United States Patent
Desjarlais et al.

(10) Patent No.: US 12,365,743 B2
(45) Date of Patent: *Jul. 22, 2025

(54) ANTI-CD28 X ANTI-PSMA ANTIBODIES

(71) Applicants: Xencor, Inc., Monrovia, CA (US); Janssen Biotech, Inc., Horsham, PA (US)

(72) Inventors: John R. Desjarlais, Pasadena, CA (US); Gregory Moore, Azusa, CA (US); Michael Hedvat, Encino, CA (US); Juan Diaz, Anaheim Hills, CA (US); Veronica Gusti Zeng, Duarte, CA (US); Matthew Adam Dragovich, Monrovia, CA (US); Joseph Erhardt, Sellersville, PA (US); Theresa McDevitt, Warminster, PA (US); Fouad Moussa, Allentown, PA (US); Pankaj Seth, Norristown, PA (US); Fei Shen, Collegeville, PA (US); Adam Zwolak, Bala Cynwyd, PA (US)

(73) Assignee: Xencor, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/172,987

(22) Filed: Feb. 22, 2023

(65) Prior Publication Data

US 2023/0265218 A1 Aug. 24, 2023

Related U.S. Application Data

(60) Provisional application No. 63/313,233, filed on Feb. 23, 2022.

(51) Int. Cl.
*C07K 16/46* (2006.01)
*C07K 16/28* (2006.01)
*C07K 16/30* (2006.01)

(52) U.S. Cl.
CPC ........ *C07K 16/468* (2013.01); *C07K 16/2818* (2013.01); *C07K 16/3069* (2013.01); *C07K 2317/31* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 5,601,819 A | 2/1997 | Wong et al. | |
| 6,551,592 B2 | 4/2003 | Lindhofer et al. | |
| 6,699,715 B1 | 3/2004 | Ledbetter et al. | |
| 6,881,557 B2 | 4/2005 | Foote | |
| 6,994,853 B1 | 2/2006 | Lindhofer et al. | |
| 7,538,196 B2 | 5/2009 | Jung | |
| 8,709,421 B2 | 4/2014 | Heiss et al. | |
| 9,017,676 B2 | 4/2015 | Lindhofer | |
| 9,382,329 B2 | 7/2016 | Chang et al. | |
| 9,441,034 B2 * | 9/2016 | Sivakumar | A61P 35/00 |
| 10,208,119 B2 | 2/2019 | Fang et al. | |
| 10,227,410 B2 | 3/2019 | Moore et al. | |
| 10,259,887 B2 | 4/2019 | Bernett et al. | |
| 10,294,300 B2 | 5/2019 | Raum et al. | |
| 10,364,287 B2 | 7/2019 | Mary et al. | |
| 10,428,155 B2 | 10/2019 | Moore et al. | |
| 10,517,949 B2 | 12/2019 | Wang et al. | |
| 10,669,337 B2 | 6/2020 | Irving et al. | |
| 10,752,697 B2 * | 8/2020 | Park | C07K 16/303 |
| 11,370,828 B2 * | 6/2022 | Westendorf | C07K 16/10 |
| 11,396,544 B2 | 7/2022 | Murphy et al. | |
| 11,591,401 B2 * | 2/2023 | Desjarlais | C07K 16/2809 |
| 11,623,957 B2 | 4/2023 | Moore et al. | |
| 11,913,023 B2 | 2/2024 | Boyle et al. | |
| 11,919,956 B2 | 3/2024 | Desjarlais et al. | |
| 12,037,604 B2 | 7/2024 | Boyle et al. | |
| 2001/0001310 A1 | 5/2001 | Weiner et al. | |
| 2002/0076406 A1 | 6/2002 | Leung | |
| 2002/0103345 A1 | 8/2002 | Zhu | |
| 2002/0115134 A1 | 8/2002 | Jung | |
| 2003/0185832 A1 | 10/2003 | Thorpe | |
| 2004/0253250 A1 | 12/2004 | Ledbetter et al. | |

(Continued)

FOREIGN PATENT DOCUMENTS

| | | | |
|---|---|---|---|
| EP | 1874821 B1 | 4/2013 | |
| EP | 3575319 A1 | 12/2019 | |
| EP | 2981281 B1 | 7/2020 | |
| EP | 3177645 B1 | 2/2021 | |

(Continued)

OTHER PUBLICATIONS

Stebbings et al., After TGN1412: Recent developments in cytokine release assays., J Immunotoxicol. Jan. 2013; 10(1): 75-82.
Waite et al., Tumor-targeted CD28 bispecific antibodies enhance the antitumor efficacy of PD-1 immunotherapy., Sci. Transl. Med. 12, eaba2325 (2020).
McCarthy et al. Altering the fine specificity of an anti-Legionella single chain antibody by a single amino acid insertion., J. Immunol. Methods, 251(1-2): 137-149, 2001.
Lin et al. Improved affinity of a chicken single-chain antibody to avian infectious bronchitis virus by site-directed mutagenesis of complementarity-determining region H3., African Journal of Biotechnology, 10(79): 18294-18302, 2011.

(Continued)

*Primary Examiner* — Marianne P Allen
(74) *Attorney, Agent, or Firm* — Louis-Vu T. Nguyen; Christopher J. Betti; Morgan, Lewis & Bockius, LLP

(57) ABSTRACT

Provided herein are novel anti-CD28× anti-PSMA antibodies and methods of using such antibodies for the treatment of PSMA-associated cancers. Subject anti-CD28× anti-PSMA antibodies are capable of agonistically binding to CD28 costimulatory molecules on T cells and PSMA on tumor cells. Thus, such antibodies selectively enhance antitumor activity at tumor sites while minimizing peripheral toxicity. The subject antibodies provided herein are particularly useful in combination with other anti-cancer therapies (e.g., anti-CD3× anti-PSMA antibodies) for the treatment of prostate cancers.

1 Claim, 173 Drawing Sheets

Specification includes a Sequence Listing.

(56) References Cited

U.S. PATENT DOCUMENTS

| | | |
|---|---|---|
| 2005/0079170 A1 | 4/2005 | Le Gall et al. |
| 2005/0175606 A1 | 8/2005 | Huang et al. |
| 2006/0115481 A1 | 6/2006 | Lindhofer et al. |
| 2006/0188493 A1 | 8/2006 | Thomas |
| 2007/0036783 A1 | 2/2007 | Humeau et al. |
| 2007/0212350 A1 | 9/2007 | Govindan et al. |
| 2008/0145362 A1 | 6/2008 | Kipriyanov et al. |
| 2008/0299137 A1 | 12/2008 | Svendsen et al. |
| 2008/0305105 A1 | 12/2008 | Kufer et al. |
| 2009/0117108 A1 | 5/2009 | Wang et al. |
| 2009/0246204 A1 | 10/2009 | Hunig |
| 2010/0291112 A1 | 11/2010 | Kellner et al. |
| 2010/0322933 A1 | 12/2010 | Lindhofer et al. |
| 2010/0330034 A1 | 12/2010 | Bigler et al. |
| 2011/0189735 A1 | 8/2011 | Hanke et al. |
| 2011/0313135 A1 | 12/2011 | Vanhove et al. |
| 2013/0078236 A1 | 3/2013 | Mary et al. |
| 2014/0348839 A1 | 11/2014 | Chowdhury et al. |
| 2015/0119555 A1 | 4/2015 | Jung et al. |
| 2016/0137980 A1 | 5/2016 | Abbot et al. |
| 2016/0355608 A1 | 12/2016 | Bernett et al. |
| 2017/0335016 A1 | 11/2017 | Takahashi |
| 2018/0079798 A1 | 3/2018 | Protzer et al. |
| 2018/0112000 A1 | 4/2018 | Nolle et al. |
| 2018/0118836 A1 | 5/2018 | Bernett et al. |
| 2018/0127501 A1 | 5/2018 | Bernett et al. |
| 2019/0106504 A1 | 4/2019 | Wu et al. |
| 2019/0233534 A1 | 8/2019 | Mehlin et al. |
| 2019/0375852 A1 | 12/2019 | Lindhofer et al. |
| 2019/0389951 A1 | 12/2019 | Murphy et al. |
| 2020/0024360 A1 | 1/2020 | Anderson et al. |
| 2020/0048350 A1 | 2/2020 | Eckelman et al. |
| 2020/0071421 A1 | 3/2020 | Zhou |
| 2020/0140552 A1 | 5/2020 | Wu et al. |
| 2020/0157213 A1 | 5/2020 | Zhu et al. |
| 2020/0157222 A1 | 5/2020 | Fang et al. |
| 2020/0199233 A1 | 6/2020 | Murphy et al. |
| 2020/0199234 A1 | 6/2020 | Georges et al. |
| 2020/0239576 A1 | 7/2020 | Murphy et al. |
| 2020/0247862 A1 | 8/2020 | Bernett et al. |
| 2020/0299388 A1 | 9/2020 | Skokos et al. |
| 2020/0376136 A1 | 12/2020 | Rudge et al. |
| 2021/0040210 A1 | 2/2021 | Ganesan et al. |
| 2021/0047435 A1 | 2/2021 | Luo et al. |
| 2021/0171596 A1 | 6/2021 | Moore et al. |
| 2022/0073876 A1 | 3/2022 | Boyle et al. |
| 2022/0089766 A1 | 3/2022 | DiLillo et al. |
| 2022/0098306 A1* | 3/2022 | Desjarlais .......... C07K 16/2809 |
| 2022/0119525 A1 | 4/2022 | Desjarlais et al. |
| 2022/0119530 A1* | 4/2022 | Desjarlais .......... C07K 16/2818 |
| 2022/0135684 A1 | 5/2022 | Desjarlais et al. |
| 2022/0233690 A1 | 7/2022 | Olson et al. |
| 2023/0040715 A1 | 2/2023 | Zwolak et al. |
| 2023/0137343 A1 | 5/2023 | Boyle et al. |
| 2023/0383012 A1 | 11/2023 | Moore et al. |
| 2024/0002793 A1 | 1/2024 | Boyle et al. |
| 2024/0034995 A1 | 2/2024 | Boyle et al. |
| 2024/0059789 A1* | 2/2024 | McDevitt .......... C07K 16/3069 |
| 2024/0218082 A1* | 7/2024 | Desjarlais ............ C07K 16/468 |
| 2025/0043001 A1 | 2/2025 | Moore et al. |
| 2025/0084179 A1 | 3/2025 | Bernett et al. |
| 2025/0084186 A1 | 3/2025 | Nisthal et al. |

FOREIGN PATENT DOCUMENTS

| | | |
|---|---|---|
| WO | WO1998004592 A1 | 2/1998 |
| WO | WO1999037791 A1 | 7/1999 |
| WO | WO200247721 A1 | 6/2002 |
| WO | WO2002051871 A2 | 7/2002 |
| WO | WO2003048194 A2 | 6/2003 |
| WO | WO2003057732 A2 | 7/2003 |
| WO | WO2003074566 A2 | 9/2003 |
| WO | WO2003078468 A2 | 9/2003 |
| WO | WO2004087876 A2 | 10/2004 |
| WO | WO2004087876 A3 | 3/2005 |
| WO | WO2005095456 A1 | 10/2005 |
| WO | WO2009062001 A1 | 5/2009 |
| WO | WO2010151792 A1 | 6/2010 |
| WO | WO 2011097603 A1 | 8/2011 |
| WO | WO2012088302 A2 | 6/2012 |
| WO | WO2014055897 A2 | 4/2014 |
| WO | WO2014110601 A1 | 7/2014 |
| WO | WO2014145806 A2 | 9/2014 |
| WO | WO2014165818 A2 | 10/2014 |
| WO | WO2014165818 A3 | 10/2014 |
| WO | WO2015112805 A1 | 7/2015 |
| WO | WO2016086186 A2 | 6/2016 |
| WO | WO2015112805 A8 | 7/2016 |
| WO | WO2016185016 A1 | 11/2016 |
| WO | WO2017023761 A1 | 2/2017 |
| WO | WO2017100372 A1 | 6/2017 |
| WO | WO2017103003 A1 | 6/2017 |
| WO | WO2017134158 A1 | 8/2017 |
| WO | WO2017205738 A1 | 11/2017 |
| WO | WO2017220990 A1 | 12/2017 |
| WO | WO2018005706 A1 | 1/2018 |
| WO | WO2018059502 A1 | 4/2018 |
| WO | WO2018184966 A1 | 10/2018 |
| WO | WO2019009726 A1 | 1/2019 |
| WO | WO2019016392 A1 | 1/2019 |
| WO | WO2019080872 A1 | 5/2019 |
| WO | WO2019190327 A2 | 10/2019 |
| WO | WO2019197583 A1 | 10/2019 |
| WO | WO2019224718 A2 | 11/2019 |
| WO | WO2019241758 A1 | 12/2019 |
| WO | WO2019245991 A1 | 12/2019 |
| WO | WO2020006509 A1 | 1/2020 |
| WO | WO2020011868 A1 | 1/2020 |
| WO | WO2020014270 A1 | 1/2020 |
| WO | WO 2020023553 A1 | 1/2020 |
| WO | WO 2020033702 A1 | 2/2020 |
| WO | WO2020076970 A1 | 4/2020 |
| WO | WO2020103100 A1 | 5/2020 |
| WO | WO2020127618 A1 | 6/2020 |
| WO | WO2020132066 A1 | 6/2020 |
| WO | WO2020180726 A1 | 9/2020 |
| WO | WO2020227515 A1 | 11/2020 |
| WO | WO2021026387 A2 | 2/2021 |
| WO | WO2021030657 A1 | 2/2021 |
| WO | WO2021155071 A1 | 8/2021 |
| WO | WO2021155380 A1 | 8/2021 |
| WO | WO2021173307 A1 | 9/2021 |
| WO | WO2021181233 A2 | 9/2021 |
| WO | WO2021197359 A1 | 10/2021 |
| WO | WO2021207242 A2 | 10/2021 |
| WO | WO2021229507 A2 | 11/2021 |
| WO | WO2021231969 A1 | 11/2021 |
| WO | WO2021259890 A1 | 12/2021 |
| WO | WO2021260064 A1 | 12/2021 |
| WO | WO2022040482 A1 | 2/2022 |
| WO | WO2022056199 A1 | 3/2022 |
| WO | WO2022061098 A1 | 3/2022 |
| WO | WO2022081886 A1 | 4/2022 |
| WO | WO 2022/162518 A3 * | 8/2022 |
| WO | WO2022056197 A1 | 8/2022 |
| WO | WO2022162518 A2 | 8/2022 |
| WO | WO2022165171 A1 | 8/2022 |
| WO | WO2022200443 A1 | 9/2022 |
| WO | WO2022201053 A1 | 9/2022 |
| WO | WO2023046322 A1 | 3/2023 |
| WO | WO2023164627 A1 | 8/2023 |
| WO | WO2023164640 A1 | 8/2023 |
| WO | WO2025049613 A1 | 3/2025 |

OTHER PUBLICATIONS

Yu, Ph.D, Hangxing, Analyzing antibody sequence for recombinant antibody expression. GenScript, May 20, 2015.

Bluemel et al., Epitope distance to the target cell membrane and antigen size determine the potency of T cell-mediated lysis by BiTE antibodies specific for a large melanoma surface antigen., Cancer Immunol Immunother. Aug. 2010;59(8):1197-209. doi: 10.1007/s00262-010- 0844-y. Epub Mar. 23, 2010.

(56) References Cited

OTHER PUBLICATIONS

Moore et al., A robust heterodimeric Fc platform engineered for efficient development of bispecific antibodies of multiple formats., Methods. Feb. 1, 2019;154:38-50. doi:10.1016/j.ymeth.2018.10.006. Epub Oct. 23, 2018.

Brinkmann et al., The making of bispecific antibodies", MABS, vol. 9, No. 2, Jan. 10, 2017 (Jan. 10, 2017), pp. 182-212".

Moore, Gregory et al., Abstract 1880: PDL1-targeted CD28 costimulatory bispecific antibodies enhance T cell activation in solid tumors., Cancer Research, Jul. 1, 2021 (Jul. 1, 2021), XP055881520, Retrieved from the Internet: URL:https://cancerres.aacrjournals.org/content/81/13_Supplement/1880.

Moore, Gregory et al., PDL1-targeted CD28 costimulatory bispecific antibodies enhance T cell activation in solid tumors., Jul. 1, 2021 (Jul. 1, 20211), XP055881523, Retrieved from the Internet: URL:https://investors.xencor.com/static-files/5adc4e21-6760-4eec-b7b3-f2b6765bddc3.

Almagro et al., Humanization of antibodies. Front Biosci. Jan. 1, 2008 ;13:1619-33. (Year: 2008).

Kussie et al. A single engineered amino acid substitution changes antibody fine specificity.J Immunol . Jan. 1, 1994 ;152(1 ): 146-52. (Year: 1994).

Edwards et al. The remarkable flexibility of the human antibody repertoire;isolation of over one thousand different antibodies to a single protein,BLyS. J Mol Biol Nov. 14, 2003;334(1):103-18. (Year: 2003).

Mullard, Asher, Trispecific antibodies take to the clinic., Nature Reviews Drug Discovery, Nature, Publishing Group, GB, vol. 19, No. 10, Sep. 11, 2020 (Sep. 11, 2020), pp. 657-658.

Singh et al., Overcoming the challenges associated with CD3+ T-cell redirection in cancer., Br J Cancer. Mar. 16, 2021; 124(6): 1037-1048.

Majocchi et al., Abstract 2884: Optimized CD28 bispecific antibodies for targeted activation of T cells within the tumor microenvironment., Cancer Res (2022) 82 (12_Supplement): 2884.

Poirier et al., CD28-Specific Immunomodulating Antibodies: What Can Be Learned From Experimental Models?: CD28-Specific Immunomodulating Antibodies., American Journal of Transplantation, vol. 12, No. 7, Jul. 1, 2012 (Jul. 1, 2012), pp. 1682-1690, XP055590905, DK ISSN: 1600-6135, DOI: 10.1111 /j.1600-6143. 2012.04032.x.

Liu et al., Bispecific antibody targeting TROP2xCD3 suppresses tumor growth of triple negative breast cancer., J Immunother Cancer. Oct. 2021;9(10):e003468. doi: 10.1136/jitc-2021-003468.

Elshiaty et al., Principles and Current Clinical Landscape of Multispecific Antibodies against Cancer., Int J Mol Sci. May 26, 2021;22(11):5632. doi: 10.3390/ijms22115632.

Zeng et al., 1073 Costimulatory CD28 trispecific antibodies targeting PDL1 and PDL2 enhance T cell activation in solid tumors., Journal for Immunotherapy of Cancer, vol. 10, No. Suppl 2,Nov. 1, 2022 (Nov. 1, 2022), p. A1115, XP093064655.

Seamen et al., Eradication of Tumors through Simultaneous Ablation of CD276/B7-H3-Positive Tumor Cells and Tumor Vasculature., Cancer Cell 31, 501-515, Apr. 10, 2017.

Skokos et al., A class of costimulatory CD28-bispecific antibodies that enhance the antitumor activity of CD3-bispecific antibodies., Sci Transl Med. Jan. 8, 2020;12(525):eaaw7888. doi: 10.1126/scitranslmed.aaw7888.

Steffen Dickopf et al, "Format and geometries matter: Structure-based design defines the functionality of bispecific antibodies", *Computational and Structural Biotechnology Journal*,vol. 18, May 14, 2020 (May 14, 2020), p. 1221-1227.

Roda-Navarro Pedro et al, "Understanding the Spatial Topology of Artificial Immunological Synapses Assembled in T Cell-Redirecting Strategies: A Major Issue in Cancer Immunotherapy", Frontiers in Cell and Developmental Biology, vol. 7, Jan. 10, 2020 (Jan. 10, 2020).

Suurs Frans V et al, "A review of bispecific antibodies and antibody constructs in oncology and clinical challenges", Apr. 24, 2019 (Apr. 24, 2019), vol. 201, p. 103-119.

Chen Shixue et al, "Immunoglobulin Gamma-Like Therapeutic Bispecific Antibody Formats for Tumor Therapy", US Feb. 11, 2019 (Feb. 11, 2019), vol. 2019, p. 1-13.

Van Blarcom, Thomas et al, "Productive common light chain libraries yield diverse panels of high affinity bispecific antibodies", MABS,vol. 10, No. 2, Dec. 14, 2017 (Dec. 14, 2017), p. 256-268.

Hedvat Michael et al, "697?Tumor-targeted CD28 costimulatory bispecific antibodies enhance T cell activation in solid tumors", Journal for Immunotherapy of Cancer,vol. 8, No. Suppl 3, Nov. 1, 2020 (Nov. 1, 2020), p. A739-A739.

Liu et al., Tumor-targeted CD28 bispecific POWERbody○ for safe and synergistic T cell-mediated immunotherapy., 2022 AACR Annual Meeting, Abstract No. 2888 (poster).

Liu et al., Abstract 2888: Tumor-targeted CD28 bispecific POWERbody ○ for safe and synergistic T cell-mediated immunotherapy., Cancer Res (2022) 82 (12_Supplement): 2888.

Ahmed et al., Humanized Affinity-matured Monoclonal Antibody 8H9 Has Potent Antitumor Activity and Binds to FG Loop of Tumor Antigen B7-H3*., The Journal of Biological Chemistry vol. 290, No. 50, pp. 30018-30029, Dec. 11, 2015.

Bohlen et al., Cytolysis of Leukemic B-Cells by T-Cells Activated via Two Bispecific Antibodies., Cancer Research 53, 4310-4314, Sep. 15, 1993.

Correnti et al., Simultaneous multiple interaction T-cell engaging (SMITE) bispecific antibodies overcome bispecific T-cell engager (BiTE) resistance via CD28 co-stimulation., Leukemia (2018) 32:1239-1243.

Hodge et al., Induction of Antitumor Immunity by Recombinant Vaccinia Viruses Expressing B7-1 or B7-2 Costimulatory Molecules., Cancer Research 54, 5552-5555, Nov. 1, 1994.

Hui et al., T cell costimulatory receptor CD28 is a primary target for PD-1-mediated inhibition., Science 10.1126/science.aaf1292, Mar. 9, 2017.

Jansen et al., An intra-tumoral niche maintains and differentiates stem-like CD8 T cells., Nature vol. 576, pp. 465-470 (2019).

Kamphorst et al., Rescue of exhausted CD8 T cells by PD-1-targeted therapies is CD28-dependent., Science 10.1126/science.aaf0683, Mar. 9, 2017.

Loo et al., Development of an Fc-Enhanced Anti-B7-H3 Monoclonal Antibody with Potent Antitumor Activity., Clin Cancer Res; 18(14) Jul. 15, 2012.

Mary et al., Antagonist properties of monoclonal antibodies targeting human CD28: role of valency and the heavy-chain constant domain., MAbs. Jan.-Feb. 2013;5(1):47-55. doi: 10.4161/mabs.22697. Epub Dec. 5, 2012.

Poirier et al., Advantages of Papio anubis for preclinical testing of immunotoxicity of candidate therapeutic antagonist antibodies targeting CD28., mAbs, 6:3, 697-706, DOI: 10.4161/mabs.28375.

Poirier et al., First-in-Human Study in Healthy Subjects with FR104, a Pegylated Monoclonal Antibody Fragment Antagonist of CD28., J Immunol. Dec. 15, 2016;197(12):4593-4602. doi: 10.4049/jimmunol.1601538. Epub Nov. 14, 2016.

Seaman et al., Genes that Distinguish Physiological and Pathological Angiogenesis., Cancer Cell. Jun. 2007; 11(6):539-54. doi: 10.1016/j.ccr.2007.04.017.

Shiao et al., Immunomodulatory Properties of FK734, a Humanized Anti-CD28 Monoclonal Antibody With Agonistic and Antagonistic Activities., Transplantation. Feb. 15, 2007;83(3):304-13. doi: 10.1097/01.tp.0000251426.46312.d5.

Moore et al., A robust heterodimeric Fc platform engineered for efficient development of bispecific antibodies of multiple formats., Methods. Feb. 1, 2019;154:38-50. doi:10.1016/j.ymeth.2018.10.006. Epub Oct. 23, 2018.

Moore, Gregory et al., PDL1-targeted CD28 costimulatory bispecific antibodies enhance T cell activation in solid tumors., Jul. 1, 2021 (Jul. 1, 2021), XP055881523, Retrieved from the Internet: URL:https://investors.xencor.com/static-files/5adc4e21-6760-4eec-b7b3-f2b6765bddc3.

Marchalonis et al., The antibody repertoire in evolution: chance, selection, and continuity., Dev Comp Immunol. 2006;30(1-2):223-47. doi: 10.1016/j.dci.2005.06.011.

(56) References Cited

OTHER PUBLICATIONS

Lippow et al., Computational design of antibody-affinity improvement beyond in vivo maturation., Nat Biotechnol. Oct. 2007;25(10):1171-6. doi: 10.1038/nbt1336. Epub Sep. 23, 2007.

Altshuler et al., Generation of Recombinant Antibodies and Means for Increasing Their Affinity., Biochemistry (Moscow), 75(13):1584-1605 (2010).

Vajda et al., Progress toward improved understanding of antibody maturation., Current Opinion in Structural Biology, 67 pp. 226-231 (2021).

Marks et al., How repertoire data are changing antibody science., J Biol Chem. Jul. 17, 2020;295(29):9823-9837. doi: 10.1074/jbc.REV120.010181.

Akbar et al., A compact vocabulary of paratope-epitope interactions enables predictability of antibody-antigen binding., Cell Rep. Mar. 16, 2021;34(11):108856. doi: 10.1016/j.celrep.2021.108856.

Lo et al., Conformational epitope matching and prediction based on protein surface spiral features., BMC Genomics 2021, 22(Suppl 2):116. https://doi.org/10.1186/s12864-020-07303-5.

David E Szymkowski et al: "Creating the next generation of protein therapeutics through rational drug design", Current Opinion in Drug Discovery & Development, Sep. 1, 2005 (Sep. 1, 2005), England, pp. 590, XP055354917, Retrieved from the Internet.

Tang Y et al: "Selection of linkers for a catalytic single-chain antibody using phage display technology", Journal of Biological Chemistry, American Society for Biochemistry and Molecular Biology, US, vol. 271, No. 26, Jan. 1, 1996 (Jan. 1, 1996), pp. 15682-15686, XP002962142, ISSN: 0021-9258, DOI: 10.1074/JBC.271.26.15682.

Cuesta et al., Multivalent antibodies: when design surpasses evolution., Trends Biotechnol. Jul. 2010;28(7):355-62. doi: 10.1016/j.tibtech.2010.03.007. Epub May 4, 2010.

Mertens, Nico, Tribodies: Fab-scFv Fusion Proteins as a Platform to Create Multifunctional Pharmaceuticals., In: "Bispecific Antibodies", Jan. 1, 2011 (Jan. 1, 2011), Springer Berlin Heidelberg, Berlin, Heidelberg, XP055261148, ISBN: 978-3-642-20910-9 pp. 135-149.

Jin Yixin et al.: "Development of STEAP1 targeting chimeric antigen receptor foradoptive cell therapy against cancer", Molecular Therapy—Oncolytics, [Online] vol. 26, Sep. 15, 2022 (Sep. 15, 2022), pp. 189-206.

Bhatia Vipul et al: "Targeting advanced prostate cancer with STEAP1 chimeric antigen receptor T cell therapy", bioRxiv, May 17, 2022 (May 17, 2022), pp. 1-47, XP093203200.

Dragovich Matthew A. et al: "Abstract 2983: Tumor-specific CD28 costimulatory bispecific antibodies enhance T cell activation in solid tumors", Cancer Research, vol. 83, No. 7_Supplement, Apr. 4, 2023 (Apr. 4, 2023), pp. 2983-2983, XP093184059.

Warwas Karsten M. et al: "Co-Stimulatory Bispecific Antibodies Induce Enhanced T Cell Activation and Tumor Cell Killing in Breast Cancer Models", Frontiers in Immunology, vol. 12, Aug. 16, 2021 (Aug. 16, 2021), XP093070636.

Brandl Martina et al.: "Bispecific antibody fragments with CD20 x CD28 specificity allow effective autologous and allogeneic T-cell activation against malignant cells in peripheral blood and bone marrow cultures from patients with B-cell lineage leukemia and lymphoma", Experimental Hematology, vol. 27, Issue 8, 1264-1270, May 19, 1999 (May 19, 1999).

Otz, T., Große-Hovest, L., Hofmann, M et al. A bispecific single-chain antibody that mediates target cell-restricted, supra-agonistic CD28 stimulation and killing of lymphoma cells. Leukemia 23, 71-77 (2009). https://doi.org/10.1038/leu.2008.271.

* cited by examiner

Figure 1A

Human CD28 sequence SEQ ID NO: 1
>sp|P10747|CD28_HUMAN T-cell-specific surface glycoprotein CD28 OS=Homo sapiens OX=9606 GN=CD28 PE=1 SV=1
MLRLLLALNLFPSIQVTGNKILVKQSPMLVAYDNAVNLSCKYSYNLFSREFRASLHKGLDSAVEVCVVYGNYSQQLQ
VYSKTGFNCDGKLGNESVTFYLQNLYVNQTDIYFCKIEVMYPPPYLDNEKSNGTIIHVKGKHLCPSPLFPGPSKPFW
VLVVVGGVLACYSLLVTVAFIIFWVRSKRSRLLHSDYMNMTPRRPGPTRKHYQPYAPPRDFAAYRS Human CD28, extracellular domain SEQ ID NO: 2
>sp|P10747|19-152
NKILVKQSPMLVAYDNAVNLSCKYSYNLFSREFRASLHKGLDSAVEVCVVYGNYSQQLQVYSKTGFNCDGKLGNESV
TFYLQNLYVNQTDIYFCKIEVMYPPPYLDNEKSNGTIIHVKGKHLCPSPLFPGPSKP Mouse CD28 sequence SEQ ID NO: 3
>sp|P31041|CD28_MOUSE T-cell-specific surface glycoprotein CD28 OS=Mus musculus OX=10090 GN=Cd28 PE=1 SV=2
MTLRLLFLALNFFSVQVTENKILVKQSPLLVVDSNEVSLSCRYSYNLLAKEFRASLYKGVNSDVEVCVGNGNFTYQP
QFRSNAEFNCDGDFDNETVTFRLWNLHVNHTDIYFCKIEFMYPPPYLDNERSNGTIIHIKEKHLCHTQSSPKLFWAL
VVVAGVLFCYGLLVTVALCVIWTNSRRNRLLQSDYMNMTPRRPGLTRKPYQPYAPARDFAAYRP Mouse CD28, extracellular domain SEQ ID NO: 4
>sp|P31041|20-150
NKILVKQSPLLVVDSNEVSLSCRYSYNLLAKEFRASLYKGVNSDVEVCVGNGNFTYQPQFRSNAEFNCDGDFDNETV
TFRLWNLHVNHTDIYFCKIEFMYPPPYLDNERSNGTIIHIKEKHLCHTQSSPKL Cynomolgus CD28 sequence SEQ ID NO: 5
>tr|Q0PDN3|Q0PDN3_MACFA CD28 OS=Macaca fascicularis OX=9541 GN=CD28 PE=2 SV=1
MLRLLLALNLLPSIQVTGNKILVKQSPMLVAYDNAVNLSCKYSYNLFSREFRASLHKGLDSAVEVCVVYGNYSQQLQ
VYSKTGFNCDGKLGNESVTFYLQNLYVNQTDIYFCKIEVMYPPPYLDNEKSNGTIIHVKGKHLCPSPLFPGPSKPFW
ALVVVGGVLACYSLLVTVAFCIFWMRSKRSRLLHSDYMNMTPRRPGPTRKHYQPYAPPRDFAAYRS Cynomolgus CD28, extracellular domain SEQ ID NO: 6
>tr|Q0PDN3|19-152
NKILVKQSPMLVAYDNAVNLSCKYSYNLFSREFRASLHKGLDSAVEVCVVYGNYSQQLQVYSKTGFNCDGKLGNESV
TFYLQNLYVNQTDIYFCKIEVMYPPPYLDNEKSNGTIIHVKGKHLCPSPLFPGPSKP Cynomolgus CD28 sequence (predicted) SEQ ID NO: 7
>XP_015308533.1 PREDICTED: CD276 antigen isoform X1 [Macaca fascicularis]
MKLSSDHVFPLFRKLQWLPAAFRIQFTPVSPSAGAAFHHGEPSCQLPHSKMLHRRGSPGMGVHVGAALGALWFCLTG
ALEVQVPEDPVVALVGTDATLRCSFSPEPGFSLAQLNLIWQLTDTKQLVHSFTEGRDQGSAYANRTALFLDLLAQGN
ASLRLQRVRVADEGSFTCFVSIRDFGSAAVSLQVAAPYSKPSMTLEPNKDLRPGDTVTITCSSYRGYPEAEVFWQDG
QGAPLTGNVTTSQMANEQGLFDVHSVLRVVLGANGTYSCLVRNPVLQQDAHGSITITPQRSPTGAVEVQVPEDPVVA
LVGTDATLRCSFSPEPGFSLAQLNLIWQLTDTKQLVHSFTEGRDQGSAYANRTALFLDLLAQGNASLRLQRVRVADE
GSFTCFVSIRDFGSAAVSLQVAAPYSKPSMTLEPNKDLRPGDTVTITCSSYRGYPEAEVFWQDGQGAPLTGNVTTSQ
MANEQGLFDVHSVLRVVLGANGTYSCLVRNPVLQQDAHGSVTITGQPMTFPPEALWVTVGLSVCLVALLVALAFVCW
RKIKQSCEEENAGAEDQDGEGEGSKTALQPLKHSDSKEDDGQELA

Figure 1B

Cynomolgus CD28, extracellular domain SEQ ID NO: 8
>XP_015308533.1|79-516
LEVQVPEDPVVALVGTDATLRCSFSPEPGFSLAQLNLIWQLTDTKQLVHSFTEGRDQGSAYANRTALFLDLLAQGNA
SLRLQRVRVADEGSFTCFVSIRDFGSAAVSLQVAAPYSKPSMTLEPNKDLRPGDTVTITCSSYRGYPEAEVFWQDGQ
GAPLTGNVTTSQMANEQGLFDVHSVLRVVLGANGTYSCLVRNPVLQQDAHGSITITPQRSPTGAVEVQVPEDPVVAL
VGTDATLRCSFSPEPGFSLAQLNLIWQLTDTKQLVHSFTEGRDQGSAYANRTALFLDLLAQGNASLRLQRVRVADEG
SFTCFVSIRDFGSAAVSLQVAAPYSKPSMTLEPNKDLRPGDTVTITCSSYRGYPEAEVFWQDGQGAPLTGNVTTSQM
ANEQGLFDVHSVLRVVLGANGTYSCLVRNPVLQQDAHGSVTITGQPMTFPPEA

Figure 2A

Human PSMA sequence SEQ ID NO: 428
>sp|Q04609
MWNLLHETDSAVATARRPRWLCAGALVLAGGFFLLGFLFGWFIKSSNEATNITPKHNMKAFLDELKAENIKKFLYNF
TQIPHLAGTEQNFQLAKQIQSQWKEFGLDSVELAHYDVLLSYPNKTHPNYISIINEDGNEIFNTSLFEPPPPGYENV
SDIVPPFSAFSPQGMPEGDLVYVNYARTEDFFKLERDMKINCSGKIVIARYGKVFRGNKVKNAQLAGAKGVILYSDP
ADYFAPGVKSYPDGWNLPGGGVQRGNILNLNGAGDPLTPGYPANEYAYRRGIAEAVGLPSIPVHPIGYYDAQKLLEK
MGGSAPPDSSWRGSLKVPYNVGPGFTGNFSTQKVKMHIHSTNEVTRIYNVIGTLRGAVEPDRYVILGGHRDSWVFGG
IDPQSGAAVVHEIVRSFGTLKKEGWRPRRTILFASWDAEEFGLLGSTEWAEENSRLLQERGVAYINADSSIEGNYTL
RVDCTPLMYSLVHNLTKELKSPDEGFEGKSLYESWTKKSPSPEFSGMPRISKLGSGNDFEVFFQRLGIASGRARYTK
NWETNKFSGYPLYHSVYETYELVEKFYDPMFKYHLTVAQVRGGMVFELANSIVLPFDCRDYAVVLRKYADKIYSISM
KHPQEMKTYSVSFDSLFSAVKNFTEIASKFSERLQDFDKSNPIVLRMMNDQLMFLERAFIDPLGLPDRPFYRHVIYA
PSSHNKYAGESFPGIYDALFDIESKVDPSKAWGEVKRQIYVAAFTVQAAAETLSEVA

Human PSMA sequence, extracellular domain SEQ ID NO: 429
>sp|Q04609|44-750
KSSNEATNITPKHNMKAFLDELKAENIKKFLYNFTQIPHLAGTEQNFQLAKQIQSQWKEFGLDSVELAHYDVLLSYP
NKTHPNYISIINEDGNEIFNTSLFEPPPPGYENVSDIVPPFSAFSPQGMPEGDLVYVNYARTEDFFKLERDMKINCS
GKIVIARYGKVFRGNKVKNAQLAGAKGVILYSDPADYFAPGVKSYPDGWNLPGGGVQRGNILNLNGAGDPLTPGYPA
NEYAYRRGIAEAVGLPSIPVHPIGYYDAQKLLEKMGGSAPPDSSWRGSLKVPYNVGPGFTGNFSTQKVKMHIHSTNE
VTRIYNVIGTLRGAVEPDRYVILGGHRDSWVFGGIDPQSGAAVVHEIVRSFGTLKKEGWRPRRTILFASWDAEEFGL
LGSTEWAEENSRLLQERGVAYINADSSIEGNYTLRVDCTPLMYSLVHNLTKELKSPDEGFEGKSLYESWTKKSPSPE
FSGMPRISKLGSGNDFEVFFQRLGIASGRARYTKNWETNKFSGYPLYHSVYETYELVEKFYDPMFKYHLTVAQVRGG
MVFELANSIVLPFDCRDYAVVLRKYADKIYSISMKHPQEMKTYSVSFDSLFSAVKNFTEIASKFSERLQDFDKSNPI
VLRMMNDQLMFLERAFIDPLGLPDRPFYRHVIYAPSSHNKYAGESFPGIYDALFDIESKVDPSKAWGEVKRQIYVAA
FTVQAAAETLSEVA

Mouse PSMA sequence SEQ ID NO: 430
>sp|O35409
MWNALQDRDSAEVLGHRQRWLRVGTLVLALTGTFLIGFLFGWFIKPSNEATGNVSHSGMKKEFLHELKAENIKKFLY
NFTRTPHLAGTQNNFELAKQIHDQWKEFGLDLVELSHYDVLLSYPNKTHPNYISIINEDGNEIFKTSLSEQPPPGYE
NISDVVPPYSAFSPQGTPEGDLVYVNYARTEDFFKLEREMKISCSGKIVIARYGKVFRGNMVKNAQLAGAKGMILYS
DPADYFVPAVKSYPDGWNLPGGGVQRGNVLNLNGAGDPLTPGYPANEHAYRHELTNAVGLPSIPVHPIGYDDAQKLL
EHMGGPAPPDSSWKGGLKVPYNVGPGFAGNFSTQKVKMHIHSYTKVTRIYNVIGTLKGALEPDRYVILGGHRDAWVF
GGIDPQSGAAVVHEIVRSFGTLKKKGRRPRRTILFASWDAEEFGLLGSTEWAEEHSRLLQERGVAYINADSSIEGNY
TLRVDCTPLMYSLVYNLTKELQSPDEGFEGKSLYDSWKEKSPSPEFIGMPRISKLGSGNDFEVFFQRLGIASGRARY
TKNWKTNKVSSYPLYHSVYETYELVVKFYDPTFKYHLTVAQVRGAMVFELANSIVLPFDCQSYAVALKKYADTIYNI
SMKHPQEMKAYMISFDSLFSAVNNFTDVASKFNQRLQELDKSNPILLRIMNDQLMYLERAFIDPLGLPGRPFYRHII
YAPSSHNKYAGESFPGIYDALFDISSKVNASKAWNEVKRQISIATFTVQAAAETLREVA

Mouse PSMA sequence, extracellular domain SEQ ID NO: 431
>sp|O35409|45-752
KPSNEATGNVSHSGMKKEFLHELKAENIKKFLYNFTRTPHLAGTQNNFELAKQIHDQWKEFGLDLVELSHYDVLLSY
PNKTHPNYISIINEDGNEIFKTSLSEQPPPGYENISDVVPPYSAFSPQGTPEGDLVYVNYARTEDFFKLEREMKISC
SGKIVIARYGKVFRGNMVKNAQLAGAKGMILYSDPADYFVPAVKSYPDGWNLPGGGVQRGNVLNLNGAGDPLTPGYP
ANEHAYRHELTNAVGLPSIPVHPIGYDDAQKLLEHMGGPAPPDSSWKGGLKVPYNVGPGFAGNFSTQKVKMHIHSYT
KVTRIYNVIGTLKGALEPDRYVILGGHRDAWVFGGIDPQSGAAVVHEIVRSFGTLKKKGRRPRRTILFASWDAEEFG
LLGSTEWAEEHSRLLQERGVAYINADSSIEGNYTLRVDCTPLMYSLVYNLTKELQSPDEGFEGKSLYDSWKEKSPSP
EFIGMPRISKLGSGNDFEVFFQRLGIASGRARYTKNWKTNKVSSYPLYHSVYETYELVVKFYDPTFKYHLTVAQVRG
AMVFELANSIVLPFDCQSYAVALKKYADTIYNISMKHPQEMKAYMISFDSLFSAVNNFTDVASKFNQRLQELDKSNP
ILLRIMNDQLMYLERAFIDPLGLPGRPFYRHIIYAPSSHNKYAGESFPGIYDALFDISSKVNASKAWNEVKRQISIA
TFTVQAAAETLREVA

Figure 2B

Macaca fascicularis PSMA sequence SEQ ID NO: 432
```
>tr|G7PNF
MWNLLHETDSAVATARRPRWLCAGALVLAGGFFLLGFLFGWFIKSSSEATNITPKHNMKAFLDELKAENIKKFLHNF
TQIPHLAGTEQNFQLAKQIQSQWKEFGLDSVELTHYDVLLSYPNKTHPNYISIINEDGNEIFNTSLFEPPPAGYENV
SDIVPPFSAFSPQGMPEGDLVYVNYARTEDFFKLERDMKINCSGKIVIARYGKVFRGNKVKNAQLAGATGVILYSDP
DDYFAPGVKSYFDGWNLPGGGVQRGNILNLNGAGDPLTPGYPANEYAYRRGMAEAVGLPSIPVHPIGYYDAQKLLEK
MGGSASPDSSWRGSLKVPYNVGPGFTGNFSTQKVKMHIHSTSEVTRIYNVIGTLRGAVEPDRYVILGGHRDSWVFGG
IDPQSGAAVVHEIVRSFGMLKKEGWRPRRTILFASWDAEEFGLLGSTEWAEENSRLLQERGVAYINADSSIEGNYTL
RVDCTPLMYSLVYNLTKELESPDEGFEGKSLYESWTKKSPSPEFSGMPRISKLGSGNDFEVFFQRLGIASGRARYTK
NWETNKFSSYPLYHSVYETYELVEKFYDPMFKYHLTVAQVRGGMVFELANSVVLPFDCRDYAVVLRKYADKIYNISM
KHPQEMKTYSVSFDSLFSAVKNFTEIASKFSERLRDFDKSNPILLRMMNDQLMFLERAFIDPLGLPDRPFYRHVIYA
PSSHNKYAGESFPGIYDALFDIESKVDPSQAWGEVKRQISIATFTVQAAAETLSEVA
```

Macaca fascicularis PSMA sequence, extracellular domain (predicted) SEQ ID NO: 433
```
>tr|G7PNF|44-750
KSSSEATNITPKHNMKAFLDELKAENIKKFLHNFTQIPHLAGTEQNFQLAKQIQSQWKEFGLDSVELTHYDVLLSYP
NKTHPNYISIINEDGNEIFNTSLFEPPPAGYENVSDIVPPFSAFSPQGMPEGDLVYVNYARTEDFFKLERDMKINCS
GKIVIARYGKVFRGNKVKNAQLAGATGVILYSDPDDYFAPGVKSYPDGWNLPGGGVQRGNILNLNGAGDPLTPGYPA
NEYAYRRGMAEAVGLPSIPVHPIGYYDAQKLLEKMGGSASPDSSWRGSLKVPYNVGPGFTGNFSTQKVKMHIHSTSE
VTRIYNVIGTLRGAVEPDRYVILGGHRDSWVFGGIDPQSGAAVVHEIVRSFGMLKKEGWRPRRTILFASWDAEEFGL
LGSTEWAEENSRLLQERGVAYINADSSIEGNYTLRVDCTPLMYSLVYNLTKELESPDEGFEGKSLYESWTKKSPSPE
FSGMPRISKLGSGNDFEVFFQRLGIASGRARYTKNWETNKFSSYPLYHSVYETYELVEKFYDPMFKYHLTVAQVRGG
MVFELANSVVLPFDCRDYAVVLRKYADKIYNISMKHPQEMKTYSVSFDSLFSAVKNFTEIASKFSERLRDFDKSNPI
LLRMMNDQLMFLERAFIDPLGLPDRPFYRHVIYAPSSHNKYAGESFPGIYDALFDIESKVDPSQAWGEVKRQISIAT
FTVQAAAETLSEVA
```

Figure 3A

| Monomer 1 | Monomer 2 |
|---|---|
| F405A | T394F |
| S364D | Y349K |
| S364E | L368K |
| S364E | Y349K |
| S364F | K370G |
| S364H | Y349K |
| S364H | Y349T |
| S364Y | K370G |
| T411K | K370E |
| V397S/F405A | T394F |
| K370R/T411K | K370E/T411E |
| L351E/S364D | Y349K/L351K |
| L351E/S364E | Y349K/L351K |
| L351E/T366D | L351K/T366K |
| P395T/V397S/F405A | T394F |
| S364D/K370G | S364Y/K370R |
| S364D/T394F | Y349K/F405A |
| S364E/F405A | Y349K/T394F |
| S364E/F405S | Y349K/T394Y |
| S364E/T411E | Y349K/D401K |
| S364H/D401K | Y349T/T411E |
| S364H/F405A | Y349T/T394F |
| S364H/T394F | Y349T/F405A |
| Y349C/S364E | Y349K/S354C |
| L351E/S364D/F405A | Y349K/L351K/T394F |
| L351K/S364H/D401K | Y349T/L351E/T411E |
| S364E/T411E/F405A | Y349K/T394F/D401K |
| S364H/D401K/F405A | Y349T/T394F/T411E |
| S364H/F405A/T411E | Y349T/T394F/D401K |

Figure 3B

| Monomer 1 | Monomer 2 |
|---|---|
| K370E/T411D | T411K |
| L368E/K409E | L368K |
| Y349T/T394F/S354C | S364H/F405A/Y349C |
| T411E | D401K |
| T411E | D401R/T411R |
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |
| L368E | S364K/K409V |
| L368D | S364K |
| L368D/K370S | S364K |
| L368D/K370S | S364K/E357L |
| L368D/K370S | S364K/E357Q |
| T411E/K360E/Q362E | D401K |
| K370S | S364K |
| L368E/K370S | S364K/E357Q |
| K370S | S364K/E357Q |
| T411E/K360D | D401K |
| T411E/K360E | D401K |
| T411E/Q362E | D401K |
| T411E/N390D | D401K |
| T411E | D401K/Q347K |
| T411E | D401K/Q347R |
| T411E/K360D/Q362E | D401K |

Figure 3C

| Monomer 1 | Monomer 2 |
|---|---|
| T411E/K360E/N390D | D401K |
| T411E/Q362E/N390D | D401K |
| T411E/Q347R | D401K/K360D |
| T411E/Q347R | D401K/K360E |
| T411E/K360 | D401K/Q347K |
| T411E/K360D | D401K/Q347R |
| T411E/K360E | D401K/Q347K |
| T411E/K360E | D401K/Q347R |
| T411E/S364K | D401K/K370S |
| T411E/K370S | D401K/S364K |
| Q347E | E357Q |
| Q347E | E357Q/Q362K |
| K360D/Q362E | Q347R |
| K360D/Q362E | D401K |
| K360D/Q362E | Q347R/D401K |
| K360E/Q362E | Q347R |
| K360E/Q362E | D401K |
| K360E/Q362E | Q347R/D401K |
| Q362E/N390D | D401K |
| Q347E/K360D | D401N |
| K360D | Q347R/N390K |
| K360D | N390K/D401N |
| K360E | Y349H |
| K370S/Q347E | S364K |
| K370S/E357L | S364K |
| K370S/E357Q | S364K |
| K370S/Q347E/E357L | S364K |
| K370S/Q347E/E357Q | S364K |

Figure 3D

| Monomer 1 | Monomer 2 |
| --- | --- |
| L368D/K370S/Q347E | S364K |
| L368D/K370S/E357L | S364K |
| L368D/K370S/E357Q | S364K |
| L368D/K370S/Q347E/E357L | S364K |
| L368D/K370S/Q347E/E357Q | S364K |
| L368E/K370S/Q347E | S364K |
| L368E/K370S/E357L | S364K |
| L368E/K370S/E357Q | S364K |
| L368E/K370S/Q347E/E357L | S364K |
| L368E/K370S/Q347E/E357Q | S364K |
| L368D/K370T/Q347E | S364K |
| L368D/K370T/E357L | S364K |
| L368D/K370T/E357Q | S364K |
| L368D/K370T/Q347E/E357L | S364K |
| L368D/K370T/Q347E/E357Q | S364K |
| L368E/K370T/Q347E | S364K |
| L368E/K370T/E357L | S364K |
| L368E/K370T/E357Q | S364K |
| L368E/K370T/Q347E/E357L | S364K |
| L368E/K370T/Q347E/E357Q | S364K |
| T411E/Q362E | D401K/T411K |
| T411E/N390D | D401K/T411K |
| T411E/Q362E | D401R/T411R |
| T411E/N390D | D401R/T411R |
| Y407T | T366Y |
| F405A | T394W |
| T366Y/F405A | T394W/Y407T |
| Y407A | T366W |
| T366S/L368A/Y407V | T366W |
| T366S/L368A/Y407V/Y349C | T366W/S354C |

Figure 3E

| Monomer 1 | Monomer 2 |
|---|---|
| T366S/L368A/Y407V/S354C | T366W/Y349C |
| S354C | Y349C |
| K392D/K409D | E356K/D399K |
| K370D/K392D/K409D | E356K/E357K/D399K |
| K274Q/R355Q/N384S/K392N/V397M/Q419E/K447_ | P217R/P228R/N276K |
| K274Q/R355Q/N384S/K392N/V397M/Q419E/K447_ | N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| K274Q/R355Q/Q419E/K447_ | P217R/P228R/N276K |
| K274Q/R355Q/Q419E/K447_ | N276K |
| I199T/N203D/K274Q/R355Q/N384S/K392N/V397M/Q419E/K447_ | Q196K/I199T/P217R/P228R/N276K |
| I199T/N203D/K274Q/R355Q/N384S/K392N/V397M/Q419E/K447_ | Q196K/I199T/N276K |
| I199T/N203D/K274Q/R355Q/Q419E/K447_ | Q196K/I199T/P217R/P228R/N276K |
| I199T/N203D/K274Q/R355Q/Q419E/K447_ | Q196K/I199T/N276K |

Figure 3F

| Monomer 1 | Monomer 2 |
|---|---|
| I199T/N203D/K274Q/R355Q/N384S/K392N/V397M/Q419E/K447_ | |
| N208D/Q295E/N384D/Q418E/N421D | |
| N208D/Q295E/Q418E/N421D | |
| Q196K/I199T/P217R/P228R/N276K | |
| Q196K/I199T/N276K | |
| K274Q/R355Q/N384S/K392N/V397M/Q419E/K447_ | |
| Q295E/N384D/Q418E/N421D | |
| Q295E/Q418E/N421D | |
| P217R/P228R/N276K | |
| N276K | |
| E269Q/E272Q/E283Q/E357Q | |
| E269Q/E272Q/E283Q | |
| E269Q/E272Q | |
| E269Q/E283Q | |
| E272Q/E283Q | |
| E269Q | |

Figure 4

| Variant constant region | Substitutions |
|---|---|
| pI-ISO(-) | I199T/N203D/K274Q/R355Q/N384S/K392N/N397M/Q418E/K447_ |
| pI_ISO(-)-Fc only | K274Q/R355Q/N384S/K392N/V397M/Q418E/K447_ |
| pI_(-)_isosteric_A | N208D/Q295E/N384D/Q418E/N421D |
| pI_(-)_isosteric A-Fc only | Q295E/N384D/Q418E/N421D |
| pI_(-)_isosteric_B | N208D/Q295E/Q418E/N421D |
| pI_(-)_isosteric_B-Fc only | Q295E/Q418E/N421D |
| pI_ISO(+RR) | Q196K/I199T/P217R/P228R/N276K |
| pI_ISO(+RR)-Fc only | P217R/P228R/N276K |
| pI_ISO(+) | Q196K/I199T/N276K |
| pI_ISO(+)-Fc only | N276K |
| pI_(+)_isosteric_A | E269Q/E272Q/E283Q/E357Q |
| pI_(+)_isosteric_B | E269Q/E272Q/E283Q |
| pI_(+)_isosteric_E269Q/E272Q | E269Q/E272Q |
| pI_(+)_isosteric_E269Q/E283Q | E269Q/E283Q |
| pI_(+)_isosteric_E272Q/E283Q | E272Q/E283Q |
| pI_(+)_isosteric_E269Q | E269Q |

Figure 5

Ablation Variants
G236R
S239G
S239K
S239Q
S239R
V266D
S267K
S267R
H268K
E269R
T299R
T299K
K322A
A327G
A327L
A327N
A327Q
L328E
L328R
P329A
P329H
P329K
A330L
A330S/P331S
I332K
I332R
V266D/A327Q
V266D/P329K
S267R/A327Q
S267R/P329K
G236R/L328R
E233P/L234V/L235A/G236_/S239K
E233P/L234V/L235A/G236_/S267K
E233P/L234V/L235A/G236_/S239K/A327G
E233P/L234V/L235A/G236_/S267K/A327G
E233P/L234V/L235A/G236_
S239K/S267K
S267K/P329K
L234A/L235A/D265S

Figure 6A

Positive Charged scFv Linkers

| Name | Sequence | Length | Charge | |
|---|---|---|---|---|
| Gly-Ser 15 | GGGGSGGGGSGGGGS | 15 | 0 | SEQ ID NO: 434 |
| Whitlow linker | GSTSGSGKPGSGEGSTKG | 18 | +1 | SEQ ID NO: 435 |
| 6paxA_1 (+A) | IRPRAIGGSKPRVA | 14 | +4 | SEQ ID NO: 436 |
| +B | GKGGSGKGGSGKGGS | 15 | +3 | SEQ ID NO: 437 |
| +C | GGKGSGGKGSGGKGS | 15 | +3 | SEQ ID NO: 438 |
| +D | GGGKSGGGKSGGGKS | 15 | +3 | SEQ ID NO: 439 |
| +E | GKGKSGKGKSGKGKS | 15 | +6 | SEQ ID NO: 440 |
| +F | GGGKSGGKGSGKGGS | 15 | +3 | SEQ ID NO: 441 |
| +G | GKPGSGKPGSGKPGS | 15 | +3 | SEQ ID NO: 442 |
| +H | /GKPGSGKPGSGKPGSGKPGS/ | 20 | +4 | SEQ ID NO: 443 |
| +I | GKGKSGKGKSGKGKSGKGKS | 20 | +8 | SEQ ID NO: 444 |

Negative Charged scFv Linkers

| Name | Sequence | Length | Charge | |
|---|---|---|---|---|
| Gly-Ser 20 | GGGGSGGGGSGGGGSGGGGS | 20 | 0 | SEQ ID NO: 445 |
| 3hsc_2 (-A) | STAGDTHLGGEDFD | 14 | -4 | SEQ ID NO: 446 |
| -B | GEGGSGEGGSGEGGS | 15 | -3 | SEQ ID NO: 447 |
| -C | GGEGSGGEGSGGEGS | 15 | -3 | SEQ ID NO: 448 |
| -D | GGGESGGGESGGGES | 15 | -3 | SEQ ID NO: 449 |
| -E | GEGESGEGESGEGES | 15 | -6 | SEQ ID NO: 450 |
| -F | GGGESGGEGSGEGGS | 15 | -3 | SEQ ID NO: 451 |
| -G | GEGESGEGESGEGESGEGES | 20 | -8 | SEQ ID NO: 452 |

Figure 6B

Additional scFv Linkers

| | |
|---|---|
| GGGGSGGGGSGGGGS | SEQ ID NO: 434 |
| GGGGSGGGGSGGGGSGGGGS | SEQ ID NO: 445 |
| GSTSGSGKPGSGEGSTKG | SEQ ID NO: 435 |
| PRGASKSGSASQTGSAPGS | SEQ ID NO: 453 |
| GTAAAGAGAAGGAAAGAAG | SEQ ID NO: 454 |
| GTSGSSGSGSGGSGSGGGG | SEQ ID NO: 455 |
| GKPGSGKPGSGKPGSGKPGS | SEQ ID NO: 443 |
| GGSEGKSSGSGSESKSTGGS | SEQ ID NO: 456 |

Staple Linkers

| | |
|---|---|
| GGGSGGSGGCPPCGGSGG | SEQ ID NO: 457 |

Figure 7

Useful domain linkers

| Name | Sequence | SEQ ID NO: |
|---|---|---|
| (GGGGS)₁ or GGGGS | GGGGS | SEQ ID NO: 458 |
| (GGGGS)₂ | GGGGSGGGGS | SEQ ID NO: 459 |
| (GGGGS)₃ | GGGGSGGGGSGGGGS | SEQ ID NO: 434 |
| (GGGGS)₄ | GGGGSGGGGSGGGGSGGGGS | SEQ ID NO: 445 |
| (GGGGS)₅ | GGGGSGGGGSGGGGSGGGGSGGGGS | SEQ ID NO: 460 |
| (GGGGS)₆ | GGGGSGGGGSGGGGSGGGGSGGGGSGGGGS | SEQ ID NO: 461 |
| (GGGGS)₇ | GGGGSGGGGSGGGGSGGGGSGGGGSGGGGSGGGGS | SEQ ID NO: 462 |
| (GGGGA)₁ or GGGGA | GGGGA | SEQ ID NO: 463 |
| (GGGGA)₂ | GGGGAGGGGA | SEQ ID NO: 464 |
| (GGGGA)₃ | GGGGAGGGGAGGGGA | SEQ ID NO: 465 |
| (GGGGA)₄ | GGGGAGGGGAGGGGAGGGGA | SEQ ID NO: 466 |
| (GGGGA)₅ | GGGGAGGGGAGGGGAGGGGAGGGGA | SEQ ID NO: 467 |
| (GGGGA)₆ | GGGGAGGGGAGGGGAGGGGAGGGGAGGGGA | SEQ ID NO: 468 |
| (GGGGA)₇ | GGGGAGGGGAGGGGAGGGGAGGGGAGGGGAGGGGA | SEQ ID NO: 469 |
| 30AA-linker | DPALVHQRPAPPGGGGSGGGGSGGGGSGGG | SEQ ID NO: 470 |
| (GKPGS)₁ or GKPGS | GKPGS | SEQ ID NO: 471 |
| (GKPGS)₅ | /GKPGSGKPGSGKPGSGKPGS/GKPGS | SEQ ID NO: 472 |
| (GKPGS)₆ | /GKPGSGKPGSGKPGSGKPGS/GKPGSGKPGS | SEQ ID NO: 473 |
| (GGGES)₁ or GGGES | GGGES | SEQ ID NO: 474 |
| "full hinge" | EPKSCDKTHTCPPCP | SEQ ID NO: 475 |
| "lower half hinge" | KTHTCPPCP | SEQ ID NO: 476 |
| "full hinge C220S variant" | EPKSSDKTHTCPPCP | SEQ ID NO: 477 |
| "flex lower half hinge" | GGGGSGGGGSKTHTCPPCP | SEQ ID NO: 478 |
| "charged lower half hinge1" | GKPGSGKPGSKTHTCPPCP | SEQ ID NO: 479 |
| "charged lower half hinge2" | GKPGSKTHTCPPCP | SEQ ID NO: 480 |
| "upper half hinge" | EPKSC | SEQ ID NO: 481 |
| "flex upper half hinge" | EPKSCGGGGSGGGGS | SEQ ID NO: 482 |
| "charged upper half hinge1" | EPKSCGKPGSGKPGS | SEQ ID NO: 483 |
| "charged upper half hinge2" | EPKSCGKPGS | SEQ ID NO: 484 |

Figure 8

Platform X

| Monomer 1 (scFv-Fc) | Monomer 2 (HC) |
|---|---|
| Heterodimer skew variants S364K/E357Q | Heterodimer skew variants L368D/K370S |
|  | Isosteric pI variant N208D/Q295E/N384D/Q418E/N421D |
| FcKO E233P/L234V/L235A/G236_/S267K | FcKO E233P/L234V/L235A/G236_/S267K |
| ±M428L/N434S for FcRn | ±M428L/N434S for FcRn |

Platform J

| Monomer 1 (scFv-Fc) | Monomer 2 (HC) |
|---|---|
| Heterodimer skew variants T366W | Heterodimer skew variants T366S/L368A/Y407V |
| FcKO L234A/L235A/D265S | FcKO L234A/L235A/D265S |
|  | Purification Variants H435R/Y436F |
| ±M252Y/S254T/T256E for FcRn | ±M252Y/S254T/T256E for FcRn |

Figure 9

| XENP | Heterodimer-skew variant, Chain 1 | Heterodimer-skew variant, Chain 2 | Heterodimer Yield (%) | CH3 Tm (°C) |
|---|---|---|---|---|
| 12757 | none | none | 52.7 | 83.1 |
| 12758 | L368D/K370S | S364K | 94.4 | 76.6 |
| 12759 | L368D/K370S | S364K/E357L | 90.2 | 77.2 |
| 12760 | L368D/K370S | S364K/E357Q | 95.2 | 77.5 |
| 12761 | T411E/K360E/Q362E | D401K | 85.6 | 80.6 |
| 12496 | L368E/K370S | S364K | 91.5 | n.d. |
| 12511 | K370S | S364K | 59.9 | n.d. |
| 12840 | L368E/K370S | S364K/E357Q | 59.5 | n.d. |
| 12841 | K370S | S364K/E357Q | 90.4 | n.d. |
| 12894 | L368E/K370S | S364K | 41.0 | n.d. |
| 12895 | K370S | S364K | 49.3 | n.d. |
| 12896 | L368E/K370S | S364K/E357Q | 73.9 | n.d. |
| 12901 | K370S | S364K/E357Q | 87.9 | n.d. |

Figure 10A

Heterodimeric Fc Backbone 1

>Heterodimeric Fc Backbone 1 monomer 1 (-) (SEQ ID NO: 485)
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK >Heterodimeric Fc Backbone 1 monomer 2 (+) (SEQ ID NO: 486)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVMHEALHNHYTQKSLSLSPGK

Heterodimeric Fc Backbone 2

>Heterodimeric Fc Backbone 2 monomer 1 (-) (SEQ ID NO: 487)
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK >Heterodimeric Fc Backbone monomer 2 (+) (SEQ ID NO: 488)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVKLTCLVKGFYPSDIAVEWESNG
QPENNYKTTPPVLDSDGSFFLYSKLTVDKSRWQQGNVFSCSVMHEALHNHYTQKSLSLSPGK

Heterodimeric Fc Backbone 3

>Heterodimeric Fc Backbone 3 monomer 1 (-) (SEQ ID NO: 489)
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCEVSGFYPSDIAVEWESDG
QPENNYKTTPPVLDSDGSFFLYSKLTVDKSRWEQGDVFSCSVMHEALHNHYTQKSLSLSPGK >Heterodimeric Fc Backbone 3 monomer 2 (+) (SEQ ID NO: 490)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVKLTCLVKGFYPSDIAVEWESNG
QPENNYKTTPPVLDSDGSFFLYSKLTVDKSRWQQGNVFSCSVMHEALHNHYTQKSLSLSPGK

Heterodimeric Fc Backbone 4

>Heterodimeric Fc Backbone 4 monomer 1 (-) (SEQ ID NO: 491)
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTENEVSLTCLVKGFYPSDIAVEWESDG
QPENNYKTTPPVLDSDGSFFLYSKLEVDKSRWEQGDVFSCSVMHEALHNHYTQKSLSLSPGK >Heterodimeric Fc Backbone 4 monomer 2 (+) (SEQ ID NO: 492)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSKGSFFLYSKLTVDKSRWQQGNVFSCSVMHEALHNHYTQKSLSLSPGK

Figure 10B

Heterodimeric Fc Backbone 5

>Heterodimeric Fc Backbone 5 monomer 1 (-) (SEQ ID NO: 493)
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSRDELTKNQVSLTCDVSGFYPSDIAVEWESDG
QPENNYKTTPPVLDSDGSFFLYSKLTVDKSRWEQGDVFSCSVMHEALHNHYTQKSLSLSPGK >Heterodimeric Fc Backbone 5 monomer 2 (+) (SEQ ID NO: 494)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSRDQLTKNQVKLTCLVKGFYPSDIAVEWESNG
QPENNYKTTPPVLDSDGSFFLYSKLTVDKSRWQQGNVFSCSVMHEALHNHYTQKSLSLSPGK

Heterodimeric Fc Backbone 6

>Heterodimeric Fc Backbone 6 monomer 1 (-) (SEQ ID NO: 495)
APPVAGPSVFLFPPKPKDTLMISRTPEVTCVVVDVKHEDPEVKFNWYVDGVEVHNAKTKPREEEYASTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK >Heterodimeric Fc Backbone 6 monomer 2 (+) (SEQ ID NO: 496)
APPVAGPSVFLFPPKPKDTLMISRTPEVTCVVVDVKHEDPEVKFNWYVDGVEVHNAKTKPREEQYASTYRVVSVLTV
LHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVMHEALHNHYTQKSLSLSPGK

Heterodimeric Fc Backbone 7

>Heterodimeric Fc Backbone 7 monomer 1 (-) (SEQ ID NO: 497)
APPVAGPSVFLFPPKPKDTLMISRTPEVTCVVVDVKHEDPEVKFNWYVDGVEVHNAKTKPREEEYSSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK >Heterodimeric Fc Backbone 7 monomer 2 (+) (SEQ ID NO: 498)
APPVAGPSVFLFPPKPKDTLMISRTPEVTCVVVDVKHEDPEVKFNWYVDGVEVHNAKTKPREEQYSSTYRVVSVLTV
LHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVMHEALHNHYTQKSLSLSPGK

Heterodimeric Fc Backbone 8

>Heterodimeric Fc Backbone 8 monomer 1 (-) (SEQ ID NO: 499)
APEFLGGPSVFLFPPKPKDTLMISRTPEVTCVVVDVSQEDPEVQFNWYVDGVEVHNAKTKPREEEFNSTYRVVSVLT
VLHQDWLNGKEYKCKVSNKGLPSSIEKTISKAKGQPREPQVYTLPPSQEEMTKNQVSLTCDVSGFYPSDIAVEWESD
GQPENNYKTTPPVLDSDGSFFLYSRLTVDKSRWEEGDVFSCSVMHEALHNHYTQKSLSLSLGK >Heterodimeric Fc Backbone 8 monomer 2 (+) (SEQ ID NO: 500)
APEFLGGPSVFLFPPKPKDTLMISRTPEVTCVVVDVSQEDPEVQFNWYVDGVEVHNAKTKPREEQFNSTYRVVSVLT
VLHQDWLNGKEYKCKVSNKGLPSSIEKTISKAKGQPREPQVYTLPPSQEQMTKNQVKLTCLVKGFYPSDIAVEWESN
GQPENNYKTTPPVLDSDGSFFLYSRLTVDKSRWQEGNVFSCSVMHEALHNHYTQKSLSLSLGK

Figure 10C

Heterodimeric Fc Backbone 9

>Heterodimeric Fc Backbone 9 monomer 1 (-) (SEQ ID NO: 501)
APPVAGPSVFLFPPKPKDTLMISRTPEVTCVVVDVSHEDPEVQFNWYVDGVEVHNAKTKPREEEFNSTFRVVSVLTV
VHQDWLNGKEYKCKVSNKGLPAPIEKTISKTKGQPREPQVYTLPPSREEMTKNQVSLTCDVSGFYPSDIAVEWESDG
QPENNYKTTPPMLDSDGSFFLYSKLTVDKSRWEQGDVFSCSVMHEALHNHYTQKSLSLSPGK

>Heterodimeric Fc Backbone 9 monomer 2 (+) (SEQ ID NO: 502)
APPVAGPSVFLFPPKPKDTLMISRTPEVTCVVVDVSHEDPEVQFNWYVDGVEVHNAKTKPREEQFNSTFRVVSVLTV
VHQDWLNGKEYKCKVSNKGLPAPIEKTISKTKGQPREPQVYTLPPSREQMTKNQVKLTCLVKGFYPSDIAVEWESNG
QPENNYKTTPPMLDSDGSFFLYSKLTVDKSRWQQGNVFSCSVMHEALHNHYTQKSLSLSPGK

Heterodimeric Fc Backbone 10

>Heterodimeric Fc Backbone 10 monomer 1 (-) (SEQ ID NO: 503)
APPVAGPSVFLFPPKPKDTLMISRTPEVTCVVVDVKHEDPEVQFNWYVDGVEVHNAKTKPREEEFNSTFRVVSVLTV
VHQDWLNGKEYKCKVSNKGLPAPIEKTISKTKGQPREPQVYTLPPSREEMTKNQVSLTCDVSGFYPSDIAVEWESDG
QPENNYKTTPPMLDSDGSFFLYSKLTVDKSRWEQGDVFSCSVMHEALHNHYTQKSLSLSPGK

>Heterodimeric Fc Backbone 10 monomer 2 (+) (SEQ ID NO: 504)
APPVAGPSVFLFPPKPKDTLMISRTPEVTCVVVDVKHEDPEVQFNWYVDGVEVHNAKTKPREEQFNSTFRVVSVLTV
VHQDWLNGKEYKCKVSNKGLPAPIEKTISKTKGQPREPQVYTLPPSREQMTKNQVKLTCLVKGFYPSDIAVEWESNG
QPENNYKTTPPMLDSDGSFFLYSKLTVDKSRWQQGNVFSCSVMHEALHNHYTQKSLSLSPGK

Heterodimeric Fc Backbone 11

>Heterodimeric Fc Backbone 11 monomer 1 (-) (SEQ ID NO: 505)
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVLHEALHSHYTQKSLSLSPGK

>Heterodimeric Fc Backbone 11 monomer 2 (+) (SEQ ID NO: 506)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVLHEALHSHYTQKSLSLSPGK

Heterodimeric Fc Backbone 12

>Heterodimeric Fc Backbone 12 monomer 1 (-) (SEQ ID NO: 507)
APPVAGPSVFLFPPKPKDTLMISRTPEVTCVVVDVKHEDPEVKFKWYVDGVEVHNAKTKPREEQYNSTYRVVSVLTV
LHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVMHEALHNHYTQKSLSLSPGK

>Heterodimeric Fc Backbone 12 monomer 2 (+) (SEQ ID NO: 508)
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK

Figure 10D

Heterodimeric Fc Backbone 13

\>Heterodimeric Fc Backbone 13 monomer 1 (SEQ ID NO: 509)
APEAAGGPSVFLFPPKPKDTLMISRTPEVTCVVVSVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLWCLVKGFYPSDIAVEWESN
GQPENNYKTTPPVLDSDGSFFLYSKLTVDKSRWQQGNVFSCSVMHEALHNHYTQKSLSLSPGK \>Heterodimeric Fc Backbone 13 monomer 2 (SEQ ID NO: 510)
APEAAGGPSVFLFPPKPKDTLMISRTPEVTCVVVSVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLSCAVKGFYPSDIAVEWESN
GQPENNYKTTPPVLDSDGSFFLVSKLTVDKSRWQQGNVFSCSVMHEALHNRFTQKSLSLSPGK

Heterodimeric Fc Backbone 14

\>Heterodimeric Fc Backbone 14 monomer 1 (SEQ ID NO: 511)
APEAAGGPSVFLFPPKPKDTLYITREPEVTCVVVSVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLWCLVKGFYPSDIAVEWESN
GQPENNYKTTPPVLDSDGSFFLYSKLTVDKSRWQQGNVFSCSVMHEALHNHYTQKSLSLSPGK \>Heterodimeric Fc Backbone 14 monomer 2 (SEQ ID NO: 512)
APEAAGGPSVFLFPPKPKDTLYITREPEVTCVVVSVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLSCAVKGFYPSDIAVEWESN
GQPENNYKTTPPVLDSDGSFFLVSKLTVDKSRWQQGNVFSCSVMHEALHNRFTQKSLSLSPGK

Heterodimeric Fc Backbone 15

\>Heterodimeric Fc Backbone 15 monomer 1 (SEQ ID NO: 513)
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSRDELTKNQVSLTCDVSGFYPSDIAVEWESDG
QPENNYKTTPPVLDSDGSFFLYSKLTVDKSRWEQGDVFSCSVLHEALHSHYTQKSLSLSPGK \>Heterodimeric Fc Backbone 15 monomer 2 (SEQ ID NO: 514)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSRDQLTKNQVKLTCLVKGFYPSDIAVEWESNG
QPENNYKTTPPVLDSDGSFFLYSKLTVDKSRWQQGNVFSCSVLHEALHSHYTQKSLSLSPGK

Heterodimeric Fc Backbone 16

\>Heterodimeric Fc Backbone 16 monomer 1 (SEQ ID NO: 515)
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVLHEALHAHYTQKSLSLSPGK \>Heterodimeric Fc Backbone 16 monomer 2 (SEQ ID NO: 516)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVLHEALHAHYTQKSLSLSPGK

Figure 10E

Heterodimeric Fc Backbone 17

>Heterodimeric Fc Backbone 17 monomer 1 (SEQ ID NO: 517)
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSRDELTKNQVSLTCDVSGFYPSDIAVEWESDG
QPENNYKTTPPVLDSDGSFFLYSKLTVDKSRWEQGDVFSCSVLHEALHAHYTQKSLSLSPGK

>Heterodimeric Fc Backbone 17 monomer 2 (SEQ ID NO: 518)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSRDQLTKNQVKLTCLVKGFYPSDIAVEWESNG
QPENNYKTTPPVLDSDGSFFLYSKLTVDKSRWQQGNVFSCSVLHEALHAHYTQKSLSLSPGK

Figure 11

2 + 1 mAb-scFv Heterodimeric Fc Backbone in Platform X

>2 + 1 mAb-scFv Heterodimeric Fc Backbone monomer 1 (SEQ ID NO: 519)
APPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDG
QPENNYKTTPPVLDSDGSFFLYSKLTVDKSRWEQGDVFSCSVMHEALHNHYTQKSLSLSPGK

>2 + 1 mAb-scFv Heterodimeric Fc Backbone monomer 2 (SEQ ID NO: 520)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVMHEALHNHYTQKSLSLSPG

2 + 1 mAb-scFv Heterodimeric Fc Backbone in Platform J

>2 + 1 mAb-scFv Heterodimeric Fc Backbone monomer 1 (SEQ ID NO: 521)
APEAAGGPSVFLFPPKPKDTLMISRTPEVTCVVVSVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLWCLVKGFYPSDIAVEWESN
GQPENNYKTTPPVLDSDGSFFLYSKLTVDKSRWQQGNVFSCSVMHEALHNHYTQKSLSLSPGK

>2 + 1 mAb-scFv Heterodimeric Fc Backbone monomer 2 (SEQ ID NO: 522)
APEAAGGPSVFLFPPKPKDTLMISRTPEVTCVVVSVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLSCAVKGFYPSDIAVEWESN
GQPENNYKTTPPVLDSDGSFFLVSKLTVDKSRWQQGNVFSCSVMHEALHNRFTQKSLSLSPG

Figure 12

IgG1 CH1(+) (SEQ ID NO: 523)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKV

IgG1 CH1(-) (SEQ ID NO: 524)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKV

IgG2 CH1(+) (SEQ ID NO: 525)
ASTKGPSVFPLAPCSRSTSESTAALGCLVKDYFPEPVTVSWNSGALTSGVHTFPAVLQSSGLYSLSSVVTVPSSNFG
TQTYTCNVDHKPSNTKVDKTV

IgG2 CH1(-) (SEQ ID NO: 526)
ASTKGPSVFPLAPCSRSTSESTAALGCLVKDYFPEPVTVSWNSGALTSGVHTFPAVLQSSGLYSLSSVVTVPSSNFG
TQTYTCNVDHKPSDTKVDKTV

IgG4 CH1(+) (SEQ ID NO: 527)
ASTKGPSVFPLAPCSRSTSESTAALGCLVKDYFPEPVTVSWNSGALTSGVHTFPAVLQSSGLYSLSSVVTVPSSSLG
TKTYTCNVDHKPSNTKVDKRV

IgG4 CH1(-) (SEQ ID NO: 528)
ASTKGPSVFPLAPCSRSTSESTAALGCLVKDYFPEPVTVSWNSGALTSGVHTFPAVLQSSGLYSLSSVVTVPSSSLG
TKTYTCNVDHKPSDTKVDKRV

Figure 13

IgG1 hinge (SEQ ID NO: 529)
EPKSCDKTHTCPPCP

IgG2 hinge (SEQ ID NO: 530)
ERKCCVECPPCP

IgG4 hinge (SEQ ID NO: 531)
ESKYGPPCPSCP

Figure 14

Light Chain Constant Domain – Kappa (SEQ ID NO: 532)
RTVAAPSVFIFPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC

Light Chain Constant Domain – Lambda (SEQ ID NO: 533)
GQPKAAPSVTLFPPSSEELQANKATLVCLISDFYPGAVTVAWKADSSPVKAGVETTTPSKQSNNKYAASSYLSLTPE
QWKSHRSYSCQVTHEGSTVEKTVAPTECS

| | sequence | SEQ ID NO: |
|---|---|---|
| Variable heavy (vh) domain | EVQLLESGGGLVQPGGSLRLSCAASGFTFSSYAMSWVRQAPGKGLEWVSTISGSGDSTYYADSVKGRFTISRDNSKNTLYLQMNSLRAEDTAVYYCAKSGPGLRQVGFDYWGQGTLVTVSS | 9 |
| vhCDR1 | SYAMS | 10 |
| vhCDR2 | TISGSGDSTYYADSVKG | 11 |
| vhCDR3 | SGPGLRQVGFDY | 12 |
| Variable light (vl) domain | DIQMTQSPSSLSASVGDRVTITCRASQSISSYLNWYQQKPGKAPKLLIYAASSLQSGVPSRFSGSGSGTDFTLTISSLQPEDFATYYCQQSYSTPFTFGQGTKLEIK | 13 |
| vlCDR1 | RASQSISSYLN | 14 |
| vlCDR2 | AASSLQS | 15 |
| vlCDR3 | QQSYSTPFT | 16 |

<u>>XENP28428 1A7[CD28]_H1L1_IgG1_PVA_/S267K</u>

Heavy Chain (SEQ ID NO: 17)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKTHTC
PPCPAPPVAGPSVFLFPPKPKDTLMISRTPEVTCVVVDVKHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSPGK Light Chain (SEQ ID NO: 18)
DIQMTQSPSSLSASVGDRVTITCRASQSISSYLNWYQQKPGKAPKLLIYAASSLQSGVPSRFSGSGSGTDFTLTISS
LQPEDFATYYCQQSYSTPFTFGQGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 16

|  | sequence | SEQ ID NO: |
|---|---|---|
| Variable heavy (vh) domain 1A7_H1.1 | EVQLLESGGGLVQPGGSLRLSCAASGFTFSSYYMSWVRQAPGKGLEWVSTISGSGDSTYYADSVKGRFTISRDNSKNTLYLQMNSLRAEDTAVYYCAKSGPGLRQVGFDYWGQGTLVTVSS | 19 |
| vhCDR1 | SYYMS | 20 |
| vhCDR2 | TISGSGDSTYYADSVKG | 21 |
| vhCDR3 | SGPGLRQVGFDY | 22 |

|  | sequence | SEQ ID NO: |
|---|---|---|
| Variable heavy (vh) domain 1A7_H1.14 | EVQLLESGGGLVQPGGSLRLSCAASGFTFSSYYMSWVRQAPGKGLEWVSTISESGDSTYYADSVKGRFTISRDNSKNTLYLQMNSLRAEDTAVYYCAKSGPGLRQVGFDYWGQGTLVTVSS | 23 |
| vhCDR1 | SYYMS | 24 |
| vhCDR2 | TISESGDSTYYADSVKG | 25 |
| vhCDR3 | SGPGLRQVGFDY | 26 |

Figure 17

| | sequence | SEQ ID NO: |
|---|---|---|
| Variable light (vl) domain 1A7_L1.71 | DIQMTQSPSSLSASVGDRVTITCRASQSISSYLNWYQQKPGKAPKLLIYAASSLQSGVPSRFSGSGSGTDFTLTISSLQPEDFATYYCQQVYSTPFTFGQGTKLEIK | 27 |
| vlCDR1 | RASQSISSYLN | 28 |
| vlCDR2 | AASSLQS | 29 |
| vlCDR3 | QQVYSTPFT | 30 |

Figure 18A

| 1A7[CD28]_H1.1_L1 | | |
|---|---|---|
| | Sequence | SEQ ID NO: |
| Variable Heavy (vh) Domain | EVQLLESGGGLVQPGGSLRLSCAASGFTFSSYYMSWVRQAPGKGLEWVSTISG SGDSTYYADSVKGRFTISRDNSKNTLYLQMNSLRAEDTAVYYCAKSGPGLRQV GFDYWGQGTLVTVSS | 31 |
| vhCDR1 | SYYMS | 32 |
| vhCDR2 | TISGSGDSTYYADSVKG | 33 |
| vhCDR3 | SGPGLRQVGFDY | 34 |
| Variable Light (vl) Domain | DIQMTQSPSSLSASVGDRVTITCRASQSISSYLNWYQQKPGKAPKLLIYAASS LQSGVPSRFSGSGSGTDFTLTISSLQPEDFATYYCQQSYSTPFTFGQGTKLEI K | 35 |
| vlCDR1 | RASQSISSYLN | 36 |
| vlCDR2 | AASSLQS | 37 |
| vlCDR3 | QQSYSTPFT | 38 |

| 1A7[CD28]_H1_L1.71 | | |
|---|---|---|
| | Sequence | SEQ ID NO: |
| Variable Heavy (vh) Domain | EVQLLESGGGLVQPGGSLRLSCAASGFTFSSYAMSWVRQAPGKGLEWVSTISG SGDSTYYADSVKGRFTISRDNSKNTLYLQMNSLRAEDTAVYYCAKSGPGLRQV GFDYWGQGTLVTVSS | 39 |
| vhCDR1 | SYAMS | 40 |
| vhCDR2 | TISGSGDSTYYADSVKG | 41 |
| vhCDR3 | SGPGLRQVGFDY | 42 |
| Variable Light (vl) Domain | DIQMTQSPSSLSASVGDRVTITCRASQSISSYLNWYQQKPGKAPKLLIYAASS LQSGVPSRFSGSGSGTDFTLTISSLQPEDFATYYCQQVYSTPFTFGQGTKLEI K | 43 |
| vlCDR1 | RASQSISSYLN | 44 |
| vlCDR2 | AASSLQS | 45 |
| vlCDR3 | QQVYSTPFT | 46 |

Figure 18B

| 1A7[CD28]_H1.1_L1.71 | | |
|---|---|---|
| | Sequence | SEQ ID NO: |
| Variable Heavy (vh) Domain | EVQLLESGGGLVQPGGSLRLSCAASGFTFSSYYMSWVRQAPGKGLEWVSTISGSGDSTYYADSVKGRFTISRDNSKNTLYLQMNSLRAEDTAVYYCAKSGPGLRQVGFDYWGQGTLVTVSS | 47 |
| vhCDR1 | SYYMS | 48 |
| vhCDR2 | TISGSGDSTYYADSVKG | 49 |
| vhCDR3 | SGPGLRQVGFDY | 50 |
| Variable Light (vl) Domain | DIQMTQSPSSLSASVGDRVTITCRASQSISSYLNWYQQKPGKAPKLLIYAASSLQSGVPSRFSGSGSGTDFTLTISSLQPEDFATYYCQQVYSTPFTFGQGTKLEIK | 51 |
| vlCDR1 | RASQSISSYLN | 52 |
| vlCDR2 | AASSLQS | 53 |
| vlCDR3 | QQVYSTPFT | 54 |

| 1A7[CD28]_H1.14_L1 | | |
|---|---|---|
| | Sequence | SEQ ID NO: |
| Variable Heavy (vh) Domain | EVQLLESGGGLVQPGGSLRLSCAASGFTFSSYYMSWVRQAPGKGLEWVSTISESGDSTYYADSVKGRFTISRDNSKNTLYLQMNSLRAEDTAVYYCAKSGPGLRQVGFDYWGQGTLVTVSS | 55 |
| vhCDR1 | SYYMS | 56 |
| vhCDR2 | TISESGDSTYYADSVKG | 57 |
| vhCDR3 | SGPGLRQVGFDY | 58 |
| Variable Light (vl) Domain | DIQMTQSPSSLSASVGDRVTITCRASQSISSYLNWYQQKPGKAPKLLIYAASSLQSGVPSRFSGSGSGTDFTLTISSLQPEDFATYYCQQSYSTPFTFGQGTKLEIK | 59 |
| vlCDR1 | RASQSISSYLN | 60 |
| vlCDR2 | AASSLQS | 61 |
| vlCDR3 | QQSYSTPFT | 62 |

Figure 18C

| 1A7[CD28] H1.14 L1.71 | | |
|---|---|---|
| | Sequence | SEQ ID NO: |
| Variable Heavy (vh) Domain | EVQLLESGGGLVQPGGSLRLSCAASGFTFSSYYMSWVRQAPGKGLEWVSTIS ESGDSTYYADSVKGRFTISRDNSKNTLYLQMNSLRAEDTAVYYCAKSGPGLR QVGFDYWGQGTLVTVSS | 63 |
| vhCDR1 | SYYMS | 64 |
| vhCDR2 | TISESGDSTYYADSVKG | 65 |
| vhCDR3 | SGPGLRQVGFDY | 66 |
| Variable Light (vl) Domain | DIQMTQSPSSLSASVGDRVTITCRASQSISSYLNWYQQKPGKAPKLLIYAAS SLQSGVPSRFSGSGSGTDFTLTISSLQPEDFATYYCQQVYSTPFTFGQGTKL EIK | 67 |
| vlCDR1 | RASQSISSYLN | 68 |
| vlCDR2 | AASSLQS | 69 |
| vlCDR3 | QQVYSTPFT | 70 |

Figure 19A

| 1A7 VH | SEQ | SEQ ID | |
|---|---|---|---|
| HFR1 | EVQLLESGGGLVQPGGSLRLSCAASGF$X_1X_2X_3$ | 71 | $X_1$ is selected from T,S,N; $X_2$ is selected from F, L; and $X_3$ is selected from S, E, R, K, G, T, A, N |
| HCDR1 | $X_1X_2X_3X_4X_5$ | | $X_1$ is selected from S, G, E, T, D, A, R, K; $X_2$ is selected from Y, N; $X_3$ is selected from A, Y, S; $X_4$ is selected from M, I; and $X_5$ is selected from S, T, N |
| HFR2 | WVRQAPGKGLEWV$X_1$ | 73 | $X_1$ is selected from S, A |
| HCDR2 | $X_1IX_2X_3X_4X_5X_6X_7$TYYADSVKG | 74 | $X_1$ is selected from T, S; $X_2$ is selected from S, D, E, Y, T; $X_3$ is selected from G, D, E, A, Y, S, N, T; $X_4$ is selected from S, D, N, G; $X_5$ is selected from D, T, Y, S, A; $X_6$ is selected from D, T, Y, S, A; and $X_7$ is selected from S, Y, A, T, D, N |
| HFR3 | RFTISRDNSKNTLYLQMNSLRAEDTAVYYCAK | 75 | |
| HCDR3 | SGPGLRQVGFDY | 76 | |
| HFR4 | WGQGTLVTVSS | 77 | |

Figure 19B

| 1A7 VL | | | |
|---|---|---|---|
| LFR1 | DIQMTQSPSSLSASVGDRVTITC | 79 | |
| LCDR1 | RASQSIS$X_1X_2$L$X_3$ | 80 | $X_1$ is selected from S, A, D, G, H, K, N, Q, T, V, Y; $X_2$ is selected from Y, A, D, F, H, K, L, N, Q, S, W; and $X_3$ is selected from N, A, D, G, H, Q, S, T, Y |
| LFR2 | WYQQKPGKAPKLLIY | 81 | |
| LCDR2 | $X_1$AS$X_2$L$X_3X_4$ | | $X_1$ is selected from A, D, G, K, L, Q, S, T, W, Y; $X_2$ is selected from S, A, D, K, N, Q, T, Y; $X_3$ is selected from Q, A, E, F, H, I, K, N, S, V, Y; and $X_4$ is selected from Q, A, E, F, H, I, K, N, S, V, Y |
| LFR3 | GVPSRFSGSGSGTDFTLTISSLQPEDFATYYC | 83 | |
| LCDR3 | QQ$X_1X_2X_3X_4$P$X_5$T | 84 | $X_1$ is selected from S, A, D, F, H, K, L, T, V, Y; $X_2$ is selected from Y, A, D, F, H, K, L, Q, V, W; $X_3$ is selected from S, A, D, G, H, K, N, Q, T, V, Y; $X_4$ is selected from T, A, D, F, I, K, L, Q, S, V, Y; and $X_5$ is selected from F, I, L, W |
| LFR4 | FGQGTKLEIK | 85 | |

Figure 20

| 1A7 VH/VL Pair | VH SEQ ID NO: | VL SQ ID NO: | scFv Orientation | K$_D$ for human CD28 (nM) |
| --- | --- | --- | --- | --- |
| H1L1 | | | VHVL | 1000 |
| H1.1_L1 | | | VHVL | 600 |
| H1.14_L1 | | | VHVL | 230 |
| H1_L1.71 | | | VHVL | 180 |
| H1.1_L1.71 | | | VHVL | 96 |
| H1.14_L1.71 | | | VHVL | 37 |
| L1.71_H1.14 | | | VLVH | 37 |
| L1_H1.14 | | | VLVH | 230 |

|  | sequence | SEQ ID NO: |
|---|---|---|
| Variable heavy (vh) domain | EVKLQQSGAELVKPGASVRLSCKASGYTFTEYIIHWIKLRSGQGLEWIGWFYPGSNDIQYNAKFKGKATLTADKSSSTVYMELTGLTSEDSAVYFCARRDDFSGYDALPYWGQGTMVTVSS | 86 |
| vhCDR1 | EYIIH | 87 |
| vhCDR2 | WFYPGSNDIQYNAKFKG | 88 |
| vhCDR3 | RDDFSGYDALPY | 89 |
| Variable light (vl) domain | DIQMTQSPASLSVSVGETVTITCRTNENIYSNLAWYQQKQGKSPQLLIYAATHLVEGVPSRFSGSGSGTQYSLKITSLQSEDFGNYYCQHFWGTPCTFGGGTKLEIK | 90 |
| vlCDR1 | RTNENIYSNLA | 91 |
| vlCDR2 | AATHLVE | 92 |
| vlCDR3 | QHFWGTPCT | 93 | hCD28.3[CD28]_H1L1

|  | sequence | SEQ ID NO: |
|---|---|---|
| Variable heavy (vh) domain | QVQLQQSGAELKKPGASVKVSCKASGYTFTEYIIHWIKLRSGQGLEWIGWFYPGSNDIQYNAQFKGKATLTADKSSSTVYMELTGLTPEDSAVYFCARRDDFSGYDALPYWGQGTLVTVSA | 94 |
| vhCDR1 | EYIIH | 95 |
| vhCDR2 | WFYPGSNDIQYNAQFKG | 96 |
| vhCDR3 | RDDFSGYDALPY | 97 |
| Variable light (vl) domain | DIQMTQSPSSLSASVGDRVTITCKTNENIYSNLAWYQQKDGKSPQLLIYAATHLVEGVPSRFSGSGSGTQYSLTISSLQPEDFGNYYCQHFWGTPCTFGGGTKLEIK | 98 |
| vlCDR1 | KTNENIYSNLA | 99 |
| vlCDR2 | AATHLVE | 100 |
| vlCDR3 | QHFWGTPCT | 101 |

|  | sequence | SEQ ID NO: |
|---|---|---|
| Variable heavy (vh) domain | QVQLQQSGPELVKPGTSVRISCEASGYTFTSYYIHWVKQRPGQGLEWIGCIYPGNVNTNYNEKFKDKATLIVDTSSNTAYMQLSRMTSEDSAVYFCTRSHYGLDWNFDVWGAGTTVTVSS | 102 |
| vhCDR1 | SYYIH | 103 |
| vhCDR2 | CIYPGNVNTNYNEKFKD | 104 |
| vhCDR3 | SHYGLDWNFDV | 105 |
| Variable light (vl) domain | DIQMNQSPSSLSASLGDTITITCHASQNIYVWLNWYQQKPGNIPKLLIYKASNLHTGVPSRFSGSGSGTGFTLTISSLQPEDIATYYCQQGQTYPYTFGGGTKLEIK | 106 |
| vlCDR1 | HASQNIYVWLN | 107 |
| vlCDR2 | KASNLHT | 108 |
| vlCDR3 | QQGQTYPYT | 109 |

TGN1412_H1L1

|  | sequence | SEQ ID NO: |
|---|---|---|
| Variable heavy (vh) domain | QVQLVQSGAEVKKPGASVKVSCKASGYTFTSYYIHWVRQAPGQGLEWIGCIYPGNVNTNYNEKFKDRATLTVDTSISTAYMELSRLRSDDTAVYFCTRSHYGLDWNFDVWGQGTTVTVSS | 110 |
| vhCDR1 | SYYIH | 111 |
| vhCDR2 | CIYPGNVNTNYNEKFKD | 112 |
| vhCDR3 | SHYGLDWNFDV | 113 |
| Variable light (vl) domain | DIQMTQSPSSLSASVGDRVTITCHASQNIYVWLNWYQQKPGKAPKLLIYKASNLHTGVPSRFSGSGSGTDFTLTISSLQPEDFATYYCQQGQTYPYTFGGGTKVEIK | 114 |
| vlCDR1 | HASQNIYVWLN | 115 |
| vlCDR2 | KASNLHT | 116 |
| vlCDR3 | QQGQTYPYT | 117 |

|  | sequence | SEQ ID NO: |
|---|---|---|
| Variable heavy (vh) domain | EVQLVESGGGLVKPGGSLRLSCGGSGFTFNNAWMNWVRQAPGKGLEWVGRIKGKTDGGTADYAAPVKGRFTISRDYSKNTLYLQMNSLTTEDTAVYYCNTDLPYYYGSGRYSGMDVWGQGTTVTVSS | 118 |
| vhCDR1 | NAWMN | 119 |
| vhCDR2 | RIKGKTDGGTADYAAPVKG | 120 |
| vhCDR3 | DLPYYYGSGRYSGMDV | 121 |
| Variable light (vl) domain | EIVLTQSPATLSLSPGERATLSCRASQSVSSYLAWYQQKPGQAPRLLIYDASNRATGIPARFSGSGSGTDFTLTISSLEPEDFAVYYCQQRSNTFGPGTKVDIK | 122 |
| vlCDR1 | RASQSVSSYLA | 123 |
| vlCDR2 | DASNRAT | 124 |
| vlCDR3 | QQRSNT | 125 |

>341VL36[CD28]_H1L1

|  | sequence | SEQ ID NO: |
|---|---|---|
| Variable heavy (vh) domain | EVQLVESGGGLVKPGGSLRLSCGGSGFTFNNAWMNWVRQAPGKGLEWVGRIKGKTDGGTADYAAPVKGRFTISRDYSKNTLYLQMNSLKTEDTGVYYCTTYLPYYYGSERWSGMDVWGQGTTVTVSS | 126 |
| vhCDR1 | NAWMN | 127 |
| vhCDR2 | RIKGKTDGGTADYAAPVKG | 128 |
| vhCDR3 | YLPYYYGSERWSGMDV | 129 |
| Variable light (vl) domain | EIVLTQSPATLSLSPGERATLSCRASQSVSSYLAWYQQKPGQAPRLLIYDASNRATGIPARFSGSGSGTDFTLTISSLEPEDFAVYYCQQRSNTFGPGTKVDIK | 130 |
| vlCDR1 | RASQSVSSYLA | 131 |
| vlCDR2 | DASNRAT | 132 |
| vlCDR3 | QQRSNT | 133 |

|  | sequence | SEQ ID NO: |
|---|---|---|
| Variable heavy (vh) domain | EVQLVQSGSELKKPGSSVKVSCKASGGTSRSFAISWVRQAPGQGLEW MGGIIPIFGPANYAQKFQGRVTITADESTSTAYMELSSLRSEDTAVY YCARHAIAMGWGVITTNYFDSWGQGTMVTVSS | 134 |
| vhCDR1 | SFAIS | 135 |
| vhCDR2 | GIIPIFGPANYAQKFQG | 136 |
| vhCDR3 | HAIAMGWGVITTNYFDS | 137 |
| Variable light (vl) domain | EIVLTQSPGTLSLSPGERATLSCRASQSVSSSYLAWYQQKPGQAPRL LIYGASSRATGIPDRFSGSGSGTDFTLTISRLEPEDFAVYYCQQYGS SPITFGQGTRLEIK | 138 |
| vlCDR1 | RASQSVSSSYLA | 139 |
| vlCDR2 | GASSRAT | 140 |
| vlCDR3 | QQYGSSPIT | 141 |

HuTN228[CD28]_H1L1

|  | sequence | SEQ ID NO: |
|---|---|---|
| Variable heavy (vh) domain | QVQLQESGPGLVKPSETLSLTCAVSGFSLTSYGVHWIRQPPGKGLEW LGVIWPGGGTNFNSALMSRLTISEDTSKNQVSLKLSSVTAADTAVYY CARDRAYGNYLYAMDYWGQGTLVTVSS | 142 |
| vhCDR1 | SYGVH | 143 |
| vhCDR2 | VIWPGGGTNFNSALMS | 144 |
| vhCDR3 | DRAYGNYLYAMDY | 145 |
| Variable light (vl) domain | DIQMTQSPSSLSASVGDRVTITCRASESVEYYVTSLMQWYQQKPGKA PKLLIYAASNVDSGVPSRFSGSGSGTDFTLTISSLQPEDIATYYCQQ SRKVPFTGGGTKVEIK | 146 |
| vlCDR1 | RASESVEYYVTSLMQ | 147 |
| vlCDR2 | AASNVDS | 148 |
| vlCDR3 | QQSRKVPFT | 149 |

| | sequence | SEQ ID NO: |
|---|---|---|
| Variable heavy (vh) domain | QVQLKQSGAELVKPGASVKISCKTSGYTFTDGYMNWVEQKPGQGLEWIGRIDPDSGNTRYNQKFQGKATLTRDKSSSTVYMDLRSLTSEDSAVYYCARDGTFYGTYGYWYFDFWGQGTQVTVSS | 150 |
| vhCDR1 | DGYMN | 151 |
| vhCDR2 | RIDPDSGNTRYNQKFQG | 152 |
| vhCDR3 | DGTFYGTYGYWYFDF | 153 |
| Variable light (vl) domain | DIVMTQSPYSLAVSAGEKVTMSCRSSQSLYYSGIKKNLLAWYQQKPGQSPKLLIYFTSTRLPGVPDRFTGSGSGTDYTLTITSVQAEDMGHYFCQQGISTPLTFGDGTKLEIR | 154 |
| vlCDR1 | RSSQSLYYSGIKKNLLA | 155 |
| vlCDR2 | FTSTRLP | 156 |
| vlCDR3 | QQGISTPLT | 157 | m9.3[CD28]_H0L0

| | sequence | SEQ ID NO: |
|---|---|---|
| Variable heavy (vh) domain | EVKLQQSGPGLVTPSQSLSITCTVSGFSLSDYGVHWVRQSPGQGLEWLGVIWAGGGTNYNSALMSRKSISKDNSKSQVFLKMNSLQADDTAVYYCARDKGYSYYYSMDYWGQGTSVTVSS | 158 |
| vhCDR1 | DYGVH | 159 |
| vhCDR2 | VIWAGGGTNYNSALMS | 160 |
| vhCDR3 | DKGYSYYYSMDY | 161 |
| Variable light (vl) domain | DIELTQSPASLAVSLGQRATISCRASESVEYYVTSLMQWYQQKPGQPPKLLIFAASNVESGVPARFSGSGSGTNFSLNIHPVDEDDVAMYFCQQSRKVPYTFGGGTKLEIK | 162 |
| vlCDR1 | RASESVEYYVTSLMQ | 163 |
| vlCDR2 | AASNVES | 164 |
| vlCDR3 | QQSRKVPYT | 165 |

Figure 21F hu9.3[CD28]_H1L1

|  | sequence | SEQ ID NO: |
|---|---|---|
| Variable heavy (vh) domain | EVQLVQSGGGLVQPGGSLRLSCAGSGFTFSDYGVHWVRQAPGKGLEWVSAIWAGGGTNYASSVMGRFTISRDNAKNSLYLQMNSLRAEDMAVYYCARDKGYSYYYSMDYWGQGTLVTVSS | 166 |
| vhCDR1 | DYGVH | 167 |
| vhCDR2 | AIWAGGGTNYASSVMG | 168 |
| vhCDR3 | DKGYSYYYSMDY | 169 |
| Variable light (vl) domain | DIVMTQSPDSLAVSLGERATINCRASESVEYYVTSLMAWYQQKPGQPPKLLIYAASNVESGVPDRFSGSGSGTNFSLTISSLQAEDVAVYYCQQSRKVPYTFGQGTKLEIK | 170 |
| vlCDR1 | RASESVEYYVTSLMA | 171 |
| vlCDR2 | AASNVES | 172 |
| vlCDR3 | QQSRKVPYT | 173 |

9G2[CD28]_H0L0

|  | sequence | SEQ ID NO: |
|---|---|---|
| Variable heavy (vh) domain | EVQLVESGGGLVQPGRSLKLSCAASGFTFSNYYMAWVRQAPTKGLEWVASITNTGGSTYYRDSVKGRFTISRDNAKSTLYLQMDSLRSEDTATYYCTRGLIYYYDGRNYYDYVMDAWGQGASVTVSS | 174 |
| vhCDR1 | NYYMA | 175 |
| vhCDR2 | SITNTGGSTYYRDSVKG | 176 |
| vhCDR3 | GLIYYYDGRNYYDYVMDA | 177 |
| Variable light (vl) domain | DIQMTQSPASLSASLGETVSIECLASEGISNSLAWYQQKPGKSPQLLIYGASSLQDGVPSRFSGSGSGTQYSLKISGMPEDEGVYYCQQGYKYPLTFGSGTKLEIK | 178 |
| vlCDR1 | LASEGISNSLA | 179 |
| vlCDR2 | GASSLQD | 180 |
| vlCDR3 | QQGYKYPLT | 181 |

| | sequence | SEQ ID NO: |
|---|---|---|
| Variable heavy (vh) domain | EVQLLESGGGLVQPGGSLRLSCAASGFTFSNYYMAWVRQAPGKGLEWVSSITNTGGSTYYRDSVKGRFTISRDNSKSTLYLQMNSLRAEDTAVYYCTRGLIYYYDGRNYYDYVMDAWGQGTTVTVSS | 182 |
| vhCDR1 | NYYMA | 183 |
| vhCDR2 | SITNTGGSTYYRDSVKG | 184 |
| vhCDR3 | GLIYYYDGRNYYDYVMDA | 185 |
| Variable light (vl) domain | DIQMTQSPSSLSASVGDRVTITCRASEGISNSLAWYQQKPGKSPKLLIYGASSLQDGVPSRFSGSGSGTDYTLTISSLQPEDFATYYCQQGYKYPLTFGSGTKVEIK | 186 |
| vlCDR1 | RASEGISNSLA | 187 |
| vlCDR2 | GASSLQD | 188 |
| vlCDR3 | QQGYKYPLT | 189 |

2F10A3.140[CD28]_H1L1

| | sequence | SEQ ID NO: |
|---|---|---|
| Variable heavy (vh) domain | EVQLLESGGGLVQPGGSLRLSCAASGFSFGGNSMSWVRQAPGKGLEWVATISDNSYSTYYADSVKGRFTISRDNSKNTLYLQMNSLRAEDTAVYYCAKSGPGLRQVGFDYWGQGTLVTVSS | 190 |
| vhCDR1 | GNSMS | 191 |
| vhCDR2 | TISDNSYSTYYADSVKG | 192 |
| vhCDR3 | SGPGLRQVGFDY | 193 |
| Variable light (vl) domain | DIQMTQSPSSLSASVGDRVTITCRASQSISSYLNWYQQKPGKAPKLLIYAASSLQSGVPSRFSGSGSGTDFTLTISSLQPEDFATYYCQQSYSTPFTFGQGTKLEIK | 194 |
| vlCDR1 | RASQSISSYLN | 195 |
| vlCDR2 | AASSLQS | 196 |
| vlCDR3 | QQSYSTPFT | 197 |

| | sequence | SEQ ID NO: |
|---|---|---|
| Variable heavy (vh) domain | QVQLQESGPGLVKPSETLSLTCTVSGFSLTSYGVHWVRQPPGKGLEWIGVIWPGGGTNYNSALKSRVTISEDTSKSQVSLKLSSVTAADTAVYYCARDRAYGNYLYAMDYWGQGTLVTVSS | 198 |
| vhCDR1 | SYGVH | 199 |
| vhCDR2 | VIWPGGGTNYNSALKS | 200 |
| vhCDR3 | DRAYGNYLYAMDY | 201 |
| Variable light (vl) domain | EIVLTQSPATLSLSPGERATLSCRASESVEYYVTSLMQWYQQKPGQAPRLLIYAASNVDSGVPARFSGSGSGTDFTLTISSLEPEDFAVYYCQQSRKVPFTFGGGTKVEIK | 202 |
| vlCDR1 | RASESVEYYVTSLMQ | 203 |
| vlCDR2 | AASNVDS | 204 |
| vlCDR3 | QQSRKVPFT | 205 |

Figure 22

>XENP27181 HuTN228[CD28]_H1L1_IgG1_PVA_/S267K
Heavy Chain (SEQ ID NO: 534)
QVQLQESGPGLVKPSETLSLTCAVSGFSLTSYGVHWIRQPPGKGLEWLGVIWPGGGTNFNSALMSRLTISEDTSKNQ
VSLKLSSVTAADTAVYYCARDRAYGNYLYAMDYWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPPVAGPSVFLFPPKPKDTLMISRTPEVTCVVVDVKHEDPEVKFNWYVDGVEVHNAKTKPREEQYNSTYRVVSV
LTVLHQDWLNGKEYKCKVSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLSLSPGK

Light Chain (SEQ ID NO: 535)
DIQMTQSPSSLSASVGDRVTITCRASESVEYYVTSLMQWYQQKPGKAPKLLIYAASNVDSGVPSRFSGSGSGTDFTL
TISSLQPEDIATYYCQQSRKVPFTFGGGTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC

>XENP29154 TGN1412
Heavy Chain - TGN1412 HC (SEQ ID NO: 536)
QVQLVQSGAEVKKPGASVKVSCKASGYTFTSYYIHWVRQAPGQGLEWIGCIYPGNVNTNYNEKFKDRATLTVDTSIS
TAYMELSRLRSDDTAVYFCTRSHYGLDWNFDVWGQGTTVTVSSASTKGPSVFPLAPCSRSTSESTAALGCLVKDYFP
EPVTVSWNSGALTSGVHTFPAVLQSSGLYSLSSVVTVPSSSLGTKTYTCNVDHKPSNTKVDKRVESKYGPPCPSCPA
PEFLGGPSVFLFPPKPKDTLMISRTPEVTCVVVDVSQEDPEVQFNWYVDGVEVHNAKTKPREEQFNSTYRVVSVLTV
LHQDWLNGKEYKCKVSNKGLPSSIEKTISKAKGQPREPQVYTLPPSQEEMTKNQVSLTCLVKGFYPSDIAVEWESNG
QPENNYKTTPPVLDSDGSFFLYSRLTVDKSRWQEGNVFSCSVMHEALHNHYTQKSLSLSLG

Light Chain - TGN1412 LC (SEQ ID NO: 537)
DIQMTQSPSSLSASVGDRVTITCHASQNIYVWLNWYQQKPGKAPKLLIYKASNLHTGVPSRFSGSGSGTDFTLTISS
LQPEDFATYYCQQGQTYPYTFGGGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

| Phage anti-CD28 Clone | $K_{Dapp}$ (M) |
|---|---|
| Phage Clone A | 3.31E-08 |
| Phage Clone B | 1.76E-08 |
| Phage Clone C | 8.66E-09 |
| Phage Clone D | 7.40E-08 |
| Phage Clone E | 1.70E-08 |
| Phage Clone F | 1.47E-08 |
| Phage Clone G | 2.84E-08 |
| Phage Clone 1A7 (XENP28428) | 1.45E-08 |

1 + 1 Fab-scFv-Fc

2 + 1 Fab₂-scFv-Fc

1 + 1 Common Light Chain

2 + 1 Common Light Chain

2+1 mAb-scFv

Dual scFv

One-arm scFv-mAb scFv-mAb

Bispecific mAb

One-arm central-scFv mAb-Fv central-Fv

Figure 25A

| A10[PSMA] | | |
|---|---|---|
| | Sequence | SEQ ID NO: |
| Variable Heavy (vh) Domain | QVQLVESGGGVVQPGRSLRLSCAASGFTFSSYNMNWVRQAPGKGLEWVAIIYYDGSNKYYADSVKGRFTISRDISKNTLYLQMNSLRAEDTAVYYCARERGRDYYGMDVWGQGTTVTVSS | 206 |
| vhCDR1 | SYNMN | 207 |
| vhCDR2 | IIYYDGSNKYYADSVKG | 208 |
| vhCDR3 | ERGRDYYGMDV | 209 |
| Variable Light (vl) Domain | SYELMQPPSVSVSPGQTARITCSGDALPKQYAYWYQQKPGQAPVLVIYKDSERPSGIPVRFSGSSSGTTVTLTITGVQAEDEADYYCQSADSSGTYVFGTGTKVTVL | 210 |
| vlCDR1 | SGDALPKQYAY | 211 |
| vlCDR2 | KDSERPS | 212 |
| vlCDR3 | QSADSSGTYV | 213 |

| A10v2[PSMA] | | |
|---|---|---|
| | Sequence | SEQ ID NO: |
| Variable Heavy (vh) Domain | QVQLVESGGGVVQPGRSLRLSCAASGFTFSSYNMNWVRQAPGKGLEWVAIIYYDESNKYYADSVKGRFTISRDISKNTLYLQMNSLRAEDTAVYYCARERGRDYYGMDVWGQGTTVTVSS | 214 |
| vhCDR1 | SYNMN | 215 |
| vhCDR2 | IIYYDESNKYYADSVKG | 216 |
| vhCDR3 | ERGRDYYGMDV | 217 |
| Variable Light (vl) Domain | SYELMQPPSVSVSPGQTARITCSGDALPKQYAYWYQQKPGQAPVLVIYKDSERPSGIPVRFSGSSSGTTVTLTITGVQAEDEADYYCQSADSSGTYVFGTGTKVTVL | 218 |
| vlCDR1 | SGDALPKQYAY | 219 |
| vlCDR2 | KDSERPS | 220 |
| vlCDR3 | QSADSSGTYV | 221 |

| D01[PSMA] | | |
|---|---|---|
| | Sequence | SEQ ID NO: |
| Variable Heavy (vh) Domain | EVQLVESGGDLVQPGGSLRLSCAASGFTFNNYNMNWVRQAPGKGLEWVSHISTSSSNKYYADSVKGRFSISRDIAKNSMYLQMNSLRDEDTAVYYCARDGVGADYGDYYYYGMDVWGQGTTVTVSS | 222 |
| vhCDR1 | NYNMN | 223 |
| vhCDR2 | HISTSSSNKYYADSVKG | 224 |
| vhCDR3 | DGVGADYGDYYYYGMDV | 225 |
| Variable Light (vl) Domain | QSVLTQPASVSGSPGQSITISCTGTSSDVGGYNYVSWYQQHPGKAPKLMIYEVSNRPSGVSNRFSGSKSGNTASLTISGLQAEDEADYYCSSYTSSYTYVFGTGTKLTVL | 226 |
| vlCDR1 | TGTSSDVGGYNYVS | 227 |
| vlCDR2 | EVSNRPS | 228 |
| vlCDR3 | SSYTSSYTYV | 229 |

Figure 25B

| D01v2[PSMA] | | |
|---|---|---|
| | Sequence | SEQ ID NO: |
| Variable Heavy (vh) Domain | EVQLVESGGDLVQPGGSLRLSCAASGFTFNNYNMNWVRQAPGKGLEWVSHISTSSSNKYYADSVKGRFSISRDIAKNSMYLQMNSLRDEDTAVYYCAREGVGADYGDYYYYGMDVWGQGTTVTVSS | 230 |
| vhCDR1 | NYNMN | 231 |
| vhCDR2 | HISTSSSNKYYADSVKG | 232 |
| vhCDR3 | EGVGADYGDYYYYGMDV | 233 |
| Variable Light (vl) Domain | QSVLTQPASVSGSPGQSITISCTGTSSDVGGYNYVSWYQQHPGKAPKLMIYEVSNRPSGVSNRFSGSKSGNTASLTISGLQAEDEADYYCSSYTSSYTYVFGTGTKLTVL | 234 |
| vlCDR1 | TGTSSDVGGYNYVS | 235 |
| vlCDR2 | EVSNRPS | 236 |
| vlCDR3 | SSYTSSYTYV | 237 |

| E07[PSMA] | | |
|---|---|---|
| | Sequence | SEQ ID NO: |
| Variable Heavy (vh) Domain | EVQLVESGGGVVQPGRSLRLSCAASGFTFITYGMHWVRQAPGKGLEWVAVVSFDESNKYYADSVKGRFTISRDNSKNTLYLQMNSLRAEDTAVYYCARALRDGNNWDYFNGMDVWGQGTTVTVSS | 238 |
| vhCDR1 | TYGMH | 239 |
| vhCDR2 | VVSFDESNKYYADSVKG | 240 |
| vhCDR3 | ALRDGNNWDYFNGMDV | 241 |
| Variable Light (vl) Domain | QSVLTQPPSASGTPGQGVTISCSGSSSNIGSNTVNWFQQLPGTAPKLLIYSDNQRPSGVPDRFSGSKSGTSASLAISGLQSEDEADYYCAAWDDSLNGYVFGTGTKVTVL | 242 |
| vlCDR1 | SGSSSNIGSNTVN | 243 |
| vlCDR2 | SDNQRPS | 244 |
| vlCDR3 | AAWDDSLNGYV | 245 |

| F02[PSMA] | | |
|---|---|---|
| | Sequence | SEQ ID NO: |
| Variable Heavy (vh) Domain | EVQLLESGPGLVKPSETLSLTCTVSGGSIISYYWSWIRQPAGKGLEWIGRIYSSGSTNYNPSLKSRVTMSVDTSKNQFSLKLSSVTAADTAVYYCAKVGVWPGAFDIWGQGTMVTVSS | 246 |
| vhCDR1 | SYYWS | 247 |
| vhCDR2 | RIYSSGSTNYNPSLKS | 248 |
| vhCDR3 | VGVWPGAFDI | 249 |
| Variable Light (vl) Domain | QSVLTQPPSASGTPGQRVTISCSGSSSNIGSNTVNWYQQLPGTAPKLLIYSSNQRPSGVPDRFSGSKSGTSASLAISGLQSEDEADYYCAAWDDSLNGVVFGGGTKLTVL | 250 |
| vlCDR1 | SGSSSNIGSNTVN | 251 |
| vlCDR2 | SSNQRPS | 252 |
| vlCDR3 | AAWDDSLNGVV | 253 |

Figure 25C

| A11[PSMA] | | |
|---|---|---|
| | Sequence | SEQ ID NO: |
| Variable Heavy (vh) Domain | QVQLQESGGDVVQPGRSLRLSCAASGFSFSGYGLHWVRQAPGRGLEWVTLISYDGSNKYYADSVKGRFTISRDNSKNTLYLQMNSLRAEDTAVYYCAKTTVSDPYYYGMDVWGQGTTVTVSS | 254 |
| vhCDR1 | GYGLH | 255 |
| vhCDR2 | LISYDGSNKYYADSVKG | 256 |
| vhCDR3 | TTVSDPYYYGMDV | 257 |
| Variable Light (vl) Domain | SYELTQPPSVSVAPGQTARITCGGNNIGSKSVHWYQQKPGQAPVLVVYDDSDRPSGIPERFSGTNSGNTATLTISRAEAGDEADYYCQVWDSSSDHVVFGGGTKLTVL | 258 |
| vlCDR1 | GGNNIGSKSVH | 259 |
| vlCDR2 | DDSDRPS | 260 |
| vlCDR3 | QVWDSSSDHVV | 261 |

| F07[PSMA] | | |
|---|---|---|
| | Sequence | SEQ ID NO: |
| Variable Heavy (vh) Domain | EVQLVESGGGVVQPGRSLRLSCAASGFTFSSYGMNWVRQAPGKGLEWVAVTSYDGSNKYYADSVKGRFTISRDISKNTLYLQMSSLRAEDTAVYYCARDPYSSSWNGAFDIWGPGTMVTVSS | 262 |
| vhCDR1 | SYGMN | 263 |
| vhCDR2 | VTSYDGSNKYYADSVKG | 264 |
| vhCDR3 | DPYSSSWNGAFDI | 265 |
| Variable Light (vl) Domain | SYELTQPPSVSVAPGQTARITCGGNNIGSKSVHWYQQKPGQAPVLVVYDDSDRPSGIPERFSGSNSGNTATLTISRVEAGDEADYYCQVWDSSTDHVVFGGGTKLTVL | 266 |
| vlCDR1 | GGNNIGSKSVH | 267 |
| vlCDR2 | DDSDRPS | 268 |
| vlCDR3 | QVWDSSTDHVV | 269 |

| F07v2[PSMA] | | |
|---|---|---|
| | Sequence | SEQ ID NO: |
| Variable Heavy (vh) Domain | EVQLVESGGGVVQPGRSLRLSCAASGFTFSSYGMNWVRQAPGKGLEWVAVTSYDESNKYYADSVKGRFTISRDISKNTLYLQMSSLRAEDTAVYYCARDPYSSSWNGAFDIWGPGTMVTVSS | 270 |
| vhCDR1 | SYGMN | 271 |
| vhCDR2 | VTSYDESNKYYADSVKG | 272 |
| vhCDR3 | DPYSSSWNGAFDI | 273 |
| Variable Light (vl) Domain | SYELTQPPSVSVAPGQTARITCGGNNIGSKSVHWYQQKPGQAPVLVVYDDSDRPSGIPERFSGSNSGNTATLTISRVEAGDEADYYCQVWDSSTDHVVFGGGTKLTVL | 274 |
| vlCDR1 | GGNNIGSKSVH | 275 |
| vlCDR2 | DDSDRPS | 276 |
| vlCDR3 | QVWDSSTDHVV | 277 |

Figure 25D

| G02[PSMA] | | |
|---|---|---|
| | Sequence | SEQ ID NO: |
| Variable Heavy (vh) Domain | EVQLVESGGGVVQPGRSLRLSCAASGFSFSGYGMHWVRQAPGKGLEWVAVISYDGSNKYYADSVKGRFTISRDNSKNTLYLQMNSLRVEDTAVYYCARDRIWGSRGYYYGMDVWGQGTTVTVSS | 278 |
| vhCDR1 | GYGMH | 279 |
| vhCDR2 | VISYDGSNKYYADSVKG | 280 |
| vhCDR3 | DRIWGSRGYYYGMDV | 281 |
| Variable Light (vl) Domain | QSALTQPASVSGSPGQSITISCTGASSDVGGYNYVSWYQQHPGKAPKLMIYEVSNRPSGVSNRFSGSKSGNTASLTISGLQAEDEADYYCSSYTITSTLVFGGGTKLTVL | 282 |
| vlCDR1 | TGASSDVGGYNYVS | 283 |
| vlCDR2 | EVSNRPS | 284 |
| vlCDR3 | SSYTITSTLV | 285 |

| G02v2[PSMA] | | |
|---|---|---|
| | Sequence | SEQ ID NO: |
| Variable Heavy (vh) Domain | EVQLVESGGGVVQPGRSLRLSCAASGFSFSGYGMHWVRQAPGKGLEWVAVISYDESNKYYADSVKGRFTISRDNSKNTLYLQMNSLRVEDTAVYYCARDRIWGSRGYYYGMDVWGQGTTVTVSS | 286 |
| vhCDR1 | GYGMH | 287 |
| vhCDR2 | VISYDESNKYYADSVKG | 288 |
| vhCDR3 | DRIWGSRGYYYGMDV | 289 |
| Variable Light (vl) Domain | QSALTQPASVSGSPGQSITISCTGASSDVGGYNYVSWYQQHPGKAPKLMIYEVSNRPSGVSNRFSGSKSGNTASLTISGLQAEDEADYYCSSYTITSTLVFGGGTKLTVL | 290 |
| vlCDR1 | TGASSDVGGYNYVS | 291 |
| vlCDR2 | EVSNRPS | 292 |
| vlCDR3 | SSYTITSTLV | 293 |

| F01[PSMA] | | |
|---|---|---|
| | Sequence | SEQ ID NO: |
| Variable Heavy (vh) Domain | QVQLQESGGGVVQPGRSLRLSCAASGFTFSTYGMHWVRQAPGKGLEWVAFISYDGSNKYYADSVKGRFTISRDNSKHTLYLQMNSLRAEDTAVYYCAGRDNLRFLEWFMDVWGQGTTVTVSS | 294 |
| vhCDR1 | TYGMH | 295 |
| vhCDR2 | FISYDGSNKYYADSVKG | 296 |
| vhCDR3 | RDNLRFLEWFMDV | 297 |
| Variable Light (vl) Domain | EIVLTQSPGTLSVSPGERATLSCRASQSVRSNLAWYQQKPGQAPRLLIYGASTRATGIPARFSGSGSGTEFTLTISSLQSEDFAVYYCHQYNDWPPYTFGQGTKLEIK | 298 |
| vlCDR1 | RASQSVRSNLA | 299 |
| vlCDR2 | GASTRAT | 300 |
| vlCDR3 | HQYNDWPPYT | 301 |

Figure 25E

| F01v2[PSMA] | | |
|---|---|---|
| | Sequence | SEQ ID NO: |
| Variable Heavy (vh) Domain | QVQLQESGGGVVQPGRSLRLSCAASGFTFSTYGMHWVRQAPGKGLEWVAFISYDESNKYYADSVKGRFTISRDNSKHTLYLQMNSLRAEDTAVYYCAGRDNLRFLEWFMDVWGQGTTVTVSS | 302 |
| vhCDR1 | TYGMH | 303 |
| vhCDR2 | FISYDESNKYYADSVKG | 304 |
| vhCDR3 | RDNLRFLEWFMDV | 305 |
| Variable Light (vl) Domain | EIVLTQSPGTLSVSPGERATLSCRASQSVRSNLAWYQQKPGQAPRLLIYGASTRATGIPARFSGSGSGTEFTLTISSLQSEDFAVYYCHQYNDWPPYTFGQGTKLEIK | 306 |
| vlCDR1 | RASQSVRSNLA | 307 |
| vlCDR2 | GASTRAT | 308 |
| vlCDR3 | HQYNDWPPYT | 309 |

Figure 26A

| 011A11[PSMA] | | |
|---|---|---|
| | Sequence | SEQ ID NO: |
| Variable Heavy (vh) Domain | EVQLVESGGGLVKPGGSLRLSCVASGFTFSFYSMNWVRQAPGKGLDWVSSISSSGNYIYYADSVKGRFTISRDNAKNSLHLHMNSLKAEDTAMYFCARSYSGSYDAFDFWGQGTMVTVSS | 310 |
| vhCDR1 | FYSMN | 311 |
| vhCDR2 | SISSSGNYIYYADSVKG | 312 |
| vhCDR3 | SYSGSYDAFDF | 313 |
| Variable Light (vl) Domain | EIVMTQSPGTLSLSPGERATLSCRASQSVSSSFLAWYQQKPGQAPRLLISGASSRATGIPDRFSVSGSGTDFTLTISRLEPEDFAVYYCQQYGVSPWTFGQGTKVEIK | 314 |
| vlCDR1 | RASQSVSSSFLA | 315 |
| vlCDR2 | GASSRAT | 316 |
| vlCDR3 | QQYGVSPWT | 317 |

| PSMB896[PSMA] | | |
|---|---|---|
| | Sequence | SEQ ID NO: |
| Variable Heavy (vh) Domain | EVQLVESGGGLVQPGGSLRLSCAASGFTFSSYAMSWVRQAPGKGLEWVSAISGGIGSTYYADSVKGRFTISRDNSKNTLWLQMNSLRAEDTAVYYCAKDAVGATPYYFDYWGQGTLVTVSS | 318 |
| vhCDR1 | SYAMS | 319 |
| vhCDR2 | AISGGIGSTYYADSVKG | 320 |
| vhCDR3 | DAVGATPYYFDY | 321 |
| Variable Light (vl) Domain | QSVLTQPPSVSAAPGQKVTISCSGSSSNIGINYVSWYQQLPGTAPKLLIYDNNKRPSGIPDRFSGSKSGTSATLGITGLQTGDEADYYCGTWDSSLSAVVFGGGTKLTVL | 322 |
| vlCDR1 | SGSSSNIGINYVS | 323 |
| vlCDR2 | DNNKRPS | 324 |
| vlCDR3 | GTWDSSLSAVV | 325 |

Figure 26B

| PSMA-H[PSMA] | | |
|---|---|---|
| | Sequence | SEQ ID NO: |
| Variable Heavy (vh) Domain | EVQLVQSGAEVKKPGASVKVSCKTSGYTFTEYTIHWVRQAPGQSLEWMGNINP NNGGTTYNQKFQGRVTITVDKSTSTAYMELSSLRSEDTAVYYCAAGWNFDYWG QGTLVTVSS | 326 |
| vhCDR1 | EYTIH | 327 |
| vhCDR2 | NINPNNGGTTYNQKFQG | 328 |
| vhCDR3 | GWNFDY | 329 |
| Variable Light (vl) Domain | DIVMTQSPDSLAVSLGERATLSCRASQDVGTAVDWYQQKPDQSPKLLIYWAST RHTGVPDRFTGSGSGTDFTLTISSLQAEDVAVYFCQQYNSYPLTFGAGTKVEI K | 330 |
| vlCDR1 | RASQDVGTAVD | 331 |
| vlCDR2 | WASTRHT | 332 |
| vlCDR3 | QQYNSYPLT | 333 |

| D7[PSMA] | | |
|---|---|---|
| | Sequence | SEQ ID NO: |
| Variable Heavy (vh) Domain | QVQLQQSGAELVEPGASVKLSCKASGYTFTYFDINWLRQRPEQGLEWIGGISP GDGNTNYNENFKGKATLTIDKSSTTAYIQLSRLTSEDSAVYFCARDGNFPYYA MDSWGQGTSVTVSS | 334 |
| vhCDR1 | YFDIN | 335 |
| vhCDR2 | GISPGDGNTNYNENFKG | 336 |
| vhCDR3 | DGNFPYYAMDS | 337 |
| Variable Light (vl) Domain | DIELTQSPLSLPVILGDQASISCRSSQSLVHSNGNTYLHWFLQKPGQSPKLLI YTVSNRFSGVPDRFSGSGSGTDFTLKISRVEAEDLGVYFCSQSTHVPTFGGGT KLEIK | 338 |
| vlCDR1 | RSSQSLVHSNGNTYLH | 339 |
| vlCDR2 | TVSNRFS | 340 |
| vlCDR3 | SQSTHVPT | 341 |

Figure 28A

>XENP31600 D7[PSMA]_H0L0_Fab-SP34_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 – D7[PSMA]_H0_IgG1_pI(-)_Isosteric_A_/PVA_/S267K/L368D/K370S (SEQ ID NO: 538)
QVQLQQSGAELVEPGASVKLSCKASGYTFTYFDINWLRQRPEQGLEWIGGISPGDGNTNYNENFKGKATLTIDKSST
TAYIQLSRLTSEDSAVYFCARDGNFPYYAMDSWGQGTSVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSDTKVDKKVEPKSCDKTHTCPP
CPAPPVAGPSVFLFPPKPKDTLMISRTPEVTCVVVDVKHEDPEVKFNWYVDGVEVHNAKTKPREEEYNSTYRVVSVL
TVLHQDWLNGKEYKCKVSNKALPAPIEKTISKAKGQPREPQVYTLPPSREEMTKNQVSLTCDVSGFYPSDIAVEWES
DGQPENNYKTTPPVLDSDGSFFLYSKLTVDKSRWEQGDVFSCSVMHEALHNHYTQKSLSLSPGK

Chain 2 – [CD3]_H1.30_L1.47_scFv(GKPGS)4_Fc(222)_IgG1_C220S/PVA_/S267K/S364K/E357Q (SEQ ID NO: 539)
EVQLVESGGGLVQPGGSLRLSCAASGFTFSTYAMNWVRQAPGKGLEWVGRIRSKYNNYATYYADSVKGRFTISRDDS
KNTLYLQMNSLRAEDTAVYYCVRHGNFGDSYVSWFAYWGQGTLVTVSSGKPGSGKPGSGKPGSGKPGSQAVVTQEPS
LTVSPGGTVTLTCGSSTGAVTTSNYANWVQQKPGKSPRGLIGGTNKRAPGVPARFSGSLLGGKAALTISGAQPEDEA
DYYCALWYSNHWVFGGGTKLTVLEPKSSDKTHTCPPCPAPPVAGPSVFLFPPKPKDTLMISRTPEVTCVVVDVKHED
PEVKFNWYVDGVEVHNAKTKPREEQYNSTYRVVSVLTVLHQDWLNGKEYKCKVSNKALPAPIEKTISKAKGQPREPQ
VYTLPPSREQMTKNQVKLTCLVKGFYPSDIAVEWESNGQPENNYKTTPPVLDSDGSFFLYSKLTVDKSRWQQGNVFS
CSVMHEALHNHYTQKSLSLSPGK

Chain 3 – D7_L0 Light Chain (SEQ ID NO: 540)
DIELTQSPLSLPVILGDQASISCRSSQSLVHSNGNTYLHWFLQKPGQSPKLLIYTVSNRFSGVPDRFSGSGSGTDFT
LKISRVEAEDLGVYFCSQSTHVPTFGGGTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC >XENP32220 PSMA-H_H1_L1.24_Fab-PSMA-H_H1_L1.24_Fab_(G4S)_[CD3]_L1.47_H1.32_scFv(GKPGS)4_(G4S)2-
IgG1_pI(-)_Isosteric_A_/PVA_/S267K/L368D/K370S-Fc(222)_IgG1_C220S/PVA_/S267K/S364K/E357Q

Chain 1 - PSMA-H_H1_IgG1_pI(-)_Isosteric_A_/PVA_/S267K/L368D/K370S (SEQ ID NO: 541)
EVQLVQSGAEVKKPGASVKVSCKTSGYTFTEYTIHWVRQAPGQSLEWMGNINPNNGGTTYNQKFQGRVTITVDKSTS
TAYMELSSLRSEDTAVYYCAAGWNFDYWGQGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSDTKVDKKVEPKSCDKTHTCPPCPAPP
VAGPSVFLFPPKPKDTLMISRTPEVTCVVVDVKHEDPEVKFNWYVDGVEVHNAKTKPREEEYNSTYRVVSVLTVLHQ
DWLNGKEYKCKVSNKALPAPIEKTISKAKGQPREPQVYTLPPSREEMTKNQVSLTCDVSGFYPSDIAVEWESDGQPE
NNYKTTPPVLDSDGSFFLYSKLTVDKSRWEQGDVFSCSVMHEALHNHYTQKSLSLSPGK

**Chain 2 - PSMA-
H_H1_(G4S)_[CD3]_L1.47_H1.32_scFv(GKPGS)4_Fc(222)_IgG1_C220S/PVA_/S267K/S364K/E357Q (SEQ ID NO: 542)**
EVQLVQSGAEVKKPGASVKVSCKTSGYTFTEYTIHWVRQAPGQSLEWMGNINPNNGGTTYNQKFQGRVTITVDKSTS
TAYMELSSLRSEDTAVYYCAAGWNFDYWGQGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVEPKSCGGGGSGGGGSQAV
VTQEPSLTVSPGGTVTLTCGSSTGAVTTSNYANWVQQKPGKSPRGLIGGTNKRAPGVPARFSGSLLGGKAALTISGA
QPEDEADYYCALWYSNHWVFGGGTKLTVLGKPGSGKPGSGKPGSGKPGSEVQLVESGGGLVQPGGSLRLSCAASGFT
FSTYAMNWVRQAPGKGLEWVGRIRSKANNYATYYADSVKGRFTISRDDSKNTLYLQMNSLRAEDTAVYYCVRHGNFG
DSYVSWFAYWGQGTLVTVSSGGGGSGGGGSKTHTCPPCPAPPVAGPSVFLFPPKPKDTLMISRTPEVTCVVVDVKHE
DPEVKFNWYVDGVEVHNAKTKPREEQYNSTYRVVSVLTVLHQDWLNGKEYKCKVSNKALPAPIEKTISKAKGQPREP
QVYTLPPSREQMTKNQVKLTCLVKGFYPSDIAVEWESNGQPENNYKTTPPVLDSDGSFFLYSKLTVDKSRWQQGNVF
SCSVMHEALHNHYTQKSLSLSPGK

Chain 3 - PSMA-H_L1.24 Light Chain (SEQ ID NO: 543)
DIVMTQSPDSLAVSLGERATLSCRASQDVGTAVDWYQQKPDQSPKLLIYYASTRHTGVPDRFTGSGSGTDFTLTISS
LQAEDVAVYFCQQYNSYPLTFGAGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

Figure 28B

>XENP33063 PSMA-H_H1_L1.58_Fab-PSMA-H_H1_L1.58_Fab_(G4S)_[CD3]_L1.47_H1.89_scFv(GKPGS)4-IgG1_pI(-)_Isosteric_A_/PVA_/S267K/L368D/K370S-Fc(216)_IgG1_C220S/PVA_/S267K/S364K/E357Q Chain 1 - PSMA-H_H1_IgG1_pI(-)_Isosteric_A_/PVA_/S267K/L368D/K370S (SEQ ID NO: 544)
EVQLVQSGAEVKKPGASVKVSCKTSGYTFTEYTIHWVRQAPGQSLEWMGNINPNNGGTTYNQKFQGRVTITVDKSTS
TAYMELSSLRSEDTAVYYCAAGWNFDYWGQGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSDTKVDKKVEPKSCDKTHTCPPCPAPP
VAGPSVFLFPPKPKDTLMISRTPEVTCVVVDVKHEDPEVKFNWYVDGVEVHNAKTKPREEEYNSTYRVVSVLTVLHQ
DWLNGKEYKCKVSNKALPAPIEKTISKAKGQPREPQVYTLPPSREEMTKNQVSLTCDVSGFYPSDIAVEWESDGQPE
NNYKTTPPVLDSDGSFFLYSKLTVDKSRWEQGDVFSCSVMHEALHNHYTQKSLSLSPGK Chain 2 - PSMA-H_H1_(G4S)_[CD3]_L1.47_H1.89_scFv(GKPGS)4_Fc(216)_IgG1_C220S/PVA_/S267K/S364K/E357Q (SEQ ID NO: 545)
EVQLVQSGAEVKKPGASVKVSCKTSGYTFTEYTIHWVRQAPGQSLEWMGNINPNNGGTTYNQKFQGRVTITVDKSTS
TAYMELSSLRSEDTAVYYCAAGWNFDYWGQGTLVTVSSASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVEPKSCGGGGSGGGGSQAV
VTQEPSLTVSPGGTVTLTCGSSTGAVTTSNYANWVQQKPGKSPRGLIGGTNKRAPGVPARFSGSLLGGKAALTISGA
QPEDEADYYCALWYSNHWVFGGGTKLTVLGKPGSGKPGSGKPGSGKPGSEVQLVESGGGLVQPGGSLRLSCAASGFT
FSTYAMNWVRQAPGKGLEWVGRIRSKYNNYATYYADSVKGRFTISRDDSKNTLYLQMNSLRAEDTAVYYCVRHGNFG
DEYVSWFAYWGQGTLVTVSSEPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - PSMA-H_L1.58 Light Chain (SEQ ID NO: 546)
DIVMTQSPDSLAVSLGERATLSCRASQDVGTAVDWYQQKPDQSPKLLIYWASTRHTGVPDRFTGSGSGTDFTLTISS
LQAEDVAVYFCQQYQSYPLTFGAGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

Figure 28C

>1391 PSMA x CD3
Chain 1 (SEQ ID NO: 547)
EIVLTQSPATLSASPGERVTLSCSASSSVSYMNWYQQKPGQAPRRWIYDSSKLASGVPARFSGSGSGRDYTLTISSL
EPEDFAVYYCQQWSRNPPTFGGGTKVEIKGGSEGKSSGSGSESKSTGGSQVQLVQSGAEVKKPGSSVKVSCKASGYT
FTRSTMHWVKQAPGQGLEWIGYINPSSAYTNYNQKFQGRVTLTADKSTSTAYMELSSLRSEDTAVYYCASPQVHYDY
AGFPYWGQGTLVTVSSEPKSSDKTHTCPPCPAPEAAGGPSVFLFPPKPKDTLMISRTPEVTCVVVSVSHEDPEVKFN
WYVDGVEVHNAKTKPREEQYNSTYRVVSVLTVLHQDWLNGKEYKCKVSNKALPAPIEKTISKAKGQPREPQVYTLPP
SREEMTKNQVSLWCLVKGFYPSDIAVEWESNGQPENNYKTTPPVLDSDGSFFLYSKLTVDKSRWQQGNVFSCSVMHE
ALHNHYTQKSLSLSPGK
Chain 2 (SEQ ID NO: 548)
EVQLVESGGGLVKPGGSLRLSCVASGFTFSFYSMNWVRQAPGKGLDWVSSISSSGNYIYYADSVKGRFTISRDNAKN
SLHLHMNSLKAEDTAMYFCARSYSGSYDAFDFWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKVDKKVEPKSCDKTHTCPP
CPAPEAAGGPSVFLFPPKPKDTLMISRTPEVTCVVVSVSHEDPEVKFNWYVDGVEVHNAKTKPREEQYNSTYRVVSV
LTVLHQDWLNGKEYKCKVSNKALPAPIEKTISKAKGQPREPQVYTLPPSREEMTKNQVSLSCAVKGFYPSDIAVEWE
SNGQPENNYKTTPPVLDSDGSFFLVSKLTVDKSRWQQGNVFSCSVMHEALHNRFTQKSLSLSPGK
Chain 3 (SEQ ID NO: 549)
EIVMTQSPGTLSLSPGERATLSCRASQSVSSSFLAWYQQKPGQAPRLLISGASSRATGIPDRFSVSGSGTDFTLTIS
RLEPEDFAVYYCQQYGVSPWTFGQGTKVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

>1508 PSMA x CD3
Chain 1 (SEQ ID NO: 550)
DIQMTQSPSSLSASVGDRVTITCRARQSIGTAIHWYQQKPGKAPKLLIKYASESISGVPSRFSGSGSGTDFTLTISS
LQPEDFATYYCQQSGSWPYTFGQGTKLEIKGGSEGKSSGSGSESKSTGGSEVQLVESGGGLVKPGGSLRLSCAASGF
TFSRYNMNWVRQAPGKGLEWVSSISTSSNYIYYADSVKGRFTFSRDNAKNSLDLQMSGLRAEDTAIYYCTRGWGPFD
YWGQGTLVTVSSEPKSSDKTHTCPPCPAPEAAGGPSVFLFPPKPKDTLMISRTPEVTCVVVSVSHEDPEVKFNWYVD
GVEVHNAKTKPREEQYNSTYRVVSVLTVLHQDWLNGKEYKCKVSNKALPAPIEKTISKAKGQPREPQVYTLPPSREE
MTKNQVSLWCLVKGFYPSDIAVEWESNGQPENNYKTTPPVLDSDGSFFLYSKLTVDKSRWQQGNVFSCSVMHEALHN
HYTQKSLSLSPGK
Chain 2 (SEQ ID NO: 551)
EVQLVESGGGLVQPGGSLRLSCAASGFTFSSYAMSWVRQAPGKGLEWVSAISGGIGSTYYADSVKGRFTISRDNSKN
TLWLQMNSLRAEDTAVYYCAKDAVGATPYYFDYWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSPGK
Chain 3 (SEQ ID NO: 552)
QSVLTQPPSVSAAPGQKVTISCSGSSSNIGINYVSWYQQLPGTAPKLLIYDNNKRPSGIPDRFSGSKSGTSATLGIT
GLQTGDEADYYCGTWDSSLSAVVFGGGTKLTVLGQPKAAPSVTLFPPSSEELQANKATLVCLISDFYPGAVTVAWKA
DSSPVKAGVETTTPSKQSNNKYAASSYLSLTPEQWKSHRSYSCQVTHEGSTVEKTVAPTECS

Figure 29A

>XENP37900 D7[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - D7[PSMA]_H0_IgG1_pI(-)_Isosteric_A_/PVA_/S267K/L368D/K370S (SEQ ID NO: 553)
QVQLQQSGAELVEPGASVKLSCKASGYTFTYFDINWLRQRPEQGLEWIGGISPGDGNTNYNENFKGKATLTIDKSST
TAYIQLSRLTSEDSAVYFCARDGNFPYYAMDSWGQGTSVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 554)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - D7[PSMA]_L0 Light Chain (SEQ ID NO: 555)
DIELTQSPLSLPVILGDQASISCRSSQSLVHSNGNTYLHWFLQKPGQSPKLLIYTVSNRFSGVPDRFSGSGSGTDFT
LKISRVEAEDLGVYFCSQSTHVPTFGGGTKLEIK/RTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC >XENP37901 D7[PSMA]_H0L0_Fab-1A7[CD28]_H1.14_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - D7[PSMA]_H0_IgG1_pI(-)_Isosteric_A_/PVA_/S267K/L368D/K370S (SEQ ID NO: 556)
QVQLQQSGAELVEPGASVKLSCKASGYTFTYFDINWLRQRPEQGLEWIGGISPGDGNTNYNENFKGKATLTIDKSST
TAYIQLSRLTSEDSAVYFCARDGNFPYYAMDSWGQGTSVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1.14_L1.71_scFv(GKPGS)4_Fc(216)_IgG1_C220S/PVA_/S267K/S364K/E357Q (SEQ ID NO: 557)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - D7[PSMA]_L0 Light Chain (SEQ ID NO: 558)
DIELTQSPLSLPVILGDQASISCRSSQSLVHSNGNTYLHWFLQKPGQSPKLLIYTVSNRFSGVPDRFSGSGSGTDFT
LKISRVEAEDLGVYFCSQSTHVPTFGGGTKLEIK/RTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC

Figure 29B

>XENP37902 PSMA-H[PSMA]_H1L1_Fab-1A7[CD28]_H1.14_L1_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - PSMA-H[PSMA]_H1_IgG1_pI(-)_Isosteric_A_/PVA_/S267K/L368D/K370S (SEQ ID NO: 559)
EVQLVQSGAEVKKPGASVKVSCKTSGYTFTEYTIHWVRQAPGQSLEWMGNINPNNGGTTYNQKFQGRVTITVDKSTS
TAYMELSSLRSEDTAVYYCAAGWNFDYWGQGTLVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAP
PVAGPSVFLFPPKPKDTLMISRTPEVTCVVVDVKHEDPEVKFNWYVDGVEVHNAKTKPREEEYNSTYRVVSVLTVLH
QDWLNGKEYKCKVSNKALPAPIEKTISKAKGQPREPQVYTLPPSREEMTKNQVSLTCDVSGFYPSDIAVEWESDGQP
ENNYKTTPPVLDSDGSFFLYSKLTVDKSRWEQGDVFSCSVMHEALHNHYTQKSLSLSPGK Chain 2 - 1A7[CD28]_H1.14_L1_scFv(GKPGS)4_Fc(216)_IgG1_C220S/PVA_/S267K/S364K/E357Q (SEQ ID NO: 1048)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - PSMA-H[PSMA]_L1 Light Chain (SEQ ID NO: 560)
DIVMTQSPDSLAVSLGERATLSCRASQDVGTAVDWYQQKPDQSPKLLIYWASTRHTGVPDRFTGSGSGTDFTLTISS
LQAEDVAVYFCQQYNSYPLTFGAGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

>XENP37903 PSMA-H[PSMA]_H1L1_Fab-1A7[CD28]_H1.14_L1.71_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - PSMA-H[PSMA]_H1_IgG1_pI(-)_Isosteric_A_/PVA_/S267K/L368D/K370S (SEQ ID NO: 561)
EVQLVQSGAEVKKPGASVKVSCKTSGYTFTEYTIHWVRQAPGQSLEWMGNINPNNGGTTYNQKFQGRVTITVDKSTS
TAYMELSSLRSEDTAVYYCAAGWNFDYWGQGTLVTVSS/ASTKGPSVFPLAPSSKSTSGGTAALGCLVKDYFPEPVT
VSWNSGALTSGVHTFPAVLQSSGLYSLSSVVTVPSSSLGTQTYICNVNHKPSDTKVDKKVEPKSCDKTHTCPPCPAP
PVAGPSVFLFPPKPKDTLMISRTPEVTCVVVDVKHEDPEVKFNWYVDGVEVHNAKTKPREEEYNSTYRVVSVLTVLH
QDWLNGKEYKCKVSNKALPAPIEKTISKAKGQPREPQVYTLPPSREEMTKNQVSLTCDVSGFYPSDIAVEWESDGQP
ENNYKTTPPVLDSDGSFFLYSKLTVDKSRWEQGDVFSCSVMHEALHNHYTQKSLSLSPGK Chain 2 - 1A7[CD28]_H1.14_L1.71_scFv(GKPGS)4_Fc(216)_IgG1_C220S/PVA_/S267K/S364K/E357Q (SEQ ID NO: 1049)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - PSMA-H[PSMA]_L1 Light Chain (SEQ ID NO: 562)
DIVMTQSPDSLAVSLGERATLSCRASQDVGTAVDWYQQKPDQSPKLLIYWASTRHTGVPDRFTGSGSGTDFTLTISS
LQAEDVAVYFCQQYNSYPLTFGAGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 29C

>XENP38931_P72_A10[PSMA]_H0L0_Fab-1A7[CD28]_H1_L1.71_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P72_A10[PSMA]_H0_IgG1_pI(-)_Isosteric_A_/PVA_/S267K/L368D/K370S (SEQ ID NO: 563)
QVQLVESGGGVVQPGRSLRLSCAASGFTFSSYNMNWVRQAPGKGLEWVAIIYYDGSNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 564)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A10[PSMA]_L0 Light Chain (SEQ ID NO: 565)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

>XENP38932_P72_D01[PSMA]_H0L0_Fab-1A7[CD28]_H1_L1.71_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P72_D01[PSMA]_H0_IgG1_pI(-)_Isosteric_A_/PVA_/S267K/L368D/K370S (SEQ ID NO: 566)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCARDGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 567)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_D01[PSMA]_L0 Light Chain (SEQ ID NO: 568)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29D

>XENP38933_P72_E07[PSMA]_H0L0_Fab-1A7[CD28]_H1_L1.71_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P72_E07[PSMA]_H0_IgG1_pI(-)_Isosteric_A_/PVA_/S267K/L368D/K370S (SEQ ID NO: 569)
EVQLVESGGGVVQPGRSLRLSCAASGFTFITYGMHWVRQAPGKGLEWVAVVSFDESNKYYADSVKGRFTISRDNSKN
TLYLQMNSLRAEDTAVYYCARALRDGNNWDYFNGMDVWGQGTTVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 570)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_E07[PSMA]_L0 Light Chain (SEQ ID NO: 571)
QSVLTQPPSASGTPGQGVTISCSGSSSNIGSNTVNWFQQLPGTAPKLLIYSDNQRPSGVPDRFSGSKSGTSASLAIS
GLQSEDEADYYCAAWDDSLNGYVFGTGTKVTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

>XENP38934_P70_F02[PSMA]_H0L0_Fab-1A7[CD28]_H1_L1.71_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P70_F02[PSMA]_H0_IgG1_pI(-)_Isosteric_A_/PVA_/S267K/L368D/K370S (SEQ ID NO: 572)
EVQLLESGPGLVKPSETLSLTCTVSGGSIISYYWSWIRQPAGKGLEWIGRIYSSGSTNYNPSLKSRVTMSVDTSKNQ
FSLKLSSVTAADTAVYYCAKVGVWPGAFDIWGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 573)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P70_F02[PSMA]_L0 Light Chain (SEQ ID NO: 574)
QSVLTQPPSASGTPGQRVTISCSGSSSNIGSNTVNWYQQLPGTAPKLLIYSSNQRPSGVPDRFSGSKSGTSASLAIS
GLQSEDEADYYCAAWDDSLNGVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29E

**>XENP38935 P72_A11[PSMA]_H0L0_Fab-1A7[CD28]_H1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q**
Chain 1 - P72_A11[PSMA]_H0_IgG1_pI(-)_Isosteric_A_/PVA_/S267K/L368D/K370S (SEQ ID NO: 575)
QVQLQESGGDVVQPGRSLRLSCAASGFSFSGYGLHWVRQAPGRGLEWVTLISYDGSNKYYADSVKGRFTISRDNSKN
TLYLQMNSLRAEDTAVYYCAKTTVSDPYYYGMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 576)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A11[PSMA]_L0 Light Chain (SEQ ID NO: 577)
SYELTQPPSVSVAPGQTARITCGGNNIGSKSVHWYQQKPGQAPVLVVYDDSDRPSGIPERFSGTNSGNTATLTISRA
EAGDEADYYCQVWDSSSDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS

**>XENP38936 a.k.a. C28PB255 P72_A10V2[PSMA]_H0L0_Fab-1A7[CD28]_H1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q**
Chain 1 - P72_A10V2[PSMA]_H0_IgG1_pI(-)_Isosteric_A_/PVA_/S267K/L368D/K370S (SEQ ID NO: 578)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 579)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A10V2[PSMA]_L0 Light Chain (SEQ ID NO: 580)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

Figure 29F

>XENP38937 a.k.a. C28PB256 P72_D01V2[PSMA]_H0L0_Fab-1A7[CD28]_H1_L1.71_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P72_D01V2[PSMA]_H0_IgG1_pI(-)_Isosteric_A_/PVA_/S267K/L368D/K370S (SEQ ID NO: 581)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCAREGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 582)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_D01V2[PSMA]_L0 Light Chain (SEQ ID NO: 583)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

>XENP38938 P72_F07[PSMA]_H0L0_Fab-1A7[CD28]_H1_L1.71_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P72_F07[PSMA]_H0_IgG1_pI(-)_Isosteric_A_/PVA_/S267K/L368D/K370S (SEQ ID NO: 584)
EVQLVESGGGVVQPGRSLRLSCAASGFTFSSYGMNWVRQAPGKGLEWVAVTSYDGSNKYYADSVKGRFTISRDISKN
TLYLQMSSLRAEDTAVYYCARDPYSSSWNGAFDIWGPGTMVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 585)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_F07[PSMA]_L0 Light Chain (SEQ ID NO: 586)
SYELTQPPSVSVAPGQTARITCGGNNIGSKSVHWYQQKPGQAPVLVVYDDSDRPSGIPERFSGSNSGNTATLTISRV
EAGDEADYYCQVWDSSTDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS

Figure 29G

>XENP38939_P72_G02[PSMA]_H0L0_Fab-1A7[CD28]_H1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_G02[PSMA]_H0_IgG1_pI(-)_Isosteric_A_/PVA_/S267K/L368D/K370S (SEQ ID NO: 587)
EVQLVESGGGVVQPGRSLRLSCAASGFSFSGYGMHWVRQAPGKGLEWVAVISYDGSNKYYADSVKGRFTISRDNSKN
TLYLQMNSLRVEDTAVYYCARDRIWGSRGYYYGMDVWGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 588)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_G02[PSMA]_L0 Light Chain (SEQ ID NO: 589)
QSALTQPASVSGSPGQSITISCTGASSDVGGYNYVSWYQQHPGKAPKLMIYEVSNRPSGVSNRFSGSKSGNTASLTI
SGLQAEDEADYYCSSYTITSTLVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP38940_P75_F01[PSMA]_H0L0_Fab-1A7[CD28]_H1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P75_F01[PSMA]_H0_IgG1_pI(-)_Isosteric_A_/PVA_/S267K/L368D/K370S (SEQ ID NO: 590)
QVQLQESGGGVVQPGRSLRLSCAASGFTFSTYGMHWVRQAPGKGLEWVAFISYDGSNKYYADSVKGRFTISRDNSKH
TLYLQMNSLRAEDTAVYYCAGRDNLRFLEWFMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 591)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P75_F01[PSMA]_L0 Light Chain (SEQ ID NO: 592)
EIVLTQSPGTLSVSPGERATLSCRASQSVRSNLAWYQQKPGQAPRLLIYGASTRATGIPARFSGSGSGTEFTLTISS
LQSEDFAVYYCHQYNDWPPYTFGQGTKLEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

Figure 29H

>XENP38941 P72_F07V2[PSMA]_H0L0_Fab-1A7[CD28]_H1_L1.71_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P72_F07V2[PSMA]_H0_IgG1_pI(-)_Isosteric_A_/PVA_/S267K/L368D/K370S (SEQ ID NO: 593)
EVQLVESGGGVVQPGRSLRLSCAASGFTFSSYGMNWVRQAPGKGLEWVAVTSYDESNKYYADSVKGRFTISRDISKN
TLYLQMSSLRAEDTAVYYCARDPYSSSWNGAFDIWGPGTMVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 594)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_F07V2[PSMA]_L0 Light Chain (SEQ ID NO: 595)
SYELTQPPSVSVAPGQTARITCGGNNIGSKSVHWYQQKPGQAPVLVVYDDSDRPSGIPERFSGSNSGNTATLTISRV
EAGDEADYYCQVWDSSTDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS

>XENP38942 P72_G02V2[PSMA]_H0L0_Fab-1A7[CD28]_H1_L1.71_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P72_G02V2[PSMA]_H0_IgG1_pI(-)_Isosteric_A_/PVA_/S267K/L368D/K370S (SEQ ID NO: 596)
EVQLVESGGGVVQPGRSLRLSCAASGFSFSGYGMHWVRQAPGKGLEWVAVISYDESNKYYADSVKGRFTISRDNSKN
TLYLQMNSLRVEDTAVYYCARDRIWGSRGYYYGMDVWGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 597)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_G02V2[PSMA]_L0 Light Chain (SEQ ID NO: 598)
QSALTQPASVSGSPGQSITISCTGASSDVGGYNYVSWYQQHPGKAPKLMIYEVSNRPSGVSNRFSGSKSGNTASLTI
SGLQAEDEADYYCSSYTITSTLVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29I

>XENP38943 P75_F01V2[PSMA]_H0L0_Fab-1A7[CD28]_H1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P75_F01V2[PSMA]_H0_IgG1_pI(-)_Isosteric_A_/PVA_/S267K/L368D/K370S (SEQ ID NO: 599)
QVQLQESGGGVVQPGRSLRLSCAASGFTFSSTYGMHWVRQAPGKGLEWVAFISYDESNKYYADSVKGRFTISRDNSKH
TLYLQMNSLRAEDTAVYYCAGRDNLRFLEWFMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 600)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P75_F01V2[PSMA]_L0 Light Chain (SEQ ID NO: 601)
EIVLTQSPGTLSVSPGERATLSCRASQSVRSNLAWYQQKPGQAPRLLIYGASTRATGIPARFSGSGSGTEFTLTISS
LQSEDFAVYYCHQYNDWPPYTFGQGTKLEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC >XENP38944 PSMB896-HC-G100A[PSMA]_H0L0_Fab-1A7[CD28]_H1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - PSMB896-HC-G100A[PSMA]_H0_IgG1_pI(-)_Isosteric_A_/PVA_/S267K/L368D/K370S (SEQ ID NO: 602)
EVQLVESGGGLVQPGGSLRLSCAASGFTFSSYAMSWVRQAPGKGLEWVSAISGGIGSTYYADSVKGRFTISRDNSKN
TLWLQMNSLRAEDTAVYYCAKDAVGATPYYFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 603)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - PSMB896-HC-G100A[PSMA]_L0 Light Chain (SEQ ID NO: 604)
QSVLTQPPSVSAAPGQKVTISCSGSSSNIGINYVSWYQQLPGTAPKLLIYDNNKRPSGIPDRFSGSKSGTSATLGIT
GLQTGDEADYYCGTWDSSLSAVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29J

>XENP38945 011A11[PSMA]_H0L0_Fab-1A7[CD28]_H1_L1.71_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - 011A11[PSMA]_H0_IgG1_pI(-)_Isosteric_A_/PVA_/S267K/L368D/K370S (SEQ ID NO: 605)
EVQLVESGGGLVKPGGSLRLSCVASGFTFSFYSMNWVRQAPGKGLDWVSSISSSGNYIYYADSVKGRFTISRDNAKN
SLHLHMNSLKAEDTAMYFCARSYSGSYDAFDFWGQGTMVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 606)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - 011A11[PSMA]_L0 Light Chain (SEQ ID NO: 607)
EIVMTQSPGTLSLSPGERATLSCRASQSVSSSFLAWYQQKPGQAPRLLISGASSRATGIPDRFSVSGSGTDFTLTIS
RLEPEDFAVYYCQQYGVSPWTFGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

>XENP39211 P72_A10[PSMA]_H0L0_Fab-1A7[CD28]_H1L1_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P72_A10[PSMA]_H0_IgG1_pI(-)_Isosteric_A_/PVA_/S267K/L368D/K370S (SEQ ID NO: 608)
QVQLVESGGGVVQPGRSLRLSCAASGFTFSSYNMNWVRQAPGKGLEWVAIIYYDGSNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1L1_scFv(GKPGS)4_Fc(216)_IgG1_C220S/PVA_/S267K/S364K/E357Q (SEQ ID NO: 609)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A10[PSMA]_L0 Light Chain (SEQ ID NO: 610)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

Figure 29K

>XENP39212 P72_A10[PSMA]_H0L0_Fab-1A7[CD28]_H1.14_L1_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P72_A10[PSMA]_H0_IgG1_pI(-)_Isosteric_A_/PVA_/S267K/L368D/K370S (SEQ ID NO: 611)
QVQLVESGGGVVQPGRSLRLSCAASGFTFSSYNMNWVRQAPGKGLEWVAIIYYDGSNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 612)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A10[PSMA]_L0 Light Chain (SEQ ID NO: 613)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS >XENP39213 P72_A10[PSMA]_H0L0_Fab-1A7[CD28]_H1.1_L1.71_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P72_A10[PSMA]_H0_IgG1_pI(-)_Isosteric_A_/PVA_/S267K/L368D/K370S (SEQ ID NO: 614)
QVQLVESGGGVVQPGRSLRLSCAASGFTFSSYNMNWVRQAPGKGLEWVAIIYYDGSNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 615)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A10[PSMA]_L0 Light Chain (SEQ ID NO: 616)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

Figure 29L

>XENP39214 P72_A10[PSMA]_H0L0_Fab-1A7[CD28]_H1.14_L1.71_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - P72_A10[PSMA]_H0_IgG1_pI(-)_Isosteric_A_/PVA_/S267K/L368D/K370S (SEQ ID NO: 617)
QVQLVESGGGVVQPGRSLRLSCAASGFTFSSYNMNWVRQAPGKGLEWVAIIYYDGSNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK Chain 2 - 1A7[CD28]_H1.14_L1.71_scFv(GKPGS)4_Fc(216)_IgG1_C220S/PVA_/S267K/S364K/E357Q (SEQ ID NO: 618)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P72_A10[PSMA]_L0 Light Chain (SEQ ID NO: 619)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

>XENP39215 P72_D01[PSMA]_H0L0_Fab-1A7[CD28]_H1L1_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - P72_D01[PSMA]_H0_IgG1_pI(-)_Isosteric_A_/PVA_/S267K/L368D/K370S (SEQ ID NO: 620)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCARDGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK Chain 2 - 1A7[CD28]_H1L1_scFv(GKPGS)4_Fc(216)_IgG1_C220S/PVA_/S267K/S364K/E357Q (SEQ ID NO: 621)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P72_D01[PSMA]_L0 Light Chain (SEQ ID NO: 622)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29M

>XENP39216 P72_D01[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_D01[PSMA]_H0_IgG1_pI(-)_Isosteric_A_/PVA_/S267K/L368D/K370S (SEQ ID NO: 623)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCARDGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 624)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_D01[PSMA]_L0 Light Chain (SEQ ID NO: 625)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39217 P72_D01[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_D01[PSMA]_H0_IgG1_pI(-)_Isosteric_A_/PVA_/S267K/L368D/K370S (SEQ ID NO: 626)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCARDGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 627)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_D01[PSMA]_L0 Light Chain (SEQ ID NO: 628)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29N

<u>>XENP39218 P72_D01[PSMA]_H0L0_Fab-1A7[CD28]_H1.14_L1.71_scFv(GKPGS)4-IgG1_pI(-</u>
<u>)_Isosteric_A_/PVA_/S267K/L368D/K370S-Fc(216)_IgG1_C220S/PVA_/S267K/S364K/E357Q</u>
Chain 1 - P72_D01[PSMA]_H0_IgG1_pI(-)_Isosteric_A_/PVA_/S267K/L368D/K370S (SEQ ID NO: 629)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCARDGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK
Chain 2 - 1A7[CD28]_H1.14_L1.71_scFv(GKPGS)4_Fc(216)_IgG1_C220S/PVA_/S267K/S364K/E357Q (SEQ ID NO: 630)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_D01[PSMA]_L0 Light Chain (SEQ ID NO: 631)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS <u>>XENP39219 P72_E07[PSMA]_H0L0_Fab-1A7[CD28]_H1L1_scFv(GKPGS)4-IgG1_pI(-</u>
<u>)_Isosteric_A_/PVA_/S267K/L368D/K370S-Fc(216)_IgG1_C220S/PVA_/S267K/S364K/E357Q</u>
Chain 1 - P72_E07[PSMA]_H0_IgG1_pI(-)_Isosteric_A_/PVA_/S267K/L368D/K370S (SEQ ID NO: 632)
EVQLVESGGGVVQPGRSLRLSCAASGFTFITYGMHWVRQAPGKGLEWVAVVSFDESNKYYADSVKGRFTISRDNSKN
TLYLQMNSLRAEDTAVYYCARALRDGNNWDYFNGMDVWGQGTTVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK
Chain 2 - 1A7[CD28]_H1L1_scFv(GKPGS)4_Fc(216)_IgG1_C220S/PVA_/S267K/S364K/E357Q (SEQ ID NO: 633)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_E07[PSMA]_L0 Light Chain (SEQ ID NO: 634)
QSVLTQPPSASGTPGQGVTISCSGSSSNIGSNTVNWFQQLPGTAPKLLIYSDNQRPSGVPDRFSGSKSGTSASLAIS
GLQSEDEADYYCAAWDDSLNGYVFGTGTKVTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29O

>XENP39220 P72_E07[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_E07[PSMA]_H0_IgG1_pI(-)_Isosteric_A_/PVA_/S267K/L368D/K370S (SEQ ID NO: 635)
EVQLVESGGGVVQPGRSLRLSCAASGFTFI<u>TYGMH</u>WVRQAPGKGLEWVA<u>VVSFDESNKYYADSVKG</u>RFTISRDNSKN
TLYLQMNSLRAEDTAVYYCARA<u>LRDGNNWDYFNGMDV</u>WGQGTTVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 636)
EVQLLESGGGLVQPGGSLRLSCAASGFTFS<u>SYYMS</u>WVRQAPGKGLEWVS<u>TISESGDSTYYADSVKG</u>RFTISRDNSKN
TLYLQMNSLRAEDTAVYYCAK<u>SGPGLRQVGFDY</u>WGQGTLVTVSS/GKPGSGKPGSGKPGSGKPGS/DIQMTQSPSSL
SASVGDRVTITC<u>RASQSISSYLN</u>WYQQKPGKAPKLLIY<u>AASSLQS</u>GVPSRFSGSGSGTDFTLTISSLQPEDFATYYC
<u>QQSYSTPFT</u>FGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_E07[PSMA]_L0 Light Chain (SEQ ID NO: 637)
QSVLTQPPSASGTPGQGVTISC<u>SGSSSNIGSNTVN</u>WFQQLPGTAPKLLIY<u>SDNQRPS</u>GVPDRFSGSKSGTSASLAIS
GLQSEDEADYYC<u>AAWDDSLNGYV</u>FGTGTKVTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39221 P72_E07[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_E07[PSMA]_H0_IgG1_pI(-)_Isosteric_A_/PVA_/S267K/L368D/K370S (SEQ ID NO: 638)
EVQLVESGGGVVQPGRSLRLSCAASGFTFI<u>TYGMH</u>WVRQAPGKGLEWVA<u>VVSFDESNKYYADSVKG</u>RFTISRDNSKN
TLYLQMNSLRAEDTAVYYCARA<u>LRDGNNWDYFNGMDV</u>WGQGTTVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 639)
EVQLLESGGGLVQPGGSLRLSCAASGFTFS<u>SYYMS</u>WVRQAPGKGLEWVS<u>TISGSGDSTYYADSVKG</u>RFTISRDNSKN
TLYLQMNSLRAEDTAVYYCAK<u>SGPGLRQVGFDY</u>WGQGTLVTVSS/GKPGSGKPGSGKPGSGKPGS/DIQMTQSPSSL
SASVGDRVTITC<u>RASQSISSYLN</u>WYQQKPGKAPKLLIY<u>AASSLQS</u>GVPSRFSGSGSGTDFTLTISSLQPEDFATYYC
<u>QQVYSTPFT</u>FGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_E07[PSMA]_L0 Light Chain (SEQ ID NO: 640)
QSVLTQPPSASGTPGQGVTISC<u>SGSSSNIGSNTVN</u>WFQQLPGTAPKLLIY<u>SDNQRPS</u>GVPDRFSGSKSGTSASLAIS
GLQSEDEADYYC<u>AAWDDSLNGYV</u>FGTGTKVTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29P

>XENP39222 P72_E07[PSMA]_H0L0_Fab-1A7[CD28]_H1.14_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_E07[PSMA]_H0_IgG1_pI(-)_Isosteric_A_/PVA_/S267K/L368D/K370S (SEQ ID NO: 641)
EVQLVESGGGVVQPGRSLRLSCAASGFTFITYGMHWVRQAPGKGLEWVAVVSFDESNKYYADSVKGRFTISRDNSKN
TLYLQMNSLRAEDTAVYYCARALRDGNNWDYFNGMDVWGQGTTVTVSS/ASTKGPSVFPLAPSSKSTSGGTAALGCL
VKDYFPEPVTVSWNSGALTSGVHTFPAVLQSSGLYSLSSVVTVPSSSLGTQTYICNVNHKPSDTKVDKKVEPKSCDK
THTCPPCPAPPVAGPSVFLFPPKPKDTLMISRTPEVTCVVVDVKHEDPEVKFNWYVDGVEVHNAKTKPREEEYNSTY
RVVSVLTVLHQDWLNGKEYKCKVSNKALPAPIEKTISKAKGQPREPQVYTLPPSREEMTKNQVSLTCDVSGFYPSDI
AVEWESDGQPENNYKTTPPVLDSDGSFFLYSKLTVDKSRWEQGDVFSCSVMHEALHNHYTQKSLSLSPGK
Chain 2 - 1A7[CD28]_H1.14_L1.71_scFv(GKPGS)4_Fc(216)_IgG1_C220S/PVA_/S267K/S364K/E357Q (SEQ ID NO: 642)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_E07[PSMA]_L0 Light Chain (SEQ ID NO: 643)
QSVLTQPPSASGTPGQGVTISCSGSSSNIGSNTVNWFQQLPGTAPKLLIYSDNQRPSGVPDRFSGSKSGTSASLAIS
GLQSEDEADYYCAAWDDSLNGYVFGTGTKVTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39223 P70_F02[PSMA]_H0L0_Fab-1A7[CD28]_H1L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P70_F02[PSMA]_H0_IgG1_pI(-)_Isosteric_A_/PVA_/S267K/L368D/K370S (SEQ ID NO: 644)
EVQLLESGPGLVKPSETLSLTCTVSGGSIISYYWSWIRQPAGKGLEWIGRIYSSGSTNYNPSLKSRVTMSVDTSKNQ
FSLKLSSVTAADTAVYYCAKVGVWPGAFDIWGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK
Chain 2 - 1A7[CD28]_H1L1_scFv(GKPGS)4_Fc(216)_IgG1_C220S/PVA_/S267K/S364K/E357Q (SEQ ID NO: 645)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P70_F02[PSMA]_L0 Light Chain (SEQ ID NO: 646)
QSVLTQPPSASGTPGQRVTISCSGSSSNIGSNTVNWYQQLPGTAPKLLIYSSNQRPSGVPDRFSGSKSGTSASLAIS
GLQSEDEADYYCAAWDDSLNGVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29Q

>XENP39224 P70_F02[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P70_F02[PSMA]_H0_IgG1_pI(-)_Isosteric_A_/PVA_/S267K/L368D/K370S (SEQ ID NO: 647)
EVQLLESGPGLVKPSETLSLTCTVSGGSIISYYWSWIRQPAGKGLEWIGRIYSSGSTNYNPSLKSRVTMSVDTSKNQ
FSLKLSSVTAADTAVYYCAKVGVWPGAFDIWGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 648)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P70_F02[PSMA]_L0 Light Chain (SEQ ID NO: 649)
QSVLTQPPSASGTPGQRVTISCSGSSSNIGSNTVNWYQQLPGTAPKLLIYSSNQRPSGVPDRFSGSKSGTSASLAIS
GLQSEDEADYYCAAWDDSLNGVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39225 P70_F02[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P70_F02[PSMA]_H0_IgG1_pI(-)_Isosteric_A_/PVA_/S267K/L368D/K370S (SEQ ID NO: 650)
EVQLLESGPGLVKPSETLSLTCTVSGGSIISYYWSWIRQPAGKGLEWIGRIYSSGSTNYNPSLKSRVTMSVDTSKNQ
FSLKLSSVTAADTAVYYCAKVGVWPGAFDIWGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 651)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P70_F02[PSMA]_L0 Light Chain (SEQ ID NO: 652)
QSVLTQPPSASGTPGQRVTISCSGSSSNIGSNTVNWYQQLPGTAPKLLIYSSNQRPSGVPDRFSGSKSGTSASLAIS
GLQSEDEADYYCAAWDDSLNGVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29R

>XENP39226_P70_F02[PSMA]_H0L0_Fab-1A7[CD28]_H1.14_L1.71_scFv(GKPGS)4-IgG1_pI(-
)_Isosteric_A_/PVA_/S267K/L368D/K370S-Fc(216)_IgG1_C220S/PVA_/S267K/S364K/E357Q Chain 1 - P70_F02[PSMA]_H0_IgG1_pI(-)_Isosteric_A_/PVA_/S267K/L368D/K370S (SEQ ID NO: 653)
EVQLLESGPGLVKPSETLSLTCTVSGGSIISYYWSWIRQPAGKGLEWIGRIYSSGSTNYNPSLKSRVTMSVDTSKNQ
FSLKLSSVTAADTAVYYCAKVGVWPGAFDIWGQGTMVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSDTKVDKKVEPKSCDKTHTCPPC
PAPPVAGPSVFLFPPKPKDTLMISRTPEVTCVVVDVKHEDPEVKFNWYVDGVEVHNAKTKPREEEYNSTYRVVSVLT
VLHQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK Chain 2 - 1A7[CD28]_H1.14_L1.71_scFv(GKPGS)4_Fc(216)_IgG1_C220S/PVA_/S267K/S364K/E357Q (SEQ ID NO: 654)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P70_F02[PSMA]_L0 Light Chain (SEQ ID NO: 655)
QSVLTQPPSASGTPGQRVTISCSGSSSNIGSNTVNWYQQLPGTAPKLLIYSSNQRPSGVPDRFSGSKSGTSASLAIS
GLQSEDEADYYCAAWDDSLNGVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39227_P72_A11[PSMA]_H0L0_Fab-1A7[CD28]_H1L1_scFv(GKPGS)4-IgG1_pI(-
)_Isosteric_A_/PVA_/S267K/L368D/K370S-Fc(216)_IgG1_C220S/PVA_/S267K/S364K/E357Q Chain 1 - P72_A11[PSMA]_H0_IgG1_pI(-)_Isosteric_A_/PVA_/S267K/L368D/K370S (SEQ ID NO: 656)
QVQLQESGGDVVQPGRSLRLSCAASGFSFSGYGLHWVRQAPGRGLEWVTLISYDGSNKYYADSVKGRFTISRDNSKN
TLYLQMNSLRAEDTAVYYCAKTTVSDPYYGMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK Chain 2 - 1A7[CD28]_H1L1_scFv(GKPGS)4_Fc(216)_IgG1_C220S/PVA_/S267K/S364K/E357Q (SEQ ID NO: 657)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P72_A11[PSMA]_L0 Light Chain (SEQ ID NO: 658)
SYELTQPPSVSVAPGQTARITCGGNNIGSKSVHWYQQKPGQAPVLVVYDDSDRPSGIPERFSGTNSGNTATLTISRA
EAGDEADYYCQVWDSSSDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS

Figure 29S

>XENP39228 P72_A11[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_A11[PSMA]_H0_IgG1_pI(-)_Isosteric_A_/PVA_/S267K/L368D/K370S (SEQ ID NO: 659)
QVQLQESGGDVVQPGRSLRLSCAASGFSFSGYGLHWVRQAPGRGLEWVTLISYDGSNKYYADSVKGRFTISRDNSKN
TLYLQMNSLRAEDTAVYYCAKTTVSDPYYYGMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 660)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A11[PSMA]_L0 Light Chain (SEQ ID NO: 661)
SYELTQPPSVSVAPGQTARITCGGNNIGSKSVHWYQQKPGQAPVLVVYDDSDRPSGIPERFSGTNSGNTATLTISRA
EAGDEADYYCQVWDSSSDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS >XENP39229 P72_A11[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_A11[PSMA]_H0_IgG1_pI(-)_Isosteric_A_/PVA_/S267K/L368D/K370S (SEQ ID NO: 662)
QVQLQESGGDVVQPGRSLRLSCAASGFSFSGYGLHWVRQAPGRGLEWVTLISYDGSNKYYADSVKGRFTISRDNSKN
TLYLQMNSLRAEDTAVYYCAKTTVSDPYYYGMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 663)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A11[PSMA]_L0 Light Chain (SEQ ID NO: 664)
SYELTQPPSVSVAPGQTARITCGGNNIGSKSVHWYQQKPGQAPVLVVYDDSDRPSGIPERFSGTNSGNTATLTISRA
EAGDEADYYCQVWDSSSDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS

Figure 29T

**>XENP39230 P72_A11[PSMA]_H0L0_Fab-1A7[CD28]_H1.14_L1.71_scFv(GKPGS)4-IgG1_pI(-
)_Isosteric_A_/PVA_/S267K/L368D/K370S-Fc(216)_IgG1_C220S/PVA_/S267K/S364K/E357Q**
Chain 1 - P72_A11[PSMA]_H0_IgG1_pI(-)_Isosteric_A_/PVA_/S267K/L368D/K370S (SEQ ID NO: 665)
QVQLQESGGDVVQPGRSLRLSCAASGFSFSGYGLHWVRQAPGRGLEWVTLISYDGSNKYYADSVKGRFTISRDNSKN
TLYLQMNSLRAEDTAVYYCAKTTVSDPYYYGMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1.14_L1.71_scFv(GKPGS)4_Fc(216)_IgG1_C220S/PVA_/S267K/S364K/E357Q (SEQ ID NO: 666)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A11[PSMA]_L0 Light Chain (SEQ ID NO: 667)
SYELTQPPSVSVAPGQTARITCGGNNIGSKSVHWYQQKPGQAPVLVVYDDSDRPSGIPERFSGTNSGNTATLTISRA
EAGDEADYYCQVWDSSSDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS

**>XENP39231 a.k.a. C28PB267 P72_A10V2[PSMA]_H0L0_Fab-1A7[CD28]_H1L1_scFv(GKPGS)4-IgG1_pI(-
)_Isosteric_A_/PVA_/S267K/L368D/K370S-Fc(216)_IgG1_C220S/PVA_/S267K/S364K/E357Q**
Chain 1 - P72_A10V2[PSMA]_H0_IgG1_pI(-)_Isosteric_A_/PVA_/S267K/L368D/K370S (SEQ ID NO: 668)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1L1_scFv(GKPGS)4_Fc(216)_IgG1_C220S/PVA_/S267K/S364K/E357Q (SEQ ID NO: 669)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A10V2[PSMA]_L0 Light Chain (SEQ ID NO: 670)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

Figure 29U

>XENP39232 a.k.a. C28PB231 P72_A10V2[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_A10V2[PSMA]_H0_IgG1_pI(-)_Isosteric_A_/PVA_/S267K/L368D/K370S (SEQ ID NO: 671)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 672)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A10V2[PSMA]_L0 Light Chain (SEQ ID NO: 673)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS >XENP39233 a.k.a. C28PB243 P72_A10V2[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_A10V2[PSMA]_H0_IgG1_pI(-)_Isosteric_A_/PVA_/S267K/L368D/K370S (SEQ ID NO: 674)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 675)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A10V2[PSMA]_L0 Light Chain (SEQ ID NO: 676)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

Figure 29V

>XENP39234 a.k.a. C28PB219 P72_A10V2[PSMA]_H0L0_Fab-1A7[CD28]_H1.14_L1.71_scFv(GKPGS)4-IgG1_pI(-)_Isosteric_A_/PVA_/S267K/L368D/K370S-Fc(216)_IgG1_C220S/PVA_/S267K/S364K/E357Q Chain 1 - P72_A10V2[PSMA]_H0_IgG1_pI(-)_Isosteric_A_/PVA_/S267K/L368D/K370S (SEQ ID NO: 677)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK Chain 2 - 1A7[CD28]_H1.14_L1.71_scFv(GKPGS)4_Fc(216)_IgG1_C220S/PVA_/S267K/S364K/E357Q (SEQ ID NO: 678)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P72_A10V2[PSMA]_L0 Light Chain (SEQ ID NO: 679)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS >XENP39235 a.k.a. C28PB268 P72_D01V2[PSMA]_H0L0_Fab-1A7[CD28]_H1L1_scFv(GKPGS)4-IgG1_pI(-)_Isosteric_A_/PVA_/S267K/L368D/K370S-Fc(216)_IgG1_C220S/PVA_/S267K/S364K/E357Q Chain 1 - P72_D01V2[PSMA]_H0_IgG1_pI(-)_Isosteric_A_/PVA_/S267K/L368D/K370S (SEQ ID NO: 680)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCAREGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK Chain 2 - 1A7[CD28]_H1L1_scFv(GKPGS)4_Fc(216)_IgG1_C220S/PVA_/S267K/S364K/E357Q (SEQ ID NO: 681)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P72_D01V2[PSMA]_L0 Light Chain (SEQ ID NO: 682)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29W

>XENP39236 a.k.a. C28PB232 P72_D01V2[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_D01V2[PSMA]_H0_IgG1_pI(-)_Isosteric_A_/PVA_/S267K/L368D/K370S (SEQ ID NO: 683)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCAREGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 684)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_D01V2[PSMA]_L0 Light Chain (SEQ ID NO: 685)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39237 a.k.a. C28PB244 P72_D01V2[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_D01V2[PSMA]_H0_IgG1_pI(-)_Isosteric_A_/PVA_/S267K/L368D/K370S (SEQ ID NO: 686)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCAREGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 687)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_D01V2[PSMA]_L0 Light Chain (SEQ ID NO: 688)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29X

>XENP39238 a.k.a. C28PB220 P72_D01V2[PSMA]_H0L0_Fab-1A7[CD28]_H1.14_L1.71_scFv(GKPGS)4-IgG1_pI(-)_Isosteric_A_/PVA_/S267K/L368D/K370S-Fc(216)_IgG1_C220S/PVA_/S267K/S364K/E357Q Chain 1 - P72_D01V2[PSMA]_H0_IgG1_pI(-)_Isosteric_A_/PVA_/S267K/L368D/K370S (SEQ ID NO: 689)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCAREGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK Chain 2 - 1A7[CD28]_H1.14_L1.71_scFv(GKPGS)4_Fc(216)_IgG1_C220S/PVA_/S267K/S364K/E357Q (SEQ ID NO: 690)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P72_D01V2[PSMA]_L0 Light Chain (SEQ ID NO: 691)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39239 P72_F07[PSMA]_H0L0_Fab-1A7[CD28]_H1L1_scFv(GKPGS)4-IgG1_pI(-)_Isosteric_A_/PVA_/S267K/L368D/K370S-Fc(216)_IgG1_C220S/PVA_/S267K/S364K/E357Q Chain 1 - P72_F07[PSMA]_H0_IgG1_pI(-)_Isosteric_A_/PVA_/S267K/L368D/K370S (SEQ ID NO: 692)
EVQLVESGGGVVQPGRSLRLSCAASGFTFSSYGMNWVRQAPGKGLEWVAVTSYDGSNKYYADSVKGRFTISRDISKN
TLYLQMSSLRAEDTAVYYCARDPYSSSWNGAFDIWGPGTMVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK Chain 2 - 1A7[CD28]_H1L1_scFv(GKPGS)4_Fc(216)_IgG1_C220S/PVA_/S267K/S364K/E357Q (SEQ ID NO: 693)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P72_F07[PSMA]_L0 Light Chain (SEQ ID NO: 694)
SYELTQPPSVSVAPGQTARITCGGNNIGSKSVHWYQQKPGQAPVLVVYDDSDRPSGIPERFSGSNSGNTATLTISRV
EAGDEADYYCQVWDSSTDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS

Figure 29Y

>XENP39240 P72_F07[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_F07[PSMA]_H0_IgG1_pI(-)_Isosteric_A_/PVA_/S267K/L368D/K370S (SEQ ID NO: 695)
EVQLVESGGGVVQPGRSLRLSCAASGFTFSSYGMNWVRQAPGKGLEWVAVTSYDGSNKYYADSVKGRFTISRDISKN
TLYLQMSSLRAEDTAVYYCARDPYSSSWNGAFDIWGPGTMVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 696)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_F07[PSMA]_L0 Light Chain (SEQ ID NO: 697)
SYELTQPPSVSVAPGQTARITCGGNNIGSKSVHWYQQKPGQAPVLVVYDDSDRPSGIPERFSGSNSGNTATLTISRV
EAGDEADYYCQVWDSSTDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS >XENP39241 P72_F07[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_F07[PSMA]_H0_IgG1_pI(-)_Isosteric_A_/PVA_/S267K/L368D/K370S (SEQ ID NO: 698)
EVQLVESGGGVVQPGRSLRLSCAASGFTFSSYGMNWVRQAPGKGLEWVAVTSYDGSNKYYADSVKGRFTISRDISKN
TLYLQMSSLRAEDTAVYYCARDPYSSSWNGAFDIWGPGTMVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 699)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_F07[PSMA]_L0 Light Chain (SEQ ID NO: 700)
SYELTQPPSVSVAPGQTARITCGGNNIGSKSVHWYQQKPGQAPVLVVYDDSDRPSGIPERFSGSNSGNTATLTISRV
EAGDEADYYCQVWDSSTDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS

Figure 29Z

>XENP39242 P72_F07[PSMA]_H0L0_Fab-1A7[CD28]_H1.14_L1.71_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P72_F07[PSMA]_H0_IgG1_pI(-)_Isosteric_A_/PVA_/S267K/L368D/K370S (SEQ ID NO: 701)
EVQLVESGGGVVQPGRSLRLSCAASGFTFSSYGMNWVRQAPGKGLEWVAVTSYDGSNKYYADSVKGRFTISRDISKN
TLYLQMSSLRAEDTAVYYCARDPYSSSWNGAFDIWGPGTMVTSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1.14_L1.71_scFv(GKPGS)4_Fc(216)_IgG1_C220S/PVA_/S267K/S364K/E357Q (SEQ ID NO: 702)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_F07[PSMA]_L0 Light Chain (SEQ ID NO: 703)
SYELTQPPSVSVAPGQTARITCGGNNIGSKSVHWYQQKPGQAPVLVVYDDSDRPSGIPERFSGSNSGNTATLTISRV
EAGDEADYYCQVWDSSTDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS

>XENP39243 P72_G02[PSMA]_H0L0_Fab-1A7[CD28]_H1L1_scFv(GKPGS)4-IgG1_pI(-)_Isosteric_A_/PVA_/S267K/L368D/K370S-Fc(216)_IgG1_C220S/PVA_/S267K/S364K/E357Q
Chain 1 - P72_G02[PSMA]_H0_IgG1_pI(-)_Isosteric_A_/PVA_/S267K/L368D/K370S (SEQ ID NO: 704)
EVQLVESGGGVVQPGRSLRLSCAASGFSFSGYGMHWVRQAPGKGLEWVAVISYDGSNKYYADSVKGRFTISRDNSKN
TLYLQMNSLRVEDTAVYYCARDRIWGSRGYYYGMDVWGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK
Chain 2 - 1A7[CD28]_H1L1_scFv(GKPGS)4_Fc(216)_IgG1_C220S/PVA_/S267K/S364K/E357Q (SEQ ID NO: 705)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_G02[PSMA]_L0 Light Chain (SEQ ID NO: 706)
QSALTQPASVSGSPGQSITISCTGASSDVGGYNYVSWYQQHPGKAPKLMIYEVSNRPSGVSNRFSGSKSGNTASLTI
SGLQAEDEADYYCSSYTITSTLVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29AA

>XENP39244 P72_G02[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_G02[PSMA]_H0_IgG1_pI(-)_Isosteric_A_/PVA_/S267K/L368D/K370S (SEQ ID NO: 707)
EVQLVESGGGVVQPGRSLRLSCAASGFSFS<u>GYGMH</u>WVRQAPGKGLEWVA<u>VISYDGSNKYYADSVKG</u>RFTISRDNSKN
TLYLQMNSLRVEDTAVYYCAR<u>DRIWGSRGYYYGMDV</u>WGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 708)
EVQLLESGGGLVQPGGSLRLSCAASGFTFS<u>SYYMS</u>WVRQAPGKGLEWVS<u>TISESGDSTYYADSVKG</u>RFTISRDNSKN
TLYLQMNSLRAEDTAVYYCAK<u>SGPGLRQVGFDY</u>WGQGTLVTVSS/GKPGSGKPGSGKPGSGKPGS/DIQMTQSPSSL
SASVGDRVTITC<u>RASQSISSYLN</u>WYQQKPGKAPKLLIY<u>AASSLQS</u>GVPSRFSGSGSGTDFTLTISSLQPEDFATYYC
<u>QQSYSTPFT</u>FGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_G02[PSMA]_L0 Light Chain (SEQ ID NO: 709)
QSALTQPASVSGSPGQSITISC<u>TGASSDVGGYNYVS</u>WYQQHPGKAPKLMIY<u>EVSNRPS</u>GVSNRFSGSKSGNTASLTI
SGLQAEDEADYYC<u>SSYTITSTLV</u>FGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39245 P72_G02[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_G02[PSMA]_H0_IgG1_pI(-)_Isosteric_A_/PVA_/S267K/L368D/K370S (SEQ ID NO: 710)
EVQLVESGGGVVQPGRSLRLSCAASGFSFS<u>GYGMH</u>WVRQAPGKGLEWVA<u>VISYDGSNKYYADSVKG</u>RFTISRDNSKN
TLYLQMNSLRVEDTAVYYCAR<u>DRIWGSRGYYYGMDV</u>WGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 711)
EVQLLESGGGLVQPGGSLRLSCAASGFTFS<u>SYYMS</u>WVRQAPGKGLEWVS<u>TISGSGDSTYYADSVKG</u>RFTISRDNSKN
TLYLQMNSLRAEDTAVYYCAK<u>SGPGLRQVGFDY</u>WGQGTLVTVSS/<u>GKPGSGKPGSGKPGSGKPGS</u>/DIQMTQSPSSL
SASVGDRVTITC<u>RASQSISSYLN</u>WYQQKPGKAPKLLIY<u>AASSLQS</u>GVPSRFSGSGSGTDFTLTISSLQPEDFATYYC
<u>QQVYSTPFT</u>FGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_G02[PSMA]_L0 Light Chain (SEQ ID NO: 712)
QSALTQPASVSGSPGQSITISC<u>TGASSDVGGYNYVS</u>WYQQHPGKAPKLMIY<u>EVSNRPS</u>GVSNRFSGSKSGNTASLTI
SGLQAEDEADYYC<u>SSYTITSTLV</u>FGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29BB

>XENP39246_P72_G02[PSMA]_H0L0_Fab-1A7[CD28]_H1.14_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_G02[PSMA]_H0_IgG1_pI(-)_Isosteric_A_/PVA_/S267K/L368D/K370S (SEQ ID NO: 713)
EVQLVESGGGVVQPGRSLRLSCAASGFSFSGYGMHWVRQAPGKGLEWVAVISYDGSNKYYADSVKGRFTISRDNSKN
TLYLQMNSLRVEDTAVYYCARDRIWGSRGYYYGMDVWGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK
Chain 2 - 1A7[CD28]_H1.14_L1.71_scFv(GKPGS)4_Fc(216)_IgG1_C220S/PVA_/S267K/S364K/E357Q (SEQ ID NO: 714)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_G02[PSMA]_L0 Light Chain (SEQ ID NO: 715)
QSALTQPASVSGSPGQSITISCTGASSDVGGYNYVSWYQQHPGKAPKLMIYEVSNRPSGVSNRFSGSKSGNTASLTI
SGLQAEDEADYYCSSYTITSTLVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39247_P75_F01[PSMA]_H0L0_Fab-1A7[CD28]_H1L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P75_F01[PSMA]_H0_IgG1_pI(-)_Isosteric_A_/PVA_/S267K/L368D/K370S (SEQ ID NO: 716)
QVQLQESGGGVVQPGRSLRLSCAASGFTFSTYGMHWVRQAPGKGLEWVAFISYDGSNKYYADSVKGRFTISRDNSKH
TLYLQMNSLRAEDTAVYYCAGRDNLRFLEWFMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1L1_scFv(GKPGS)4_Fc(216)_IgG1_C220S/PVA_/S267K/S364K/E357Q (SEQ ID NO: 717)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P75_F01[PSMA]_L0 Light Chain (SEQ ID NO: 718)
EIVLTQSPGTLSVSPGERATLSCRASQSVRSNLAWYQQKPGQAPRLLIYGASTRATGIPARFSGSGSGTEFTLTISS
LQSEDFAVYYCHQYNDWPPYTFGQGTKLEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

Figure 29CC

>XENP39248 P75_F01[PSMA]_H0L0_Fab-1A7[CD28]_H1.14_L1_scFv(GKPGS)4-IgG1_pI(-)_Isosteric_A_/PVA_/S267K/L368D/K370S-Fc(216)_IgG1_C220S/PVA_/S267K/S364K/E357Q Chain 1 - P75_F01[PSMA]_H0_IgG1_pI(-)_Isosteric_A_/PVA_/S267K/L368D/K370S (SEQ ID NO: 719)
QVQLQESGGGVVQPGRSLRLSCAASGFTFSTYGMHWVRQAPGKGLEWVAFISYDGSNKYYADSVKGRFTISRDNSKH
TLYLQMNSLRAEDTAVYYCAGRDNLRFLEWFMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK Chain 2 - 1A7[CD28]_H1.14_L1_scFv(GKPGS)4_Fc(216)_IgG1_C220S/PVA_/S267K/S364K/E357Q (SEQ ID NO: 720)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P75_F01[PSMA]_L0 Light Chain (SEQ ID NO: 721)
EIVLTQSPGTLSVSPGERATLSCRASQSVRSNLAWYQQKPGQAPRLLIYGASTRATGIPARFSGSGSGTEFTLTISS
LQSEDFAVYYCHQYNDWPPYTFGQGTKLEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC >XENP39249 P75_F01[PSMA]_H0L0_Fab-1A7[CD28]_H1.1_L1.71_scFv(GKPGS)4-IgG1_pI(-)_Isosteric_A_/PVA_/S267K/L368D/K370S-Fc(216)_IgG1_C220S/PVA_/S267K/S364K/E357Q Chain 1 - P75_F01[PSMA]_H0_IgG1_pI(-)_Isosteric_A_/PVA_/S267K/L368D/K370S (SEQ ID NO: 722)
QVQLQESGGGVVQPGRSLRLSCAASGFTFSTYGMHWVRQAPGKGLEWVAFISYDGSNKYYADSVKGRFTISRDNSKH
TLYLQMNSLRAEDTAVYYCAGRDNLRFLEWFMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK Chain 2 - 1A7[CD28]_H1.1_L1.71_scFv(GKPGS)4_Fc(216)_IgG1_C220S/PVA_/S267K/S364K/E357Q (SEQ ID NO: 723)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P75_F01[PSMA]_L0 Light Chain (SEQ ID NO: 724)
EIVLTQSPGTLSVSPGERATLSCRASQSVRSNLAWYQQKPGQAPRLLIYGASTRATGIPARFSGSGSGTEFTLTISS
LQSEDFAVYYCHQYNDWPPYTFGQGTKLEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

Figure 29DD

>XENP39250 P75_F01[PSMA]_H0L0_Fab-1A7[CD28]_H1.14_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P75_F01[PSMA]_H0_IgG1_pI(-)_Isosteric_A_/PVA_/S267K/L368D/K370S (SEQ ID NO: 725)
QVQLQESGGGVVQPGRSLRLSCAASGFTFSTYGMHWVRQAPGKGLEWVAFISYDGSNKYYADSVKGRFTISRDNSKH
TLYLQMNSLRAEDTAVYYCAGRDNLRFLEWFMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1.14_L1.71_scFv(GKPGS)4_Fc(216)_IgG1_C220S/PVA_/S267K/S364K/E357Q (SEQ ID NO: 726)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P75_F01[PSMA]_L0 Light Chain (SEQ ID NO: 727)
EIVLTQSPGTLSVSPGERATLSCRASQSVRSNLAWYQQKPGQAPRLLIYGASTRATGIPARFSGSGSGTEFTLTISS
LQSEDFAVYYCHQYNDWPPYTFGQGTKLEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC >XENP39251 P72_F07V2[PSMA]_H0L0_Fab-1A7[CD28]_H1L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_F07V2[PSMA]_H0_IgG1_pI(-)_Isosteric_A_/PVA_/S267K/L368D/K370S (SEQ ID NO: 728)
EVQLVESGGGVVQPGRSLRLSCAASGFTFSSYGMNWVRQAPGKGLEWVAVTSYDESNKYYADSVKGRFTISRDISKN
TLYLQMSSLRAEDTAVYYCARDPYSSSWNGAFDIWGPGTMVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1L1_scFv(GKPGS)4_Fc(216)_IgG1_C220S/PVA_/S267K/S364K/E357Q (SEQ ID NO: 729)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_F07V2[PSMA]_L0 Light Chain (SEQ ID NO: 730)
SYELTQPPSVSVAPGQTARITCGGNNIGSKSVHWYQQKPGQAPVLVVYDDSDRPSGIPERFSGSNSGNTATLTISRV
EAGDEADYYCQVWDSSTDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS

Figure 29EE

>XENP39252 P72_F07V2[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_F07V2[PSMA]_H0_IgG1_pI(-)_Isosteric_A_/PVA_/S267K/L368D/K370S (SEQ ID NO: 731)
EVQLVESGGGVVQPGRSLRLSCAASGFTFSSYGMNWVRQAPGKGLEWVAVTSYDESNKYYADSVKGRFTISRDISKN
TLYLQMSSLRAEDTAVYYCARDPYSSSWNGAFDIWGPGTMVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 732)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_F07V2[PSMA]_L0 Light Chain (SEQ ID NO: 733)
SYELTQPPSVSVAPGQTARITCGGNNIGSKSVHWYQQKPGQAPVLVVYDDSDRPSGIPERFSGSNSGNTATLTISRV
EAGDEADYYCQVWDSSTDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS >XENP39253 P72_F07V2[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_F07V2[PSMA]_H0_IgG1_pI(-)_Isosteric_A_/PVA_/S267K/L368D/K370S (SEQ ID NO: 734)
EVQLVESGGGVVQPGRSLRLSCAASGFTFSSYGMNWVRQAPGKGLEWVAVTSYDESNKYYADSVKGRFTISRDISKN
TLYLQMSSLRAEDTAVYYCARDPYSSSWNGAFDIWGPGTMVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 735)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_F07V2[PSMA]_L0 Light Chain (SEQ ID NO: 736)
SYELTQPPSVSVAPGQTARITCGGNNIGSKSVHWYQQKPGQAPVLVVYDDSDRPSGIPERFSGSNSGNTATLTISRV
EAGDEADYYCQVWDSSTDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS

Figure 29FF

>XENP39254_P72_F07V2[PSMA]_H0L0_Fab-1A7[CD28]_H1.14_L1.71_scFv(GKPGS)4-IgG1_pI(-)_Isosteric_A_/PVA_/S267K/L368D/K370S-Fc(216)_IgG1_C220S/PVA_/S267K/S364K/E357Q Chain 1 - P72_F07V2[PSMA]_H0_IgG1_pI(-)_Isosteric_A_/PVA_/S267K/L368D/K370S (SEQ ID NO: 737)
EVQLVESGGGVVQPGRSLRLSCAASGFTFSSYGMNWVRQAPGKGLEWVAVTSYDESNKYYADSVKGRFTISRDISKN
TLYLQMSSLRAEDTAVYYCARDPYSSSWNGAFDIWGPGTMVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK Chain 2 - 1A7[CD28]_H1.14_L1.71_scFv(GKPGS)4_Fc(216)_IgG1_C220S/PVA_/S267K/S364K/E357Q (SEQ ID NO: 738)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P72_F07V2[PSMA]_L0 Light Chain (SEQ ID NO: 739)
SYELTQPPSVSVAPGQTARITCGGNNIGSKSVHWYQQKPGQAPVLVVYDDSDRPSGIPERFSGSNSGNTATLTISRV
EAGDEADYYCQVWDSSTDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS >XENP39255_P72_G02V2[PSMA]_H0L0_Fab-1A7[CD28]_H1L1_scFv(GKPGS)4-IgG1_pI(-)_Isosteric_A_/PVA_/S267K/L368D/K370S-Fc(216)_IgG1_C220S/PVA_/S267K/S364K/E357Q Chain 1 - P72_G02V2[PSMA]_H0_IgG1_pI(-)_Isosteric_A_/PVA_/S267K/L368D/K370S (SEQ ID NO: 740)
EVQLVESGGGVVQPGRSLRLSCAASGFSFSGYGMHWVRQAPGKGLEWVAVISYDESNKYYADSVKGRFTISRDNSKN
TLYLQMNSLRVEDTAVYYCARDRIWGSRGYYYGMDVWGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK Chain 2 - 1A7[CD28]_H1L1_scFv(GKPGS)4_Fc(216)_IgG1_C220S/PVA_/S267K/S364K/E357Q (SEQ ID NO: 741)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P72_G02V2[PSMA]_L0 Light Chain (SEQ ID NO: 742)
QSALTQPASVSGSPGQSITISCTGASSDVGGYNYVSWYQQHPGKAPKLMIYEVSNRPSGVSNRFSGSKSGNTASLTI
SGLQAEDEADYYCSSYTITSTLVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29GG

>XENP39256_P72_G02V2[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_G02V2[PSMA]_H0_IgG1_pI(-)_Isosteric_A_/PVA_/S267K/L368D/K370S (SEQ ID NO: 743)
EVQLVESGGGVVQPGRSLRLSCAASGFSFSGYGMHWVRQAPGKGLEWVAVISYDESNKYYADSVKGRFTISRDNSKN
TLYLQMNSLRVEDTAVYYCARDRIWGSRGYYYGMDVWGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 744)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_G02V2[PSMA]_L0 Light Chain (SEQ ID NO: 745)
QSALTQPASVSGSPGQSITISCTGASSDVGGYNYVSWYQQHPGKAPKLMIYEVSNRPSGVSNRFSGSKSGNTASLTI
SGLQAEDEADYYCSSYTITSTLVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39257_P72_G02V2[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_G02V2[PSMA]_H0_IgG1_pI(-)_Isosteric_A_/PVA_/S267K/L368D/K370S (SEQ ID NO: 746)
EVQLVESGGGVVQPGRSLRLSCAASGFSFSGYGMHWVRQAPGKGLEWVAVISYDESNKYYADSVKGRFTISRDNSKN
TLYLQMNSLRVEDTAVYYCARDRIWGSRGYYYGMDVWGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 747)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_G02V2[PSMA]_L0 Light Chain (SEQ ID NO: 748)
QSALTQPASVSGSPGQSITISCTGASSDVGGYNYVSWYQQHPGKAPKLMIYEVSNRPSGVSNRFSGSKSGNTASLTI
SGLQAEDEADYYCSSYTITSTLVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29HH

>XENP39258 P72_G02V2[PSMA]_H0L0_Fab-1A7[CD28]_H1.14_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_G02V2[PSMA]_H0_IgG1_pI(-)_Isosteric_A_/PVA_/S267K/L368D/K370S (SEQ ID NO: 749)
EVQLVESGGGVVQPGRSLRLSCAASGFSFSGYGMHWVRQAPGKGLEWVAVISYDESNKYYADSVKGRFTISRDNSKN
TLYLQMNSLRVEDTAVYYCARDRIWGSRGYYYGMDVWGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK
Chain 2 - 1A7[CD28]_H1.14_L1.71_scFv(GKPGS)4_Fc(216)_IgG1_C220S/PVA_/S267K/S364K/E357Q (SEQ ID NO: 750)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_G02V2[PSMA]_L0 Light Chain (SEQ ID NO: 751)
QSALTQPASVSGSPGQSITISCTGASSDVGGYNYVSWYQQHPGKAPKLMIYEVSNRPSGVSNRFSGSKSGNTASLTI
SGLQAEDEADYYCSSYTITSTLVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39259 P75_F01V2[PSMA]_H0L0_Fab-1A7[CD28]_H1L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P75_F01V2[PSMA]_H0_IgG1_pI(-)_Isosteric_A_/PVA_/S267K/L368D/K370S (SEQ ID NO: 752)
QVQLQESGGGVVQPGRSLRLSCAASGFTFSTYGMHWVRQAPGKGLEWVAFISYDESNKYYADSVKGRFTISRDNSKH
TLYLQMNSLRAEDTAVYYCAGRDNLRFLEWFMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_H1L1_scFv(GKPGS)4_Fc(216)_IgG1_C220S/PVA_/S267K/S364K/E357Q (SEQ ID NO: 753)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P75_F01V2[PSMA]_L0 Light Chain (SEQ ID NO: 754)
EIVLTQSPGTLSVSPGERATLSCRASQSVRSNLAWYQQKPGQAPRLLIYGASTRATGIPARFSGSGSGTEFTLTISS
LQSEDFAVYYCHQYNDWPPYTFGQGTKLEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

Figure 29II

>XENP39260 P75_F01V2[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - P75_F01V2[PSMA]_H0_IgG1_pI(-)_Isosteric_A_/PVA_/S267K/L368D/K370S (SEQ ID NO: 755)
QVQLQESGGGVVQPGRSLRLSCAASGFTFS<u>TYGMH</u>WVRQAPGKGLEWVA<u>FISYDESNKYYADSVKG</u>RFTISRDNSKH
TLYLQMNSLRAEDTAVYYCAG<u>RDNLRFLEWFMDV</u>WGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK

Chain 2 - 1A7[CD28]_H1.14_L1_scFv(GKPGS)4_Fc(216)_IgG1_C220S/PVA_/S267K/S364K/E357Q (SEQ ID NO: 756)
EVQLLESGGGLVQPGGSLRLSCAASGFTFS<u>SYYMS</u>WVRQAPGKGLEWVS<u>TISESGDSTYYADSVKG</u>RFTISRDNSKN
TLYLQMNSLRAEDTAVYYCAK<u>SGPGLRQVGFDY</u>WGQGTLVTVSS/GKPGSGKPGSGKPGSGKPGS/DIQMTQSPSSL
SASVGDRVTITC<u>RASQSISSYLN</u>WYQQKPGKAPKLLIY<u>AASSLQS</u>GVPSRFSGSGSGTDFTLTISSLQPEDFATYYC
<u>QQSYSTPFT</u>FGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK

Chain 3 - P75_F01V2[PSMA]_L0 Light Chain (SEQ ID NO: 757)
EIVLTQSPGTLSVSPGERATLSC<u>RASQSVRSNLA</u>WYQQKPGQAPRLLIY<u>GASTRAT</u>GIPARFSGSGSGTEFTLTISS
LQSEDFAVYYC<u>HQYNDWPPYT</u>FGQGTKLEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC >XENP39261 P75_F01V2[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - P75_F01V2[PSMA]_H0_IgG1_pI(-)_Isosteric_A_/PVA_/S267K/L368D/K370S (SEQ ID NO: 758)
QVQLQESGGGVVQPGRSLRLSCAASGFTFS<u>TYGMH</u>WVRQAPGKGLEWVA<u>FISYDESNKYYADSVKG</u>RFTISRDNSKH
TLYLQMNSLRAEDTAVYYCAG<u>RDNLRFLEWFMDV</u>WGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK

Chain 2 - 1A7[CD28]_H1.1_L1.71_scFv(GKPGS)4_Fc(216)_IgG1_C220S/PVA_/S267K/S364K/E357Q (SEQ ID NO: 759)
EVQLLESGGGLVQPGGSLRLSCAASGFTFS<u>SYYMS</u>WVRQAPGKGLEWVS<u>TISGSGDSTYYADSVKG</u>RFTISRDNSKN
TLYLQMNSLRAEDTAVYYCAK<u>SGPGLRQVGFDY</u>WGQGTLVTVSS/GKPGSGKPGSGKPGSGKPGS/DIQMTQSPSSL
SASVGDRVTITC<u>RASQSISSYLN</u>WYQQKPGKAPKLLIY<u>AASSLQS</u>GVPSRFSGSGSGTDFTLTISSLQPEDFATYYC
<u>QQVYSTPFT</u>FGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK

Chain 3 - P75_F01V2[PSMA]_L0 Light Chain (SEQ ID NO: 760)
EIVLTQSPGTLSVSPGERATLSC<u>RASQSVRSNLA</u>WYQQKPGQAPRLLIY<u>GASTRAT</u>GIPARFSGSGSGTEFTLTISS
LQSEDFAVYYC<u>HQYNDWPPYT</u>FGQGTKLEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

Figure 29JJ

>XENP39262 P75_F01V2[PSMA]_H0L0_Fab-1A7[CD28]_H1.14_L1.71_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - P75_F01V2[PSMA]_H0_IgG1_pI(-)_Isosteric_A_/PVA_/S267K/L368D/K370S (SEQ ID NO: 761)
QVQLQESGGGVVQPGRSLRLSCAASGFTFSTYGMHWVRQAPGKGLEWVAFISYDESNKYYADSVKGRFTISRDNSKH
TLYLQMNSLRAEDTAVYYCAGRDNLRFLEWFMDVWGQGTTVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK Chain 2 - 1A7[CD28]_H1.14_L1.71_scFv(GKPGS)4_Fc(216)_IgG1_C220S/PVA_/S267K/S364K/E357Q (SEQ ID NO: 762)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P75_F01V2[PSMA]_L0 Light Chain (SEQ ID NO: 763)
EIVLTQSPGTLSVSPGERATLSCRASQSVRSNLAWYQQKPGQAPRLLIYGASTRATGIPARFSGSGSGTEFTLTISS
LQSEDFAVYYCHQYNDWPPYTFGQGTKLEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

>XENP39263 PSMB896-HC-G100A[PSMA]_H0L0_Fab-1A7[CD28]_H1L1_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - PSMB896-HC-G100A[PSMA]_H0_IgG1_pI(-)_Isosteric_A_/PVA_/S267K/L368D/K370S (SEQ ID NO: 764)
EVQLVESGGGLVQPGGSLRLSCAASGFTFSSYAMSWVRQAPGKGLEWVSAISGGIGSTYYADSVKGRFTISRDNSKN
TLWLQMNSLRAEDTAVYYCAKDAVGATPYYFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK Chain 2 - 1A7[CD28]_H1L1_scFv(GKPGS)4_Fc(216)_IgG1_C220S/PVA_/S267K/S364K/E357Q (SEQ ID NO: 765)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - PSMB896-HC-G100A[PSMA]_L0 Light Chain (SEQ ID NO: 766)
QSVLTQPPSVSAAPGQKVTISCSGSSSNIGINYVSWYQQLPGTAPKLLIYDNNKRPSGIPDRFSGSKSGTSATLGIT
GLQTGDEADYYCGTWDSSLSAVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29KK

>XENP39264 PSMB896-HC-G100A[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - PSMB896-HC-G100A[PSMA]_H0_IgG1_pI(-)_Isosteric_A_/PVA_/S267K/L368D/K370S (SEQ ID NO: 767)
EVQLVESGGGLVQPGGSLRLSCAASGFTFSSYAMSWVRQAPGKGLEWVSAISGGIGSTYYADSVKGRFTISRDNSKN
TLWLQMNSLRAEDTAVYYCAKDAVGATPYYFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 768)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - PSMB896-HC-G100A[PSMA]_L0 Light Chain (SEQ ID NO: 769)
QSVLTQPPSVSAAPGQKVTISCSGSSSNIGINYVSWYQQLPGTAPKLLIYDNNKRPSGIPDRFSGSKSGTSATLGIT
GLQTGDEADYYCGTWDSSLSAVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39265 PSMB896-HC-G100A[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - PSMB896-HC-G100A[PSMA]_H0_IgG1_pI(-)_Isosteric_A_/PVA_/S267K/L368D/K370S (SEQ ID NO: 770)
EVQLVESGGGLVQPGGSLRLSCAASGFTFSSYAMSWVRQAPGKGLEWVSAISGGIGSTYYADSVKGRFTISRDNSKN
TLWLQMNSLRAEDTAVYYCAKDAVGATPYYFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 771)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - PSMB896-HC-G100A[PSMA]_L0 Light Chain (SEQ ID NO: 772)
QSVLTQPPSVSAAPGQKVTISCSGSSSNIGINYVSWYQQLPGTAPKLLIYDNNKRPSGIPDRFSGSKSGTSATLGIT
GLQTGDEADYYCGTWDSSLSAVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29LL

>XENP39266 PSMB896-HC-G100A[PSMA]_H0L0_Fab-1A7[CD28]_H1.14_L1.71_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - PSMB896-HC-G100A[PSMA]_H0_IgG1_pI(-)_Isosteric_A_/PVA_/S267K/L368D/K370S (SEQ ID NO: 773)
EVQLVESGGGLVQPGGSLRLSCAASGFTFSSYAMSWVRQAPGKGLEWVSAISGGIGSTYYADSVKGRFTISRDNSKN
TLWLQMNSLRAEDTAVYYCAKDAVGATPYYFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK

Chain 2 - 1A7[CD28]_H1.14_L1.71_scFv(GKPGS)4_Fc(216)_IgG1_C220S/PVA_/S267K/S364K/E357Q (SEQ ID NO: 774)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK

Chain 3 - PSMB896-HC-G100A[PSMA]_L0 Light Chain (SEQ ID NO: 775)
QSVLTQPPSVSAAPGQKVTISCSGSSSNIGINYVSWYQQLPGTAPKLLIYDNNKRPSGIPDRFSGSKSGTSATLGIT
GLQTGDEADYYCGTWDSSLSAVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39267 011A11[PSMA]_H0L0_Fab-1A7[CD28]_H1L1_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - 011A11[PSMA]_H0_IgG1_pI(-)_Isosteric_A_/PVA_/S267K/L368D/K370S (SEQ ID NO: 776)
EVQLVESGGGLVKPGGSLRLSCVASGFTFSFYSMNWVRQAPGKGLDWVSSISSSGNYIYYADSVKGRFTISRDNAKN
SLHLHMNSLKAEDTAMYFCARSYSGSYDAFDFWGQGTMVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK

Chain 2 - 1A7[CD28]_H1L1_scFv(GKPGS)4_Fc(216)_IgG1_C220S/PVA_/S267K/S364K/E357Q (SEQ ID NO: 777)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK

Chain 3 - 011A11[PSMA]_L0 Light Chain (SEQ ID NO: 778)
EIVMTQSPGTLSLSPGERATLSCRASQSVSSSFLAWYQQKPGQAPRLLISGASSRATGIPDRFSVSGSGTDFTLTIS
RLEPEDFAVYYCQQYGVSPWTFGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

Figure 29MM

>XENP39268 011A11[PSMA]_H0L0_Fab-1A7[CD28]_H1.14_L1_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - 011A11[PSMA]_H0_IgG1_pI(-)_Isosteric_A_/PVA_/S267K/L368D/K370S (SEQ ID NO: 779)
EVQLVESGGGLVKPGGSLRLSCVASGFTFSFYSMNWVRQAPGKGLDWVSSISSSGNYIYYADSVKGRFTISRDNAKN
SLHLHMNSLKAEDTAMYFCARSYSGSYDAFDFWGQGTMVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1.14_L1_scFv(GKPGS)4_Fc(216)_IgG1_C220S/PVA_/S267K/S364K/E357Q (SEQ ID NO: 780)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - 011A11[PSMA]_L0 Light Chain (SEQ ID NO: 781)
EIVMTQSPGTLSLSPGERATLSCRASQSVSSSFLAWYQQKPGQAPRLLISGASSRATGIPDRFSVSGSGTDFTLTIS
RLEPEDFAVYYCQQYGVSPWTFGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC >XENP39269 011A11[PSMA]_H0L0_Fab-1A7[CD28]_H1.1_L1.71_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - 011A11[PSMA]_H0_IgG1_pI(-)_Isosteric_A_/PVA_/S267K/L368D/K370S (SEQ ID NO: 782)
EVQLVESGGGLVKPGGSLRLSCVASGFTFSFYSMNWVRQAPGKGLDWVSSISSSGNYIYYADSVKGRFTISRDNAKN
SLHLHMNSLKAEDTAMYFCARSYSGSYDAFDFWGQGTMVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_H1.1_L1.71_scFv(GKPGS)4_Fc(216)_IgG1_C220S/PVA_/S267K/S364K/E357Q (SEQ ID NO: 783)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - 011A11[PSMA]_L0 Light Chain (SEQ ID NO: 784)
EIVMTQSPGTLSLSPGERATLSCRASQSVSSSFLAWYQQKPGQAPRLLISGASSRATGIPDRFSVSGSGTDFTLTIS
RLEPEDFAVYYCQQYGVSPWTFGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

Figure 29NN

>XENP39270 011A11[PSMA]_H0L0_Fab-1A7[CD28]_H1.14_L1.71_scFv(GKPGS)4-IgG1_pI(-
)_Isosteric_A_/PVA_/S267K/L368D/K370S-Fc(216)_IgG1_C220S/PVA_/S267K/S364K/E357Q Chain 1 - 011A11[PSMA]_H0_IgG1_pI(-)_Isosteric_A_/PVA_/S267K/L368D/K370S (SEQ ID NO: 785)
EVQLVESGGGLVKPGGSLRLSCVASGFTFSFYSMNWVRQAPGKGLDWVSSISSSGNYIYYADSVKGRFTISRDNAKN
SLHLHMNSLKAEDTAMYFCARSYSGSYDAFDFWGQGTMVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK Chain 2 - 1A7[CD28]_H1.14_L1.71_scFv(GKPGS)4_Fc(216)_IgG1_C220S/PVA_/S267K/S364K/E357Q (SEQ ID NO: 786)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - 011A11[PSMA]_L0 Light Chain (SEQ ID NO: 787)
EIVMTQSPGTLSLSPGERATLSCRASQSVSSSFLAWYQQKPGQAPRLLISGASSRATGIPDRFSVSGSGTDFTLTIS
RLEPEDFAVYYCQQYGVSPWTFGQGTKVEIK/RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC >XENP39274 P72_A10V2[PSMA]_H0L0_Fab-1A7[CD28]_L1_H1.14_scFv(GKPGS)4-IgG1_pI(-
)_Isosteric_A_/PVA_/S267K/L368D/K370S-Fc(216)_IgG1_C220S/PVA_/S267K/S364K/E357Q Chain 1 - P72_A10V2[PSMA]_H0_IgG1_pI(-)_Isosteric_A_/PVA_/S267K/L368D/K370S (SEQ ID NO: 788)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK Chain 2 - 1A7[CD28]_L1_H1.14_scFv(GKPGS)4_Fc(216)_IgG1_C220S/PVA_/S267K/S364K/E357Q (SEQ ID NO: 789)
DIQMTQSPSSLSASVGDRVTITCRASQSISSYLNWYQQKPGKAPKLLIYAASSLQSGVPSRFSGSGSGTDFTLTISS
LQPEDFATYYCQQSYSTPFTFGQGTKLEIK/GKPGSGKPGSGKPGSGKPGS/EVQLLESGGGLVQPGGSLRLSCAAS
GFTFSSYYMSWVRQAPGKGLEWVSTISESGDSTYYADSVKGRFTISRDNSKNTLYLQMNSLRAEDTAVYYCAKSGPG
LRQVGFDYWGQGTLVTVSS/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P72_A10V2[PSMA]_L0 Light Chain (SEQ ID NO: 790)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

Figure 2900

>XENP39275 P72_D01V2[PSMA]_H0L0_Fab-1A7[CD28]_L1_H1.14_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_D01V2[PSMA]_H0_IgG1_pI(-)_Isosteric_A_/PVA_/S267K/L368D/K370S (SEQ ID NO: 791)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCAREGVGADYGDYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK
Chain 2 - 1A7[CD28]_L1_H1.14_scFv(GKPGS)4_Fc(216)_IgG1_C220S/PVA_/S267K/S364K/E357Q (SEQ ID NO: 792)
DIQMTQSPSSLSASVGDRVTITCRASQSISSYLNWYQQKPGKAPKLLIYAASSLQSGVPSRFSGSGSGTDFTLTISS
LQPEDFATYYCQQSYSTPFTFGQGTKLEIK/GKPGSGKPGSGKPGSGKPGS/EVQLLESGGGLVQPGGSLRLSCAAS
GFTFSSYYMSWVRQAPGKGLEWVSTISESGDSTYYADSVKGRFTISRDNSKNTLYLQMNSLRAEDTAVYYCAKSGPG
LRQVGFDYWGQGTLVTVSS/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_D01V2[PSMA]_L0 Light Chain (SEQ ID NO: 793)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS >XENP39276 P72_F07[PSMA]_H0L0_Fab-1A7[CD28]_L1_H1.14_scFv(GKPGS)4-IgG1_pI(-
)_Isosteric_A_/PVA_/S267K/L368D/K370S-Fc(216)_IgG1_C220S/PVA_/S267K/S364K/E357Q
Chain 1 - P72_F07[PSMA]_H0_IgG1_pI(-)_Isosteric_A_/PVA_/S267K/L368D/K370S (SEQ ID NO: 794)
EVQLVESGGGVVQPGRSLRLSCAASGFTFSSYGMNWVRQAPGKGLEWVAVTSYDGSNKYYADSVKGRFTISRDISKN
TLYLQMSSLRAEDTAVYYCARDPYSSSWNGAFDIWGPGTMVTVSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK
Chain 2 - 1A7[CD28]_L1_H1.14_scFv(GKPGS)4_Fc(216)_IgG1_C220S/PVA_/S267K/S364K/E357Q (SEQ ID NO: 795)
DIQMTQSPSSLSASVGDRVTITCRASQSISSYLNWYQQKPGKAPKLLIYAASSLQSGVPSRFSGSGSGTDFTLTISS
LQPEDFATYYCQQSYSTPFTFGQGTKLEIK/GKPGSGKPGSGKPGSGKPGS/EVQLLESGGGLVQPGGSLRLSCAAS
GFTFSSYYMSWVRQAPGKGLEWVSTISESGDSTYYADSVKGRFTISRDNSKNTLYLQMNSLRAEDTAVYYCAKSGPG
LRQVGFDYWGQGTLVTVSS/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_F07[PSMA]_L0 Light Chain (SEQ ID NO: 796)
SYELTQPPSVSVAPGQTARITCGGNNIGSKSVHWYQQKPGQAPVLVVYDDSDRPSGIPERFSGSNSGNTATLTISRV
EAGDEADYYCQVWDSSTDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS

Figure 29PP

<u>>XENP39277 P72_A10V2[PSMA]_H0L0_Fab-1A7[CD28]_L1.71_H1.14_scFv(GKPGS)4-IgG1_pI(-)_Isosteric_A_/PVA_/S267K/L368D/K370S-Fc(216)_IgG1_C220S/PVA_/S267K/S364K/E357Q</u>
Chain 1 - P72_A10V2[PSMA]_H0_IgG1_pI(-)_Isosteric_A_/PVA_/S267K/L368D/K370S (SEQ ID NO: 797)
QVQLVESGGGVVQPGRSLRLSCAASGFTFS<u>SYNMN</u>WVRQAPGKGLEWVA<u>IIYYDESNKYYADSVKG</u>RFTISRDISKN
TLYLQMNSLRAEDTAVYYCAR<u>ERGRDYYGMDV</u>WGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK
Chain 2 - 1A7[CD28]_L1.71_H1.14_scFv(GKPGS)4_Fc(216)_IgG1_C220S/PVA_/S267K/S364K/E357Q (SEQ ID NO: 798)
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQVYSTPFT</u>FGQGTKLEIK/GKPGSGKPGSGKPGSGKPGS/EVQLLESGGGLVQPGGSLRLSCAAS
GFTFS<u>SYYMS</u>WVRQAPGKGLEWVS<u>TISESGDSTYYADSVKG</u>RFTISRDNSKNTLYLQMNSLRAEDTAVYYCAKS<u>GPG</u>
<u>LRQVGFDY</u>WGQGTLVTVSS/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_A10V2[PSMA]_L0 Light Chain (SEQ ID NO: 799)
SYELMQPPSVSVSPGQTARITC<u>SGDALPKQYAY</u>WYQQKPGQAPVLVIY<u>KDSERPS</u>GIPVRFSGSSSGTTVTLTITGV
QAEDEADYYC<u>QSADSSGTYV</u>FGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS <u>>XENP39278 P72_D01V2[PSMA]_H0L0_Fab-1A7[CD28]_L1.71_H1.14_scFv(GKPGS)4-IgG1_pI(-)_Isosteric_A_/PVA_/S267K/L368D/K370S-Fc(216)_IgG1_C220S/PVA_/S267K/S364K/E357Q</u>
Chain 1 - P72_D01V2[PSMA]_H0_IgG1_pI(-)_Isosteric_A_/PVA_/S267K/L368D/K370S (SEQ ID NO: 800)
EVQLVESGGDLVQPGGSLRLSCAASGFTF<u>NNYNMN</u>WVRQAPGKGLEWVS<u>HISTSSSNKYYADSVKG</u>RFSISRDIAKN
SMYLQMNSLRDEDTAVYYCARE<u>GVGADYGDYYYGMDV</u>WGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK
Chain 2 - 1A7[CD28]_L1.71_H1.14_scFv(GKPGS)4_Fc(216)_IgG1_C220S/PVA_/S267K/S364K/E357Q (SEQ ID NO: 801)
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQVYSTPFT</u>FGQGTKLEIK/GKPGSGKPGSGKPGSGKPGS/EVQLLESGGGLVQPGGSLRLSCAAS
GFTFS<u>SYYMS</u>WVRQAPGKGLEWVS<u>TISESGDSTYYADSVKG</u>RFTISRDNSKNTLYLQMNSLRAEDTAVYYCAKS<u>GPG</u>
<u>LRQVGFDY</u>WGQGTLVTVSS/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_D01V2[PSMA]_L0 Light Chain (SEQ ID NO: 802)
QSVLTQPASVSGSPGQSITISC<u>TGTSSDVGGYNYVS</u>WYQQHPGKAPKLMIY<u>EVSNRPS</u>GVSNRFSGSKSGNTASLTI
SGLQAEDEADYYC<u>SSYTSSYTYV</u>FGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 29QQ

>XENP39279_P72_F07[PSMA]_H0L0_Fab-1A7[CD28]_L1.71_H1.14_scFv(GKPGS)4-IgG1_pI(-
)_Isosteric_A_/PVA_/S267K/L368D/K370S-Fc(216)_IgG1_C220S/PVA_/S267K/S364K/E357Q Chain 1 - P72_F07[PSMA]_H0_IgG1_pI(-)_Isosteric_A_/PVA_/S267K/L368D/K370S (SEQ ID NO: 803)
EVQLVESGGGVVQPGRSLRLSCAASGFTFSSYGMNWVRQAPGKGLEWVAVTSYDGSNKYYADSVKGRFTISRDISKN
TLYLQMSSLRAEDTAVYYCARDPYSSSWNGAFDIWGPGTMVTSS/ASTKGPSVFPLAPSSKSTSGGTAALGCLVKD
YFPEPVTVSWNSGALTSGVHTFPAVLQSSGLYSLSSVVTVPSSSLGTQTYICNVNHKPSDTKVDKKVEPKSCDKTHT
CPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVE
WESDGQPENNYKTTPPVLDSDGSFFLYSKLTVDKSRWEQGDVFSCSVMHEALHNHYTQKSLSLSPGK Chain 2 - 1A7[CD28]_L1.71_H1.14_scFv(GKPGS)4_Fc(216)_IgG1_C220S/PVA_/S267K/S364K/E357Q (SEQ ID NO: 804)
DIQMTQSPSSLSASVGDRVTITCRASQSISSYLNWYQQKPGKAPKLLIYAASSLQSGVPSRFSGSGSGTDFTLTISS
LQPEDFATYYCQQVYSTPFTFGQGTKLEIK/GKPGSGKPGSGKPGSGKPGS/EVQLLESGGGLVQPGGSLRLSCAAS
GFTFSSYYMSWVRQAPGKGLEWVSTISESGDSTYYADSVKGRFTISRDNSKNTLYLQMNSLRAEDTAVYYCAKSGPG
LRQVGFDYWGQGTLVTVSS/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P72_F07[PSMA]_L0 Light Chain (SEQ ID NO: 805)
SYELTQPPSVSVAPGQTARITCGGNNIGSKSVHWYQQKPGQAPVLVVYDDSDRPSGIPERFSGSNSGNTATLTISRV
EAGDEADYYCQVWDSSTDHVVFGGGTKLTVL/GQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECS >XENP40470_P72_A10V2[PSMA]_H0L0_Fab-1A7[CD28]_H1.1_L1_scFv(GKPGS)4-IgG1_pI(-
)_Isosteric_A_/PVA_/S267K/L368D/K370S-Fc(216)_IgG1_C220S/PVA_/S267K/S364K/E357Q Chain 1 - P72_A10V2[PSMA]_H0_IgG1_pI(-)_Isosteric_A_/PVA_/S267K/L368D/K370S (SEQ ID NO: 806)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK Chain 2 - 1A7[CD28]_H1.1_L1_scFv(GKPGS)4_Fc(216)_IgG1_C220S/PVA_/S267K/S364K/E357Q (SEQ ID NO: 807)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK Chain 3 - P72_A10V2[PSMA]_L0 Light Chain (SEQ ID NO: 808)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

Figure 29RR

<u>>XENP41406 P72_D01[PSMA]_H0L0_Fab-1A7[CD28]_L1.71_H1_scFv(GKPGS)4-IgG1_pI(-
)_Isosteric_A_/PVA_/S267K/L368D/K370S-Fc(216)_IgG1_C220S/PVA_/S267K/S364K/E357Q</u>
Chain 1 - P72_D01[PSMA]_H0_IgG1_pI(-)_Isosteric_A_/PVA_/S267K/L368D/K370S (SEQ ID NO: 809)
EVQLVESGGDLVQPGGSLRLSCAASGFTF<u>NNYNMN</u>WVRQAPGKGLEWVS<u>HISTSSSNKYYADSVKG</u>RFSISRDIAKN
SMYLQMNSLRDEDTAVYYCAR<u>DGVGADYGDYYYYGMDV</u>WGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSDTKVDKKVEPKSCD
KTHTCPPCPAPPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTCDVSGFYPSD
IAVEWESDGQPENNYKTTPPVLDSDGSFFLYSKLTVDKSRWEQGDVFSCSVMHEALHNHYTQKSLSLSPGK
Chain 2 - 1A7[CD28]_L1.71_H1_scFv(GKPGS)4_Fc(216)_IgG1_C220S/PVA_/S267K/S364K/E357Q (SEQ ID NO: 810)
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQVYSTPFT</u>FGQGTKLEIK/GKPGSGKPGSGKPGSGKPGS/EVQLLESGGGLVQPGGSLRLSCAAS
GTFS<u>SYAMS</u>WVRQAPGKGLEWVS<u>TISGSGDSTYYADSVKG</u>RFTISRDNSKNTLYLQMNSLRAEDTAVYYCAKS<u>GPG
LRQVGFDY</u>WGQGTLVTVSS/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - P72_D01[PSMA]_L0 Light Chain (SEQ ID NO: 811)
QSVLTQPASVSGSPGQSITISC<u>TGTSSDVGGYNYVS</u>WYQQHPGKAPKLMIY<u>EVSNRPS</u>GVSNRFSGSKSGNTASLTI
SGLQAEDEADYYC<u>SSYTSSYTYV</u>FGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS <u>>XENP42268 a.k.a. C28PB247 (PSMB896-HC-G100A[PSMA]_H0L0_Fab-1A7[CD28]_H1_L1.71_scFv(GKPGS)4-
IgG1_pI(-)_Isosteric_A_/PVA_/S267K/L368D/K370S-Fc(216)_IgG1_C220S/PVA_/S267K/S364K/E357Q)</u>
Chain 1 - C28PB247 (PSMB896-HC-G100A[PSMA]_H0_IgG1_pI(-)_Isosteric_A_/PVA_/S267K/L368D/K370S (SEQ ID NO: 812)
EVQLVESGGGLVQPGGSLRLSCAASGFTFS<u>SYAMS</u>WVRQAPGKGLEWVS<u>AISGGIGSTYYADSVKG</u>RFTISRDNSKN
TLWLQMNSLRAEDTAVYYCAK<u>DAVGATPYYFDY</u>WGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSDTKVDKKVEPKSCDKTHTC
PPCPAPPVAGPSVFLFPPKPKDTLMISRTPEVTCVVVDVKHEDPEVKFNWYVDGVEVHNAKTKPREEEYNSTYRVVS
VLTVLHQDWLNGKEYKCKVSNKALPAPIEKTISKAKGQPREPQVYTLPPSREEMTKNQVSLTCDVSGFYPSDIAVEW
ESDGQPENNYKTTPPVLDSDGSFFLYSKLTVDKSRWEQGDVFSCSVMHEALHNHYTQKSLSLSPGK
Chain 2 - 1A7[CD28]_H1_L1.71_scFv(GKPGS)4_Fc(216)_IgG1_C220S/PVA_/S267K/S364K/E357Q (SEQ ID NO: 813)
EVQLLESGGGLVQPGGSLRLSCAASGFTFS<u>SYAMS</u>WVRQAPGKGLEWVS<u>TISGSGDSTYYADSVKG</u>RFTISRDNSKN
TLYLQMNSLRAEDTAVYYCAKS<u>GPGLRQVGFDY</u>WGQGTLVTVSS/GKPGSGKPGSGKPGSGKPGS/DIQMTQSPSSL
SASVGDRVTITC<u>RASQSISSYLN</u>WYQQKPGKAPKLLIY<u>AASSLQS</u>GVPSRFSGSGSGTDFTLTISSLQPEDFATYYC
<u>QQVYSTPFT</u>FGQGTKLEIK/EPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTISKAKGQPREPQVYT
LPPSREQMTKNQVKLTCLVKGFYPSDIAVEWESNGQPENNYKTTPPVLDSDGSFFLYSKLTVDKSRWQQGNVFSCSV
MHEALHNHYTQKSLSLSPGK
Chain 3 - PSMB896-HC-G100A[PSMA]_L0 Light Chain (SEQ ID NO: 814)
QSVLTQPPSVSAAPGQKVTISC<u>SGSSSNIGINYVS</u>WYQQLPGTAPKLLIY<u>DNNKRPS</u>GIPDRFSGSKSGTSATLGIT
GLQTGDEADYYC<u>GTWDSSLSAVV</u>FGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 30A

>C28PB405 HC1 (AAS_knob3): 1A7[CD28]_h1.14_l1-spFv HL, HC2 (AAS_hole3_RF): P72_A10V2-Fab
Chain 1 - 1A7[CD28]_h1.14_l1-spFv (SEQ ID NO: 815)
EVQLLESGGGLVQPGGSLRLSCAASGFTFSSYAMSWVRQAPGCGLEWVSTISGSGDSTYYADSVKGRFTISRDNSKN
TLYLQMNSLRAEDTAVYYCAKSGPGLRQVGFDYWGQGTLVTVSS/GGGSGGSGGCPPCGGSGG/DIQMTQSPSSLSA
SVGDRVTITCRASQSISSYLNWYQQKPGKAPKLLIYAASSLQSGVPSRFSGSGSGTDFTLTISSLQPEDFATYYCQQ
SYSTPFTFGCGTKLEIK/EPKSSDKTHTCPPCPAPEAAGGPSVFLFPPKPKDTLMISRTPEVTCVVVSVSHEDPEVK
FNWYVDGVEVHNAKTKPREEQYNSTYRVVSVLTVLHQDWLNGKEYKCKVSNKALPAPIEKTISKAKGQPREPQVYTL
PPSREEMTKNQVSLWCLVKGFYPSDIAVEWESNGQPENNYKTTPPVLDSDGSFFLYSKLTVDKSRWQQGNVFSCSVM
HEALHNHYTQKSLSLSPGK
Chain 2 - HC1 (AAS_knob3): P72_A10V2 (SEQ ID NO: 816)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSPGK
Chain 3 - LC: P72_A10V2 (SEQ ID NO: 817)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

>C28PB404 HC1 (AAS_knob3): 1A7[CD28]_h1.14_l1-spFv HL, HC2 (AAS_hole3_RF): PSMB896-G100A-Fab
Chain 1 - 1A7[CD28]_h1.14_l1-spFv (SEQ ID NO: 818)
EVQLLESGGGLVQPGGSLRLSCAASGFTFSSYAMSWVRQAPGCGLEWVSTISGSGDSTYYADSVKGRFTISRDNSKN
TLYLQMNSLRAEDTAVYYCAKSGPGLRQVGFDYWGQGTLVTVSS/GGGSGGSGGCPPCGGSGG/DIQMTQSPSSLSA
SVGDRVTITCRASQSISSYLNWYQQKPGKAPKLLIYAASSLQSGVPSRFSGSGSGTDFTLTISSLQPEDFATYYCQQ
SYSTPFTFGCGTKLEIK/EPKSSDKTHTCPPCPAPEAAGGPSVFLFPPKPKDTLMISRTPEVTCVVVSVSHEDPEVK
FNWYVDGVEVHNAKTKPREEQYNSTYRVVSVLTVLHQDWLNGKEYKCKVSNKALPAPIEKTISKAKGQPREPQVYTL
PPSREEMTKNQVSLWCLVKGFYPSDIAVEWESNGQPENNYKTTPPVLDSDGSFFLYSKLTVDKSRWQQGNVFSCSVM
HEALHNHYTQKSLSLSPGK
Chain 2 - HC1 (AAS_knob3): PSMB896-G100A (SEQ ID NO: 819)
EVQLVESGGGLVQPGGSLRLSCAASGFTFSSYAMSWVRQAPGKGLEWVSAISGGIGSTYYADSVKGRFTISRDNSKN
TLWLQMNSLRAEDTAVYYCAKDAVGATPYYFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKTHTC
PPCPAPEAAGGPSVFLFPPKPKDTLMISRTPEVTCVVVSVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSLSCAVKGFYPSDIAVE
WESNGQPENNYKTTPPVLDSDGSFFLVSKLTVDKSRWQQGNVFSCSVMHEALHNRFTQKSLSLSPGK
Chain 3 - LC: PSMB896-G100A (SEQ ID NO: 820)
QSVLTQPPSVSAAPGQKVTISCSGSSSNIGINYVSWYQQLPGTAPKLLIYDNNKRPSGIPDRFSGSKSGTSATLGIT
GLQTGDEADYYCGTWDSSLSAVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 30B

>C28PB403 HC1 (AAS_knob3): 1A7_H1.1_L1-spFv HL, HC2 (AAS_hole3_RF): P72_A10V2-Fab
Chain 1 - 1A7_H1.1_L1-spFv (SEQ ID NO: 821)
EVQLLESGGGLVQPGGSLRLSCAASGFTFSSYYMSWVRQAPGCGLEWVSTISGSGDSTYYADSVKGRFTISRDNSKN
TLYLQMNSLRAEDTAVYYCAKSGPGLRQVGFDYWGQGTLVTVSS/GGGSGGSGGCPPCGGSGG/DIQMTQSPSSLSA
SVGDRVTITCRASQSISSYLNWYQQKPGKAPKLLIYAASSLQSGVPSRFSGSGSGTDFTLTISSLQPEDFATYYCQQ
SYSTPFTFGCGTKLEIK/EPKSSDKTHTCPPCPAPEAAGGPSVFLFPPKPKDTLMISRTPEVTCVVVSVSHEDPEVK
FNWYVDGVEVHNAKTKPREEQYNSTYRVVSVLTVLHQDWLNGKEYKCKVSNKALPAPIEKTISKAKGQPREPQVYTL
PPSREEMTKNQVSLWCLVKGFYPSDIAVEWESNGQPENNYKTTPPVLDSDGSFFLYSKLTVDKSRWQQGNVFSCSVM
HEALHNHYTQKSLSLSPGK
Chain 2 - HC1 (AAS_knob3): P72_A10V2 (SEQ ID NO: 822)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSPGK
Chain 3 - LC: P72_A10V2 (SEQ ID NO: 823)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

>C28PB402 HC1 (AAS_knob3): 1A7_H1.1_L1-spFv HL, HC2 (AAS_hole3_RF): PSMB896-G100A-Fab
Chain 1 - 1A7_H1.1_L1-spFv (SEQ ID NO: 824)
EVQLLESGGGLVQPGGSLRLSCAASGFTFSSYYMSWVRQAPGCGLEWVSTISGSGDSTYYADSVKGRFTISRDNSKN
TLYLQMNSLRAEDTAVYYCAKSGPGLRQVGFDYWGQGTLVTVSS/GGGSGGSGGCPPCGGSGG/DIQMTQSPSSLSA
SVGDRVTITCRASQSISSYLNWYQQKPGKAPKLLIYAASSLQSGVPSRFSGSGSGTDFTLTISSLQPEDFATYYCQQ
SYSTPFTFGCGTKLEIK/EPKSSDKTHTCPPCPAPEAAGGPSVFLFPPKPKDTLMISRTPEVTCVVVSVSHEDPEVK
FNWYVDGVEVHNAKTKPREEQYNSTYRVVSVLTVLHQDWLNGKEYKCKVSNKALPAPIEKTISKAKGQPREPQVYTL
PPSREEMTKNQVSLWCLVKGFYPSDIAVEWESNGQPENNYKTTPPVLDSDGSFFLYSKLTVDKSRWQQGNVFSCSVM
HEALHNHYTQKSLSLSPGK
Chain 2 - HC1 (AAS_knob3): PSMB896-G100A (SEQ ID NO: 825)
EVQLVESGGGLVQPGGSLRLSCAASGFTFSSYAMSWVRQAPGKGLEWVSAISGGIGSTYYADSVKGRFTISRDNSKN
TLWLQMNSLRAEDTAVYYCAKDAVGATPYYFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKTHTC
PPCPAPEAAGGPSVFLFPPKPKDTLMISRTPEVTCVVVSVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSLSCAVKGFYPSDIAVE
WESNGQPENNYKTTPPVLDSDGSFFLVSKLTVDKSRWQQGNVFSCSVMHEALHNRFTQKSLSLSPGK
Chain 3 - LC: PSMB896-G100A (SEQ ID NO: 826)
QSVLTQPPSVSAAPGQKVTISCSGSSSNIGINYVSWYQQLPGTAPKLLIYDNNKRPSGIPDRFSGSKSGTSATLGIT
GLQTGDEADYYCGTWDSSLSAVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 30C

>C28PB401 HC1 (AAS_knob3): 1A7[CD28]_h1.14_l1-spFv HL, HC2 (AAS_hole3_RF): P72_A10V2-Fab
Chain 1 - 1A7[CD28]_h1.14_l1-spFv (SEQ ID NO: 827)
EVQLLESGGGLVQPGGSLRLSCAASGFTFSSYYMSWVRQAPGCGLEWVSTISESGDSTYYADSVKGRFTISRDNSKN
TLYLQMNSLRAEDTAVYYCAKSGPGLRQVGFDYWGQGTLVTVSS/GGGSGGSGGCPPCGGSGG/DIQMTQSPSSLSA
SVGDRVTITCRASQSISSYLNWYQQKPGKAPKLLIYAASSLQSGVPSRFSGSGSGTDFTLTISSLQPEDFATYYCQQ
SYSTPFTFGCGTKLEIK/EPKSSDKTHTCPPCPAPEAAGGPSVFLFPPKPKDTLMISRTPEVTCVVVSVSHEDPEVK
FNWYVDGVEVHNAKTKPREEQYNSTYRVVSVLTVLHQDWLNGKEYKCKVSNKALPAPIEKTISKAKGQPREPQVYTL
PPSREEMTKNQVSLWCLVKGFYPSDIAVEWESNGQPENNYKTTPPVLDSDGSFFLYSKLTVDKSRWQQGNVFSCSVM
HEALHNHYTQKSLSLSPGK
Chain 2 - HC1 (AAS_knob3): P72_A10V2 (SEQ ID NO: 828)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSPGK
Chain 3 - LC: P72_A10V2 (SEQ ID NO: 829)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

>C28PB400 HC1 (AAS_knob3): 1A7[CD28]_H1_L1.71-spFv HL, HC2 (AAS_hole3_RF): PSMB896-G100A-Fab
Chain 1 - 1A7[CD28]_H1_L1.71-spFv (SEQ ID NO: 830)
EVQLLESGGGLVQPGGSLRLSCAASGFTFSSYAMSWVRQAPGCGLEWVSTISGSGDSTYYADSVKGRFTISRDNSKN
TLYLQMNSLRAEDTAVYYCAKSGPGLRQVGFDYWGQGTLVTVSS/GGGSGGSGGCPPCGGSGG/DIQMTQSPSSLSA
SVGDRVTITCRASQSISSYLNWYQQKPGKAPKLLIYAASSLQSGVPSRFSGSGSGTDFTLTISSLQPEDFATYYCQQ
VYSTPFTFGCGTKLEIK/EPKSSDKTHTCPPCPAPEAAGGPSVFLFPPKPKDTLMISRTPEVTCVVVSVSHEDPEVK
FNWYVDGVEVHNAKTKPREEQYNSTYRVVSVLTVLHQDWLNGKEYKCKVSNKALPAPIEKTISKAKGQPREPQVYTL
PPSREEMTKNQVSLWCLVKGFYPSDIAVEWESNGQPENNYKTTPPVLDSDGSFFLYSKLTVDKSRWQQGNVFSCSVM
HEALHNHYTQKSLSLSPGK
Chain 2 - HC1 (AAS_knob3): PSMB896-G100A (SEQ ID NO: 831)
EVQLVESGGGLVQPGGSLRLSCAASGFTFSSYAMSWVRQAPGKGLEWVSAISGGIGSTYYADSVKGRFTISRDNSKN
TLWLQMNSLRAEDTAVYYCAKDAVGATPYYFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKTHTC
PPCPAPEAAGGPSVFLFPPKPKDTLMISRTPEVTCVVVSVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSLSCAVKGFYPSDIAVE
WESNGQPENNYKTTPPVLDSDGSFFLVSKLTVDKSRWQQGNVFSCSVMHEALHNRFTQKSLSLSPGK
Chain 3 - LC: PSMB896-G100A (SEQ ID NO: 832)
QSVLTQPPSVSAAPGQKVTISCSGSSSNIGINYVSWYQQLPGTAPKLLIYDNNKRPSGIPDRFSGSKSGTSATLGIT
GLQTGDEADYYCGTWDSSLSAVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 30D

<u>>C28PB397 1A7[CD28]_H1_L1.71 spFv HL (knob) x PSMA_P72_A10V2-Fab (hole3 RF): IgG1 AAS</u>
Chain 1 - 1A7[CD28]_H1_L1.71 spFv (SEQ ID NO:342)
EVQLLESGGGLVQPGGSLRLSCAASGFTFSSYAMSWVRQAPGCGLEWVSTISGSGDSTYYADSVKGRFTISRDNSKN
TLYLQMNSLRAEDTAVYYCAKSGPGLRQVGFDYWGQGTLVTVSS/GGGSGGSGGCPPCGGSGG/DIQMTQSPSSLSA
SVGDRVTITCRASQSISSYLNWYQQKPGKAPKLLIYAASSLQSGVPSRFSGSGSGTDFTLTISSLQPEDFATYYCQQ
VYSTPFTFGCGTKLEIK/EPKSSDKTHTCPPCPAPEAAGGPSVFLFPPKPKDTLMISRTPEVTCVVVSVSHEDPEVK
FNWYVDGVEVHNAKTKPREEQYNSTYRVVSVLTVLHQDWLNGKEYKCKVSNKALPAPIEKTISKAKGQPREPQVYTL
PPSREEMTKNQVSLWCLVKGFYPSDIAVEWESNGQPENNYKTTPPVLDSDGSFFLYSKLTVDKSRWQQGNVFSCSVM
HEALHNHYTQKSLSLSPGK
Chain 2 - HC1 (hole3 RF): PSMA_P72_A10V2 (SEQ ID NO:343)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSPGK
Chain 3 - LC: PSMA_P72_A10V2 (SEQ ID NO:344)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS <u>>C28PB397[(K447del)] 1A7[CD28]_H1_L1.71 spFv HL (knob) x PSMA_P72_A10V2-Fab (hole3 RF): IgG1 AAS (K447_)</u>
Chain 1 - 1A7[CD28]_H1_L1.71 spFv (K447del) (SEQ ID NO:345)
EVQLLESGGGLVQPGGSLRLSCAASGFTFSSYAMSWVRQAPGCGLEWVSTISGSGDSTYYADSVKGRFTISRDNSKN
TLYLQMNSLRAEDTAVYYCAKSGPGLRQVGFDYWGQGTLVTVSS/GGGSGGSGGCPPCGGSGG/DIQMTQSPSSLSA
SVGDRVTITCRASQSISSYLNWYQQKPGKAPKLLIYAASSLQSGVPSRFSGSGSGTDFTLTISSLQPEDFATYYCQQ
VYSTPFTFGCGTKLEIK/EPKSSDKTHTCPPCPAPEAAGGPSVFLFPPKPKDTLMISRTPEVTCVVVSVSHEDPEVK
FNWYVDGVEVHNAKTKPREEQYNSTYRVVSVLTVLHQDWLNGKEYKCKVSNKALPAPIEKTISKAKGQPREPQVYTL
PPSREEMTKNQVSLWCLVKGFYPSDIAVEWESNGQPENNYKTTPPVLDSDGSFFLYSKLTVDKSRWQQGNVFSCSVM
HEALHNHYTQKSLSLSPG
Chain 2 - HC1 (hole3 RF): PSMA_P72_A10V2 (K447del) (SEQ ID NO:346)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSPG
Chain 3 - LC: PSMA_P72_A10V2 (SEQ ID NO:347)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

Figure 30E

>C28PB397[(G446del/K447del)] 1A7[CD28]_H1_L1.71 spFv HL (knob) x PSMA_P72_A10V2-Fab (hole3 RF): IgG1 AAS (G446_/K447_)
Chain 1 - 1A7[CD28]_H1_L1.71 spFv (G446del/K447del) (SEQ ID NO:348)
EVQLLESGGGLVQPGGSLRLSCAASGFTFSSYAMSWVRQAPGCGLEWVSTISGSGDSTYYADSVKGRFTISRDNSKN
TLYLQMNSLRAEDTAVYYCAKSGPGLRQVGFDYWGQGTLVTVSS/GGGSGGSGGCPPCGGSGG/DIQMTQSPSSLSA
SVGDRVTITCRASQSISSYLNWYQQKPGKAPKLLIYAASSLQSGVPSRFSGSGSGTDFTLTISSLQPEDFATYYCQQ
VYSTPFTFGCGTKLEIK/EPKSSDKTHTCPPCPAPEAAGGPSVFLFPPKPKDTLMISRTPEVTCVVVSVSHEDPEVK
FNWYVDGVEVHNAKTKPREEQYNSTYRVVSVLTVLHQDWLNGKEYKCKVSNKALPAPIEKTISKAKGQPREPQVYTL
PPSREEMTKNQVSLWCLVKGFYPSDIAVEWESNGQPENNYKTTPPVLDSDGSFFLYSKLTVDKSRWQQGNVFSCSVM
HEALHNHYTQKSLSLSP
Chain 2 - HC1 (hole3 RF): PSMA_P72_A10V2 (G446del/K447del) (SEQ ID NO:349)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSP
Chain 3 - LC: PSMA_P72_A10V2 (SEQ ID NO:350)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

>C28PB343 HC1 (knob): 1A7[CD28]_H1L1-HL-scFv x HC2 (hole, RF): PSMA_P72_D01V2-Fab
Chain 1 - 1A7[CD28]_H1L1-HL-scFv (SEQ ID NO: 833)
EVQLLESGGGLVQPGGSLRLSCAASGFTFS<u>SYAMS</u>WVRQAPGKGLEWVS<u>TISGSGDSTYYADSVKG</u>RFTISRDNSKN
TLYLQMNSLRAEDTAVYYCAK<u>SGPGLRQVGFDY</u>WGQGTLVTVSS/GKPGSGKPGSGKPGSGKPGS/DIQMTQSPSSL
SASVGDRVTITC<u>RASQSISSYLN</u>WYQQKPGKAPKLLIY<u>AASSLQS</u>GVPSRFSGSGSGTDFTLTISSLQPEDFATYYC
<u>QQSYSTPFT</u>FGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK
Chain 2 - HC1 (knob): PSMA_P72_D01V2 (SEQ ID NO: 834)
EVQLVESGGDLVQPGGSLRLSCAASGFTFN<u>NYNMN</u>WVRQAPGKGLEWVS<u>HISTSSSNKYYADSVKG</u>RFSISRDIAKN
SMYLQMNSLRDEDTAVYYCAR<u>EGVGADYGDYYYGMDV</u>WGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKKVEPKSCD
KTHTCPPCPAPEAAGGPSVFLFPPKPKDTLMISRTPEVTCVVVSVSHEDPEVKFNWYVDGVEVHNAKTKPREEQYNS
TYRVVSVLTVLHQDWLNGKEYKCKVSNKALPAPIEKTISKAKGQPREPQVYTLPPSREEMTKNQVSLSCAVKGFYPS
DIAVEWESNGQPENNYKTTPPVLDSDGSFFLVSKLTVDKSRWQQGNVFSCSVMHEALHNRFTQKSLSLSPGK
Chain 3 - LC: PSMA_P72_D01V2 (SEQ ID NO: 835)
QSVLTQPASVSGSPGQSITISC<u>TGTSSDVGGYNYVS</u>WYQQHPGKAPKLMIY<u>EVSNRPS</u>GVSNRFSGSKSGNTASLTI
SGLQAEDEADYYC<u>SSYTSSYTYV</u>FGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 30F

>C28PB342 HC1 (knob): 1A7[CD28]_H1L1-HL-scFv x HC2 (hole, RF):  PSMA_P72_A10V2-Fab
Chain 1 - 1A7[CD28]_H1L1-HL-scFv (SEQ ID NO: 836)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK
Chain 2 - HC1 (knob):  PSMA_P72_A10V2 (SEQ ID NO: 837)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSPGK
Chain 3 - LC:  PSMA_P72_A10V2 (SEQ ID NO: 838)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

>C28PB341 HC1 (knob): 1A7[CD28]_H1L1-HL-scFv x HC2 (hole, RF):  PSMB896-HC-G100A-Fab
Chain 1 - 1A7[CD28]_H1L1-HL-scFv (SEQ ID NO: 839)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK
Chain 2 - HC1 (knob):  PSMB896-HC-G100A (SEQ ID NO: 840)
EVQLVESGGGLVQPGGSLRLSCAASGFTFSSYAMSWVRQAPGKGLEWVSAISGGIGSTYYADSVKGRFTISRDNSKN
TLWLQMNSLRAEDTAVYYCAKDAVGATPYYFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKTHTC
PPCPAPEAAGGPSVFLFPPKPKDTLMISRTPEVTCVVVSVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSLSCAVKGFYPSDIAVE
WESNGQPENNYKTTPPVLDSDGSFFLVSKLTVDKSRWQQGNVFSCSVMHEALHNRFTQKSLSLSPGK
Chain 3 - LC:  PSMB896-HC-G100A (SEQ ID NO: 841)
QSVLTQPPSVSAAPGQKVTISCSGSSSNIGINYVSWYQQLPGTAPKLLIYDNNKRPSGIPDRFSGSKSGTSATLGIT
GLQTGDEADYYCGTWDSSLSAVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 30G

>C28PB331 HC1 (knob): 1A7[CD28]_H1_L1.71-HL-scFv x HC2 (hole, RF): PSMA_P72_D01V2-Fab
Chain 1 - 1A7[CD28]_H1_L1.71-HL-scFv (SEQ ID NO: 842)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK
Chain 2 - HC1 (knob): PSMA_P72_D01V2 (SEQ ID NO: 843)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCAREGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKKVEPKSCD
KTHTCPPCPAPEAAGGPSVFLFPPKPKDTLMISRTPEVTCVVVSVSHEDPEVKFNWYVDGVEVHNAKTKPREEQYNS
TYRVVSVLTVLHQDWLNGKEYKCKVSNKALPAPIEKTISKAKGQPREPQVYTLPPSREEMTKNQVSLSCAVKGFYPS
DIAVEWESNGQPENNYKTTPPVLDSDGSFFLVSKLTVDKSRWQQGNVFSCSVMHEALHNRFTQKSLSLSPGK
Chain 3 - LC: PSMA_P72_D01V2 (SEQ ID NO: 844)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

>C28PB330 HC1 (knob): 1A7[CD28]_H1_L1.71-HL-scFv x HC2 (hole, RF): PSMA_P72_A10V2-Fab
Chain 1 - 1A7[CD28]_H1_L1.71-HL-scFv (SEQ ID NO:351)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK
Chain 2 - HC1 (knob): PSMA_P72_A10V2 (SEQ ID NO:352)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSPGK
Chain 3 - LC: PSMA_P72_A10V2 (SEQ ID NO:353)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

Figure 30H

>C28PB330[(K447del)] HC1 (knob): 1A7[CD28]_H1_L1.71-HL-scFv x HC2 (hole, RF): PSMA_P72_A10V2-Fab (K447_)

Chain 1 - 1A7[CD28]_H1_L1.71-HL-scFv (K447del) (SEQ ID NO:354)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPG

Chain 2 - HC1 (knob): PSMA_P72_A10V2 (K447del) (SEQ ID NO:355)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSPG

Chain 3 - LC: PSMA_P72_A10V2 (SEQ ID NO:356)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

>C28PB330[(G446del/K447del)] HC1 (knob): 1A7[CD28]_H1_L1.71-HL-scFv x HC2 (hole, RF): PSMA_P72_A10V2-Fab (G446del/K447del)

Chain 1 - 1A7[CD28]_H1_L1.71-HL-scFv (G446del/K447del) (SEQ ID NO:357)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSP

Chain 2 - HC1 (knob): PSMA_P72_A10V2 (G446del/K447del) (SEQ ID NO:358)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSP

Chain 3 - LC: PSMA_P72_A10V2 (SEQ ID NO:359)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

Figure 30I

>C28PB329 HC1 (knob): 1A7[CD28]_H1_L1.71-HL-scFv x HC2 (hole, RF): PSMB896-HC-G100A-Fab
Chain 1 - 1A7[CD28]_H1_L1.71-HL-scFv (SEQ ID NO: 845)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK
Chain 2 - HC1 (knob): PSMB896-HC-G100A (SEQ ID NO: 846)
EVQLVESGGGLVQPGGSLRLSCAASGFTFSSYAMSWVRQAPGKGLEWVSAISGGIGSTYYADSVKGRFTISRDNSKN
TLWLQMNSLRAEDTAVYYCAKDAVGATPYYFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKTHTC
PPCPAPEAAGGPSVFLFPPKPKDTLMISRTPEVTCVVVSVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSLSCAVKGFYPSDIAVE
WESNGQPENNYKTTPPVLDSDGSFFLVSKLTVDKSRWQQGNVFSCSVMHEALHNRFTQKSLSLSPGK
Chain 3 - LC: PSMB896-HC-G100A (SEQ ID NO: 847)
QSVLTQPPSVSAAPGQKVTISCSGSSSNIGINYVSWYQQLPGTAPKLLIYDNNKRPSGIPDRFSGSKSGTSATLGIT
GLQTGDEADYYCGTWDSSLSAVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

>C28PB319 HC1 (knob): 1A7[CD28]_H1.1_L1.71-HL-scFv x HC2 (hole, RF): PSMA_P72_D01V2-Fab
Chain 1 - 1A7[CD28]_H1.1_L1.71-HL-scFv (SEQ ID NO: 848)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK
Chain 2 - HC1 (knob): PSMA_P72_D01V2 (SEQ ID NO: 849)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCAREGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKKVEPKSCD
KTHTCPPCPAPEAAGGPSVFLFPPKPKDTLMISRTPEVTCVVVSVSHEDPEVKFNWYVDGVEVHNAKTKPREEQYNS
TYRVVSVLTVLHQDWLNGKEYKCKVSNKALPAPIEKTISKAKGQPREPQVYTLPPSREEMTKNQVSLSCAVKGFYPS
DIAVEWESNGQPENNYKTTPPVLDSDGSFFLVSKLTVDKSRWQQGNVFSCSVMHEALHNRFTQKSLSLSPGK
Chain 3 - LC: PSMA_P72_D01V2 (SEQ ID NO: 850)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 30J

>C28PB318 HC1 (knob): 1A7[CD28]_H1.1_L1.71-HL-scFv x HC2 (hole, RF): PSMA_P72_A10V2-Fab
Chain 1 - 1A7[CD28]_H1.1_L1.71-HL-scFv (SEQ ID NO: 851)
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK Chain 2 - HC1 (knob): PSMA_P72_A10V2 (SEQ ID NO: 852)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSPGK Chain 3 - LC: PSMA_P72_A10V2 (SEQ ID NO: 853)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS

>C28PB307 HC1 (knob): 1A7[CD28]_H1.14_L1-HL-scFv x HC2 (hole, RF): PSMA_P72_D01V2-Fab
Chain 1 - 1A7[CD28]_H1.14_L1-HL-scFv (SEQ ID NO: 854)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQSYSTPFTFGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK Chain 2 - HC1 (knob): PSMA_P72_D01V2 (SEQ ID NO: 855)
EVQLVESGGDLVQPGGSLRLSCAASGFTFNNYNMNWVRQAPGKGLEWVSHISTSSSNKYYADSVKGRFSISRDIAKN
SMYLQMNSLRDEDTAVYYCAREGVGADYGDYYYYGMDVWGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKKVEPKSCD
KTHTCPPCPAPEAAGGPSVFLFPPKPKDTLMISRTPEVTCVVVSVSHEDPEVKFNWYVDGVEVHNAKTKPREEQYNS
TYRVVSVLTVLHQDWLNGKEYKCKVSNKALPAPIEKTISKAKGQPREPQVYTLPPSREEMTKNQVSLSCAVKGFYPS
DIAVEWESNGQPENNYKTTPPVLDSDGSFFLVSKLTVDKSRWQQGNVFSCSVMHEALHNRFTQKSLSLSPGK Chain 3 - LC: PSMA_P72_D01V2 (SEQ ID NO: 856)
QSVLTQPASVSGSPGQSITISCTGTSSDVGGYNYVSWYQQHPGKAPKLMIYEVSNRPSGVSNRFSGSKSGNTASLTI
SGLQAEDEADYYCSSYTSSYTYVFGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 30K

><ins>C28PB306 HC1 (knob): 1A7[CD28]_H1.14_L1-HL-scFv x HC2 (hole, RF): PSMA_P72_A10V2-Fab</ins>
Chain 1 - 1A7[CD28]_H1.14_L1-HL-scFv (SEQ ID NO: 857)
EVQLLESGGGLVQPGGSLRLSCAASGFTFS<ins>SYYMS</ins>WVRQAPGKGLEWVS<ins>TISESGDSTYYADSVKG</ins>RFTISRDNSKN
TLYLQMNSLRAEDTAVYYCAK<ins>SGPGLRQVGFDY</ins>WGQGTLVTVSS/GKPGSGKPGSGKPGSGKPGS/DIQMTQSPSSL
SASVGDRVTITC<ins>RASQSISSYLN</ins>WYQQKPGKAPKLLIY<ins>AASSLQS</ins>GVPSRFSGSGSGTDFTLTISSLQPEDFATYYC
<ins>QQSYSTPFT</ins>FGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK
Chain 2 - HC1 (knob): PSMA_P72_A10V2 (SEQ ID NO: 858)
QVQLVESGGGVVQPGRSLRLSCAASGFTFS<ins>SYNMN</ins>WVRQAPGKGLEWVA<ins>IIYYDESNKYYADSVKG</ins>RFTISRDISKN
TLYLQMNSLRAEDTAVYYCAR<ins>ERGRDYYGMDV</ins>WGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSPGK
Chain 3 - LC: PSMA_P72_A10V2 (SEQ ID NO: 859)
SYELMQPPSVSVSPGQTARITC<ins>SGDALPKQYAY</ins>WYQQKPGQAPVLVIY<ins>KDSERPS</ins>GIPVRFSGSSSGTTVTLTITGV
QAEDEADYYC<ins>QSADSSGTYV</ins>FGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS ><ins>C28PB295 HC1 (knob): 1A7[CD28]_H1.14_L1.71-HL-scFv x HC2 (hole, RF): PSMA_P72_D01V2-Fab</ins>
Chain 1 - 1A7[CD28]_H1.14_L1.71-HL-scFv (SEQ ID NO: 860)
EVQLLESGGGLVQPGGSLRLSCAASGFTFS<ins>SYYMS</ins>WVRQAPGKGLEWVS<ins>TISESGDSTYYADSVKG</ins>RFTISRDNSKN
TLYLQMNSLRAEDTAVYYCAK<ins>SGPGLRQVGFDY</ins>WGQGTLVTVSS/GKPGSGKPGSGKPGSGKPGS/DIQMTQSPSSL
SASVGDRVTITC<ins>RASQSISSYLN</ins>WYQQKPGKAPKLLIY<ins>AASSLQS</ins>GVPSRFSGSGSGTDFTLTISSLQPEDFATYYC
<ins>QQVYSTPFT</ins>FGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK
Chain 2 - HC1 (knob): PSMA_P72_D01V2 (SEQ ID NO: 861)
EVQLVESGGDLVQPGGSLRLSCAASGFTFN<ins>NYNMN</ins>WVRQAPGKGLEWVS<ins>HISTSSSNKYYADSVKG</ins>RFSISRDIAKN
SMYLQMNSLRDEDTAVYYCAR<ins>EGVGADYGDYYYGMDV</ins>WGQGTTVTVSS/ASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKKVEPKSCD
KTHTCPPCPAPEAAGGPSVFLFPPKPKDTLMISRTPEVTCVVVSVSHEDPEVKFNWYVDGVEVHNAKTKPREEQYNS
TYRVVSVLTVLHQDWLNGKEYKCKVSNKALPAPIEKTISKAKGQPREPQVYTLPPSREEMTKNQVSLSCAVKGFYPS
DIAVEWESNGQPENNYKTTPPVLDSDGSFFLVSKLTVDKSRWQQGNVFSCSVMHEALHNRFTQKSLSLSPGK
Chain 3 - LC: PSMA_P72_D01V2 (SEQ ID NO: 862)
QSVLTQPASVSGSPGQSITISCT<ins>GTSSDVGGYNYVS</ins>WYQQHPGKAPKLMIY<ins>EVSNRPS</ins>GVSNRFSGSKSGNTASLTI
SGLQAEDEADYYC<ins>SSYTSSYTYV</ins>FGTGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

Figure 30L

<u>>C28PB294 HC1 (knob): 1A7[CD28]_H1.14_L1.71-HL-scFv x HC2 (hole, RF): PSMA_P72_A10V2-Fab</u>
Chain 1 - 1A7[CD28]_H1.14_L1.71-HL-scFv (SEQ ID NO: 863)
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK
Chain 2 - HC1 (knob): PSMA_P72_A10V2 (SEQ ID NO: 864)
QVQLVESGGGVVQPGRSLRLSCAASGFTFSSYNMNWVRQAPGKGLEWVAIIYYDESNKYYADSVKGRFTISRDISKN
TLYLQMNSLRAEDTAVYYCARERGRDYYGMDVWGQGTTVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPEAAGGPSVFLFPPKPKDTLMISRTPEVTCVVVSVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEW
ESNGQPENNYKTTPPVLDSDGSFFLVSKLTVDKSRWQQGNVFSCSVMHEALHNRFTQKSLSLSPGK
Chain 3 - LC: PSMA_P72_A10V2 (SEQ ID NO: 865)
SYELMQPPSVSVSPGQTARITCSGDALPKQYAYWYQQKPGQAPVLVIYKDSERPSGIPVRFSGSSSGTTVTLTITGV
QAEDEADYYCQSADSSGTYVFGTGTKVTVL/GQPKAAPSVTLFPPSSEELQANKATLVCLISDFYPGAVTVAWKADS
SPVKAGVETTTPSKQSNNKYAASSYLSLTPEQWKSHRSYSCQVTHEGSTVEKTVAPTECS <u>> C28PB329 a.k.a. XENP42269 (PSMB896-HC-G100A[PSMA]_H0L0_Fab-1A7[CD28]_H1_L1.71_scFv(GKPGS)4-IgG1_L234A/L235A/D265S/T366S/L368A/Y407V/H435R/Y436F-Fc(216)_IgG1_C220S/L234A/L235A/D265S/T366W)</u>
Chain 1 - PSMB896-HC-G100A[PSMA]_H0_IgG1_L234A/L235A/D265S/T366S/L368A/Y407V/H435R/Y436F (SEQ ID NO: 866)
EVQLVESGGGLVQPGGSLRLSCAASGFTFSSYAMSWVRQAPGKGLEWVSAISGGIGSTYYADSVKGRFTISRDNSKN
TLWLQMNSLRAEDTAVYYCAKDAVGATPYYFDYWGQGTLVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKTHTC
PPCPAPEAAGGPSVFLFPPKPKDTLMISRTPEVTCVVVSVSHEDPEVKFNWYVDGVEVHNAKTKPREEQYNSTYRVV
SVLTVLHQDWLNGKEYKCKVSNKALPAPIEKTISKAKGQPREPQVYTLPPSREEMTKNQVSLSCAVKGFYPSDIAVE
WESNGQPENNYKTTPPVLDSDGSFFLVSKLTVDKSRWQQGNVFSCSVMHEALHNRFTQKSLSLSPGK
Chain 2 - 1A7[CD28]_H1_L1.71_scFv(GKPGS)4_Fc(216)_IgG1_C220S/L234A/L235A/D265S/T366W (SEQ ID NO: 867)
EVQLLESGGGLVQPGGSLRLSCAASGFTFSSYAMSWVRQAPGKGLEWVSTISGSGDSTYYADSVKGRFTISRDNSKN
TLYLQMNSLRAEDTAVYYCAKSGPGLRQVGFDYWGQGTLVTVSS/GKPGSGKPGSGKPGSGKPGS/DIQMTQSPSSL
SASVGDRVTITCRASQSISSYLNWYQQKPGKAPKLLIYAASSLQSGVPSRFSGSGSGTDFTLTISSLQPEDFATYYC
QQVYSTPFTFGQGTKLEIK/EPKSSDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLWCLVKGFYPSDIAVEWESNGQPENNYKTTPPVLDSDGSFFLYSKLTVDKSRWQQGNVFSCS
VMHEALHNHYTQKSLSLSPGK
Chain 3 - PSMB896-HC-G100A[PSMA]_L0 Light Chain (SEQ ID NO: 868)
QSVLTQPPSVSAAPGQKVTISCSGSSSNIGINYVSWYQQLPGTAPKLLIYDNNKRPSGIPDRFSGSKSGTSATLGIT
GLQTGDEADYYCGTWDSSLSAVVFGGGTKLTVL/GQPKAAPSVTLFPPSSEELQANKATLVCLISDFYPGAVTVAWK
ADSSPVKAGVETTTPSKQSNNKYAASSYLSLTPEQWKSHRSYSCQVTHEGSTVEKTVAPTECS

- ✳ Target Only; no T-cells
- ✚ PBS
- ★ B7H3 x CD3 Only
- ● B7H3 x CD3 + XENP37902 PSMA x CD28 (1A7_H1.14_L1; 230nM)
- ◆ B7H3 x CD3 + XENP37903 PSMA x CD28 (1A7_H1.14_L1.71; 37nM)

- ✳ Target Only; no T-cells
- ┼ PBS
- ▲ XENP31600 PSMA x CD3 Only
- ● XENP31600 + XENP37902 PSMA x CD28 (1A7_H1.14_L1; 230nM)
- ■ XENP31600 + XENP37903 PSMA x CD28 (1A7_H1.14_L1.71; 37nM)

✳ Target Only; no T-cells
╋ PBS
★ XENP31600 PSMA x CD3 Only
● XENP31600 + XENP37902 PSMA x CD28 (1A7_H1.14_L1; 230nM)
■ XENP31600 + XENP37903 PSMA x CD28 (1A7_H1.14_L1.71; 37nM)

Figure 36A
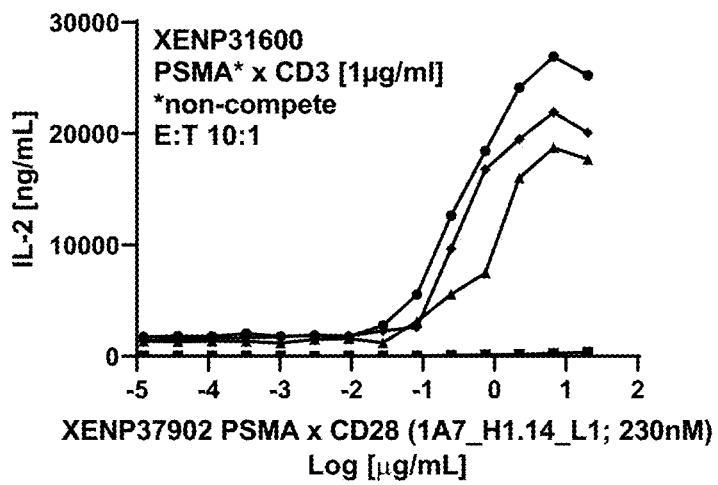
Figure 36B
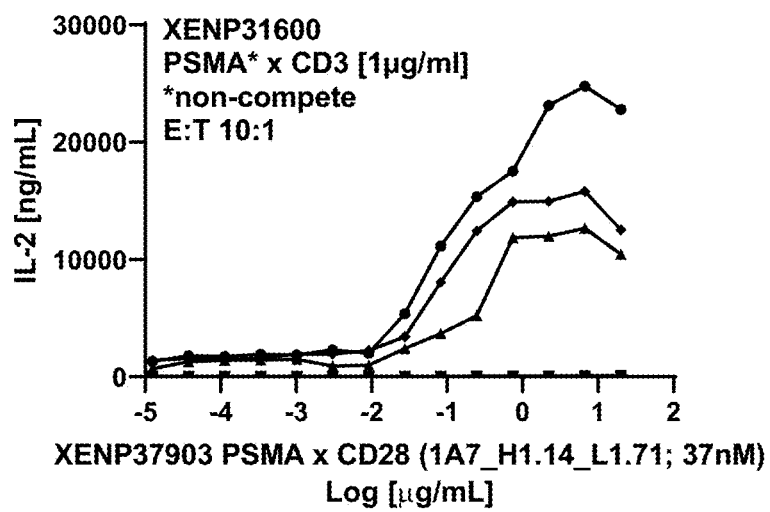
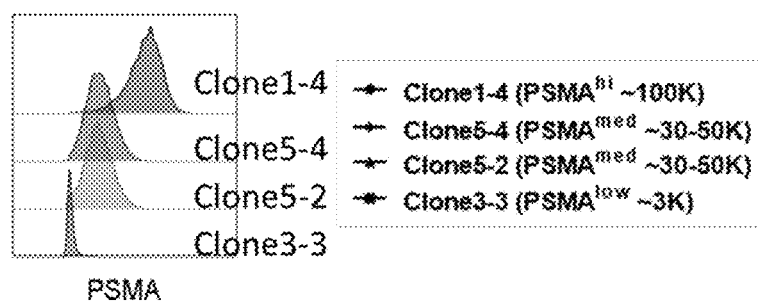

Figure 37A
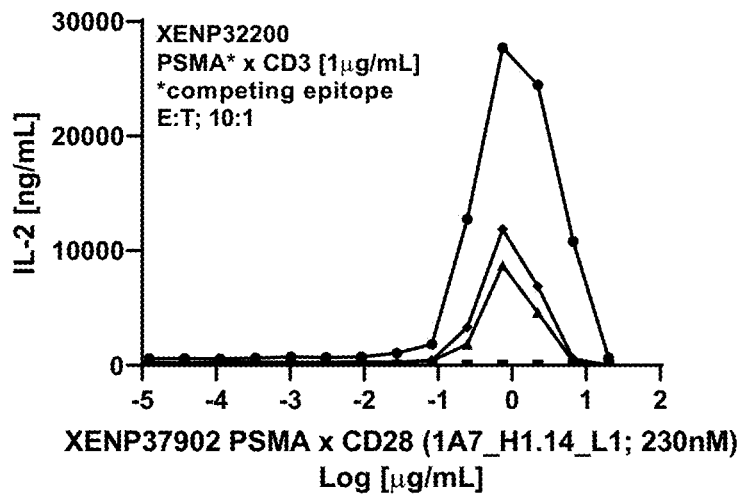
Figure 37B
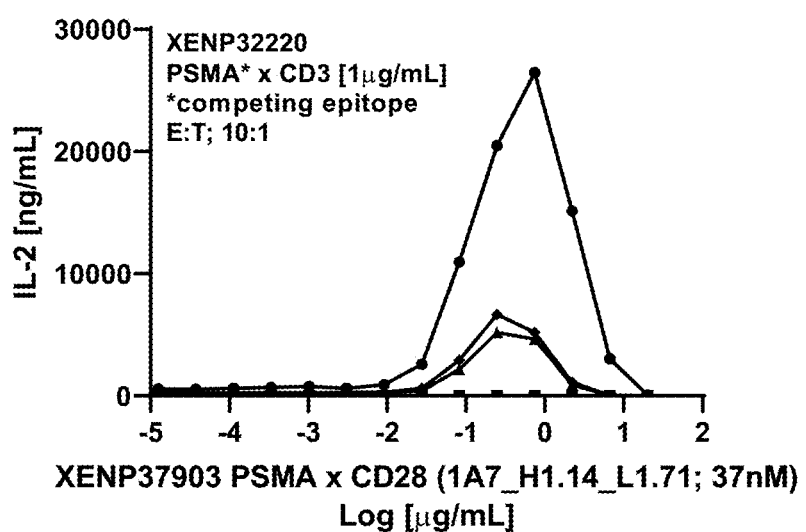
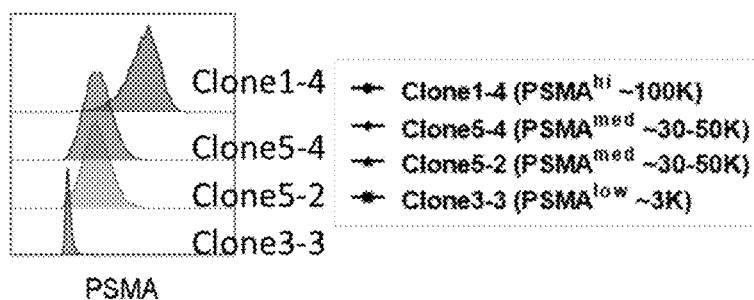

Figure 41
A)
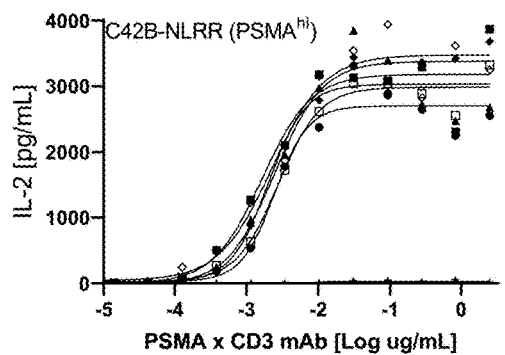
B)
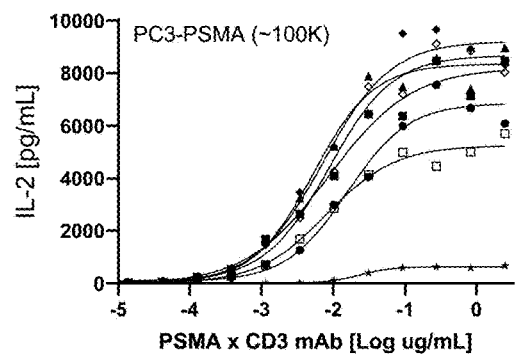
C)
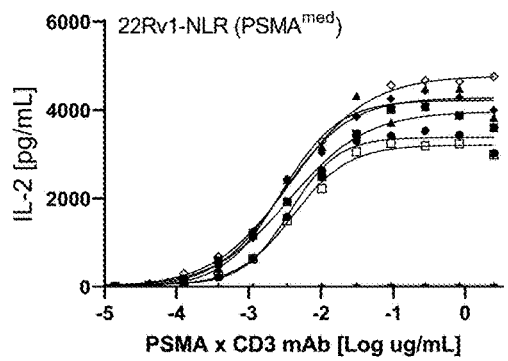
D)
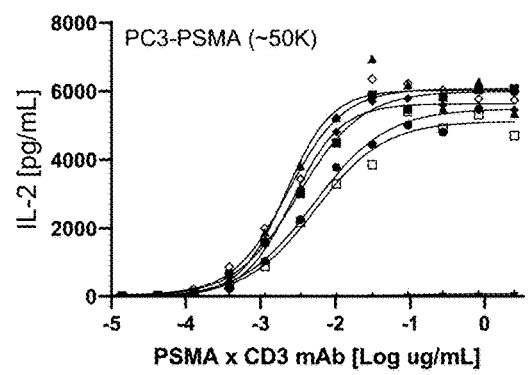
- 1391 PSMA x CD3 Only
- XENP39232 PSMA (A10v2) x CD28 (1A7_H1.14_L1; 230 nM)
- XENP38936 PSMA (A10v2) x CD28 (1A7_H1_L1.71; 180 nM)
- XENP39233 PSMA (A10v2) x CD28 (1A7_H1.1_L1.71; 96 nM)
- XENP39234 PSMA (A10v2) x CD28 (1A7_H1.14_L1.71; 37 nM)
- XENP39274 PSMA (A10v2) x CD28 (1A7_L1_H1.14; 230nM)
- XENP39277 PSMA (A10v2) x CD28 (1A7_L1.71_H1.14; 37nM)

Figure 42
A)
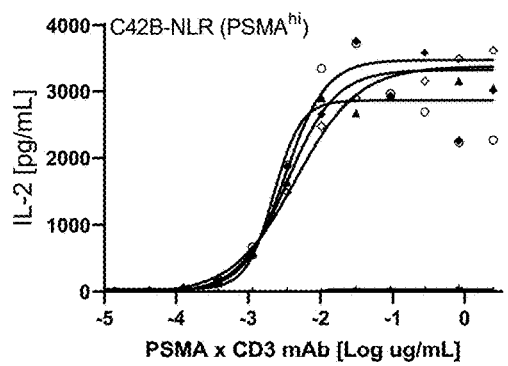
B)
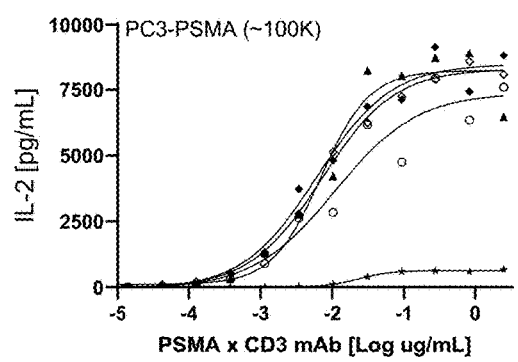
C)
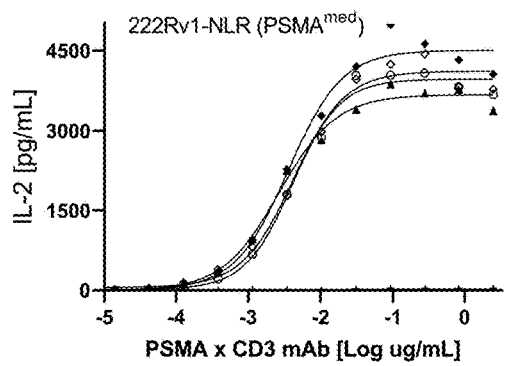
D)
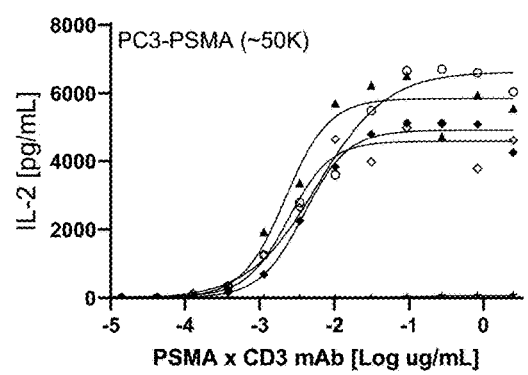
- 1391 PSMA x CD3 Only
- XENP39236 PSMA (D01v2) x CD28 (1A7_H1.14_L1; 230 nM)
- XENP39275 PSMA (D01v2) x CD28 (1A7_L1_H1.14; 230nM)
- XENP38937 PSMA (D01v2) x CD28 (1A7_H1_L1.71; 180 nM)
- XENP39278 PSMA (D01v2) x CD28 (1A7_L1.71_H1.14; 37nM)

Figure 43
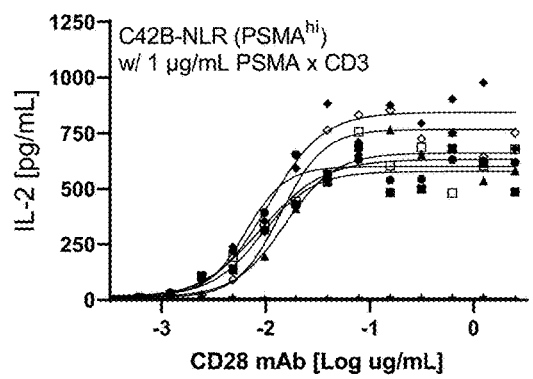
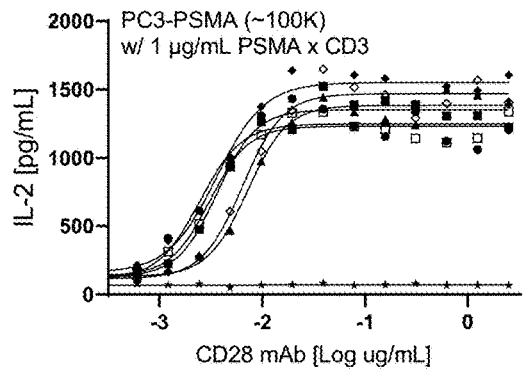
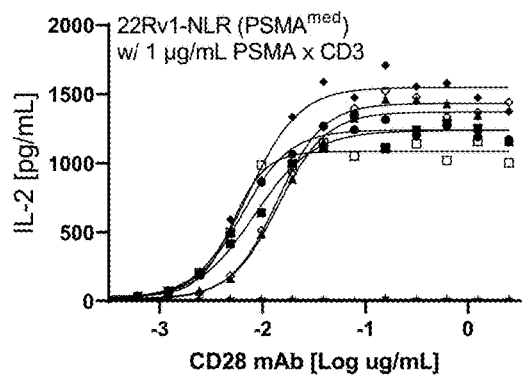
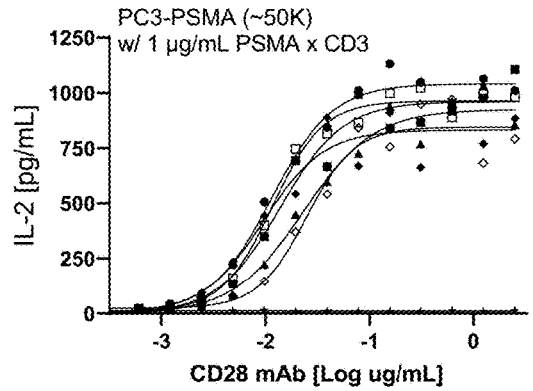
- 1391 PSMA x CD3 Only
- XENP39232 PSMA (A10v2) x CD28 (1A7_H1.14_L1; 230 nM)
- XENP38936 PSMA (A10v2) x CD28 (1A7_H1_L1.71; 180 nM)
- XENP39233 PSMA (A10v2) x CD28 (1A7_H1.1_L1.71; 96 nM)
- XENP39234 PSMA (A10v2) x CD28 (1A7_H1.14_L1.71; 37 nM)
- XENP39274 PSMA (A10v2) x CD28 (1A7_L1_H1.14; 230nM)
- XENP39277 PSMA (A10v2) x CD28 (1A7_L1.71_H1.14; 96nM)

Figure 44
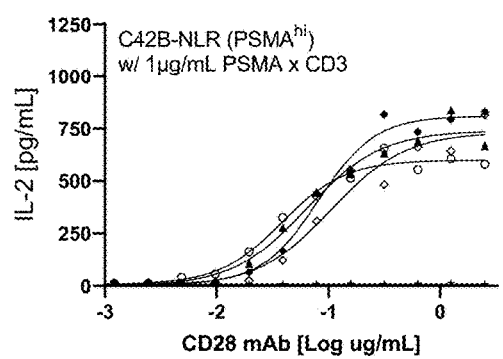
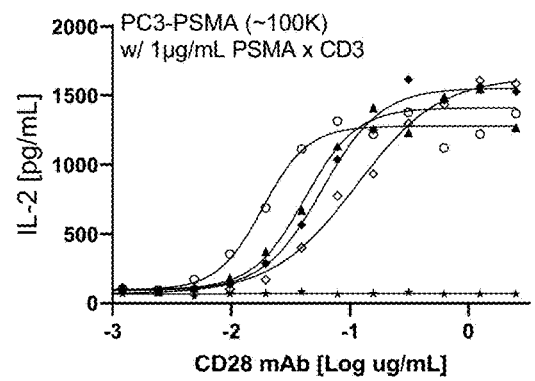
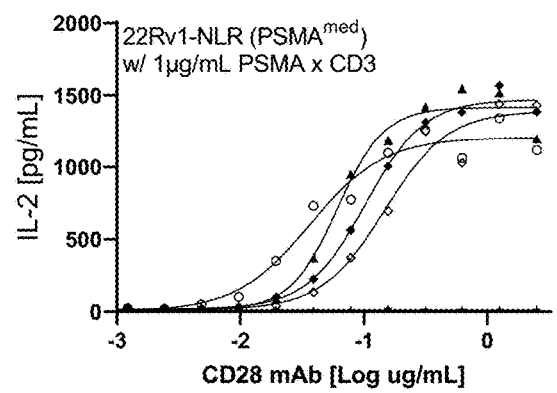
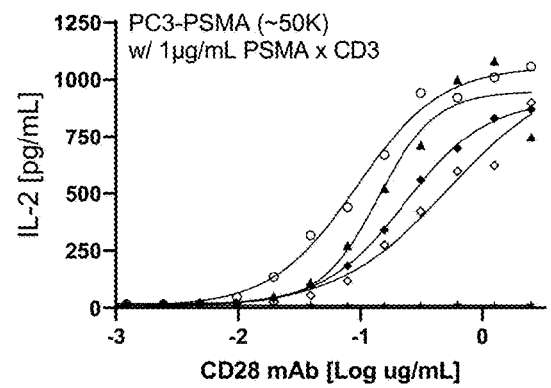
- 1391 PSMA x CD3 Only
- XENP39236 PSMA (D01v2) x CD28 (1A7_H1.14_L1; 230 nM)
- XENP38937 PSMA (D01v2) x CD28 (1A7_H1_L1.71; 180 nM)
- XENP39275 PSMA (D01v2) x CD28 (1A7_L1_H1.14; 230nM)
- XENP39278 PSMA (D01v2) x CD28 (1A7_L1.71_H1.14; 37nM)

Figure 45
A)
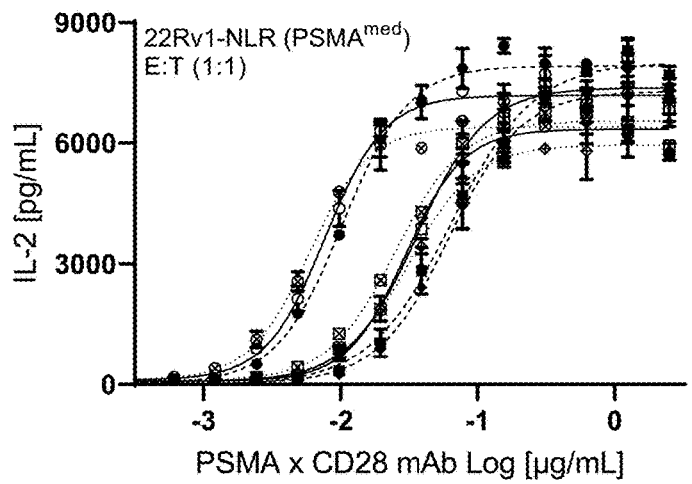
B)
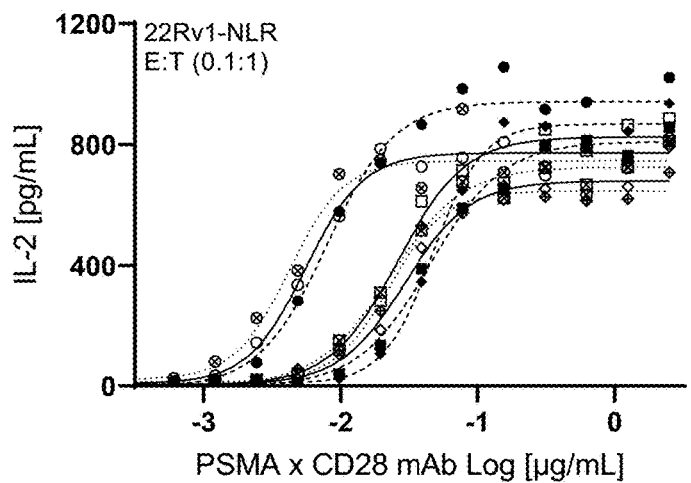
- ⊗ XENP39234 PSMA (A10v2) x CD28 (1A7_H1.14_L1.71; 37nM)
- ○ XENP39233 PSMA (A10v2) x CD28 (1A7_H1.1_L1.71; 96nM)
- ● XENP38936 PSMA (A10v2) x CD28 (1A7_H1_L1.71; 180nM)
- ◇ XENP39222 PSMA (E07) x CD28 (1A7_H1.14_L1.71; 37nM)
- ◊ XENP39221 PSMA (E07) x CD28 (1A7_H1.1_L1.71; 96nM)
- ◆ XENP38933 PSMA (E07) x CD28 (1A7_H1_L1.71; 180nM)
- ⊠ XENP39238 PSMA (D01v2) x CD28 (1A7_H1.14_L1.71; 37nM)
- ⊟ XENP39237 PSMA (D01v2) x CD28 (1A7_H1.1_L1.71; 96nM)
- ■ XENP38937 PSMA (D01v2) x CD28 (1A7_H1_L1.71; 180nM)
w/ 1µg/mL 1391 PSMA x CD3

Figure 46
A)
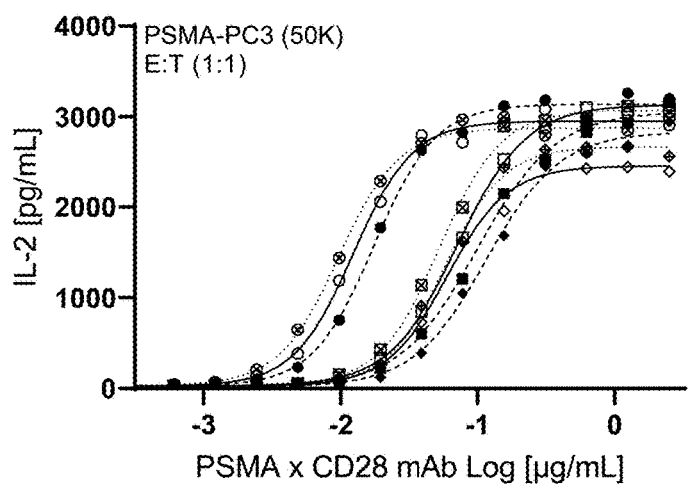
B)
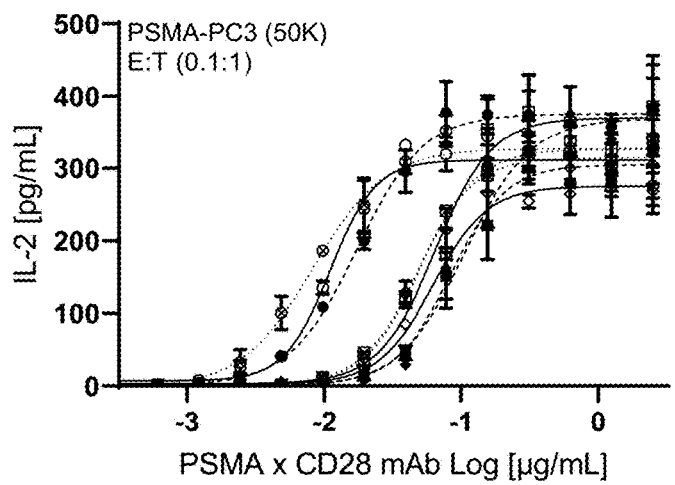
- ⊗ XENP39234 PSMA (A10v2) x CD28 (1A7_H1.14_L1.71; 37nM)
- ⊖ XENP39233 PSMA (A10v2) x CD28 (1A7_H1.1_L1.71; 96nM)
- ● XENP38936 PSMA (A10v2) x CD28 (1A7_H1_L1.71; 180nM)
- ⊠ XENP39238 PSMA (D01v2) x CD28 (1A7_H1.14_L1.71; 37nM)
- ⊟ XENP39237 PSMA (D01v2) x CD28 (1A7_H1.1_L1.71; 96nM)
- ■ XENP38937 PSMA (D01v2) x CD28 (1A7_H1_L1.71; 180nM)
- ⬦ XENP39222 PSMA (E07) x CD28 (1A7_H1.14_L1.71; 37nM)
- ⬨ XENP39221 PSMA (E07) x CD28 (1A7_H1.1_L1.71; 96nM)
- ◆ XENP38933 PSMA (E07) x CD28 (1A7_H1_L1.71; 180nM)
w/ 1μg/mL 1391 PSMA x CD3

- XENP39231 PSMA (A10v2) x CD28 (1A7_H1L1; 1000 nM)
- XENP40470 PSMA (A10v2) x CD28 (1A7_H1.1_L1; 600 nM)
- XENP38936 PSMA (A10v2) x CD28 (1A7_H1_L1.71; 180 nM)

Figure 52
A) B7H3 x CD3
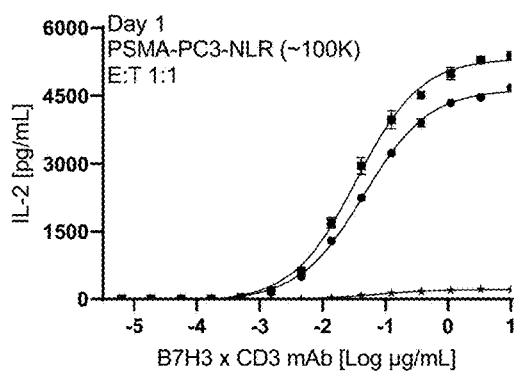
B) PSMA x CD3 XENP33063
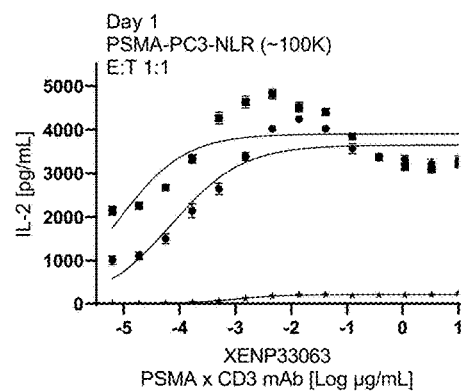
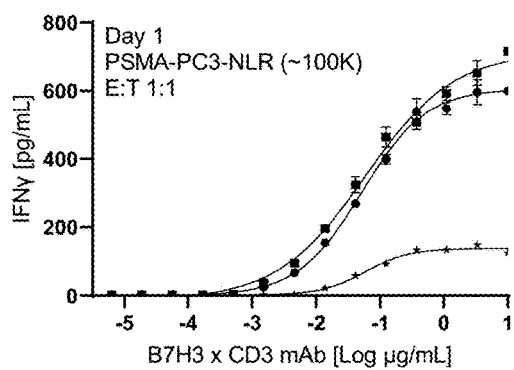
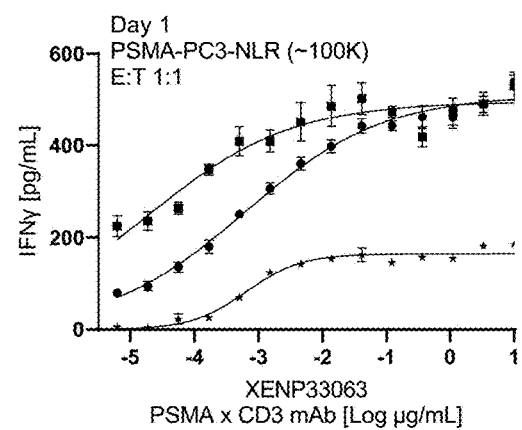
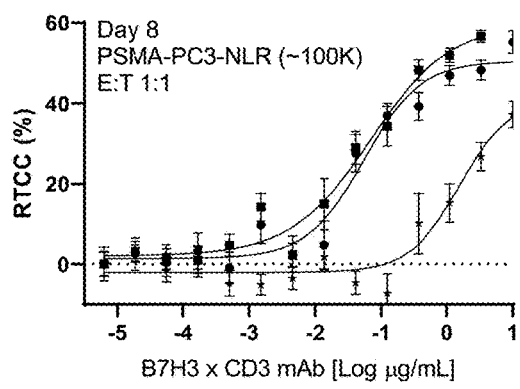
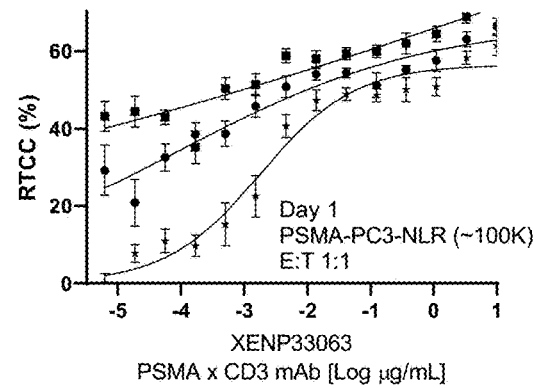
- ─★─ CD3 Only
- ─●─ XENP39234 PSMA (A10v2) x CD28 (1A7_H1.14_L1.71; 37 nM)
- ─■─ XENP38936 PSMA (A10v2) x CD28 (1A7_H1_L1.71; 180 nM)

Figure 55
A)
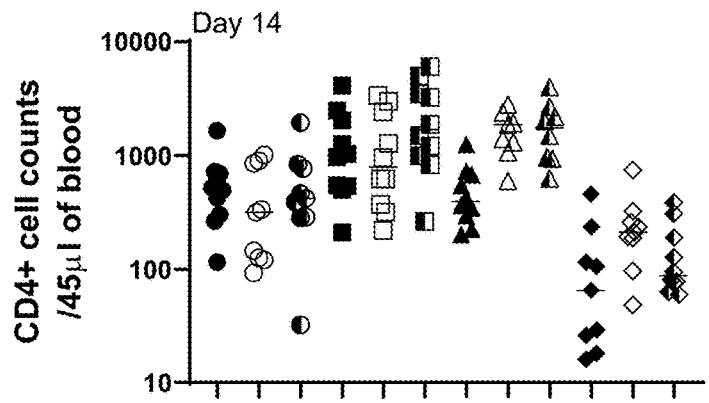
B)
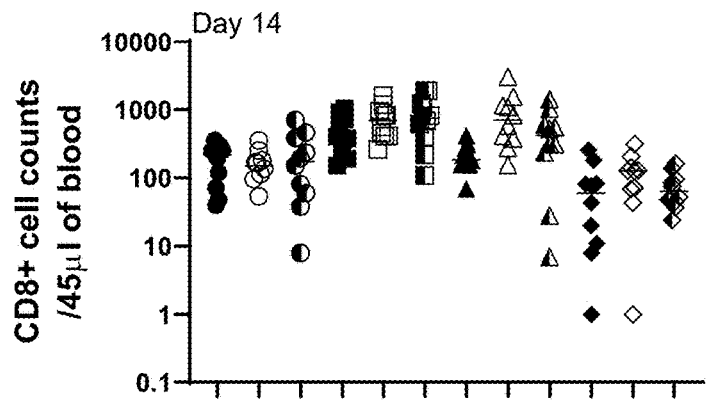
- ● PBS
- ○ 38936 PSMA (A10v2) x CD28 (180 nM), 1 mg/Kg
- ◐ 39231 PSMA (A10v2) x CD28 (1 uM), 1 mg/Kg
- ■ 33063 PSMA x CD3, 0.1 mg/Kg
- ☐ 33063, 0.1 mg/Kg + 38936, 1 mg/Kg
- ⊞ 33063, 0.1 mg/Kg + 39231, 1 mg/Kg
- ▲ 33063 PSMA x CD3, 0.01 mg/Kg
- △ 33063, 0.01 mg/Kg + 38936, 1 mg/Kg
- △ 33063, 0.01 mg/Kg + 39231, 1 mg/Kg
- ◆ B7H3 x CD3, 0.5 mg/Kg
- ◇ B7H3 x CD3, 0.5 mg/Kg + 38936, 1 mg/Kg
- ◇ B7H3 x CD3, 0.5 mg/Kg + 39231, 1 mg/Kg Figure 58
A)
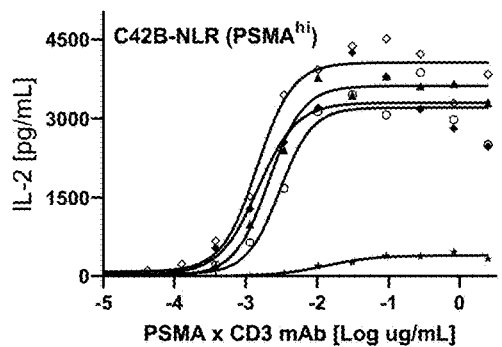
B)
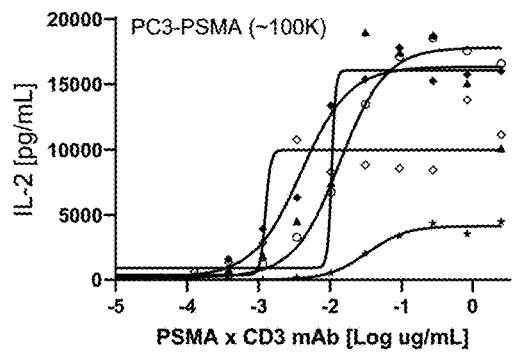
C)
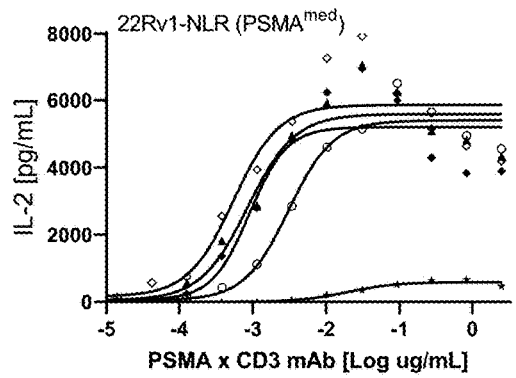
D)
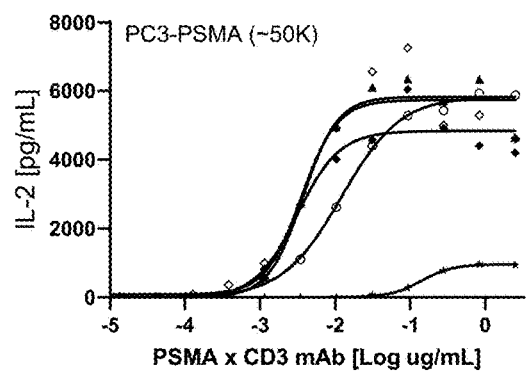
- 1508 PSMA x CD3 Only
- XENP39236 PSMA (D01v2) x CD28 (1A7_H1.14_L1; 230 nM)
- XENP39275 PSMA (D01v2) x CD28 (1A7_L1_H1.14; 230nM)
- XENP38937 PSMA (D01v2) x CD28 (1A7_H1_L1.71; 180 nM)
- XENP39278 PSMA (D01v2) x CD28 (1A7_L1.71_H1.14; 37nM)

Figure 59
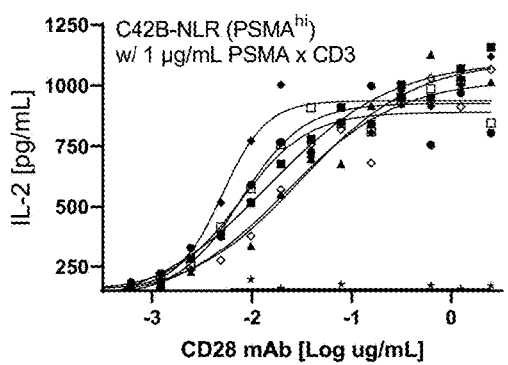
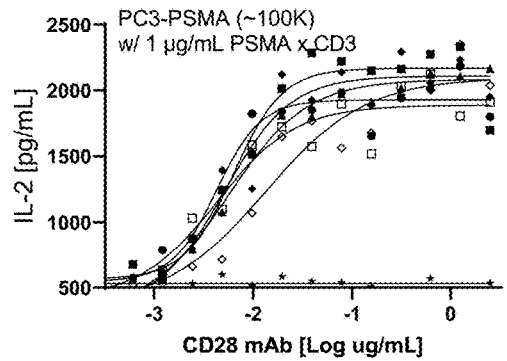
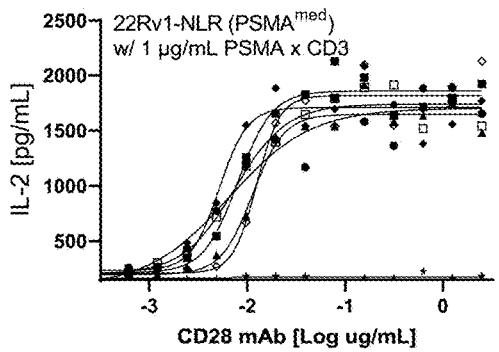
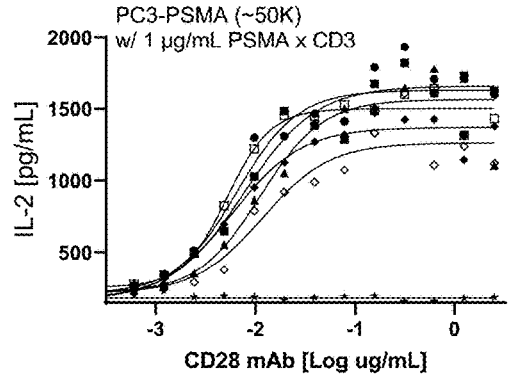
- 1508 PSMA x CD3 Only
- XENP39232 PSMA (A10v2) x CD28 (1A7_H1.14_L1; 230 nM)
- XENP39274 PSMA (A10v2) x CD28 (1A7_L1_H1.14; 230nM)
- XENP38936 PSMA (A10v2) x CD28 (1A7_H1_L1.71; 180 nM)
- XENP39233 PSMA (A10v2) x CD28 (1A7_H1.1_L1.71; 96 nM)
- XENP39234 PSMA (A10v2) x CD28 (1A7_H1.14_L1.71; 37 nM)
- XENP39277 PSMA (A10v2) x CD28 (1A7_L1.71_H1.14; 96nM)

Figure 60
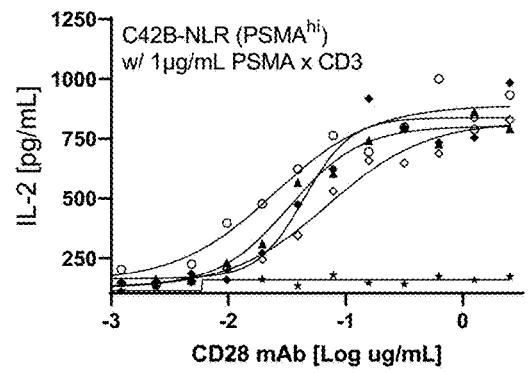
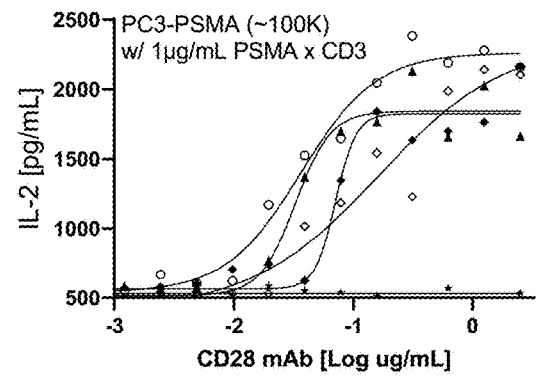
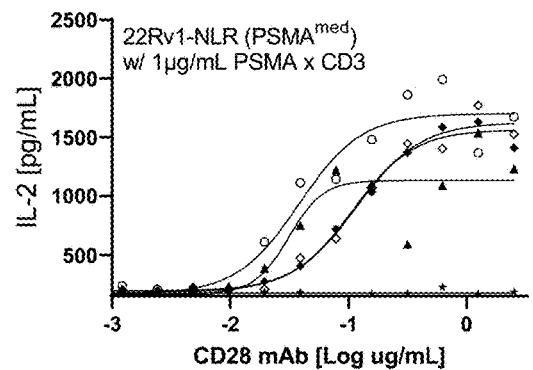
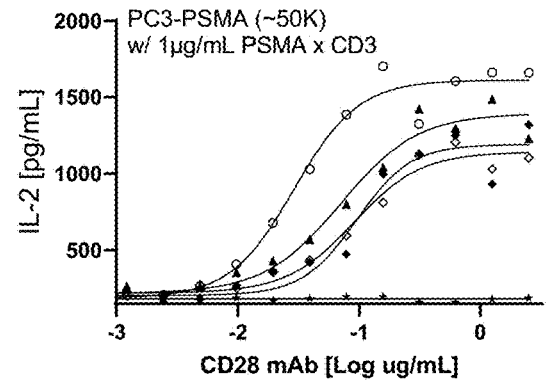
→ 1508 PSMA x CD3 Only
→ XENP39236 PSMA (D01v2) x CD28 (1A7_H1.14_L1; 230 nM)  → XENP39275 PSMA (D01v2) x CD28 (1A7_L1_H1.14; 230nM)
→ XENP38937 PSMA (D01v2) x CD28 (1A7_H1_L1.71; 180 nM)
→ XENP39278 PSMA (D01v2) x CD28 (1A7_L1.71_H1.14; 37nM)

Figure 61
A)
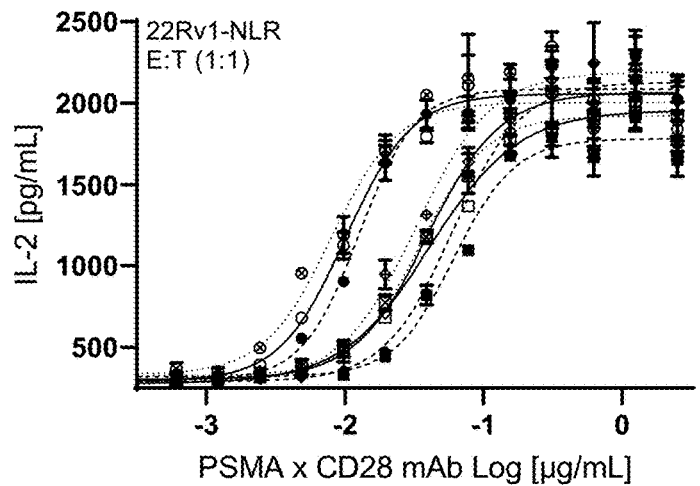
B)
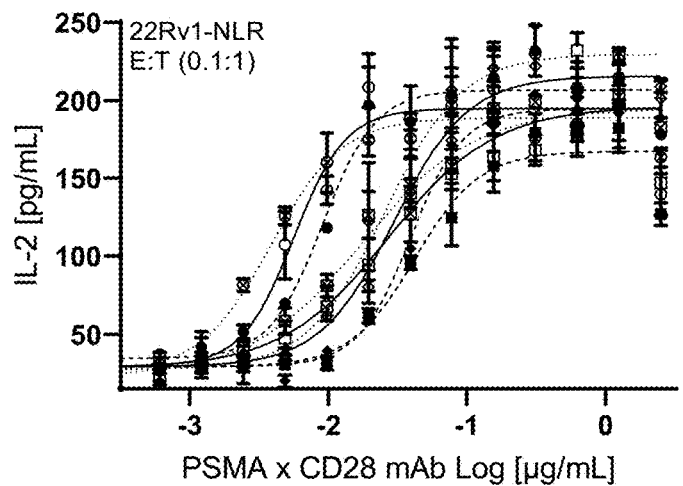
- ⊗ XENP39234 PSMA (A10v2) x CD28 (1A7_H1.14_L1.71; 37nM)
- ○ XENP39233 PSMA (A10v2) x CD28 (1A7_H1.1_L1.71; 96nM)
- ● XENP38936 PSMA (A10v2) x CD28 (1A7_H1_L1.71; 180nM)
- ◇ XENP39222 PSMA (E07) x CD28 (1A7_H1.14_L1.71; 37nM)
- ◊ XENP39221 PSMA (E07) x CD28 (1A7_H1.1_L1.71; 96nM)
- ◆ XENP38933 PSMA (E07) x CD28 (1A7_H1_L1.71; 180nM)
- ⊠ XENP39238 PSMA (D01v2) x CD28 (1A7_H1.14_L1.71; 37nM)
- ⊟ XENP39237 PSMA (D01v2) x CD28 (1A7_H1.1_L1.71; 96nM)
- ■ XENP38937 PSMA (D01v2) x CD28 (1A7_H1_L1.71; 180nM)
w/ 1µg/mL 1508 PSMA x CD3

Figure 62
A)
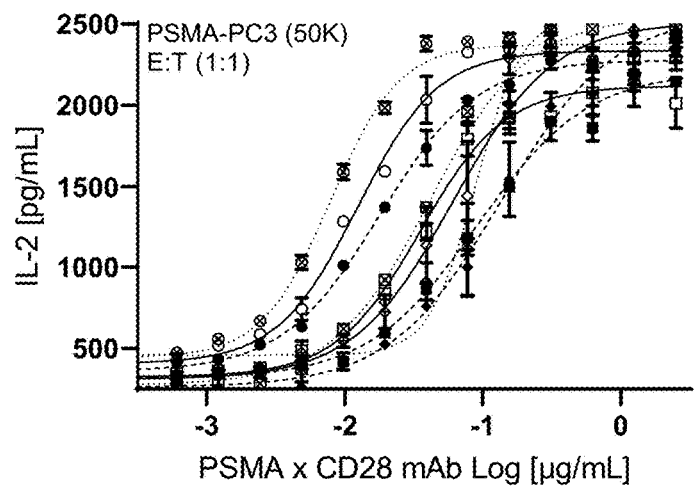
B)
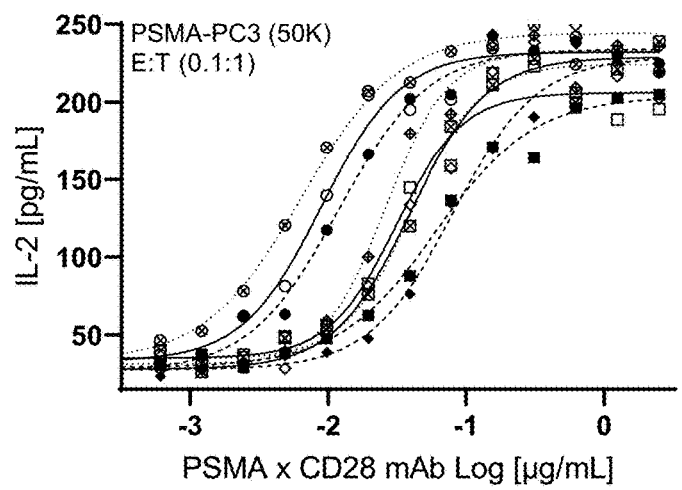
- ⊗ XENP39234 PSMA (A10v2) x CD28 (1A7_H1.14_L1.71; 37nM)
- ○ XENP39233 PSMA (A10v2) x CD28 (1A7_H1.1_L1.71; 96nM)
- ● XENP38936 PSMA (A10v2) x CD28 (1A7_H1_L1.71; 180nM)
- ⊠ XENP39238 PSMA (D01v2) x CD28 (1A7_H1.14_L1.71; 37nM)
- ⊟ XENP39237 PSMA (D01v2) x CD28 (1A7_H1.1_L1.71; 96nM)
- ■ XENP38937 PSMA (D01v2) x CD28 (1A7_H1_L1.71; 180nM)
- ◇ XENP39222 PSMA (E07) x CD28 (1A7_H1.14_L1.71; 37nM)
- ◊ XENP39221 PSMA (E07) x CD28 (1A7_H1.1_L1.71; 96nM)
- ◆ XENP38933 PSMA (E07) x CD28 (1A7_H1_L1.71; 180nM)
w/ 1µg/mL 1508 PSMA x CD3

→ XENP39231 PSMA (A10v2) x CD28 (1A7_H1L1; 1000 nM)
→ XENP40470 PSMA (A10v2) x CD28 (1A7_H1.1_L1; 600 nM)
→ XENP38936 PSMA (A10v2) x CD28 (1A7_H1_L1.71; 180 nM)

Figure 67

|  | sequence | SEQ ID NO: |
|---|---|---|
| Variable heavy (vh) domain 1A7_H1sp | EVQLLESGGGLVQPGGSLRLSCAASGFTFSSYAMSWVRQAPGCGLEWVSTISGSGDSTYYADSVKGRFTISRDNSKNTLYLQMNSLRAEDTAVYYCAKSGPGLRQVGFDYWGQGTLVTVSS | 360 |
| vhCDR1 | SYAMS | 361 |
| vhCDR2 | TISGSGDSTYYADSVKG | 362 |
| vhCDR3 | SGPGLRQVGFDY | 363 |

|  | sequence | SEQ ID NO: |
|---|---|---|
| Variable heavy (vh) domain 1A7_H1.1sp | EVQLLESGGGLVQPGGSLRLSCAASGFTFSSYYMSWVRQAPGCGLEWVSTISGSGDSTYYADSVKGRFTISRDNSKNTLYLQMNSLRAEDTAVYYCAKSGPGLRQVGFDYWGQGTLVTVSS | 364 |
| vhCDR1 | SYYMS | 365 |
| vhCDR2 | TISGSGDSTYYADSVKG | 366 |
| vhCDR3 | SGPGLRQVGFDY | 367 |

|  | sequence | SEQ ID NO: |
|---|---|---|
| Variable heavy (vh) domain 1A7_H1.14sp | EVQLLESGGGLVQPGGSLRLSCAASGFTFSSYYMSWVRQAPGCGLEWVSTISESGDSTYYADSVKGRFTISRDNSKNTLYLQMNSLRAEDTAVYYCAKSGPGLRQVGFDYWGQGTLVTVSS | 368 |
| vhCDR1 | SYYMS | 369 |
| vhCDR2 | TISESGDSTYYADSVKG | 370 |
| vhCDR3 | SGPGLRQVGFDY | 371 |

Figure 68

| | sequence | SEQ ID NO: |
|---|---|---|
| Variable light (vl) domain 1A7_L1sp | DIQMTQSPSSLSASVGDRVTITCRASQSISSYLNWYQQKPGKAPKLL IYAASSLQSGVPSRFSGSGSGTDFTLTISSLQPEDFATYYCQQSYST PFTFGCGTKLEIK | 372 |
| vlCDR1 | RASQSISSYLN | 373 |
| vlCDR2 | AASSLQS | 374 |
| vlCDR3 | QQSYSTPFT | 375 |

| | sequence | SEQ ID NO: |
|---|---|---|
| Variable light (vl) domain 1A7_L1.71sp | DIQMTQSPSSLSASVGDRVTITCRASQSISSYLNWYQQKPGKAPKLL IYAASSLQSGVPSRFSGSGSGTDFTLTISSLQPEDFATYYCQQVYST PFTFGCGTKLEIK | 376 |
| vlCDR1 | RASQSISSYLN | 377 |
| vlCDR2 | AASSLQS | 378 |
| vlCDR3 | QQVYSTPFT | 379 |

Figure 69A

| 1A7[CD28]_H1sp_L1sp | | |
|---|---|---|
| | Sequence | SEQ ID NO: |
| Variable Heavy (vh) Domain | EVQLLESGGGLVQPGGSLRLSCAASGFTFSSYAMSWVRQAPGCGLEWVSTISG SGDSTYYADSVKGRFTISRDNSKNTLYLQMNSLRAEDTAVYYCAKSGPGLRQV GFDYWGQGTLVTVSS | 380 |
| vhCDR1 | SYAMS | 381 |
| vhCDR2 | TISGSGDSTYYADSVKG | 382 |
| vhCDR3 | SGPGLRQVGFDY | 383 |
| Variable Light (vl) Domain | DIQMTQSPSSLSASVGDRVTITCRASQSISSYLNWYQQKPGKAPKLLIYAASS LQSGVPSRFSGSGSGTDFTLTISSLQPEDFATYYCQQSYSTPFTFGCGTKLEI K | 384 |
| vlCDR1 | RASQSISSYLN | 385 |
| vlCDR2 | AASSLQS | 386 |
| vlCDR3 | QQSYSTPFT | 387 |

| 1A7[CD28]_H1.1sp_L1sp | | |
|---|---|---|
| | Sequence | SEQ ID NO: |
| Variable Heavy (vh) Domain | EVQLLESGGGLVQPGGSLRLSCAASGFTFSSYYMSWVRQAPGCGLEWVSTISG SGDSTYYADSVKGRFTISRDNSKNTLYLQMNSLRAEDTAVYYCAKSGPGLRQV GFDYWGQGTLVTVSS | 388 |
| vhCDR1 | SYYMS | 389 |
| vhCDR2 | TISGSGDSTYYADSVKG | 390 |
| vhCDR3 | SGPGLRQVGFDY | 391 |
| Variable Light (vl) Domain | DIQMTQSPSSLSASVGDRVTITCRASQSISSYLNWYQQKPGKAPKLLIYAASS LQSGVPSRFSGSGSGTDFTLTISSLQPEDFATYYCQQSYSTPFTFGCGTKLEI K | 392 |
| vlCDR1 | RASQSISSYLN | 393 |
| vlCDR2 | AASSLQS | 394 |
| vlCDR3 | QQSYSTPFT | 395 |

Figure 69B

| 1A7[CD28]_H1sp_L1.71sp | | |
|---|---|---|
| | Sequence | SEQ ID NO: |
| Variable Heavy (vh) Domain | EVQLLESGGGLVQPGGSLRLSCAASGFTFSSYAMSWVRQAPGCGLEWVSTISGSGDSTYYADSVKGRFTISRDNSKNTLYLQMNSLRAEDTAVYYCAKSGPGLRQVGFDYWGQGTLVTVSS | 396 |
| vhCDR1 | SYAMS | 397 |
| vhCDR2 | TISGSGDSTYYADSVKG | 398 |
| vhCDR3 | SGPGLRQVGFDY | 399 |
| Variable Light (vl) Domain | DIQMTQSPSSLSASVGDRVTITCRASQSISSYLNWYQQKPGKAPKLLIYAASSLQSGVPSRFSGSGSGTDFTLTISSLQPEDFATYYCQQVYSTPFTFGCGTKLEIK | 400 |
| vlCDR1 | RASQSISSYLN | 401 |
| vlCDR2 | AASSLQS | 402 |
| vlCDR3 | QQVYSTPFT | 403 |

| 1A7[CD28]_H1.1sp_L1.71sp | | |
|---|---|---|
| | Sequence | SEQ ID NO: |
| Variable Heavy (vh) Domain | EVQLLESGGGLVQPGGSLRLSCAASGFTFSSYYMSWVRQAPGCGLEWVSTISGSGDSTYYADSVKGRFTISRDNSKNTLYLQMNSLRAEDTAVYYCAKSGPGLRQVGFDYWGQGTLVTVSS | 404 |
| vhCDR1 | SYYMS | 405 |
| vhCDR2 | TISGSGDSTYYADSVKG | 406 |
| vhCDR3 | SGPGLRQVGFDY | 407 |
| Variable Light (vl) Domain | DIQMTQSPSSLSASVGDRVTITCRASQSISSYLNWYQQKPGKAPKLLIYAASSLQSGVPSRFSGSGSGTDFTLTISSLQPEDFATYYCQQVYSTPFTFGCGTKLEIK | 408 |
| vlCDR1 | RASQSISSYLN | 409 |
| vlCDR2 | AASSLQS | 410 |
| vlCDR3 | QQVYSTPFT | 411 |

Figure 69C

| 1A7[CD28]_H1.14sp_L1sp | | |
|---|---|---|
| | Sequence | SEQ ID NO: |
| Variable Heavy (vh) Domain | EVQLLESGGGLVQPGGSLRLSCAASGFTFSSYYMSWVRQAPGCGLEWVSTISES GDSTYYADSVKGRFTISRDNSKNTLYLQMNSLRAEDTAVYYCAKSGPGLRQVGF DYWGQGTLVTVSS | 412 |
| vhCDR1 | SYYMS | 413 |
| vhCDR2 | TISESGDSTYYADSVKG | 414 |
| vhCDR3 | SGPGLRQVGFDY | 415 |
| Variable Light (vl) Domain | DIQMTQSPSSLSASVGDRVTITCRASQSISSYLNWYQQKPGKAPKLLIYAASSL QSGVPSRFSGSGSGTDFTLTISSLQPEDFATYYCQQSYSTPFTFGCGTKLEIK | 416 |
| vlCDR1 | RASQSISSYLN | 417 |
| vlCDR2 | AASSLQS | 418 |
| vlCDR3 | QQSYSTPFT | 419 |

| 1A7[CD28]_H1.14sp_L1.71sp | | |
|---|---|---|
| | Sequence | SEQ ID NO: |
| Variable Heavy (vh) Domain | EVQLLESGGGLVQPGGSLRLSCAASGFTFSSYYMSWVRQAPGCGLEWVSTIS ESGDSTYYADSVKGRFTISRDNSKNTLYLQMNSLRAEDTAVYYCAKSGPGLR QVGFDYWGQGTLVTVSS | 420 |
| vhCDR1 | SYYMS | 421 |
| vhCDR2 | TISESGDSTYYADSVKG | 422 |
| vhCDR3 | SGPGLRQVGFDY | 423 |
| Variable Light (vl) Domain | DIQMTQSPSSLSASVGDRVTITCRASQSISSYLNWYQQKPGKAPKLLIYAAS SLQSGVPSRFSGSGSGTDFTLTISSLQPEDFATYYCQQVYSTPFTFGCGTKL EIK | 424 |
| vlCDR1 | RASQSISSYLN | 425 |
| vlCDR2 | AASSLQS | 426 |
| vlCDR3 | QQVYSTPFT | 427 |

Figure 70A

>1A7[CD28]_H1.1 SEQ ID NO: 869
EVQLLESGGGLVQPGGSLRLSCAASGFTFSSYYMSWVRQAPGKGLEWVSTISGSGDSTYYADSVKGRFTISRDNSKN
TLYLQMNSLRAEDTAVYYCAKSGPGLRQVGFDYWGQGTLVTVSS

>1A7[CD28]_H1.2 SEQ ID NO: 870
EVQLLESGGGLVQPGGSLRLSCAASGFTFSSYAMSWVRQAPGKGLEWVSTIDGSGDSTYYADSVKGRFTISRDNSKN
TLYLQMNSLRAEDTAVYYCAKSGPGLRQVGFDYWGQGTLVTVSS

>1A7[CD28]_H1.3 SEQ ID NO: 871
EVQLLESGGGLVQPGGSLRLSCAASGFTFSSYAMSWVRQAPGKGLEWVSTIEGSGDSTYYADSVKGRFTISRDNSKN
TLYLQMNSLRAEDTAVYYCAKSGPGLRQVGFDYWGQGTLVTVSS

>1A7[CD28]_H1.4 SEQ ID NO: 872
EVQLLESGGGLVQPGGSLRLSCAASGFTFSSYAMSWVRQAPGKGLEWVSTIYGSGDSTYYADSVKGRFTISRDNSKN
TLYLQMNSLRAEDTAVYYCAKSGPGLRQVGFDYWGQGTLVTVSS

>1A7[CD28]_H1.5 SEQ ID NO: 873
EVQLLESGGGLVQPGGSLRLSCAASGFTFSSYAMSWVRQAPGKGLEWVSTISDSGDSTYYADSVKGRFTISRDNSKN
TLYLQMNSLRAEDTAVYYCAKSGPGLRQVGFDYWGQGTLVTVSS

>1A7[CD28]_H1.6 SEQ ID NO: 874
EVQLLESGGGLVQPGGSLRLSCAASGFTFSSYAMSWVRQAPGKGLEWVSTISESGDSTYYADSVKGRFTISRDNSKN
TLYLQMNSLRAEDTAVYYCAKSGPGLRQVGFDYWGQGTLVTVSS

>1A7[CD28]_H1.7 SEQ ID NO: 875
EVQLLESGGGLVQPGGSLRLSCAASGFTFSSYAMSWVRQAPGKGLEWVSTISGSGTSTYYADSVKGRFTISRDNSKN
TLYLQMNSLRAEDTAVYYCAKSGPGLRQVGFDYWGQGTLVTVSS

>1A7[CD28]_H1.8 SEQ ID NO: 876
EVQLLESGGGLVQPGGSLRLSCAASGFTFSSYAMSWVRQAPGKGLEWVSTISGSGYSTYYADSVKGRFTISRDNSKN
TLYLQMNSLRAEDTAVYYCAKSGPGLRQVGFDYWGQGTLVTVSS

>1A7[CD28]_H1.9 SEQ ID NO: 877
EVQLLESGGGLVQPGGSLRLSCAASGFTFSSYAMSWVRQAPGKGLEWVSTISGSGDYTYYADSVKGRFTISRDNSKN
TLYLQMNSLRAEDTAVYYCAKSGPGLRQVGFDYWGQGTLVTVSS

>1A7[CD28]_H1.10 SEQ ID NO: 878
EVQLLESGGGLVQPGGSLRLSCAASGFTFSSYYMSWVRQAPGKGLEWVSTIDGSGDSTYYADSVKGRFTISRDNSKN
TLYLQMNSLRAEDTAVYYCAKSGPGLRQVGFDYWGQGTLVTVSS

>1A7[CD28]_H1.11 SEQ ID NO: 879
EVQLLESGGGLVQPGGSLRLSCAASGFTFSSYYMSWVRQAPGKGLEWVSTIEGSGDSTYYADSVKGRFTISRDNSKN
TLYLQMNSLRAEDTAVYYCAKSGPGLRQVGFDYWGQGTLVTVSS

>1A7[CD28]_H1.12 SEQ ID NO: 880
EVQLLESGGGLVQPGGSLRLSCAASGFTFSSYYMSWVRQAPGKGLEWVSTIYGSGDSTYYADSVKGRFTISRDNSKN
TLYLQMNSLRAEDTAVYYCAKSGPGLRQVGFDYWGQGTLVTVSS

>1A7[CD28]_H1.13 SEQ ID NO: 881
EVQLLESGGGLVQPGGSLRLSCAASGFTFSSYYMSWVRQAPGKGLEWVSTISDSGDSTYYADSVKGRFTISRDNSKN
TLYLQMNSLRAEDTAVYYCAKSGPGLRQVGFDYWGQGTLVTVSS

Figure 70B

>1A7[CD28]_H1.14 SEQ ID NO: 882
EVQLLESGGGLVQPGGSLRLSCAASGFTFSSYYMSWVRQAPGKGLEWVSTISESGDSTYYADSVKGRFTISRDNSKN
TLYLQMNSLRAEDTAVYYCAKSGPGLRQVGFDYWGQGTLVTVSS

>1A7[CD28]_H1.15 SEQ ID NO: 883
EVQLLESGGGLVQPGGSLRLSCAASGFTFSSYYMSWVRQAPGKGLEWVSTISGSGTSTYYADSVKGRFTISRDNSKN
TLYLQMNSLRAEDTAVYYCAKSGPGLRQVGFDYWGQGTLVTVSS

>1A7[CD28]_H1.16 SEQ ID NO: 884
EVQLLESGGGLVQPGGSLRLSCAASGFTFSSYYMSWVRQAPGKGLEWVSTISGSGYSTYYADSVKGRFTISRDNSKN
TLYLQMNSLRAEDTAVYYCAKSGPGLRQVGFDYWGQGTLVTVSS

>1A7[CD28]_H1.17 SEQ ID NO: 885
EVQLLESGGGLVQPGGSLRLSCAASGFTFSSYYMSWVRQAPGKGLEWVSTISGSGDYTYYADSVKGRFTISRDNSKN
TLYLQMNSLRAEDTAVYYCAKSGPGLRQVGFDYWGQGTLVTVSS

>1A7[CD28]_H1.18 SEQ ID NO: 886
EVQLLESGGGLVQPGGSLRLSCAASGFTFSSYAMSWVRQAPGKGLEWVSTIDDSGDSTYYADSVKGRFTISRDNSKN
TLYLQMNSLRAEDTAVYYCAKSGPGLRQVGFDYWGQGTLVTVSS

>1A7[CD28]_H1.19 SEQ ID NO: 887
EVQLLESGGGLVQPGGSLRLSCAASGFTFSSYAMSWVRQAPGKGLEWVSTIDESGDSTYYADSVKGRFTISRDNSKN
TLYLQMNSLRAEDTAVYYCAKSGPGLRQVGFDYWGQGTLVTVSS

>1A7[CD28]_H1.20 SEQ ID NO: 888
EVQLLESGGGLVQPGGSLRLSCAASGFTFSSYAMSWVRQAPGKGLEWVSTIDGSGTSTYYADSVKGRFTISRDNSKN
TLYLQMNSLRAEDTAVYYCAKSGPGLRQVGFDYWGQGTLVTVSS

>1A7[CD28]_H1.21 SEQ ID NO: 889
EVQLLESGGGLVQPGGSLRLSCAASGFTFSSYAMSWVRQAPGKGLEWVSTIDGSGYSTYYADSVKGRFTISRDNSKN
TLYLQMNSLRAEDTAVYYCAKSGPGLRQVGFDYWGQGTLVTVSS

>1A7[CD28]_H1.22 SEQ ID NO: 890
EVQLLESGGGLVQPGGSLRLSCAASGFTFSSYAMSWVRQAPGKGLEWVSTIDGSGDYTYYADSVKGRFTISRDNSKN
TLYLQMNSLRAEDTAVYYCAKSGPGLRQVGFDYWGQGTLVTVSS

>1A7[CD28]_H1.23 SEQ ID NO: 891
EVQLLESGGGLVQPGGSLRLSCAASGFTFSSYAMSWVRQAPGKGLEWVSTIEDSGDSTYYADSVKGRFTISRDNSKN
TLYLQMNSLRAEDTAVYYCAKSGPGLRQVGFDYWGQGTLVTVSS

>1A7[CD28]_H1.24 SEQ ID NO: 892
EVQLLESGGGLVQPGGSLRLSCAASGFTFSSYAMSWVRQAPGKGLEWVSTIEESGDSTYYADSVKGRFTISRDNSKN
TLYLQMNSLRAEDTAVYYCAKSGPGLRQVGFDYWGQGTLVTVSS

>1A7[CD28]_H1.25 SEQ ID NO: 893
EVQLLESGGGLVQPGGSLRLSCAASGFTFSSYAMSWVRQAPGKGLEWVSTIEGSGTSTYYADSVKGRFTISRDNSKN
TLYLQMNSLRAEDTAVYYCAKSGPGLRQVGFDYWGQGTLVTVSS

>1A7[CD28]_H1.26 SEQ ID NO: 894
EVQLLESGGGLVQPGGSLRLSCAASGFTFSSYAMSWVRQAPGKGLEWVSTIEGSGYSTYYADSVKGRFTISRDNSKN
TLYLQMNSLRAEDTAVYYCAKSGPGLRQVGFDYWGQGTLVTVSS

Figure 70C

>1A7[CD28]_H1.27 SEQ ID NO: 895
EVQLLESGGGLVQPGGSLRLSCAASGFTFSSYAMSWVRQAPGKGLEWVSTIEGSGDYTYYADSVKGRFTISRDNSKN
TLYLQMNSLRAEDTAVYYCAKSGPGLRQVGFDYWGQGTLVTVSS

>1A7[CD28]_H1.28 SEQ ID NO: 896
EVQLLESGGGLVQPGGSLRLSCAASGFTFSSYAMSWVRQAPGKGLEWVSTIYDSGDSTYYADSVKGRFTISRDNSKN
TLYLQMNSLRAEDTAVYYCAKSGPGLRQVGFDYWGQGTLVTVSS

>1A7[CD28]_H1.29 SEQ ID NO: 897
EVQLLESGGGLVQPGGSLRLSCAASGFTFSSYAMSWVRQAPGKGLEWVSTIYESGDSTYYADSVKGRFTISRDNSKN
TLYLQMNSLRAEDTAVYYCAKSGPGLRQVGFDYWGQGTLVTVSS

>1A7[CD28]_H1.30 SEQ ID NO: 898
EVQLLESGGGLVQPGGSLRLSCAASGFTFSSYAMSWVRQAPGKGLEWVSTIYGSGTSTYYADSVKGRFTISRDNSKN
TLYLQMNSLRAEDTAVYYCAKSGPGLRQVGFDYWGQGTLVTVSS

>1A7[CD28]_H1.31 SEQ ID NO: 899
EVQLLESGGGLVQPGGSLRLSCAASGFTFSSYAMSWVRQAPGKGLEWVSTIYGSGYSTYYADSVKGRFTISRDNSKN
TLYLQMNSLRAEDTAVYYCAKSGPGLRQVGFDYWGQGTLVTVSS

>1A7[CD28]_H1.32 SEQ ID NO: 900
EVQLLESGGGLVQPGGSLRLSCAASGFTFSSYAMSWVRQAPGKGLEWVSTIYGSGDYTYYADSVKGRFTISRDNSKN
TLYLQMNSLRAEDTAVYYCAKSGPGLRQVGFDYWGQGTLVTVSS

>1A7[CD28]_H1.33 SEQ ID NO: 901
EVQLLESGGGLVQPGGSLRLSCAASGFTFSSYAMSWVRQAPGKGLEWVSTISDSGTSTYYADSVKGRFTISRDNSKN
TLYLQMNSLRAEDTAVYYCAKSGPGLRQVGFDYWGQGTLVTVSS

>1A7[CD28]_H1.34 SEQ ID NO: 902
EVQLLESGGGLVQPGGSLRLSCAASGFTFSSYAMSWVRQAPGKGLEWVSTISDSGYSTYYADSVKGRFTISRDNSKN
TLYLQMNSLRAEDTAVYYCAKSGPGLRQVGFDYWGQGTLVTVSS

>1A7[CD28]_H1.35 SEQ ID NO: 903
EVQLLESGGGLVQPGGSLRLSCAASGFTFSSYAMSWVRQAPGKGLEWVSTISDSGDYTYYADSVKGRFTISRDNSKN
TLYLQMNSLRAEDTAVYYCAKSGPGLRQVGFDYWGQGTLVTVSS

>1A7[CD28]_H1.36 SEQ ID NO: 904
EVQLLESGGGLVQPGGSLRLSCAASGFTFSSYAMSWVRQAPGKGLEWVSTISESGTSTYYADSVKGRFTISRDNSKN
TLYLQMNSLRAEDTAVYYCAKSGPGLRQVGFDYWGQGTLVTVSS

>1A7[CD28]_H1.37 SEQ ID NO: 905
EVQLLESGGGLVQPGGSLRLSCAASGFTFSSYAMSWVRQAPGKGLEWVSTISESGYSTYYADSVKGRFTISRDNSKN
TLYLQMNSLRAEDTAVYYCAKSGPGLRQVGFDYWGQGTLVTVSS

>1A7[CD28]_H1.38 SEQ ID NO: 906
EVQLLESGGGLVQPGGSLRLSCAASGFTFSSYAMSWVRQAPGKGLEWVSTISESGDYTYYADSVKGRFTISRDNSKN
TLYLQMNSLRAEDTAVYYCAKSGPGLRQVGFDYWGQGTLVTVSS

>1A7[CD28]_H1.39 SEQ ID NO: 907
EVQLLESGGGLVQPGGSLRLSCAASGFTFSSYAMSWVRQAPGKGLEWVSTISGSGTYTYYADSVKGRFTISRDNSKN
TLYLQMNSLRAEDTAVYYCAKSGPGLRQVGFDYWGQGTLVTVSS

Figure 70D

>1A7[CD28]_H1.40 SEQ ID NO: 908
EVQLLESGGGLVQPGGSLRLSCAASGFTFS<u>SYAMS</u>WVRQAPGKGLEWVS<u>TISGSGYYTYYADSVKG</u>RFTISRDNSKN
TLYLQMNSLRAEDTAVYYCAK<u>SGPGLRQVGFDY</u>WGQGTLVTVSS

>1A7[CD28]_H1.41 SEQ ID NO: 909
EVQLLESGGGLVQPGGSLRLSCAASGFTFS<u>SYYMS</u>WVRQAPGKGLEWVS<u>TIEGSGDYTYYADSVKG</u>RFTISRDNSKN
TLYLQMNSLRAEDTAVYYCAK<u>SGPGLRQVGFDY</u>WGQGTLVTVSS

>1A7[CD28]_H1.42 SEQ ID NO: 910
EVQLLESGGGLVQPGGSLRLSCAASGFTFS<u>SYYMS</u>WVRQAPGKGLEWVS<u>TISESGDYTYYADSVKG</u>RFTISRDNSKN
TLYLQMNSLRAEDTAVYYCAK<u>SGPGLRQVGFDY</u>WGQGTLVTVSS

>1A7[CD28]_H1.43 SEQ ID NO: 911
EVQLLESGGGLVQPGGSLRLSCAASGFSFS<u>GNYMT</u>WVRQAPGKGLEWVA<u>TITADSDATYYADSVKG</u>RFTISRDNSKN
TLYLQMNSLRAEDTAVYYCAK<u>SGPGLRQVGFDY</u>WGQGTLVTVSS

>1A7[CD28]_H1.44 SEQ ID NO: 912
EVQLLESGGGLVQPGGSLRLSCAASGFTFS<u>GYSMN</u>WVRQAPGKGLEWVA<u>TIYANGSYTYYADSVKG</u>RFTISRDNSKN
TLYLQMNSLRAEDTAVYYCAK<u>SGPGLRQVGFDY</u>WGQGTLVTVSS

>1A7[CD28]_H1.45 SEQ ID NO: 913
EVQLLESGGGLVQPGGSLRLSCAASGFNFE<u>EYSMN</u>WVRQAPGKGLEWVA<u>TITYNGDYTYYADSVKG</u>RFTISRDNSKN
TLYLQMNSLRAEDTAVYYCAK<u>SGPGLRQVGFDY</u>WGQGTLVTVSS

>1A7[CD28]_H1.46 SEQ ID NO: 914
EVQLLESGGGLVQPGGSLRLSCAASGFSFR<u>TYYMT</u>WVRQAPGKGLEWVA<u>TITSDGDYTYYADSVKG</u>RFTISRDNSKN
TLYLQMNSLRAEDTAVYYCAK<u>SGPGLRQVGFDY</u>WGQGTLVTVSS

>1A7[CD28]_H1.47 SEQ ID NO: 915
EVQLLESGGGLVQPGGSLRLSCAASGFSFK<u>GYSMN</u>WVRQAPGKGLEWVA<u>TIYASSDSTYYADSVKG</u>RFTISRDNSKN
TLYLQMNSLRAEDTAVYYCAK<u>SGPGLRQVGFDY</u>WGQGTLVTVSS

>1A7[CD28]_H1.48 SEQ ID NO: 916
EVQLLESGGGLVQPGGSLRLSCAASGFSFG<u>EYSMN</u>WVRQAPGKGLEWVS<u>TIYADGDYTYYADSVKG</u>RFTISRDNSKN
TLYLQMNSLRAEDTAVYYCAK<u>SGPGLRQVGFDY</u>WGQGTLVTVSS

>1A7[CD28]_H1.49 SEQ ID NO: 917
EVQLLESGGGLVQPGGSLRLSCAASGFTFT<u>DYSMN</u>WVRQAPGKGLEWVA<u>TIYADSSTYYADSVKG</u>RFTISRDNSKN
TLYLQMNSLRAEDTAVYYCAK<u>SGPGLRQVGFDY</u>WGQGTLVTVSS

>1A7[CD28]_H1.50 SEQ ID NO: 918
EVQLLESGGGLVQPGGSLRLSCAASGFTFG<u>GYSMN</u>WVRQAPGKGLEWVA<u>TIYYDSTTYYADSVKG</u>RFTISRDNSKN
TLYLQMNSLRAEDTAVYYCAK<u>SGPGLRQVGFDY</u>WGQGTLVTVSS

>1A7[CD28]_H1.51 SEQ ID NO: 919
EVQLLESGGGLVQPGGSLRLSCAASGFTFG<u>AYSMN</u>WVRQAPGKGLEWVS<u>TIYNDGATTYYADSVKG</u>RFTISRDNSKN
TLYLQMNSLRAEDTAVYYCAK<u>SGPGLRQVGFDY</u>WGQGTLVTVSS

>1A7[CD28]_H1.52 SEQ ID NO: 920
EVQLLESGGGLVQPGGSLRLSCAASGFSFE<u>AYSMN</u>WVRQAPGKGLEWVA<u>TIYYDSSYTYYADSVKG</u>RFTISRDNSKN
TLYLQMNSLRAEDTAVYYCAK<u>SGPGLRQVGFDY</u>WGQGTLVTVSS

Figure 70E

>1A7[CD28]_H1.53 SEQ ID NO: 921
EVQLLESGGGLVQPGGSLRLSCAASGFSFGSYYMSWVRQAPGKGLEWVASIYYGGYDTYYADSVKGRFTISRDNSKN
TLYLQMNSLRAEDTAVYYCAKSGPGLRQVGFDYWGQGTLVTVSS

>1A7[CD28]_H1.54 SEQ ID NO: 922
EVQLLESGGGLVQPGGSLRLSCAASGFNFAEYSMSWVRQAPGKGLEWVATIYAGSDYTYYADSVKGRFTISRDNSKN
TLYLQMNSLRAEDTAVYYCAKSGPGLRQVGFDYWGQGTLVTVSS

>1A7[CD28]_H1.55 SEQ ID NO: 923
EVQLLESGGGLVQPGGSLRLSCAASGFTFGAYSINWVRQAPGKGLEWVATIYYDGSYTYYADSVKGRFTISRDNSKN
TLYLQMNSLRAEDTAVYYCAKSGPGLRQVGFDYWGQGTLVTVSS

>1A7[CD28]_H1.56 SEQ ID NO: 924
EVQLLESGGGLVQPGGSLRLSCAASGFTFSRYYINWVRQAPGKGLEWVASIYDGGADTYYADSVKGRFTISRDNSKN
TLYLQMNSLRAEDTAVYYCAKSGPGLRQVGFDYWGQGTLVTVSS

>1A7[CD28]_H1.57 SEQ ID NO: 925
EVQLLESGGGLVQPGGSLRLSCAASGFSFGTYSINWVRQAPGKGLEWVSTIYYDGASTYYADSVKGRFTISRDNSKN
TLYLQMNSLRAEDTAVYYCAKSGPGLRQVGFDYWGQGTLVTVSS

>1A7[CD28]_H1.58 SEQ ID NO: 926
EVQLLESGGGLVQPGGSLRLSCAASGFTFGKYSISWVRQAPGKGLEWVATIYNDGYYTYYADSVKGRFTISRDNSKN
TLYLQMNSLRAEDTAVYYCAKSGPGLRQVGFDYWGQGTLVTVSS

>1A7[CD28]_H1.59 SEQ ID NO: 927
EVQLLESGGGLVQPGGSLRLSCAASGFSFEKYYISWVRQAPGKGLEWVASIYDGSYDTYYADSVKGRFTISRDNSKN
TLYLQMNSLRAEDTAVYYCAKSGPGLRQVGFDYWGQGTLVTVSS

>1A7[CD28]_H1.60 SEQ ID NO: 928
EVQLLESGGGLVQPGGSLRLSCAASGFSFGTYSMNWVRQAPGKGLEWVATIDYDGSNTYYADSVKGRFTISRDNSKN
TLYLQMNSLRAEDTAVYYCAKSGPGLRQVGFDYWGQGTLVTVSS

>1A7[CD28]_H1.61 SEQ ID NO: 929
EVQLLESGGGLVQPGGSLRLSCAASGFSFAAYSMSWVRQAPGKGLEWVATIYAGSDYTYYADSVKGRFTISRDNSKN
TLYLQMNSLRAEDTAVYYCAKSGPGLRQVGFDYWGQGTLVTVSS

>1A7[CD28]_H1.62 SEQ ID NO: 930
EVQLLESGGGLVQPGGSLRLSCAASGFTFTTYSMTWVRQAPGKGLEWVATIYNDGYYTYYADSVKGRFTISRDNSKN
TLYLQMNSLRAEDTAVYYCAKSGPGLRQVGFDYWGQGTLVTVSS

>1A7[CD28]_H1.63 SEQ ID NO: 931
EVQLLESGGGLVQPGGSLRLSCAASGFSFKDYSMNWVRQAPGKGLEWVATIYYDGTYTYYADSVKGRFTISRDNSKN
TLYLQMNSLRAEDTAVYYCAKSGPGLRQVGFDYWGQGTLVTVSS

>1A7[CD28]_H1.64 SEQ ID NO: 932
EVQLLESGGGLVQPGGSLRLSCAASGFSFAAYSMNWVRQAPGKGLEWVATIYAGGAYTYYADSVKGRFTISRDNSKN
TLYLQMNSLRAEDTAVYYCAKSGPGLRQVGFDYWGQGTLVTVSS

>1A7[CD28]_H1.65 SEQ ID NO: 933
EVQLLESGGGLVQPGGSLRLSCAASGFNFAEYYISWVRQAPGKGLEWVASIYNGGSDTYYADSVKGRFTISRDNSKN
TLYLQMNSLRAEDTAVYYCAKSGPGLRQVGFDYWGQGTLVTVSS

Figure 70F

>1A7[CD28]_H1.66 SEQ ID NO: 934
EVQLLESGGGLVQPGGSLRLSCAASGFSLGEYYMNWVRQAPGKGLEWVSTIDYDGTYTYYADSVKGRFTISRDNSKN
TLYLQMNSLRAEDTAVYYCAKSGPGLRQVGFDYWGQGTLVTVSS

>1A7[CD28]_H1.67 SEQ ID NO: 935
EVQLLESGGGLVQPGGSLRLSCAASGFTFNEYYITWVRQAPGKGLEWVSSIYSSSYDTYYADSVKGRFTISRDNSKN
TLYLQMNSLRAEDTAVYYCAKSGPGLRQVGFDYWGQGTLVTVSS

>1A7[CD28]_H1.68 SEQ ID NO: 936
EVQLLESGGGLVQPGGSLRLSCAASGFTFKDYYITWVRQAPGKGLEWVSSIYTSGYDTYYADSVKGRFTISRDNSKN
TLYLQMNSLRAEDTAVYYCAKSGPGLRQVGFDYWGQGTLVTVSS

>1A7[CD28]_H1.69 SEQ ID NO: 937
EVQLLESGGGLVQPGGSLRLSCAASGFSFGKYSINWVRQAPGKGLEWVATIYSDGTDTYYADSVKGRFTISRDNSKN
TLYLQMNSLRAEDTAVYYCAKSGPGLRQVGFDYWGQGTLVTVSS

Figure 71A

>1A7[CD28]_L1.1 SEQ ID NO: 938
DIQMTQSPSSLSASVGDRVTITCRASQSISAYLNWYQQKPGKAPKLLIYAASSLQSGVPSRFSGSGSGTDFTLTISS
LQPEDFATYYCQQSYSTPFTFGQGTKLEIK

>1A7[CD28]_L1.2 SEQ ID NO: 939
DIQMTQSPSSLSASVGDRVTITCRASQSISDYLNWYQQKPGKAPKLLIYAASSLQSGVPSRFSGSGSGTDFTLTISS
LQPEDFATYYCQQSYSTPFTFGQGTKLEIK

>1A7[CD28]_L1.3 SEQ ID NO: 940
DIQMTQSPSSLSASVGDRVTITCRASQSISGYLNWYQQKPGKAPKLLIYAASSLQSGVPSRFSGSGSGTDFTLTISS
LQPEDFATYYCQQSYSTPFTFGQGTKLEIK

>1A7[CD28]_L1.4 SEQ ID NO: 941
DIQMTQSPSSLSASVGDRVTITCRASQSISHYLNWYQQKPGKAPKLLIYAASSLQSGVPSRFSGSGSGTDFTLTISS
LQPEDFATYYCQQSYSTPFTFGQGTKLEIK

>1A7[CD28]_L1.5 SEQ ID NO: 942
DIQMTQSPSSLSASVGDRVTITCRASQSISKYLNWYQQKPGKAPKLLIYAASSLQSGVPSRFSGSGSGTDFTLTISS
LQPEDFATYYCQQSYSTPFTFGQGTKLEIK

>1A7[CD28]_L1.6 SEQ ID NO: 943
DIQMTQSPSSLSASVGDRVTITCRASQSISNYLNWYQQKPGKAPKLLIYAASSLQSGVPSRFSGSGSGTDFTLTISS
LQPEDFATYYCQQSYSTPFTFGQGTKLEIK

>1A7[CD28]_L1.7 SEQ ID NO: 944
DIQMTQSPSSLSASVGDRVTITCRASQSISQYLNWYQQKPGKAPKLLIYAASSLQSGVPSRFSGSGSGTDFTLTISS
LQPEDFATYYCQQSYSTPFTFGQGTKLEIK

>1A7[CD28]_L1.8 SEQ ID NO: 945
DIQMTQSPSSLSASVGDRVTITCRASQSISTYLNWYQQKPGKAPKLLIYAASSLQSGVPSRFSGSGSGTDFTLTISS
LQPEDFATYYCQQSYSTPFTFGQGTKLEIK

>1A7[CD28]_L1.9 SEQ ID NO: 946
DIQMTQSPSSLSASVGDRVTITCRASQSISVYLNWYQQKPGKAPKLLIYAASSLQSGVPSRFSGSGSGTDFTLTISS
LQPEDFATYYCQQSYSTPFTFGQGTKLEIK

>1A7[CD28]_L1.10 SEQ ID NO: 947
DIQMTQSPSSLSASVGDRVTITCRASQSISYYLNWYQQKPGKAPKLLIYAASSLQSGVPSRFSGSGSGTDFTLTISS
LQPEDFATYYCQQSYSTPFTFGQGTKLEIK

>1A7[CD28]_L1.11 SEQ ID NO: 948
DIQMTQSPSSLSASVGDRVTITCRASQSISSALNWYQQKPGKAPKLLIYAASSLQSGVPSRFSGSGSGTDFTLTISS
LQPEDFATYYCQQSYSTPFTFGQGTKLEIK

>1A7[CD28]_L1.12 SEQ ID NO: 949
DIQMTQSPSSLSASVGDRVTITCRASQSISSDLNWYQQKPGKAPKLLIYAASSLQSGVPSRFSGSGSGTDFTLTISS
LQPEDFATYYCQQSYSTPFTFGQGTKLEIK

>1A7[CD28]_L1.13 SEQ ID NO: 950
DIQMTQSPSSLSASVGDRVTITCRASQSISSFLNWYQQKPGKAPKLLIYAASSLQSGVPSRFSGSGSGTDFTLTISS
LQPEDFATYYCQQSYSTPFTFGQGTKLEIK

Figure 71B

>1A7[CD28]_L1.14 SEQ ID NO: 951
DIQMTQSPSSLSASVGDRVTITC<u>RASQSISSHLN</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.15 SEQ ID NO: 952
DIQMTQSPSSLSASVGDRVTITC<u>RASQSISSKLN</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.16 SEQ ID NO: 953
DIQMTQSPSSLSASVGDRVTITC<u>RASQSISSLLN</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.17 SEQ ID NO: 954
DIQMTQSPSSLSASVGDRVTITC<u>RASQSISSNLN</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.18 SEQ ID NO: 955
DIQMTQSPSSLSASVGDRVTITC<u>RASQSISSQLN</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.19 SEQ ID NO: 956
DIQMTQSPSSLSASVGDRVTITC<u>RASQSISSSLN</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.20 SEQ ID NO: 957
DIQMTQSPSSLSASVGDRVTITC<u>RASQSISSWLN</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.21 SEQ ID NO: 958
DIQMTQSPSSLSASVGDRVTITC<u>RASQSISSYLA</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.22 SEQ ID NO: 959
DIQMTQSPSSLSASVGDRVTITC<u>RASQSISSYLD</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.23 SEQ ID NO: 960
DIQMTQSPSSLSASVGDRVTITC<u>RASQSISSYLG</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.24 SEQ ID NO: 961
DIQMTQSPSSLSASVGDRVTITC<u>RASQSISSYLH</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.25 SEQ ID NO: 962
DIQMTQSPSSLSASVGDRVTITC<u>RASQSISSYLQ</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.26 SEQ ID NO: 963
DIQMTQSPSSLSASVGDRVTITC<u>RASQSISSYLS</u>WYQQKPGKAPKLLIY<u>AASSLQS</u>GVPSRFSGSGSGTDFTLTISS
LQPEDFATYYC<u>QQSYSTPFT</u>FGQGTKLEIK

Figure 71C

>1A7[CD28]_L1.27 SEQ ID NO: 964
DIQMTQSPSSLSASVGDRVTITC<u>RASQSISSYLT</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.28 SEQ ID NO: 965
DIQMTQSPSSLSASVGDRVTITC<u>RASQSISSYLY</u>WYQQKPGKAPKLLIY<u>AASSLQS</u>GVPSRFSGSGSGTDFTLTISS
LQPEDFATYYC<u>QQSYSTPFT</u>FGQGTKLEIK

>1A7[CD28]_L1.29 SEQ ID NO: 966
DIQMTQSPSSLSASVGDRVTITC<u>RASQSISSYLN</u>WYQQKPGKAPKLLIY<u>DASSLQS</u>GVPSRFSGSGSGTDFTLTISS
LQPEDFATYYC<u>QQSYSTPFT</u>FGQGTKLEIK

>1A7[CD28]_L1.30 SEQ ID NO: 967
DIQMTQSPSSLSASVGDRVTITC<u>RASQSISSYLN</u>WYQQKPGKAPKLLIY<u>GASSLQS</u>GVPSRFSGSGSGTDFTLTISS
LQPEDFATYYC<u>QQSYSTPFT</u>FGQGTKLEIK

>1A7[CD28]_L1.31 SEQ ID NO: 968
DIQMTQSPSSLSASVGDRVTITC<u>RASQSISSYLN</u>WYQQKPGKAPKLLIY<u>KASSLQS</u>GVPSRFSGSGSGTDFTLTISS
LQPEDFATYYC<u>QQSYSTPFT</u>FGQGTKLEIK

>1A7[CD28]_L1.32 SEQ ID NO: 969
DIQMTQSPSSLSASVGDRVTITC<u>RASQSISSYLN</u>WYQQKPGKAPKLLIY<u>LASSLQS</u>GVPSRFSGSGSGTDFTLTISS
LQPEDFATYYC<u>QQSYSTPFT</u>FGQGTKLEIK

>1A7[CD28]_L1.33 SEQ ID NO: 970
DIQMTQSPSSLSASVGDRVTITC<u>RASQSISSYLN</u>WYQQKPGKAPKLLIY<u>QASSLQS</u>GVPSRFSGSGSGTDFTLTISS
LQPEDFATYYC<u>QQSYSTPFT</u>FGQGTKLEIK

>1A7[CD28]_L1.34 SEQ ID NO: 971
DIQMTQSPSSLSASVGDRVTITC<u>RASQSISSYLN</u>WYQQKPGKAPKLLIY<u>SASSLQS</u>GVPSRFSGSGSGTDFTLTISS
LQPEDFATYYC<u>QQSYSTPFT</u>FGQGTKLEIK

>1A7[CD28]_L1.35 SEQ ID NO: 972
DIQMTQSPSSLSASVGDRVTITC<u>RASQSISSYLN</u>WYQQKPGKAPKLLIY<u>TASSLQS</u>GVPSRFSGSGSGTDFTLTISS
LQPEDFATYYC<u>QQSYSTPFT</u>FGQGTKLEIK

>1A7[CD28]_L1.36 SEQ ID NO: 973
DIQMTQSPSSLSASVGDRVTITC<u>RASQSISSYLN</u>WYQQKPGKAPKLLIY<u>WASSLQS</u>GVPSRFSGSGSGTDFTLTISS
LQPEDFATYYC<u>QQSYSTPFT</u>FGQGTKLEIK

>1A7[CD28]_L1.37 SEQ ID NO: 974
DIQMTQSPSSLSASVGDRVTITC<u>RASQSISSYLN</u>WYQQKPGKAPKLLIY<u>YASSLQS</u>GVPSRFSGSGSGTDFTLTISS
LQPEDFATYYC<u>QQSYSTPFT</u>FGQGTKLEIK

>1A7[CD28]_L1.38 SEQ ID NO: 975
DIQMTQSPSSLSASVGDRVTITC<u>RASQSISSYLN</u>WYQQKPGKAPKLLIY<u>AASALQS</u>GVPSRFSGSGSGTDFTLTISS
LQPEDFATYYC<u>QQSYSTPFT</u>FGQGTKLEIK

>1A7[CD28]_L1.39 SEQ ID NO: 976
DIQMTQSPSSLSASVGDRVTITC<u>RASQSISSYLN</u>WYQQKPGKAPKLLIY<u>AASDLQS</u>GVPSRFSGSGSGTDFTLTISS
LQPEDFATYYC<u>QQSYSTPFT</u>FGQGTKLEIK

Figure 71D

>1A7[CD28]_L1.40 SEQ ID NO: 977
DIQMTQSPSSLSASVGDRVTITCRASQSISSYLNWYQQKPGKAPKLLIYAASKLQSGVPSRFSGSGSGTDFTLTISS
LQPEDFATYYCQQSYSTPFTFGQGTKLEIK

>1A7[CD28]_L1.41 SEQ ID NO: 978
DIQMTQSPSSLSASVGDRVTITCRASQSISSYLNWYQQKPGKAPKLLIYAASNLQSGVPSRFSGSGSGTDFTLTISS
LQPEDFATYYCQQSYSTPFTFGQGTKLEIK

>1A7[CD28]_L1.42 SEQ ID NO: 979
DIQMTQSPSSLSASVGDRVTITCRASQSISSYLNWYQQKPGKAPKLLIYAASQLQSGVPSRFSGSGSGTDFTLTISS
LQPEDFATYYCQQSYSTPFTFGQGTKLEIK

>1A7[CD28]_L1.43 SEQ ID NO: 980
DIQMTQSPSSLSASVGDRVTITCRASQSISSYLNWYQQKPGKAPKLLIYAASTLQSGVPSRFSGSGSGTDFTLTISS
LQPEDFATYYCQQSYSTPFTFGQGTKLEIK

>1A7[CD28]_L1.44 SEQ ID NO: 981
DIQMTQSPSSLSASVGDRVTITCRASQSISSYLNWYQQKPGKAPKLLIYAASYLQSGVPSRFSGSGSGTDFTLTISS
LQPEDFATYYCQQSYSTPFTFGQGTKLEIK

>1A7[CD28]_L1.45 SEQ ID NO: 982
DIQMTQSPSSLSASVGDRVTITCRASQSISSYLNWYQQKPGKAPKLLIYAASSLASGVPSRFSGSGSGTDFTLTISS
LQPEDFATYYCQQSYSTPFTFGQGTKLEIK

>1A7[CD28]_L1.46 SEQ ID NO: 983
DIQMTQSPSSLSASVGDRVTITCRASQSISSYLNWYQQKPGKAPKLLIYAASSLESGVPSRFSGSGSGTDFTLTISS
LQPEDFATYYCQQSYSTPFTFGQGTKLEIK

>1A7[CD28]_L1.47 SEQ ID NO: 984
DIQMTQSPSSLSASVGDRVTITCRASQSISSYLNWYQQKPGKAPKLLIYAASSLFSGVPSRFSGSGSGTDFTLTISS
LQPEDFATYYCQQSYSTPFTFGQGTKLEIK

>1A7[CD28]_L1.48 SEQ ID NO: 985
DIQMTQSPSSLSASVGDRVTITCRASQSISSYLNWYQQKPGKAPKLLIYAASSLHSGVPSRFSGSGSGTDFTLTISS
LQPEDFATYYCQQSYSTPFTFGQGTKLEIK

>1A7[CD28]_L1.49 SEQ ID NO: 986
DIQMTQSPSSLSASVGDRVTITCRASQSISSYLNWYQQKPGKAPKLLIYAASSLISGVPSRFSGSGSGTDFTLTISS
LQPEDFATYYCQQSYSTPFTFGQGTKLEIK

>1A7[CD28]_L1.50 SEQ ID NO: 987
DIQMTQSPSSLSASVGDRVTITCRASQSISSYLNWYQQKPGKAPKLLIYAASSLKSGVPSRFSGSGSGTDFTLTISS
LQPEDFATYYCQQSYSTPFTFGQGTKLEIK

>1A7[CD28]_L1.51 SEQ ID NO: 988
DIQMTQSPSSLSASVGDRVTITCRASQSISSYLNWYQQKPGKAPKLLIYAASSLNSGVPSRFSGSGSGTDFTLTISS
LQPEDFATYYCQQSYSTPFTFGQGTKLEIK

>1A7[CD28]_L1.52 SEQ ID NO: 989
DIQMTQSPSSLSASVGDRVTITCRASQSISSYLNWYQQKPGKAPKLLIYAASSLSSGVPSRFSGSGSGTDFTLTISS
LQPEDFATYYCQQSYSTPFTFGQGTKLEIK

Figure 71E

>1A7[CD28]_L1.53 SEQ ID NO: 990
DIQMTQSPSSLSASVGDRVTITCRASQSISSYLNWYQQKPGKAPKLLIYAASSLVSGVPSRFSGSGSGTDFTLTISS
LQPEDFATYYCQQSYSTPFTFGQGTKLEIK

>1A7[CD28]_L1.54 SEQ ID NO: 991
DIQMTQSPSSLSASVGDRVTITCRASQSISSYLNWYQQKPGKAPKLLIYAASSLYSGVPSRFSGSGSGTDFTLTISS
LQPEDFATYYCQQSYSTPFTFGQGTKLEIK

>1A7[CD28]_L1.55 SEQ ID NO: 992
DIQMTQSPSSLSASVGDRVTITCRASQSISSYLNWYQQKPGKAPKLLIYAASSLQAGVPSRFSGSGSGTDFTLTISS
LQPEDFATYYCQQSYSTPFTFGQGTKLEIK

>1A7[CD28]_L1.56 SEQ ID NO: 993
DIQMTQSPSSLSASVGDRVTITCRASQSISSYLNWYQQKPGKAPKLLIYAASSLQDGVPSRFSGSGSGTDFTLTISS
LQPEDFATYYCQQSYSTPFTFGQGTKLEIK

>1A7[CD28]_L1.57 SEQ ID NO: 994
DIQMTQSPSSLSASVGDRVTITCRASQSISSYLNWYQQKPGKAPKLLIYAASSLQGGVPSRFSGSGSGTDFTLTISS
LQPEDFATYYCQQSYSTPFTFGQGTKLEIK

>1A7[CD28]_L1.58 SEQ ID NO: 995
DIQMTQSPSSLSASVGDRVTITCRASQSISSYLNWYQQKPGKAPKLLIYAASSLQHGVPSRFSGSGSGTDFTLTISS
LQPEDFATYYCQQSYSTPFTFGQGTKLEIK

>1A7[CD28]_L1.59 SEQ ID NO: 996
DIQMTQSPSSLSASVGDRVTITCRASQSISSYLNWYQQKPGKAPKLLIYAASSLQKGVPSRFSGSGSGTDFTLTISS
LQPEDFATYYCQQSYSTPFTFGQGTKLEIK

>1A7[CD28]_L1.60 SEQ ID NO: 997
DIQMTQSPSSLSASVGDRVTITCRASQSISSYLNWYQQKPGKAPKLLIYAASSLQQGVPSRFSGSGSGTDFTLTISS
LQPEDFATYYCQQSYSTPFTFGQGTKLEIK

>1A7[CD28]_L1.61 SEQ ID NO: 998
DIQMTQSPSSLSASVGDRVTITCRASQSISSYLNWYQQKPGKAPKLLIYAASSLQTGVPSRFSGSGSGTDFTLTISS
LQPEDFATYYCQQSYSTPFTFGQGTKLEIK

>1A7[CD28]_L1.62 SEQ ID NO: 999
DIQMTQSPSSLSASVGDRVTITCRASQSISSYLNWYQQKPGKAPKLLIYAASSLQVGVPSRFSGSGSGTDFTLTISS
LQPEDFATYYCQQSYSTPFTFGQGTKLEIK

>1A7[CD28]_L1.63 SEQ ID NO: 1000
DIQMTQSPSSLSASVGDRVTITCRASQSISSYLNWYQQKPGKAPKLLIYAASSLQYGVPSRFSGSGSGTDFTLTISS
LQPEDFATYYCQQSYSTPFTFGQGTKLEIK

>1A7[CD28]_L1.64 SEQ ID NO: 1001
DIQMTQSPSSLSASVGDRVTITCRASQSISSYLNWYQQKPGKAPKLLIYAASSLQSGVPSRFSGSGSGTDFTLTISS
LQPEDFATYYCQQAYSTPFTFGQGTKLEIK

>1A7[CD28]_L1.65 SEQ ID NO: 1002
DIQMTQSPSSLSASVGDRVTITCRASQSISSYLNWYQQKPGKAPKLLIYAASSLQSGVPSRFSGSGSGTDFTLTISS
LQPEDFATYYCQQDYSTPFTFGQGTKLEIK

Figure 71F

>1A7[CD28]_L1.66 SEQ ID NO: 1003
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQFYSTPFT</u>FGQGTKLEIK

>1A7[CD28]_L1.67 SEQ ID NO: 1004
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQHYSTPFT</u>FGQGTKLEIK

>1A7[CD28]_L1.68 SEQ ID NO: 1005
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQKYSTPFT</u>FGQGTKLEIK

>1A7[CD28]_L1.69 SEQ ID NO: 1006
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQLYSTPFT</u>FGQGTKLEIK

>1A7[CD28]_L1.70 SEQ ID NO: 1007
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQTYSTPFT</u>FGQGTKLEIK

>1A7[CD28]_L1.71 SEQ ID NO: 1008
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQVYSTPFT</u>FGQGTKLEIK

>1A7[CD28]_L1.72 SEQ ID NO: 1009
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQYYSTPFT</u>FGQGTKLEIK

>1A7[CD28]_L1.73 SEQ ID NO: 1010
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSASTPFT</u>FGQGTKLEIK

>1A7[CD28]_L1.74 SEQ ID NO: 1011
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSDSTPFT</u>FGQGTKLEIK

>1A7[CD28]_L1.75 SEQ ID NO: 1012
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSFSTPFT</u>FGQGTKLEIK

>1A7[CD28]_L1.76 SEQ ID NO: 1013
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSHSTPFT</u>FGQGTKLEIK

>1A7[CD28]_L1.77 SEQ ID NO: 1014
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSKSTPFT</u>FGQGTKLEIK

>1A7[CD28]_L1.78 SEQ ID NO: 1015
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSLSTPFT</u>FGQGTKLEIK

Figure 71G

>1A7[CD28]_L1.79 SEQ ID NO: 1016
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSQSTPFT</u>FGQGTKLEIK

>1A7[CD28]_L1.80 SEQ ID NO: 1017
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSVSTPFT</u>FGQGTKLEIK

>1A7[CD28]_L1.81 SEQ ID NO: 1018
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSWSTPFT</u>FGQGTKLEIK

>1A7[CD28]_L1.82 SEQ ID NO: 1019
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSYATPFT</u>FGQGTKLEIK

>1A7[CD28]_L1.83 SEQ ID NO: 1020
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSYDTPFT</u>FGQGTKLEIK

>1A7[CD28]_L1.84 SEQ ID NO: 1021
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSYGTPFT</u>FGQGTKLEIK

>1A7[CD28]_L1.85 SEQ ID NO: 1022
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSYHTPFT</u>FGQGTKLEIK

>1A7[CD28]_L1.86 SEQ ID NO: 1023
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSYKTPFT</u>FGQGTKLEIK

>1A7[CD28]_L1.87 SEQ ID NO: 1024
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSYNTPFT</u>FGQGTKLEIK

>1A7[CD28]_L1.88 SEQ ID NO: 1025
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSYQTPFT</u>FGQGTKLEIK

>1A7[CD28]_L1.89 SEQ ID NO: 1026
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSYTTPFT</u>FGQGTKLEIK

>1A7[CD28]_L1.90 SEQ ID NO: 1027
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSYVTPFT</u>FGQGTKLEIK

>1A7[CD28]_L1.91 SEQ ID NO: 1028
DIQMTQSPSSLSASVGDRVTITC<u>RASQSISSYLN</u>WYQQKPGKAPKLLIY<u>AASSLQS</u>GVPSRFSGSGSGTDFTLTISS
LQPEDFATYYC<u>QQSYYTPFT</u>FGQGTKLEIK

Figure 71H

>1A7[CD28]_L1.92 SEQ ID NO: 1029
DIQMTQSPSSLSASVGDRVTITCRASQSISSYLNWYQQKPGKAPKLLIYAASSLQSGVPSRFSGSGSGTDFTLTISS
LQPEDFATYYCQQSYSAPFTFGQGTKLEIK

>1A7[CD28]_L1.93 SEQ ID NO: 1030
DIQMTQSPSSLSASVGDRVTITCRASQSISSYLNWYQQKPGKAPKLLIYAASSLQSGVPSRFSGSGSGTDFTLTISS
LQPEDFATYYCQQSYSDPFTFGQGTKLEIK

>1A7[CD28]_L1.94 SEQ ID NO: 1031
DIQMTQSPSSLSASVGDRVTITCRASQSISSYLNWYQQKPGKAPKLLIYAASSLQSGVPSRFSGSGSGTDFTLTISS
LQPEDFATYYCQQSYSFPFTFGQGTKLEIK

>1A7[CD28]_L1.95 SEQ ID NO: 1032
DIQMTQSPSSLSASVGDRVTITCRASQSISSYLNWYQQKPGKAPKLLIYAASSLQSGVPSRFSGSGSGTDFTLTISS
LQPEDFATYYCQQSYSIPFTFGQGTKLEIK

>1A7[CD28]_L1.96 SEQ ID NO: 1033
DIQMTQSPSSLSASVGDRVTITCRASQSISSYLNWYQQKPGKAPKLLIYAASSLQSGVPSRFSGSGSGTDFTLTISS
LQPEDFATYYCQQSYSKPFTFGQGTKLEIK

>1A7[CD28]_L1.97 SEQ ID NO: 1034
DIQMTQSPSSLSASVGDRVTITCRASQSISSYLNWYQQKPGKAPKLLIYAASSLQSGVPSRFSGSGSGTDFTLTISS
LQPEDFATYYCQQSYSLPFTFGQGTKLEIK

>1A7[CD28]_L1.98 SEQ ID NO: 1035
DIQMTQSPSSLSASVGDRVTITCRASQSISSYLNWYQQKPGKAPKLLIYAASSLQSGVPSRFSGSGSGTDFTLTISS
LQPEDFATYYCQQSYSQPFTFGQGTKLEIK

>1A7[CD28]_L1.99 SEQ ID NO: 1036
DIQMTQSPSSLSASVGDRVTITCRASQSISSYLNWYQQKPGKAPKLLIYAASSLQSGVPSRFSGSGSGTDFTLTISS
LQPEDFATYYCQQSYSSPFTFGQGTKLEIK

>1A7[CD28]_L1.100 SEQ ID NO: 1037
DIQMTQSPSSLSASVGDRVTITCRASQSISSYLNWYQQKPGKAPKLLIYAASSLQSGVPSRFSGSGSGTDFTLTISS
LQPEDFATYYCQQSYSVPFTFGQGTKLEIK

>1A7[CD28]_L1.101 SEQ ID NO: 1038
DIQMTQSPSSLSASVGDRVTITCRASQSISSYLNWYQQKPGKAPKLLIYAASSLQSGVPSRFSGSGSGTDFTLTISS
LQPEDFATYYCQQSYSYPFTFGQGTKLEIK

>1A7[CD28]_L1.102 SEQ ID NO: 1039
DIQMTQSPSSLSASVGDRVTITCRASQSISSYLNWYQQKPGKAPKLLIYAASSLQSGVPSRFSGSGSGTDFTLTISS
LQPEDFATYYCQQSYSTPITFGQGTKLEIK

>1A7[CD28]_L1.103 SEQ ID NO: 1040
DIQMTQSPSSLSASVGDRVTITCRASQSISSYLNWYQQKPGKAPKLLIYAASSLQSGVPSRFSGSGSGTDFTLTISS
LQPEDFATYYCQQSYSTPLTFGQGTKLEIK

>1A7[CD28]_L1.104 SEQ ID NO: 1041
DIQMTQSPSSLSASVGDRVTITCRASQSISSYLNWYQQKPGKAPKLLIYAASSLQSGVPSRFSGSGSGTDFTLTISS
LQPEDFATYYCQQSYSTPWTFGQGTKLEIK

Figure 71I

>1A7[CD28]_L1.105 SEQ ID NO: 1042
DIQMTQSPSSLSASVGDRVTITCRASQSISSYLTWYQQKPGKAPKLLIYAASSLQSGVPSRFSGSGSGTDFTLTISS
LQPEDFATYYCQQVYSTPFTFGQGTKLEIK

>1A7[CD28]_L1.106 SEQ ID NO: 1043
DIQMTQSPSSLSASVGDRVTITCRASQSISSYLTWYQQKPGKAPKLLIYAASSLQSGVPSRFSGSGSGTDFTLTISS
LQPEDFATYYCQQSYNTPFTFGQGTKLEIK

ANTI-CD28 X ANTI-PSMA ANTIBODIES

PRIORITY CLAIM

This application claims priority to and benefit of U.S. Provisional Application No. 63/313,233, filed on Feb. 23, 2022, the contents of which are hereby incorporated by reference in their entirety.

SEQUENCE LISTING

The instant application contains a Sequence Listing which has been submitted electronically in XML format and is hereby incorporated by reference in its entirety. Said XML copy, created on Feb. 22, 2023, is named 067461-5297-WO_SL.xml and is 1,295,846 bytes in size.

BACKGROUND

Prostate cancer (PC) is one of the most prevalent cancers in men, and end stage (castration-resistant prostate cancer) has no curative treatment option. Prostate Specific Membrane Antigen (PSMA), a type II transmembrane protein with a large extracellular domain, has long generated interest as a therapeutic target. PSMA is highly overexpressed in PC compared to normal tissue, and its expression has been shown to correlate with malignancy. Previous attempts to target PSMA include antibody-based radiotherapy and antibody drug conjugates, which have shown some success but can be hampered by the inherent toxicity of the modality.

Antibody-based therapeutics have been used successfully to treat a variety of diseases, including cancer. An increasingly prevalent avenue being explored is the engineering of single immunoglobulin molecules that co-engage two different antigens. Such alternate antibody formats that engage two different antigens are often referred to as bispecific antibodies. One particular approach for bispecific antibodies is to engineer a first binding domain which engages CD3 and a second binding domain which engages an antigen associated with or upregulated on cancer cells (e.g., PSMA) so that the bispecific antibody redirects CD3+ T cells to destroy the cancer cells.

TILs, however, lose their cytotoxic ability over time due to upregulation of inhibitory immune checkpoints. While checkpoint blockade has demonstrated increased clinical response rates relative to other treatment options, many patients still fail to achieve a response to checkpoint blockade. Engagement of costimulatory receptors on TILs could provide a positive signal capable of overcoming negative signals of immune checkpoints. Preclinical and clinical studies of agonistic costimulatory receptor antibodies have indeed demonstrated that agonism of costimulatory receptors can result in impressive anti-tumor responses, activating T cells to attack tumor cells.

It is also important for cancer therapy to enhance anti-tumor activity by specifically destroying tumor cells while minimizing peripheral toxicity. In this context, it is crucial that only T cells in the presence of the target tumor cells are provided a costimulatory signal. However, agonism of costimulatory receptors with monospecific full-length antibodies is likely nondiscriminatory with regards to TILs vs. peripheral T cells vs. autoantigen-reactive T cells that contribute to autoimmune toxicities. Thus, there remains a need for novel immune response enhancing compositions for the treatment of cancers, including PSMA-associated cancers.

SUMMARY

Provided herein are novel anti-CD28× anti-PSMA antibodies and methods of using such antibodies for the treatment of PSMA-associated cancers. Subject anti-CD28× anti-PSMA antibodies are capable of agonistically binding to CD28 costimulatory molecules on T cells and PSMA on tumor cells. Thus, such antibodies selectively enhance anti-tumor activity at tumor sites while minimizing peripheral toxicity. The subject antibodies provided herein are particularly useful in combination with other anti-cancer therapies (e.g., anti-CD3× anti-PSMA antibodies) for the treatment of prostate cancers.

In a first aspect, provided herein are heterodimeric anti-CD28× anti-PSMA antibodies in the 1+1 Fab-scFv-Fc format. These antibodies comprise: a) a first monomer; b) a second monomer; and c) a light chain. The first monomer comprises: i) a single chain variable fragment (scFv); and ii) a first Fc domain, wherein the scFv is covalently attached to the N-terminus of the first Fc domain using a domain linker. The second monomer comprises, from N-terminal to C-terminal, a VH1-CH1-hinge-CH2-CH3, wherein VH1 is a first variable heavy domain and CH2-CH3 is a second Fc domain. The light chain comprises, from N-terminal to C-terminal, VL1-CL, wherein VL1 is a first variable light domain and CL is a constant light domain. The scFv comprises a second VH domain (VH2), a scFv linker, and a second variable light domain (VL2). The VH1 and the VL1 together form a first antigen binding domain (ABD) and the VH2 and the VL2 together form a second ABD, Further, one of the first ABD and second ABD binds CD28 and the other of the first ABD and second ABD binds Prostate Specific Membrane Antigen (PSMA).

In some embodiments, the first ABD binds human CD28 and the second ABD binds PSMA. In certain embodiments, the first ABD binds PSMA and the second ABD binds human CD28.

In some embodiments, the scFv comprises, from N-terminal to C-terminal, VH2-scFv linker-VL2. In certain embodiments, the scFv comprises, from N-terminal to C-terminal, VL2-scFv linker-VH2.

In some embodiments, the first ABD binds to human PSMA, and VH1 and VL1 are selected from the following:
 (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:206; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:210; or
 (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:214; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:218; or
 (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:222; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:226; or
 (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:230;

and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:234; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:238; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:242; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:246; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:250; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:254; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:258; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:262; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:266; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:270; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:274; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:278; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:282; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 286; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:290; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:294; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:298; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:302; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:306; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:310; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:314; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:318; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:322; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:326; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:330; or (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:334; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:338.

In some embodiments, VH1 and VL1 are selected from the following:

(i) a VH1 comprising a vhCDR1 having an amino acid sequence of SEQ ID NO:207; a vhCDR2 having an amino acid sequence of SEQ ID NO:208; and a vhCDR3 having an amino acid sequence of SEQ ID NO:209; and (ii) a VL1 comprising a vlCDR1 having an amino acid sequence of SEQ ID NO:211, a vlCDR2 having an amino acid sequence of SEQ ID NO: 212, and a vlCDR3 having an amino acid sequence of SEQ ID NO:213; or (i) a VH1 comprising a vhCDR1 having an amino acid sequence of SEQ ID NO:215; a vhCDR2 having an amino acid sequence of SEQ ID NO:216; and a vhCDR3 having an amino acid sequence of SEQ ID NO:217; and (ii) a VL1 comprising a vlCDR1 having an amino acid sequence of SEQ ID NO:219, a vlCDR2 having an amino acid sequence of SEQ ID NO: 220, and a vlCDR3 having an amino acid sequence of SEQ ID NO:221;

(i) a VH1 comprising a vhCDR1 having an amino acid sequence of SEQ ID NO:223; a vhCDR2 having an amino acid sequence of SEQ ID NO:224; and a vhCDR3 having an amino acid sequence of SEQ ID NO:225; and (ii) a VL1 comprising a vlCDR1 having an amino acid sequence of SEQ ID NO:227, a vlCDR2 having an amino acid sequence of SEQ ID NO: 228, and a vlCDR3 having an amino acid sequence of SEQ ID NO:229; or (i) a VH1 comprising a vhCDR1 having an amino acid sequence of SEQ ID NO:231; a vhCDR2 having an amino acid sequence of SEQ ID NO:232; and a vhCDR3 having an amino acid sequence of SEQ ID NO:233; and (ii) a VL1 comprising a vlCDR1 having an amino acid sequence of SEQ ID NO:235, a vlCDR2 having an amino acid sequence of SEQ ID NO: 236, and a vlCDR3 having an amino acid sequence of SEQ ID NO:237; or (i) a VH1 comprising a vhCDR1 having an amino acid sequence of SEQ ID NO:239; a vhCDR2 having an amino acid sequence of SEQ ID NO:240; and a vhCDR3 having an amino acid sequence of SEQ ID NO:241; and (ii) a VL1 comprising a vlCDR1 having an amino acid sequence of SEQ ID NO:243, a vlCDR2 having an amino acid sequence of SEQ ID NO: 244, and a vlCDR3 having an amino acid sequence of SEQ ID NO:245; or (i) a VH1 comprising a vhCDR1 having an amino acid sequence of SEQ ID NO:247; a vhCDR2 having an amino acid sequence of SEQ ID NO:248; and a vhCDR3 having an amino acid sequence of SEQ ID NO:249; and (ii) a VL1 comprising a vlCDR1 having an amino acid sequence of SEQ ID NO:251, a vlCDR2 having an amino acid sequence of SEQ ID NO: 252, and a vlCDR3 having an amino acid sequence of SEQ ID NO:253; or (i) a VH1 comprising a vhCDR1 having an amino acid sequence of SEQ ID NO:255; a vhCDR2 having an amino acid sequence of SEQ ID NO:256; and a vhCDR3 having an amino acid sequence of SEQ ID NO:257; and (ii) a VL1 comprising a vlCDR1 having an amino acid sequence of SEQ ID NO:259, a vlCDR2 having an amino acid sequence of SEQ ID NO: 260, and a vlCDR3 having an amino acid sequence of SEQ ID NO:261; or (i) a VH1 comprising a vhCDR1 having an amino acid sequence of SEQ ID NO:263; a vhCDR2 having an amino acid sequence of SEQ ID NO:264; and a vhCDR3 having an amino acid sequence of SEQ ID NO:265; and (ii) a VL1 comprising a vlCDR1 having an amino acid sequence of SEQ ID NO:267, a vlCDR2 having an amino acid sequence of SEQ ID NO: 268, and a vlCDR3 having an amino acid sequence of SEQ ID NO:269; or (i) a VH1 comprising a vhCDR1 having an amino acid sequence of SEQ ID NO:271; a vhCDR2 having an amino acid sequence of SEQ ID NO:212; and a vhCDR3 having an amino acid sequence of SEQ ID NO:273; and (ii) a VL1 comprising a vlCDR1 having an amino acid sequence of SEQ ID NO:275, a vlCDR2 having an amino acid sequence of SEQ ID NO: 276, and a vlCDR3 having an amino acid sequence of SEQ ID NO:277; or (i) a VH1 comprising a vhCDR1 having an amino acid sequence of SEQ ID NO:279; a vhCDR2 having an amino acid sequence of SEQ ID NO:280; and a vhCDR3 having an amino acid sequence of SEQ ID NO:281; and (ii) a VL1 comprising a vlCDR1 having an amino acid sequence of SEQ ID NO:283, a vlCDR2 having an amino acid sequence of SEQ ID NO: 284, and a vlCDR3 having an amino acid sequence of SEQ ID NO:285; or (i) a VH1 comprising a vhCDR1 having an amino acid sequence of SEQ ID NO:287; a vhCDR2 having an amino acid sequence of SEQ ID NO:288; and a vhCDR3 having an amino acid sequence of SEQ ID NO:289; and (ii) a VL1 comprising a vlCDR1 having an amino acid sequence of SEQ ID NO:291, a vlCDR2 having an amino acid sequence of SEQ ID NO: 292, and a vlCDR3 having an amino acid sequence of SEQ ID NO:293; or (i) a VH1 comprising a vhCDR1 having an amino acid sequence of SEQ ID NO:295; a vhCDR2 having an amino acid sequence of SEQ ID NO:296; and a vhCDR3 having an amino acid sequence of SEQ ID NO:297; and (ii) a VL1 comprising a vlCDR1 having an amino acid sequence of SEQ ID NO:299, a vlCDR2 having an amino acid sequence of SEQ ID NO: 300, and a vlCDR3 having an amino acid sequence of SEQ ID NO:301; or (i) a VH1 comprising a vhCDR1 having an amino acid sequence of SEQ ID NO:303; a vhCDR2 having an amino acid sequence of SEQ ID NO:304; and a vhCDR3 having an amino acid sequence of SEQ ID NO:305; and (ii) a VL1 comprising a vlCDR1 having an amino acid sequence of SEQ ID NO:307, a vlCDR2 having an amino acid sequence of SEQ ID NO: 308, and a vlCDR3 having an amino acid sequence of SEQ ID NO:309; or (i) a VH1 comprising a vhCDR1 having an amino acid sequence of SEQ ID NO:311; a vhCDR2 having an amino acid sequence of SEQ ID NO:312; and a vhCDR3 having an amino acid sequence of SEQ ID NO:313; and (ii) a VL1 comprising a vlCDR1 having an amino acid sequence of SEQ ID NO: 315, a vlCDR2 having an amino acid sequence of SEQ ID NO: 316, and a vlCDR3 having an amino acid sequence of SEQ ID NO:317; or (i) a VH1 comprising a vhCDR1 having an amino acid sequence of SEQ ID NO:319; a vhCDR2 having an amino acid sequence of SEQ ID NO:320; and a vhCDR3 having an amino acid sequence of SEQ ID NO:321; and (ii) a VL1 comprising a vlCDR1 having an amino acid sequence of SEQ ID NO:323, a vlCDR2 having an amino acid sequence of SEQ ID NO: 324, and a vlCDR3 having an amino acid sequence of SEQ ID NO:325; or (i) a VH1 comprising a vhCDR1 having an amino acid sequence of SEQ ID NO:327; a vhCDR2 having an amino acid sequence of SEQ ID NO:328; and a vhCDR3 having an amino acid sequence of SEQ ID NO:329; and (ii) a VL1 comprising a vlCDR1 having an amino acid sequence of SEQ ID NO:331, a vlCDR2 having an amino acid sequence of SEQ ID NO: 332, and a vlCDR3 having an amino acid sequence of SEQ ID NO:333; or (i) a VH1 comprising a vhCDR1 having an amino acid sequence of SEQ ID NO:335; a vhCDR2 having an amino acid sequence of SEQ ID NO:336; and a vhCDR3 having an amino acid sequence of SEQ ID NO:337; and (ii) a VL1 comprising a vlCDR1 having an amino acid sequence of SEQ ID NO:339, a vlCDR2 having an amino acid sequence of SEQ ID NO: 340, and a vlCDR3 having an amino acid sequence of SEQ ID NO:341.

In exemplary embodiments, VH1 and VL1 are selected from the following:
- (i) a VH1 having an amino acid sequence of SEQ ID NO:206; and (ii) a VL1 having an amino acid sequence of SEQ ID NO:210; or
- (i) a VH1 having an amino acid sequence of SEQ ID NO:214; and (ii) a VL1 having an amino acid sequence of SEQ ID NO:218; or
- (i) a VH1 having an amino acid sequence of SEQ ID NO:222; and (ii) a VL1 having an amino acid sequence of SEQ ID NO:226; or
- (i) a VH1 having an amino acid sequence of SEQ ID NO:230; and (ii) a VL1 having an amino acid sequence of SEQ ID NO:234; or
- (i) a VH1 having an amino acid sequence of SEQ ID NO:238; and (ii) a VL1 having an amino acid sequence of SEQ ID NO:242; or
- (i) a VH1 having an amino acid sequence of SEQ ID NO:246; and (ii) a VL1 having an amino acid sequence of SEQ ID NO:250; or
- (i) a VH1 having an amino acid sequence of SEQ ID NO:254; and (ii) a VL1 having an amino acid sequence of SEQ ID NO:258; or
- (i) a VH1 having an amino acid sequence of SEQ ID NO:262; and (ii) a VL1 having an amino acid sequence of SEQ ID NO:266; or
- (i) a VH1 having an amino acid sequence of SEQ ID NO:270; and (ii) a VL1 having an amino acid sequence of SEQ ID NO:274; or
- (i) a VH1 having an amino acid sequence of SEQ ID NO:278; and (ii) a VL1 having an amino acid sequence of SEQ ID NO:282; or
- (i) a VH1 having an amino acid sequence of SEQ ID NO:286; and (ii) a VL1 having an amino acid sequence of SEQ ID NO:290; or
- (i) a VH1 having an amino acid sequence of SEQ ID NO:294; and (ii) a VL1 having an amino acid sequence of SEQ ID NO:298; or
- (i) a VH1 having an amino acid sequence of SEQ ID NO:302; and (ii) a VL1 having an amino acid sequence of SEQ ID NO:306; or
- (i) a VH1 having an amino acid sequence of SEQ ID NO:310; and (ii) a VL1 having an amino acid sequence of SEQ ID NO:314; or
- (i) a VH1 having an amino acid sequence of SEQ ID NO:318; and (ii) a VL1 having an amino acid sequence of SEQ ID NO:322; or
- (i) a VH1 having an amino acid sequence of SEQ ID NO:326; and (ii) a VL1 having an amino acid sequence of SEQ ID NO:330; or
- (i) a VH1 having an amino acid sequence of SEQ ID NO:334; and (ii) a VL1 having an amino acid sequence of SEQ ID NO:338.

In some embodiments, the second ABD binds to human CD28, and VH2 and VL2 are selected from the following:
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:9; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:13; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:31; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:35; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:39; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:43; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:47; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:51; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:55; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:59; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 63; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:67; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:86; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:90; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:94; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:98; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 102; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:106; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:110; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:114; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:118; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:122; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 126; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:130; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 134; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:138; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 142; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:146; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 150; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:154; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 158; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:162; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 166; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:170; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 174; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:178; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:182; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:186; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 190; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:194; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 198; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:202; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:380; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:384; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:388; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:392; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:396; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:400; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 404; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:408; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:412; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:416; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:420; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:424.

In certain embodiments, VH2 and VL2 are selected from the following:

(i) a VH2 comprising a vhCDR1 having an amino acid sequence of SEQ ID NO: 10; a vhCDR2 having an amino acid sequence of SEQ ID NO:11; and a vhCDR3 having an amino acid sequence of SEQ ID NO: 12; and (ii) a VL2 comprising a vlCDR1 having an amino acid sequence of SEQ ID NO:14, a vlCDR2 having an amino acid sequence of SEQ ID NO: 15, and a vlCDR3 having an amino acid sequence of SEQ ID NO:16; or (i) a VH2 comprising a vhCDR1 having an amino acid sequence of SEQ ID NO:32; a vhCDR2 having an amino acid sequence of SEQ ID NO:33; and a vhCDR3 having an amino acid sequence of SEQ ID NO:34; and (ii) a VL2 comprising a vlCDR1 having an amino acid sequence of SEQ ID NO:36, a vlCDR2 having an amino acid sequence of SEQ ID NO: 37, and a vlCDR3 having an amino acid sequence of SEQ ID NO:38; or i) a VH2 comprising a vhCDR1 having an amino acid sequence of SEQ ID NO:40; a vhCDR2 having an amino acid sequence of SEQ ID NO:41; and a vhCDR3 having an amino acid sequence of SEQ ID NO:42; and (ii) a VL2 comprising a vlCDR1 having an amino acid sequence of SEQ ID NO:44, a vlCDR2 having an amino acid sequence of SEQ ID NO: 45, and a vlCDR3 having an amino acid sequence of SEQ ID NO:46; or i) a VH2 comprising a vhCDR1 having an amino acid sequence of SEQ ID NO:48; a vhCDR2 having an amino acid sequence of SEQ ID NO:49; and a vhCDR3 having an amino acid sequence of SEQ ID NO: 50; and (ii) a VL2 comprising a vlCDR1 having an amino acid sequence of SEQ ID NO:52, a vlCDR2 having an amino acid sequence of SEQ ID NO: 53, and a vlCDR3 having an amino acid sequence of SEQ ID NO:54; or i) a VH2 comprising a vhCDR1 having an amino acid sequence of SEQ ID NO:56; a vhCDR2 having an amino acid sequence of SEQ ID NO:57; and a vhCDR3 having an amino acid sequence of SEQ ID NO:58; and (ii) a VL2 comprising a vlCDR1 having an amino acid sequence of SEQ ID NO:60, a vlCDR2 having an amino acid sequence of SEQ ID NO:61, and a vlCDR3 having an amino acid sequence of SEQ ID NO:62; or i) a VH2 comprising a vhCDR1 having an amino acid sequence of SEQ ID NO:64; a vhCDR2 having an amino acid sequence of SEQ ID NO:65; and a vhCDR3 having an amino acid sequence of SEQ ID NO:66; and (ii) a VL2 comprising a vlCDR1 having an amino acid sequence of SEQ ID NO:68, a vlCDR2 having an amino acid sequence of SEQ ID NO:69, and a vlCDR3 having an amino acid sequence of SEQ ID NO:70; or i) a VH2 comprising a vhCDR1 having an amino acid sequence of SEQ ID NO:87; a vhCDR2 having an amino acid sequence of SEQ ID NO:88; and a vhCDR3 having an amino acid sequence of SEQ ID NO:89; and (ii) a VL2 comprising a vlCDR1 having an amino acid sequence of SEQ ID NO: 91, a vlCDR2 having an amino acid sequence of SEQ ID NO:92, and a vlCDR3 having an amino acid sequence of SEQ ID NO:93; or i) a VH2 comprising a vhCDR1 having an amino acid sequence of SEQ ID NO:95; a vhCDR2 having an amino acid sequence of SEQ ID NO:96; and a vhCDR3 having an amino acid sequence of SEQ ID NO:97; and (ii) a VL2 comprising a vlCDR1 having an amino acid sequence of SEQ ID NO:99, a vlCDR2 having an amino acid sequence of SEQ ID NO:100, and a vlCDR3 having an amino acid sequence of SEQ ID NO:101; or i) a VH2 comprising a vhCDR1 having an amino acid sequence of SEQ ID NO:103; a vhCDR2 having an amino acid sequence of SEQ ID NO:104; and a vhCDR3 having an amino acid sequence of SEQ ID NO:105; and (ii) a VL2 comprising a vlCDR1 having an amino acid sequence of SEQ ID NO: 107, a vlCDR2 having an amino acid sequence of SEQ ID NO:108, and a vlCDR3 having an amino acid sequence of SEQ ID NO:109; or i) a VH2 comprising a vhCDR1 having an amino acid sequence of SEQ ID NO:111; a vhCDR2 having an amino acid sequence of SEQ ID NO:112; and a vhCDR3 having an amino acid sequence of SEQ ID NO:113; and (ii) a VL2 comprising a vlCDR1 having an amino acid sequence of SEQ ID NO:115, a vlCDR2 having an amino acid sequence of SEQ ID NO:116, and a vlCDR3 having an amino acid sequence of SEQ ID NO:117; or i) a VH2 comprising a vhCDR1 having an amino acid sequence of SEQ ID NO:119; a vhCDR2 having an amino acid sequence of SEQ ID NO:120; and a vhCDR3 having an amino acid sequence of SEQ ID NO:121; and (ii) a VL2 comprising a vlCDR1 having an amino acid sequence of SEQ ID NO: 123, a vlCDR2 having an amino acid sequence of SEQ ID NO:124, and a vlCDR3 having an amino acid sequence of SEQ ID NO:125; or i) a VH2 comprising a vhCDR1 having an amino acid sequence of SEQ ID NO:127; a vhCDR2 having an amino acid sequence of SEQ ID NO:128; and a vhCDR3 having an amino acid sequence of SEQ ID NO:129; and (ii) a VL2 comprising a vlCDR1 having an amino acid sequence of SEQ ID NO:131, a vlCDR2 having an amino acid sequence of SEQ ID NO:132, and a vlCDR3 having an amino acid sequence of SEQ ID NO:133; or i) a VH2 comprising a vhCDR1 having an amino acid sequence of SEQ ID NO:135; a vhCDR2 having an amino acid sequence of SEQ ID NO:136; and a vhCDR3 having an amino acid sequence of SEQ ID NO:137; and (ii) a VL2 comprising a vlCDR1 having an amino acid sequence of SEQ ID NO: 139, a vlCDR2 having an amino acid sequence of SEQ ID NO:140, and a vlCDR3 having an amino acid sequence of SEQ ID NO:141; or i) a VH2 comprising a vhCDR1 having an amino acid sequence of SEQ ID NO:143; a vhCDR2 having an amino acid sequence of SEQ ID NO:144; and a vhCDR3 having an amino acid sequence of SEQ ID NO:115; and (ii) a VL2 comprising a vlCDR1 having an amino acid sequence of SEQ ID NO: 147, a vlCDR2 having an amino acid sequence of SEQ ID NO:149, and a vlCDR3 having an amino acid sequence of SEQ ID NO:149; or i) a VH2 comprising a vhCDR1 having an amino acid sequence of SEQ ID NO:151; a vhCDR2 having an amino acid sequence of SEQ ID NO:152; and a vhCDR3 having an amino acid sequence of SEQ ID NO:153; and (ii) a VL2 comprising a vlCDR1 having an amino acid sequence of SEQ ID NO: 155, a vlCDR2 having an amino acid sequence of SEQ ID NO:156, and a vlCDR3 having an amino acid sequence of SEQ ID NO:157; or
i) a VH2 comprising a vhCDR1 having an amino acid sequence of SEQ ID NO:159; a vhCDR2 having an amino acid sequence of SEQ ID NO:160; and a vhCDR3 having an amino acid sequence of SEQ ID NO:161; and (ii) a VL2 comprising a vlCDR1 having an amino acid sequence of SEQ ID NO: 163, a vlCDR2 having an amino acid sequence of SEQ ID NO:164, and a vlCDR3 having an amino acid sequence of SEQ ID NO:165; or
i) a VH2 comprising a vhCDR1 having an amino acid sequence of SEQ ID NO:167; a vhCDR2 having an amino acid sequence of SEQ ID NO:168; and a vhCDR3 having an amino acid sequence of SEQ ID NO:169; and (ii) a VL2 comprising a vlCDR1 having an amino acid sequence of SEQ ID NO:171, a vlCDR2 having an amino acid sequence of SEQ ID NO:172, and a vlCDR3 having an amino acid sequence of SEQ ID NO:173; or
i) a VH2 comprising a vhCDR1 having an amino acid sequence of SEQ ID NO:175; a vhCDR2 having an amino acid sequence of SEQ ID NO:176; and a vhCDR3 having an amino acid sequence of SEQ ID NO:177; and (ii) a VL2 comprising a vlCDR1 having an amino acid sequence of SEQ ID NO: 179, a vlCDR2 having an amino acid sequence of SEQ ID NO:180, and a vlCDR3 having an amino acid sequence of SEQ ID NO:181; or
i) a VH2 comprising a vhCDR1 having an amino acid sequence of SEQ ID NO:183; a vhCDR2 having an amino acid sequence of SEQ ID NO:184; and a vhCDR3 having an amino acid sequence of SEQ ID NO:185; and (ii) a VL2 comprising a vlCDR1 having an amino acid sequence of SEQ ID NO: 187, a vlCDR2 having an amino acid sequence of SEQ ID NO:188, and a vlCDR3 having an amino acid sequence of SEQ ID NO:189; or
i) a VH2 comprising a vhCDR1 having an amino acid sequence of SEQ ID NO:191; a vhCDR2 having an amino acid sequence of SEQ ID NO:192; and a vhCDR3 having an amino acid sequence of SEQ ID NO:193; and (ii) a VL2 comprising a vlCDR1 having an amino acid sequence of SEQ ID NO: 195, a vlCDR2 having an amino acid sequence of SEQ ID NO:196, and a vlCDR3 having an amino acid sequence of SEQ ID NO:197; or
i) a VH2 comprising a vhCDR1 having an amino acid sequence of SEQ ID NO:199; a vhCDR2 having an amino acid sequence of SEQ ID NO:200; and a vhCDR3 having an amino acid sequence of SEQ ID NO:201; and (ii) a VL2 comprising a vlCDR1 having an amino acid sequence of SEQ ID NO:203, a vlCDR2 having an amino acid sequence of SEQ ID NO:204, and a vlCDR3 having an amino acid sequence of SEQ ID NO:205; or
i) a VH2 comprising a vhCDR1 having an amino acid sequence of SEQ ID NO:381; a vhCDR2 having an amino acid sequence of SEQ ID NO:382; and a vhCDR3 having an amino acid sequence of SEQ ID NO:383; and (ii) a VL2 comprising a vlCDR1 having an amino acid sequence of SEQ ID NO:385, a vlCDR2 having an amino acid sequence of SEQ ID NO:386, and a vlCDR3 having an amino acid sequence of SEQ ID NO:387; or i) a VH2 comprising a vhCDR1 having an amino acid sequence of SEQ ID NO:389; a vhCDR2 having an amino acid sequence of SEQ ID NO:390; and a vhCDR3 having an amino acid sequence of SEQ ID NO:391; and (ii) a VL2 comprising a vlCDR1 having an amino acid sequence of SEQ ID NO:393, a vlCDR2 having an amino acid sequence of SEQ ID NO:394, and a vlCDR3 having an amino acid sequence of SEQ ID NO:395; or
i) a VH2 comprising a vhCDR1 having an amino acid sequence of SEQ ID NO:397; a vhCDR2 having an amino acid sequence of SEQ ID NO:398; and a vhCDR3 having an amino acid sequence of SEQ ID NO:399; and (ii) a VL2 comprising a vlCDR1 having an amino acid sequence of SEQ ID NO:401, a vlCDR2 having an amino acid sequence of SEQ ID NO:402, and a vlCDR3 having an amino acid sequence of SEQ ID NO:403; or
i) a VH2 comprising a vhCDR1 having an amino acid sequence of SEQ ID NO:405; a vhCDR2 having an amino acid sequence of SEQ ID NO:406; and a vhCDR3 having an amino acid sequence of SEQ ID NO:407; and (ii) a VL2 comprising a vlCDR1 having an amino acid sequence of SEQ ID NO:409, a vlCDR2 having an amino acid sequence of SEQ ID NO:410, and a vlCDR3 having an amino acid sequence of SEQ ID NO:411; or
i) a VH2 comprising a vhCDR1 having an amino acid sequence of SEQ ID NO:413; a vhCDR2 having an amino acid sequence of SEQ ID NO:414; and a vhCDR3 having an amino acid sequence of SEQ ID NO:415; and (ii) a VL2 comprising a vlCDR1 having an amino acid sequence of SEQ ID NO:417, a vlCDR2 having an amino acid sequence of SEQ ID NO:418, and a vlCDR3 having an amino acid sequence of SEQ ID NO:419; or
i) a VH2 comprising a vhCDR1 having an amino acid sequence of SEQ ID NO:421; a vhCDR2 having an amino acid sequence of SEQ ID NO:422; and a vhCDR3 having an amino acid sequence of SEQ ID NO:423; and (ii) a VL2 comprising a vlCDR1 having an amino acid sequence of SEQ ID NO:425, a vlCDR2 having an amino acid sequence of SEQ ID NO:426, and a vlCDR3 having an amino acid sequence of SEQ ID NO:427.

In exemplary embodiments, VH2 and VL2 are selected from the following:
(i) a VH2 having an amino acid sequence of SEQ ID NO:9; and (ii) a VL2 having an amino acid sequence of SEQ ID NO:13; or
(i) a VH2 having an amino acid sequence of SEQ ID NO:31; and (ii) a VL2 having an amino acid sequence of SEQ ID NO:35; or
(i) a VH2 having an amino acid sequence of SEQ ID NO:39; and (ii) a VL2 having an amino acid sequence of SEQ ID NO:43; or
(i) a VH2 having an amino acid sequence of SEQ ID NO:47; and (ii) a VL2 having an amino acid sequence of SEQ ID NO:51; or
(i) a VH2 having an amino acid sequence of SEQ ID NO:55; and (ii) a VL2 having an amino acid sequence of SEQ ID NO:59; or
(i) a VH2 having an amino acid sequence of SEQ ID NO:63; and (ii) a VL2 having an amino acid sequence of SEQ ID NO:67; or (i) a VH2 having an amino acid sequence of SEQ ID NO:86; and (ii) a VL2 having an amino acid sequence of SEQ ID NO:90; or
(i) a VH2 having an amino acid sequence of SEQ ID NO:94; and (ii) a VL2 having an amino acid sequence of SEQ ID NO:98; or
(i) a VH2 having an amino acid sequence of SEQ ID NO:102; and (ii) a VL2 having an amino acid sequence of SEQ ID NO:106; or
(i) a VH2 having an amino acid sequence of SEQ ID NO:110; and (ii) a VL2 having an amino acid sequence of SEQ ID NO:114; or
(i) a VH2 having an amino acid sequence of SEQ ID NO:118; and (ii) a VL2 having an amino acid sequence of SEQ ID NO:122; or
(i) a VH2 having an amino acid sequence of SEQ ID NO:126; and (ii) a VL2 having an amino acid sequence of SEQ ID NO:130; or
(i) a VH2 having an amino acid sequence of SEQ ID NO:134; and (ii) a VL2 having an amino acid sequence of SEQ ID NO:138; or
(i) a VH2 having an amino acid sequence of SEQ ID NO:142; and (ii) a VL2 having an amino acid sequence of SEQ ID NO:146; or
(i) a VH2 having an amino acid sequence of SEQ ID NO:150; and (ii) a VL2 having an amino acid sequence of SEQ ID NO:154; or
(i) a VH2 having an amino acid sequence of SEQ ID NO:158; and (ii) a VL2 having an amino acid sequence of SEQ ID NO:162; or
(i) a VH2 having an amino acid sequence of SEQ ID NO:166; and (ii) a VL2 having an amino acid sequence of SEQ ID NO:170; or
(i) a VH2 having an amino acid sequence of SEQ ID NO:174; and (ii) a VL2 having an amino acid sequence of SEQ ID NO:178; or
(i) a VH2 having an amino acid sequence of SEQ ID NO:182; and (ii) a VL2 having an amino acid sequence of SEQ ID NO:186; or
(i) a VH2 having an amino acid sequence of SEQ ID NO:190; and (ii) a VL2 having an amino acid sequence of SEQ ID NO:194; or
(i) a VH2 having an amino acid sequence of SEQ ID NO:198; and (ii) a VL2 having an amino acid sequence of SEQ ID NO:202; or
(i) a VH2 having an amino acid sequence of SEQ ID NO:380; and (ii) a VL2 having an amino acid sequence of SEQ ID NO:384; or
(i) a VH2 having an amino acid sequence of SEQ ID NO:388; and (ii) a VL2 having an amino acid sequence of SEQ ID NO:392; or
(i) a VH2 having an amino acid sequence of SEQ ID NO:396; and (ii) a VL2 having an amino acid sequence of SEQ ID NO:400; or
(i) a VH2 having an amino acid sequence of SEQ ID NO:404; and (ii) a VL2 having an amino acid sequence of SEQ ID NO:408; or
(i) a VH2 having an amino acid sequence of SEQ ID NO:412; and (ii) a VL2 having an amino acid sequence of SEQ ID NO:416; or
(i) a VH2 having an amino acid sequence of SEQ ID NO:420; and (ii) a VL2 having an amino acid sequence of SEQ ID NO:424.

In some embodiments, VH1 comprises a vhCDR1, a vhCDR2, and a vhCDR3 having an amino acid sequence of a vhCDR1, a vhCDR2, and a vhCDR3, respectively, of a VH having an amino acid sequence of SEQ ID NO:214; VL1 comprises a vlCDR1, a vlCDR2, and a vlCDR3 having an amino acid sequence of a vlCDR1, a vlCDR2, and a vlCDR3, respectively, of a VL having an amino acid sequence of SEQ ID NO:218; VH2 comprises a vhCDR1, a vhCDR2, and a vhCDR3 having an amino acid sequence of a vhCDR1, a vhCDR2, and a vhCDR3, respectively, of a VH having an amino acid sequence of SEQ ID NO:39; and VL2 comprises a vlCDR1, a vlCDR2, and a vlCDR3 having an amino acid sequence of a vlCDR1, a vlCDR2, and a vlCDR3, respectively, of a VL having an amino acid sequence of SEQ ID NO:43.

In exemplary embodiments, VH1 comprises a vhCDR1 having an amino acid sequence of SEQ ID NO:215; a vhCDR2 having an amino acid sequence of SEQ ID NO:216; and a vhCDR3 having an amino acid sequence of SEQ ID NO:217; VL1 comprises a vlCDR1 having an amino acid sequence of SEQ ID NO:219, a vlCDR2 having an amino acid sequence of SEQ ID NO: 220, and a vlCDR3 having an amino acid sequence of SEQ ID NO:221, VH2 comprises a vhCDR1 having an amino acid sequence of SEQ ID NO:40; a vhCDR2 having an amino acid sequence of SEQ ID NO:41; and a vhCDR3 having an amino acid sequence of SEQ ID NO:42; and VL2 comprises a vlCDR1 having an amino acid sequence of SEQ ID NO:44, a vlCDR2 having an amino acid sequence of SEQ ID NO:45, and a vlCDR3 having an amino acid sequence of SEQ ID NO:46.

In some embodiments, the first Fc domain and second Fc domain are each variant Fc domains. In exemplary embodiments, one of the first and second Fc domains comprises heterodimerization variant T366W, and the other of the first and second Fc domains comprises heterodimerization variants T366S/L368A/Y407V, wherein numbering is according to EU numbering. In some embodiments, the first Fc domain comprises heterodimerization variant T366W, and the second Fc domain comprises heterodimerization variants T366S/L368A/Y407V.

In certain embodiments, the first and second Fc domains each comprise one or more ablation variants. In some embodiments, one or more ablation variants comprise L234A/L235A/D265S, wherein numbering is according to EU numbering.

In some embodiments, the first or second Fc domain comprises purification variants H435R/Y436F, wherein numbering is according to EU numbering.

In exemplary embodiments, the second Fc domain comprises purification variants H435R/Y436F.

In exemplary embodiments, the first Fc domain comprises amino acid substitutions L234A/L235A/D265S/LT366W, and the second Fc domain comprises amino acid substitutions L234A/L235A/D265S/T366S/L368A/Y407V/H435R/Y436F, wherein numbering is according to EU numbering. In some embodiments, the first and second Fc domains each further comprise amino acid substitutions M252Y/S254T/T256E, wherein numbering is according to EU numbering.

In some embodiments, the first and second Fc domains comprise a set of heterodimerization skew variants selected from the following heterodimerization variants: S364K/E357Q:L368D/K370S; S364K:L368D/K370S; S364K:L368E/K370S; D401K: T411E/K360E/Q362E; and T366W:T366S/L368A/Y407V, wherein numbering is according to EU numbering. In some embodiments, the first and second Fc domains comprise heterodimerization skew variants S364K/E357Q:L368D/K370S, wherein numbering is according to EU numbering.

In certain embodiments, the first and second Fc domains each comprise one or more ablation variants. In exemplary embodiments, the one or more ablation variants comprise E233P/L234V/L235A/G236del/S267K, wherein numbering is according to EU numbering.

In some embodiments, the one of the first or second monomer further comprises a pI variant. In some embodiments, the CH1-hinge-CH2-CH3 of the second monomer comprises pI variants N208D/Q295E/N384D/Q418E/N421D, wherein numbering is according to EU numbering.

In some embodiments, the CH1-hinge-CH2-CH3 of the second monomer comprises amino acid variants E233P/L234V/L235A/G236del/S267K/L368D/K370S/N208D/Q295E/N384D/Q418E/N421 D, the first Fc domain comprises amino acid variants E233P/L234V/L235A/G236del/S267K/S364K/E357Q, wherein numbering is according to EU numbering. In exemplary embodiments, the first and second variant Fc domains each further comprise amino acid variants 428L/434S.

In some embodiments, of the anti-CD28× anti-PSMA antibody, the scFv linker is selected from GKPGSGKPGSGKPGSGKPGS (SEQ ID NO: 443), GGSEGKSSGSGSESKSTGGS (SEQ ID NO: 456), and GGGSGGSGGCPPCGGSGG (SEQ ID NO: 457).

In a second aspect, provided herein are heterodimeric anti-CD28× anti-PSMA antibodies in the 2+1 Fab$_2$-scFv-Fc format. These antibodies comprise: a) a first monomer; b) a second monomer; and c) a light chain. The first monomer comprises, from N-terminal to C-terminal, VH1-CH1-first domain linker-scFv-second domain linker-CH2-CH3, wherein VH1 is a first variable heavy domain, and CH2-CH3 is a first Fc domain. The second monomer comprises, from N-terminal to C-terminal, a VH1-CH1-hinge-CH2-CH3, wherein CH2-CH3 is a second Fc domain. The light chain comprises, from N-terminal to C-terminal, VL1-CL, wherein VL1 is a first variable light domain and CL is a constant light domain. The scFv comprises a second VH domain (VH2), a scFv linker, and a second variable light domain (VL2). Each of the VH1s and the VL1 together form a first antigen binding domain (ABD), and the VH2 and the VL2 form a second ABD. Further, one of the first and second ABDs bind human CD28 and the other of the first and second ABDs binds PSMA.

In some embodiments, the first ABDs bind human CD28 and the second ABD binds PSMA. In certain embodiments, the first ABDs bind PSMA and the second ABD binds human CD28.

In some embodiments, the scFv comprises, from N-terminal to C-terminal, VH2-scFv linker-VL2. In certain embodiments, the scFv comprises, from N-terminal to C-terminal, VL2-scFv linker-VH2.

In some embodiments, the first ABDs bind to human PSMA, and VH1 and VL1 are selected from the following:
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:206; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:210; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:214; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:218; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:222; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:226; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:230; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:234; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:238; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:242; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:246; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:250; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:254; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:258; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:262; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:266; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:270; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:274; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:278; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:282; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:286; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:290; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:294; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:298; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:302; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:306; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:310; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:314; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:318; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:322; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:326; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:330; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:334; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:338.

In some embodiments, VH1 and VL1 are selected from the following:
- (i) a VH1 comprising a vhCDR1 having an amino acid sequence of SEQ ID NO:207; a vhCDR2 having an amino acid sequence of SEQ ID NO:208; and a vhCDR3 having an amino acid sequence of SEQ ID NO:209; and (ii) a VL1 comprising a vlCDR1 having an amino acid sequence of SEQ ID NO:211, a vlCDR2 having an amino acid sequence of SEQ ID NO: 212, and a vlCDR3 having an amino acid sequence of SEQ ID NO:213; or
- (i) a VH1 comprising a vhCDR1 having an amino acid sequence of SEQ ID NO:215; a vhCDR2 having an amino acid sequence of SEQ ID NO:216; and a vhCDR3 having an amino acid sequence of SEQ ID NO: 217; and (ii) a VL1 comprising a vlCDR1 having an amino acid sequence of SEQ ID NO:219, a vlCDR2 having an amino acid sequence of SEQ ID NO: 220, and a vlCDR3 having an amino acid sequence of SEQ ID NO:221;
- (i) a VH1 comprising a vhCDR1 having an amino acid sequence of SEQ ID NO:223; a vhCDR2 having an amino acid sequence of SEQ ID NO:224; and a vhCDR3 having an amino acid sequence of SEQ ID NO:225; and (ii) a VL1 comprising a vlCDR1 having an amino acid sequence of SEQ ID NO:227, a vlCDR2 having an amino acid sequence of SEQ ID NO: 228, and a vlCDR3 having an amino acid sequence of SEQ ID NO:229; or
- (i) a VH1 comprising a vhCDR1 having an amino acid sequence of SEQ ID NO:231; a vhCDR2 having an amino acid sequence of SEQ ID NO:232; and a vhCDR3 having an amino acid sequence of SEQ ID NO:233; and (ii) a VL1 comprising a vlCDR1 having an amino acid sequence of SEQ ID NO:235, a vlCDR2 having an amino acid sequence of SEQ ID NO: 236, and a vlCDR3 having an amino acid sequence of SEQ ID NO:237; or
- (i) a VH1 comprising a vhCDR1 having an amino acid sequence of SEQ ID NO:239; a vhCDR2 having an amino acid sequence of SEQ ID NO:240; and a vhCDR3 having an amino acid sequence of SEQ ID NO:241; and (ii) a VL1 comprising a vlCDR1 having an amino acid sequence of SEQ ID NO:243, a vlCDR2 having an amino acid sequence of SEQ ID NO: 244, and a vlCDR3 having an amino acid sequence of SEQ ID NO:245; or
- (i) a VH1 comprising a vhCDR1 having an amino acid sequence of SEQ ID NO:247; a vhCDR2 having an amino acid sequence of SEQ ID NO:248; and a vhCDR3 having an amino acid sequence of SEQ ID NO:249; and (ii) a VL1 comprising a vlCDR1 having an amino acid sequence of SEQ ID NO:251, a vlCDR2 having an amino acid sequence of SEQ ID NO: 252, and a vlCDR3 having an amino acid sequence of SEQ ID NO:253; or
- (i) a VH1 comprising a vhCDR1 having an amino acid sequence of SEQ ID NO:255; a vhCDR2 having an amino acid sequence of SEQ ID NO:256; and a vhCDR3 having an amino acid sequence of SEQ ID NO:257; and (ii) a VL1 comprising a vlCDR1 having an amino acid sequence of SEQ ID NO:259, a vlCDR2 having an amino acid sequence of SEQ ID NO: 260, and a vlCDR3 having an amino acid sequence of SEQ ID NO:261; or
- (i) a VH1 comprising a vhCDR1 having an amino acid sequence of SEQ ID NO:263; a vhCDR2 having an amino acid sequence of SEQ ID NO:264; and a vhCDR3 having an amino acid sequence of SEQ ID NO:265; and (ii) a VL1 comprising a vlCDR1 having an amino acid sequence of SEQ ID NO:267, a vlCDR2 having an amino acid sequence of SEQ ID NO: 268, and a vlCDR3 having an amino acid sequence of SEQ ID NO:269; or
- (i) a VH1 comprising a vhCDR1 having an amino acid sequence of SEQ ID NO:271; a vhCDR2 having an amino acid sequence of SEQ ID NO:212; and a vhCDR3 having an amino acid sequence of SEQ ID NO:273; and (ii) a VL1 comprising a vlCDR1 having an amino acid sequence of SEQ ID NO:275, a vlCDR2 having an amino acid sequence of SEQ ID NO: 276, and a vlCDR3 having an amino acid sequence of SEQ ID NO:277; or (i) a VH1 comprising a vhCDR1 having an amino acid sequence of SEQ ID NO:279; a vhCDR2 having an amino acid sequence of SEQ ID NO:280; and a vhCDR3 having an amino acid sequence of SEQ ID NO:281; and (ii) a VL1 comprising a vlCDR1 having an amino acid sequence of SEQ ID NO:283, a vlCDR2 having an amino acid sequence of SEQ ID NO: 284, and a vlCDR3 having an amino acid sequence of SEQ ID NO:285; or (i) a VH1 comprising a vhCDR1 having an amino acid sequence of SEQ ID NO:287; a vhCDR2 having an amino acid sequence of SEQ ID NO:288; and a vhCDR3 having an amino acid sequence of SEQ ID NO:289; and (ii) a VL1 comprising a vlCDR1 having an amino acid sequence of SEQ ID NO:291, a vlCDR2 having an amino acid sequence of SEQ ID NO: 292, and a vlCDR3 having an amino acid sequence of SEQ ID NO:293; or (i) a VH1 comprising a vhCDR1 having an amino acid sequence of SEQ ID NO:295; a vhCDR2 having an amino acid sequence of SEQ ID NO:296; and a vhCDR3 having an amino acid sequence of SEQ ID NO:297; and (ii) a VL1 comprising a vlCDR1 having an amino acid sequence of SEQ ID NO:299, a vlCDR2 having an amino acid sequence of SEQ ID NO: 300, and a vlCDR3 having an amino acid sequence of SEQ ID NO:301; or (i) a VH1 comprising a vhCDR1 having an amino acid sequence of SEQ ID NO:303; a vhCDR2 having an amino acid sequence of SEQ ID NO:304; and a vhCDR3 having an amino acid sequence of SEQ ID NO:305; and (ii) a VL1 comprising a vlCDR1 having an amino acid sequence of SEQ ID NO:307, a vlCDR2 having an amino acid sequence of SEQ ID NO: 308, and a vlCDR3 having an amino acid sequence of SEQ ID NO:309; or (i) a VH1 comprising a vhCDR1 having an amino acid sequence of SEQ ID NO:311; a vhCDR2 having an amino acid sequence of SEQ ID NO:312; and a vhCDR3 having an amino acid sequence of SEQ ID NO:313; and (ii) a VL1 comprising a vlCDR1 having an amino acid sequence of SEQ ID NO: 315, a vlCDR2 having an amino acid sequence of SEQ ID NO: 316, and a vlCDR3 having an amino acid sequence of SEQ ID NO:317; or (i) a VH1 comprising a vhCDR1 having an amino acid sequence of SEQ ID NO:319; a vhCDR2 having an amino acid sequence of SEQ ID NO:320; and a vhCDR3 having an amino acid sequence of SEQ ID NO:321; and (ii) a VL1 comprising a vlCDR1 having an amino acid sequence of SEQ ID NO: 323, a vlCDR2 having an amino acid sequence of SEQ ID NO: 324, and a vlCDR3 having an amino acid sequence of SEQ ID NO:325; or (i) a VH1 comprising a vhCDR1 having an amino acid sequence of SEQ ID NO:327; a vhCDR2 having an amino acid sequence of SEQ ID NO:328; and a vhCDR3 having an amino acid sequence of SEQ ID NO:329; and (ii) a VL1 comprising a vlCDR1 having an amino acid sequence of SEQ ID NO:331, a vlCDR2 having an amino acid sequence of SEQ ID NO: 332, and a vlCDR3 having an amino acid sequence of SEQ ID NO:333; or (i) a VH1 comprising a vhCDR1 having an amino acid sequence of SEQ ID NO:335; a vhCDR2 having an amino acid sequence of SEQ ID NO:336; and a vhCDR3 having an amino acid sequence of SEQ ID NO:337; and (ii) a VL1 comprising a vlCDR1 having an amino acid sequence of SEQ ID NO: 339, a vlCDR2 having an amino acid sequence of SEQ ID NO: 340, and a vlCDR3 having an amino acid sequence of SEQ ID NO:341.

In exemplary embodiments, VH1 and VL1 are selected from the following:

(i) a VH1 having an amino acid sequence of SEQ ID NO:206; and (ii) a VL1 having an amino acid sequence of SEQ ID NO:210; or (i) a VH1 having an amino acid sequence of SEQ ID NO:214; and (ii) a VL1 having an amino acid sequence of SEQ ID NO:218; or (i) a VH1 having an amino acid sequence of SEQ ID NO:222; and (ii) a VL1 having an amino acid sequence of SEQ ID NO:226; or (i) a VH1 having an amino acid sequence of SEQ ID NO:230; and (ii) a VL1 having an amino acid sequence of SEQ ID NO:234; or (i) a VH1 having an amino acid sequence of SEQ ID NO:238; and (ii) a VL1 having an amino acid sequence of SEQ ID NO:242; or (i) a VH1 having an amino acid sequence of SEQ ID NO:246; and (ii) a VL1 having an amino acid sequence of SEQ ID NO:250; or (i) a VH1 having an amino acid sequence of SEQ ID NO:254; and (ii) a VL1 having an amino acid sequence of SEQ ID NO:258; or (i) a VH1 having an amino acid sequence of SEQ ID NO:262; and (ii) a VL1 having an amino acid sequence of SEQ ID NO:266; or (i) a VH1 having an amino acid sequence of SEQ ID NO:270; and (ii) a VL1 having an amino acid sequence of SEQ ID NO:274; or (i) a VH1 having an amino acid sequence of SEQ ID NO:278; and (ii) a VL1 having an amino acid sequence of SEQ ID NO:282; or (i) a VH1 having an amino acid sequence of SEQ ID NO:286; and (ii) a VL1 having an amino acid sequence of SEQ ID NO:290; or (i) a VH1 having an amino acid sequence of SEQ ID NO:294; and (ii) a VL1 having an amino acid sequence of SEQ ID NO:298; or (i) a VH1 having an amino acid sequence of SEQ ID NO:302; and (ii) a VL1 having an amino acid sequence of SEQ ID NO:306; or (i) a VH1 having an amino acid sequence of SEQ ID NO:310; and (ii) a VL1 having an amino acid sequence of SEQ ID NO:314; or (i) a VH1 having an amino acid sequence of SEQ ID NO:318; and (ii) a VL1 having an amino acid sequence of SEQ ID NO:322; or (i) a VH1 having an amino acid sequence of SEQ ID NO:326; and (ii) a VL1 having an amino acid sequence of SEQ ID NO:330; or (i) a VH1 having an amino acid sequence of SEQ ID NO:334; and (ii) a VL1 having an amino acid sequence of SEQ ID NO:338.

In some embodiments, the second ABD binds to human CD28, and VH2 and VL2 are selected from the following:

(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:9; and
(ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:13; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:31; and
(ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:35; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:39; and
(ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:43; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:47; and
(ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:51; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:55; and
(ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:59; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:63; and
(ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:67; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:86; and
(ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:90; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:94; and
(ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:98; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 102; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:106; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:110; and
(ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:114; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:118; and
(ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:122; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 126; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:130; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 134; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:138; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 142; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:146; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 150; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:154; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 158; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:162; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 166; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:170; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 174; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:178; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:182; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:186; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 190; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:194; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 198; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:202; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:380; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:384; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:388; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:392; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:396; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:400; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:404; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:408; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:412; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:416; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:420; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:424.

In certain embodiments, VH2 and VL2 are selected from the following:

(i) a VH2 comprising a vhCDR1 having an amino acid sequence of SEQ ID NO:10; a vhCDR2 having an amino acid sequence of SEQ ID NO:11; and a vhCDR3 having an amino acid sequence of SEQ ID NO: 12; and (ii) a VL2 comprising a vlCDR1 having an amino acid sequence of SEQ ID NO: 14, a vlCDR2 having an amino acid sequence of SEQ ID NO: 15, and a vlCDR3 having an amino acid sequence of SEQ ID NO:16; or (i) a VH2 comprising a vhCDR1 having an amino acid sequence of SEQ ID NO:32; a vhCDR2 having an amino acid sequence of SEQ ID NO:33; and a vhCDR3 having an amino acid sequence of SEQ ID NO:34; and (ii) a VL2 comprising a vlCDR1 having an amino acid sequence of SEQ ID NO:36, a vlCDR2 having an amino acid sequence of SEQ ID NO: 37, and a vlCDR3 having an amino acid sequence of SEQ ID NO:38; or i) a VH2 comprising a vhCDR1 having an amino acid sequence of SEQ ID NO:40; a vhCDR2 having an amino acid sequence of SEQ ID NO:41; and a vhCDR3 having an amino acid sequence of SEQ ID NO:42; and (ii) a VL2 comprising a vlCDR1 having an amino acid sequence of SEQ ID NO:44, a vlCDR2 having an amino acid sequence of SEQ ID NO: 45, and a vlCDR3 having an amino acid sequence of SEQ ID NO:46; or i) a VH2 comprising a vhCDR1 having an amino acid sequence of SEQ ID NO:48; a vhCDR2 having an amino acid sequence of SEQ ID NO:49; and a vhCDR3 having an amino acid sequence of SEQ ID NO:50; and (ii) a VL2 comprising a vlCDR1 having an amino acid sequence of SEQ ID NO:52, a vlCDR2 having an amino acid sequence of SEQ ID NO: 53, and a vlCDR3 having an amino acid sequence of SEQ ID NO:54; or i) a VH2 comprising a vhCDR1 having an amino acid sequence of SEQ ID NO:56; a vhCDR2 having an amino acid sequence of SEQ ID NO:57; and a vhCDR3 having an amino acid sequence of SEQ ID NO:58; and (ii) a VL2 comprising a vlCDR1 having an amino acid sequence of SEQ ID NO:60, a vlCDR2 having an amino acid sequence of SEQ ID NO:61, and a vlCDR3 having an amino acid sequence of SEQ ID NO:62; or i) a VH2 comprising a vhCDR1 having an amino acid sequence of SEQ ID NO:64; a vhCDR2 having an amino acid sequence of SEQ ID NO:65; and a vhCDR3 having an amino acid sequence of SEQ ID NO:66; and (ii) a VL2 comprising a vlCDR1 having an amino acid sequence of SEQ ID NO:68, a vlCDR2 having an amino acid sequence of SEQ ID NO:69, and a vlCDR3 having an amino acid sequence of SEQ ID NO:70; or i) a VH2 comprising a vhCDR1 having an amino acid sequence of SEQ ID NO:87; a vhCDR2 having an amino acid sequence of SEQ ID NO:88; and a vhCDR3 having an amino acid sequence of SEQ ID NO:89; and (ii) a VL2 comprising a vlCDR1 having an amino acid sequence of SEQ ID NO: 91, a vlCDR2 having an amino acid sequence of SEQ ID NO:92, and a vlCDR3 having an amino acid sequence of SEQ ID NO:93; or i) a VH2 comprising a vhCDR1 having an amino acid sequence of SEQ ID NO:95; a vhCDR2 having an amino acid sequence of SEQ ID NO:96; and a vhCDR3 having an amino acid sequence of SEQ ID NO:97; and (ii) a VL2 comprising a vlCDR1 having an amino acid sequence of SEQ ID NO:99, a vlCDR2 having an amino acid sequence of SEQ ID NO:100, and a vlCDR3 having an amino acid sequence of SEQ ID NO:101; or i) a VH2 comprising a vhCDR1 having an amino acid sequence of SEQ ID NO:103; a vhCDR2 having an amino acid sequence of SEQ ID NO:104; and a vhCDR3 having an amino acid sequence of SEQ ID NO:105; and (ii) a VL2 comprising a vlCDR1 having an amino acid sequence of SEQ ID NO: 107, a vlCDR2 having an amino acid sequence of SEQ ID NO:108, and a vlCDR3 having an amino acid sequence of SEQ ID NO:109; or i) a VH2 comprising a vhCDR1 having an amino acid sequence of SEQ ID NO:111; a vhCDR2 having an amino acid sequence of SEQ ID NO:112; and a vhCDR3 having an amino acid sequence of SEQ ID NO:113; and (ii) a VL2 comprising a vlCDR1 having an amino acid sequence of SEQ ID NO: 115, a vlCDR2 having an amino acid sequence of SEQ ID NO:116, and a vlCDR3 having an amino acid sequence of SEQ ID NO:117; or i) a VH2 comprising a vhCDR1 having an amino acid sequence of SEQ ID NO:119; a vhCDR2 having an amino acid sequence of SEQ ID NO:120; and a vhCDR3 having an amino acid sequence of SEQ ID NO:121; and (ii) a VL2 comprising a vlCDR1 having an amino acid sequence of SEQ ID NO: 123, a vlCDR2 having an amino acid sequence of SEQ ID NO:124, and a vlCDR3 having an amino acid sequence of SEQ ID NO:125; or i) a VH2 comprising a vhCDR1 having an amino acid sequence of SEQ ID NO:127; a vhCDR2 having an amino acid sequence of SEQ ID NO:128; and a vhCDR3 having an amino acid sequence of SEQ ID NO:129; and (ii) a VL2 comprising a vlCDR1 having an amino acid sequence of SEQ ID NO:131, a vlCDR2 having an amino acid sequence of SEQ ID NO:132, and a vlCDR3 having an amino acid sequence of SEQ ID NO:133; or i) a VH2 comprising a vhCDR1 having an amino acid sequence of SEQ ID NO:135; a vhCDR2 having an amino acid sequence of SEQ ID NO:136; and a vhCDR3 having an amino acid sequence of SEQ ID NO:137; and (ii) a VL2 comprising a vlCDR1 having an amino acid sequence of SEQ ID NO: 139, a vlCDR2 having an amino acid sequence of SEQ ID NO:140, and a vlCDR3 having an amino acid sequence of SEQ ID NO:141; or i) a VH2 comprising a vhCDR1 having an amino acid sequence of SEQ ID NO:143; a vhCDR2 having an amino acid sequence of SEQ ID NO:144; and a vhCDR3 having an amino acid sequence of SEQ ID NO:115; and (ii) a VL2 comprising a vlCDR1 having an amino acid sequence of SEQ ID NO: 147, a vlCDR2 having an amino acid sequence of SEQ ID NO:149, and a vlCDR3 having an amino acid sequence of SEQ ID NO:149; or i) a VH2 comprising a vhCDR1 having an amino acid sequence of SEQ ID NO:151; a vhCDR2 having an amino acid sequence of SEQ ID NO:152; and a vhCDR3 having an amino acid sequence of SEQ ID NO:153; and (ii) a VL2 comprising a vlCDR1 having an amino acid sequence of SEQ ID NO: 155, a vlCDR2 having an amino acid sequence of SEQ ID NO:156, and a vlCDR3 having an amino acid sequence of SEQ ID NO:157; or i) a VH2 comprising a vhCDR1 having an amino acid sequence of SEQ ID NO:159; a vhCDR2 having an amino acid sequence of SEQ ID NO:160; and a vhCDR3 having an amino acid sequence of SEQ ID NO:161; and (ii) a VL2 comprising a vlCDR1 having an amino acid sequence of SEQ ID NO: 163, a vlCDR2 having an amino acid sequence of SEQ ID NO:164, and a vlCDR3 having an amino acid sequence of SEQ ID NO:165; or i) a VH2 comprising a vhCDR1 having an amino acid sequence of SEQ ID NO:167; a vhCDR2 having an amino acid sequence of SEQ ID NO:168; and a vhCDR3 having an amino acid sequence of SEQ ID NO:169; and (ii) a VL2 comprising a vlCDR1 having an amino acid sequence of SEQ ID NO:171, a vlCDR2 having an amino acid sequence of SEQ ID NO:172, and a vlCDR3 having an amino acid sequence of SEQ ID NO:173; or i) a VH2 comprising a vhCDR1 having an amino acid sequence of SEQ ID NO:175; a vhCDR2 having an amino acid sequence of SEQ ID NO:176; and a vhCDR3 having an amino acid sequence of SEQ ID NO:177; and (ii) a VL2 comprising a vlCDR1 having an amino acid sequence of SEQ ID NO: 179, a vlCDR2 having an amino acid sequence of SEQ ID NO:180, and a vlCDR3 having an amino acid sequence of SEQ ID NO:181; or i) a VH2 comprising a vhCDR1 having an amino acid sequence of SEQ ID NO:183; a vhCDR2 having an amino acid sequence of SEQ ID NO:184; and a vhCDR3 having an amino acid sequence of SEQ ID NO:185; and (ii) a VL2 comprising a vlCDR1 having an amino acid sequence of SEQ ID NO: 187, a vlCDR2 having an amino acid sequence of SEQ ID NO:188, and a vlCDR3 having an amino acid sequence of SEQ ID NO:189; or i) a VH2 comprising a vhCDR1 having an amino acid sequence of SEQ ID NO:191; a vhCDR2 having an amino acid sequence of SEQ ID NO:192; and a vhCDR3 having an amino acid sequence of SEQ ID NO: 193; and (ii) a VL2 comprising a vlCDR1 having an amino acid sequence of SEQ ID NO:195, a vlCDR2 having an amino acid sequence of SEQ ID NO:196, and a vlCDR3 having an amino acid sequence of SEQ ID NO:197; or i) a VH2 comprising a vhCDR1 having an amino acid sequence of SEQ ID NO:199; a vhCDR2 having an amino acid sequence of SEQ ID NO:200; and a vhCDR3 having an amino acid sequence of SEQ ID NO:201; and (ii) a VL2 comprising a vlCDR1 having an amino acid sequence of SEQ ID NO:203, a vlCDR2 having an amino acid sequence of SEQ ID NO:204, and a vlCDR3 having an amino acid sequence of SEQ ID NO:205; or i) a VH2 comprising a vhCDR1 having an amino acid sequence of SEQ ID NO:381; a vhCDR2 having an amino acid sequence of SEQ ID NO:382; and a vhCDR3 having an amino acid sequence of SEQ ID NO:383; and (ii) a VL2 comprising a vlCDR1 having an amino acid sequence of SEQ ID NO:385, a vlCDR2 having an amino acid sequence of SEQ ID NO:386, and a vlCDR3 having an amino acid sequence of SEQ ID NO:387; or
i) a VH2 comprising a vhCDR1 having an amino acid sequence of SEQ ID NO:389; a vhCDR2 having an amino acid sequence of SEQ ID NO:390; and a vhCDR3 having an amino acid sequence of SEQ ID NO:391; and (ii) a VL2 comprising a vlCDR1 having an amino acid sequence of SEQ ID NO:393, a vlCDR2 having an amino acid sequence of SEQ ID NO:394, and a vlCDR3 having an amino acid sequence of SEQ ID NO:395; or
i) a VH2 comprising a vhCDR1 having an amino acid sequence of SEQ ID NO:397; a vhCDR2 having an amino acid sequence of SEQ ID NO:398; and a vhCDR3 having an amino acid sequence of SEQ ID NO:399; and (ii) a VL2 comprising a vlCDR1 having an amino acid sequence of SEQ ID NO:401, a vlCDR2 having an amino acid sequence of SEQ ID NO:402, and a vlCDR3 having an amino acid sequence of SEQ ID NO:403; or
i) a VH2 comprising a vhCDR1 having an amino acid sequence of SEQ ID NO:405; a vhCDR2 having an amino acid sequence of SEQ ID NO:406; and a vhCDR3 having an amino acid sequence of SEQ ID NO:407; and (ii) a VL2 comprising a vlCDR1 having an amino acid sequence of SEQ ID NO:409, a vlCDR2 having an amino acid sequence of SEQ ID NO:410, and a vlCDR3 having an amino acid sequence of SEQ ID NO:411; or
i) a VH2 comprising a vhCDR1 having an amino acid sequence of SEQ ID NO:413; a vhCDR2 having an amino acid sequence of SEQ ID NO:414; and a vhCDR3 having an amino acid sequence of SEQ ID NO:415; and (ii) a VL2 comprising a vlCDR1 having an amino acid sequence of SEQ ID NO:417, a vlCDR2 having an amino acid sequence of SEQ ID NO:418, and a vlCDR3 having an amino acid sequence of SEQ ID NO:419; or
i) a VH2 comprising a vhCDR1 having an amino acid sequence of SEQ ID NO:421; a vhCDR2 having an amino acid sequence of SEQ ID NO:422; and a vhCDR3 having an amino acid sequence of SEQ ID NO:423; and (ii) a VL2 comprising a vlCDR1 having an amino acid sequence of SEQ ID NO:425, a vlCDR2 having an amino acid sequence of SEQ ID NO:426, and a vlCDR3 having an amino acid sequence of SEQ ID NO:427.

In exemplary embodiments, VH2 and VL2 are selected from the following:
(i) a VH2 having an amino acid sequence of SEQ ID NO:9; and (ii) a VL2 having an amino acid sequence of SEQ ID NO:13; or
(i) a VH2 having an amino acid sequence of SEQ ID NO:31; and (ii) a VL2 having an amino acid sequence of SEQ ID NO:35; or
(i) a VH2 having an amino acid sequence of SEQ ID NO:39; and (ii) a VL2 having an amino acid sequence of SEQ ID NO:43; or
(i) a VH2 having an amino acid sequence of SEQ ID NO:47; and (ii) a VL2 having an amino acid sequence of SEQ ID NO:51; or
(i) a VH2 having an amino acid sequence of SEQ ID NO:55; and (ii) a VL2 having an amino acid sequence of SEQ ID NO:59; or
(i) a VH2 having an amino acid sequence of SEQ ID NO:63; and (ii) a VL2 having an amino acid sequence of SEQ ID NO:67; or
(i) a VH2 having an amino acid sequence of SEQ ID NO:86; and (ii) a VL2 having an amino acid sequence of SEQ ID NO:90; or
(i) a VH2 having an amino acid sequence of SEQ ID NO:94; and (ii) a VL2 having an amino acid sequence of SEQ ID NO:98; or
(i) a VH2 having an amino acid sequence of SEQ ID NO:102; and (ii) a VL2 having an amino acid sequence of SEQ ID NO:106; or
(i) a VH2 having an amino acid sequence of SEQ ID NO:110; and (ii) a VL2 having an amino acid sequence of SEQ ID NO:114; or
(i) a VH2 having an amino acid sequence of SEQ ID NO:118; and (ii) a VL2 having an amino acid sequence of SEQ ID NO:122; or
(i) a VH2 having an amino acid sequence of SEQ ID NO:126; and (ii) a VL2 having an amino acid sequence of SEQ ID NO:130; or
(i) a VH2 having an amino acid sequence of SEQ ID NO:134; and (ii) a VL2 having an amino acid sequence of SEQ ID NO:138; or
(i) a VH2 having an amino acid sequence of SEQ ID NO:142; and (ii) a VL2 having an amino acid sequence of SEQ ID NO:146; or
(i) a VH2 having an amino acid sequence of SEQ ID NO:150; and (ii) a VL2 having an amino acid sequence of SEQ ID NO:154; or
(i) a VH2 having an amino acid sequence of SEQ ID NO:158; and (ii) a VL2 having an amino acid sequence of SEQ ID NO:162; or
(i) a VH2 having an amino acid sequence of SEQ ID NO:166; and (ii) a VL2 having an amino acid sequence of SEQ ID NO:170; or
(i) a VH2 having an amino acid sequence of SEQ ID NO:174; and (ii) a VL2 having an amino acid sequence of SEQ ID NO:178; or
(i) a VH2 having an amino acid sequence of SEQ ID NO:182; and (ii) a VL2 having an amino acid sequence of SEQ ID NO:186; or
(i) a VH2 having an amino acid sequence of SEQ ID NO:190; and (ii) a VL2 having an amino acid sequence of SEQ ID NO:194; or
(i) a VH2 having an amino acid sequence of SEQ ID NO:198; and (ii) a VL2 having an amino acid sequence of SEQ ID NO:202; or
(i) a VH2 having an amino acid sequence of SEQ ID NO:380; and (ii) a VL2 having an amino acid sequence of SEQ ID NO:384; or
(i) a VH2 having an amino acid sequence of SEQ ID NO:388; and (ii) a VL2 having an amino acid sequence of SEQ ID NO:392; or
(i) a VH2 having an amino acid sequence of SEQ ID NO:396; and (ii) a VL2 having an amino acid sequence of SEQ ID NO:400; or
(i) a VH2 having an amino acid sequence of SEQ ID NO:404; and (ii) a VL2 having an amino acid sequence of SEQ ID NO:408; or
(i) a VH2 having an amino acid sequence of SEQ ID NO:412; and (ii) a VL2 having an amino acid sequence of SEQ ID NO:416; or
(i) a VH2 having an amino acid sequence of SEQ ID NO:420; and (ii) a VL2 having an amino acid sequence of SEQ ID NO:424.

In some embodiments, VH1 comprises a vhCDR1, a vhCDR2, and a vhCDR3 having an amino acid sequence of a vhCDR1, a vhCDR2, and a vhCDR3, respectively, of a VH having an amino acid sequence of SEQ ID NO:214; VL1 comprises a vlCDR1, a vlCDR2, and a vlCDR3 having an amino acid sequence of a vlCDR1, a vlCDR2, and a vlCDR3, respectively, of a VL having an amino acid sequence of SEQ ID NO:218; VH2 comprises a vhCDR1, a vhCDR2, and a vhCDR3 having an amino acid sequence of a vhCDR1, a vhCDR2, and a vhCDR3, respectively, of a VH having an amino acid sequence of SEQ ID NO:39; and VL2 comprises a vlCDR1, a vlCDR2, and a vlCDR3 having an amino acid sequence of a vlCDR1, a vlCDR2, and a vlCDR3, respectively, of a VL having an amino acid sequence of SEQ ID NO:43.

In exemplary embodiments, VH1 comprises a vhCDR1 having an amino acid sequence of SEQ ID NO:215; a vhCDR2 having an amino acid sequence of SEQ ID NO:216; and a vhCDR3 having an amino acid sequence of SEQ ID NO:217; VL1 comprises a vlCDR1 having an amino acid sequence of SEQ ID NO:219, a vlCDR2 having an amino acid sequence of SEQ ID NO: 220, and a vlCDR3 having an amino acid sequence of SEQ ID NO:221; VH2 comprises a vhCDR1 having an amino acid sequence of SEQ ID NO:40; a vhCDR2 having an amino acid sequence of SEQ ID NO:41; and a vhCDR3 having an amino acid sequence of SEQ ID NO:42; and VL2 comprises a vlCDR1 having an amino acid sequence of SEQ ID NO:44, a vlCDR2 having an amino acid sequence of SEQ ID NO:45, and a vlCDR3 having an amino acid sequence of SEQ ID NO:46.

In some embodiments, the first Fc domain and second Fc domain are each variant Fc domains. In exemplary embodiments, one of the first and second Fc domains comprises heterodimerization variant T366W, and the other of the first and second Fc domains comprises heterodimerization variants T366S/L368A/Y407V, wherein numbering is according to EU numbering. In some embodiments, the first Fc domain comprises heterodimerization variant T366W, and the second Fc domain comprises heterodimerization variants T366S/L368A/Y407V.

In certain embodiments, the first and second Fc domains each comprise one or more ablation variants. In some embodiments, one or more ablation variants comprise L234A/L235A/D265S, wherein numbering is according to EU numbering.

In some embodiments, the first or second Fc domain comprises purification variants H435R/Y436F, wherein numbering is according to EU numbering.

In exemplary embodiments, the second Fc domain comprises purification variants H435R/Y436F.

In exemplary embodiments, the first Fc domain comprises amino acid substitutions L234A/L235A/D265S/LT366W, and the second Fc domain comprises amino acid substitutions L234A/L235A/D265S/T366S/L368A/Y407V/H435R/Y436F, wherein numbering is according to EU numbering. In some embodiments, the first and second Fc domains each further comprise amino acid substitutions M252Y/S254T/T256E, wherein numbering is according to EU numbering.

In some embodiments, the first and second Fc domains comprise a set of heterodimerization skew variants selected from the following heterodimerization variants: S364K/E357Q:L368D/K370S; S364K:L368D/K370S; S364K:L368E/K370S; D401K: T411E/K360E/Q362E; and T366W: T366S/L368A/Y407V, wherein numbering is according to EU numbering. In some embodiments, the first and second Fc domains comprise heterodimerization skew variants S364K/E357Q:L368D/K370S, wherein numbering is according to EU numbering.

In certain embodiments, the first and second Fc domains each comprise one or more ablation variants. In exemplary embodiments, the one or more ablation variants comprise E233P/L234V/L235A/G236del/S267K, wherein numbering is according to EU numbering.

In some embodiments, the one of the first or second monomer further comprises a pI variant. In some embodiments, the CH1-hinge-CH2-CH3 of the second monomer comprises pI variants N208D/Q295E/N384D/Q418E/N421D, wherein numbering is according to EU numbering.

In some embodiments, the CH1-hinge-CH2-CH3 of the second monomer comprises amino acid variants E233P/L234V/L235A/G236del/S267K/L368D/K370S/N208D/Q295E/N384D/Q418E/N421 D, the first Fc domain comprises amino acid variants E233P/L234V/L235A/G236del/S267K/S364K/E357Q, wherein numbering is according to EU numbering. In exemplary embodiments, the first and second variant Fc domains each further comprise amino acid variants 428L/434S.

In some embodiments, of the anti-CD28× anti-PSMA antibody, the scFv linker is selected from GKPGSGKPGSGKPGSGKPGS (SEQ ID NO: 443), GGSEGKSSGSGSESKSTGGS (SEQ ID NO: 456), and GGGSGGSGGCPPCGGSGG (SEQ ID NO: 457).

In another aspect, provided herein are heterodimeric anti-CD28× anti-PSMA antibodies in the 2+1 mAb-scFv format. These antibodies comprise: a) a first monomer; b) a second monomer; and c) a light chain. The first monomer comprises, from N-terminal to C-terminal, VH1-CH1-hinge-CH2-CH3-domain linker-scFv, wherein VH1 is a first variable heavy domain, and CH2-CH3 is a first Fc domain. The second monomer comprises, from N-terminal to C-terminal, a VH1-CH1-hinge-CH2-CH3, wherein VH1 is a first variable heavy domain and CH2-CH3 is a second Fc domain. The light chain comprises, from N-terminal to C-terminal, VL1-CL, wherein VL1 is a first variable light domain and CL is a constant light domain. The scFv comprises a second VH domain (VH2), a scFv linker, and a second variable light domain (VL2). Each of the VH1s and the VL1 together form a first antigen binding domain (ABD), and the VH2 and the VL2 form a second ABD. Further, one of the first and second ABDs bind human CD28 and the other of the first and second ABDs binds PSMA.

In some embodiments, the first ABDs bind human CD28 and the second ABD binds PSMA. In certain embodiments, the first ABDs bind PSMA and the second ABD binds human CD28.

In some embodiments, the scFv comprises, from N-terminal to C-terminal, VH2-scFv linker-VL2. In certain embodiments, the scFv comprises, from N-terminal to C-terminal, VL2-scFv linker-VH2.

In some embodiments, the first ABDs bind to human PSMA, and VH1 and VL1 are selected from the following:
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:206; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:210; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:214; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:218; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:222; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:226; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:230; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:234; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:238; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:242; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:246; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:250; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:254; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:258; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:262; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:266; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:270; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:274; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:278; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:282; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:286; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:290; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:294; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:298; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:302; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:306; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:310; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:314; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:318; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:322; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:326; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:330; or
(i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:334; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:338.
In some embodiments, VH1 and VL1 are selected from the following:
(i) a VH1 comprising a vhCDR1 having an amino acid sequence of SEQ ID NO:207; a vhCDR2 having an amino acid sequence of SEQ ID NO:208; and a vhCDR3 having an amino acid sequence of SEQ ID NO:209; and (ii) a VL1 comprising a vlCDR1 having an amino acid sequence of SEQ ID NO:211, a vlCDR2 having an amino acid sequence of SEQ ID NO: 212, and a vlCDR3 having an amino acid sequence of SEQ ID NO:213; or (i) a VH1 comprising a vhCDR1 having an amino acid sequence of SEQ ID NO:215; a vhCDR2 having an amino acid sequence of SEQ ID NO:216; and a vhCDR3 having an amino acid sequence of SEQ ID NO:217; and (ii) a VL1 comprising a vlCDR1 having an amino acid sequence of SEQ ID NO:219, a vlCDR2 having an amino acid sequence of SEQ ID NO: 220, and a vlCDR3 having an amino acid sequence of SEQ ID NO:221;

(i) a VH1 comprising a vhCDR1 having an amino acid sequence of SEQ ID NO:223; a vhCDR2 having an amino acid sequence of SEQ ID NO:224; and a vhCDR3 having an amino acid sequence of SEQ ID NO:225; and (ii) a VL1 comprising a vlCDR1 having an amino acid sequence of SEQ ID NO:227, a vlCDR2 having an amino acid sequence of SEQ ID NO: 228, and a vlCDR3 having an amino acid sequence of SEQ ID NO:229; or (i) a VH1 comprising a vhCDR1 having an amino acid sequence of SEQ ID NO:231; a vhCDR2 having an amino acid sequence of SEQ ID NO:232; and a vhCDR3 having an amino acid sequence of SEQ ID NO:233; and (ii) a VL1 comprising a vlCDR1 having an amino acid sequence of SEQ ID NO:235, a vlCDR2 having an amino acid sequence of SEQ ID NO: 236, and a vlCDR3 having an amino acid sequence of SEQ ID NO:237; or (i) a VH1 comprising a vhCDR1 having an amino acid sequence of SEQ ID NO:239; a vhCDR2 having an amino acid sequence of SEQ ID NO:240; and a vhCDR3 having an amino acid sequence of SEQ ID NO:241; and (ii) a VL1 comprising a vlCDR1 having an amino acid sequence of SEQ ID NO:243, a vlCDR2 having an amino acid sequence of SEQ ID NO: 244, and a vlCDR3 having an amino acid sequence of SEQ ID NO:245; or (i) a VH1 comprising a vhCDR1 having an amino acid sequence of SEQ ID NO:247; a vhCDR2 having an amino acid sequence of SEQ ID NO:248; and a vhCDR3 having an amino acid sequence of SEQ ID NO: 249; and (ii) a VL1 comprising a vlCDR1 having an amino acid sequence of SEQ ID NO:251, a vlCDR2 having an amino acid sequence of SEQ ID NO: 252, and a vlCDR3 having an amino acid sequence of SEQ ID NO:253; or (i) a VH1 comprising a vhCDR1 having an amino acid sequence of SEQ ID NO:255; a vhCDR2 having an amino acid sequence of SEQ ID NO:256; and a vhCDR3 having an amino acid sequence of SEQ ID NO:257; and (ii) a VL1 comprising a vlCDR1 having an amino acid sequence of SEQ ID NO:259, a vlCDR2 having an amino acid sequence of SEQ ID NO: 260, and a vlCDR3 having an amino acid sequence of SEQ ID NO:261; or (i) a VH1 comprising a vhCDR1 having an amino acid sequence of SEQ ID NO:263; a vhCDR2 having an amino acid sequence of SEQ ID NO:264; and a vhCDR3 having an amino acid sequence of SEQ ID NO:265; and (ii) a VL1 comprising a vlCDR1 having an amino acid sequence of SEQ ID NO:267, a vlCDR2 having an amino acid sequence of SEQ ID NO: 268, and a vlCDR3 having an amino acid sequence of SEQ ID NO:269; or (i) a VH1 comprising a vhCDR1 having an amino acid sequence of SEQ ID NO:271; a vhCDR2 having an amino acid sequence of SEQ ID NO:212; and a vhCDR3 having an amino acid sequence of SEQ ID NO:273; and (ii) a VL1 comprising a vlCDR1 having an amino acid sequence of SEQ ID NO:275, a vlCDR2 having an amino acid sequence of SEQ ID NO: 276, and a vlCDR3 having an amino acid sequence of SEQ ID NO:277; or (i) a VH1 comprising a vhCDR1 having an amino acid sequence of SEQ ID NO:279; a vhCDR2 having an amino acid sequence of SEQ ID NO:280; and a vhCDR3 having an amino acid sequence of SEQ ID NO:281; and (ii) a VL1 comprising a vlCDR1 having an amino acid sequence of SEQ ID NO:283, a vlCDR2 having an amino acid sequence of SEQ ID NO: 284, and a vlCDR3 having an amino acid sequence of SEQ ID NO:285; or (i) a VH1 comprising a vhCDR1 having an amino acid sequence of SEQ ID NO:287; a vhCDR2 having an amino acid sequence of SEQ ID NO:288; and a vhCDR3 having an amino acid sequence of SEQ ID NO:289; and (ii) a VL1 comprising a vlCDR1 having an amino acid sequence of SEQ ID NO:291, a vlCDR2 having an amino acid sequence of SEQ ID NO: 292, and a vlCDR3 having an amino acid sequence of SEQ ID NO:293; or (i) a VH1 comprising a vhCDR1 having an amino acid sequence of SEQ ID NO:295; a vhCDR2 having an amino acid sequence of SEQ ID NO:296; and a vhCDR3 having an amino acid sequence of SEQ ID NO:297; and (ii) a VL1 comprising a vlCDR1 having an amino acid sequence of SEQ ID NO:299, a vlCDR2 having an amino acid sequence of SEQ ID NO: 300, and a vlCDR3 having an amino acid sequence of SEQ ID NO:301; or (i) a VH1 comprising a vhCDR1 having an amino acid sequence of SEQ ID NO:303; a vhCDR2 having an amino acid sequence of SEQ ID NO:304; and a vhCDR3 having an amino acid sequence of SEQ ID NO:305; and (ii) a VL1 comprising a vlCDR1 having an amino acid sequence of SEQ ID NO:307, a vlCDR2 having an amino acid sequence of SEQ ID NO: 308, and a vlCDR3 having an amino acid sequence of SEQ ID NO:309; or (i) a VH1 comprising a vhCDR1 having an amino acid sequence of SEQ ID NO:311; a vhCDR2 having an amino acid sequence of SEQ ID NO:312; and a vhCDR3 having an amino acid sequence of SEQ ID NO:313; and (ii) a VL1 comprising a vlCDR1 having an amino acid sequence of SEQ ID NO: 315, a vlCDR2 having an amino acid sequence of SEQ ID NO: 316, and a vlCDR3 having an amino acid sequence of SEQ ID NO:317; or (i) a VH1 comprising a vhCDR1 having an amino acid sequence of SEQ ID NO:319; a vhCDR2 having an amino acid sequence of SEQ ID NO:320; and a vhCDR3 having an amino acid sequence of SEQ ID NO:321; and (ii) a VL1 comprising a vlCDR1 having an amino acid sequence of SEQ ID NO: 323, a vlCDR2 having an amino acid sequence of SEQ ID NO: 324, and a vlCDR3 having an amino acid sequence of SEQ ID NO:325; or (i) a VH1 comprising a vhCDR1 having an amino acid sequence of SEQ ID NO:327; a vhCDR2 having an amino acid sequence of SEQ ID NO:328; and a vhCDR3 having an amino acid sequence of SEQ ID NO:329; and (ii) a VL1 comprising a vlCDR1 having an amino acid sequence of SEQ ID NO:331, a vlCDR2 having an amino acid sequence of SEQ ID NO: 332, and a vlCDR3 having an amino acid sequence of SEQ ID NO:333; or
(i) a VH1 comprising a vhCDR1 having an amino acid sequence of SEQ ID NO:335; a vhCDR2 having an amino acid sequence of SEQ ID NO:336; and a vhCDR3 having an amino acid sequence of SEQ ID NO:337; and (ii) a VL1 comprising a vlCDR1 having an amino acid sequence of SEQ ID NO: 339, a vlCDR2 having an amino acid sequence of SEQ ID NO: 340, and a vlCDR3 having an amino acid sequence of SEQ ID NO:341.

In exemplary embodiments, VH1 and VL1 are selected from the following:
- (i) a VH1 having an amino acid sequence of SEQ ID NO:206; and (ii) a VL1 having an amino acid sequence of SEQ ID NO:210; or
- (i) a VH1 having an amino acid sequence of SEQ ID NO:214; and (ii) a VL1 having an amino acid sequence of SEQ ID NO:218; or
- (i) a VH1 having an amino acid sequence of SEQ ID NO:222; and (ii) a VL1 having an amino acid sequence of SEQ ID NO:226; or
- (i) a VH1 having an amino acid sequence of SEQ ID NO:230; and (ii) a VL1 having an amino acid sequence of SEQ ID NO:234; or
- (i) a VH1 having an amino acid sequence of SEQ ID NO:238; and (ii) a VL1 having an amino acid sequence of SEQ ID NO:242; or
- (i) a VH1 having an amino acid sequence of SEQ ID NO:246; and (ii) a VL1 having an amino acid sequence of SEQ ID NO:250; or
- (i) a VH1 having an amino acid sequence of SEQ ID NO:254; and (ii) a VL1 having an amino acid sequence of SEQ ID NO:258; or
- (i) a VH1 having an amino acid sequence of SEQ ID NO:262; and (ii) a VL1 having an amino acid sequence of SEQ ID NO:266; or
- (i) a VH1 having an amino acid sequence of SEQ ID NO:270; and (ii) a VL1 having an amino acid sequence of SEQ ID NO:274; or
- (i) a VH1 having an amino acid sequence of SEQ ID NO:278; and (ii) a VL1 having an amino acid sequence of SEQ ID NO:282; or
- (i) a VH1 having an amino acid sequence of SEQ ID NO:286; and (ii) a VL1 having an amino acid sequence of SEQ ID NO:290; or
- (i) a VH1 having an amino acid sequence of SEQ ID NO:294; and (ii) a VL1 having an amino acid sequence of SEQ ID NO:298; or
- (i) a VH1 having an amino acid sequence of SEQ ID NO:302; and (ii) a VL1 having an amino acid sequence of SEQ ID NO:306; or
- (i) a VH1 having an amino acid sequence of SEQ ID NO:310; and (ii) a VL1 having an amino acid sequence of SEQ ID NO:314; or
- (i) a VH1 having an amino acid sequence of SEQ ID NO:318; and (ii) a VL1 having an amino acid sequence of SEQ ID NO:322; or
- (i) a VH1 having an amino acid sequence of SEQ ID NO:326; and (ii) a VL1 having an amino acid sequence of SEQ ID NO:330; or
- (i) a VH1 having an amino acid sequence of SEQ ID NO:334; and (ii) a VL1 having an amino acid sequence of SEQ ID NO:338.

In some embodiments, the second ABD binds to human CD28, and VH2 and VL2 are selected from the following:
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:9; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:13; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:31; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:35; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:39; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:43; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:47; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:51; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:55; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:59; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:63; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:67; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:86; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:90; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:94; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:98; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 102; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:106; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:110; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:114; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:118; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:122; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 126; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:130; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 134; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:138; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 142; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:146; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 150; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:154; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 158; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:162; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 166; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:170; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 174; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:178; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:182; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:186; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 190; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:194; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 198; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:202; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:380; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:384; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:388; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:392; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:396; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:400; or (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:404; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:408; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:412; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:416; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:420; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:424.

In certain embodiments, VH2 and VL2 are selected from the following:
(i) a VH2 comprising a vhCDR1 having an amino acid sequence of SEQ ID NO:10; a vhCDR2 having an amino acid sequence of SEQ ID NO:11; and a vhCDR3 having an amino acid sequence of SEQ ID NO: 12; and (ii) a VL2 comprising a vlCDR1 having an amino acid sequence of SEQ ID NO: 14, a vlCDR2 having an amino acid sequence of SEQ ID NO: 15, and a vlCDR3 having an amino acid sequence of SEQ ID NO:16; or
(i) a VH2 comprising a vhCDR1 having an amino acid sequence of SEQ ID NO:32; a vhCDR2 having an amino acid sequence of SEQ ID NO:33; and a vhCDR3 having an amino acid sequence of SEQ ID NO:34; and (ii) a VL2 comprising a vlCDR1 having an amino acid sequence of SEQ ID NO:36, a vlCDR2 having an amino acid sequence of SEQ ID NO: 37, and a vlCDR3 having an amino acid sequence of SEQ ID NO:38; or
i) a VH2 comprising a vhCDR1 having an amino acid sequence of SEQ ID NO:40; a vhCDR2 having an amino acid sequence of SEQ ID NO:41; and a vhCDR3 having an amino acid sequence of SEQ ID NO:42; and (ii) a VL2 comprising a vlCDR1 having an amino acid sequence of SEQ ID NO:44, a vlCDR2 having an amino acid sequence of SEQ ID NO: 45, and a vlCDR3 having an amino acid sequence of SEQ ID NO:46; or
i) a VH2 comprising a vhCDR1 having an amino acid sequence of SEQ ID NO:48; a vhCDR2 having an amino acid sequence of SEQ ID NO:49; and a vhCDR3 having an amino acid sequence of SEQ ID NO:50; and (ii) a VL2 comprising a vlCDR1 having an amino acid sequence of SEQ ID NO:52, a vlCDR2 having an amino acid sequence of SEQ ID NO: 53, and a vlCDR3 having an amino acid sequence of SEQ ID NO:54; or
i) a VH2 comprising a vhCDR1 having an amino acid sequence of SEQ ID NO:56; a vhCDR2 having an amino acid sequence of SEQ ID NO:57; and a vhCDR3 having an amino acid sequence of SEQ ID NO:58; and (ii) a VL2 comprising a vlCDR1 having an amino acid sequence of SEQ ID NO:60, a vlCDR2 having an amino acid sequence of SEQ ID NO:61, and a vlCDR3 having an amino acid sequence of SEQ ID NO:62; or
i) a VH2 comprising a vhCDR1 having an amino acid sequence of SEQ ID NO:64; a vhCDR2 having an amino acid sequence of SEQ ID NO:65; and a vhCDR3 having an amino acid sequence of SEQ ID NO:66; and (ii) a VL2 comprising a vlCDR1 having an amino acid sequence of SEQ ID NO:68, a vlCDR2 having an amino acid sequence of SEQ ID NO:69, and a vlCDR3 having an amino acid sequence of SEQ ID NO:70; or
i) a VH2 comprising a vhCDR1 having an amino acid sequence of SEQ ID NO:87; a vhCDR2 having an amino acid sequence of SEQ ID NO:88; and a vhCDR3 having an amino acid sequence of SEQ ID NO:89; and (ii) a VL2 comprising a vlCDR1 having an amino acid sequence of SEQ ID NO: 91, a vlCDR2 having an amino acid sequence of SEQ ID NO:92, and a vlCDR3 having an amino acid sequence of SEQ ID NO:93; or
i) a VH2 comprising a vhCDR1 having an amino acid sequence of SEQ ID NO:95; a vhCDR2 having an amino acid sequence of SEQ ID NO:96; and a vhCDR3 having an amino acid sequence of SEQ ID NO:97; and (ii) a VL2 comprising a vlCDR1 having an amino acid sequence of SEQ ID NO:99, a vlCDR2 having an amino acid sequence of SEQ ID NO:100, and a vlCDR3 having an amino acid sequence of SEQ ID NO:101; or
i) a VH2 comprising a vhCDR1 having an amino acid sequence of SEQ ID NO:103; a vhCDR2 having an amino acid sequence of SEQ ID NO:104; and a vhCDR3 having an amino acid sequence of SEQ ID NO:105; and (ii) a VL2 comprising a vlCDR1 having an amino acid sequence of SEQ ID NO: 107, a vlCDR2 having an amino acid sequence of SEQ ID NO:108, and a vlCDR3 having an amino acid sequence of SEQ ID NO:109; or
i) a VH2 comprising a vhCDR1 having an amino acid sequence of SEQ ID NO:111; a vhCDR2 having an amino acid sequence of SEQ ID NO:112; and a vhCDR3 having an amino acid sequence of SEQ ID NO:113; and (ii) a VL2 comprising a vlCDR1 having an amino acid sequence of SEQ ID NO: 115, a vlCDR2 having an amino acid sequence of SEQ ID NO:116, and a vlCDR3 having an amino acid sequence of SEQ ID NO:117; or
i) a VH2 comprising a vhCDR1 having an amino acid sequence of SEQ ID NO:119; a vhCDR2 having an amino acid sequence of SEQ ID NO:120; and a vhCDR3 having an amino acid sequence of SEQ ID NO:121; and (ii) a VL2 comprising a vlCDR1 having an amino acid sequence of SEQ ID NO: 123, a vlCDR2 having an amino acid sequence of SEQ ID NO:124, and a vlCDR3 having an amino acid sequence of SEQ ID NO:125; or
i) a VH2 comprising a vhCDR1 having an amino acid sequence of SEQ ID NO:127; a vhCDR2 having an amino acid sequence of SEQ ID NO:128; and a vhCDR3 having an amino acid sequence of SEQ ID NO:129; and (ii) a VL2 comprising a vlCDR1 having an amino acid sequence of SEQ ID NO:131, a vlCDR2 having an amino acid sequence of SEQ ID NO:132, and a vlCDR3 having an amino acid sequence of SEQ ID NO:133; or
i) a VH2 comprising a vhCDR1 having an amino acid sequence of SEQ ID NO:135; a vhCDR2 having an amino acid sequence of SEQ ID NO:136; and a vhCDR3 having an amino acid sequence of SEQ ID NO:137; and (ii) a VL2 comprising a vlCDR1 having an amino acid sequence of SEQ ID NO: 139, a vlCDR2 having an amino acid sequence of SEQ ID NO:140, and a vlCDR3 having an amino acid sequence of SEQ ID NO:141; or
i) a VH2 comprising a vhCDR1 having an amino acid sequence of SEQ ID NO:143; a vhCDR2 having an amino acid sequence of SEQ ID NO:144; and a vhCDR3 having an amino acid sequence of SEQ ID NO:115; and (ii) a VL2 comprising a vlCDR1 having an amino acid sequence of SEQ ID NO: 147, a vlCDR2 having an amino acid sequence of SEQ ID NO:149, and a vlCDR3 having an amino acid sequence of SEQ ID NO:149; or
i) a VH2 comprising a vhCDR1 having an amino acid sequence of SEQ ID NO:151; a vhCDR2 having an amino acid sequence of SEQ ID NO:152; and a vhCDR3 having an amino acid sequence of SEQ ID NO:153; and (ii) a VL2 comprising a vlCDR1 having an amino acid sequence of SEQ ID NO: 155, a vlCDR2 having an amino acid sequence of SEQ ID NO:156, and a vlCDR3 having an amino acid sequence of SEQ ID NO:157; or
i) a VH2 comprising a vhCDR1 having an amino acid sequence of SEQ ID NO:159; a vhCDR2 having an amino acid sequence of SEQ ID NO:160; and a vhCDR3 having an amino acid sequence of SEQ ID NO:161; and (ii) a VL2 comprising a vlCDR1 having an amino acid sequence of SEQ ID NO: 163, a vlCDR2 having an amino acid sequence of SEQ ID NO:164, and a vlCDR3 having an amino acid sequence of SEQ ID NO:165; or
i) a VH2 comprising a vhCDR1 having an amino acid sequence of SEQ ID NO:167; a vhCDR2 having an amino acid sequence of SEQ ID NO:168; and a vhCDR3 having an amino acid sequence of SEQ ID NO:169; and (ii) a VL2 comprising a vlCDR1 having an amino acid sequence of SEQ ID NO:171, a vlCDR2 having an amino acid sequence of SEQ ID NO:172, and a vlCDR3 having an amino acid sequence of SEQ ID NO:173; or
i) a VH2 comprising a vhCDR1 having an amino acid sequence of SEQ ID NO:175; a vhCDR2 having an amino acid sequence of SEQ ID NO:176; and a vhCDR3 having an amino acid sequence of SEQ ID NO:177; and (ii) a VL2 comprising a vlCDR1 having an amino acid sequence of SEQ ID NO: 179, a vlCDR2 having an amino acid sequence of SEQ ID NO:180, and a vlCDR3 having an amino acid sequence of SEQ ID NO:181; or
i) a VH2 comprising a vhCDR1 having an amino acid sequence of SEQ ID NO:183; a vhCDR2 having an amino acid sequence of SEQ ID NO:184; and a vhCDR3 having an amino acid sequence of SEQ ID NO:185; and (ii) a VL2 comprising a vlCDR1 having an amino acid sequence of SEQ ID NO: 187, a vlCDR2 having an amino acid sequence of SEQ ID NO:188, and a vlCDR3 having an amino acid sequence of SEQ ID NO:189; or
i) a VH2 comprising a vhCDR1 having an amino acid sequence of SEQ ID NO:191; a vhCDR2 having an amino acid sequence of SEQ ID NO:192; and a vhCDR3 having an amino acid sequence of SEQ ID NO:193; and (ii) a VL2 comprising a vlCDR1 having an amino acid sequence of SEQ ID NO: 195, a vlCDR2 having an amino acid sequence of SEQ ID NO:196, and a vlCDR3 having an amino acid sequence of SEQ ID NO:197; or
i) a VH2 comprising a vhCDR1 having an amino acid sequence of SEQ ID NO:199; a vhCDR2 having an amino acid sequence of SEQ ID NO:200; and a vhCDR3 having an amino acid sequence of SEQ ID NO:201; and (ii) a VL2 comprising a vlCDR1 having an amino acid sequence of SEQ ID NO:203, a vlCDR2 having an amino acid sequence of SEQ ID NO:204, and a vlCDR3 having an amino acid sequence of SEQ ID NO:205; or
i) a VH2 comprising a vhCDR1 having an amino acid sequence of SEQ ID NO:381; a vhCDR2 having an amino acid sequence of SEQ ID NO:382; and a vhCDR3 having an amino acid sequence of SEQ ID NO:383; and (ii) a VL2 comprising a vlCDR1 having an amino acid sequence of SEQ ID NO:385, a vlCDR2 having an amino acid sequence of SEQ ID NO:386, and a vlCDR3 having an amino acid sequence of SEQ ID NO:387; or
i) a VH2 comprising a vhCDR1 having an amino acid sequence of SEQ ID NO:389; a vhCDR2 having an amino acid sequence of SEQ ID NO:390; and a vhCDR3 having an amino acid sequence of SEQ ID NO:391; and (ii) a VL2 comprising a vlCDR1 having an amino acid sequence of SEQ ID NO:393, a vlCDR2 having an amino acid sequence of SEQ ID NO:394, and a vlCDR3 having an amino acid sequence of SEQ ID NO:395; or
i) a VH2 comprising a vhCDR1 having an amino acid sequence of SEQ ID NO:397; a vhCDR2 having an amino acid sequence of SEQ ID NO:398; and a vhCDR3 having an amino acid sequence of SEQ ID NO:399; and (ii) a VL2 comprising a vlCDR1 having an amino acid sequence of SEQ ID NO:401, a vlCDR2 having an amino acid sequence of SEQ ID NO:402, and a vlCDR3 having an amino acid sequence of SEQ ID NO:403; or
i) a VH2 comprising a vhCDR1 having an amino acid sequence of SEQ ID NO:405; a vhCDR2 having an amino acid sequence of SEQ ID NO:406; and a vhCDR3 having an amino acid sequence of SEQ ID NO:407; and (ii) a VL2 comprising a vlCDR1 having an amino acid sequence of SEQ ID NO:409, a vlCDR2 having an amino acid sequence of SEQ ID NO:410, and a vlCDR3 having an amino acid sequence of SEQ ID NO:411; or
i) a VH2 comprising a vhCDR1 having an amino acid sequence of SEQ ID NO:413; a vhCDR2 having an amino acid sequence of SEQ ID NO:414; and a vhCDR3 having an amino acid sequence of SEQ ID NO:415; and (ii) a VL2 comprising a vlCDR1 having an amino acid sequence of SEQ ID NO:417, a vlCDR2 having an amino acid sequence of SEQ ID NO:418, and a vlCDR3 having an amino acid sequence of SEQ ID NO:419; or
i) a VH2 comprising a vhCDR1 having an amino acid sequence of SEQ ID NO:421; a vhCDR2 having an amino acid sequence of SEQ ID NO:422; and a vhCDR3 having an amino acid sequence of SEQ ID NO:423; and (ii) a VL2 comprising a vlCDR1 having an amino acid sequence of SEQ ID NO:425, a vlCDR2 having an amino acid sequence of SEQ ID NO:426, and a vlCDR3 having an amino acid sequence of SEQ ID NO:427.

In exemplary embodiments, VH2 and VL2 are selected from the following:
(i) a VH2 having an amino acid sequence of SEQ ID NO:9; and (ii) a VL2 having an amino acid sequence of SEQ ID NO:13; or
(i) a VH2 having an amino acid sequence of SEQ ID NO:31; and (ii) a VL2 having an amino acid sequence of SEQ ID NO:35; or (i) a VH2 having an amino acid sequence of SEQ ID NO:39; and (ii) a VL2 having an amino acid sequence of SEQ ID NO:43; or
(i) a VH2 having an amino acid sequence of SEQ ID NO:47; and (ii) a VL2 having an amino acid sequence of SEQ ID NO:51; or
(i) a VH2 having an amino acid sequence of SEQ ID NO:55; and (ii) a VL2 having an amino acid sequence of SEQ ID NO:59; or
(i) a VH2 having an amino acid sequence of SEQ ID NO:63; and (ii) a VL2 having an amino acid sequence of SEQ ID NO:67; or
(i) a VH2 having an amino acid sequence of SEQ ID NO:86; and (ii) a VL2 having an amino acid sequence of SEQ ID NO:90; or
(i) a VH2 having an amino acid sequence of SEQ ID NO:94; and (ii) a VL2 having an amino acid sequence of SEQ ID NO:98; or
(i) a VH2 having an amino acid sequence of SEQ ID NO:102; and (ii) a VL2 having an amino acid sequence of SEQ ID NO:106; or
(i) a VH2 having an amino acid sequence of SEQ ID NO:110; and (ii) a VL2 having an amino acid sequence of SEQ ID NO:114; or
(i) a VH2 having an amino acid sequence of SEQ ID NO:118; and (ii) a VL2 having an amino acid sequence of SEQ ID NO:122; or
(i) a VH2 having an amino acid sequence of SEQ ID NO:126; and (ii) a VL2 having an amino acid sequence of SEQ ID NO:130; or
(i) a VH2 having an amino acid sequence of SEQ ID NO:134; and (ii) a VL2 having an amino acid sequence of SEQ ID NO:138; or
(i) a VH2 having an amino acid sequence of SEQ ID NO:142; and (ii) a VL2 having an amino acid sequence of SEQ ID NO:146; or
(i) a VH2 having an amino acid sequence of SEQ ID NO:150; and (ii) a VL2 having an amino acid sequence of SEQ ID NO:154; or
(i) a VH2 having an amino acid sequence of SEQ ID NO:158; and (ii) a VL2 having an amino acid sequence of SEQ ID NO:162; or
(i) a VH2 having an amino acid sequence of SEQ ID NO:166; and (ii) a VL2 having an amino acid sequence of SEQ ID NO:170; or
(i) a VH2 having an amino acid sequence of SEQ ID NO:174; and (ii) a VL2 having an amino acid sequence of SEQ ID NO:178; or
(i) a VH2 having an amino acid sequence of SEQ ID NO:182; and (ii) a VL2 having an amino acid sequence of SEQ ID NO:186; or
(i) a VH2 having an amino acid sequence of SEQ ID NO:190; and (ii) a VL2 having an amino acid sequence of SEQ ID NO:194; or
(i) a VH2 having an amino acid sequence of SEQ ID NO:198; and (ii) a VL2 having an amino acid sequence of SEQ ID NO:202; or
(i) a VH2 having an amino acid sequence of SEQ ID NO:380; and (ii) a VL2 having an amino acid sequence of SEQ ID NO:384; or
(i) a VH2 having an amino acid sequence of SEQ ID NO:388; and (ii) a VL2 having an amino acid sequence of SEQ ID NO:392; or
(i) a VH2 having an amino acid sequence of SEQ ID NO:396; and (ii) a VL2 having an amino acid sequence of SEQ ID NO:400; or
(i) a VH2 having an amino acid sequence of SEQ ID NO:404; and (ii) a VL2 having an amino acid sequence of SEQ ID NO:408; or
(i) a VH2 having an amino acid sequence of SEQ ID NO:412; and (ii) a VL2 having an amino acid sequence of SEQ ID NO:416; or
(i) a VH2 having an amino acid sequence of SEQ ID NO:420; and (ii) a VL2 having an amino acid sequence of SEQ ID NO:424.

In some embodiments, VH1 comprises a vhCDR1, a vhCDR2, and a vhCDR3 having an amino acid sequence of a vhCDR1, a vhCDR2, and a vhCDR3, respectively, of a VH having an amino acid sequence of SEQ ID NO:214; VL1 comprises a vlCDR1, a vlCDR2, and a vlCDR3 having an amino acid sequence of a vlCDR1, a vlCDR2, and a vlCDR3, respectively, of a VL having an amino acid sequence of SEQ ID NO:218; VH2 comprises a vhCDR1, a vhCDR2, and a vhCDR3 having an amino acid sequence of a vhCDR1, a vhCDR2, and a vhCDR3, respectively, of a VH having an amino acid sequence of SEQ ID NO:39; and VL2 comprises a vlCDR1, a vlCDR2, and a vlCDR3 having an amino acid sequence of a vlCDR1, a vlCDR2, and a vlCDR3, respectively, of a VL having an amino acid sequence of SEQ ID NO:43.

In exemplary embodiments, VH1 comprises a vhCDR1 having an amino acid sequence of SEQ ID NO:215; a vhCDR2 having an amino acid sequence of SEQ ID NO:216; and a vhCDR3 having an amino acid sequence of SEQ ID NO:217; VL1 comprises a vlCDR1 having an amino acid sequence of SEQ ID NO:219, a vlCDR2 having an amino acid sequence of SEQ ID NO: 220, and a vlCDR3 having an amino acid sequence of SEQ ID NO:221, VH2 comprises a vhCDR1 having an amino acid sequence of SEQ ID NO:40; a vhCDR2 having an amino acid sequence of SEQ ID NO:41; and a vhCDR3 having an amino acid sequence of SEQ ID NO:42; and VL2 comprises a vlCDR1 having an amino acid sequence of SEQ ID NO:44, a vlCDR2 having an amino acid sequence of SEQ ID NO:45, and a vlCDR3 having an amino acid sequence of SEQ ID NO:46.

In some embodiments, the first Fc domain and second Fc domain are each variant Fc domains. In exemplary embodiments, one of the first and second Fc domains comprises heterodimerization variant T366W, and the other of the first and second Fc domains comprises heterodimerization variants T366S/L368A/Y407V, wherein numbering is according to EU numbering. In some embodiments, the first Fc domain comprises heterodimerization variant T366W, and the second Fc domain comprises heterodimerization variants T366S/L368A/Y407V.

In certain embodiments, the first and second Fc domains each comprise one or more ablation variants. In some embodiments, one or more ablation variants comprise L234A/L235A/D265S, wherein numbering is according to EU numbering.

In some embodiments, the first or second Fc domain comprises purification variants H435R/Y436F, wherein numbering is according to EU numbering.

In exemplary embodiments, the second Fc domain comprises purification variants H435R/Y436F.

In exemplary embodiments, the first Fc domain comprises amino acid substitutions L234A/L235A/D265S/LT366W, and the second Fc domain comprises amino acid substitutions L234A/L235A/D265S/T366S/L368A/Y407V/H435R/Y436F, wherein numbering is according to EU numbering. In some embodiments, the first and second Fc domains each further comprise amino acid substitutions M252Y/S254T/T256E, wherein numbering is according to EU numbering.

In some embodiments, the first and second Fc domains comprise a set of heterodimerization skew variants selected from the following heterodimerization variants: S364K/E357Q:L368D/K370S; S364K:L368D/K370S; S364K:L368E/K370S; D401K: T411E/K360E/Q362E; and T366W:T366S/L368A/Y407V, wherein numbering is according to EU numbering. In some embodiments, the first and second Fc domains comprise heterodimerization skew variants S364K/E357Q:L368D/K370S, wherein numbering is according to EU numbering.

In certain embodiments, the first and second Fc domains each comprise one or more ablation variants. In exemplary embodiments, the one or more ablation variants comprise E233P/L234V/L235A/G236del/S267K, wherein numbering is according to EU numbering.

In some embodiments, the one of the first or second monomer further comprises a pI variant. In some embodiments, the CH1-hinge-CH2-CH3 of the second monomer comprises pI variants N208D/Q295E/N384D/Q418E/N421D, wherein numbering is according to EU numbering.

In some embodiments, the CH1-hinge-CH2-CH3 of the second monomer comprises amino acid variants E233P/L234V/L235A/G236del/S267K/L368D/K370S/N208D/Q295E/N384D/Q418E/N421 D, the first Fc domain comprises amino acid variants E233P/L234V/L235A/G236del/S267K/S364K/E357Q, wherein numbering is according to EU numbering. In exemplary embodiments, the first and second variant Fc domains each further comprise amino acid variants 428L/434S.

In some embodiments, of the anti-CD28× anti-PSMA antibody, the scFv linker is selected from GKPGSGKPGSGKPGSGKPGS (SEQ ID NO: 443), GGSEGKSSGSGSESKSTGGS (SEQ ID NO: 456), and GGGSGGSGGCPPCGGSGG (SEQ ID NO: 457).

In another aspect, provided herein are bispecific antibodies that include a first antigen binding domain that binds to PSMA, and a second antigen binding domain that binds to CD28.

The first antigen binding domain (i.e., the PSMA binding domain) comprises:
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:206; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:210; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:214; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:218; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:222; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:226; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:230; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:234; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:238; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:242; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:246; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:250; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:254; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:258; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:262; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:266; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:270; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:274; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:278; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:282; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:286; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:290; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:294; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:298; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:302; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:306; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:310; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:314; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:318; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:322; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:326; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:330; or
- (i) a VH1 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:334; and (ii) a VL1 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:338.

The second antigen binding domain (i.e., the CD28 binding domain) comprises:
- i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:9; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:13; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:31; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:35; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:39; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:43; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:47; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:51; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:55; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:59; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:63; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:67; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:86; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:90; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:94; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:98; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 102; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:106; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:110; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:114; or
- (i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:118; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:122; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 126; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:130; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 134; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:138; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 142; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:146; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 150; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:154; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 158; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:162; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 166; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:170; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 174; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:178; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:182; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:186; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 190; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:194; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 198; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:202; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:380; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:384; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:388; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:392; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:396; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:400; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:404; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:408; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:412; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:416; or
(i) a VH2 comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:420; and (ii) a VL2 comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:424.
In some embodiments, (i) the vhCDR1, vhCDR2, vhCDR3, vlCDR1, vlCDR2, and vlCDR3 amino acid sequences are according to the Kabat numbering system; (ii)

the vhCDR1, vhCDR2, vhCDR3, vlCDR1, vlCDR2, and vlCDR3 amino acid sequences are according to the Chothia numbering system; (iii) the vhCDR1, vhCDR2, vhCDR3, vlCDR1, vlCDR2, and vlCDR3 amino acid sequences are according to the AbM numbering system; (iv) the vhCDR1, vhCDR2, vhCDR3, vlCDR1, vlCDR2, and vlCDR3 amino acid sequences are according to the Contact numbering system; (v) wherein the vhCDR1, vhCDR2, vhCDR3, vlCDR1, vlCDR2, and vlCDR3 amino acid sequences are according to the IMGT numbering system; (vi) wherein the vhCDR1, vhCDR2, vhCDR3, vlCDR1, vlCDR2, and vlCDR3 amino acid sequences are according to the Kabat+ Chothia numbering system; and/or the vhCDR1, vhCDR2, vhCDR3, vlCDR1, vlCDR2, and vlCDR3 amino acid sequences are according to the Xencor numbering system.

In another aspect, provided herein are bispecific antibodies that include a first antigen binding domain that binds to PSMA, and a second antigen binding domain that binds to CD28.

The first antigen binding domain (i.e., the PSMA binding domain) comprises:

(i) a VH1 comprising a vhCDR1 having an amino acid sequence of SEQ ID NO:207; a vhCDR2 having an amino acid sequence of SEQ ID NO:208; and a vhCDR3 having an amino acid sequence of SEQ ID NO:209; and (ii) a VL1 comprising a vlCDR1 having an amino acid sequence of SEQ ID NO:211, a vlCDR2 having an amino acid sequence of SEQ ID NO: 212, and a vlCDR3 having an amino acid sequence of SEQ ID NO:213; or (i) a VH1 comprising a vhCDR1 having an amino acid sequence of SEQ ID NO:215; a vhCDR2 having an amino acid sequence of SEQ ID NO:216; and a vhCDR3 having an amino acid sequence of SEQ ID NO:217; and (ii) a VL1 comprising a vlCDR1 having an amino acid sequence of SEQ ID NO:219, a vlCDR2 having an amino acid sequence of SEQ ID NO: 220, and a vlCDR3 having an amino acid sequence of SEQ ID NO:221;

(i) a VH1 comprising a vhCDR1 having an amino acid sequence of SEQ ID NO:223; a vhCDR2 having an amino acid sequence of SEQ ID NO:224; and a vhCDR3 having an amino acid sequence of SEQ ID NO:225; and (ii) a VL1 comprising a vlCDR1 having an amino acid sequence of SEQ ID NO:227, a vlCDR2 having an amino acid sequence of SEQ ID NO: 228, and a vlCDR3 having an amino acid sequence of SEQ ID NO:229; or (i) a VH1 comprising a vhCDR1 having an amino acid sequence of SEQ ID NO:231; a vhCDR2 having an amino acid sequence of SEQ ID NO:232; and a vhCDR3 having an amino acid sequence of SEQ ID NO: 233; and (ii) a VL1 comprising a vlCDR1 having an amino acid sequence of SEQ ID NO:235, a vlCDR2 having an amino acid sequence of SEQ ID NO: 236, and a vlCDR3 having an amino acid sequence of SEQ ID NO:237; or (i) a VH1 comprising a vhCDR1 having an amino acid sequence of SEQ ID NO:239; a vhCDR2 having an amino acid sequence of SEQ ID NO:240; and a vhCDR3 having an amino acid sequence of SEQ ID NO:241; and (ii) a VL1 comprising a vlCDR1 having an amino acid sequence of SEQ ID NO:243, a vlCDR2 having an amino acid sequence of SEQ ID NO: 244, and a vlCDR3 having an amino acid sequence of SEQ ID NO:245; or (i) a VH1 comprising a vhCDR1 having an amino acid sequence of SEQ ID NO:247; a vhCDR2 having an amino acid sequence of SEQ ID NO:248; and a vhCDR3 having an amino acid sequence of SEQ ID NO:249; and (ii) a VL1 comprising a vlCDR1 having an amino acid sequence of SEQ ID NO:251, a vlCDR2 having an amino acid sequence of SEQ ID NO: 252, and a vlCDR3 having an amino acid sequence of SEQ ID NO:253; or (i) a VH1 comprising a vhCDR1 having an amino acid sequence of SEQ ID NO:255; a vhCDR2 having an amino acid sequence of SEQ ID NO:256; and a vhCDR3 having an amino acid sequence of SEQ ID NO:257; and (ii) a VL1 comprising a vlCDR1 having an amino acid sequence of SEQ ID NO:259, a vlCDR2 having an amino acid sequence of SEQ ID NO: 260, and a vlCDR3 having an amino acid sequence of SEQ ID NO:261; or (i) a VH1 comprising a vhCDR1 having an amino acid sequence of SEQ ID NO:263; a vhCDR2 having an amino acid sequence of SEQ ID NO:264; and a vhCDR3 having an amino acid sequence of SEQ ID NO:265; and (ii) a VL1 comprising a vlCDR1 having an amino acid sequence of SEQ ID NO:267, a vlCDR2 having an amino acid sequence of SEQ ID NO: 268, and a vlCDR3 having an amino acid sequence of SEQ ID NO:269; or (i) a VH1 comprising a vhCDR1 having an amino acid sequence of SEQ ID NO:271; a vhCDR2 having an amino acid sequence of SEQ ID NO:212; and a vhCDR3 having an amino acid sequence of SEQ ID NO:273; and (ii) a VL1 comprising a vlCDR1 having an amino acid sequence of SEQ ID NO:275, a vlCDR2 having an amino acid sequence of SEQ ID NO: 276, and a vlCDR3 having an amino acid sequence of SEQ ID NO:277; or (i) a VH1 comprising a vhCDR1 having an amino acid sequence of SEQ ID NO:279; a vhCDR2 having an amino acid sequence of SEQ ID NO:280; and a vhCDR3 having an amino acid sequence of SEQ ID NO:281; and (ii) a VL1 comprising a vlCDR1 having an amino acid sequence of SEQ ID NO:283, a vlCDR2 having an amino acid sequence of SEQ ID NO: 284, and a vlCDR3 having an amino acid sequence of SEQ ID NO:285; or (i) a VH1 comprising a vhCDR1 having an amino acid sequence of SEQ ID NO:287; a vhCDR2 having an amino acid sequence of SEQ ID NO:288; and a vhCDR3 having an amino acid sequence of SEQ ID NO:289; and (ii) a VL1 comprising a vlCDR1 having an amino acid sequence of SEQ ID NO:291, a vlCDR2 having an amino acid sequence of SEQ ID NO: 292, and a vlCDR3 having an amino acid sequence of SEQ ID NO:293; or (i) a VH1 comprising a vhCDR1 having an amino acid sequence of SEQ ID NO:295; a vhCDR2 having an amino acid sequence of SEQ ID NO:296; and a vhCDR3 having an amino acid sequence of SEQ ID NO:297; and (ii) a VL1 comprising a vlCDR1 having an amino acid sequence of SEQ ID NO:299, a vlCDR2 having an amino acid sequence of SEQ ID NO: 300, and a vlCDR3 having an amino acid sequence of SEQ ID NO:301; or (i) a VH1 comprising a vhCDR1 having an amino acid sequence of SEQ ID NO:303; a vhCDR2 having an amino acid sequence of SEQ ID NO:304; and a vhCDR3 having an amino acid sequence of SEQ ID NO:305; and (ii) a VL1 comprising a vlCDR1 having an amino acid sequence of SEQ ID NO:307, a vlCDR2 having an amino acid sequence of SEQ ID NO: 308, and a vlCDR3 having an amino acid sequence of SEQ ID NO:309; or
- (i) a VH1 comprising a vhCDR1 having an amino acid sequence of SEQ ID NO:311; a vhCDR2 having an amino acid sequence of SEQ ID NO:312; and a vhCDR3 having an amino acid sequence of SEQ ID NO:313; and (ii) a VL1 comprising a vlCDR1 having an amino acid sequence of SEQ ID NO: 315, a vlCDR2 having an amino acid sequence of SEQ ID NO: 316, and a vlCDR3 having an amino acid sequence of SEQ ID NO:317; or
- (i) a VH1 comprising a vhCDR1 having an amino acid sequence of SEQ ID NO:319; a vhCDR2 having an amino acid sequence of SEQ ID NO:320; and a vhCDR3 having an amino acid sequence of SEQ ID NO:321; and (ii) a VL1 comprising a vlCDR1 having an amino acid sequence of SEQ ID NO: 323, a vlCDR2 having an amino acid sequence of SEQ ID NO: 324, and a vlCDR3 having an amino acid sequence of SEQ ID NO:325; or
- (i) a VH1 comprising a vhCDR1 having an amino acid sequence of SEQ ID NO:327; a vhCDR2 having an amino acid sequence of SEQ ID NO:328; and a vhCDR3 having an amino acid sequence of SEQ ID NO:329; and (ii) a VL1 comprising a vlCDR1 having an amino acid sequence of SEQ ID NO:331, a vlCDR2 having an amino acid sequence of SEQ ID NO: 332, and a vlCDR3 having an amino acid sequence of SEQ ID NO:333; or
- (i) a VH1 comprising a vhCDR1 having an amino acid sequence of SEQ ID NO:335; a vhCDR2 having an amino acid sequence of SEQ ID NO:336; and a vhCDR3 having an amino acid sequence of SEQ ID NO:337; and (ii) a VL1 comprising a vlCDR1 having an amino acid sequence of SEQ ID NO: 339, a vlCDR2 having an amino acid sequence of SEQ ID NO: 340, and a vlCDR3 having an amino acid sequence of SEQ ID NO:341.

The second antigen binding domain (i.e., the CD28 binding domain) comprises:
- (i) a VH2 comprising a vhCDR1 having an amino acid sequence of SEQ ID NO:10; a vhCDR2 having an amino acid sequence of SEQ ID NO:11; and a vhCDR3 having an amino acid sequence of SEQ ID NO: 12; and (ii) a VL2 comprising a vlCDR1 having an amino acid sequence of SEQ ID NO: 14, a vlCDR2 having an amino acid sequence of SEQ ID NO: 15, and a vlCDR3 having an amino acid sequence of SEQ ID NO:16; or
- (i) a VH2 comprising a vhCDR1 having an amino acid sequence of SEQ ID NO:32; a vhCDR2 having an amino acid sequence of SEQ ID NO:33; and a vhCDR3 having an amino acid sequence of SEQ ID NO:34; and (ii) a VL2 comprising a vlCDR1 having an amino acid sequence of SEQ ID NO: 36, a vlCDR2 having an amino acid sequence of SEQ ID NO: 37, and a vlCDR3 having an amino acid sequence of SEQ ID NO:38; or
- i) a VH2 comprising a vhCDR1 having an amino acid sequence of SEQ ID NO:40; a vhCDR2 having an amino acid sequence of SEQ ID NO:41; and a vhCDR3 having an amino acid sequence of SEQ ID NO:42; and (ii) a VL2 comprising a vlCDR1 having an amino acid sequence of SEQ ID NO:44, a vlCDR2 having an amino acid sequence of SEQ ID NO: 45, and a vlCDR3 having an amino acid sequence of SEQ ID NO:46; or
- i) a VH2 comprising a vhCDR1 having an amino acid sequence of SEQ ID NO:48; a vhCDR2 having an amino acid sequence of SEQ ID NO:49; and a vhCDR3 having an amino acid sequence of SEQ ID NO:50; and (ii) a VL2 comprising a vlCDR1 having an amino acid sequence of SEQ ID NO:52, a vlCDR2 having an amino acid sequence of SEQ ID NO: 53, and a vlCDR3 having an amino acid sequence of SEQ ID NO:54; or
- i) a VH2 comprising a vhCDR1 having an amino acid sequence of SEQ ID NO:56; a vhCDR2 having an amino acid sequence of SEQ ID NO:57; and a vhCDR3 having an amino acid sequence of SEQ ID NO:58; and (ii) a VL2 comprising a vlCDR1 having an amino acid sequence of SEQ ID NO:60, a vlCDR2 having an amino acid sequence of SEQ ID NO:61, and a vlCDR3 having an amino acid sequence of SEQ ID NO:62; or
- i) a VH2 comprising a vhCDR1 having an amino acid sequence of SEQ ID NO:64; a vhCDR2 having an amino acid sequence of SEQ ID NO:65; and a vhCDR3 having an amino acid sequence of SEQ ID NO:66; and (ii) a VL2 comprising a vlCDR1 having an amino acid sequence of SEQ ID NO:68, a vlCDR2 having an amino acid sequence of SEQ ID NO:69, and a vlCDR3 having an amino acid sequence of SEQ ID NO:70; or
- i) a VH2 comprising a vhCDR1 having an amino acid sequence of SEQ ID NO:87; a vhCDR2 having an amino acid sequence of SEQ ID NO:88; and a vhCDR3 having an amino acid sequence of SEQ ID NO:89; and (ii) a VL2 comprising a vlCDR1 having an amino acid sequence of SEQ ID NO:91, a vlCDR2 having an amino acid sequence of SEQ ID NO:92, and a vlCDR3 having an amino acid sequence of SEQ ID NO:93; or
- i) a VH2 comprising a vhCDR1 having an amino acid sequence of SEQ ID NO:95; a vhCDR2 having an amino acid sequence of SEQ ID NO:96; and a vhCDR3 having an amino acid sequence of SEQ ID NO:97; and (ii) a VL2 comprising a vlCDR1 having an amino acid sequence of SEQ ID NO:99, a vlCDR2 having an amino acid sequence of SEQ ID NO:100, and a vlCDR3 having an amino acid sequence of SEQ ID NO:101; or
- i) a VH2 comprising a vhCDR1 having an amino acid sequence of SEQ ID NO:103; a vhCDR2 having an amino acid sequence of SEQ ID NO:104; and a vhCDR3 having an amino acid sequence of SEQ ID NO:105; and (ii) a VL2 comprising a vlCDR1 having an amino acid sequence of SEQ ID NO: 107, a vlCDR2 having an amino acid sequence of SEQ ID NO:108, and a vlCDR3 having an amino acid sequence of SEQ ID NO:109; or
- i) a VH2 comprising a vhCDR1 having an amino acid sequence of SEQ ID NO:111; a vhCDR2 having an amino acid sequence of SEQ ID NO:112; and a vhCDR3 having an amino acid sequence of SEQ ID NO:113; and (ii) a VL2 comprising a vlCDR1 having an amino acid sequence of SEQ ID NO: 115, a vlCDR2 having an amino acid sequence of SEQ ID NO:116, and a vlCDR3 having an amino acid sequence of SEQ ID NO:117; or
- i) a VH2 comprising a vhCDR1 having an amino acid sequence of SEQ ID NO:119; a vhCDR2 having an amino acid sequence of SEQ ID NO:120; and a vhCDR3 having an amino acid sequence of SEQ ID NO:121; and (ii) a VL2 comprising a vlCDR1 having an amino acid sequence of SEQ ID NO: 123, a vlCDR2 having an amino acid sequence of SEQ ID NO:124, and a vlCDR3 having an amino acid sequence of SEQ ID NO:125; or i) a VH2 comprising a vhCDR1 having an amino acid sequence of SEQ ID NO:127; a vhCDR2 having an amino acid sequence of SEQ ID NO:128; and a vhCDR3 having an amino acid sequence of SEQ ID NO:129; and (ii) a VL2 comprising a vlCDR1 having an amino acid sequence of SEQ ID NO:131, a vlCDR2 having an amino acid sequence of SEQ ID NO:132, and a vlCDR3 having an amino acid sequence of SEQ ID NO:133; or i) a VH2 comprising a vhCDR1 having an amino acid sequence of SEQ ID NO:135; a vhCDR2 having an amino acid sequence of SEQ ID NO:136; and a vhCDR3 having an amino acid sequence of SEQ ID NO:137; and (ii) a VL2 comprising a vlCDR1 having an amino acid sequence of SEQ ID NO: 139, a vlCDR2 having an amino acid sequence of SEQ ID NO:140, and a vlCDR3 having an amino acid sequence of SEQ ID NO:141; or i) a VH2 comprising a vhCDR1 having an amino acid sequence of SEQ ID NO:143; a vhCDR2 having an amino acid sequence of SEQ ID NO:144; and a vhCDR3 having an amino acid sequence of SEQ ID NO:115; and (ii) a VL2 comprising a vlCDR1 having an amino acid sequence of SEQ ID NO: 147, a vlCDR2 having an amino acid sequence of SEQ ID NO:149, and a vlCDR3 having an amino acid sequence of SEQ ID NO:149; or i) a VH2 comprising a vhCDR1 having an amino acid sequence of SEQ ID NO:151; a vhCDR2 having an amino acid sequence of SEQ ID NO:152; and a vhCDR3 having an amino acid sequence of SEQ ID NO:153; and (ii) a VL2 comprising a vlCDR1 having an amino acid sequence of SEQ ID NO: 155, a vlCDR2 having an amino acid sequence of SEQ ID NO:156, and a vlCDR3 having an amino acid sequence of SEQ ID NO:157; or i) a VH2 comprising a vhCDR1 having an amino acid sequence of SEQ ID NO:159; a vhCDR2 having an amino acid sequence of SEQ ID NO:160; and a vhCDR3 having an amino acid sequence of SEQ ID NO:161; and (ii) a VL2 comprising a vlCDR1 having an amino acid sequence of SEQ ID NO: 163, a vlCDR2 having an amino acid sequence of SEQ ID NO:164, and a vlCDR3 having an amino acid sequence of SEQ ID NO:165; or i) a VH2 comprising a vhCDR1 having an amino acid sequence of SEQ ID NO:167; a vhCDR2 having an amino acid sequence of SEQ ID NO:168; and a vhCDR3 having an amino acid sequence of SEQ ID NO:169; and (ii) a VL2 comprising a vlCDR1 having an amino acid sequence of SEQ ID NO:171, a vlCDR2 having an amino acid sequence of SEQ ID NO:172, and a vlCDR3 having an amino acid sequence of SEQ ID NO:173; or i) a VH2 comprising a vhCDR1 having an amino acid sequence of SEQ ID NO:175; a vhCDR2 having an amino acid sequence of SEQ ID NO:176; and a vhCDR3 having an amino acid sequence of SEQ ID NO:177; and (ii) a VL2 comprising a vlCDR1 having an amino acid sequence of SEQ ID NO: 179, a vlCDR2 having an amino acid sequence of SEQ ID NO:180, and a vlCDR3 having an amino acid sequence of SEQ ID NO:181; or i) a VH2 comprising a vhCDR1 having an amino acid sequence of SEQ ID NO:183; a vhCDR2 having an amino acid sequence of SEQ ID NO:184; and a vhCDR3 having an amino acid sequence of SEQ ID NO:185; and (ii) a VL2 comprising a vlCDR1 having an amino acid sequence of SEQ ID NO: 187, a vlCDR2 having an amino acid sequence of SEQ ID NO:188, and a vlCDR3 having an amino acid sequence of SEQ ID NO:189; or i) a VH2 comprising a vhCDR1 having an amino acid sequence of SEQ ID NO:191; a vhCDR2 having an amino acid sequence of SEQ ID NO:192; and a vhCDR3 having an amino acid sequence of SEQ ID NO: 193; and (ii) a VL2 comprising a vlCDR1 having an amino acid sequence of SEQ ID NO:195, a vlCDR2 having an amino acid sequence of SEQ ID NO:196, and a vlCDR3 having an amino acid sequence of SEQ ID NO:197; or i) a VH2 comprising a vhCDR1 having an amino acid sequence of SEQ ID NO:199; a vhCDR2 having an amino acid sequence of SEQ ID NO:200; and a vhCDR3 having an amino acid sequence of SEQ ID NO:201; and (ii) a VL2 comprising a vlCDR1 having an amino acid sequence of SEQ ID NO:203, a vlCDR2 having an amino acid sequence of SEQ ID NO:204, and a vlCDR3 having an amino acid sequence of SEQ ID NO:205; or i) a VH2 comprising a vhCDR1 having an amino acid sequence of SEQ ID NO:381; a vhCDR2 having an amino acid sequence of SEQ ID NO:382; and a vhCDR3 having an amino acid sequence of SEQ ID NO:383; and (ii) a VL2 comprising a vlCDR1 having an amino acid sequence of SEQ ID NO:385, a vlCDR2 having an amino acid sequence of SEQ ID NO:386, and a vlCDR3 having an amino acid sequence of SEQ ID NO:387; or i) a VH2 comprising a vhCDR1 having an amino acid sequence of SEQ ID NO:389; a vhCDR2 having an amino acid sequence of SEQ ID NO:390; and a vhCDR3 having an amino acid sequence of SEQ ID NO:391; and (ii) a VL2 comprising a vlCDR1 having an amino acid sequence of SEQ ID NO:393, a vlCDR2 having an amino acid sequence of SEQ ID NO:394, and a vlCDR3 having an amino acid sequence of SEQ ID NO:395; or i) a VH comprising a vhCDR1 having an amino acid sequence of SEQ ID NO:397; a vhCDR2 having an amino acid sequence of SEQ ID NO:398; and a vhCDR3 having an amino acid sequence of SEQ ID NO:399; and (ii) a VL comprising a vlCDR1 having an amino acid sequence of SEQ ID NO:401, a vlCDR2 having an amino acid sequence of SEQ ID NO:402, and a vlCDR3 having an amino acid sequence of SEQ ID NO:403; or i) a VH2 comprising a vhCDR1 having an amino acid sequence of SEQ ID NO:405; a vhCDR2 having an amino acid sequence of SEQ ID NO:406; and a vhCDR3 having an amino acid sequence of SEQ ID NO:407; and (ii) a VL2 comprising a vlCDR1 having an amino acid sequence of SEQ ID NO:409, a vlCDR2 having an amino acid sequence of SEQ ID NO:410, and a vlCDR3 having an amino acid sequence of SEQ ID NO:411; or i) a VH2 comprising a vhCDR1 having an amino acid sequence of SEQ ID NO:413; a vhCDR2 having an amino acid sequence of SEQ ID NO:414; and a vhCDR3 having an amino acid sequence of SEQ ID NO:415; and (ii) a VL2 comprising a vlCDR1 having an amino acid sequence of SEQ ID NO:417, a vlCDR2 having an amino acid sequence of SEQ ID NO:418, and a vlCDR3 having an amino acid sequence of SEQ ID NO:419; or i) a VH2 comprising a vhCDR1 having an amino acid sequence of SEQ ID NO:421; a vhCDR2 having an amino acid sequence of SEQ ID NO:422; and a vhCDR3 having an amino acid sequence of SEQ ID NO:423; and (ii) a VL2 comprising a vlCDR1 having an amino acid sequence of SEQ ID NO:425, a vlCDR2 having an amino acid sequence of SEQ ID NO:426, and a vlCDR3 having an amino acid sequence of SEQ ID NO:427.

In another aspect, provided herein are bispecific antibodies that include a first antigen binding domain that binds to PSMA, and a second antigen binding domain that binds to CD28.

The first antigen binding domain (i.e., the PSMA binding domain) comprises:
- (i) a VH1 having an amino acid sequence that is at least about 95% identical to SEQ ID NO: 206; and (ii) a VL1 having an amino acid sequence that is at least about 95% identical to SEQ ID NO:210; or
- (i) a VH1 having an amino acid sequence that is at least about 95% identical to SEQ ID NO: 214; and (ii) a VL1 having an amino acid sequence that is at least about 95% identical to SEQ ID NO:218; or
- (i) a VH1 having an amino acid sequence that is at least about 95% identical to SEQ ID NO:222; and (ii) a VL1 having an amino acid sequence that is at least about 95% identical to SEQ ID NO:226; or
- (i) a VH1 having an amino acid sequence that is at least about 95% identical to SEQ ID NO:230; and (ii) a VL1 having an amino acid sequence that is at least about 95% identical to SEQ ID NO:234; or
- (i) a VH1 having an amino acid sequence that is at least about 95% identical to SEQ ID NO:238; and (ii) a VL1 having an amino acid sequence that is at least about 95% identical to SEQ ID NO:242; or
- (i) a VH1 having an amino acid sequence that is at least about 95% identical to SEQ ID NO:246; and (ii) a VL1 having an amino acid sequence that is at least about 95% identical to SEQ ID NO:250; or
- (i) a VH1 having an amino acid sequence that is at least about 95% identical to SEQ ID NO:254; and (ii) a VL1 having an amino acid sequence that is at least about 95% identical to SEQ ID NO:258; or
- (i) a VH1 having an amino acid sequence that is at least about 95% identical to SEQ ID NO: 262; and (ii) a VL1 having an amino acid sequence that is at least about 95% identical to SEQ ID NO:266; or
- (i) a VH1 having an amino acid sequence that is at least about 95% identical to SEQ ID NO:270; and (ii) a VL1 having an amino acid sequence that is at least about 95% identical to SEQ ID NO:274; or
- (i) a VH1 having an amino acid sequence that is at least about 95% identical to SEQ ID NO:278; and (ii) a VL1 having an amino acid sequence that is at least about 95% identical to SEQ ID NO:282; or
- (i) a VH1 having an amino acid sequence that is at least about 95% identical to SEQ ID NO:286; and (ii) a VL1 having an amino acid sequence that is at least about 95% identical to SEQ ID NO:290; or
- (i) a VH1 having an amino acid sequence that is at least about 95% identical to SEQ ID NO: 294; and (ii) a VL1 having an amino acid sequence that is at least about 95% identical to SEQ ID NO:298; or
- (i) a VH1 having an amino acid sequence that is at least about 95% identical to SEQ ID NO: 302; and (ii) a VL1 having an amino acid sequence that is at least about 95% identical to SEQ ID NO:306; or
- (i) a VH1 having an amino acid sequence that is at least about 95% identical to SEQ ID NO:310; and (ii) a VL1 having an amino acid sequence that is at least about 95% identical to SEQ ID NO: 314; or
- (i) a VH1 having an amino acid sequence that is at least about 95% identical to SEQ ID NO: 318; and (ii) a VL1 having an amino acid sequence that is at least about 95% identical to SEQ ID NO:322; or
- (i) a VH1 having an amino acid sequence that is at least about 95% identical to SEQ ID NO:326; and (ii) a VL1 having an amino acid sequence that is at least about 95% identical to SEQ ID NO:330; or
- (i) a VH1 having an amino acid sequence that is at least about 95% identical to SEQ ID NO: 334; and (ii) a VL1 having an amino acid sequence that is at least about 95% identical to SEQ ID NO:338.

The second antigen binding domain (i.e., the CD28 binding domain) comprises:
- (i) a VH2 having an amino acid sequence that is at least about 95% identical to SEQ ID NO:9; and (ii) a VL2 having an amino acid sequence that is at least about 95% identical to SEQ ID NO: 13; or
- (i) a VH2 having an amino acid sequence that is at least about 95% identical to SEQ ID NO:31; and (ii) a VL2 having an amino acid sequence that is at least about 95% identical to SEQ ID NO:35; or
- (i) a VH2 having an amino acid sequence that is at least about 95% identical to SEQ ID NO: 39; and (ii) a VL2 having an amino acid sequence that is at least about 95% identical to SEQ ID NO:43; or
- (i) a VH2 having an amino acid sequence that is at least about 95% identical to SEQ ID NO:47; and (ii) a VL2 having an amino acid sequence that is at least about 95% identical to SEQ ID NO:51; or
- (i) a VH2 having an amino acid sequence that is at least about 95% identical to SEQ ID NO:55; and (ii) a VL2 having an amino acid sequence that is at least about 95% identical to SEQ ID NO:59; or
- (i) a VH2 having an amino acid sequence that is at least about 95% identical to SEQ ID NO: 63; and (ii) a VL2 having an amino acid sequence that is at least about 95% identical to SEQ ID NO: 67; or
- (i) a VH2 having an amino acid sequence that is at least about 95% identical to SEQ ID NO: 86; and (ii) a VL2 having an amino acid sequence that is at least about 95% identical to SEQ ID NO: 90; or
- (i) a VH2 having an amino acid sequence that is at least about 95% identical to SEQ ID NO:94; and (ii) a VL2 having an amino acid sequence that is at least about 95% identical to SEQ ID NO:98; or
- (i) a VH2 having an amino acid sequence that is at least about 95% identical to SEQ ID NO: 102; and (ii) a VL2 having an amino acid sequence that is at least about 95% identical to SEQ ID NO: 106; or
- (i) a VH2 having an amino acid sequence that is at least about 95% identical to SEQ ID NO:110; and (ii) a VL2 having an amino acid sequence that is at least about 95% identical to SEQ ID NO: 114; or
- (i) a VH2 having an amino acid sequence that is at least about 95% identical to SEQ ID NO: 118; and (ii) a VL2 having an amino acid sequence that is at least about 95% identical to SEQ ID NO: 122; or
(i) a VH2 having an amino acid sequence that is at least about 95% identical to SEQ ID NO:126; and (ii) a VL2 having an amino acid sequence that is at least about 95% identical to SEQ ID NO: 130; or
(i) a VH2 having an amino acid sequence that is at least about 95% identical to SEQ ID NO: 134; and (ii) a VL2 having an amino acid sequence that is at least about 95% identical to SEQ ID NO:138; or
(i) a VH2 having an amino acid sequence that is at least about 95% identical to SEQ ID NO: 142; and (ii) a VL2 having an amino acid sequence that is at least about 95% identical to SEQ ID NO: 146; or
(i) a VH2 having an amino acid sequence that is at least about 95% identical to SEQ ID NO: 150; and (ii) a VL2 having an amino acid sequence that is at least about 95% identical to SEQ ID NO: 154; or
(i) a VH2 having an amino acid sequence that is at least about 95% identical to SEQ ID NO:158; and (ii) a VL2 having an amino acid sequence that is at least about 95% identical to SEQ ID NO: 162; or
(i) a VH2 having an amino acid sequence that is at least about 95% identical to SEQ ID NO: 166; and (ii) a VL2 having an amino acid sequence that is at least about 95% identical to SEQ ID NO: 170; or
(i) a VH2 having an amino acid sequence that is at least about 95% identical to SEQ ID NO:174; and (ii) a VL2 having an amino acid sequence that is at least about 95% identical to SEQ ID NO: 178; or
(i) a VH2 having an amino acid sequence that is at least about 95% identical to SEQ ID NO: 182; and (ii) a VL2 having an amino acid sequence that is at least about 95% identical to SEQ ID NO: 186; or
(i) a VH2 having an amino acid sequence that is at least about 95% identical to SEQ ID NO: 190; and (ii) a VL2 having an amino acid sequence that is at least about 95% identical to SEQ ID NO: 194; or
(i) a VH2 having an amino acid sequence that is at least about 95% identical to SEQ ID NO: 198; and (ii) a VL2 having an amino acid sequence that is at least about 95% identical to SEQ ID NO:202; or
(i) a VH2 having an amino acid sequence that is at least about 95% identical to SEQ ID NO:380; and (ii) a VL2 having an amino acid sequence that is at least about 95% identical to SEQ ID NO: 384; or
(i) a VH2 having an amino acid sequence that is at least about 95% identical to SEQ ID NO:388; and (ii) a VL2 having an amino acid sequence that is at least about 95% identical to SEQ ID NO:392; or
(i) a VH2 having an amino acid sequence that is at least about 95% identical to SEQ ID NO: 396; and (ii) a VL2 having an amino acid sequence that is at least about 95% identical to SEQ ID NO:400; or
(i) a VH2 having an amino acid sequence that is at least about 95% identical to SEQ ID NO:404; and (ii) a VL2 having an amino acid sequence that is at least about 95% identical to SEQ ID NO:408; or
(i) a VH2 having an amino acid sequence that is at least about 95% identical to SEQ ID NO:412; and (ii) a VL2 having an amino acid sequence that is at least about 95% identical to SEQ ID NO:416; or
(i) a VH2 having an amino acid sequence that is at least about 95% identical to SEQ ID NO:420; and (ii) a VL2 having an amino acid sequence that is at least about 95% identical to SEQ ID NO:424.

In some embodiments of the bispecific antibodies, the antibody is a humanized antibody. In certain embodiments, the antibody is a human antibody.

In some embodiments of the bispecific antibodies, the antibody is an IgG antibody. In some embodiments, IgG antibody is an IgG1, IgG2, IgG3, or IgG4 antibody. In exemplary embodiments, the IgG antibody is an IgG1 antibody.

In some embodiments of the bispecific antibodies, the first antigen binding domain binds a PSMA antigen. In exemplary embodiments, the first antigen binding domain binds a PSMA epitope. In some embodiments, the first antigen binding domain specifically binds to PSMA.

In some embodiments of the bispecific antibodies, the vhCDR1, vhCDR2, vhCDR3, vlCDR1, vlCDR2 and vlCDR3 of the first antigen binding domain form a binding site for an antigen of the PSMA. In certain embodiments, the vhCDR1, vhCDR2, vhCDR3, vlCDR1, vlCDR2 and vlCDR3 of the first antigen binding domain form a binding site for an epitope of the PSMA.

In some embodiments of the bispecific antibodies, the second antigen binding domain binds a CD28 antigen. In exemplary embodiments, the second antigen binding domain binds a CD28 epitope. In some embodiments, the second antigen binding domain specifically binds to CD28.

In some embodiments of the bispecific antibodies, the vhCDR1, vhCDR2, vhCDR3, vlCDR1, vlCDR2 and vlCDR3 of the second antigen binding domain form a binding site for an antigen of the CD28. In exemplary embodiments, the vhCDR1, vhCDR2, vhCDR3, vlCDR1, vlCDR2 and vlCDR3 of the second antigen binding domain form a binding site for an epitope of the CD28.

In some embodiments of the bispecific antibodies, the PSMA is present on the surface of a cell. In certain embodiments, the cell is a prostate cell. In exemplary embodiments, the cell is a prostate cancer cell.

In some embodiments of the bispecific antibodies, the antibody comprises a first Fc domain and a second Fc domain. In exemplary embodiments, the first Fc domain and the second Fc domain are each variant Fc domains.

In some embodiments, one of the first and second Fc domains comprises heterodimerization variant T366W, and the other of the first and second Fc domains comprises heterodimerization variants T366S/L368A/Y407V, wherein numbering is according to EU numbering. In exemplary embodiments, the first Fc domain comprises heterodimerization variant T366W, and the second Fc domain comprises heterodimerization variants T366S/L368A/Y407V.

In some embodiments, the first and second Fc domains each comprise one or more ablation variants. In exemplary embodiments, the one or more ablation variants comprise L234A/L235A/D265S, wherein numbering is according to EU numbering. I In some embodiments, the first or second Fc domain comprises purification variants H435R/Y436F, wherein numbering is according to EU numbering. In exemplary embodiments, the second Fc domain comprises purification variants H435R/Y436F.

In certain embodiments, the first Fc domain comprises amino acid substitutions L234A/L235A/D265S/LT366W, and the second Fc domain comprises amino acid substitutions L234A/L235A/D265S/T366S/L368A/Y407V/H435R/Y436F, wherein numbering is according to EU numbering. In exemplary embodiments, the first and second Fc domains each further comprise amino acid substitutions M252Y/S254T/T256E, wherein numbering is according to EU numbering.

In some embodiments, the first and second Fc domains comprise a set of heterodimerization skew variants selected from the following heterodimerization skew variants: S364K/E357Q:L368D/K370S; S364K:L368D/K370S; S364K:L368E/K370S; D401K: T411E/K360E/Q362E; and T366W: T366S/L368A/Y407V, wherein numbering is according to EU numbering. In exemplary embodiments, the first and second Fc domains comprise heterodimerization skew variants S364K/E357Q:L368D/K370S, wherein numbering is according to EU numbering.

In some embodiments, the first and second Fc domains each comprise one or more ablation variants. In some embodiments, the one or more ablation variants comprise E233P/L234V/L235A/G236del/S267K, wherein numbering is according to EU numbering.

In some embodiments of the bispecific antibody, the bispecific antibody is in the 1+1 Fab-scFv-Fc format. These antibodies comprise: a) a first monomer; b) a second monomer; and c) a light chain. The first monomer comprises: i) a single chain variable fragment (scFv); and ii) the first Fc domain, wherein the scFv is covalently attached to the N-terminus of the first Fc domain using a domain linker. The second monomer comprises, from N-terminal to C-terminal, a VH1-CH1-hinge-CH2-CH3, wherein VH1 is the first variable heavy domain and CH2-CH3 is the second Fc domain. The light chain comprises, from N-terminal to C-terminal, VL1-CL, wherein VL1 is the first variable light domain and CL is a constant light domain. The scFv comprises the second VH domain (VH2), a scFv linker, and the second variable light domain (VL2). The VH1 and the VL1 together form the first antigen binding domain (ABD) and the VH2 and the VL2 together form the second ABD.

In some embodiments, one of the first or second monomer further comprises a pI variant. In some embodiments, the CH1-hinge-CH2-CH3 of the second monomer comprises pI variants N208D/Q295E/N384D/Q418E/N421D, wherein numbering is according to EU numbering.

In exemplary embodiments, the CH1-hinge-CH2-CH3 of the second monomer comprises amino acid variants E233P/L234V/L235A/G236del/S267K/L368D/K370S/N208D/Q295E/N384D/Q418E/N421 D, the first Fc domain comprises amino acid variants E233P/L234V/L235A/G236del/S267K/S364K/E357Q, wherein numbering is according to EU numbering. In exemplary embodiments, the first and second variant Fc domains each further comprise amino acid variants 428L/434S.

In exemplary embodiments of the bispecific 1+1 Fab-scFv-Fc format antibody, the scFv linker is selected from GKPGSGKPGSGKPGSGKPGS (SEQ ID NO: 443), GGSEGKSSGSGSESKSTGGS (SEQ ID NO: 456), and GGGSGGSGGCPPCGGSGG (SEQ ID NO: 457).

In another aspect, provided herein is a heterodimeric antibody comprising: a) a first monomer having an amino acid sequence of SEQ ID NO:351; b) a second monomer having an amino acid sequence of SEQ ID NO:352; and c) a light chain having an amino acid sequence of SEQ ID NO:353.

In yet another aspect, provided herein is a heterodimeric antibody comprising: a) a first monomer having an amino acid sequence of SEQ ID NO:342; b) a second monomer having an amino acid sequence of SEQ ID NO:343; and c) a light chain having an amino acid sequence of SEQ ID NO:344.

In one aspect, provided herein is a bispecific antibody comprising: a) a first antigen binding domain having: (i) a VH1 having an amino acid sequence of SEQ ID NO:214; and (ii) a VL1 having an amino acid sequence of SEQ ID NO:218; and b) a second antigen binding domain having: (i) a VH2 having an amino acid sequence of SEQ ID NO:39; and (ii) a VL2 having an amino acid sequence of SEQ ID NO:43.

In one aspect, provided herein is a bispecific antibody comprising: a) a first antigen binding domain having: (i) a VH1 comprising a vhCDR1 having an amino acid sequence of SEQ ID NO:215; a vhCDR2 having an amino acid sequence of SEQ ID NO:216; and a vhCDR3 having an amino acid sequence of SEQ ID NO:217; and (ii) a VL1 comprising a vlCDR1 having an amino acid sequence of SEQ ID NO:219, a vlCDR2 having an amino acid sequence of SEQ ID NO: 220, and a vlCDR3 having an amino acid sequence of SEQ ID NO:221; and b) a second antigen binding domain having: (i) a VH2 comprising a vhCDR1 having an amino acid sequence of SEQ ID NO:40; a vhCDR2 having an amino acid sequence of SEQ ID NO:41; and a vhCDR3 having an amino acid sequence of SEQ ID NO:42; and (ii) a VL2 comprising a vlCDR1 having an amino acid sequence of SEQ ID NO:44, a vlCDR2 having an amino acid sequence of SEQ ID NO: 45, and a vlCDR3 having an amino acid sequence of SEQ ID NO:46.

In another aspect, provided herein is a bispecific antibody comprising: a) a first antigen binding domain having: (i) a VH1 having an amino acid sequence of SEQ ID NO:214; and (ii) a VL1 having an amino acid sequence of SEQ ID NO:218; and b) a second antigen binding domain having: (i) a VH2 having an amino acid sequence of SEQ ID NO:396; and (ii) a VL2 having an amino acid sequence of SEQ ID NO:400.

In one aspect, provided herein is a bispecific antibody comprising: a) a first antigen binding domain having: (i) a VH1 comprising a vhCDR1 having an amino acid sequence of SEQ ID NO:215; a vhCDR2 having an amino acid sequence of SEQ ID NO:216; and a vhCDR3 having an amino acid sequence of SEQ ID NO:217; and (ii) a VL1 comprising a vlCDR1 having an amino acid sequence of SEQ ID NO:219, a vlCDR2 having an amino acid sequence of SEQ ID NO: 220, and a vlCDR3 having an amino acid sequence of SEQ ID NO:221; and b) a second antigen binding domain having: (i) a VH2 comprising a vhCDR1 having an amino acid sequence of SEQ ID NO:397; a vhCDR2 having an amino acid sequence of SEQ ID NO:398; and a vhCDR3 having an amino acid sequence of SEQ ID NO:399; and (ii) a VL2 comprising a vlCDR1 having an amino acid sequence of SEQ ID NO: 401, a vlCDR2 having an amino acid sequence of SEQ ID NO:402, and a vlCDR3 having an amino acid sequence of SEQ ID NO:403.

Also provided herein are nucleic acid compositions comprising nucleic acids encoding the antibodies described herein, expression vector compositions that include such nucleic acids, host cells for making the antibodies that comprise the expression vector compositions, and methods of making the antibodies.

In another aspect, provided herein is a method of treating prostate cancer in a patient in need thereof, comprising administering to the patient an anti-CD28× anti-PSMA antibody described herein.

In yet another aspect, provided herein is a method of treating prostate cancer in a patient in need thereof, comprising administering to the patient: a) an anti-CD28× anti-PSMA as described herein; and b) an anti-CD3× anti-PSMA an anti-CD3× anti-B7H3, an anti-CD3× anti-hK2 or an anti-CD3× anti-TMEFF2 antibody.

In one aspect, provided herein is a method of enhancing T cell proliferation in the presence of PSMA-expressing cells, comprising contacting the cells with an anti-CD28×anti-PSMA as described herein. In some embodiments, the PSMA-expressing cells are prostate cells.

In another aspect, provided herein is a method of inhibiting the growth or proliferation of PSMA-expressing cells, comprising contacting the cells with with an anti-CD28×anti-PSMA as described herein. In some embodiments, the PSMA-expressing cells are prostate cells.

BRIEF DESCRIPTION OF THE DRAWINGS

FIGS. 1A-1B depict the sequences for human, mouse, and cynomolgus CD28. Such CD28 are useful for the development of cross-reactive CD28 antigen binding domains for ease of clinical development.

FIGS. 2A-2B depicts the sequences for human, mouse, and cynomolgus PSMA. Such PSMA are useful for the development of cross-reactive PSMA antigen binding domains for ease of clinical development.

FIGS. 3A-3F depict useful pairs of heterodimerization variant sets (including skew and pI variants). In FIG. 3F, there are variants for which there are no corresponding "monomer 2" variants. Such variants are pI variants that can be used alone on either monomer of a bispecific antibody (e.g., PSMA×CD28 bsAb), or included, for example, on the non-scFv side of a format that utilizes an scFv as a component and an appropriate charged scFv linker can be used on the second monomer that utilizes an scFv as the CD28 binding domain. Suitable charged linkers are shown in FIGS. 6A-6B.

FIG. 4 depicts a list of isosteric variant antibody constant regions and their respective substitutions. pI_(−) indicates lower pI variants, while pI_(+) indicates higher pI variants. These variants can be optionally and independently combined with other variants, including heterodimerization variants, outlined herein.

FIG. 5 depict useful ablation variants that ablate FcγR binding (also referred to as "knockouts" or "KO" variants). In some embodiments, such ablation variants are included in the Fc domain of both monomers of the subject antibody described herein. In other embodiments, the ablation variants are only included on only one variant Fc domain.

FIGS. 6A-6B depicts a number of charged scFv linkers that find use in increasing or decreasing the pI of the subject heterodimeric bispecific antibodies that utilize one or more scFv as a component, as described herein (e.g., PSMA×CD28 bsAbs). The (+H) positive linker finds particular use herein, particularly with anti-CD28 VL and VH sequences shown herein. A single prior art scFv linker with a single charge is referenced as "Whitlow," from Whitlow et al., Protein Engineering 6(8):989-995 (1993). It should be noted that this linker was used for reducing aggregation and enhancing proteolytic stability in scFvs. Such charged scFv linkers can be used in any of the subject antibody formats disclosed herein that include scFvs (e.g., 1+1 Fab-scFv-Fc and 2+1 Fab2-scFv-Fc formats).

FIG. 7 depicts a number of exemplary domain linkers. In some embodiments, these linkers find use linking a single-chain Fv to an Fc chain. In some embodiments, these linkers may be combined in any orientation. For example, a GGGGS (SEQ ID NO: 458) linker may be combined with a "lower half hinge" linker at the N-terminus or at the C-terminus.

FIG. 8 shows a particularly useful bispecific antibody platforms for the PSMA×CD28 bsAbs of the invention. Although the platforms are described here in the context of the 1+1 Fab-scFv-Fc format, they can be adapted for use in other bispecific antibody formats.

FIG. 9 depicts various heterodimeric skew variant amino acid substitutions that can be used with the heterodimeric antibodies described herein.

FIGS. 10A-10E shows the sequences of several useful heterodimeric PSMA×CD28 bsAb backbones based on human IgG1, without the cytokine sequences. Heterodimeric Fc backbone 1 is based on human IgG1 (356E/358M allotype), and includes the L368D/K370S skew variants and the Q295E/N384D/Q418E/N421D pI variants on a first heterodimeric Fc chain, the S364K/E357Q skew variants on a second heterodimeric Fc chain, and the E233P/L234V/L235A/G236del/S267K ablation variants on both chains. Heterodimeric Fc backbone 2 is based on human IgG1 (356E/358M allotype), and includes the L368D/K370S skew variants and the Q295E/N384D/Q418E/N421D pI variants on a first heterodimeric Fc chain, the S364K skew variant on a second heterodimeric Fc chain, and the E233P/L234V/L235A/G236del/S267K ablation variants on both chains. Heterodimeric Fc backbone 3 is based on human IgG1 (356E/358M allotype), and includes the L368E/K370S skew variants and the Q295E/N384D/Q418E/N421D pI variants on a first heterodimeric Fc chain, the S364K skew variant on a second heterodimeric Fc chain, and the E233P/L234V/L235A/G236del/S267K ablation variants on both chains. Heterodimeric Fc backbone 4 is based on human IgG1 (356E/358M allotype), and includes the K360E/Q362E/T411E skew variants and the Q295E/N384D/Q418E/N421D pI variants on a first heterodimeric Fc chain, the D401K skew variant on a second heterodimeric Fc chain, and the E233P/L234V/L235A/G236del/S267K ablation variants on both chains. Heterodimeric Fc backbone 5 is based on human IgG1 (356D/358L allotype), and includes the L368D/K370S skew variants and the Q295E/N384D/Q418E/N421D pI variants on a first heterodimeric Fc chain, the S364K/E357Q skew variants on a second heterodimeric Fc chain, and the E233P/L234V/L235A/G236del/S267K ablation variants on both chains. Heterodimeric Fc backbone 6 is based on human IgG1 (356E/358M allotype), and includes the L368D/K370S skew variants and the Q295E/N384D/Q418E/N421D pI variants on a first heterodimeric Fc chain, the S364K/E357Q skew variants on a second heterodimeric Fc chain, and the E233P/L234V/L235A/G236del/S267K ablation variants and N297A variant that removes glycosylation on both chains. Heterodimeric Fc backbone 7 is based on human IgG1 (356E/358M allotype), and includes the L368D/K370S skew variants and the Q295E/N384D/Q418E/N421D pI variants on a first heterodimeric Fc chain, the S364K/E357Q skew variants on a second heterodimeric Fc chain, and the E233P/L234V/L235A/G236del/S267K ablation variants and N297S variant that removes glycosylation on both chains. Heterodimeric Fc backbone 8 is based on human IgG4, and includes the L368D/K370S skew variants and the Q295E/N384D/Q418E/N421D pI variants on a first heterodimeric Fc chain, the S364K/E357Q skew variants on a second heterodimeric Fc chain, and the S228P (according to EU numbering, S241P in Kabat) variant that ablates Fab arm exchange (as is known in the art) on both chains. Heterodimeric Fc backbone 9 is based on human IgG2, and includes the L368D/K370S skew variants and the Q295E/N384D/Q418E/N421D pI variants on a first heterodimeric Fc chain, the S364K/E357Q skew variants on a second heterodimeric Fc chain. Heterodimeric Fc backbone 10 is based on human IgG2, and includes the L368D/K370S skew variants and the Q295E/N384D/Q418E/N421D pI variants on a first heterodimeric Fc chain, the S364K/E357Q skew variants on a second heterodimeric Fc chain, and the S267K ablation variant on both chains. Heterodimeric Fc backbone 11 is based on human IgG1 (356E/358M allotype), and includes the L368D/K370S skew variants and the Q295E/N384D/Q418E/N421D pI variants on a first heterodimeric Fc chain, the S364K/E357Q skew variants on a second heterodimeric Fc chain, and the E233P/L234V/L235A/G236del/S267K ablation variants and M428L/N434S Xtend variants on both chains. Heterodimeric Fc backbone 12 is based on human IgG1 (356E/358M allotype), and includes the L368D/K370S skew variants on a first heterodimeric Fc chain, the S364K/E357Q skew variants and P217R/P229R/N276K pI variants on a second heterodimeric Fc chain, and the E233P/L234V/L235A/G236del/S267K ablation variants on both chains. Heterodimeric Fc backbone 13 is based on human IgG1 (356E/358M allotype), and includes the T366W skew variant on a first heterodimeric Fc chain, the T366S/L368A/Y407V skew variants and H435R/Y436F purification variants on a second heterodimeric Fc chain, and the L234A/L235A/D265S ablation variants on both chains. Heterodimeric Fc backbone 14 is based on human IgG1 (356E/358M allotype), and includes the T366W skew variant on a first heterodimeric Fc chain, the T366S/L368A/Y407V skew variants and H435R/Y436F purification variants on a second heterodimeric Fc chain, and the L234A/L235A/D265S ablation variants and M252Y/S254T/T256E half-life extension variants on both chains. Heterodimeric Fc backbone 15 is based on human IgG1 (356D/358L allotype), and includes the L368D/K370S skew variants and the Q295E/N384D/Q418E/N421D pI variants on a first heterodimeric Fc chain, the S364K/E357Q skew variants on a second heterodimeric Fc chain, and the E233P/L234V/L235A/G236del/S267K ablation variants and M428L/N434S Xtend variants on both chains. Heterodimeric Fc backbone 16 is based on human IgG1 (356E/358M allotype), and includes the L368D/K370S skew variants and the Q295E/N384D/Q418E/N421D pI variants on a first heterodimeric Fc chain, the S364K/E357Q skew variants on a second heterodimeric Fc chain, and the E233P/L234V/L235A/G236del/S267K ablation variants and M428L/N434A Xtend variants on both chains. Heterodimeric Fc backbone 17 is based on human IgG1 (356D/358L allotype), and includes the L368D/K370S skew variants and the Q295E/N384D/Q418E/N421D pI variants on a first heterodimeric Fc chain, the S364K/E357Q skew variants on a second heterodimeric Fc chain, and the E233P/L234V/L235A/G236del/S267K ablation variants and M428L/N434A Xtend variants on both chains.

Figure 23:
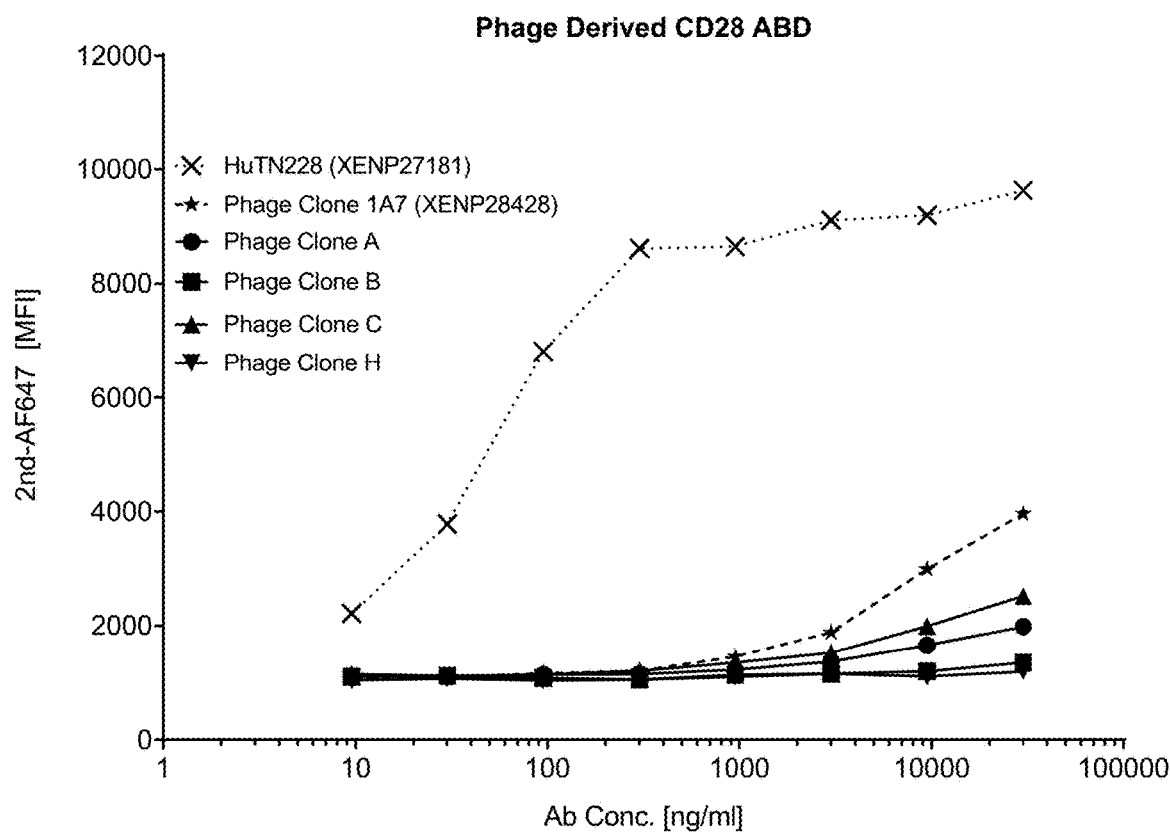

Included within each of these backbones are sequences that are 90, 95, 98 and 99% identical (as defined herein) to the recited sequences, and/or contain from 1, 2, 3, 4, 5, 6, 7, 8, 9 or 10 additional amino acid substitutions (as compared to the "parent" of the Figure, which, as will be appreciated by those in the art, already contain a number of amino acid modifications as compared to the parental human IgG1 (or IgG2 or IgG4, depending on the backbone). That is, the recited backbones may contain additional amino acid modifications (generally amino acid substitutions) in addition or as an alternative to the skew, pI and ablation variants contained within the backbones of this Figure. Additionally, the backbones depicted herein may include deletion of the C-terminal glycine (K446_) and/or lysine (K447_). The C-terminal glycine and/or lysine deletion may be intentionally engineered to reduce heterogeneity or in the context of certain bispecific formats, such as the mAb-scFv format. Additionally, C-terminal glycine and/or lysine deletion may occur naturally for example during production and storage.

FIG. 11 depicts illustrative sequences of heterodimeric PSMA×CD28 bsAb backbone for use in the 2+1 mAb-scFv format. The format depicted here is based on heterodimeric Fc backbone 1 as depicted in FIGS. 10A-10E, except further including G446_on monomer 1 (–) and G446_/K447_on monomer 2 (+). It should be noted that any of the additional backbones depicted in FIGS. 10A-10E may be adapted for use in the 2+1 mAb-scFv format with or without including K447_on one or both chains. It should be noted that these sequences may further include the M428L/N434S variants or M252Y/S254T/T256E half-life extension variants.

FIG. 12 depicts sequences for "CH1" that find use in embodiments of PSMA×CD28 bsAbs.

FIG. 13 depicts sequences for "hinge" that find use in embodiments of PSMA×CD28 bsAbs.

FIG. 14 depicts the constant domain of the cognate light chains that find use in the subject PSMA×CD28 bsAbs that utilize a Fab binding domain.

FIG. 15 depicts the variable heavy and variable light chain sequences for 1A7, an exemplary phage-derived CD28 binding domain, as well as the sequences for XENP28428, an anti-CD28 mAb based on 1A7 and IgG1 backbone with E233P/L234V/L235A/G236del/S267K ablation variant. CDRs are underlined and slashes indicate the border(s) between the variable regions and constant domain. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

FIG. 16 depicts the sequences for affinity-optimized variable heavy domains from anti-CD28 clone 1A7. It should be noted that the variable heavy domains can be paired with any of the other variable light domains depicted herein, including those depicted in FIGS. 17, 18A-18C and 21A-21H (e.g. 1A7_H1.1_L1.71 as utilized in XENP37559).

FIG. 17 depicts the sequences for affinity-optimized variable light domain from anti-CD28 clone 1A7. It should be noted that the variable light domains can be paired with any of the other variable light domains depicted herein, including those depicted in FIGS. 16, 18 and 21 (e.g. 1A7_H1.1_L1.71 as utilized in XENP37559).

FIGS. 18A-18C depicts the sequence for illustrative affinity-optimized 1A7 VH/VH pairs. It should be noted that these pairs may be formatted as Fabs or as scFvs. Additionally, in the scFv format, these pairs may be formatted in the VHVL orientation or the VLVH orientation.

FIGS. 19A-19B depicts consensus framework regions (FR) and complementarity determining regions (CDRs) (as in Kabat) for anti-CD28 clone 1A7 variable heavy and variable light domain variants.

FIG. 20 depicts illustrative affinity-engineered 1A7 VH/VL pairs and their binding affinities in the context of scFvs (in the context of 1+1 Fab-scFv-Fc bsAb format).

FIGS. 21A-21H depicts the variable heavy and variable light chain sequences for additional CD28 binding domains which find use in the PSMA×CD28 bsAbs of the invention. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

FIG. 22 depicts the sequences for XENP27181, a bivalent anti-CD28 mAb based on HuTN228 binding domain and IgG1 backbone with E233P/L234V/L235A/G236del/S267K ablation variant; and XENP29154 which is an in-house produced version of TGN1412.

FIG. 23 depicts binding of illustrative bivalent anti-CD28 mAbs based on phage-derived clones on human PBMCs. The data show that the phage campaign generated CD28 binding domains having weaker maximum binding than prior art HuTN228 (which is related to the humanized CD28 binding domains described in Example 1A).

Figure 24A:
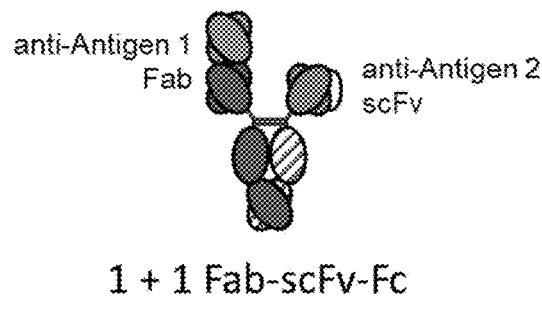
Figure 24B:
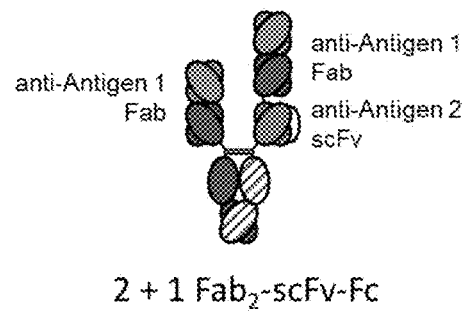
Figure 24C:
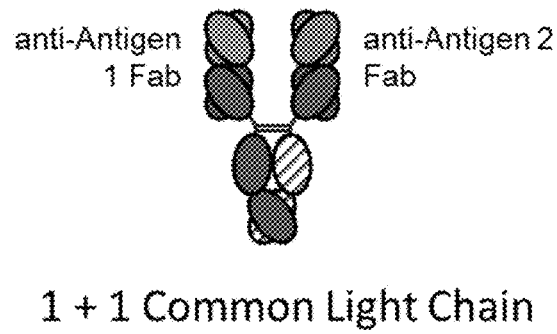
Figure 24D:
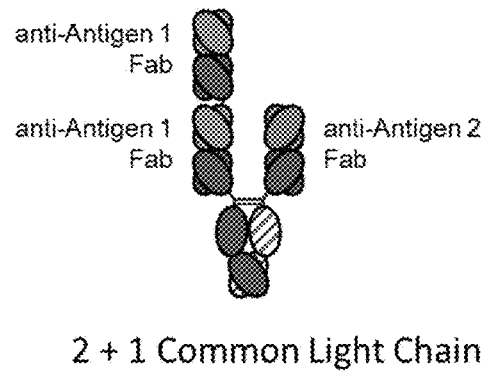
Figure 24E:
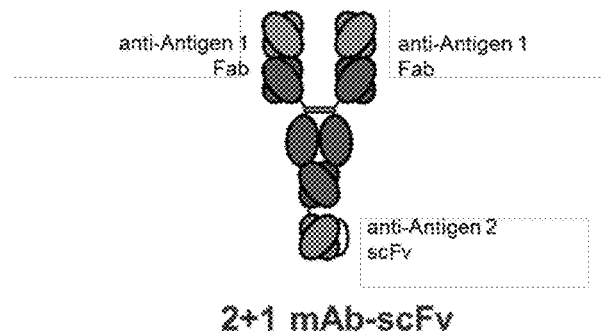

FIGS. 24A-24M depicts bispecific formats of the present invention. FIG. 24A depicts the "1+1 Fab-scFv-Fc" format, with a first Fab arm binding a first antigen and a second scFv arm binding second antigen. The 1+1 Fab-scFv-Fc format comprises a first monomer comprising a first heavy chain variable region (VH1) covalently attached to the N-terminus of a first heterodimeric Fc backbone (optionally via a linker), a second monomer comprising a single-chain Fv covalently attached to the N-terminus of a second corresponding heterodimeric Fc backbone (optionally via a linker), and a third monomer comprising a light chain variable region covalently to a light chain constant domain, wherein the light chain variable region is complementary to the VH1. FIG. 24B depicts the "2+1 Fab2-scFv-Fc" format, with a first Fab arm and a second Fab-scFv arm, wherein the Fab binds a first antigen and the scFv binds second antigen. The 2+1 Fab2-scFv-Fc format comprises a first monomer comprising a first heavy chain variable region (VH1) covalently attached to the N-terminus of a first heterodimeric Fc backbone (optionally via a linker), a second monomer comprising the VH1 covalently attached (optionally via a linker) to a single-chain Fv covalently attached (optionally via a linker) to the N-terminus of a second corresponding heterodimeric Fc backbone, and a third monomer comprising a light chain variable region covalently to a light chain constant domain, wherein the light chain variable region is complementary to the VH1. FIG. 24C depicts the "1+1 Common Light Chain" or "1+1 CLC" format, with a first Fc comprising a first Fab arm binding a first antigen and a second Fc comprising a second Fab arm binding second antigen. The 1+1 CLC format comprises a first monomer comprising VH1-CH1-hinge-CH2-CH3, a second monomer comprising VH2-CH1-hinge-CH2-CH3, and a third monomer comprising VL-CL. The VL pairs with the VH1 to form a binding domain with a first antigen binding specificity; and the VL pairs with the VH2 to form a binding domain with a second antigen binding specificity. FIG. 24D depicts the "2+1 Common Light Chain" or "2+1 CLC" format, with a first Fc comprising 2 Fab arms each binding a first antigen and a second Fc comprising 1 Fab arm binding a second antigen. The 2+1 CLC format comprises a first monomer comprising VH1-CH1-hinge-VH1-CH1-hinge-CH2-CH3, a second monomer comprising VH2-CH1-hinge-CH2-CH3, and a third monomer comprising VL-CL. The VL pairs with the first and second VH1 to form binding domains with a first antigen binding specificity; and the VL pairs with the VH2 to form a binding domain with a second antigen binding specificity. FIG. 24E depicts the "2+1 mAb-scFv" format, with a first Fc comprising an N-terminal Fab arm binding a first antigen and a second Fc comprising an N-terminal Fab arm binding the first antigen and a C-terminal scFv binding a second antigen. The 2+1 mAb-scFv format comprises a first monomer comprising VH1-CH1-hinge-CH2-CH3, a second monomer comprising VH1-CH1-hinge-CH2-CH3-scFv, and a third monomer comprising VL-CL. The VL pairs with the first and second VH1 to form binding domains with binding specificity for the first antigen. Additional bispecific formats include F) dual scFv, G) one-arm scFv-mAb, H) scFv-mAb, I) bispecific mAb, J) one-arm central-scFv, K) mAb-Fv, L) central-Fv, and M) trident.

FIGS. 25A-25E depicts the variable heavy and variable light chain sequences for exemplary PSMA binding domains which find use in the PSMA×CD28 bsAbs of the invention. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

FIGS. 26A-26B depicts the variable heavy and variable light chain sequences for additional PSMA binding domains which find use in the PSMA×CD28 bsAbs of the invention. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

Figure 27A:
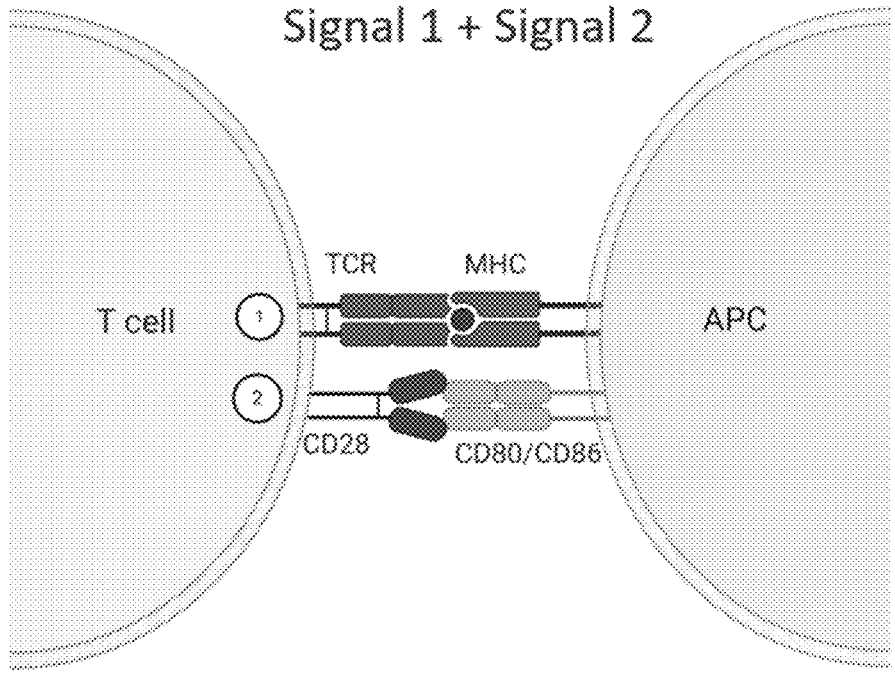
Figure 27B:
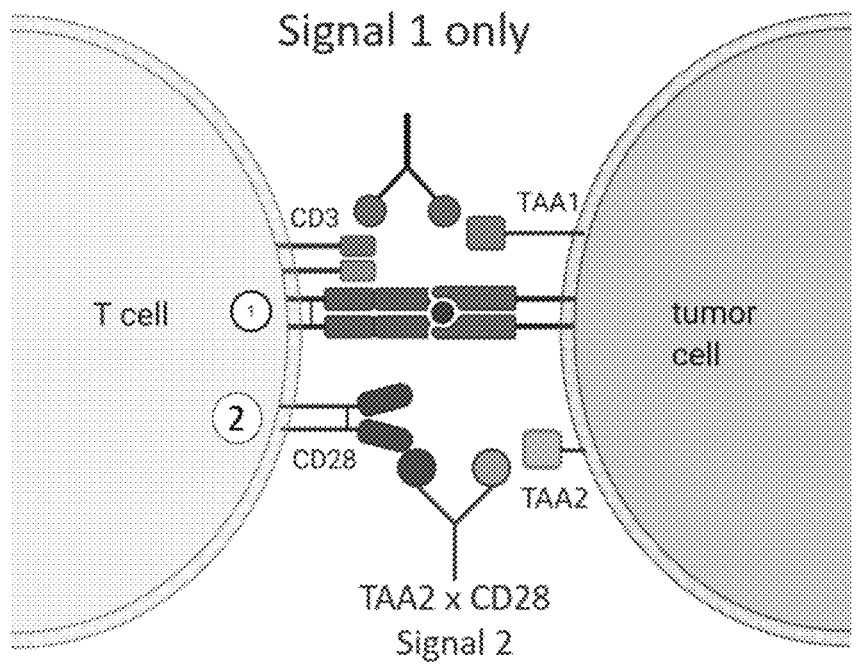

FIGS. 27A-27B depicts A) classic T cell/APC interaction and B) replication of the classic T cell/APC interaction by combining CD3 bispecific antibodies with CD28 bispecific antibodies. In classic T cell/APC interaction, there is a first signal provided by TCR reactivity with peptide-MHC (Signal 1) and a second signal provided by CD28 crosslinking by CD80/CD86 being expressed on APCs (Signal 2) which together fully activate T cells. In contrast in treatment with CD3 bispecifics, only the first signal is provided. The CD28 signal may be provided by a CD28 bispecific with the idea to promote activation and proliferation through CD28 costimulation. In some embodiments, TAA1 and TAA2 may be different antigens. In some embodiments, TAA1 and TAA2 may be same antigen but different epitopes. In some embodiments, TAA1 and TAA2 may be same antigen and same epitope.

FIGS. 28A-28C depicts sequences for illustrative PSMA× CD3 bsAbs that may be combined with the PSMA×CD28 bsAbs of the invention.

FIGS. 29A-29RR depict the sequences for illustrative PSMA×CD28 bsAbs in the 1+1 Fab-scFv-Fc format using Platform X. Although these sequences utilize Platform X, they can use Platform J or any other suitable backbones including those depicted in FIGS. 10A-10E. CDRs are underlined, and slashes indicate the border(s) between the variable regions, Fc regions, and constant domains. It should be noted that the PSMA×CD28 bsAbs can utilize variable region, Fc region, and constant domain sequences that are 90, 95, 98 and 99% identical (as defined herein), and/or contain from 1, 2, 3, 4, 5, 6, 7, 8, 9 or 10 amino acid substitutions. In addition, each sequence outlined herein can include or exclude the M428L/N434S variants in one or preferably both Fc domains, which including M428L/N434S results in longer half-life in serum.

FIGS. 30A-30L depict the sequences for illustrative PSMA×CD28 bsAbs in the 1+1 Fab-scFv-Fc format using Platform J. Although these sequences utilize Platform J, they can use Platform X or any other suitable backbones including those depicted in FIGS. 10A-10E. CDRs are underlined, and slashes indicate the border(s) between the variable regions, Fc regions, and constant domains. It should be noted that the PSMA×CD28 bsAbs can utilize variable region, Fc region, and constant domain sequences that are 90, 95, 98 and 99% identical (as defined herein), and/or contain from 1, 2, 3, 4, 5, 6, 7, 8, 9 or 10 amino acid substitutions. In addition, each sequence outlined herein can include or exclude the M252Y/S254T/T256E variants in one or preferably both Fc domains, which including M252Y/S254T/T256E results in longer half-life in serum.

Figure 31:
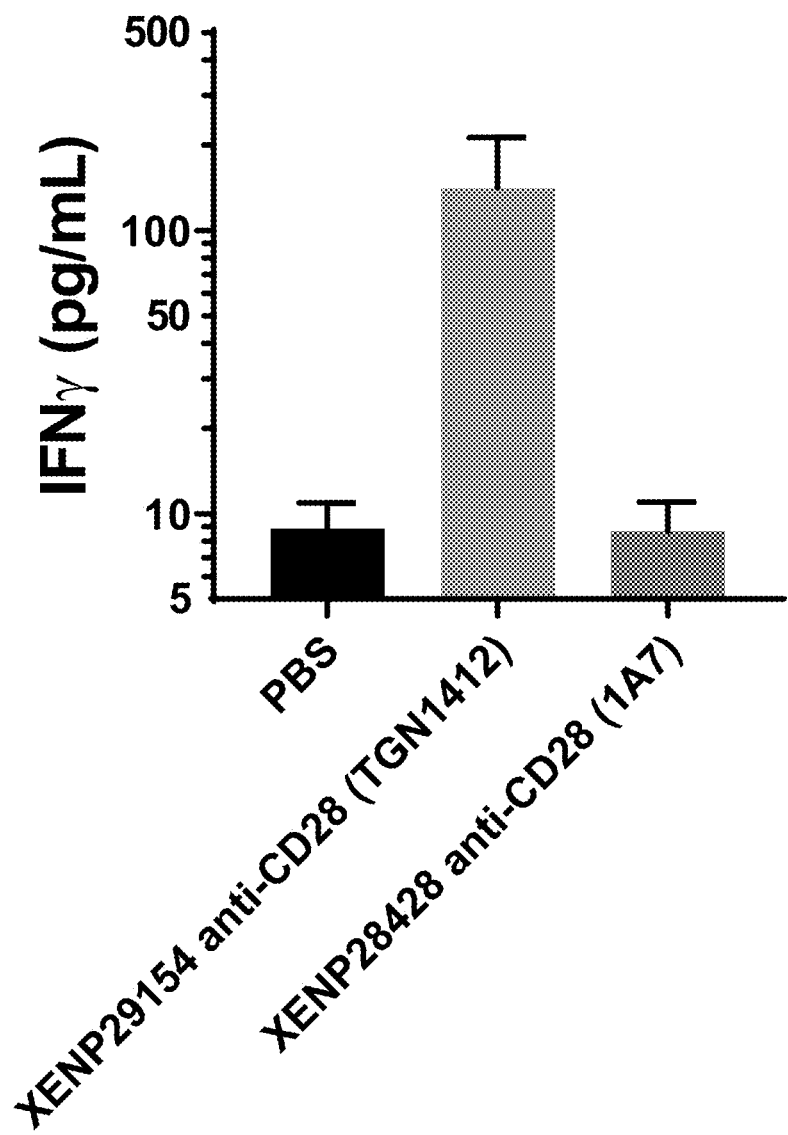

FIG. 31 depicts the release of IFNγ from human PBMCs treated with air-dried XENP28428 (anti-CD28 clone 1A7), TGN1412 (XENP29154), or negative control PBS.

Figure 32A:
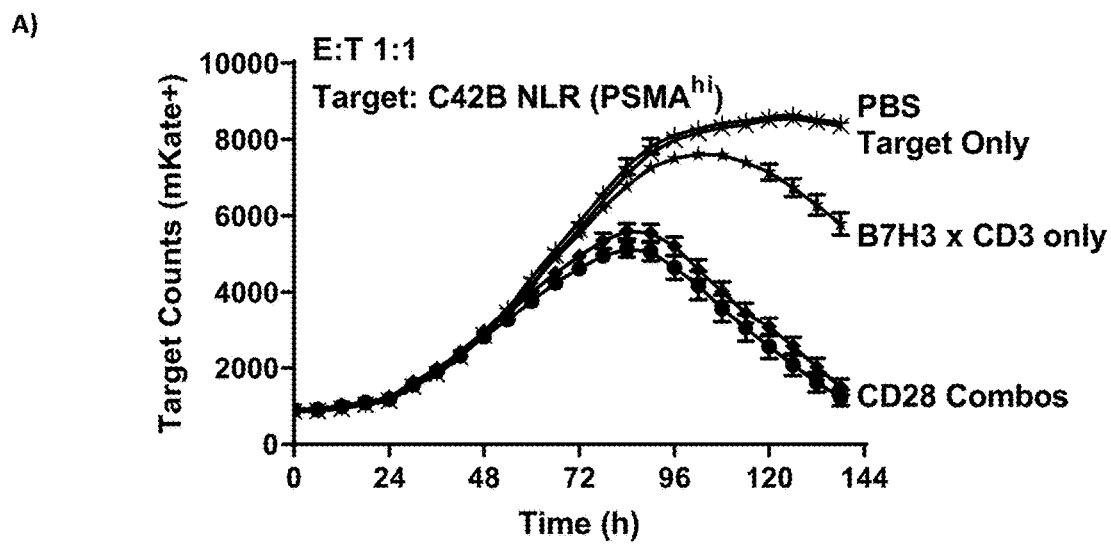
Figure 32B:
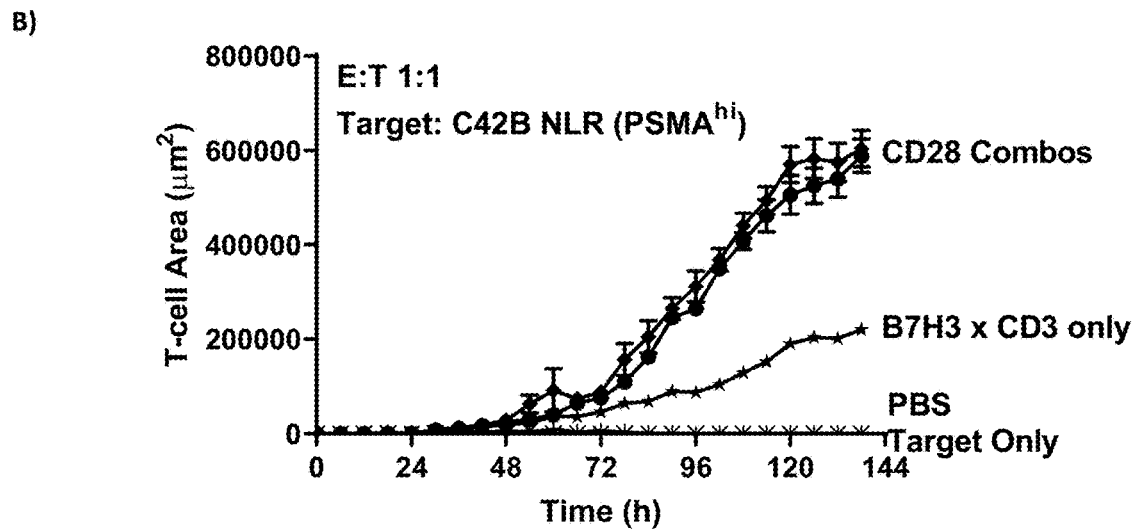

FIGS. 32A-32B depicts A) Redirected T Cell Cytotoxicity (RTCC) (as indicated by decrease in target cell count over time) and B) T cell proliferation (as indicated by increase in T cell area over time) after incubating C42B-NLR (PSMA$^{hi}$) cells with T cells (E:T 1:1) and 1 μg/mL B7H3×CD3 bsAb alone or in combination with 1 μg/mL prototype PSMA×CD28 bsAbs XENP37902 or XENP37903. The data show that combination with PSMA×CD28 bsAb enhances both RTCC and T cell proliferation in the presence of PSMA$^{hi}$ cells. Notably, the low affinity CD28 binding domain in XENP37902 is sufficient to enhance activity.

Figure 33A:
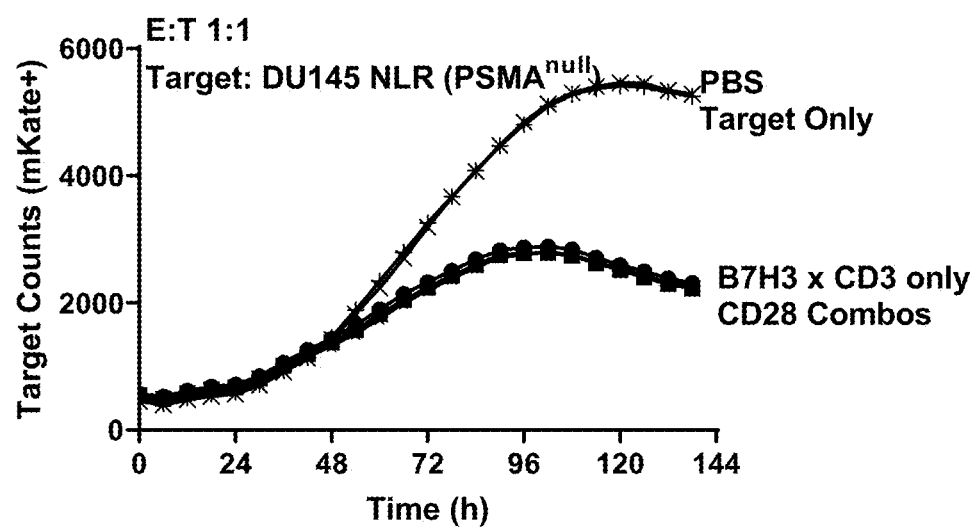
Figure 33B:
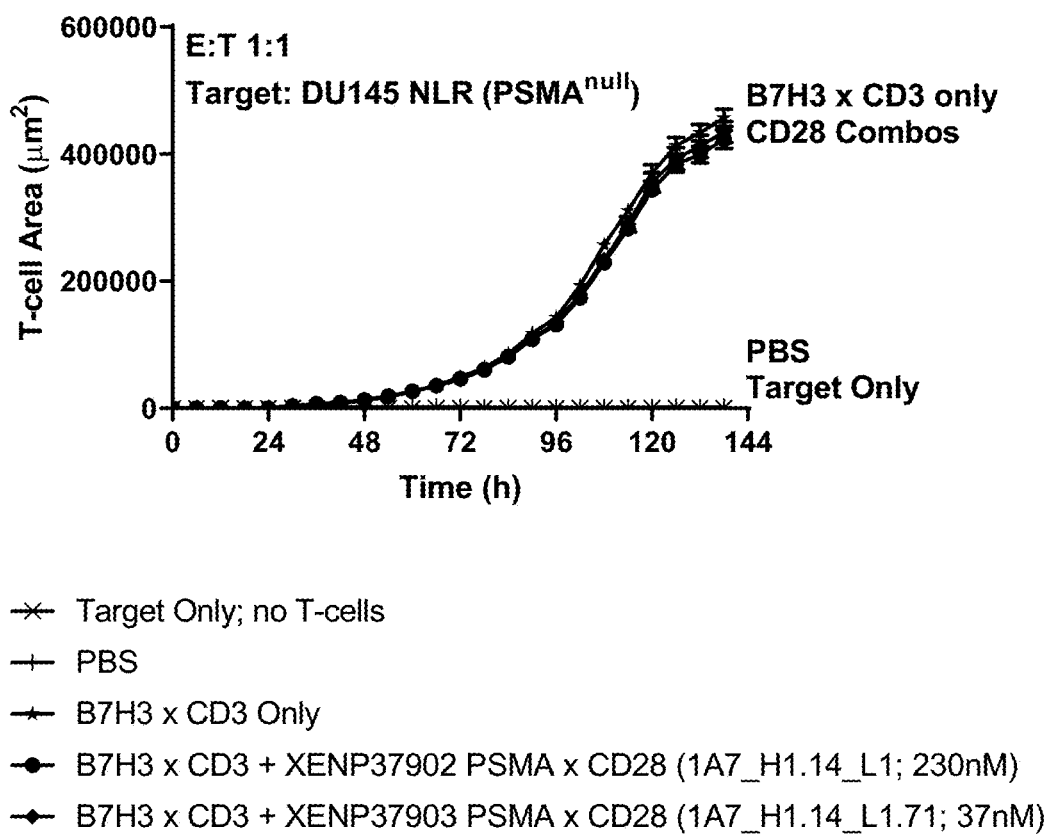

FIGS. 33A-33B depicts A) RTCC (as indicated by decrease in target cell count over time) and B) T cell proliferation (as indicated by increase in T cell area over time) after incubating DU145 (PSMA$^{null}$) cells with T cells (E:T 1:1) and 1 μg/mL B7H3×CD3 bsAb alone or in combination with prototype 1 μg/mL PSMA×CD28 bsAbs XENP37902 or XENP37903. The data show that combination with PSMA×CD28 bsAb does not enhance RTCC or T cell proliferation in the presence of PSMA$^{null}$ cells.

Figure 34A:
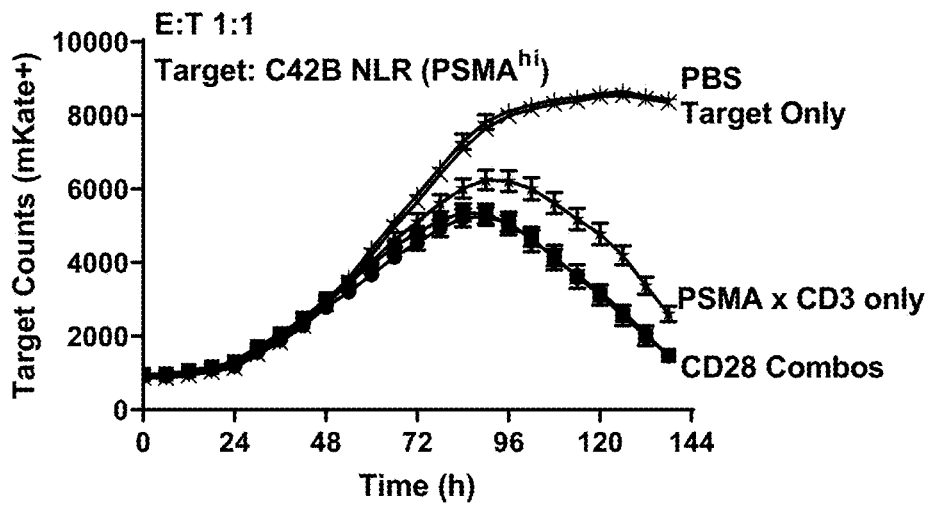
Figure 34B:
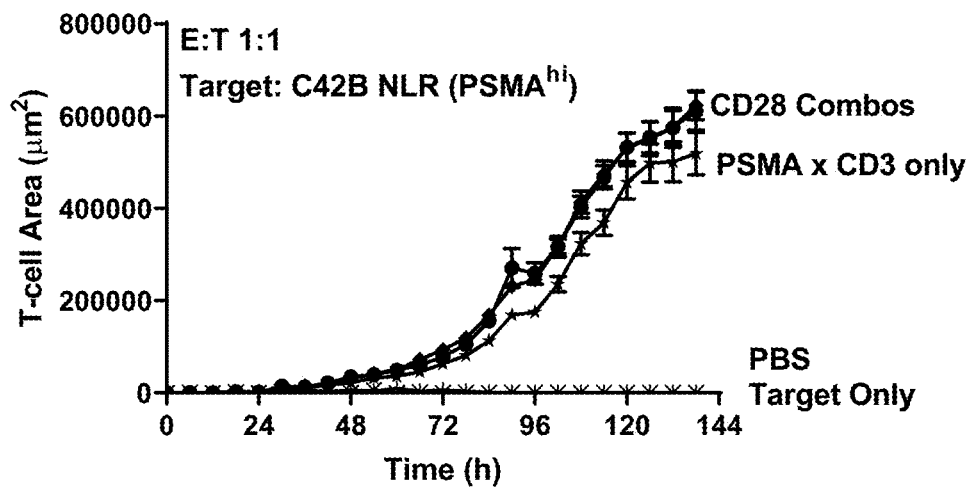

FIGS. 34A-34B depicts A) RTCC (as indicated by decrease in target cell count over time) and B) T cell proliferation (as indicated by increase in T cell area over time) after incubating C42B-NLR (PSMA$^{hi}$) cells with T cells (E:T 1:1) and 1 μg/mL PSMA×CD3 bsAb alone or in combination with 1 μg/mL prototype PSMA×CD28 bsAbs XENP37902 or XENP37903. It should be noted that the PSMA×CD3 and PSMA×CD28 bsAbs bind non-competing PSMA epitopes. The data show that combination with PSMA×CD28 bsAb enhances both RTCC and T cell proliferation in the presence of PSMA$^{hi}$ cells. Notably, the low affinity CD28 binding domain in XENP37902 is sufficient to enhance activity.

Figure 35A:
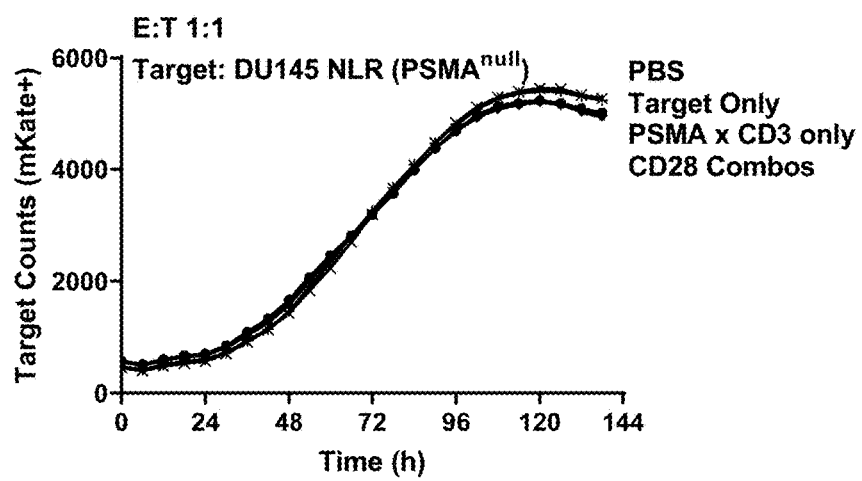
Figure 35B:
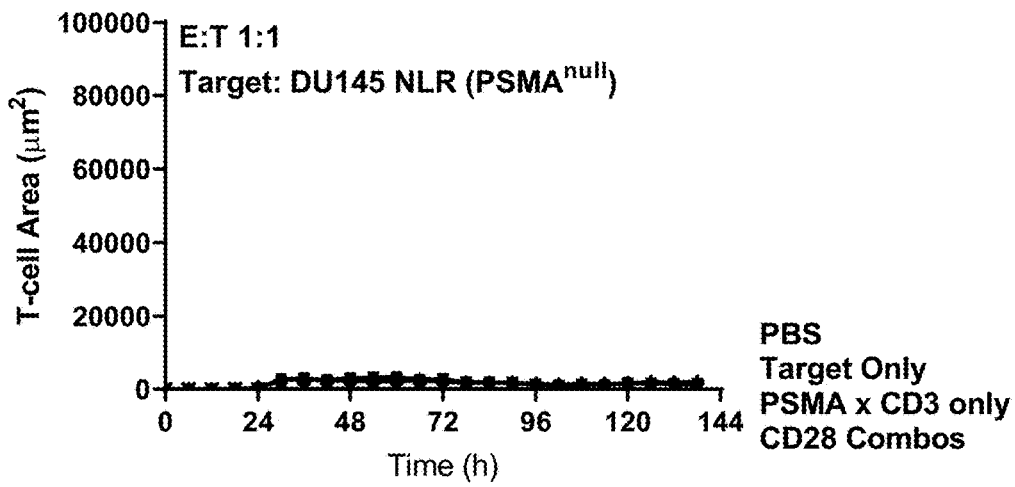

FIGS. 35A-35B depicts A) RTCC (as indicated by decrease in target cell count over time) and B) T cell proliferation (as indicated by increase in T cell area over time) after incubating DU145-NLR (PSMA$^{null}$) cells with T cells (E:T 1:1) and 1 μg/mL PSMA×CD3 bsAb alone or in combination with 1 μg/mL prototype PSMA×CD28 bsAbs XENP37902 or XENP37903. It should be noted that the PSMA×CD3 and PSMA×CD28 bsAbs bind non-competing PSMA epitopes. The data show that combination with PSMA×CD28 bsAb does not enhance RTCC or T cell proliferation in the presence of PSMA$^{null}$ cells.

FIGS. 36A-36B depicts induction of IL-2 secretion by A) XENP37902 PSMA×CD28 having 230 nM CD28 binding affinity and B) XENP37903 PSMA×CD28 having 37 nM CD28 binding affinity in combination with an illustrative non-competing PSMA×CD3 bsAb incubated with T cells and PC3 cells transfected with varying surface PSMA densities. The data show that the PSMA×CD28 bsAb enhanced cytokine secretion in the presence of PSMA$^{hi}$ and PSMA$^{med}$ cell lines. Notably, the low affinity CD28 binding domain in XENP37902 is sufficient to enhance activity.

FIGS. 37A-37B depicts induction of IL-2 secretion by A) XENP37902 PSMA×CD28 having 230 nM CD28 binding affinity and B) XENP37903 PSMA×CD28 having 37 nM CD28 binding affinity in combination with an illustrative competing PSMA×CD3 bsAb (i.e. binding the same PSMA epitope) incubated with T cells and PC3 cells transfected with varying surface PSMA densities. The data show that the PSMA×CD28 bsAb enhanced cytokine secretion in the presence of PSMA$^{hi}$ and PSMA$^{med}$ cell lines. Notably, a hooking effect is observed at higher concentrations.

Figure 38:
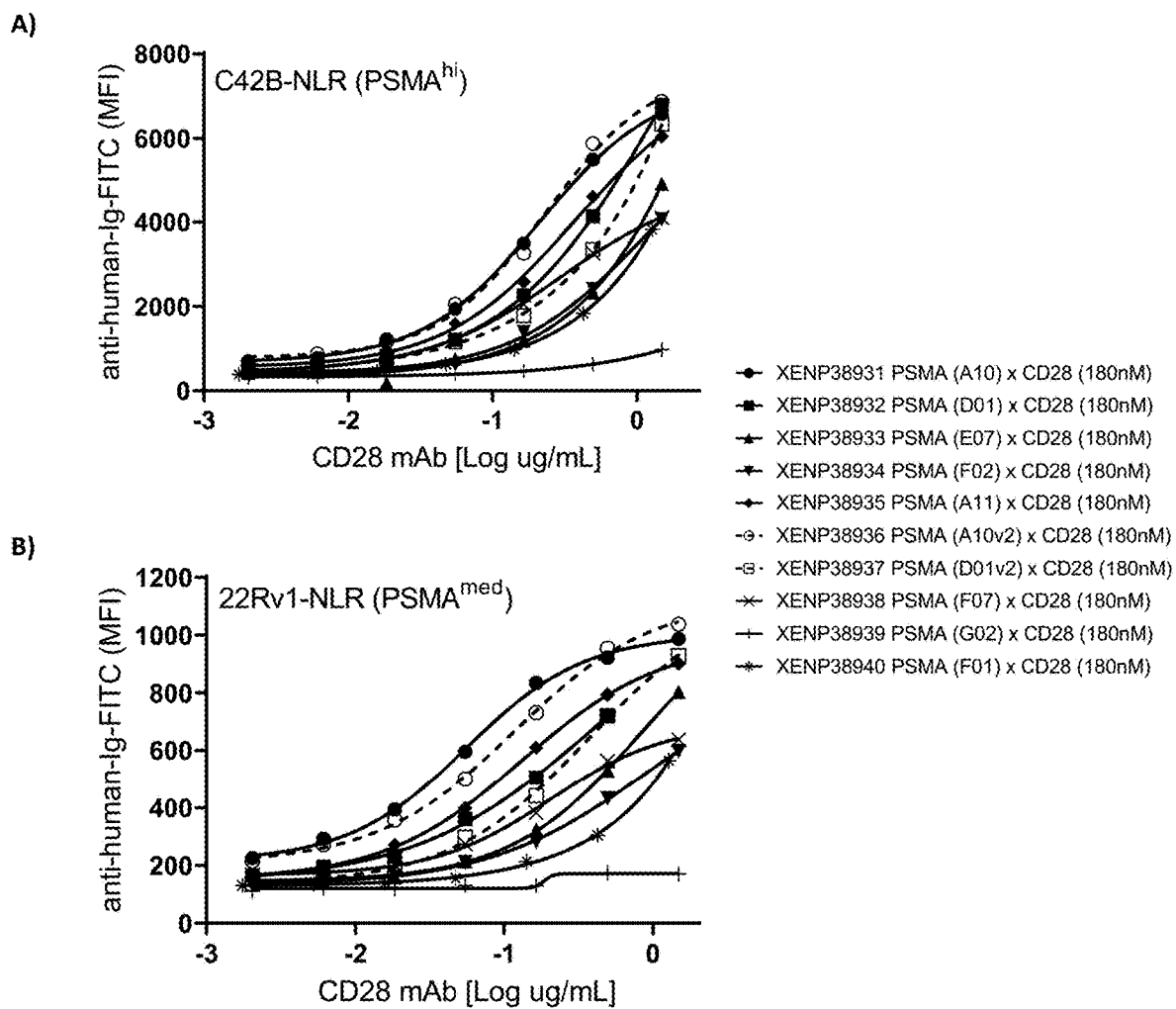

FIG. 38 depicts binding to A) C42B-NLR (PSMA$^{hi}$) and B) 22Rv1-NLR (PSMA$^{med}$) cells by PSMA×CD28 bsAbs incorporating a 1A7_H1_L1.71 180 nM CD28 binding domain and various PSMA binding domains.

Figure 39:
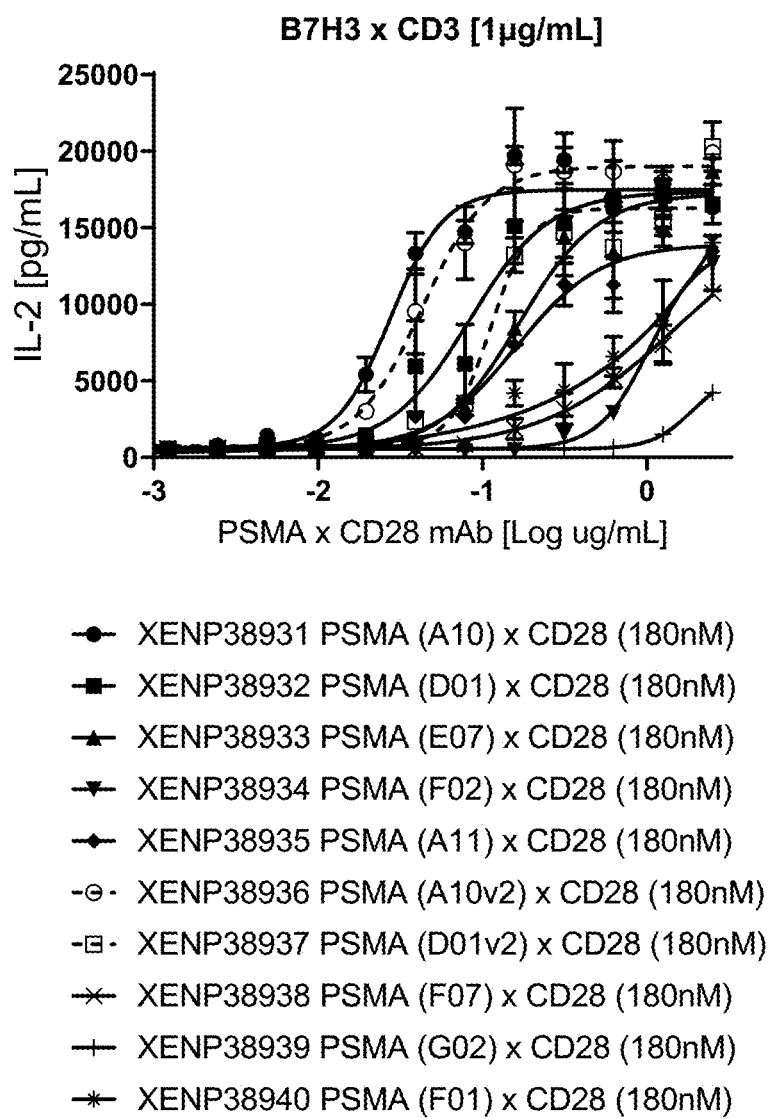

FIG. 39 depicts induction of IL-2 secretion by PSMA×CD28 bsAbs incorporating a 1A7_H1_L1.71 180 nM CD28 binding domain and various PSMA binding domains in combination with an illustrative B7H3×CD3 bsAb incubated with T cells and 22Rv1-NLR (PSMA$^{med}$) cells. The data show a range of potency consistent with cell binding.

Figure 40:
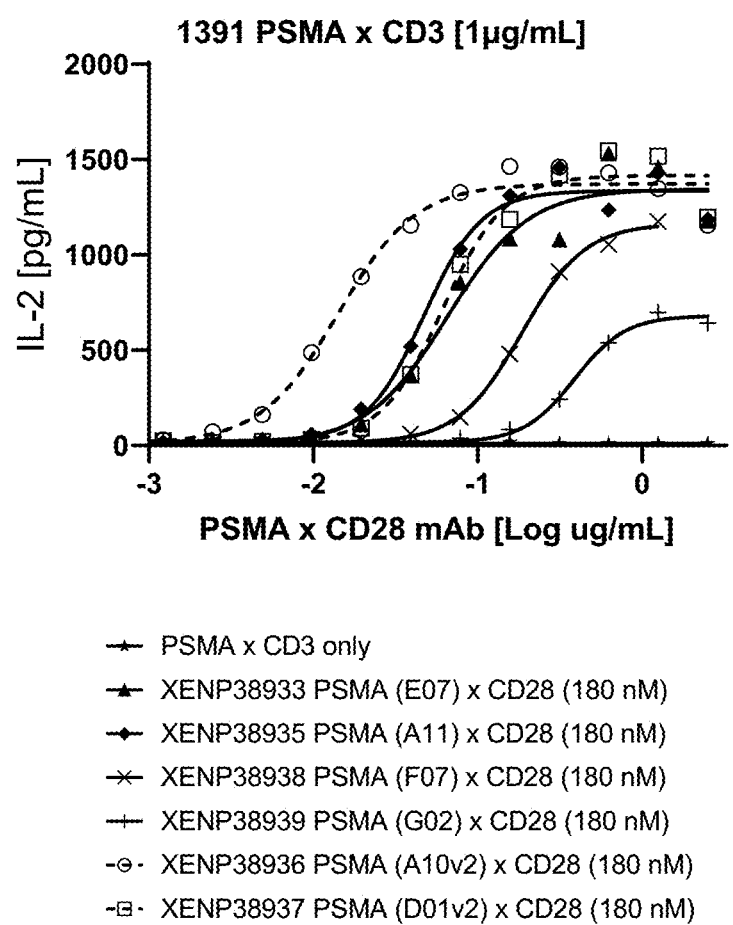

FIG. 40 depicts induction of IL-2 secretion by PSMA×CD28 bsAbs incorporating a 1A7_H1_L1.71 180 nM CD28 binding domain and various PSMA binding domains in combination with 1391 PSMA×CD3 incubated with T cells and 22Rv1-NLR (PSMA$^{med}$) cells.

FIG. 41 depicts induction of IL-2 secretion by PSMA×CD28 bsAbs incorporating A10v2 PSMA binding domain and CD28 binding domains of varying affinities in combination with 1391 PSMA×CD3 (constant 1 μg/mL PSMA×CD28 and dose titration of PSMA×CD3) incubated with T cells and A) C42B-NLR (PSMA$^{hi}$), B) PC3-PSMA (~100K), C) 22Rv1-NLR (PSMA$^{med}$), and D) PC3-PSMA (~50K) cells.

FIG. 42 depicts induction of IL-2 secretion by PSMA×CD28 bsAbs incorporating D01v2 PSMA binding domain and CD28 binding domains of varying affinities in combination with 1391 PSMA×CD3 (constant 1 μg/mL PSMA×CD28 and dose titration of PSMA×CD3) incubated with T cells and A) C42B-NLR (PSMA$^{hi}$), B) PC3-PSMA (~100K), C) 22Rv1-NLR (PSMA$^{med}$), and D) PC3-PSMA (~50K) cells.

FIG. 43 depicts induction of IL-2 secretion by PSMA×CD28 bsAbs incorporating A10v2 PSMA binding domain and CD28 binding domains of varying affinities in combination with 1391 PSMA×CD3 (constant 1 μg/mL PSMA×CD3 and dose titration of PSMA×CD28) incubated with T cells and A) C42B-NLR (PSMA$^{hi}$), B) PC3-PSMA (~100K), C) 22Rv1-NLR (PSMA$^{med}$), and D) PC3-PSMA (~50K) cells.

FIG. 44 depicts induction of IL-2 secretion by PSMA×CD28 bsAbs incorporating D01v2 PSMA binding domain and CD28 binding domains of varying affinities in combination with 1391 PSMA×CD3 (constant 1 μg/mL PSMA×CD3 and dose titration of PSMA×CD28) incubated with T cells and A) C42B-NLR (PSMA$^{hi}$), B) PC3-PSMA (~100K), C) 22Rv1-NLR (PSMA$^{med}$), and D) PC3-PSMA (~50K) cells.

FIG. 45 depicts induction of IL-2 secretion by PSMA×CD28 bsAbs incorporating various PSMA binding domain and CD28 binding domains of varying affinities in combination with 1391 PSMA×CD3 (constant 1 µg/mL PSMA× CD3 and dose titration of PSMA×CD28) incubated with T cells and 22Rv1-NLR (PSMA$^{med}$) at A) 1:1 and B) 0.1:1 effector:target ratios.

FIG. 46 depicts induction of IL-2 secretion by PSMA× CD28 bsAbs incorporating various PSMA binding domain and CD28 binding domains of varying affinities in combination with 1391 PSMA×CD3 (constant 1 µg/mL PSMA× CD3 and dose titration of PSMA×CD28) incubated with T cells and PSMA-PC3 (~50K) at A) 1:1 and B) 0.1:1 effector: target ratios.

Figure 47:
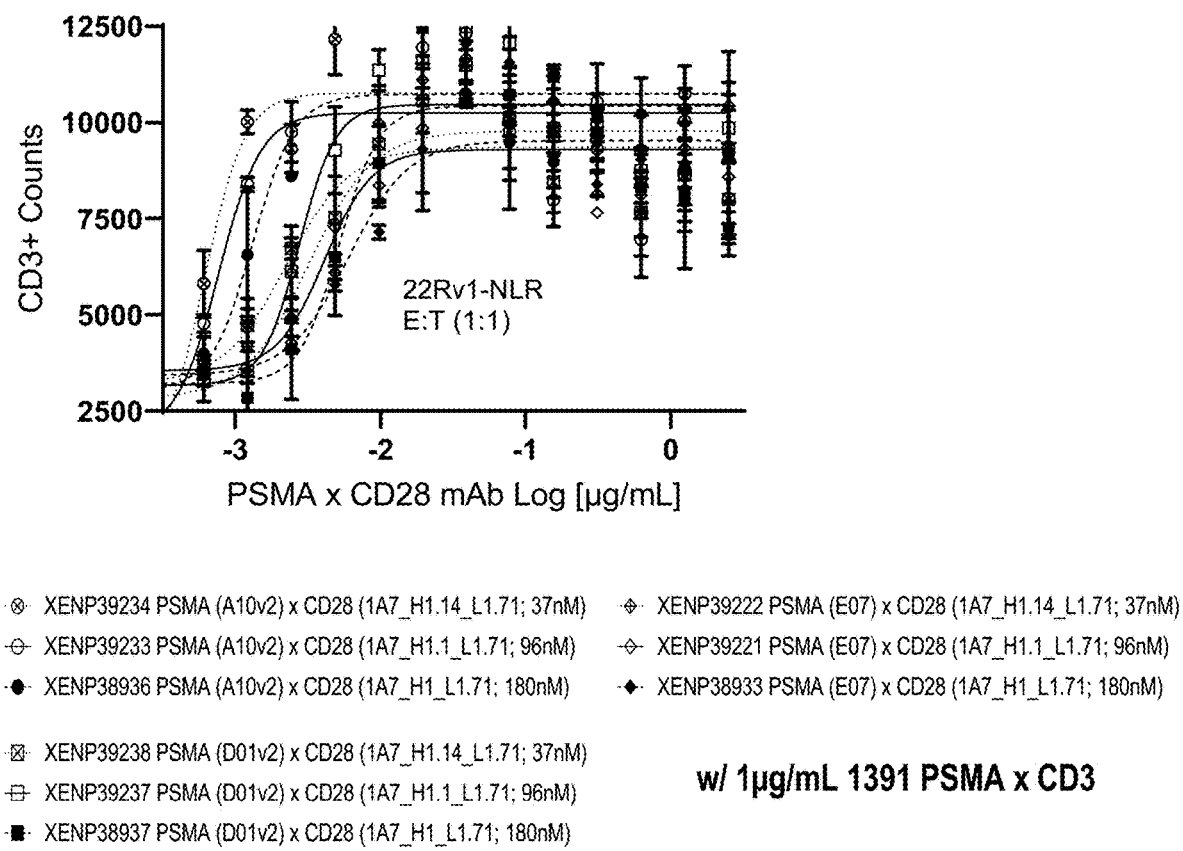

FIG. 47 depicts induction of T cell proliferation by PSMA×CD28 bsAbs incorporating various PSMA binding domain and CD28 binding domains of varying affinities in combination with 1391 PSMA×CD3 (constant 1 µg/mL PSMA×CD3 and dose titration of PSMA×CD28) incubated with T cells and 22Rv1-NLR (PSMA$^{med}$) at 1:1 effector: target ratios.

Figure 48:
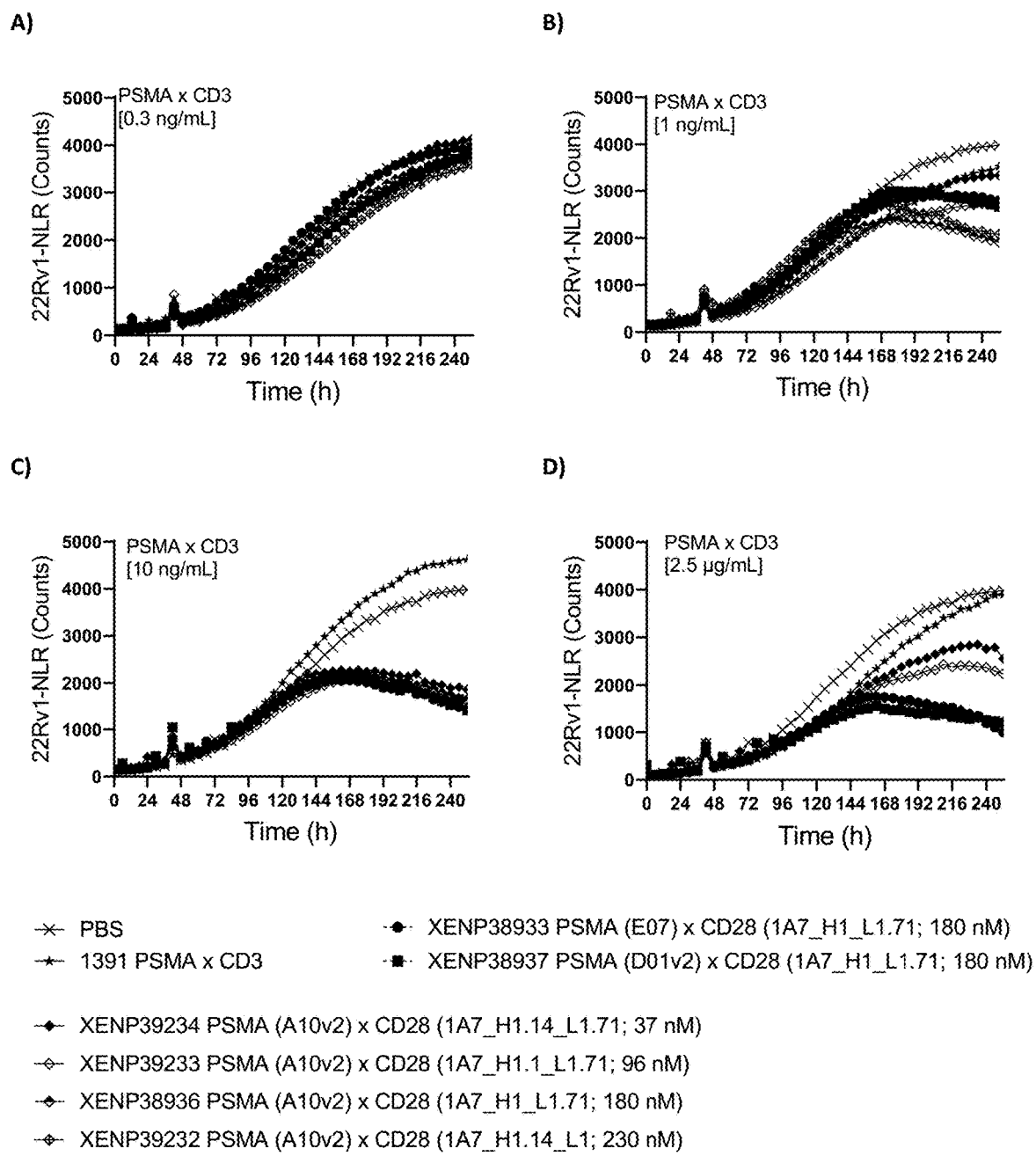

FIG. 48 depicts induction of RTCC (as indicated by decrease in target cell count over time) after incubating 22Rv1-NLR (PSMA$^{med}$) cells with T cells (E:T 1:1) and A) 0.3 mg/mL, B) 1 ng/mL, C) 10 ng/mL, or D) 2.5 µg/mL 1391 PSMA×CD3 alone or in combination with 1 µg/mL PSMA× CD28 bsAbs incorporating various PSMA binding domain and CD28 binding domains of varying affinities. The data show that combination with PSMA×CD28 bsAb enhances RTCC. Notably at higher 2.5 µg/mL concentration, high affinity CD28 binding domain as in XENP39234 and XENP39233 does not perform as well as low affinity CD28 binding domains as in XENP38936 and XENP39232.

Figure 49:
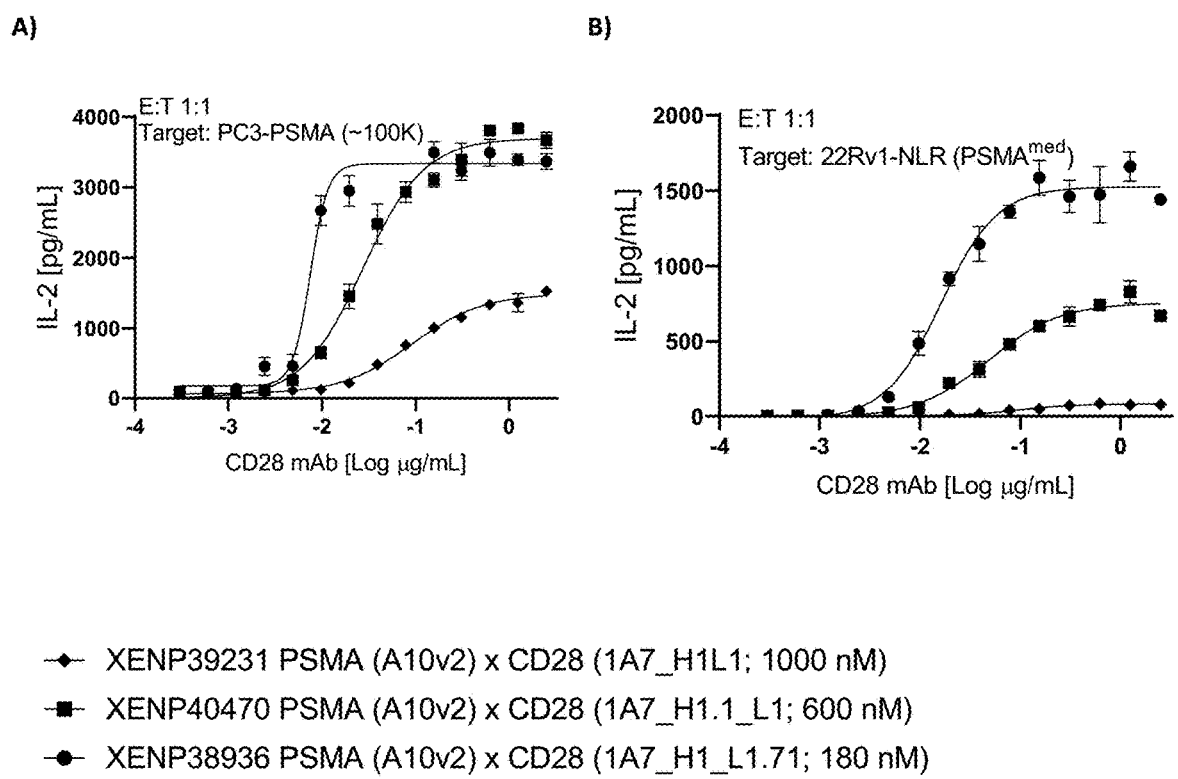

FIG. 49 depicts induction of IL-2 secretion by PSMA× CD28 bsAbs incorporating A10v2 PSMA binding domain and CD28 binding domains of additional lower affinities in combination with 1391 PSMA×CD3 (constant 1 µg/mL PSMA×CD3 and dose titration of PSMA×CD28) incubated with T cells and A) PSMA-PC3 (~100K) or B) 22Rv1-NLR (PSMA$^{med}$).

Figure 50:
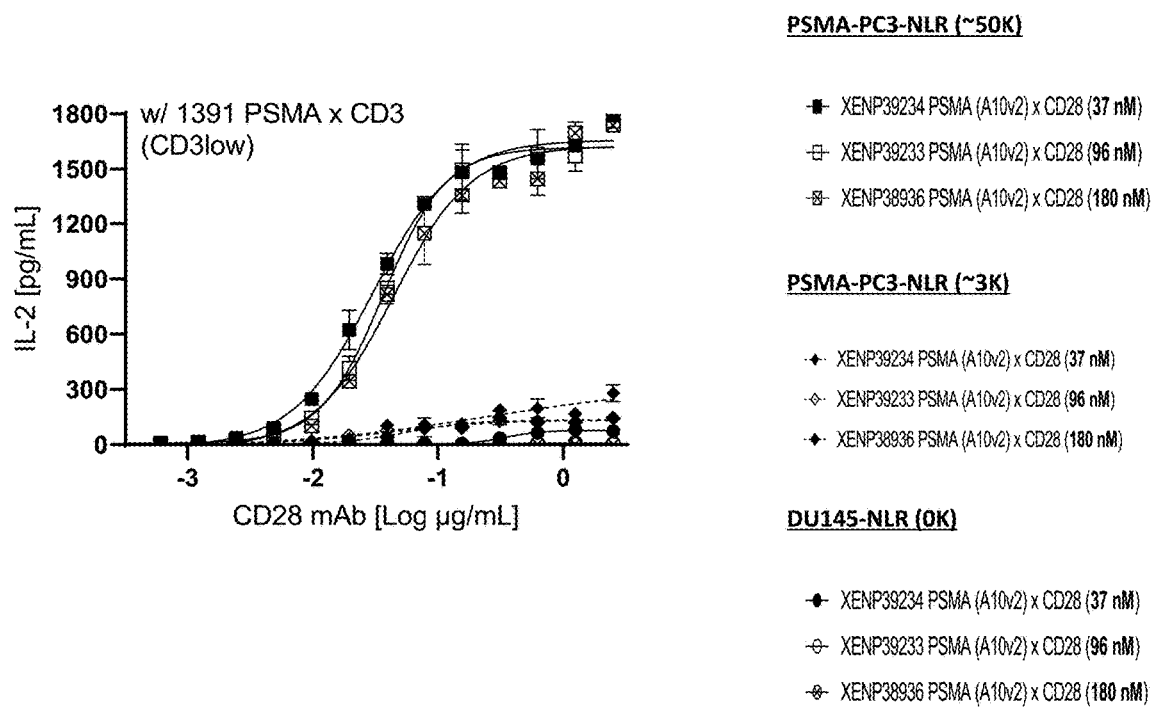

FIG. 50 depicts induction of IL-2 secretion by PSMA× CD28 bsAbs incorporating A10v2 PSMA binding domain and CD28 binding domains of varying affinities in combination with 1391 PSMA×CD3 (constant 1 µg/mL PSMA× CD3 and dose titration of PSMA×CD28) incubated with T cells and PSMA-PC3-NLR (~50K PSMA), PSMA-PC3-NLR (~3K PSMA), or DU145-NLR (OK PSMA).

Figure 51:
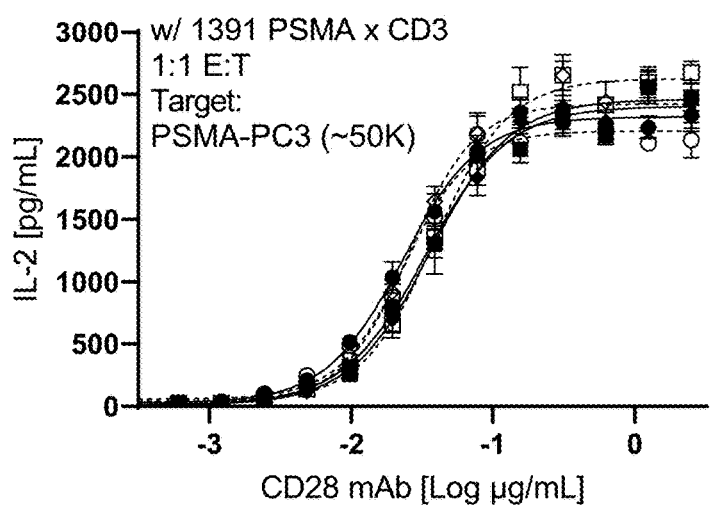

FIG. 51 depicts induction of IL-2 secretion by PSMA× CD28 bsAbs incorporating A10v2 PSMA binding domain and CD28 binding domains of varying affinities built on Platform X or Platform J in combination with 1391 PSMA× CD3 (constant 1 µg/mL PSMA×CD3 and dose titration of PSMA×CD28) incubated with T cells and PSMA-PC3 (~50K).

FIG. 52 depicts induction of IL-2 secretion, IFNγ secretion, and RTCC by XENP39234 and XENP38936 in combination with A) a B7H3×CD3 bsAb and B) XENP33063 PSMA×CD3 bsAb. PSMA×CD28 combine more potently with tumor antigen matched CD3 bispecific.

Figure 53:
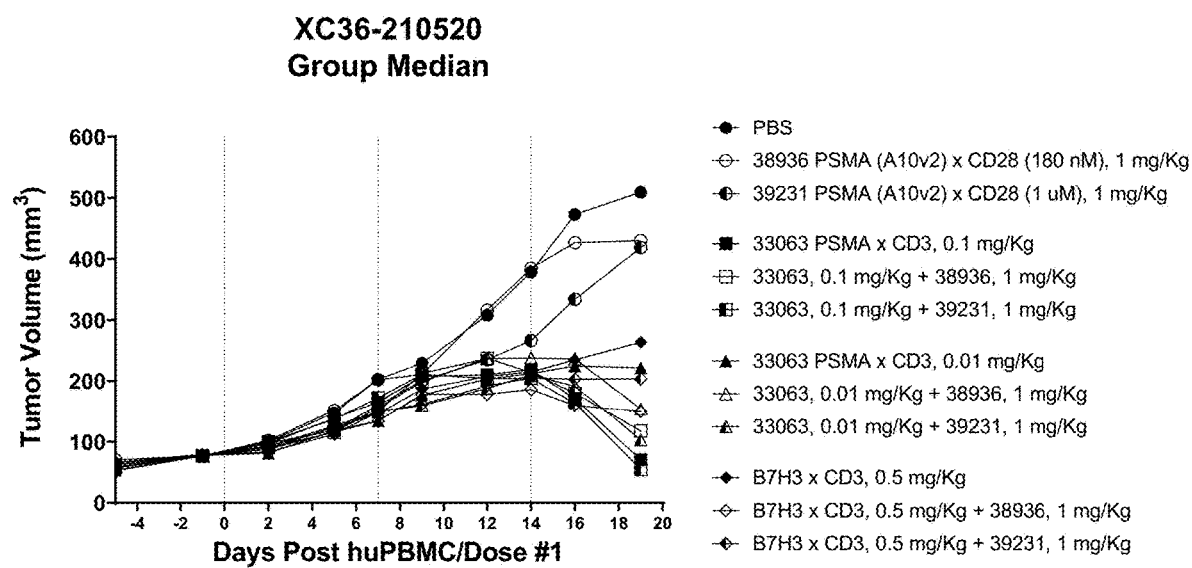

FIG. 53 depicts the change in tumor volume (as determined by caliper measurements) over time in PSMA-transfected PC3 (~100K) and huPBMC-engrafted NSG-DKO mice dosed with XENP33063 PSMA×CD3 or B7H3×CD3 bsAbs alone or in combination with XENP38936 (PSMA× CD28 180 nM) or XENP39231 (PSMA×CD28 1 µM).

Figure 54:
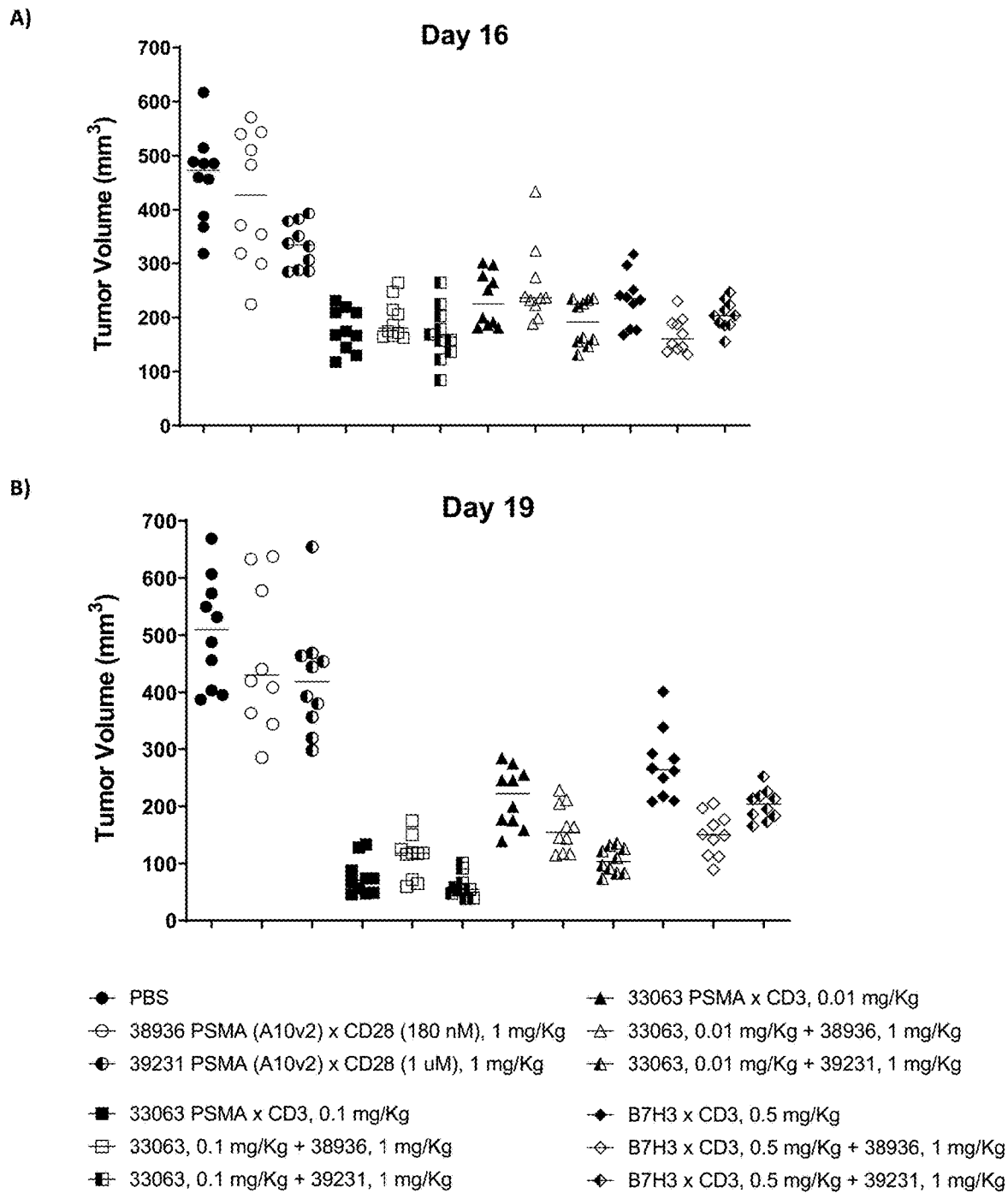

FIG. 54 depicts tumor volume (as determined by caliper measurements) on A) Day 16 and B) Day 19 in PSMA-transfected PC3 (~100K) and huPBMC-engrafted NSG-DKO mice dosed with PSMA×CD3 or B7H3×CD3 bsAbs alone or in combination with XENP38936 (PSMA×CD28 180 nM) or XENP39231 (PSMA×CD28 1 µM).

FIG. 55 depicts A) human CD4+ and B) human CD8+ cell counts on Day 14 in PSMA-transfected PC3 (~100K) and huPBMC-engrafted NSG-DKO mice dosed with PSMA× CD3 or B7H3×CD3 bsAbs alone or in combination with XENP38936 (PSMA×CD28 180 nM) or XENP39231 (PSMA×CD28 1 µM).

Figure 56:
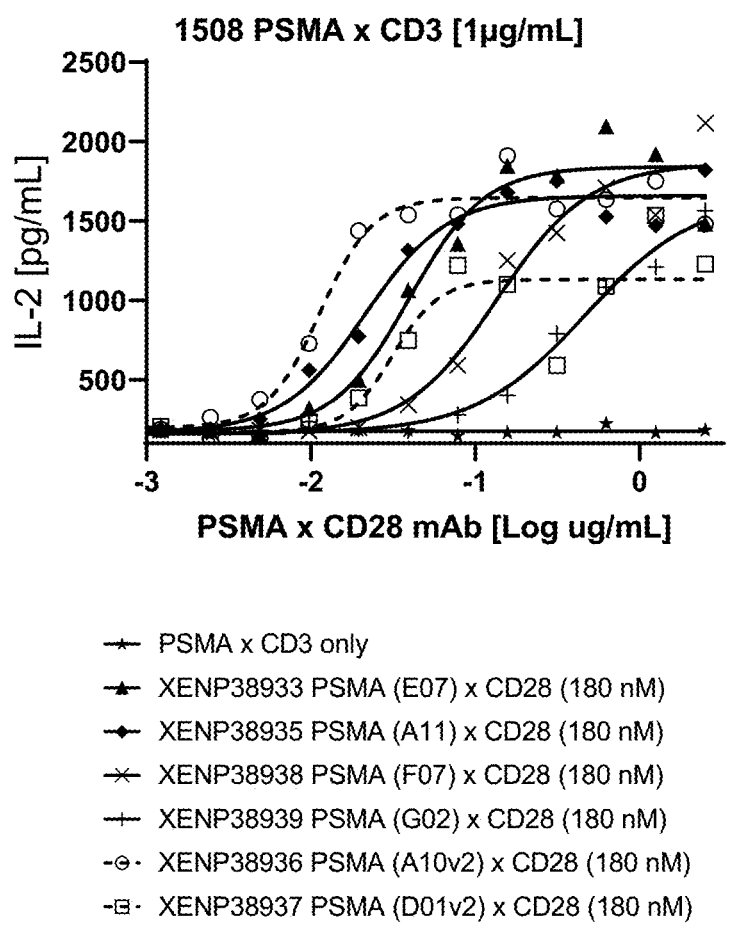

FIG. 56 depicts induction of IL-2 secretion by PSMA× CD28 bsAbs incorporating a 1A7_H1_L1.71 180 nM CD28 binding domain and various PSMA binding domains in combination with 1508 PSMA×CD3 incubated with T cells and 22Rv1-NLR (PSMA$^{med}$) cells.

Figure 57:
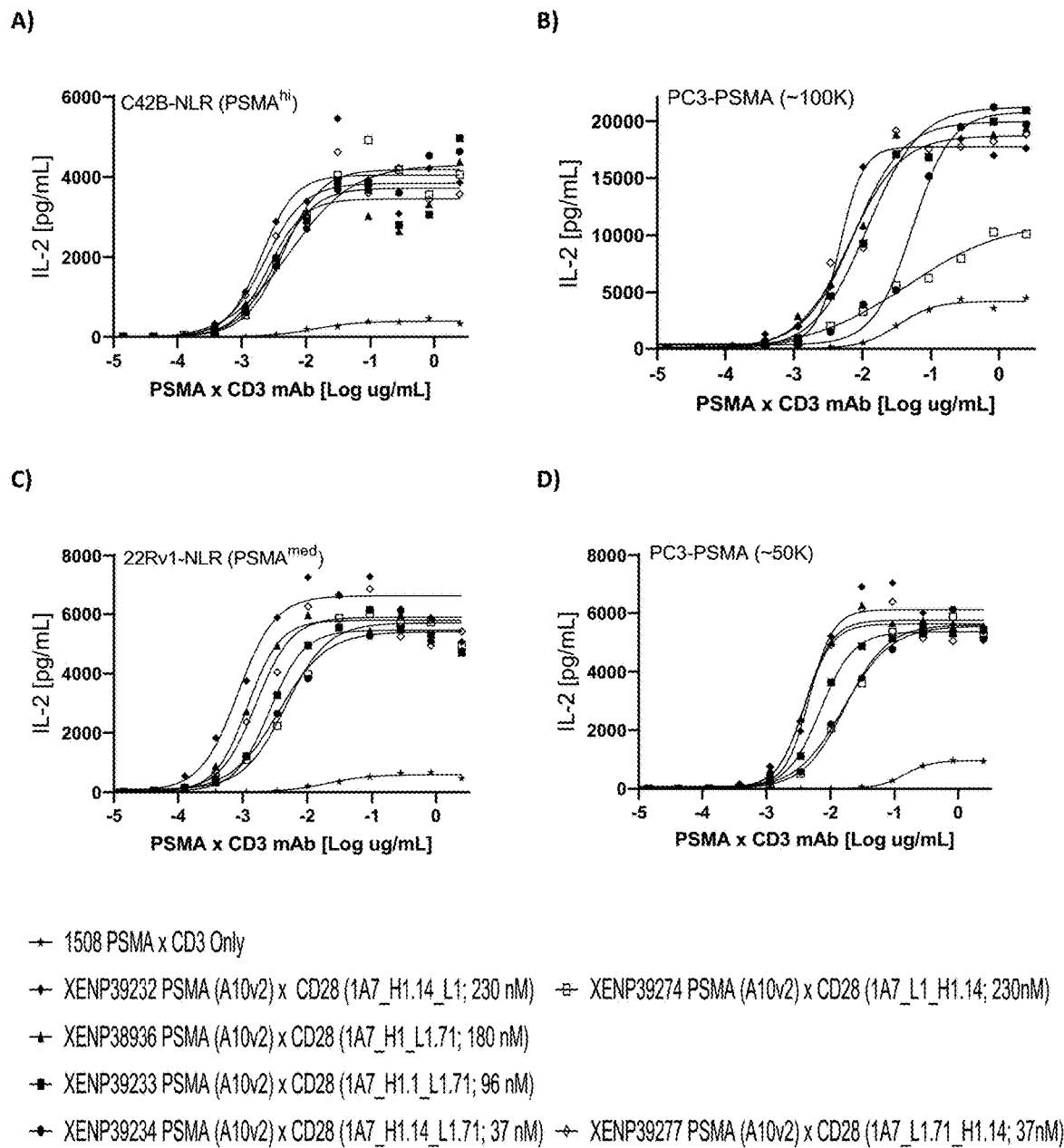

FIG. 57 depicts induction of IL-2 secretion by PSMA× CD28 bsAbs incorporating A10v2 PSMA binding domain and CD28 binding domains of varying affinities in combination with 1508 PSMA×CD3 (constant 1 µg/mL PSMA× CD28 and dose titration of PSMA×CD3) incubated with T cells and A) C42B-NLR (PSMA$^{hi}$), B) PC3-PSMA (~100K), C) 22Rv1-NLR (PSMA$^{med}$), and D) PC3-PSMA (~50K) cells.

FIG. 58 depicts induction of IL-2 secretion by PSMA× CD28 bsAbs incorporating D01v2 PSMA binding domain and CD28 binding domains of varying affinities in combination with 1508 PSMA×CD3 (constant 1 µg/mL PSMA× CD28 and dose titration of PSMA×CD3) incubated with T cells and A) C42B-NLR (PSMA$^{hi}$), B) PC3-PSMA (~100K), C) 22Rv1-NLR (PSMA$^{med}$), and D) PC3-PSMA (~50K) cells.

FIG. 59 depicts induction of IL-2 secretion by PSMA× CD28 bsAbs incorporating A10v2 PSMA binding domain and CD28 binding domains of varying affinities in combination with 1508 PSMA×CD3 (constant 1 µg/mL PSMA× CD3 and dose titration of PSMA×CD28) incubated with T cells and A) C42B-NLR (PSMA$^{hi}$), B) PC3-PSMA (~100K), C) 22Rv1-NLR (PSMA$^{med}$), and D) PC3-PSMA (~50K) cells.

FIG. 60 depicts induction of IL-2 secretion by PSMA× CD28 bsAbs incorporating D01v2 PSMA binding domain and CD28 binding domains of varying affinities in combination with 1508 PSMA×CD3 (constant 1 µg/mL PSMA× CD3 and dose titration of PSMA×CD28) incubated with T cells and A) C42B-NLR (PSMA$^{hi}$), B) PC3-PSMA (~100K), C) 22Rv1-NLR (PSMA$^{med}$), and D) PC3-PSMA (~50K) cells.

FIG. 61 depicts induction of IL-2 secretion by PSMA× CD28 bsAbs incorporating various PSMA binding domain and CD28 binding domains of varying affinities in combination with 1508 PSMA×CD3 (constant 1 µg/mL PSMA× CD3 and dose titration of PSMA×CD28) incubated with T cells and 22Rv1-NLR (PSMA$^{med}$) at A) 1:1 and B) 0.1:1 effector:target ratios.

FIG. 62 depicts induction of IL-2 secretion by PSMA× CD28 bsAbs incorporating various PSMA binding domain and CD28 binding domains of varying affinities in combination with 1508 PSMA×CD3 (constant 1 µg/mL PSMA× CD3 and dose titration of PSMA×CD28) incubated with T cells and PSMA-PC3 (~50K) at A) 1:1 and B) 0.1:1 effector: target ratios.

Figure 63:
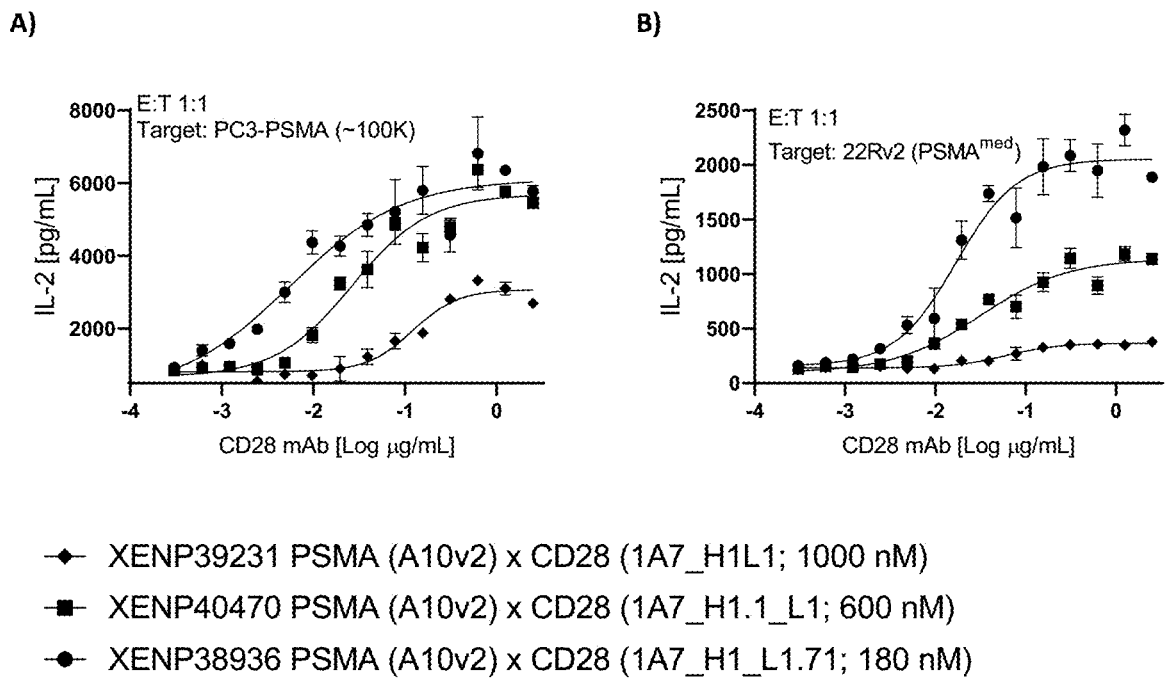

FIG. 63 depicts induction of IL-2 secretion by PSMA× CD28 bsAbs incorporating A10v2 PSMA binding domain and CD28 binding domains of additional lower affinities in combination with 1508 PSMA×CD3 (constant 1 µg/mL PSMA×CD3 and dose titration of PSMA×CD28) incubated with T cells and A) PSMA-PC3 (~100K) or B) 22Rv1-NLR (PSMA$^{med}$).

Figure 64:
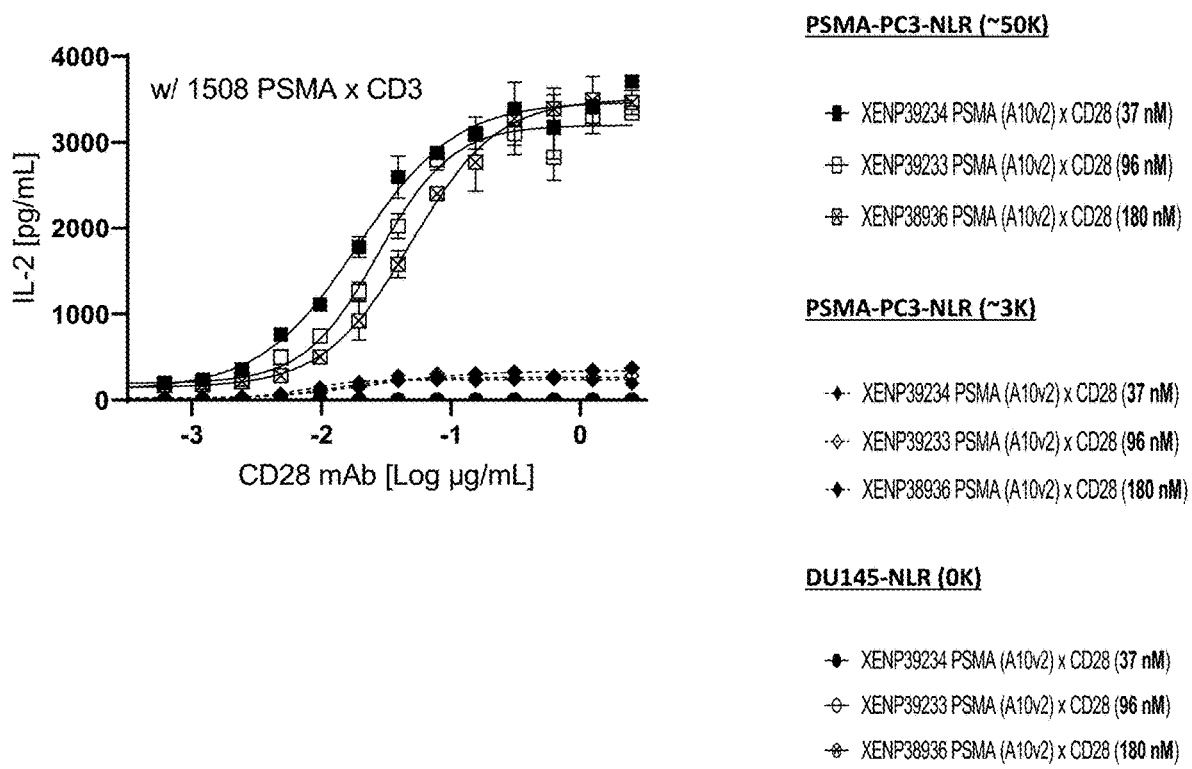

FIG. 64 depicts induction of IL-2 secretion by PSMA× CD28 bsAbs incorporating A10v2 PSMA binding domain and CD28 binding domains of varying affinities in combination with 1508 PSMA×CD3 (constant 1 µg/mL PSMA× CD3 and dose titration of PSMA×CD28) incubated with T cells and PSMA-PC3-NLR (~50K PSMA), PSMA-PC3-NLR (~3K PSMA), or DU145-NLR (OK PSMA).

Figure 65:
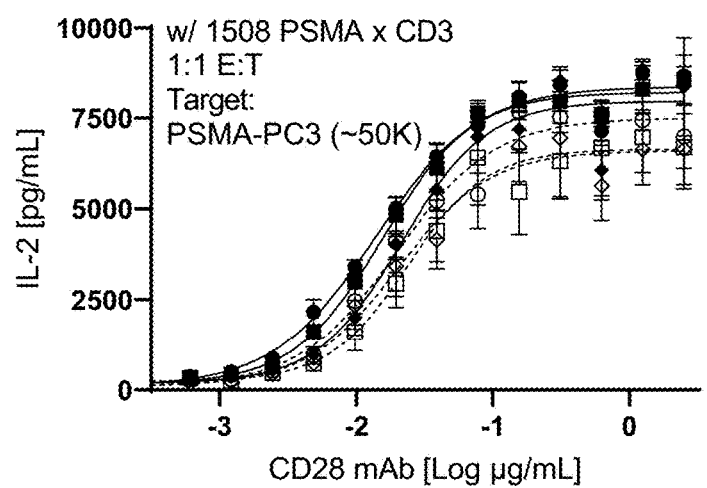

FIG. 65 depicts induction of IL-2 secretion by PSMA× CD28 bsAbs incorporating A10v2 PSMA binding domain and CD28 binding domains of varying affinities built on Platform X or Platform J in combination with 1508 PSMA× CD3 (constant 1 µg/mL PSMA×CD3 and dose titration of PSMA×CD28) incubated with T cells and PSMA-PC3 (~50K).

Figure 66:
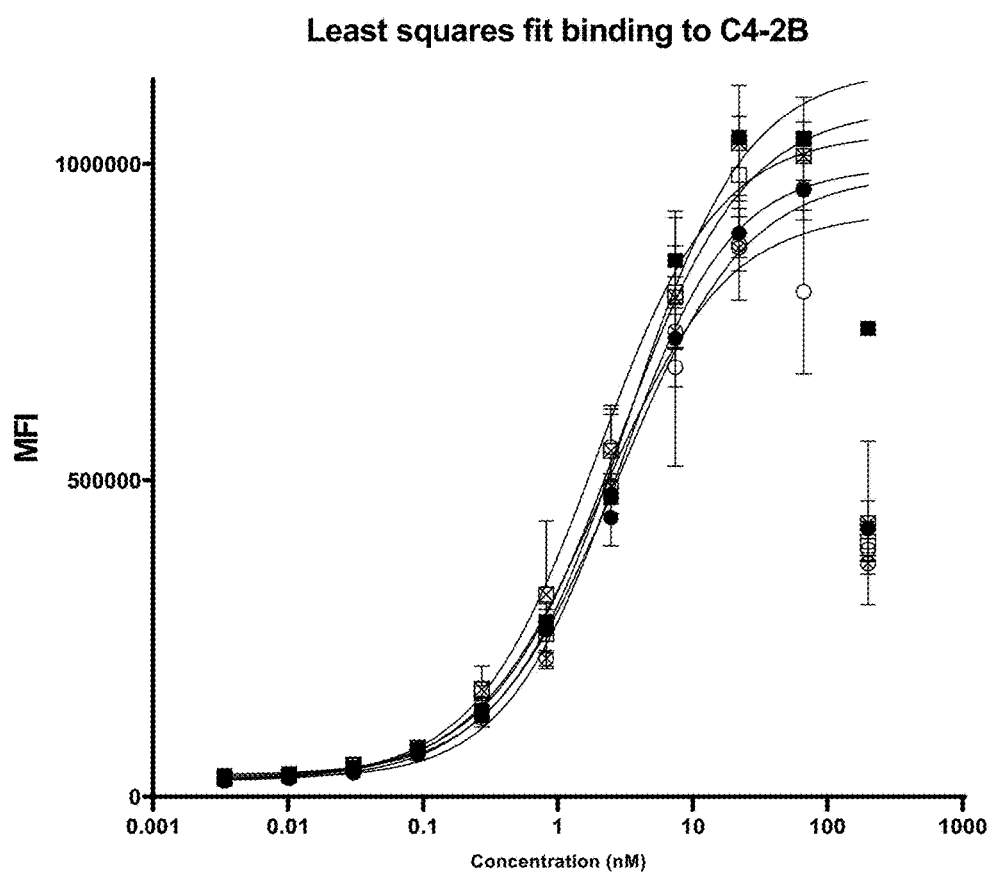

FIG. 66 depicts binding to C42B (PSMA$^{hi}$) by PSMA× CD28 bsAbs incorporating A10v2 PSMA binding domain and CD28 binding domains of varying affinities built on Platform X or Platform J.

FIG. 67 depicts the sequences for illustrative variable heavy domains from anti-CD28 clone 1A7 with an introduced cysteine to allow for "stapling" of the scFv. It should be noted that the variable heavy domains can be paired with any of the other CD28 binding domain variable light domains depicted herein, including those depicted in FIG. 68 (e.g. as utilized in C28PB405, C28PB404, C28PB403, C28PB402, C28PB401, C28PB400, and C28PB397).

FIG. 68 depicts the sequences for illustrative variable light domain from anti-CD28 clone 1A7 with an introduced cysteine to allow for "stapling" of the scFv. It should be noted that the variable heavy domains can be paired with any of the other CD28 binding domain variable heavy domains depicted herein, including those depicted in FIG. 67 (e.g. as utilized in C28PB405, C28PB404, C28PB403, C28PB402, C28PB401, C28PB400, and C28PB397).

FIGS. 69A-69C depicts the sequence for illustrative stapled 1A7 VH/VL pairs. These pairs may be formatted in the VHVL orientation or the VLVH orientation.

FIGS. 70A-70F depicts additional sequences for affinity-optimized variable heavy domains from anti-CD28 clone 1A7. It should be noted that the variable heavy domains can be paired with any of the other CD28 binding domain variable light domains depicted herein, including those depicted in FIGS. 71A-71I.

FIGS. 71A-71I depicts additional sequences for affinity-optimized variable light domains from anti-CD28 clone 1A7. It should be noted that the variable light domains can be paired with any of the other CD28 binding domain variable heavy domains depicted herein, including those depicted in FIGS. 70-70F.

Figure 72:
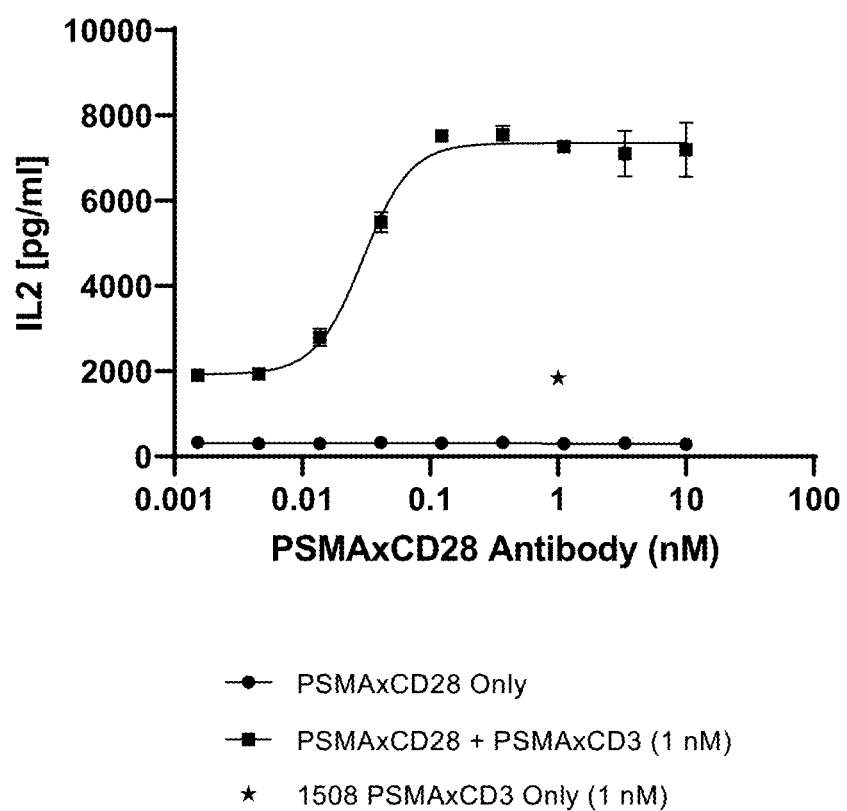

FIG. 72 shows addition of PSMA×CD28 increased IL2 production of PSMA×CD3 in a dose dependent manner in C42B cells using human PBMCs.

DETAILED DESCRIPTION

I. Overview

Prostate cancer (PC) is one of the most prevalent cancers in men, and end stage (castration-resistant prostate cancer) has no curative treatment option. Prostate Specific Membrane Antigen (PSMA), a type II transmembrane protein with a large extracellular domain, has long generated interest as a therapeutic target. PSMA is highly overexpressed in PC compared to normal tissue, and its expression has been shown to correlate with malignancy. Previous attempts to target PSMA include antibody-based radiotherapy and antibody drug conjugates, which have shown some success but can be hampered by the inherent toxicity of the modality.

The activation of T cells in the treatment of cancer is being widely investigated. T cells require multiple signals for complete activation and differentiation. As shown in FIG. 27A, Signal 1, promoted by recognition of a peptide-MHC (pMHC) complex by the T cell receptor (TCR), is absolutely required for T cell activation. Signal 2, which synergizes with, and amplifies signal 1, is typically provided by the interaction of the CD28 ligands CD80 and CD86 with CD28 itself. Although CD28 engagement alone is typically inert, when combined with signal 1 activation, it promotes additional activation, survival, and proliferative signals, including IL-2 secretion. As CD80 and CD86 are only naturally expressed by professional antigen-presenting cells (APC), the extent of CD28 costimulation in the tumor setting can be highly variable. Accordingly, the present invention is directed to a novel class of tumor-targeted anti-CD28× anti-PSMA bispecific antibodies that mimick the CD80/CD86 engagement of CD28, thereby providing an artificial source of signal 2. Notably, signal 1 can either be provided by the natural TCR:pMHC recognition of tumor cells, or it can be provided by combination of the CD28 bispecific with a CD3 bispecific (e.g., anti-CD3× anti-PSMA), which can mimic signal 1.

Accordingly, provided herein are novel anti-CD28× anti-PSMA (also referred to as "uCD28×αPSMA" and sometimes "CD28×PSMA") bispecific antibodies and methods of using such antibodies for the treatment of PSMA-associated cancers. In many cases, these bispecific antibodies are heterodimeric. Subject uCD28×αPSMA antibodies are capable of agonistically binding to CD28 costimulatory molecules on T cells and targeting to PSMA on PSMA-expressing tumor cells. Thus, such antibodies selectively enhance anti-tumor activity at PSMA-expressing tumor sites while minimizing peripheral toxicity. The subject antibodies provided herein are particularly useful for enhancing anti-tumor activity either alone, as a monotherapy, or when used in combination with other anti-cancer therapies as more fully described herein.

Accordingly, in one aspect, provided herein are heterodimeric antibodies that bind to two different antigens, e.g., the antibodies are "bispecific," in that they bind two different target antigens, generally CD28 and PSMA as described below. These heterodimeric antibodies can bind each of the target antigens either monovalently (e.g., there is a single antigen binding domain such as a variable heavy and variable light domain pair) or bivalently (there are two antigen binding domains that each independently bind the antigen). In some embodiments, the heterodimeric antibody provided herein includes one CD28 binding domain and one PSMA binding domain (e.g., heterodimeric antibodies in the "1+1 Fab-scFv-Fc" format described herein, which are thus bispecific and bivalent). In other embodiments, the heterodimeric antibody provided herein includes one CD28 binding domain and two PSMA binding domains (e.g., heterodimeric antibodies in the "2+1 Fab2-scFv-Fc" formats described herein, which are thus bispecific but trivalent, as they contain three antigen binding domains (ABDs)). The heterodimeric antibodies provided herein are based on the use of different monomers that contain amino acid substitutions (i.e., skew variants") that "skew" formation of heterodimers over homodimers, as is more fully outlined below. In some embodiments, the heterodimer antibodies are also coupled with purification variants (e.g., "pI variants") that allow simple purification of the heterodimers away from the homodimers, as is similarly outlined below. The heterodimeric bispecific antibodies provided generally rely on the use of engineered or variant Fc domains that can self-assemble in production cells to produce heterodimeric proteins, and methods to generate and purify such heterodimeric proteins.

II. Nomenclature

The naming nomenclature of particular antigen binding domains (e.g., PSMA and CD28 binding domains) use a "Hx.xx_Ly.yy" type of format, with the numbers being unique identifiers to particular variable chain sequences. Thus, for example, the CD28 binding domain "1A7[CD28] H1 L1" (FIG. 15) includes a variable heavy domain, H1, and a variable light domain L1. In the case that these sequences are used as scFvs, the designation "H1_L1", indicates that the binding domain includes a variable heavy domain "H1" combined with a variable light domain "L1," and is in VH-linker-VL orientation, from N- to C-terminus. This molecule with the identical sequences of the heavy and light variable domains but in the reverse order (VL-linker-VH orientation, from N- to C-terminus) would be designated "L1_H1". Similarly, different constructs may "mix and match" the heavy and light chains as will be evident from the sequence listing and the Figures.

III. Definitions

In order that the application may be more completely understood, several definitions are set forth below. Such definitions are meant to encompass grammatical equivalents.

By "CD28," "Cluster of Differentiation 28," and "Tp44" (e.g., Genebank Accession Numbers NP_001230006 (human), NP_001230007 (human), NP_006130 (human), and NP_031668 (mouse)) herein is meant a B7 receptor expressed on T cells that provides co-stimulatory signals required for T cell activation and survival. T cell stimulation through CD28 in addition to the T cell receptor (TCR) provides a potent signal for the production of various interleukins. CD28 is the receptor for CD80 (B7.1) and CD86 (B7.2) proteins. CD28 includes an intercellular domain with a YMNM motif (SEQ ID NO: 1044) critical for the recruitment of SH2-domain containing proteins, particularly PI3K. CD28 also includes two proline-rich motifs that are able to bind SH3-containing proteins. Exemplary CD28 sequences are depicted in FIGS. 1A-1B. Unless otherwise noted, references to CD28 are to the human CD28 sequence.

By "PSMA" or "Prostate Specific Membrane Antigen" (e.g., Genebank Accession Number NP 005012.2) herein is meant a type II transmembrane protein that is expressed in prostatic tissues, including primary prostate adenocarcinomas, metastatic prostate cancer, and in the tumor neovasculature of many solid tumors. In prostate cancer (PCa), PSMA is highly expressed in poorly differentiated, highly metastatic prostatic cells and in castrate-resistant models. Exemplary PSMA sequences are disclosed in FIGS. 2A-2B. Unless otherwise noted, references to PSMA are to the human PSMA sequence.

By "B7H3," "B7-H3," "B7RP-2," "CD276," "Cluster of Differentiation 276," (e.g., Genebank Accession Numbers NP_001019907 (human), NP_001316557 (human), NP_001316558 (human), NP 079516 (human), and NP_598744 (mouse)) herein is meant a type-1 transmembrane protein that is a member of the B7 family possessing an ectodomain composed of a single IgV-IgC domain pair. B7H3 is an immune checkpoint molecule and is aberrantly overexpressed in many types of cancers. Unless otherwise noted, references to B7H3 are to the human B7H3 sequence.

By "ablation" herein is meant a decrease or removal of activity. Thus, for example, "ablating FcγR binding" means the Fc region amino acid variant has less than 50% starting binding as compared to an Fc region not containing the specific variant, with more than 70-80-90-95-98% loss of activity being preferred, and in general, with the activity being below the level of detectable binding in a Biacore, SPR or BLI assay. Of particular use in the ablation of FcγR binding are those shown in FIG. 5, which generally are added to both monomers.

By "ADCC" or "antibody dependent cell-mediated cytotoxicity" as used herein is meant the cell-mediated reaction, wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity.

By "ADCP" or antibody dependent cell-mediated phagocytosis as used herein is meant the cell-mediated reaction wherein nonspecific phagocytic cells that express FcγRs recognize bound antibody on a target cell and subsequently cause phagocytosis of the target cell.

As used herein, the term "antibody" is used generally. Antibodies provided herein can take on a number of formats as described herein, including traditional antibodies as well as antibody derivatives, fragments and mimetics, described herein.

Traditional immunoglobulin (Ig) antibodies are "Y" shaped tetramers. Each tetramer is typically composed of two identical pairs of polypeptide chains, each pair having one "light chain" monomer (typically having a molecular weight of about 25 kDa) and one "heavy chain" monomer (typically having a molecular weight of about 50-70 kDa).

Other useful antibody formats include, but are not limited to, the "1+1 Fab-scFv-Fc," and "2+1 Fab$_2$-scFv-Fc" formats provided herein (see, e.g., FIGS. 24A-24M). Additional useful antibody formats include, but are not limited to, "1+1 common light chain," and "2+1 common light chain," "mAb-Fv," "mAb-scFv," "central-Fv", "one armed scFv-mAb," "scFv-mAb," "dual scFv," and "trident" format antibodies (FIGS. 24A-24M). See also, US20180127501A1, which is incorporated by reference herein, particularly in pertinent part relating to antibody formats (see, e.g., FIG. 2 of US20180127501A1).

Antibody heavy chains typically include a variable heavy (VH) domain, which includes vhCDR1-3, and an Fc domain, which includes a CH2-CH3 monomer. In some embodiments, antibody heavy chains include a hinge and CH1 domain. Traditional antibody heavy chains are monomers that are organized, from N- to C-terminus: VH-CH1-hinge-CH2-CH3. The CH1-hinge-CH2-CH3 is collectively referred to as the heavy chain "constant domain" or "constant region" of the antibody, of which there are five different categories or "isotypes": IgA, IgD, IgG, IgE and IgM.

In some embodiments, the antibodies provided herein include IgG isotype constant domains, which has several subclasses, including, but not limited to IgG1, IgG2, IgG3, and IgG4. In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH"

domains in the context of IgG are as follows: "CH1" refers to positions 118-215 according to the EU index as in Kabat. "Hinge" refers to positions 216-230 according to the EU index as in Kabat. "CH2" refers to positions 231-340 according to the EU index as in Kabat, and "CH3" refers to positions 341-447 according to the EU index as in Kabat. As shown in Table 1, the exact numbering and placement of the heavy chain domains can be different among different numbering systems. As shown herein and described below, the pI variants can be in one or more of the CH regions, as well as the hinge region, discussed below.

It should be noted that IgG1 has different allotypes with polymorphisms at 356 (D or E) and 358 (L or M). The sequences depicted herein use the 356E/358M allotype, however the other allotype is included herein. That is, any sequence inclusive of an IgG1 Fc domain included herein can have 356D/358L replacing the 356E/358M allotype. It should be understood that therapeutic antibodies can also comprise hybrids of isotypes and/or subclasses. For example, as shown in US Publication 2009/0163699, incorporated by reference, the present antibodies, in some embodiments, include human IgG1/G2 hybrids.

By "Fc" or "Fc region" or "Fc domain" as used herein is meant the polypeptide comprising the constant region of an antibody, in some instances, excluding all of the first constant region immunoglobulin domain (e.g., CH1) or a portion thereof, and in some cases, optionally including all or part of the hinge. For IgG, the Fc domain comprises immunoglobulin domains CH2 and CH3 (Cγ2 and Cγ3), and optionally all or a portion of the hinge region between CH1 (Cγ1) and CH2 (Cγ2). Thus, in some cases, the Fc domain includes, from N- to C-terminal, CH2-CH3 and hinge-CH2-CH3. In some embodiments, the Fc domain is that from IgG1, IgG2, IgG3 or IgG4, with IgG1 hinge-CH2-CH3 and IgG4 hinge-CH2-CH3 finding particular use in many embodiments. Additionally, in the case of human IgG1 Fc domains, the hinge may include a C220S amino acid substitution. Furthermore, in the case of human IgG4 Fc domains, the hinge may include a S228P amino acid substitution. Although the boundaries of the Fc region may vary, the human IgG heavy chain Fc region is usually defined to include residues E216, C226, or A231 to its carboxyl-terminal, wherein the numbering is according to the EU index as in Kabat. In some embodiments, as is more fully described below, amino acid modifications are made to the Fc region, for example to alter binding to one or more FcγR or to the FcRn.

By "heavy chain constant region" herein is meant the CH1-hinge-CH2-CH3 portion of an antibody (or fragments thereof), excluding the variable heavy domain; in EU numbering of human IgG1 this is amino acids 118-447. By "heavy chain constant region fragment" herein is meant a heavy chain constant region that contains fewer amino acids from either or both of the N- and C-termini but still retains the ability to form a dimer with another heavy chain constant region.

Another type of domain of the heavy chain is the hinge region. By "hinge" or "hinge region" or "antibody hinge region" or "hinge domain" herein is meant the flexible polypeptide comprising the amino acids between the first and second constant domains of an antibody. Structurally, the IgG CH1 domain ends at EU position 215, and the IgG CH2 domain begins at residue EU position 231. Thus for IgG the antibody hinge is herein defined to include positions 216 (E216 in IgG1) to 230 (P230 in IgG1), wherein the numbering is according to the EU index as in Kabat. In some cases, a "hinge fragment" is used, which contains fewer amino acids at either or both of the N- and C-termini of the hinge domain. As noted herein, pI variants can be made in the hinge region as well. Many of the antibodies herein have at least one the cysteines at position 220 according to EU numbering (hinge region) replaced by a serine. Generally, this modification is on the "scFv monomer" side (when 1+1 or 2+1 formats are used) for most of the sequences depicted herein, although it can also be on the "Fab monomer" side, or both, to reduce disulfide formation. Specifically included within the sequences herein are one or both of these cysteines replaced (C220S).

As will be appreciated by those in the art, the exact numbering and placement of the heavy chain constant region domains (i.e., CH1, hinge, CH2 and CH3 domains) can be different among different numbering systems. A useful comparison of heavy constant region numbering according to EU and Kabat is as below, see Edelman et al., 1969, Proc Natl Acad Sci USA 63:78-85 and Kabat et al., 1991, Sequences of Proteins of Immunological Interest, 5th Ed., United States Public Health Service, National Institutes of Health, Bethesda, entirely incorporated by reference.

TABLE 1

| | EU Numbering | Kabat Numbering |
|---|---|---|
| CH1 | 118-215 | 114-223 |
| Hinge | 216-230 | 226-243 |
| CH2 | 231-340 | 244-360 |
| CH3 | 341-447 | 361-478 |

The antibody light chain generally comprises two domains: the variable light domain (VL), which includes light chain CDRs vlCDR1-3, and a constant light chain region (often referred to as CL or Cκ). The antibody light chain is typically organized from N- to C-terminus: VL-CL.

By "antigen binding domain" or "ABD" herein is meant a set of six Complementary Determining Regions (CDRs) that, when present as part of a polypeptide sequence, specifically binds a target antigen (e.g., PSMA or CD28) as discussed herein. As is known in the art, these CDRs are generally present as a first set of variable heavy CDRs (vhCDRs or VHCDRs) and a second set of variable light CDRs (vlCDRs or VLCDRs), each comprising three CDRs: vhCDR1, vhCDR2, vhCDR3 variable heavy CDRs and vlCDR1, vlCDR2 and vlCDR3 vhCDR3 variable light CDRs. The CDRs are present in the variable heavy domain (vhCDR1-3) and variable light domain (vlCDR1-3). The variable heavy domain and variable light domain from an Fv region.

The present invention provides a large number of different CDR sets. In this case, a "full CDR set" comprises the three variable light and three variable heavy CDRs, e.g., a vlCDR1, vlCDR2, vlCDR3, vhCDR1, vhCDR2 and vhCDR3. These can be part of a larger variable light or variable heavy domain, respectfully. In addition, as more fully outlined herein, the variable heavy and variable light domains can be on separate polypeptide chains, when a heavy and light chain is used (for example when Fabs are used), or on a single polypeptide chain in the case of scFv sequences.

As will be appreciated by those in the art, the exact numbering and placement of the CDRs can be different among different numbering systems. However, it should be understood that the disclosure of a variable heavy and/or variable light sequence includes the disclosure of the associated (inherent) CDRs. Accordingly, the disclosure of each variable heavy region is a disclosure of the vhCDRs (e.g., vhCDR1, vhCDR2 and vhCDR3) and the disclosure of each variable light region is a disclosure of the vlCDRs (e.g., vlCDR1, vlCDR2 and vlCDR3). A useful comparison of CDR numbering is as below, see Lafranc et al., Dev. Comp. Immunol. 27(1):55-77 (2003):

TABLE 2

|        | Kabat + Chothia | IMGT    | Kabat  | AbM    | Chothia | Contact | Xencor  |
|--------|-----------------|---------|--------|--------|---------|---------|---------|
| vhCDR1 | 26-35           | 27-38   | 31-35  | 26-35  | 26-32   | 30-35   | 27-35   |
| vhCDR2 | 50-65           | 56-65   | 50-65  | 50-58  | 52-56   | 47-58   | 54-61   |
| vhCDR3 | 95-102          | 105-117 | 95-102 | 95-102 | 95-102  | 93-101  | 103-116 |
| vlCDR1 | 24-34           | 27-38   | 24-34  | 24-34  | 24-34   | 30-36   | 27-38   |
| vlCDR2 | 50-56           | 56-65   | 50-56  | 50-56  | 50-56   | 46-55   | 56-62   |
| vlCDR3 | 89-97           | 105-117 | 89-97  | 89-97  | 89-97   | 89-96   | 97-105  |

Throughout the present specification, the Kabat numbering system is generally used when referring to a residue in the variable domain (approximately, residues 1-107 of the light chain variable region and residues 1-113 of the heavy chain variable region) and the EU numbering system for Fc regions (e.g., Kabat et al., supra (1991)).

The CDRs contribute to the formation of the antigen-binding, or more specifically, epitope binding site of the antigen binding domains and antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning." As outlined below, the invention not only includes the enumerated antigen binding domains and antibodies herein, but those that compete for binding with the epitopes bound by the enumerated antigen binding domains.

In some embodiments, the six CDRs of the antigen binding domain are contributed by a variable heavy and a variable light domain. In a "Fab" format, the set of 6 CDRs are contributed by two different polypeptide sequences, the variable heavy domain (vh or VH; containing the vhCDR1, vhCDR2 and vhCDR3) and the variable light domain (vl or VL; containing the vlCDR1, vlCDR2 and vlCDR3), with the C-terminus of the vh domain being attached to the N-terminus of the CH1 domain of the heavy chain and the C-terminus of the vl domain being attached to the N-terminus of the constant light domain (and thus forming the light chain). In a scFv format, the vh and vl domains are covalently attached, generally through the use of a linker (a "scFv linker") as outlined herein, into a single polypeptide sequence, which can be either (starting from the N-terminus) vh-linker-vl or vl-linker-vh, with the former being generally preferred (including optional domain linkers on each side, depending on the format used. In general, the C-terminus of the scFv domain is attached to the N-terminus of all or part of the hinge in the second monomer.

By "variable region" or "variable domain" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively, and contains the CDRs that confer antigen specificity. Thus, a "variable heavy domain" pairs with a "variable light domain" to form an antigen binding domain ("ABD"). In addition, each variable domain comprises three hypervariable regions ("complementary determining regions," "CDRs") (vhCDR1, vhCDR2 and vhCDR3 for the variable heavy domain and vlCDR1, vlCDR2 and vlCDR3 for the variable light domain) and four framework (FR) regions, arranged from amino-terminus to carboxy-terminus in the following order: FR1-CDR1-FR2-CDR2-FR3-CDR3-FR4.

By "Fab" or "Fab region" as used herein is meant the antibody region that comprises the VH, CH1, VL, and CL immunoglobulin domains, generally on two different polypeptide chains (e.g., VH-CH1 on one chain and VL-CL on the other). Fab may refer to this region in isolation, or this region in the context of a bispecific antibody of the invention. In the context of a Fab, the Fab comprises an Fv region in addition to the CH1 and CL domains.

By "Fv" or "Fv fragment" or "Fv region" as used herein is meant the antibody region that comprises the VL and VH domains. Fv regions can be formatted as both Fabs (as discussed above, generally two different polypeptides that also include the constant regions as outlined above) and single chain Fvs (scFvs), where the vl and vh domains are included in a single peptide, attached generally with a linker as discussed herein.

By "single chain Fv" or "scFv" herein is meant a variable heavy domain covalently attached to a variable light domain, generally using a scFv linker as discussed herein, to form a scFv or scFv domain. A scFv domain can be in either orientation from N to C-terminus (vh-linker-vl or vl-linker-vh). In the sequences depicted in the sequence listing and in the figures, the order of the vh and vl domain is indicated in the name, e.g., H.X_L.Y means N- to C-terminal is vh-linker-vl, and L.Y_H.X is vl-linker-vh.

Some embodiments of the subject antibodies provided herein comprise at least one scFv domain, which, while not naturally occurring, generally includes a variable heavy domain and a variable light domain, linked together by a scFv linker. As outlined herein, while the scFv domain is generally from N- to C-terminus oriented as VH-scFv linker-VL, this can be reversed for any of the scFv domains (or those constructed using vh and vl sequences from Fabs), to VL-scFv linker-VH, with optional linkers at one or both ends depending on the format.

By "modification" or "variant" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g., the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in this case an Fc variant, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution;" that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, -233E or 233E designates an insertion of glutamic acid after position 233 and before position 234. Additionally, -233ADE or A233ADE designates an insertion of AlaAsp-Glu after position 233 and before position 234.

By "amino acid deletion" or "deletion" as used herein is meant the removal of an amino acid sequence at a particular position in a parent polypeptide sequence. For example, E233- or E233 #, E233( ) or E233del designates a deletion of glutamic acid at position 233. Additionally, EDA233- or EDA233 #designates a deletion of the sequence GluAspAla that begins at position 233.

By "variant protein" or "protein variant", or "variant" as used herein is meant a protein that differs from that of a parent protein by virtue of at least one amino acid modification. The protein variant has at least one amino acid modification compared to the parent protein, yet not so many that the variant protein will not align with the parental protein using an alignment program such as that described below. In general, variant proteins (such as variant Fc domains, etc., outlined herein, are generally at least 75, 80, 85, 90, 91, 92, 93, 94, 95, 96, 97, 98 or 99% identical to the parent protein, using the alignment programs described below, such as BLAST.

"Variant" as used herein also refers to particular amino acid modifications that confer particular function (e.g., a "heterodimerization variant," "pI variant," "ablation variant," etc.).

As described below, in some embodiments the parent polypeptide, for example an Fc parent polypeptide, is a human wild type sequence, such as the heavy constant domain or Fc region from IgG1, IgG2, IgG3 or IgG4, although human sequences with variants can also serve as "parent polypeptides", for example the IgG1/2 hybrid of US Publication 2006/0134105 can be included. The protein variant sequence herein will preferably possess at least about 80% identity with a parent protein sequence, and most preferably at least about 90% identity, more preferably at least about 95-98-99% identity. Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain as compared to an Fc domain of human IgG1, IgG2 or IgG4.

"Fc variant" or "variant Fc" as used herein is meant a protein comprising an amino acid modification in an Fc domain. The modification can be an addition, deletion, or substitution. The Fc variants are defined according to the amino acid modifications that compose them. Thus, for example, N434S or 434S is an Fc variant with the substitution for seine at position 434 relative to the parent Fc polypeptide, wherein the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, 428L/434S is the same Fc variant as 434S/428L, and so on. For all positions discussed herein that relate to antibodies or derivatives and fragments thereof (e.g., Fc domains), unless otherwise noted, amino acid position numbering is according to the EU index. The "EU index" or "EU index as in Kabat" or "EU numbering" scheme refers to the numbering of the EU antibody (Edelman et al., 1969, Proc Natl Acad Sci USA 63:78-85, hereby entirely incorporated by reference). The modification can be an addition, deletion, or substitution.

In general, variant Fc domains have at least about 80, 85, 90, 95, 97, 98 or 99 percent identity to the corresponding parental human IgG Fc domain (using the identity algorithms discussed below, with one embodiment utilizing the BLAST algorithm as is known in the art, using default parameters). Alternatively, the variant Fc domains can have from 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental Fc domain. Alternatively, the variant Fc domains can have up to 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental Fc domain. Additionally, as discussed herein, the variant Fc domains described herein still retain the ability to form a dimer with another Fc domain as measured using known techniques as described herein, such as non-denaturing gel electrophoresis.

By "protein" as used herein is meant at least two covalently attached amino acids, which includes proteins, polypeptides, oligopeptides and peptides. In addition, polypeptides that make up the antibodies of the invention may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Asparagine 297 (also referred to as Asn297 or N297) is a residue at position 297 in the human antibody IgG1.

By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification.

By "non-naturally occurring modification" as used herein is meant an amino acid modification that is not isotypic. For example, because none of the human IgGs comprise a serine at position 434, the substitution 434S in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "IgG Fc ligand" as used herein is meant a molecule, preferably a polypeptide, from any organism that binds to the Fc region of an IgG antibody to form an Fc/Fc ligand complex. Fc ligands include but are not limited to FcγRIs, FcγRIIs, FcγRIIIs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. A variety of FcRn variants used to increase binding to the FcRn receptor, and in some cases, to increase serum half-life. An "FcRn variant" is an amino acid modification that contributes to increased binding to the FcRn receptor, and suitable FcRn variants are shown below.

By "parent polypeptide" as used herein is meant a starting polypeptide that is subsequently modified to generate a variant. The parent polypeptide may be a naturally occurring polypeptide, or a variant or engineered version of a naturally occurring polypeptide. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below. In this context, a "parent Fc domain" will be relative to the recited variant; thus, a "variant human IgG1 Fc domain" is compared to the parent Fc domain of human IgG1, a "variant human IgG4 Fc domain" is compared to the parent Fc domain human IgG4, etc.

By "position" as used herein is meant a location in the sequence of a protein. Positions may be numbered sequentially, or according to an established format, for example the EU index for numbering of antibody domains (e.g., a CH1, CH2, CH3 or hinge domain).

By "target antigen" as used herein is meant the molecule that is bound specifically by the antigen binding domain comprising the variable regions of a given antibody.

By "strandedness" in the context of the monomers of the heterodimeric antibodies of the invention herein is meant that, similar to the two strands of DNA that "match", heterodimerization variants are incorporated into each monomer so as to preserve the ability to "match" to form heterodimers. For example, if some pI variants are engineered into monomer A (e.g., making the pI higher) then steric variants that are "charge pairs" that can be utilized as well do not interfere with the pI variants, e.g., the charge variants that make a pI higher are put on the same "strand" or "monomer" to preserve both functionalities. Similarly, for "skew" variants that come in pairs of a set as more fully outlined below, the skilled artisan will consider pI in deciding into which strand or monomer one set of the pair will go, such that pI separation is maximized using the pI of the skews as well.

By "target cell" as used herein is meant a cell that expresses a target antigen.

By "host cell" in the context of producing a bispecific antibody according to the invention herein is meant a cell that contains the exogeneous nucleic acids encoding the components of the bispecific antibody and is capable of expressing the bispecific antibody under suitable conditions. Suitable host cells are discussed below.

By "wild type" or "WT" herein is meant an amino acid sequence or a nucleotide sequence that is found in nature, including allelic variations. A WT protein has an amino acid sequence or a nucleotide sequence that has not been intentionally modified.

Provided herein are a number of antibody domains (e.g., Fc domains) that have sequence identity to human antibody domains. Sequence identity between two similar sequences (e.g., antibody variable domains) can be measured by algorithms such as that of Smith, T. F. & Waterman, M. S. (1981) "Comparison Of Biosequences," Adv. Appl. Math. 2:482 [local homology algorithm]; Needleman, S. B. & Wunsch, CD. (1970) "A General Method Applicable To The Search For Similarities In The Amino Acid Sequence Of Two Proteins," J. Mol. Biol. 48:443 [homology alignment algorithm], Pearson, W. R. & Lipman, D. J. (1988) "Improved Tools For Biological Sequence Comparison," Proc. Natl. Acad. Sci. (U.S.A.) 85:2444 [search for similarity method]; or Altschul, S. F. et al, (1990) "Basic Local Alignment Search Tool," J. Mol. Biol. 215:403-10, the "BLAST" algorithm, see https://blast.ncbi.nlm.nih.gov/Blast.cgi. When using any of the aforementioned algorithms, the default parameters (for Window length, gap penalty, etc.) are used. In one embodiment, sequence identity is done using the BLAST algorithm, using default parameters The antibodies of the present invention are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities. "Recombinant" means the antibodies are generated using recombinant nucleic acid techniques in exogenous host cells, and they can be isolated as well.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction. Binding affinity is generally measured using a Biacore, SPR or BLI assay.

IV. Anti-CD28× Anti-PSMA Antibodies

In one aspect, provided herein are novel anti-CD28× anti-PSMA antibodies In some embodiments, the anti-CD28× anti-PSMA antibodies described herein are capable of agonistically binding to CD28 costimulatory molecules on T cells and PSMA on tumor cells. Such antibodies selectively enhance anti-tumor activity at PSMA-associated tumor sites while minimizing peripheral toxicity. The subject antibodies provided herein are particularly useful in combination with other anti-cancer therapies, including, for example, multivalent antibodies for the treatment of prostate cancers.

The anti-CD28× anti-PSMA antibodies are multivalent and include at least two antigen binding domains (ABDs), wherein at least one antigen binding domain is a CD28 binding domain and at least one antigen binding domain is a PSMA binding domain. Any suitable CD28 binding domain and PSMA binding domain can be included in the subject anti-CD28× anti-PSMA antibodies, including, for example, the CD28 binding domains and PSMA binding domains provided herein.

The antigen binding domains provided herein generally include a variable heavy domain (VH) having VH-CDR1, VH-CDR-2, and VH-CDR-3; and a variable light domain (VL), and a variable light domain (VL) having VL-CDR1, VL-CDR-2, and VL-CDR-3.

In addition, as discussed above, the numbering used in the sequence listing and figures for the identification of the CDRs is Kabat, however, different numbering can be used, which will change the amino acid sequences of the CDRs as shown in Table 2.

For all of the variable heavy and light domains listed herein, further variants can be made. As outlined herein, in some embodiments the set of 6 CDRs can have from 0, 1, 2, 3, 4 or 5 amino acid modifications (with amino acid substitutions finding particular use), as well as changes in the framework regions of the variable heavy and light domains, as long as the frameworks (excluding the CDRs) retain at least about 80, 85 or 90% identity to a human germline sequence selected from those listed in FIG. 1 of U.S. Pat. No. 7,657,380, which Figure and Legend is incorporated by reference in its entirety herein. Thus, for example, the identical CDRs as described herein can be combined with different framework sequences from human germline sequences, as long as the framework regions retain at least 80, 85 90, 95 or 99% identity to a human germline sequence selected from those listed in FIG. 1 of U.S. Pat. No. 7,657,380. Alternatively, the CDRs can have amino acid modifications (e.g., from 1, 2, 3, 4 or 5 amino acid modifications in the set of CDRs (that is, the CDRs can be modified as long as the total number of changes in the set of 6 CDRs is less than 6 amino acid modifications, with any combination of CDRs being changed; e.g., there may be one change in vlCDR1, two in vhCDR2, none in vhCDR3, etc.)), as well as having framework region changes, as long as the framework regions retain at least 80, 85 90, 95 or 99% identity to a human germline sequence selected from those listed in FIG. 1 of U.S. Pat. No. 7,657,380.

As will be appreciated by those in the art, any set of 6 CDRs or VH and VL domains can be in the scFv format or in the Fab format, which is then added to the heavy and light constant domains, where the heavy constant domains comprise variants (including within the CH1 domain as well as the Fc domain).

In addition, in embodiments wherein the subject antibody includes an scFv, the scFv can be in an orientation from N- to C-terminus of VH-scFv linker-VL or VL-scFv linker-VH. In some formats, one or more of the ABDs generally is a Fab that includes a VH domain on one protein chain (generally as a component of a heavy chain) and a VL on another protein chain (generally as a component of a light chain). Exemplary scFv linkers for use in the subject antibodies are depicted in FIGS. 6A-6B.

Useful CD28 binding domains and PSMA binding domains that can be included in the subject anti-CD28× anti-PSMA antibodies are further detailed herein.

In some embodiments, the anti-CD28× anti-PSMA antibody is a bispecific antibody. In some embodiments, the anti-CD28× anti-PSMA antibody is a bivalent antibody. In some embodiments, the anti-CD28× anti-PSMA antibody is a trivalent antibody. In some embodiments, the anti-CD28× anti-PSMA antibody is a bispecific, bivalent antibody. In some embodiments, the anti-CD28× anti-PSMA antibodies include one CD28 binding domain and one PSMA binding domain. In exemplary embodiments, the anti-CD28× anti-PSMA antibody is a bispecific, trivalent antibody. In some embodiments, the anti-CD28× anti-PSMA antibodies include one CD28 binding domain and two PSMA binding domains.

The anti-CD28× anti-PSMA antibodies provided herein can be in any useful format, including, including, for example, canonical immunoglobulin, as well as the "1+1 Fab-scFv-Fc," "2+1 Fab$_2$-scFv-Fc," described herein (FIGS. 24A-24M). Additional useful formats include, but are not limited to: "1+1 common light chain," and "2+1 common light chain," "mAb-Fv," "mAb-scFv," "central-Fv", "one armed scFv-mAb," "scFv-mAb," "dual scFv," and "trident" formats provided herein (see, e.g., FIGS. 24A-24M). See also, US20180127501A1, which is incorporated by reference herein, particularly in pertinent part relating to antibody formats (see, e.g., FIG. 2). In some embodiments, the anti-CD28× anti-PSMA antibodies are heterodimeric bispecific antibodies that include variant Fc domains having any of the heterodimerization skew variants, pI variants and/or ablation variants described herein. See, e.g. FIG. 8.

Note that unless specified herein, the order of the antigen list in the name does not confer structure; that is an anti-PSMA× anti-CD28 1+1 Fab-scFv-Fc antibody can have the scFv bind to PSMA or CD28, although in some cases, the order specifies structure as indicated.

The anti-CD28× anti-PSMA antibodies provided herein further include different antibody domains. As described herein and known in the art, the antibodies described herein include different domains within the heavy and light chains, which can be overlapping as well. These domains include, but are not limited to, the Fc domain, the CH1 domain, the CH2 domain, the CH3 domain, the hinge domain, the heavy constant domain (CH1-hinge-Fc domain or CH1-hinge-CH2-CH3), the variable heavy domain, the variable light domain, the light constant domain, Fab domains and scFv domains.

As shown herein, there are a number of suitable linkers (for use as either domain linkers or scFv linkers) that can be used to covalently attach the recited domains (e.g., scFvs, Fabs, Fc domains, VH domains, VL domains, etc.), including traditional peptide bonds, generated by recombinant techniques. Exemplary linkers to attach domains of the subject antibody to each other are depicted in FIG. 7. In some embodiments, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used, with from about 5 to about 10 amino acids finding use in some embodiments. Useful linkers include glycine-serine polymers, including for example (GS)n, (GSGGS)n (SEQ ID NO: 1045), (GGGGS)n (SEQ ID NO: 1046), and (GGGS)n (SEQ ID NO: 1047), where n is an integer of at least one (and generally from 3 to 4), glycine-alanine polymers, alanine-serine polymers, and other flexible linkers. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers.

Other linker sequences may include any sequence of any length of CL/CH1 domain but not all residues of CL/CH1 domain; for example the first 5-12 amino acid residues of the CL/CH1 domains. Linkers can be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ Linker sequences may also be derived from other proteins such as Ig-like proteins (e.g., TCR, FcR, KIR), hinge region-derived sequences, and other natural sequences from other proteins.

In some embodiments, the linker is a "domain linker", used to link any two domains as outlined herein together. For example, in the 2+1 Fab2-scFv-Fc format, there may be a domain linker that attaches the C-terminus of the CH1 domain of the Fab to the N-terminus of the scFv, with another optional domain linker attaching the C-terminus of the scFv to the CH2 domain (although in many embodiments the hinge is used as this domain linker). While any suitable linker can be used, many embodiments utilize a glycine-serine polymer as the domain linker, including for example (GS)n, (GSGGS)n (SEQ ID NO: 1045), (GGGGS)n (SEQ ID NO: 1046), and (GGGS)n (SEQ ID NO: 1047), where n is an integer of at least one (and generally from 3 to 4 to 5) as well as any peptide sequence that allows for recombinant attachment of the two domains with sufficient length and flexibility to allow each domain to retain its biological function. In some cases, and with attention being paid to "strandedness", as outlined below, charged domain linkers, as used in some embodiments of scFv linkers can be used. Exemplary useful domain linkers are depicted in FIG. 7.

In some embodiments, the linker is a scFv linker that is used to covalently attach the VH and VL domains as discussed herein. In many cases, the scFv linker is a charged scFv linker, a number of which are shown in FIGS. 6A-6B. Accordingly, provided herein are charged scFv linkers, to facilitate the separation in pI between a first and a second monomer. That is, by incorporating a charged scFv linker, either positive or negative (or both, in the case of scaffolds that use scFvs on different monomers), this allows the monomer comprising the charged linker to alter the pI without making further changes in the Fc domains. These charged linkers can be substituted into any scFv containing standard linkers. Again, as will be appreciated by those in the art, charged scFv linkers are used on the correct "strand" or monomer, according to the desired changes in pI. For example, as discussed herein, to make 1+1 Fab-scFv-Fc format heterodimeric antibody, the original pI of the Fv region for each of the desired antigen binding domains are calculated, and one is chosen to make an scFv, and depending on the pI, either positive or negative linkers are chosen. Charged domain linkers can also be used to increase the pI separation of the monomers of the invention as well, and thus those included in FIGS. 6A-6B can be used in any embodiment herein where a linker is utilized. In some embodiments, the scFv is a "stapled" scFv that includes a "staple linker." "Stapled" scFvs that exhibit improved stability and/or reduced aggregation are further described in detail herein. Exemplary staple linkers that are useful for inclusion in such "stapled" scFvs are provided in FIGS. 6A-6B.

In some embodiments, wherein an scFv is included in the anti-CD28× anti-PSMA antibody (e.g., the 1+1 Fab-scFv-Fc format or 2+1 Fab2-scFv-Fc format antibody), the scFv includes "staple" modifications that improve scFv stability and/or reduces aggregation. In exemplary embodiments, such "stapled" scFvs include: a) a first disulfide bond between a structurally conserved surface exposed VH cysteine and a first scFv linker cysteine; b) a second disulfide bond between a structurally conserved surface exposed VL cysteine and a second scFv linker cysteine; or c) the first disulfide bond between the structurally conserved surface exposed VH cysteine and the first scFv linker cysteine and the second disulfide bond between the structurally considered surface exposed VL cysteine and the second scFv linker cysteine. Exemplary scFv "staple linkers" for inclusion in "stapled" scFvs are provided in FIGS. 6A-6B. Methods for making "stapled" scFvs are described in WO 2021/030657, which is incorporated by reference in its entirety, including pertinent parts relating to methods for making "stapled" scFvs, and "stapled" scFv compositions.

Exemplary subject anti-CD28× anti-PSMA antibodies are depicted, for example, in FIGS. 29A-29RR and 30A-30L. During the cell culture production of the anti-CD28× anti-PSMA antibodies provided herein, the C-terminal lysine residue or C-terminal lysine and glycine residues may be cleaved from the heavy chain monomers, thereby leading to variants with C-terminal "clipping." See, e.g., Jiang et al., Journal of Pharmaceutical Sciences 105:2066-2072 (2016). Thus, in some embodiments provided herein, the anti-CD28× anti-PSMA antibody is a variant of one of the anti-CD28× anti-PSMA antibodies depicted in FIGS. 29A-29RR and 30A-30L that includes a deletion of a C-terminal lysine (-K) residues or lysine and glycine (-GK) residues in "chain 1" and/or "chain 2." In some embodiments, the deletion is G446del and/or K447del. In some embodiments, the anti-CD28× anti-PSMA antibody is engineered to include a G446del and/or K447del modification in one or both Fc domains of a anti-CD28× anti-PSMA antibody described herein. In some embodiments, the anti-CD28× anti-PSMA antibody includes a naturally occurring G446del and/or K447del modification in one or both Fc domains as compared to an anti-CD28× anti-PSMA antibody provided herein.

Aspects of the anti-CD28× anti-PSMA antibodies are further described in detail below.

A. CD28 Binding Domains

The anti-CD28× anti-PSMA antibodies provided herein include at least one CD28 binding domain. Any suitable CD28 binding domain can be included in the anti-CD28× anti-PSMA antibodies provided herein. In exemplary embodiments, the CD28 binding domain is an agonistic CD28 ABDs that advantageously provide T cell costimulatory activity.

As will be appreciated by those in the art, suitable CD28 binding domains can comprise a set of 6 CDRs as depicted in the figures, either as they are underlined or, in the case where a different numbering scheme is used, as described herein and as shown in Table 2, as the CDRs that are identified using other alignments within the variable heavy (VH) domain and variable light domain (VL) sequences of those depicted in FIGS. 15 18C, 21A-21H and 22. Suitable CD28 ABDs can also include the entire VH and VL sequences as depicted in these sequences and figures, used as scFvs or as Fabs.

In one embodiment, the CD28 antigen binding domain includes the 6 CDRs (i.e., vhCDR1-3 and vlCDR1-3) of any of the CD28 binding domains described herein, including, but not limited to those depicted in FIGS. 1518C and 21A-21H. In some embodiments, the CD28 ABD that binds human CD28 is one of the following CD28 ABDs: 1A7[CD28]_H1L1, 1A7[CD28]_H1.1_L1, 1A7[CD28]_H1_L1.71, 1A7[CD28]_H1.1_L1.71, 1A7[CD28]H1.14_L1, 1A7[CD28]_H1.14_L1.71, 1A7[CD28]_H1sp_L1sp, 1A7[CD28]_H1.1sp_L1sp, 1A7[CD28]H1sp_L1.71sp, 1A7[CD28]_H1.1sp_L1.71sp, 1A7[CD28]_H1.14sp_L1sp, 1A7[CD28]_H1.14sp_L1.71sp, CD28.3[CD28]_H0L0, hCD28.3[CD28]_H1L1, 5.11A1[CD28]_H0L0, TGN1412_H1L1, 341VL34[CD28]_H1L1, 341VL36[CD28]_H1L1, 281VL4[CD28]_H1L1, HuTN228[CD28]_H1L1, PV1[CD28]H0L0, m9.3[CD28]_H0L0, hu9.3[CD28]_H1L1, 9G2[CD28]_H0L0, 9G2[CD28]_H1L1, 2F10A3.140[CD28]_H1L1, and TN228[CD28]_H4L2 (FIGS. 1518C, 21A-21H, and 69A-69C). In exemplary embodiments, the CD28 ABD is CD28 ABDs: 1A7[CD28]H1L1, 1A7[CD28]_H1.14L1.

In addition to the parental CDR sets disclosed in the figures and sequence listing that form an ABD to CD28, provided herein are variant CD28 ABDS having CDRs that include at least one modification of the CD28 ABD CDRs disclosed herein (e.g., (FIGS. 1518C, and 21A-21H and the sequence listing). In one embodiment, the CD28 ABD of the subject anti-CD28× anti-PSMA antibody includes a set of 6 CDRs with 1, 2, 3, 4, 5, 6, 7, 8, 9, 10 amino acid modifications as compared to the 6 CDRs of a CD28 ABD as described herein, including the figures and sequence listing. In exemplary embodiments, the CD28 ABD of the subject anti-CD28× anti-PSMA antibody includes a set of 6 CDRs with 1, 2, 3, 4, 5, 6, 7, 8, 9, 10 amino acid modifications as compared to the 6 CDRs of one of the following CD28 ABDs: 1A7[CD28]_H1L1, 1A7[CD28]_H1.1_L1, 1A7[CD28]_H1_L1.71, 1A7[CD28]_H1.1_L1.71, 1A7[CD28]H1.14_L1, 1A7[CD28]_H1.14_L1.71, 1A7[CD28]_H1sp_L1sp, 1A7[CD28]_H1.1sp_L1sp, 1A7[CD28]H1sp_L1.71sp, 1A7[CD28]_H1.1sp_L1.71sp, 1A7[CD28]_H1.14sp_L1sp, 1A7[CD28]_H1.14sp_L1.71sp, CD28.3[CD28]_H0L0, hCD28.3[CD28]_H1L1, 5.11A1[CD28]_H0L0, TGN1412_H1L1, 341VL34[CD28]_H1L1, 341VL36[CD28]_H1L1, 281VL4[CD28]_H1L1, HuTN228[CD28]_H1L1, PV1[CD28]H0L0, m9.3[CD28]_H0L0, hu9.3[CD28]_H1L1, 9G2[CD28]_H0L0, 9G2[CD28]_H1L1, 2F10A3.140[CD28]_H1L1, and TN228[CD28]_H4L2 (FIGS. 1518C, 21A-21H, and 69A-69C). In certain embodiments, the CD28 ABD of the subject anti-CD28× anti-PSMA antibody is capable of binding CD28 antigen, as measured by at least one of a Biacore, surface plasmon resonance (SPR), flow cytometry, and/or BLI (biolayer interferometry, e.g., Octet assay) assay, with the latter finding particular use in many embodiments. In particular embodiments, the CD28 ABD is capable of binding human CD28 antigen (see FIGS. 1A-1B).

In some embodiments, the CD28 ABD of the subject anti-CD28× anti-PSMA antibody includes 6 CDRs that are at least 90, 95, 97, 98 or 99% identical to the 6 CDRs of a CD28 ABD as described herein, including the figures and sequence listing. In exemplary embodiments, the CD28 ABD of the subject anti-CD28× anti-PSMA antibody includes 6 CDRs that are at least 90, 95, 97, 98 or 99% identical to the 6 CDRs of one of the following CD28 ABDs: 1A7[CD28]_H1L1, 1A7[CD28]_H1.1_L1, 1A7[CD28]_H1_L1.71, 1A7[CD28]_H1.1_L1.71, 1A7[CD28]H1.14_L1, 1A7[CD28]_H1.14_L1.71, 1A7[CD28]

_H1sp_L1sp, 1A7[CD28]_H1.1sp_L1sp, 1A7[CD28]H1sp_L1.71sp, 1A7[CD28]_H1.1sp_L1.71sp, 1A7[CD28]_H1.14sp_L1sp, 1A7[CD28]_H1.14sp_L1.71sp, CD28.3[CD28]_H0L0, hCD28.3[CD28]_H1L1, 5.11A1[CD28]_H0L0, TGN1412_H1L1, 341VL34[CD28]_H1L1, 341VL36[CD28]_H1L1, 281VL4[CD28]_H1L1, HuTN228[CD28]_H1L1, PV1[CD28]H0L0, m9.3[CD28]_H0L0, hu9.3[CD28]_H1L1, 9G2[CD28]_H0L0, 9G2[CD28]_H1L1, 2F10A3.140[CD28]_H1L1, and TN228[CD28]_H4L2 (FIGS. 15-18C, 21A-21H, and 69A-69C). In certain embodiments, the CD28 ABD is capable of binding to the CD28, as measured by at least one of a Biacore, surface plasmon resonance (SPR), flow cytometry, and/or BLI (biolayer interferometry, e.g., Octet assay) assay, with the latter finding particular use in many embodiments. In particular embodiments, the CD28 ABD is capable of binding human CD28 antigen (see FIGS. 1A-1B).

In another exemplary embodiment, the CD28 ABD of the subject anti-CD28× anti-PSMA antibody includes the variable heavy (VH) domain and variable light (VL) domain of any one of the CD28 ABDs described herein, including the figures and sequence listing. In exemplary embodiments, the CD28 ABD is one of the following CD28 ABDs: 1A7[CD28]_H1L1, 1A7[CD28]_H1.1_L1, 1A7[CD28]_H1_L1.71, 1A7[CD28]_H1.1_L1.71, 1A7[CD28]_H1.14_L1, 1A7[CD28]_H1.14_L1.71, 1A7[CD28]_H1sp_L1sp, 1A7[CD28]_H1.1sp_L1sp, 1A7[CD28]H1sp_L1.71sp, 1A7[CD28]_H1.1sp_L1.71sp, 1A7[CD28]_H1.14sp_L1sp, 1A7[CD28]_H1.14sp_L1.71sp, CD28.3[CD28]_H0L0, hCD28.3[CD28]_H1L1, 5.11A1[CD28]_H0L0, TGN1412_H1L1, 341VL34[CD28]_H1L1, 341VL36[CD28]_H1L1, 281VL4[CD28]_H1L1, HuTN228[CD28]_H1L1, PV1[CD28]H0L0, m9.3[CD28]_H0L0, hu9.3[CD28]_H1L1, 9G2[CD28]_H0L0, 9G2[CD28]_H1L1, 2F10A3.140[CD28]_H1L1, and TN228[CD28]_H4L2 (FIGS. 15-18C, 21A-21H, and 69A-69C). In some embodiments, the CD28 ABD includes a VH/VL pair selected from the VHs and VLs depicted in FIGS. 67, 68, 70A-70F and 71A-71I, respectively.

In some embodiments, the anti-CD28× anti-PSMA antibody includes a CD28 ABD that includes a variable heavy domain and/or a variable light domain that are variants of a CD28 ABD VH and VL domain disclosed herein. In one embodiment, the variant VH domain and/or VL domain has from 1, 2, 3, 4, 5, 6, 7, 8, 9 or 10 amino acid changes from a VH and/or VL domain of a CD28 ABD described herein, including the figures and sequence listing. In exemplary embodiments, the variant VH domain and/or VL domain has from 1, 2, 3, 4, 5, 6, 7, 8, 9 or 10 amino acid changes from a VH and/or VL domain of one of the following CD28 ABDs: 1A7[CD28]_H1L1, 1A7[CD28]_H1.1_L1, 1A7[CD28]_H1_L1.71, 1A7[CD28]_H1.1_L1.71, 1A7[CD28]_H1.14_L1, 1A7[CD28]_H1.14_L1.71, 1A7[CD28]_H1sp_L1sp, 1A7[CD28]_H1.1sp_L1sp, 1A7[CD28]H1sp_L1.71sp, 1A7[CD28]_H1.1sp_L1.71sp, 1A7[CD28]_H1.14sp_L1sp, 1A7[CD28]_H1.14sp_L1.71sp, CD28.3[CD28]_H0L0, hCD28.3[CD28]_H1L1, 5.11A1[CD28]_H0L0, TGN1412_H1L1, 341VL34[CD28]_H1L1, 341VL36[CD28]_H1L1, 281VL4[CD28]_H1L1, HuTN228[CD28]_H1L1, PV1[CD28]H0L0, m9.3[CD28]_H0L0, hu9.3[CD28]_H1L1, 9G2[CD28]_H0L0, 9G2[CD28]_H1L1, 2F10A3.140[CD28]_H1L1, and TN228[CD28]_H4L2 (FIGS. 15-18C, 21A-21H, and 67-69C). In some embodiments, the changes are in a VH domain depicted in FIGS. 15-18C, 21A-21H, and 67-71I. In some embodiments, the changes are in a VL domain are depicted in 15-18C, 21A-21H, and 67-71I. In some embodiments, the changes are in a VH and VL domain are depicted in FIGS. 15-18C, 21A-21H, and 67-71I. In exemplary embodiments, the CD28 ABD is an scFv and the amino acid changes introduce cysteine residues in the VH and/or VL framework regions (FR1-FR4) to allow for "stapling" of the scFv, as described herein. See also WO 2021/030657, which is incorporated by reference in its entirety, including pertinent parts relating to methods for making "stapled" scFvs, and "stapled" scFv compositions. Exemplary "stapled" CD28 binding domains and VH/VL domains that can be included in the subject anti-CD28× anti-PSMA antibodies depicted herein are included in FIGS. 67-69C. In certain embodiments, the CD28 ABD of the anti-CD28× anti-PSMA antibody is capable of binding to CD28, as measured at least one of a Biacore, surface plasmon resonance (SPR), flow cytometry, and/or BLI (biolayer interferometry, e.g., Octet assay) assay, with the latter finding particular use in many embodiments. In particular embodiments, the CD28 ABD is capable of binding human CD28 antigen (see FIGS. 1A-1B).

In one embodiment, the variant VH and/or VL domain is at least 90, 95, 97, 98 or 99% identical to the VH and/or VL of a CD28 ABD as described herein, including the figures and sequence listing. In exemplary embodiments, the variant VH and/or VL domain is at least 90, 95, 97, 98 or 99% identical to the VH and/or VL of one of the following CD28 ABDs: 1A7[CD28]_H1L1, 1A7[CD28]H1.1_L1, 1A7[CD28]_H1_L1.71, 1A7[CD28]_H1.1_L1.71, 1A7[CD28]_H1.14_L1, 1A7[CD28]_H1.14_L1.71, 1A7[CD28]_H1sp_L1sp, 1A7[CD28]_H1.1sp_L1sp, 1A7[CD28]H1sp_L1.71sp, 1A7[CD28]_H1.1sp_L1.71sp, 1A7[CD28]_H1.14sp_L1sp, 1A7[CD28]_H1.14sp_L1.71sp, CD28.3[CD28]_H0L0, hCD28.3[CD28]_H1L1, 5.11A1[CD28]_H0L0, TGN1412_H1L1, 341VL34[CD28]_H1L1, 341VL36[CD28]_H1L1, 281VL4[CD28]_H1L1, HuTN228[CD28]_H1L1, PV1[CD28]H0L0, m9.3[CD28]_H0L0, hu9.3[CD28]_H1L1, 9G2[CD28]_H0L0, 9G2[CD28]_H1L1, 2F10A3.140[CD28]_H1L1, and TN228[CD28]_H4L2 (FIGS. 15-18C, 21A-21H, and 69A-69C). In some embodiments, the CD28 ABD includes a VH that is at least 90, 95, 97, 98 or 99% identical to VH domain depicted in FIGS. 15-18C, 21A-21H, and 67-71I. In some embodiments, the CD28 ABD includes a VL that is at least 90, 95, 97, 98 or 99% identical to VL domain depicted in FIGS. 15-18C, 21A-21H, and 67-71I. In some embodiments, the CD28 ABD includes a VH and a VL that is at least 90, 95, 97, 98 or 99% identical to a VH domain and a VL domain depicted in FIGS. 15-18C, 21A-21H, and 67-71I. In certain embodiments, the CD28 ABD is capable of binding to CD28, as measured by at least one of a Biacore, surface plasmon resonance (SPR), flow cytometry, and/or BLI (biolayer interferometry, e.g., Octet assay) assay, with the latter finding particular use in many embodiments. In particular embodiments, the CD28 ABD is capable of binding human CD28 antigen (see FIGS. 1A-1B).

In one embodiment, the CD28 antigen binding domain of the anti-CD28× anti-PSMA antibody includes a variable heavy domain (VH) having the vhCDR1-3 (i.e., vhCDR1-3) of 1A7_H1 (SEQ ID NO:39, FIG. 18A). In some embodiments, the CD28 antigen binding domain of the anti-CD28× anti-PSMA antibody further includes any of the CD28 binding domain variable light domains provided herein. In exemplary embodiments, the variable light domain is 1A7_L1.71 (SEQ ID NO:43, FIG. 18A) or a variant thereof. In certain embodiments, the CD28 ABD of the anti-CD28× anti-PSMA antibody is capable of binding CD28 antigen, as measured by at least one of a Biacore, surface plasmon resonance (SPR), flow cytometry, and/or BLI (biolayer interferometry, e.g., Octet assay) assay, with the latter finding particular use in many embodiments. In particular embodiments, the CD28 ABD of the anti-CD28× anti-PSMA antibody is capable of binding human CD28 antigen (see FIGS. 1A-1B). In exemplary embodiments, the anti-CD28× anti-PSMA antibody is a "1+1 Fab-scFv-Fc," "2+1 Fab2-scFv-Fc," or "2+1 mAb-scFv" antibody.

In one embodiment, the CD28 ABD of the anti-CD28× anti-PSMA antibody includes a variable heavy domain (VH) having vhCDR1-3s with 1, 2, 3, 4, 5, 6, 7, 8, 9, 10 amino acid modifications as compared to the vhCDR1-3 of 1A7_H1 (SEQ ID NO:39, FIG. 18A). In some embodiments, the CD28 antigen binding domain of the anti-CD28× anti-PSMA antibody further includes any of the CD28 binding domain variable light domains provided herein. In exemplary embodiments, the variable light domain is 1A7_L1.71 (SEQ ID NO:43, FIG. 18A) or a variant thereof. In certain embodiments, the CD28 ABD of the anti-CD28× anti-PSMA antibody is capable of binding CD28 antigen, as measured by at least one of a Biacore, surface plasmon resonance (SPR), flow cytometry, and/or BLI (biolayer interferometry, e.g., Octet assay) assay, with the latter finding particular use in many embodiments. In particular embodiments, the CD28 ABD of the anti-CD28× anti-PSMA antibody is capable of binding human CD28 antigen (see FIGS. 1A-1B). In particular embodiments, the CD28 ABD of the anti-CD28× anti-PSMA antibody is capable of binding human CD28 antigen (see FIGS. 1A-1B). In exemplary embodiments, the anti-CD28× anti-PSMA antibody is a "1+1 Fab-scFv-Fc," "2+1 Fab2-scFv-Fc," or "2+1 mAb-scFv" antibody.

In some embodiments, the CD28 ABD of the anti-CD28× anti-PSMA antibody includes a variable heavy domain (VH) having vhCDR1-3s that are at least 90, 95, 97, 98 or 99% identical to the vhCDR1-3 of 1A7_H1 (SEQ ID NO:39, FIG. 18A). In some embodiments, the CD28 antigen binding domain of the anti-CD28× anti-PSMA antibody further includes any of the CD28 binding domain variable light domains provided herein. In exemplary embodiments, the variable light domain is 1A7_L1.71 (SEQ ID NO:43, FIG. 18A) or a variant thereof. In certain embodiments, the CD28 ABD of the anti-CD28× anti-PSMA antibody is capable of binding to the CD28, as measured by at least one of a Biacore, surface plasmon resonance (SPR), flow cytometry, and/or BLI (biolayer interferometry, e.g., Octet assay) assay, with the latter finding particular use in many embodiments. In particular embodiments, the CD28 ABD of the anti-CD28× anti-PSMA antibody is capable of binding human CD28 antigen (see FIGS. 1A-1B). In exemplary embodiments, the anti-CD28× anti-PSMA antibody is a "1+1 Fab-scFv-Fc," "2+1 Fab$_2$-scFv-Fc," or "2+1 mAb-scFv" antibody.

In exemplary embodiments, the CD28 binding domain of the anti-CD28× anti-PSMA antibody is an scFv. In some embodiments, the anti-CD28 scFv includes one of the CD28 ABD VH and/or VLs described herein or a variant thereof. In some embodiments, the anti-CD28 scFv of the anti-CD28× anti-PSMA antibody includes one or more "staple" modifications that improves the stability or reduce aggregation of the scFv. In some embodiments, the anti-CD28× anti-PSMA antibody includes a "stapled" scFv, wherein the stapled scFv includes: a) a first disulfide bond between a structurally conserved surface exposed VH cysteine and a first scFv linker cysteine; b) a second disulfide bond between a structurally conserved surface exposed VL cysteine and a second scFv linker cysteine; or c) the first disulfide bond between the structurally conserved surface exposed VH cysteine and the first scFv linker cysteine and the second disulfide bond between the structurally considered surface exposed VL cysteine and the second scFv linker cysteine. In exemplary embodiments, the "stapled" scFv is a variant of one of the CD28 ABDs described herein, wherein the variant CD28 ABD includes: a) an amino acid substitution to introduce a surface exposed VH cysteine; b) an amino acid substitution to introduce a surface exposed VL cysteine; or c) amino acid substitutions to introduce both a surface exposed VH cysteine and a surface exposed VH cysteine. In some embodiments, the amino acid change(s) is in the VH and/or VL framework regions (FR1, FR2, FR3, and/or FR4). Exemplary scFv "staple linkers" for inclusion in "stapled" scFvs are provided in FIGS. 6A-6B. Methods for making "stapled" scFvs are described, for example, in WO 2021/030657, which is incorporated by reference in its entirety, including pertinent parts relating to methods for making "stapled" scFvs, and "stapled" scFv compositions. In exemplary embodiments, the anti-CD28× anti-PSMA antibody includes a "stapled" scFv that includes a modified VH and VL of any of the following CD28 ABDs: 1A7[CD28]_H1L1, 1A7[CD28]_H1.1_L1, 1A7[CD28]_H1_L1.71, 1A7[CD28]_H1.1_L1.71, 1A7[CD28]H1.14_L1, 1A7[CD28]_H1.14_L1.71, CD28.3[CD28]_H0L0, hCD28.3[CD28]_H1L1, 5.11A1[CD28]_H0L0, TGN1412_H1L1, 341VL34[CD28]_H1L1, 341VL36[CD28]_H1L1, 281VL4[CD28]_H1L1, HuTN228[CD28]_H1L1, PV1[CD28]H0L0, m9.3[CD28]_H0L0, hu9.3[CD28]_H1L1, 9G2[CD28]_H0L0, 9G2[CD28]_H1L1, 2F10A3.140[CD28]_H1L1, and TN228[CD28]_H4L2 (FIGS. 15-18C, and 21A-21H). Exemplary "stapled" CD28 binding domains include, but are not limited to: 1A7[CD28]H1sp_L1sp, 1A7[CD28]_H1.1sp_L1sp, 1A7[CD28]_H1sp_L1.71sp, 1A7[CD28]_H1.1sp_L1.71sp, 1A7[CD28]_H1.14sp_L1sp, and 1A7[CD28]_H1.14sp_L1.71sp (FIGS. 70A-70F).

In some embodiments, the anti-CD28× anti-PSMA antibody includes a CD28 binding domain that includes a VH and VL selected from the following:
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:9; and
  (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:13; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:31; and
  (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:35; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:39; and
  (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:43; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:47; and
  (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:51; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:55; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:59; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:63; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:67; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:86; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:90; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:94; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:98; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 102; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:106; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:110; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:114; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:118; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:122; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 126; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:130; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 134; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:138; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 142; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:146; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 150; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:154; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 158; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:162; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 166; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:170; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 174; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:178; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:182; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:186; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 190; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:194; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 198; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:202; or
- (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:380; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:384; or
- (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:388; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:392; or
- (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:396; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:400; or
- (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:404; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:408; or
- (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:412; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:416; or
- (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:420; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:424.

In some embodiments, the anti-CD28× anti-PSMA antibody includes a CD28 binding domain that includes a VH and VL selected from the following:
- (i) a VH comprising a vhCDR1 having an amino acid sequence of SEQ ID NO:10; a vhCDR2 having an amino acid sequence of SEQ ID NO:11; and a vhCDR3 having an amino acid sequence of SEQ ID NO: 12; and (ii) a VL comprising a vlCDR1 having an amino acid sequence of SEQ ID NO: 14, a vlCDR2 having an amino acid sequence of SEQ ID NO: 15, and a vlCDR3 having an amino acid sequence of SEQ ID NO:16; or
- (i) a VH comprising a vhCDR1 having an amino acid sequence of SEQ ID NO:32; a vhCDR2 having an amino acid sequence of SEQ ID NO:33; and a vhCDR3 having an amino acid sequence of SEQ ID NO:34; and (ii) a VL comprising a vlCDR1 having an amino acid sequence of SEQ ID NO: 36, a vlCDR2 having an amino acid sequence of SEQ ID NO: 37, and a vlCDR3 having an amino acid sequence of SEQ ID NO:38; or
- i) a VH comprising a vhCDR1 having an amino acid sequence of SEQ ID NO:40; a vhCDR2 having an amino acid sequence of SEQ ID NO:41; and a vhCDR3 having an amino acid sequence of SEQ ID NO:42; and (ii) a VL comprising a vlCDR1 having an amino acid sequence of SEQ ID NO:44, a vlCDR2 having an amino acid sequence of SEQ ID NO: 45, and a vlCDR3 having an amino acid sequence of SEQ ID NO:46; or
- i) a VH comprising a vhCDR1 having an amino acid sequence of SEQ ID NO:48; a vhCDR2 having an amino acid sequence of SEQ ID NO:49; and a vhCDR3 having an amino acid sequence of SEQ ID NO:50; and (ii) a VL comprising a vlCDR1 having an amino acid sequence of SEQ ID NO:52, a vlCDR2 having an amino acid sequence of SEQ ID NO: 53, and a vlCDR3 having an amino acid sequence of SEQ ID NO:54; or
- i) a VH comprising a vhCDR1 having an amino acid sequence of SEQ ID NO:56; a vhCDR2 having an amino acid sequence of SEQ ID NO:57; and a vhCDR3 having an amino acid sequence of SEQ ID NO:58; and (ii) a VL comprising a vlCDR1 having an amino acid sequence of SEQ ID NO:60, a vlCDR2 having an amino acid sequence of SEQ ID NO:61, and a vlCDR3 having an amino acid sequence of SEQ ID NO:62; or
- i) a VH comprising a vhCDR1 having an amino acid sequence of SEQ ID NO:64; a vhCDR2 having an amino acid sequence of SEQ ID NO:65; and a vhCDR3 having an amino acid sequence of SEQ ID NO:66; and (ii) a VL comprising a vlCDR1 having an amino acid sequence of SEQ ID NO:68, a vlCDR2 having an amino acid sequence of SEQ ID NO:69, and a vlCDR3 having an amino acid sequence of SEQ ID NO:70; or
- i) a VH comprising a vhCDR1 having an amino acid sequence of SEQ ID NO:87; a vhCDR2 having an amino acid sequence of SEQ ID NO:88; and a vhCDR3 having an amino acid sequence of SEQ ID NO:89; and (ii) a VL comprising a vlCDR1 having an amino acid sequence of SEQ ID NO:91, a vlCDR2 having an amino acid sequence of SEQ ID NO:92, and a vlCDR3 having an amino acid sequence of SEQ ID NO:93; or
- i) a VH comprising a vhCDR1 having an amino acid sequence of SEQ ID NO:95; a vhCDR2 having an amino acid sequence of SEQ ID NO:96; and a vhCDR3 having an amino acid sequence of SEQ ID NO:97; and (ii) a VL comprising a vlCDR1 having an amino acid sequence of SEQ ID NO:99, a vlCDR2 having an amino acid sequence of SEQ ID NO:100, and a vlCDR3 having an amino acid sequence of SEQ ID NO:101; or
- i) a VH comprising a vhCDR1 having an amino acid sequence of SEQ ID NO:103; a vhCDR2 having an amino acid sequence of SEQ ID NO:104; and a vhCDR3 having an amino acid sequence of SEQ ID NO:105; and (ii) a VL comprising a vlCDR1 having an amino acid sequence of SEQ ID NO: 107, a vlCDR2 having an amino acid sequence of SEQ ID NO:108, and a vlCDR3 having an amino acid sequence of SEQ ID NO:109; or
- i) a VH comprising a vhCDR1 having an amino acid sequence of SEQ ID NO:111; a vhCDR2 having an amino acid sequence of SEQ ID NO:112; and a vhCDR3 having an amino acid sequence of SEQ ID NO:113; and (ii) a VL comprising a vlCDR1 having an amino acid sequence of SEQ ID NO: 115, a vlCDR2 having an amino acid sequence of SEQ ID NO:116, and a vlCDR3 having an amino acid sequence of SEQ ID NO:117; or i) a VH comprising a vhCDR1 having an amino acid sequence of SEQ ID NO:119; a vhCDR2 having an amino acid sequence of SEQ ID NO:120; and a vhCDR3 having an amino acid sequence of SEQ ID NO:121; and (ii) a VL comprising a vlCDR1 having an amino acid sequence of SEQ ID NO: 123, a vlCDR2 having an amino acid sequence of SEQ ID NO:124, and a vlCDR3 having an amino acid sequence of SEQ ID NO:125; or i) a VH comprising a vhCDR1 having an amino acid sequence of SEQ ID NO:127; a vhCDR2 having an amino acid sequence of SEQ ID NO:128; and a vhCDR3 having an amino acid sequence of SEQ ID NO:129; and (ii) a VL comprising a vlCDR1 having an amino acid sequence of SEQ ID NO:131, a vlCDR2 having an amino acid sequence of SEQ ID NO:132, and a vlCDR3 having an amino acid sequence of SEQ ID NO:133; or i) a VH comprising a vhCDR1 having an amino acid sequence of SEQ ID NO:135; a vhCDR2 having an amino acid sequence of SEQ ID NO:136; and a vhCDR3 having an amino acid sequence of SEQ ID NO:137; and (ii) a VL comprising a vlCDR1 having an amino acid sequence of SEQ ID NO: 139, a vlCDR2 having an amino acid sequence of SEQ ID NO:140, and a vlCDR3 having an amino acid sequence of SEQ ID NO:141; or i) a VH comprising a vhCDR1 having an amino acid sequence of SEQ ID NO:143; a vhCDR2 having an amino acid sequence of SEQ ID NO:144; and a vhCDR3 having an amino acid sequence of SEQ ID NO:115; and (ii) a VL comprising a vlCDR1 having an amino acid sequence of SEQ ID NO: 147, a vlCDR2 having an amino acid sequence of SEQ ID NO:149, and a vlCDR3 having an amino acid sequence of SEQ ID NO:149; or i) a VH comprising a vhCDR1 having an amino acid sequence of SEQ ID NO:151; a vhCDR2 having an amino acid sequence of SEQ ID NO:152; and a vhCDR3 having an amino acid sequence of SEQ ID NO:153; and (ii) a VL comprising a vlCDR1 having an amino acid sequence of SEQ ID NO: 155, a vlCDR2 having an amino acid sequence of SEQ ID NO:156, and a vlCDR3 having an amino acid sequence of SEQ ID NO:157; or i) a VH comprising a vhCDR1 having an amino acid sequence of SEQ ID NO:159; a vhCDR2 having an amino acid sequence of SEQ ID NO:160; and a vhCDR3 having an amino acid sequence of SEQ ID NO:161; and (ii) a VL comprising a vlCDR1 having an amino acid sequence of SEQ ID NO:163, a vlCDR2 having an amino acid sequence of SEQ ID NO:164, and a vlCDR3 having an amino acid sequence of SEQ ID NO:165; or i) a VH comprising a vhCDR1 having an amino acid sequence of SEQ ID NO:167; a vhCDR2 having an amino acid sequence of SEQ ID NO:168; and a vhCDR3 having an amino acid sequence of SEQ ID NO:169; and (ii) a VL comprising a vlCDR1 having an amino acid sequence of SEQ ID NO:171, a vlCDR2 having an amino acid sequence of SEQ ID NO:172, and a vlCDR3 having an amino acid sequence of SEQ ID NO:173; or i) a VH comprising a vhCDR1 having an amino acid sequence of SEQ ID NO:175; a vhCDR2 having an amino acid sequence of SEQ ID NO:176; and a vhCDR3 having an amino acid sequence of SEQ ID NO:177; and (ii) a VL comprising a vlCDR1 having an amino acid sequence of SEQ ID NO: 179, a vlCDR2 having an amino acid sequence of SEQ ID NO:180, and a vlCDR3 having an amino acid sequence of SEQ ID NO:181; or i) a VH comprising a vhCDR1 having an amino acid sequence of SEQ ID NO:183; a vhCDR2 having an amino acid sequence of SEQ ID NO:184; and a vhCDR3 having an amino acid sequence of SEQ ID NO:185; and (ii) a VL comprising a vlCDR1 having an amino acid sequence of SEQ ID NO: 187, a vlCDR2 having an amino acid sequence of SEQ ID NO:188, and a vlCDR3 having an amino acid sequence of SEQ ID NO:189; or i) a VH comprising a vhCDR1 having an amino acid sequence of SEQ ID NO:191; a vhCDR2 having an amino acid sequence of SEQ ID NO:192; and a vhCDR3 having an amino acid sequence of SEQ ID NO:193; and (ii) a VL comprising a vlCDR1 having an amino acid sequence of SEQ ID NO: 195, a vlCDR2 having an amino acid sequence of SEQ ID NO:196, and a vlCDR3 having an amino acid sequence of SEQ ID NO:197; or i) a VH comprising a vhCDR1 having an amino acid sequence of SEQ ID NO:199; a vhCDR2 having an amino acid sequence of SEQ ID NO:200; and a vhCDR3 having an amino acid sequence of SEQ ID NO:201; and (ii) a VL comprising a vlCDR1 having an amino acid sequence of SEQ ID NO:203, a vlCDR2 having an amino acid sequence of SEQ ID NO:204, and a vlCDR3 having an amino acid sequence of SEQ ID NO:205; or i) a VH comprising a vhCDR1 having an amino acid sequence of SEQ ID NO:381; a vhCDR2 having an amino acid sequence of SEQ ID NO:382; and a vhCDR3 having an amino acid sequence of SEQ ID NO:383; and (ii) a VL comprising a vlCDR1 having an amino acid sequence of SEQ ID NO:385, a vlCDR2 having an amino acid sequence of SEQ ID NO:386, and a vlCDR3 having an amino acid sequence of SEQ ID NO:387; or i) a VH comprising a vhCDR1 having an amino acid sequence of SEQ ID NO:389; a vhCDR2 having an amino acid sequence of SEQ ID NO:390; and a vhCDR3 having an amino acid sequence of SEQ ID NO:391; and (ii) a VL comprising a vlCDR1 having an amino acid sequence of SEQ ID NO:393, a vlCDR2 having an amino acid sequence of SEQ ID NO:394, and a vlCDR3 having an amino acid sequence of SEQ ID NO:395; or i) a VH comprising a vhCDR1 having an amino acid sequence of SEQ ID NO:397; a vhCDR2 having an amino acid sequence of SEQ ID NO:398; and a vhCDR3 having an amino acid sequence of SEQ ID NO:399; and (ii) a VL comprising a vlCDR1 having an amino acid sequence of SEQ ID NO:401, a vlCDR2 having an amino acid sequence of SEQ ID NO:402, and a vlCDR3 having an amino acid sequence of SEQ ID NO:403; or i) a VH comprising a vhCDR1 having an amino acid sequence of SEQ ID NO:405; a vhCDR2 having an amino acid sequence of SEQ ID NO:406; and a vhCDR3 having an amino acid sequence of SEQ ID NO:407; and (ii) a VL comprising a vlCDR1 having an amino acid sequence of SEQ ID NO:409, a vlCDR2 having an amino acid sequence of SEQ ID NO:410, and a vlCDR3 having an amino acid sequence of SEQ ID NO:411; or i) a VH comprising a vhCDR1 having an amino acid sequence of SEQ ID NO:413; a vhCDR2 having an amino acid sequence of SEQ ID NO:414; and a vhCDR3 having an amino acid sequence of SEQ ID NO:415; and (ii) a VL comprising a vlCDR1 having an amino acid sequence of SEQ ID NO:417, a vlCDR2 having an amino acid sequence of SEQ ID NO:418, and a vlCDR3 having an amino acid sequence of SEQ ID NO:419; or i) a VH comprising a vhCDR1 having an amino acid sequence of SEQ ID NO:421; a vhCDR2 having an amino acid sequence of SEQ ID NO:422; and a vhCDR3 having an amino acid sequence of SEQ ID NO:423; and (ii) a VL comprising a vlCDR1 having an amino acid sequence of SEQ ID NO:425, a vlCDR2 having an amino acid sequence of SEQ ID NO:426, and a vlCDR3 having an amino acid sequence of SEQ ID NO:427.

In some embodiments, the anti-CD28× anti-PSMA antibody includes a CD28 binding domain that includes a VH and VL selected from the following:

(i) a VH having an amino acid sequence that is at least about 95% identical to SEQ ID NO: 9; and (ii) a VL having an amino acid sequence that is at least about 95% identical to SEQ ID NO: 13; or (i) a VH having an amino acid sequence that is at least about 95% identical to SEQ ID NO:31; and (ii) a VL having an amino acid sequence that is at least about 95% identical to SEQ ID NO:35; or (i) a VH having an amino acid sequence that is at least about 95% identical to SEQ ID NO: 39; and (ii) a VL having an amino acid sequence that is at least about 95% identical to SEQ ID NO:43; or (i) a VH having an amino acid sequence that is at least about 95% identical to SEQ ID NO: 47; and (ii) a VL having an amino acid sequence that is at least about 95% identical to SEQ ID NO:51; or (i) a VH having an amino acid sequence that is at least about 95% identical to SEQ ID NO: 55; and (ii) a VL having an amino acid sequence that is at least about 95% identical to SEQ ID NO:59; or (i) a VH having an amino acid sequence that is at least about 95% identical to SEQ ID NO:63; and (ii) a VL having an amino acid sequence that is at least about 95% identical to SEQ ID NO: 67; or (i) a VH having an amino acid sequence that is at least about 95% identical to SEQ ID NO: 86; and (ii) a VL having an amino acid sequence that is at least about 95% identical to SEQ ID NO: 90; or (i) a VH having an amino acid sequence that is at least about 95% identical to SEQ ID NO: 94; and (ii) a VL having an amino acid sequence that is at least about 95% identical to SEQ ID NO:98; or (i) a VH having an amino acid sequence that is at least about 95% identical to SEQ ID NO:102; and (ii) a VL having an amino acid sequence that is at least about 95% identical to SEQ ID NO: 106; or (i) a VH having an amino acid sequence that is at least about 95% identical to SEQ ID NO:110; and (ii) a VL having an amino acid sequence that is at least about 95% identical to SEQ ID NO: 114; or (i) a VH having an amino acid sequence that is at least about 95% identical to SEQ ID NO: 118; and (ii) a VL having an amino acid sequence that is at least about 95% identical to SEQ ID NO: 122; or (i) a VH having an amino acid sequence that is at least about 95% identical to SEQ ID NO: 126; and (ii) a VL having an amino acid sequence that is at least about 95% identical to SEQ ID NO: 130; or (i) a VH having an amino acid sequence that is at least about 95% identical to SEQ ID NO:134; and (ii) a VL having an amino acid sequence that is at least about 95% identical to SEQ ID NO:138; or (i) a VH having an amino acid sequence that is at least about 95% identical to SEQ ID NO: 142; and (ii) a VL having an amino acid sequence that is at least about 95% identical to SEQ ID NO: 146; or (i) a VH having an amino acid sequence that is at least about 95% identical to SEQ ID NO: 150; and (ii) a VL having an amino acid sequence that is at least about 95% identical to SEQ ID NO: 154; or (i) a VH having an amino acid sequence that is at least about 95% identical to SEQ ID NO:158; and (ii) a VL having an amino acid sequence that is at least about 95% identical to SEQ ID NO: 162; or (i) a VH having an amino acid sequence that is at least about 95% identical to SEQ ID NO:166; and (ii) a VL having an amino acid sequence that is at least about 95% identical to SEQ ID NO: 170; or (i) a VH having an amino acid sequence that is at least about 95% identical to SEQ ID NO: 174; and (ii) a VL having an amino acid sequence that is at least about 95% identical to SEQ ID NO: 178; or (i) a VH having an amino acid sequence that is at least about 95% identical to SEQ ID NO:182; and (ii) a VL having an amino acid sequence that is at least about 95% identical to SEQ ID NO: 186; or (i) a VH having an amino acid sequence that is at least about 95% identical to SEQ ID NO: 190; and (ii) a VL having an amino acid sequence that is at least about 95% identical to SEQ ID NO: 194; or (i) a VH having an amino acid sequence that is at least about 95% identical to SEQ ID NO: 198; and (ii) a VL having an amino acid sequence that is at least about 95% identical to SEQ ID NO:202; or (i) a VH having an amino acid sequence that is at least about 95% identical to SEQ ID NO: 380; and (ii) a VL having an amino acid sequence that is at least about 95% identical to SEQ ID NO: 384; or (i) a VH having an amino acid sequence that is at least about 95% identical to SEQ ID NO:388; and (ii) a VL having an amino acid sequence that is at least about 95% identical to SEQ ID NO:392; or (i) a VH having an amino acid sequence that is at least about 95% identical to SEQ ID NO: 396; and (ii) a VL having an amino acid sequence that is at least about 95% identical to SEQ ID NO:400; or (i) a VH having an amino acid sequence that is at least about 95% identical to SEQ ID NO:404; and (ii) a VL having an amino acid sequence that is at least about 95% identical to SEQ ID NO:408; or (i) a VH having an amino acid sequence that is at least about 95% identical to SEQ ID NO:412; and (ii) a VL having an amino acid sequence that is at least about 95% identical to SEQ ID NO:416; or
(i) a VH having an amino acid sequence that is at least about 95% identical to SEQ ID NO:420; and (ii) a VL having an amino acid sequence that is at least about 95% identical to SEQ ID NO:424.

In some embodiments, the anti-CD28× anti-PSMA antibody includes a CD28 binding domain that includes a VH and VL selected from the following:
(i) a VH having an amino acid sequence of SEQ ID NO: 9; and (ii) a VL having an amino acid sequence of SEQ ID NO:13; or
(i) a VH having an amino acid sequence of SEQ ID NO:31; and (ii) a VL having an amino acid sequence of SEQ ID NO:35; or
(i) a VH having an amino acid sequence of SEQ ID NO:39; and (ii) a VL having an amino acid sequence of SEQ ID NO:43; or
(i) a VH having an amino acid sequence of SEQ ID NO:47; and (ii) a VL having an amino acid sequence of SEQ ID NO:51; or
(i) a VH having an amino acid sequence of SEQ ID NO:55; and (ii) a VL having an amino acid sequence of SEQ ID NO:59; or
(i) a VH having an amino acid sequence of SEQ ID NO:63; and (ii) a VL having an amino acid sequence of SEQ ID NO:67; or
(i) a VH having an amino acid sequence of SEQ ID NO:86; and (ii) a VL having an amino acid sequence of SEQ ID NO:90; or
(i) a VH having an amino acid sequence of SEQ ID NO:94; and (ii) a VL having an amino acid sequence of SEQ ID NO:98; or
(i) a VH having an amino acid sequence of SEQ ID NO:102; and (ii) a VL having an amino acid sequence of SEQ ID NO:106; or
(i) a VH having an amino acid sequence of SEQ ID NO:110; and (ii) a VL having an amino acid sequence of SEQ ID NO:114; or
(i) a VH having an amino acid sequence of SEQ ID NO:118; and (ii) a VL having an amino acid sequence of SEQ ID NO:122; or
(i) a VH having an amino acid sequence of SEQ ID NO:126; and (ii) a VL having an amino acid sequence of SEQ ID NO:130; or
(i) a VH having an amino acid sequence of SEQ ID NO:134; and (ii) a VL having an amino acid sequence of SEQ ID NO:138; or
(i) a VH having an amino acid sequence of SEQ ID NO:142; and (ii) a VL having an amino acid sequence of SEQ ID NO:146; or
(i) a VH having an amino acid sequence of SEQ ID NO:150; and (ii) a VL having an amino acid sequence of SEQ ID NO:154; or
(i) a VH having an amino acid sequence of SEQ ID NO:158; and (ii) a VL having an amino acid sequence of SEQ ID NO:162; or
(i) a VH having an amino acid sequence of SEQ ID NO:166; and (ii) a VL having an amino acid sequence of SEQ ID NO:170; or
(i) a VH having an amino acid sequence of SEQ ID NO:174; and (ii) a VL having an amino acid sequence of SEQ ID NO:178; or
(i) a VH having an amino acid sequence of SEQ ID NO:182; and (ii) a VL having an amino acid sequence of SEQ ID NO:186; or
(i) a VH having an amino acid sequence of SEQ ID NO:190; and (ii) a VL having an amino acid sequence of SEQ ID NO:194; or
(i) a VH having an amino acid sequence of SEQ ID NO:198; and (ii) a VL having an amino acid sequence of SEQ ID NO:202; or
(i) a VH having an amino acid sequence of SEQ ID NO:380; and (ii) a VL having an amino acid sequence of SEQ ID NO:384; or
(i) a VH having an amino acid sequence of SEQ ID NO:388; and (ii) a VL having an amino acid sequence of SEQ ID NO:392; or
(i) a VH having an amino acid sequence of SEQ ID NO:396; and (ii) a VL having an amino acid sequence of SEQ ID NO:400; or
(i) a VH having an amino acid sequence of SEQ ID NO:404; and (ii) a VL having an amino acid sequence of SEQ ID NO:408; or
(i) a VH having an amino acid sequence of SEQ ID NO:412; and (ii) a VL having an amino acid sequence of SEQ ID NO:416; or
(i) a VH having an amino acid sequence of SEQ ID NO:420; and (ii) a VL having an amino acid sequence of SEQ ID NO:424.

In some embodiments, the CD28 binding domain included in the anti-CD28× anti-PSMA antibody includes a vhCDR1 having an amino acid of SEQ ID NO:72, a vhCDR2 having an amino acid sequence of SEQ ID NO:74, and/or a vhCDR3 having an amino acid sequence of SEQ ID NO: 76. In some embodiments, the CD28 binding domain included in the anti-CD28× anti-PSMA antibody includes a vlCDR1 having an amino acid of SEQ ID NO:80, a vlCDR2 having an amino acid sequence of SEQ ID NO:82, and/or a vlCDR3 having an amino acid sequence of SEQ ID NO: 84.

B. PSMA Binding Domains

The anti-CD28× anti-PSMA antibodies provided herein include at least one PSMA binding domain. Subject antibodies that include such PSMA antigen binding domains (e.g., anti-PSMA× anti-CD3 bispecific antibodies) advantageously target cells that express high levels of PSMA over those that express levels of PSMA (e.g., normal cells).

As will be appreciated by those in the art, suitable PSMA binding domains can comprise a set of 6 CDRs as depicted in the sequence listing and FIGS. 25A-25E and 26A-26B, either as the CDRs are underlined or, in the case where a different numbering scheme is used as described herein and as shown in Table 2, as the CDRs that are identified using other alignments within the variable heavy (VH) domain and variable light domain (VL) sequences of those depicted in FIGS. 25A-25E and 26A-26B and the sequence listing (see Table 2). Suitable PSMA ABDs can also include the entire VH and VL sequences as depicted in these sequences and figures, used as scFvs or as Fab domains.

In one embodiment, the PSMA antigen binding domain of the anti-CD28× anti-PSMA antibody includes the 6 CDRs (i.e., vhCDR1-3 and vlCDR1-3) of a PSMA ABD described herein, including the Figures and sequence listing. In exemplary embodiments, the PSMA ABD is one of the following PSMA ABDs: A10[PSMA], A10v2[PSMA], D01[PSMA], D01v2[PSMA], E07[PSMA], F02[PSMA], A11[PSMA], F07[PSMA], F07v2[PSMA], G02[PSMA], F01[PSMA], F01v2[PSMA], 011A11[PSMA], PSMB896[PSMA], PSMA-H[PSMA], and D7[PSMA](FIGS. 25A-25E and 26A-26B).

In addition to the parental CDR sets disclosed in the figures and sequence listing that form an ABD to PSMA, provided herein are variant PSMA ABDS having CDRs that include at least one modification of the PSMA ABD CDRs disclosed herein. In one embodiment, the PSMA ABD includes a set of 6 CDRs with 1, 2, 3, 4, 5, 6, 7, 8, 9, 10 amino acid modifications as compared to the 6 CDRs of a PSMA ABD described herein, including the figures and sequence listing. In exemplary embodiments, the PSMA ABD of the anti-CD28× anti-PSMA antibody includes a set of 6 CDRs with 1, 2, 3, 4, 5, 6, 7, 8, 9, 10 amino acid modifications as compared to the 6 CDRs of one of the following PSMA ABDs: A10[PSMA], A10v2[PSMA], D01[PSMA], D01v2[PSMA], E07[PSMA], F02[PSMA], A11[PSMA], F07[PSMA], F07v2[PSMA], G02[PSMA], F01[PSMA], F01v2[PSMA], 011A11[PSMA], PSMB896[PSMA], PSMA-H[PSMA], and D7[PSMA](FIGS. 25A-25E and 26A-26B). In certain embodiments, the variant PSMA ABD is capable of binding PSMA antigen, as measured by at least one of a Biacore, surface plasmon resonance (SPR), flow cytometry, and/or BLI (biolayer interferometry, e.g., Octet assay) assay, with the latter finding particular use in many embodiments. In particular embodiments, the PSMA ABD is capable of binding human PSMA antigen (see Example 5).

In one embodiment, the PSMA ABD of the anti-CD28× anti-PSMA antibody includes 6 CDRs that are at least 90, 95, 97, 98 or 99% identical to the 6 CDRs of a PSMA ABD as described herein, including the figures and sequence listing. In exemplary embodiments, the PSMA ABD includes 6 CDRs that are at least 90, 95, 97, 98 or 99% identical to the 6 CDRs of one of the following PSMA ABDs: A10[PSMA], A10v2[PSMA], D01[PSMA], D01v2[PSMA], E07[PSMA], F02[PSMA], A11[PSMA], F07[PSMA], F07v2[PSMA], G02[PSMA], F01[PSMA], F01v2[PSMA], 011A11[PSMA], PSMB896[PSMA], PSMA-H[PSMA], and D7[PSMA](FIGS. 25A-25E and 26A-26B). In certain embodiments, the PSMA ABD is capable of binding to PSMA antigen, as measured by at least one of a Biacore, surface plasmon resonance (SPR), flow cytometry, and/or BLI (biolayer interferometry, e.g., Octet assay) assay, with the latter finding particular use in many embodiments. In particular embodiments, the PSMA ABD is capable of binding human PSMA antigen (see FIGS. 2A-2B).

In another exemplary embodiment, the PSMA ABD of the anti-CD28× anti-PSMA antibody include the variable heavy (VH) domain and variable light (VL) domain of any one of the PSMA ABDs described herein, including the figures and sequence listing. In exemplary embodiments, the PSMA ABD is one of the following PSMA ABDs: A10[PSMA], A10v2[PSMA], D01[PSMA], D01v2[PSMA], E07[PSMA], F02[PSMA], A11[PSMA], F07[PSMA], F07v2[PSMA], G02[PSMA], F01[PSMA], F01v2[PSMA], 011A11[PSMA], PSMB896[PSMA], PSMA-H[PSMA], and D7[PSMA](FIGS. 25A-25E and 26A-26B).

In addition to the parental PSMA variable heavy and variable light domains disclosed herein, provided herein are PSMA ABDs that include a variable heavy domain and/or a variable light domain that are variants of a PSMA ABD VH and VL domain disclosed herein. In one embodiment, the variant VH domain and/or VL domain has from 1, 2, 3, 4, 5, 6, 7, 8, 9 or 10 amino acid changes from a VH and/or VL domain of a PSMA ABD described herein, including the figures and sequence listing. In exemplary embodiments, the variant VH domain and/or VL domain has from 1, 2, 3, 4, 5, 6, 7, 8, 9 or 10 amino acid changes from a VH and/or VL domain of one of the following PSMA ABDs: A10[PSMA], A10v2[PSMA], D01[PSMA], D01v2[PSMA], E07[PSMA], F02[PSMA], A11[PSMA], F07[PSMA], F07v2[PSMA], G02[PSMA], F01[PSMA], F01v2[PSMA], 011A11[PSMA], PSMB896[PSMA], PSMA-H[PSMA], and D7[PSMA](FIGS. 25A-25E and 26A-26B). In some embodiments, the changes are in a VH domain depicted in FIGS. 25A-25E and 26A-26B. In some embodiments, the changes are in a VL domain are depicted in FIGS. 25A-25E and 26A-26B. In some embodiments, the changes are in a VH and VL domain are depicted in FIGS. 25A-25E and 26A-26B. In some embodiments, the amino acid change(s) is in the VH and/or VL framework regions (FR1, FR2, FR3, and/or FR4). In certain embodiments, the PSMA ABD of the anti-CD28× anti-PSMA antibody is capable of binding to PSMA, as measured at least one of a Biacore, surface plasmon resonance (SPR), flow cytometry, and/or BLI (biolayer interferometry, e.g., Octet assay) assay, with the latter finding particular use in many embodiments. In particular embodiments, the PSMA ABD is capable of binding human PSMA antigen.

In one embodiment, the variant VH and/or VL domain is at least 90, 95, 97, 98 or 99% identical to the VH and/or VL of a PSMA ABD as described herein, including the figures and sequence listing. In exemplary embodiments, the variant VH and/or VL domain is at least 90, 95, 97, 98 or 99% identical to the VH and/or VL of one of the following PSMA ABDs: A10[PSMA], A10v2[PSMA], D01[PSMA], D01v2[PSMA], E07[PSMA], F02[PSMA], A11[PSMA], F07[PSMA], F07v2[PSMA], G02[PSMA], F01[PSMA], F01v2[PSMA], 011A11[PSMA], PSMB896[PSMA], PSMA-H[PSMA], and D7[PSMA](FIGS. 25A-25E and 26A-26B). In some embodiments, the PSMA ABD includes a VH that is at least 90, 95, 97, 98 or 99% identical to VH domain depicted in FIGS. 25A-25E and 26A-26B. In some embodiments, the CD28 PSMA includes a VL that is at least 90, 95, 97, 98 or 99% identical to VL domain depicted in FIGS. 25A-25E and 26A-26B. In some embodiments, the PSMA ABD includes a VH and a VL that is at least 90, 95, 97, 98 or 99% identical to a VH and a VL domains depicted in FIGS. 25A-25E and 26A-26B. In certain embodiments, the PSMA ABD of the anti-CD28× anti-PSMA antibody is capable of binding to the PSMA, as measured by at least one of a Biacore, surface plasmon resonance (SPR), flow cytometry, and/or BLI (biolayer interferometry, e.g., Octet assay) assay, with the latter finding particular use in many embodiments. In particular embodiments, the PSMA ABD is capable of binding human PSMA antigen.

In some embodiments, the anti-CD28× anti-PSMA antibody is a bivalent antibody (e.g., 1+1 Fab-scFv-Fc format antibody) that includes one PSMA binding domain. In other embodiments, the anti-CD28× anti-PSMA antibody is a trivalent antibody (e.g., 2+1 Fab2scFv-Fc format antibody) that includes two PSMA binding domains.

In some embodiments, the VH and VL of the PSMA binding domain(s) are selected from the following:
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:206; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:210; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:214; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:218; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:222; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:226; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:230; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:234; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:238; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:242; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:246; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:250; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:254; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:258; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:262; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:266; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:270; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:274; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:278; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:282; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:286; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:290; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:294; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:298; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:302; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:306; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:310; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:314; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:318; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:322; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:326; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:330; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:334; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:338.

In some embodiments, the VH and VL of the PSMA binding domain(s) are selected from the following:
(i) a VH comprising a vhCDR1 having an amino acid sequence of SEQ ID NO:207; a vhCDR2 having an amino acid sequence of SEQ ID NO:208; and a vhCDR3 having an amino acid sequence of SEQ ID NO:209; and (ii) a VL comprising a vlCDR1 having an amino acid sequence of SEQ ID NO:211, a vlCDR2 having an amino acid sequence of SEQ ID NO: 212, and a vlCDR3 having an amino acid sequence of SEQ ID NO:213; or (i) a VH comprising a vhCDR1 having an amino acid sequence of SEQ ID NO:215; a vhCDR2 having an amino acid sequence of SEQ ID NO:216; and a vhCDR3 having an amino acid sequence of SEQ ID NO:217; and (ii) a VL comprising a vlCDR1 having an amino acid sequence of SEQ ID NO:219, a vlCDR2 having an amino acid sequence of SEQ ID NO: 220, and a vlCDR3 having an amino acid sequence of SEQ ID NO:221;

(i) a VH comprising a vhCDR1 having an amino acid sequence of SEQ ID NO:223; a vhCDR2 having an amino acid sequence of SEQ ID NO:224; and a vhCDR3 having an amino acid sequence of SEQ ID NO:225; and (ii) a VL comprising a vlCDR1 having an amino acid sequence of SEQ ID NO:227, a vlCDR2 having an amino acid sequence of SEQ ID NO: 228, and a vlCDR3 having an amino acid sequence of SEQ ID NO:229; or (i) a VH comprising a vhCDR1 having an amino acid sequence of SEQ ID NO:231; a vhCDR2 having an amino acid sequence of SEQ ID NO:232; and a vhCDR3 having an amino acid sequence of SEQ ID NO:233; and (ii) a VL comprising a vlCDR1 having an amino acid sequence of SEQ ID NO:235, a vlCDR2 having an amino acid sequence of SEQ ID NO: 236, and a vlCDR3 having an amino acid sequence of SEQ ID NO:237; or (i) a VH comprising a vhCDR1 having an amino acid sequence of SEQ ID NO:239; a vhCDR2 having an amino acid sequence of SEQ ID NO:240; and a vhCDR3 having an amino acid sequence of SEQ ID NO:241; and (ii) a VL comprising a vlCDR1 having an amino acid sequence of SEQ ID NO:243, a vlCDR2 having an amino acid sequence of SEQ ID NO: 244, and a vlCDR3 having an amino acid sequence of SEQ ID NO:245; or (i) a VH comprising a vhCDR1 having an amino acid sequence of SEQ ID NO:247; a vhCDR2 having an amino acid sequence of SEQ ID NO:248; and a vhCDR3 having an amino acid sequence of SEQ ID NO:249; and (ii) a VL comprising a vlCDR1 having an amino acid sequence of SEQ ID NO:251, a vlCDR2 having an amino acid sequence of SEQ ID NO: 252, and a vlCDR3 having an amino acid sequence of SEQ ID NO:253; or (i) a VH comprising a vhCDR1 having an amino acid sequence of SEQ ID NO:255; a vhCDR2 having an amino acid sequence of SEQ ID NO:256; and a vhCDR3 having an amino acid sequence of SEQ ID NO:257; and (ii) a VL comprising a vlCDR1 having an amino acid sequence of SEQ ID NO:259, a vlCDR2 having an amino acid sequence of SEQ ID NO: 260, and a vlCDR3 having an amino acid sequence of SEQ ID NO:261; or (i) a VH comprising a vhCDR1 having an amino acid sequence of SEQ ID NO:263; a vhCDR2 having an amino acid sequence of SEQ ID NO:264; and a vhCDR3 having an amino acid sequence of SEQ ID NO:265; and (ii) a VL comprising a vlCDR1 having an amino acid sequence of SEQ ID NO:267, a vlCDR2 having an amino acid sequence of SEQ ID NO: 268, and a vlCDR3 having an amino acid sequence of SEQ ID NO:269; or (i) a VH comprising a vhCDR1 having an amino acid sequence of SEQ ID NO:271; a vhCDR2 having an amino acid sequence of SEQ ID NO:212; and a vhCDR3 having an amino acid sequence of SEQ ID NO:273; and (ii) a VL comprising a vlCDR1 having an amino acid sequence of SEQ ID NO:275, a vlCDR2 having an amino acid sequence of SEQ ID NO: 276, and a vlCDR3 having an amino acid sequence of SEQ ID NO:277; or (i) a VH comprising a vhCDR1 having an amino acid sequence of SEQ ID NO:279; a vhCDR2 having an amino acid sequence of SEQ ID NO:280; and a vhCDR3 having an amino acid sequence of SEQ ID NO:281; and (ii) a VL comprising a vlCDR1 having an amino acid sequence of SEQ ID NO:283, a vlCDR2 having an amino acid sequence of SEQ ID NO: 284, and a vlCDR3 having an amino acid sequence of SEQ ID NO:285; or (i) a VH comprising a vhCDR1 having an amino acid sequence of SEQ ID NO:287; a vhCDR2 having an amino acid sequence of SEQ ID NO:288; and a vhCDR3 having an amino acid sequence of SEQ ID NO:289; and (ii) a VL comprising a vlCDR1 having an amino acid sequence of SEQ ID NO:291, a vlCDR2 having an amino acid sequence of SEQ ID NO: 292, and a vlCDR3 having an amino acid sequence of SEQ ID NO:293; or (i) a VH comprising a vhCDR1 having an amino acid sequence of SEQ ID NO:295; a vhCDR2 having an amino acid sequence of SEQ ID NO:296; and a vhCDR3 having an amino acid sequence of SEQ ID NO:297; and (ii) a VL comprising a vlCDR1 having an amino acid sequence of SEQ ID NO:299, a vlCDR2 having an amino acid sequence of SEQ ID NO: 300, and a vlCDR3 having an amino acid sequence of SEQ ID NO:301; or (i) a VH comprising a vhCDR1 having an amino acid sequence of SEQ ID NO:303; a vhCDR2 having an amino acid sequence of SEQ ID NO:304; and a vhCDR3 having an amino acid sequence of SEQ ID NO:305; and (ii) a VL comprising a vlCDR1 having an amino acid sequence of SEQ ID NO:307, a vlCDR2 having an amino acid sequence of SEQ ID NO: 308, and a vlCDR3 having an amino acid sequence of SEQ ID NO:309; or (i) a VH comprising a vhCDR1 having an amino acid sequence of SEQ ID NO:311; a vhCDR2 having an amino acid sequence of SEQ ID NO:312; and a vhCDR3 having an amino acid sequence of SEQ ID NO:313; and (ii) a VL comprising a vlCDR1 having an amino acid sequence of SEQ ID NO: 315, a vlCDR2 having an amino acid sequence of SEQ ID NO: 316, and a vlCDR3 having an amino acid sequence of SEQ ID NO:317; or (i) a VH comprising a vhCDR1 having an amino acid sequence of SEQ ID NO:319; a vhCDR2 having an amino acid sequence of SEQ ID NO:320; and a vhCDR3 having an amino acid sequence of SEQ ID NO:321; and (ii) a VL comprising a vlCDR1 having an amino acid sequence of SEQ ID NO: 323, a vlCDR2 having an amino acid sequence of SEQ ID NO: 324, and a vlCDR3 having an amino acid sequence of SEQ ID NO:325; or (i) a VH comprising a vhCDR1 having an amino acid sequence of SEQ ID NO:327; a vhCDR2 having an amino acid sequence of SEQ ID NO:328; and a vhCDR3 having an amino acid sequence of SEQ ID NO: 329; and (ii) a VL comprising a vlCDR1 having an amino acid sequence of SEQ ID NO:331, a vlCDR2 having an amino acid sequence of SEQ ID NO: 332, and a vlCDR3 having an amino acid sequence of SEQ ID NO:333; or (i) a VH comprising a vhCDR1 having an amino acid sequence of SEQ ID NO:335; a vhCDR2 having an amino acid sequence of SEQ ID NO:336; and a vhCDR3 having an amino acid sequence of SEQ ID NO:337; and (ii) a VL comprising a vlCDR1 having an amino acid sequence of SEQ ID NO: 339, a vlCDR2 having an amino acid sequence of SEQ ID NO: 340, and a vlCDR3 having an amino acid sequence of SEQ ID NO:341.

In some embodiments, the VH and VL of the PSMA binding domain(s) are selected from the following:
- (i) a VH1 having an amino acid sequence that is at least about 95% identical to SEQ ID NO: 206; and (ii) a VL1 having an amino acid sequence that is at least about 95% identical to SEQ ID NO:210; or
- (i) a VH1 having an amino acid sequence that is at least about 95% identical to SEQ ID NO:214; and (ii) a VL1 having an amino acid sequence that is at least about 95% identical to SEQ ID NO:218; or
- (i) a VH1 having an amino acid sequence that is at least about 95% identical to SEQ ID NO: 222; and (ii) a VL1 having an amino acid sequence that is at least about 95% identical to SEQ ID NO:226; or
- (i) a VH1 having an amino acid sequence that is at least about 95% identical to SEQ ID NO:230; and (ii) a VL1 having an amino acid sequence that is at least about 95% identical to SEQ ID NO:234; or
- (i) a VH1 having an amino acid sequence that is at least about 95% identical to SEQ ID NO:238; and (ii) a VL1 having an amino acid sequence that is at least about 95% identical to SEQ ID NO:242; or
- (i) a VH1 having an amino acid sequence that is at least about 95% identical to SEQ ID NO:246; and (ii) a VL1 having an amino acid sequence that is at least about 95% identical to SEQ ID NO:250; or
- (i) a VH1 having an amino acid sequence that is at least about 95% identical to SEQ ID NO:254; and (ii) a VL1 having an amino acid sequence that is at least about 95% identical to SEQ ID NO:258; or
- (i) a VH1 having an amino acid sequence that is at least about 95% identical to SEQ ID NO:262; and (ii) a VL1 having an amino acid sequence that is at least about 95% identical to SEQ ID NO:266; or
- (i) a VH1 having an amino acid sequence that is at least about 95% identical to SEQ ID NO:270; and (ii) a VL1 having an amino acid sequence that is at least about 95% identical to SEQ ID NO:274; or
- (i) a VH1 having an amino acid sequence that is at least about 95% identical to SEQ ID NO:278; and (ii) a VL1 having an amino acid sequence that is at least about 95% identical to SEQ ID NO:282; or
- (i) a VH1 having an amino acid sequence that is at least about 95% identical to SEQ ID NO:286; and (ii) a VL1 having an amino acid sequence that is at least about 95% identical to SEQ ID NO:290; or
- (i) a VH1 having an amino acid sequence that is at least about 95% identical to SEQ ID NO:294; and (ii) a VL1 having an amino acid sequence that is at least about 95% identical to SEQ ID NO:298; or
- (i) a VH1 having an amino acid sequence that is at least about 95% identical to SEQ ID NO: 302; and (ii) a VL1 having an amino acid sequence that is at least about 95% identical to SEQ ID NO:306; or
- (i) a VH1 having an amino acid sequence that is at least about 95% identical to SEQ ID NO:310; and (ii) a VL1 having an amino acid sequence that is at least about 95% identical to SEQ ID NO: 314; or
- (i) a VH1 having an amino acid sequence that is at least about 95% identical to SEQ ID NO: 318; and (ii) a VL1 having an amino acid sequence that is at least about 95% identical to SEQ ID NO:322; or
- (i) a VH1 having an amino acid sequence that is at least about 95% identical to SEQ ID NO:326; and (ii) a VL1 having an amino acid sequence that is at least about 95% identical to SEQ ID NO:330; or
- (i) a VH1 having an amino acid sequence that is at least about 95% identical to SEQ ID NO: 334; and (ii) a VL1 having an amino acid sequence that is at least about 95% identical to SEQ ID NO:338; and In some embodiments, the VH and VL of the PSMA binding domain(s) are selected from the following:
- (i) a VH having an amino acid sequence of SEQ ID NO:206; and (ii) a VL having an amino acid sequence of SEQ ID NO:210; or
- (i) a VH having an amino acid sequence of SEQ ID NO:214; and (ii) a VL having an amino acid sequence of SEQ ID NO:218; or
- (i) a VH having an amino acid sequence of SEQ ID NO:222; and (ii) a VL having an amino acid sequence of SEQ ID NO:226; or
- (i) a VH having an amino acid sequence of SEQ ID NO:230; and (ii) a VL having an amino acid sequence of SEQ ID NO:234; or
- (i) a VH having an amino acid sequence of SEQ ID NO:238; and (ii) a VL having an amino acid sequence of SEQ ID NO:242; or
- (i) a VH having an amino acid sequence of SEQ ID NO:246; and (ii) a VL having an amino acid sequence of SEQ ID NO:250; or
- (i) a VH having an amino acid sequence of SEQ ID NO:254; and (ii) a VL having an amino acid sequence of SEQ ID NO:258; or
- (i) a VH having an amino acid sequence of SEQ ID NO:262; and (ii) a VL having an amino acid sequence of SEQ ID NO:266; or
- (i) a VH having an amino acid sequence of SEQ ID NO:270; and (ii) a VL having an amino acid sequence of SEQ ID NO:274; or
- (i) a VH having an amino acid sequence of SEQ ID NO:278; and (ii) a VL having an amino acid sequence of SEQ ID NO:282; or
- (i) a VH having an amino acid sequence of SEQ ID NO:286; and (ii) a VL having an amino acid sequence of SEQ ID NO:290; or
- (i) a VH having an amino acid sequence of SEQ ID NO:294; and (ii) a VL having an amino acid sequence of SEQ ID NO:298; or
- (i) a VH having an amino acid sequence of SEQ ID NO:302; and (ii) a VL having an amino acid sequence of SEQ ID NO:306; or
- (i) a VH having an amino acid sequence of SEQ ID NO:310; and (ii) a VL having an amino acid sequence of SEQ ID NO:314; or
- (i) a VH having an amino acid sequence of SEQ ID NO:318; and (ii) a VL having an amino acid sequence of SEQ ID NO:322; or
- (i) a VH having an amino acid sequence of SEQ ID NO:326; and (ii) a VL having an amino acid sequence of SEQ ID NO:330; or (i) a VH having an amino acid sequence of SEQ ID NO:334; and (ii) a VL having an amino acid sequence of SEQ ID NO:338.

C. Chimeric and Humanized Antibodies

In certain embodiments, the subject antibodies provided herein include a heavy chain variable region from a particular germline heavy chain immunoglobulin gene and/or a light chain variable region from a particular germline light chain immunoglobulin gene. For example, such antibodies may comprise or consist of a human antibody comprising heavy or light chain variable regions that are "the product of" or "derived from" a particular germline sequence. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody (using the methods outlined herein). A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a humanized antibody typically is at least 90% identical in amino acids sequence to an amino acid sequence encoded by a human germline immunoglobulin gene and contains amino acid residues that identify the antibody as being derived from human sequences when compared to the germline immunoglobulin amino acid sequences of other species (e.g., murine germline sequences). In certain cases, a humanized antibody may be at least 95, 96, 97, 98 or 99%, or even at least 96%, 97%, 98%, or 99% identical in amino acid sequence to the amino acid sequence encoded by the germline immunoglobulin gene. Typically, a humanized antibody derived from a particular human germline sequence will display no more than $10^{-20}$ amino acid differences from the amino acid sequence encoded by the human germline immunoglobulin gene (prior to the introduction of any skew, pI and ablation variants herein; that is, the number of variants is generally low, prior to the introduction of the variants of the invention). In certain cases, the humanized antibody may display no more than 5, or even no more than 4, 3, 2, or 1 amino acid difference from the amino acid sequence encoded by the germline immunoglobulin gene (again, prior to the introduction of any skew, pI and ablation variants herein; that is, the number of variants is generally low, prior to the introduction of the variants of the invention).

In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

D. Heterodimeric Antibodies

In exemplary embodiments, the anti-CD28× anti-PSMA antibodies provided herein are heterodimeric bispecific antibodies that include two variant Fc domain sequences. Such variant Fc domains include amino acid modifications to facilitate the self-assembly and/or purification of the heterodimeric antibodies.

An ongoing problem in antibody technologies is the desire for "bispecific" antibodies that bind to two different antigens simultaneously, in general thus allowing the different antigens to be brought into proximity and resulting in new functionalities and new therapies. In general, these antibodies are made by including genes for each heavy and light chain into the host cells. This generally results in the formation of the desired heterodimer (A-B), as well as the two homodimers (A-A and B-B (not including the light chain heterodimeric issues)). However, a major obstacle in the formation of bispecific antibodies is the difficulty in biasing the formation of the desired heterodimeric antibody over the formation of the homodimers and/or purifying the heterodimeric antibody away from the homodimers.

There are a number of mechanisms that can be used to generate the subject heterodimeric antibodies. In addition, as will be appreciated by those in the art, these different mechanisms can be combined to ensure high heterodimerization. Amino acid modifications that facilitate the production and purification of heterodimers are collectively referred to generally as "heterodimerization variants." As discussed below, heterodimerization variants include "skew" variants (e.g., the "knobs and holes" and the "charge pairs" variants described below) as well as "pI variants," which allow purification of heterodimers from homodimers. As is generally described in U.S. Pat. No. 9,605,084, hereby incorporated by reference in its entirety and specifically as below for the discussion of heterodimerization variants, useful mechanisms for heterodimerization include "knobs and holes" ("KIH") as described in U.S. Pat. No. 9,605,084, "electrostatic steering" or "charge pairs" as described in U.S. Pat. No. 9,605,084, pI variants as described in U.S. Pat. No. 9,605,084, and general additional Fc variants as outlined in U.S. Pat. No. 9,605,084 and below.

Heterodimerization variants that are useful for the formation and purification of the subject heterodimeric antibody (e.g., bispecific antibodies) are further discussed in detailed below.

1. Skew Variants

In some embodiments, the heterodimeric antibody includes skew variants which are one or more amino acid modifications in a first Fc domain (A) and/or a second Fc domain (B) that favor the formation of Fc heterodimers (Fc dimers that include the first and the second Fc domain; (A-B) over Fc homodimers (Fc dimers that include two of the first Fc domain or two of the second Fc domain; A-A or B-B). Suitable skew variants are included in the FIG. 29 of US Publ. App. No. 2016/0355608, hereby incorporated by reference in its entirety and specifically for its disclosure of skew variants, as well as in FIGS. 3A-3F and 9.

One particular type of skew variants is generally referred to in the art as "knobs and holes," referring to amino acid engineering that creates steric influences to favor heterodimeric formation and disfavor homodimeric formation, as described in U.S. Ser. No. 61/596,846, Ridgway et al., Protein Engineering 9(7):617 (1996); Atwell et al., J. Mol. Biol. 1997 270:26; U.S. Pat. No. 8,216,805, all of which are hereby incorporated by reference in their entirety and specifically for the disclosure of "knobs and holes" mutations. This is sometime referred to herein as "steric variants." The figures identify a number of "monomer A—monomer B" pairs that rely on "knobs and holes". In addition, as described in Merchant et al., Nature Biotech. 16:677 (1998), these "knobs and holes" mutations can be combined with disulfide bonds to further favor formation of Fc heterodimers.

Another method that finds use in the generation of heterodimers is sometimes referred to as "electrostatic steering" as described in Gunasekaran et al., J. Biol. Chem. 285(25): 19637 (2010), hereby incorporated by reference in its entirety. This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "skew variants". These include, but are not limited to, D221E/P228E/L368E paired with D221R/P228R/K409R (e.g., these are "monomer corresponding sets) and C220E/P228E/368E paired with C220R/E224R/P228R/K409R.

In some embodiments, the skew variants advantageously and simultaneously favor heterodimerization based on both the "knobs and holes" mechanism as well as the "electrostatic steering" mechanism. In some embodiments, the heterodimeric antibody includes one or more sets of such heterodimerization skew variants. These variants come in "pairs" of "sets". That is, one set of the pair is incorporated into the first monomer and the other set of the pair is incorporated into the second monomer. It should be noted that these sets do not necessarily behave as "knobs in holes" variants, with a one-to-one correspondence between a residue on one monomer and a residue on the other. That is, these pairs of sets may instead form an interface between the two monomers that encourages heterodimer formation and discourages homodimer formation, allowing the percentage of heterodimers that spontaneously form under biological conditions to be over 90%, rather than the expected 50% (25% homodimer A/A:50% heterodimer A/B:25% homodimer B/B). Exemplary heterodimerization "skew" variants are depicted in FIGS. 3A-3F. Such "skew" variants include, but are not limited to: S364K/E357Q:L368D/K370S; L368D/K370S:S364K; L368E/K370S:S364K; T411T/E360E/Q362E:D401K; L368D/K370S:S364K/E357L; K370S:S364K/E357Q (EU numbering).

In exemplary embodiments, the heterodimeric antibody includes a S364K/E357Q:L368D/K370S; L368D/K370S: S364K; L368E/K370S:S364K; T411T/E360E/Q362E: D401K; L368D/K370S:S364K/E357L; K370S:S364K/ E357Q; or a T366S/L368A/Y407V:T366W (optionally including a bridging disulfide, T366S/L368A/Y407V/ Y349C:T366W/S354C) "skew" variant amino acid substitution set (EU numbering). In an exemplary embodiment, the heterodimeric antibody includes a "S364K/E357Q: L368D/K370S" amino acid substitution set. In terms of nomenclature, the pair "S364K/E357Q:L368D/K370S" means that one of the monomers includes an Fc domain that includes the amino acid substitutions S364K and E357Q and the other monomer includes an Fc domain that includes the amino acid substitutions L368D and K370S; as above, the "strandedness" of these pairs depends on the starting pI.

In some embodiments, the skew variants provided herein can be optionally and independently incorporated with any other modifications, including, but not limited to, other skew variants (see, e.g., in FIG. 37 of US Publ. App. No. 2012/0149876, herein incorporated by reference, particularly for its disclosure of skew variants), pI variants, isotpypic variants, FcRn variants, ablation variants, etc. into one or both of the first and second Fc domains of the heterodimeric antibody. Further, individual modifications can also independently and optionally be included or excluded from the subject the heterodimeric antibody.

In some embodiments, the skew variants outlined herein can be optionally and independently incorporated with any pI variant (or other variants such as Fc variants, FcRn variants, etc.) into one or both heavy chain monomers, and can be independently and optionally included or excluded from the subject heterodimeric antibodies.

2. Purification Variants

In some embodiments, the heterodimeric antibody includes purification variants that advantageously allow for the separation of heterodimeric proteins (e.g., anti-CD28× anti-PSMA bispecific antibody) from homodimeric proteins.

There are several basic mechanisms that can lead to ease of purifying heterodimeric antibodies. For example, modifications to one or both of the antibody heavy chain monomers A and B such that each monomer has a different pI allows for the isoelectric purification of heterodimeric A-B antibody from monomeric A-A and B-B proteins. Alternatively, some scaffold formats, such as the "1+1 Fab-scFv-Fc" format, and the "2+1 Fab2-scFv-Fc" format, allows separation on the basis of size. As described above, it is also possible to "skew" the formation of heterodimers over homodimers using skew variants. Thus, a combination of heterodimerization skew variants and purification variants find particular use in the heterodimeric antibodies provided herein.

Additionally, as more fully outlined below, depending on the format of the heterodimeric antibody, purification variants either contained within the constant region and/or Fc domains of a monomer, and/or domain linkers can be used. In some embodiments, the heterodimeric antibody includes additional modifications for alternative functionalities that can also create pI changes, such as Fc, FcRn and KO variants.

In some embodiments, the subject heterodimeric antibodies provided herein include at least one monomer with one or more modifications that alter the pI of the monomer (i.e., a "pI variant"). In general, as will be appreciated by those in the art, there are two general categories of pI variants: those that increase the pI of the protein (basic changes) and those that decrease the pI of the protein (acidic changes). As described herein, all combinations of these variants can be done: one monomer may be wild type, or a variant that does not display a significantly different pI from wild-type, and the other can be either more basic or more acidic. Alternatively, each monomer is changed, one to more basic and one to more acidic.

Depending on the format of the heterodimer antibody, pI variants can be either contained within the constant and/or Fc domains of a monomer, or charged linkers, either domain linkers or scFv linkers, can be used. That is, antibody formats that utilize scFv(s) such as "1+1 Fab-scFv-Fc", format can include charged scFv linkers (either positive or negative), that give a further pI boost for purification purposes. As will be appreciated by those in the art, some 1+1 Fab-scFv-Fc and 2+1 Fab$_2$-scFv-Fc formats are useful with just charged scFv linkers and no additional pI adjustments, although the invention does provide pI variants that are on one or both of the monomers, and/or charged domain linkers as well. In addition, additional amino acid engineering for alternative functionalities may also confer pI changes, such as Fc, FcRn and KO variants.

In subject heterodimeric antibodies that utilizes pI as a separation mechanism to allow the purification of heterodimeric proteins, amino acid variants are introduced into one or both of the monomer polypeptides. That is, the pI of one of the monomers (referred to herein for simplicity as "monomer A") can be engineered away from monomer B, or both monomer A and B change be changed, with the pI of monomer A increasing and the pI of monomer B decreasing. As is outlined more fully below, the pI changes of either or both monomers can be done by removing or adding a charged residue (e.g., a neutral amino acid is replaced by a positively or negatively charged amino acid residue, e.g., glycine to glutamic acid), changing a charged residue from positive or negative to the opposite charge (aspartic acid to lysine) or changing a charged residue to a neutral residue (e.g., loss of a charge; lysine to serine). A number of these variants are shown in the FIGS. 3A-3F and 4.

Thus, in some embodiments, the subject heterodimeric antibody includes amino acid modifications in the constant regions that alter the isoelectric point (pI) of at least one, if not both, of the monomers of a dimeric protein to form "pI antibodies") by incorporating amino acid substitutions ("pI variants" or "pI substitutions") into one or both of the monomers. As shown herein, the separation of the heterodimers from the two homodimers can be accomplished if the pIs of the two monomers differ by as little as 0.1 pH unit, with 0.2, 0.3, 0.4 and 0.5 or greater all finding use in the present invention.

As will be appreciated by those in the art, the number of pI variants to be included on each or both monomer(s) to get good separation will depend in part on the starting pI of the components, for example in the 1+1 Fab-scFv-Fc, 2+1 Fab$_2$-scFv-Fc, 1+1 CLC and 2+1 CLC formats, the starting pI of the scFv (1+1 Fab-scFv-Fc, 2+1 Fab$_2$-scFv-Fc) and Fab(s) of interest. That is, to determine which monomer to engineer or in which "direction" (e.g., more positive or more negative), the Fv sequences of the two target antigens are calculated and a decision is made from there. As is known in the art, different Fvs will have different starting pIs which are exploited in the present invention. In general, as outlined herein, the pIs are engineered to result in a total pI difference of each monomer of at least about 0.1 logs, with 0.2 to 0.5 being preferred as outlined herein.

In the case where pI variants are used to achieve heterodimerization, by using the constant region(s) of the heavy chain(s), a more modular approach to designing and purifying bispecific proteins, including antibodies, is provided. Thus, in some embodiments, heterodimerization variants (including skew and pI heterodimerization variants) are not included in the variable regions, such that each individual antibody must be engineered. In addition, in some embodiments, the possibility of immunogenicity resulting from the pI variants is significantly reduced by importing pI variants from different IgG isotypes such that pI is changed without introducing significant immunogenicity. Thus, an additional problem to be solved is the elucidation of low pI constant domains with high human sequence content, e.g., the minimization or avoidance of non-human residues at any particular position. Alternatively or in addition to isotypic substitutions, the possibility of immunogenicity resulting from the pI variants is significantly reduced by utilizing isosteric substitutions (e.g. Asn to Asp; and Gln to Glu).

As discussed below, a side benefit that can occur with this pI engineering is also the extension of serum half-life and increased FcRn binding. That is, as described in US Publ. App. No. US 2012/0028304 (incorporated by reference in its entirety), lowering the pI of antibody constant domains (including those found in antibodies and Fc fusions) can lead to longer serum retention in vivo. These pI variants for increased serum half-life also facilitate pI changes for purification.

In addition, it should be noted that the pI variants give an additional benefit for the analytics and quality control process of bispecific antibodies, as the ability to either eliminate, minimize and distinguish when homodimers are present is significant. Similarly, the ability to reliably test the reproducibility of the heterodimeric antibody production is important.

In general, embodiments of particular use rely on sets of variants that include skew variants, which encourage heterodimerization formation over homodimerization formation, coupled with pI variants, which increase the pI difference between the two monomers to facilitate purification of heterodimers away from homodimers.

Exemplary combinations of pI variants are shown in FIGS. 4 and 5, and FIG. 30 of US Publ. App. No. 2016/0355608, all of which are herein incorporated by reference in its entirety and specifically for the disclosure of pI variants. Preferred combinations of pI variants are shown in FIGS. 3A-3F and 4. As outlined herein and shown in the figures, these changes are shown relative to IgG1, but all isotypes can be altered this way, as well as isotype hybrids. In the case where the heavy chain constant domain is from IgG2-4, R133E and R133Q can also be used.

In one embodiment, a preferred combination of pI variants has one monomer (the negative Fab side) comprising 208D/295E/384D/418E/421D variants (N208D/Q295E/N384D/Q418E/N421D when relative to human IgG1) and a second monomer (the positive scFv side) comprising a positively charged scFv linker, including (GKPGS)$_4$ (SEQ ID NO:443). However, as will be appreciated by those in the art, the first monomer includes a CH1 domain, including position 208. Accordingly, in constructs that do not include a CH1 domain (for example for antibodies that do not utilize a CH1 domain on one of the domains), a preferred negative pI variant Fc set includes 295E/384D/418E/421D variants (Q295E/N384D/Q418E/N421D when relative to human IgG1).

Accordingly, in some embodiments, one monomer has a set of substitutions from FIG. 8 and the other monomer has a charged linker (either in the form of a charged scFv linker because that monomer comprises an scFv or a charged domain linker, as the format dictates, which can be selected from those depicted in FIG. 6A-6B).

In some embodiments, modifications are made in the hinge of the Fc domain, including positions 216, 217, 218, 219, 220, 221, 222, 223, 224, 225, 226, 227, 228, 229, and 230 based on EU numbering. Thus, pI mutations and particularly substitutions can be made in one or more of positions 216-230, with 1, 2, 3, 4 or 5 mutations finding use. Again, all possible combinations are contemplated, alone or with other pI variants in other domains.

Specific substitutions that find use in lowering the pI of hinge domains include, but are not limited to, a deletion at position 221, a non-native valine or threonine at position 222, a deletion at position 223, a non-native glutamic acid at position 224, a deletion at position 225, a deletion at position 235 and a deletion or a non-native alanine at position 236. In some cases, only pI substitutions are done in the hinge domain, and in others, these substitution(s) are added to other pI variants in other domains in any combination.

In some embodiments, mutations can be made in the CH2 region, including positions 233, 234, 235, 236, 274, 296, 300, 309, 320, 322, 326, 327, 334 and 339, based on EU numbering. It should be noted that changes in 233-236 can be made to increase effector function (along with 327A) in the IgG2 backbone. Again, all possible combinations of these 14 positions can be made; e.g., an antibody provided herein may include a variant Fc domain with 1, 2, 3, 4, 5, 6, 7, 8, 9 or 10 CH2 pI substitutions.

Specific substitutions that find use in lowering the pI of CH2 domains include, but are not limited to, a non-native glutamine or glutamic acid at position 274, a non-native phenylalanine at position 296, a non-native phenylalanine at position 300, a non-native valine at position 309, a non-native glutamic acid at position 320, a non-native glutamic acid at position 322, a non-native glutamic acid at position 326, a non-native glycine at position 327, a non-native glutamic acid at position 334, a non-native threonine at position 339, and all possible combinations within CH2 and with other domains.

In this embodiment, the modifications can be independently and optionally selected from position 355, 359, 362, 384, 389,392, 397, 418, 419, 444 and 447 (EU numbering) of the CH3 region. Specific substitutions that find use in lowering the pI of CH3 domains include, but are not limited to, a non-native glutamine or glutamic acid at position 355, a non-native serine at position 384, a non-native asparagine or glutamic acid at position 392, a non-native methionine at position 397, a non-native glutamic acid at position 419, a non-native glutamic acid at position 359, a non-native glutamic acid at position 362, a non-native glutamic acid at position 389, a non-native glutamic acid at position 418, a non-native glutamic acid at position 444, and a deletion or non-native aspartic acid at position 447.

In some embodiments, the anti-CD28× anti-PSMA antibody includes amino acid substitutions in one of its Fc domains that reduces binding to Protein A. Such purification variants produces heterodimers with asymmetric binding to Protein A, which can in turn be used for separation of heterodimeric from homodimeric populations by a pH gradient. Exemplary purification amino acid substitutions that reduce binding to Protein A include, but are not limited to H435R and Y436F (IgG1 CH3 domain, EU numbering). See, e.g., US2010331527, which is incorporated by reference in its entirety, and specifically for pertinent disclosures relating to Fc domain modifications to reduce Protein A binding.

3. Isotypic Variants

In addition, many embodiments of the subject heterodimeric antibodies rely on the "importation" of pI amino acids at particular positions from one IgG isotype into another, thus reducing or eliminating the possibility of unwanted immunogenicity being introduced into the variants. A number of these are shown in FIG. 21 of US Publ. 2014/0370013, hereby incorporated by reference. That is, IgG1 is a common isotype for therapeutic antibodies for a variety of reasons, including high effector function. However, the heavy constant region of IgG1 has a higher pI than that of IgG2 (8.10 versus 7.31). By introducing IgG2 residues at particular positions into the IgG1 backbone, the pI of the resulting monomer is lowered (or increased) and additionally exhibits longer serum half-life. For example, IgG1 has a glycine (pI 5.97) at position 137, and IgG2 has a glutamic acid (pI 3.22); importing the glutamic acid will affect the pI of the resulting protein. As is described below, a number of amino acid substitutions are generally required to significant affect the pI of the variant antibody. However, it should be noted as discussed below that even changes in IgG2 molecules allow for increased serum half-life.

In other embodiments, non-isotypic amino acid changes are made, either to reduce the overall charge state of the resulting protein (e.g., by changing a higher pI amino acid to a lower pI amino acid), or to allow accommodations in structure for stability, etc. as is more further described below.

In addition, by pI engineering both the heavy and light constant domains, significant changes in each monomer of the heterodimer can be seen. As discussed herein, having the pIs of the two monomers differ by at least 0.5 can allow separation by ion exchange chromatography or isoelectric focusing, or other methods sensitive to isoelectric point.

4. Calculating pI

The pI of each monomer of the antibodies provided herein can depend on the pI of the variant heavy chain constant domain and the pI of the total monomer, including the variant heavy chain constant domain and the fusion partner. Thus, in some embodiments, the change in pI is calculated on the basis of the variant heavy chain constant domain, using the chart in the FIG. 19 of US Pub. 2014/0370013. As discussed herein, which monomer to engineer is generally decided by the inherent pI of the Fv and scaffold regions. Alternatively, the pI of each monomer can be compared.

5. pI Variants that Also Confer Better FcRn In Vivo Binding

In the case where the pI variant decreases the pI of the monomer, the pI variant can have the added benefit of improving serum retention in vivo.

Although still under examination, Fc regions are believed to have longer half-lives in vivo, because binding to FcRn at pH 6 in an endosome sequesters the Fc (Ghetie and Ward, 1997 Immunol Today. 18(12): 592-598, entirely incorporated by reference). The endosomal compartment then recycles the Fc to the cell surface. Once the compartment opens to the extracellular space, the higher pH, ~7.4, induces the release of Fc back into the blood. In mice, Dall' Acqua et al. showed that Fc mutants with increased FcRn binding at pH 6 and pH 7.4 actually had reduced serum concentrations and the same half-life as wild-type Fc (Dall' Acqua et al. 2002, J. Immunol. 169:5171-5180, entirely incorporated by reference). The increased affinity of Fc for FcRn at pH 7.4 is thought to forbid the release of the Fc back into the blood. Therefore, the Fc mutations that will increase Fc's half-life in vivo will ideally increase FcRn binding at the lower pH while still allowing release of Fc at higher pH. The amino acid histidine changes its charge state in the pH range of 6.0 to 7.4. Therefore, it is not surprising to find His residues at important positions in the Fc/FcRn complex.

Recently it has been suggested that antibodies with variable regions that have lower isoelectric points may also have longer serum half-lives (Igawa et al., 2010 PEDS. 23(5): 385-392, entirely incorporated by reference). However, the mechanism of this is still poorly understood. Moreover, variable regions differ from antibody to antibody. Constant region variants with reduced pI and extended half-life would provide a more modular approach to improving the pharmacokinetic properties of antibodies, as described herein.

E. Additional Fc Variants for Additional Functionality

In addition to the heterodimerization variants discussed above, there are a number of useful Fc amino acid modification that can be made for a variety of reasons, including, but not limited to, altering binding to one or more FcγR receptors, altered binding to FcRn receptors, etc., as discussed below.

Accordingly, the antibodies provided herein (heterodimeric, as well as homodimeric) can include such amino acid modifications with or without the heterodimerization variants outlined herein (e.g., the pI variants and steric variants). Each set of variants can be independently and optionally included or excluded from any particular heterodimeric protein.

1. FcγR and FcRn Variants

Accordingly, there are a number of useful Fc substitutions that can be made to alter binding to one or more of the FcγR receptors. In certain embodiments, the subject antibody includes modifications that alter the binding to one or more FcγR receptors (i.e., "FcγR variants"). Substitutions that result in increased binding as well as decreased binding can be useful. For example, it is known that increased binding to FcγRIIIa generally results in increased ADCC (antibody dependent cell-mediated cytotoxicity; the cell-mediated reaction wherein nonspecific cytotoxic cells that express FcγRs recognize bound antibody on a target cell and subsequently cause lysis of the target cell). Similarly, decreased binding to FcγRIIb (an inhibitory receptor) can be beneficial as well in some circumstances. Amino acid substitutions that find use in the subject antibodies include those listed in U.S. Pat. No. 8,188,321 (particularly FIG. 41) and U.S. Pat. No. 8,084,582, and US Publ. App. Nos. 20060235208 and 20070148170, all of which are expressly incorporated herein by reference in their entirety and specifically for the variants disclosed therein that affect Fcγ receptor binding. Particular variants that find use include, but are not limited to, 236A, 239D, 239E, 332E, 332D, 239D/332E, 267D, 267E, 328F, 267E/328F, 236A/332E, 239D/332E/330Y, 239D, 332E/330L, 243A, 243L, 264A, 264V and 299T. Such modification may be included in one or both Fc domains of the subject antibody.

In some embodiments, the subject antibody includes one or more Fc modifications that increase serum half-life. Fc substitutions that find use in increased binding to the FcRn receptor and increased serum half-life, as specifically disclosed in U.S. Ser. No. 12/341,769, hereby incorporated by reference in its entirety, including, but not limited to, 434S, 434A, 428L, 308F, 259I, 428L/434S, 259I/308F, 436I/428L, 436I or V/434S, 436V/428L, 259I/308F/428L, and M252Y/S254T/T256E. Such modification may be included in one or both Fc domains of the subject antibody.

2. Ablation Variants

In some embodiments, the heterodimeric antibody includes one or more modifications that reduce or remove the normal binding of the Fc domain to one or more or all of the Fcγ receptors (e.g., FcγR1, FcγRIIa, FcγRIIb, FcγRIIIa, etc.) to avoid additional mechanisms of action. Such modifications are referred to as "FcγR ablation variants" or "Fc knock out (FcKO or KO)" variants. In these embodiments, for some therapeutic applications, it is desirable to reduce or remove the normal binding of the Fc domain to one or more or all of the Fcγ receptors (e.g., FcγR1, FcγRIIa, FcγRIIb, FcγRIIIa, etc.) to avoid additional mechanisms of action. That is, for example, in many embodiments, particularly in the use of bispecific antibodies that bind CD28 monovalently, it is generally desirable to ablate FcγRIIIa binding to eliminate or significantly reduce ADCC activity. In some embodiments, of the subject antibodies described herein, at least one of the Fc domains comprises one or more Fcγ receptor ablation variants. In some embodiments, of the subject antibodies described herein, both of the Fc domains comprises one or more Fcγ receptor ablation variants. These ablation variants are depicted in FIG. 5, and each can be independently and optionally included or excluded, with preferred aspects utilizing ablation variants selected from the group consisting of: L234A/L235A/D265S, G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del. It should be noted that the ablation variants referenced herein ablate FcγR binding but generally not FcRn binding.

As is known in the art, the Fc domain of human IgG1 has the highest binding to the Fcγ receptors, and thus ablation variants can be used when the constant domain (or Fc domain) in the backbone of the heterodimeric antibody is IgG1. Alternatively, or in addition to ablation variants in an IgG1 background, mutations at the glycosylation position 297 (generally to A or S) can significantly ablate binding to FcγRIIIa, for example. Human IgG2 and IgG4 have naturally reduced binding to the Fcγ receptors, and thus those backbones can be used with or without the ablation variants.

F. Combination of Heterodimeric and Fc Variants

As will be appreciated by those in the art, all of the recited heterodimerization variants (including skew and/or purification variants) can be optionally and independently combined in any way, as long as they retain their "strandedness" or "monomer partition". In addition, all of these variants can be combined into any of the heterodimerization formats.

In the case of pI variants, while embodiments finding particular use are shown in the figures, other combinations can be generated, following the basic rule of altering the pI difference between two monomers to facilitate purification.

In addition, any of the heterodimerization variants (skew and purification variants), are also independently and optionally combined with Fc ablation variants, Fc variants, FcRn variants, as generally outlined herein.

Exemplary combination of variants that are included in some embodiments of the heterodimeric 1+1 Fab-scFv-Fc, and 2+1 Fab$_2$-scFv-Fc format antibodies are included in FIG. 8. In some embodiments, the heterodimeric antibody includes a combination of variants as depicted in FIG. 8. In certain embodiments, the antibody is a heterodimeric 1+1 Fab-scFv-Fc, or 2+1 Fab2-scFv-Fc format antibody that includes the "platform X" combination of variants depicted in FIG. 8. In certain embodiments, the antibody is a heterodimeric 1+1 Fab-scFv-Fc, or 2+1 Fab$_2$-scFv-Fc format antibody that includes the "platform J" combination of variants depicted in FIG. 8.

G. Useful Antibody Formats

As will be appreciated by those in the art and discussed more fully below, the heterodimeric bispecific antibodies provided herein can take on several different configurations as generally depicted in FIG. 24A-24M.

As will be appreciated by those in the art, the heterodimeric formats of the invention can have different valencies as well as be bispecific. That is, heterodimeric antibodies of the invention can be bivalent and bispecific, or trivalent and bispecific, wherein the first antigen is bound by two binding domains and the second antigen by a second binding domain. As is outlined herein, when CD28 is one of the target antigens, it is preferable that the CD28 is bound only monovalently.

The present invention utilizes CD28 binding domains in combination with PSMA binding domains. As will be appreciated by those in the art, any collection of anti-CD28 CDRs, anti-CD28 variable light and variable heavy domains, Fabs and scFvs as depicted in any of the Figures (see particularly FIGS. 15-18C, and 21A-21H) can be used. Similarly, any of the PSMA antigen binding domains can be used, whether CDRs, variable light and variable heavy domains, Fabs and scFvs as depicted in any of the Figures (e.g., FIGS. 25A-25E and 26A-26B) can be used, optionally and independently combined in any combination.

1. 1+1 Fab-scFv-Fc Format

One heterodimeric antibody format that finds particular use in subject anti-CD28× anti-PSMA antibodies provided herein is the "1+1 Fab-scFv-Fc" or "bottle opener" format as shown in FIG. 24A. The 1+1 Fab-scFv-Fc format antibody includes a first monomer that is a "regular" heavy chain (VH1-CH1-hinge-CH2-CH3), wherein VH1 is a first variable heavy domain and CH2-CH3 is a first Fc domain. The 1+1 Fab-scFv-Fc also includes a light chain that includes a first variable light domain VL1 and a constant light domain CL. The light chain interacts with the VH1-CH1 of the first monomer to form a first antigen binding domain that is a Fab. The second monomer of the antibody includes a second binding domain that is a single chain Fv ("scFv", as defined below) and a second Fc domain. The scFv includes a second variable heavy domain (VH2) and a second variable light domain (VL2), wherein the VH2 is attached to the VL2 using an scFv linker that can be charged (see, e.g., FIGS. 6A-6B). The scFv is attached to the heavy chain using a domain linker (see, e.g., FIG. 7). The two monomers are brought together by the use of amino acid variants (e.g., heterodimerization variants, discussed above) in the constant regions (e.g., the Fc domain, the CH1 domain and/or the hinge region) that promote the formation of heterodimeric antibodies as is described more fully below. This structure is sometimes referred to herein as the "bottle-opener" format, due to a rough visual similarity to a bottle-opener. In some embodiments, the 1+1 Fab-scFv-Fc format antibody is a bivalent antibody.

There are several distinct advantages to the present "1+1 Fab-scFv-Fc" format. As is known in the art, antibody analogs relying on two scFv constructs often have stability and aggregation problems, which can be alleviated in the present invention by the addition of a "regular" heavy and light chain pairing. In addition, as opposed to formats that rely on two heavy chains and two light chains, there is no issue with the incorrect pairing of heavy and light chains (e.g., heavy 1 pairing with light 2, etc.).

In some embodiments of the 1+1 Fab-scFv-Fc format antibody, one of the first or second antigen binding domain is a CD28 binding domain and the other binding domain is a PSMA binding domain. In some embodiments where the 1+1 Fab-scFv-Fc, it is the scFv that binds to the CD28, and the Fab that binds PSMA. Exemplary anti-CD28× anti-PSMA bispecific antibodies in the 1+1 Fab-scFv-Fc format are depicted in FIGS. 29A-29RR and 30A-30L.

In some embodiments, the first and second Fc domains of the 1+1 Fab-scFv-Fc format antibody are variant Fc domains that include heterodimerization skew variants (e.g., a set of amino acid substitutions as shown in FIGS. 3A-3F and 9). Particularly useful heterodimerization skew variants include S364K/E357Q:L368D/K370S; L368D/K370S: S364K; L368E/K370S:S364K; T411T/E360E/Q362E:D401K; L368D/K370S:S364K/E357L; K370S:S364K/E357Q; T366S/L368A/Y407V:T366W and T366S/L368A/Y407V/Y349C:T366W/S354C (EU numbering)). In exemplary embodiments, one of the first or second variant Fc domains includes heterodimerization skew variants L368D/K370S and the other of the first or second variant Fc domains includes heterodimerization skew variants S364K/E357Q, wherein numbering is according to EU numbering. In exemplary embodiments, the first variant Fc domain includes heterodimerization skew variants L368D/K370S and the second variant Fc domain includes heterodimerization skew variants S364K/E357Q, wherein numbering is according to EU numbering.

In some embodiments, the variant Fc domains include ablation variants (including those shown in FIG. 5). In some embodiments, each of the first and second variant Fc domains include ablation variants E233P/L234V/L235A/G236_/S267K, wherein numbering is according to EU numbering.

In some embodiments, the constant domain (CH1-hinge-CH2-CH3) of the first monomer includes pI variants (including those shown in FIG. 4). In exemplary embodiments, the constant domain (CH1-hinge-CH2-CH3) of the first monomer includes pI variants N208D/Q295E/N384D/Q418E/N421D, wherein numbering is according to EU numbering.

In exemplary embodiments, the 1+1 Fab-scFv-Fc format antibody include "Platform X" amino acid modifications as depicted in FIG. 8. In such embodiments, the CH1-hinge-CH2-CH3 of the first monomer comprises amino acid variants L368D/K370S/N208D/Q295E/N384D/Q418E/N421D/E233P/L234V/L235A/G236del/S267 K, the second Fc domain comprises amino acid variants S364K/E357Q/E233P/L234V/L235A/G236del/S267K, wherein numbering is according to EU numbering.

In some embodiments, the scFv of the 1+1 Fab-scFv-Fc format antibody provided herein includes a charged scFv linker (including those shown in FIGS. 6A-6B). In some embodiments, the 1+1 Fab-scFv-Fc format antibody provided herein includes FcRn variants M428L/N434S, wherein numbering is according to EU numbering.

In exemplary embodiments 1+1 Fab-scFv-Fc format antibody with "Platform X" variants, the first Fc domain includes heterodimerization skew variants L368D/K370S and the second Fc domain includes heterodimerization skew variants S364K/E357Q; each of the first and second Fc domains include ablation variants E233P/L234V/L235A/G236_/S267K; and the constant domain (CH1-hinge-CH2-CH3) of the first monomer includes pI variants N208D/Q295E/N384D/Q418E/N421D, wherein numbering is according to EU numbering. In some embodiments, the scFv of the 1+1 Fab-scFv-Fc format antibody provided herein includes a (GKPGS)$_4$ charged scFv linker (SEQ ID NO:443). In some embodiments, the 1+1 Fab-scFv-Fc format antibody provided herein includes FcRn variants M428L/N434S, wherein numbering is according to EU numbering. In some embodiments, the scFv of the 1+1 Fab-scFv-Fc format antibody provided herein includes a charged scFv linker (including those shown in FIGS. 6A-6B).

In exemplary embodiments, the 1+1 Fab-scFv-Fc format antibody include "Platform J" amino acid modifications as depicted in FIG. 8. In such embodiments, the first Fc domain comprises amino acid substitutions L234A/L235A/D265S/T366S/L368A/Y407V/H435R/Y436F, and the first Fc domain comprises amino acid substitutions L234A/L235A/D265S/LT366W, wherein numbering is according to EU numbering.

In exemplary embodiments 1+1 Fab-scFv-Fc format antibody with Platform J variants, the first Fc domain includes heterodimerization skew variants T366S/L368A/Y407V and the second Fc domain includes heterodimerization skew variants T366W; each of the first and second variant Fc domains include ablation variants L234A/L235A/D265S; and the second Fc domain includes purification variants H435R/Y436F, wherein numbering is according to EU numbering. In some embodiments, the scFv of the 1+1 Fab-scFv-Fc format antibody provided herein includes a (GKPGS)4 charged scFv linker (SEQ ID NO:443). In some embodiments, the 1+1 Fab-scFv-Fc format antibody provided herein includes FcRn variants M252Y/S254T/T256E, wherein numbering is according to EU numbering. In some embodiments, the scFv of the 1+1 Fab-scFv-Fc format antibody provided herein includes a charged scFv linker (including those shown in FIGS. 6A-6B).

In exemplary embodiments, the 1+1 Fab-scFv-Fc format antibody with Platform J variants further includes a "stapled" scFv (e.g., a "stapled" anti-CD28 scFv). Stapled" scFvs that exhibit improved stability and/or reduced aggregation are further described in detail herein. Exemplary staple linkers that are useful for inclusion in such "stapled" scFvs are provided in FIGS. 6A-6B. In exemplary embodiments, the stapled linker is GGGSGGSGGCPPCGGSGG (SEQ ID NO:457).

In some embodiments, one of the first binding domain or the second binding domain binds CD28 and the other binding domain binds a tumor associated antigen (TAA) (see FIG. 34A). Any suitable CD28 binding domain can be included in subject 1+1 Fab-scFv-Fc format antibody, including any of the CD28 binding domains provided herein. In some embodiments, the CD28 binding domain is one of the following CD28 binding domains or a variant thereof: 1A7[CD28]_H1L1, 1A7[CD28]_H1. 1_L1, 1A7[CD28]_H1_L1.71, 1A7[CD28]_H1.1_L1.71, 1A7[CD28] H1.14_L1, 1A7[CD28]_H1.14_L1.71, 1A7[CD28]_ H1sp_L1sp, 1A7[CD28]_H1.1sp_L1sp, 1A7[CD28] H1sp_L1.71sp, 1A7[CD28]_H1.1sp_L1.71sp, 1A7[CD28]_ H1.14sp_L1sp, 1A7[CD28]_H1.14sp_L1.71sp, CD28.3 [CD28]_H0L0, hCD28.3[CD28]_H1L1, 5.11A1[CD28]_ H0L0, TGN1412_H1L1, 341VL34[CD28]_H1L1, 341VL36[CD28]_H1L1, 281VL4[CD28]_H1L1, HuTN228 [CD28]_H1L1, PV1[CD28]H0L0, m9.3[CD28]_H0L0, hu9.3[CD28]_H1L1, 9G2[CD28]_H0L0, 9G2[CD28]_ H1L1, 2F10A3.140[CD28]_H1L1, and TN228[CD28]_ H4L2 (FIGS. 15-18C, 21A-21H, and 69A-69C).

In some embodiments of the 1+1 Fab-scFv-Fc format, the anti-CD28 ABD has a VH and VL domain selected from the following:
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:9; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:13; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:31; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:35; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:39; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:43; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:47; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:51; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:55; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:59; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:63; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:67; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:86; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:90; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:94; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:98; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 102; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:106; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:110; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:114; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:118; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:122; or
  (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 126; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:130; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 134; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:138; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 142; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:146; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 150; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:154; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 158; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:162; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 166; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:170; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 174; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:178; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:182; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:186; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 190; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:194; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 198; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:202; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:380; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:384; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:388; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:392; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:396; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:400; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:404; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:408; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:412; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:416; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:420; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:424.

In some embodiments of the 1+1 Fab-scFv-Fc format, the anti-CD28 ABD has a VH and VL domain selected from the following:
(i) a VH comprising a vhCDR1 having an amino acid sequence of SEQ ID NO:10; a vhCDR2 having an amino acid sequence of SEQ ID NO:11; and a vhCDR3 having an amino acid sequence of SEQ ID NO: 12; and (ii) a VL comprising a vlCDR1 having an amino acid sequence of SEQ ID NO: 14, a vlCDR2 having an amino acid sequence of SEQ ID NO: 15, and a vlCDR3 having an amino acid sequence of SEQ ID NO:16; or (i) a VH comprising a vhCDR1 having an amino acid sequence of SEQ ID NO:32; a vhCDR2 having an amino acid sequence of SEQ ID NO:33; and a vhCDR3 having an amino acid sequence of SEQ ID NO:34; and (ii) a VL comprising a vlCDR1 having an amino acid sequence of SEQ ID NO: 36, a vlCDR2 having an amino acid sequence of SEQ ID NO: 37, and a vlCDR3 having an amino acid sequence of SEQ ID NO:38; or i) a VH comprising a vhCDR1 having an amino acid sequence of SEQ ID NO:40; a vhCDR2 having an amino acid sequence of SEQ ID NO:41; and a vhCDR3 having an amino acid sequence of SEQ ID NO:42; and (ii) a VL comprising a vlCDR1 having an amino acid sequence of SEQ ID NO:44, a vlCDR2 having an amino acid sequence of SEQ ID NO: 45, and a vlCDR3 having an amino acid sequence of SEQ ID NO:46; or i) a VH comprising a vhCDR1 having an amino acid sequence of SEQ ID NO:48; a vhCDR2 having an amino acid sequence of SEQ ID NO:49; and a vhCDR3 having an amino acid sequence of SEQ ID NO:50; and (ii) a VL comprising a vlCDR1 having an amino acid sequence of SEQ ID NO:52, a vlCDR2 having an amino acid sequence of SEQ ID NO: 53, and a vlCDR3 having an amino acid sequence of SEQ ID NO:54; or i) a VH comprising a vhCDR1 having an amino acid sequence of SEQ ID NO:56; a vhCDR2 having an amino acid sequence of SEQ ID NO:57; and a vhCDR3 having an amino acid sequence of SEQ ID NO:58; and (ii) a VL comprising a vlCDR1 having an amino acid sequence of SEQ ID NO:60, a vlCDR2 having an amino acid sequence of SEQ ID NO:61, and a vlCDR3 having an amino acid sequence of SEQ ID NO:62; or i) a VH comprising a vhCDR1 having an amino acid sequence of SEQ ID NO:64; a vhCDR2 having an amino acid sequence of SEQ ID NO:65; and a vhCDR3 having an amino acid sequence of SEQ ID NO:66; and (ii) a VL comprising a vlCDR1 having an amino acid sequence of SEQ ID NO:68, a vlCDR2 having an amino acid sequence of SEQ ID NO:69, and a vlCDR3 having an amino acid sequence of SEQ ID NO:70; or i) a VH comprising a vhCDR1 having an amino acid sequence of SEQ ID NO:87; a vhCDR2 having an amino acid sequence of SEQ ID NO:88; and a vhCDR3 having an amino acid sequence of SEQ ID NO:89; and (ii) a VL comprising a vlCDR1 having an amino acid sequence of SEQ ID NO:91, a vlCDR2 having an amino acid sequence of SEQ ID NO:92, and a vlCDR3 having an amino acid sequence of SEQ ID NO:93; or i) a VH comprising a vhCDR1 having an amino acid sequence of SEQ ID NO:95; a vhCDR2 having an amino acid sequence of SEQ ID NO:96; and a vhCDR3 having an amino acid sequence of SEQ ID NO:97; and (ii) a VL comprising a vlCDR1 having an amino acid sequence of SEQ ID NO:99, a vlCDR2 having an amino acid sequence of SEQ ID NO:100, and a vlCDR3 having an amino acid sequence of SEQ ID NO:101; or i) a VH comprising a vhCDR1 having an amino acid sequence of SEQ ID NO:103; a vhCDR2 having an amino acid sequence of SEQ ID NO:104; and a vhCDR3 having an amino acid sequence of SEQ ID NO:105; and (ii) a VL comprising a vlCDR1 having an amino acid sequence of SEQ ID NO: 107, a vlCDR2 having an amino acid sequence of SEQ ID NO:108, and a vlCDR3 having an amino acid sequence of SEQ ID NO:109; or i) a VH comprising a vhCDR1 having an amino acid sequence of SEQ ID NO:111; a vhCDR2 having an amino acid sequence of SEQ ID NO:112; and a vhCDR3 having an amino acid sequence of SEQ ID NO:113; and (ii) a VL comprising a vlCDR1 having an amino acid sequence of SEQ ID NO: 115, a vlCDR2 having an amino acid sequence of SEQ ID NO:116, and a vlCDR3 having an amino acid sequence of SEQ ID NO:117; or i) a VH comprising a vhCDR1 having an amino acid sequence of SEQ ID NO:119; a vhCDR2 having an amino acid sequence of SEQ ID NO:120; and a vhCDR3 having an amino acid sequence of SEQ ID NO:121; and (ii) a VL comprising a vlCDR1 having an amino acid sequence of SEQ ID NO: 123, a vlCDR2 having an amino acid sequence of SEQ ID NO:124, and a vlCDR3 having an amino acid sequence of SEQ ID NO:125; or i) a VH comprising a vhCDR1 having an amino acid sequence of SEQ ID NO:127; a vhCDR2 having an amino acid sequence of SEQ ID NO:128; and a vhCDR3 having an amino acid sequence of SEQ ID NO:129; and (ii) a VL comprising a vlCDR1 having an amino acid sequence of SEQ ID NO:131, a vlCDR2 having an amino acid sequence of SEQ ID NO:132, and a vlCDR3 having an amino acid sequence of SEQ ID NO:133; or i) a VH comprising a vhCDR1 having an amino acid sequence of SEQ ID NO:135; a vhCDR2 having an amino acid sequence of SEQ ID NO:136; and a vhCDR3 having an amino acid sequence of SEQ ID NO:137; and (ii) a VL comprising a vlCDR1 having an amino acid sequence of SEQ ID NO: 139, a vlCDR2 having an amino acid sequence of SEQ ID NO:140, and a vlCDR3 having an amino acid sequence of SEQ ID NO:141; or i) a VH comprising a vhCDR1 having an amino acid sequence of SEQ ID NO:143; a vhCDR2 having an amino acid sequence of SEQ ID NO:144; and a vhCDR3 having an amino acid sequence of SEQ ID NO:115; and (ii) a VL comprising a vlCDR1 having an amino acid sequence of SEQ ID NO: 147, a vlCDR2 having an amino acid sequence of SEQ ID NO:149, and a vlCDR3 having an amino acid sequence of SEQ ID NO:149; or i) a VH comprising a vhCDR1 having an amino acid sequence of SEQ ID NO:151; a vhCDR2 having an amino acid sequence of SEQ ID NO:152; and a vhCDR3 having an amino acid sequence of SEQ ID NO:153; and (ii) a VL comprising a vlCDR1 having an amino acid sequence of SEQ ID NO: 155, a vlCDR2 having an amino acid sequence of SEQ ID NO:156, and a vlCDR3 having an amino acid sequence of SEQ ID NO:157; or i) a VH comprising a vhCDR1 having an amino acid sequence of SEQ ID NO:159; a vhCDR2 having an amino acid sequence of SEQ ID NO:160; and a vhCDR3 having an amino acid sequence of SEQ ID NO:161; and (ii) a VL comprising a vlCDR1 having an amino acid sequence of SEQ ID NO: 163, a vlCDR2 having an amino acid sequence of SEQ ID NO:164, and a vlCDR3 having an amino acid sequence of SEQ ID NO:165; or i) a VH comprising a vhCDR1 having an amino acid sequence of SEQ ID NO:167; a vhCDR2 having an amino acid sequence of SEQ ID NO:168; and a vhCDR3 having an amino acid sequence of SEQ ID NO:169; and (ii) a VL comprising a vlCDR1 having an amino acid sequence of SEQ ID NO:171, a vlCDR2 having an amino acid sequence of SEQ ID NO:172, and a vlCDR3 having an amino acid sequence of SEQ ID NO:173; or i) a VH comprising a vhCDR1 having an amino acid sequence of SEQ ID NO:175; a vhCDR2 having an amino acid sequence of SEQ ID NO:176; and a vhCDR3 having an amino acid sequence of SEQ ID NO: 177; and (ii) a VL comprising a vlCDR1 having an amino acid sequence of SEQ ID NO:179, a vlCDR2 having an amino acid sequence of SEQ ID NO:180, and a vlCDR3 having an amino acid sequence of SEQ ID NO:181; or i) a VH comprising a vhCDR1 having an amino acid sequence of SEQ ID NO:183; a vhCDR2 having an amino acid sequence of SEQ ID NO:184; and a vhCDR3 having an amino acid sequence of SEQ ID NO:185; and (ii) a VL comprising a vlCDR1 having an amino acid sequence of SEQ ID NO: 187, a vlCDR2 having an amino acid sequence of SEQ ID NO:188, and a vlCDR3 having an amino acid sequence of SEQ ID NO:189; or i) a VH comprising a vhCDR1 having an amino acid sequence of SEQ ID NO:191; a vhCDR2 having an amino acid sequence of SEQ ID NO:192; and a vhCDR3 having an amino acid sequence of SEQ ID NO:193; and (ii) a VL comprising a vlCDR1 having an amino acid sequence of SEQ ID NO: 195, a vlCDR2 having an amino acid sequence of SEQ ID NO:196, and a vlCDR3 having an amino acid sequence of SEQ ID NO:197; or i) a VH comprising a vhCDR1 having an amino acid sequence of SEQ ID NO:199; a vhCDR2 having an amino acid sequence of SEQ ID NO:200; and a vhCDR3 having an amino acid sequence of SEQ ID NO:201; and (ii) a VL comprising a vlCDR1 having an amino acid sequence of SEQ ID NO:203, a vlCDR2 having an amino acid sequence of SEQ ID NO:204, and a vlCDR3 having an amino acid sequence of SEQ ID NO:205; or i) a VH comprising a vhCDR1 having an amino acid sequence of SEQ ID NO:381; a vhCDR2 having an amino acid sequence of SEQ ID NO:382; and a vhCDR3 having an amino acid sequence of SEQ ID NO:383; and (ii) a VL comprising a vlCDR1 having an amino acid sequence of SEQ ID NO:385, a vlCDR2 having an amino acid sequence of SEQ ID NO:386, and a vlCDR3 having an amino acid sequence of SEQ ID NO:387; or i) a VH comprising a vhCDR1 having an amino acid sequence of SEQ ID NO:389; a vhCDR2 having an amino acid sequence of SEQ ID NO:390; and a vhCDR3 having an amino acid sequence of SEQ ID NO:391; and (ii) a VL comprising a vlCDR1 having an amino acid sequence of SEQ ID NO:393, a vlCDR2 having an amino acid sequence of SEQ ID NO:394, and a vlCDR3 having an amino acid sequence of SEQ ID NO:395; or i) a VH comprising a vhCDR1 having an amino acid sequence of SEQ ID NO:397; a vhCDR2 having an amino acid sequence of SEQ ID NO:398; and a vhCDR3 having an amino acid sequence of SEQ ID NO:399; and (ii) a VL comprising a vlCDR1 having an amino acid sequence of SEQ ID NO:401, a vlCDR2 having an amino acid sequence of SEQ ID NO:402, and a vlCDR3 having an amino acid sequence of SEQ ID NO:403; or i) a VH comprising a vhCDR1 having an amino acid sequence of SEQ ID NO:405; a vhCDR2 having an amino acid sequence of SEQ ID NO:406; and a vhCDR3 having an amino acid sequence of SEQ ID NO:407; and (ii) a VL comprising a vlCDR1 having an amino acid sequence of SEQ ID NO:409, a vlCDR2 having an amino acid sequence of SEQ ID NO:410, and a vlCDR3 having an amino acid sequence of SEQ ID NO:411; or i) a VH comprising a vhCDR1 having an amino acid sequence of SEQ ID NO:413; a vhCDR2 having an amino acid sequence of SEQ ID NO:414; and a vhCDR3 having an amino acid sequence of SEQ ID NO:415; and (ii) a VL comprising a vlCDR1 having an amino acid sequence of SEQ ID NO:417, a vlCDR2 having an amino acid sequence of SEQ ID NO:418, and a vlCDR3 having an amino acid sequence of SEQ ID NO:419; or i) a VH comprising a vhCDR1 having an amino acid sequence of SEQ ID NO:421; a vhCDR2 having an amino acid sequence of SEQ ID NO:422; and a vhCDR3 having an amino acid sequence of SEQ ID NO:423; and (ii) a VL comprising a vlCDR1 having an amino acid sequence of SEQ ID NO:425, a vlCDR2 having an amino acid sequence of SEQ ID NO:426, and a vlCDR3 having an amino acid sequence of SEQ ID NO:427.

In some embodiments of the 1+1 Fab-scFv-Fc format, the anti-CD28 ABD has a VH and VL domain selected from the following:

(i) a VH having an amino acid sequence of SEQ ID NO:9; and (ii) a VL having an amino acid sequence of SEQ ID NO:13; or (i) a VH having an amino acid sequence of SEQ ID NO:31; and (ii) a VL having an amino acid sequence of SEQ ID NO:35; or (i) a VH having an amino acid sequence of SEQ ID NO:39; and (ii) a VL having an amino acid sequence of SEQ ID NO:43; or (i) a VH having an amino acid sequence of SEQ ID NO:47; and (ii) a VL having an amino acid sequence of SEQ ID NO:51; or (i) a VH having an amino acid sequence of SEQ ID NO:55; and (ii) a VL having an amino acid sequence of SEQ ID NO:59; or (i) a VH having an amino acid sequence of SEQ ID NO:63; and (ii) a VL having an amino acid sequence of SEQ ID NO:67; or (i) a VH having an amino acid sequence of SEQ ID NO:86; and (ii) a VL having an amino acid sequence of SEQ ID NO:90; or (i) a VH having an amino acid sequence of SEQ ID NO:94; and (ii) a VL having an amino acid sequence of SEQ ID NO:98; or (i) a VH having an amino acid sequence of SEQ ID NO:102; and (ii) a VL having an amino acid sequence of SEQ ID NO:106; or (i) a VH having an amino acid sequence of SEQ ID NO:110; and (ii) a VL having an amino acid sequence of SEQ ID NO:114; or (i) a VH having an amino acid sequence of SEQ ID NO:118; and (ii) a VL having an amino acid sequence of SEQ ID NO:122; or (i) a VH having an amino acid sequence of SEQ ID NO:126; and (ii) a VL having an amino acid sequence of SEQ ID NO:130; or
(i) a VH having an amino acid sequence of SEQ ID NO:134; and (ii) a VL having an amino acid sequence of SEQ ID NO:138; or
(i) a VH having an amino acid sequence of SEQ ID NO:142; and (ii) a VL having an amino acid sequence of SEQ ID NO:146; or
(i) a VH having an amino acid sequence of SEQ ID NO:150; and (ii) a VL having an amino acid sequence of SEQ ID NO:154; or
(i) a VH having an amino acid sequence of SEQ ID NO:158; and (ii) a VL having an amino acid sequence of SEQ ID NO:162; or
(i) a VH having an amino acid sequence of SEQ ID NO:166; and (ii) a VL having an amino acid sequence of SEQ ID NO:170; or
(i) a VH having an amino acid sequence of SEQ ID NO:174; and (ii) a VL having an amino acid sequence of SEQ ID NO:178; or
(i) a VH having an amino acid sequence of SEQ ID NO:182; and (ii) a VL having an amino acid sequence of SEQ ID NO:186; or
(i) a VH having an amino acid sequence of SEQ ID NO:190; and (ii) a VL having an amino acid sequence of SEQ ID NO:194; or
(i) a VH having an amino acid sequence of SEQ ID NO:198; and (ii) a VL having an amino acid sequence of SEQ ID NO:202; or
(i) a VH having an amino acid sequence of SEQ ID NO:380; and (ii) a VL having an amino acid sequence of SEQ ID NO:384; or
(i) a VH having an amino acid sequence of SEQ ID NO:388; and (ii) a VL having an amino acid sequence of SEQ ID NO:392; or
(i) a VH having an amino acid sequence of SEQ ID NO:396; and (ii) a VL having an amino acid sequence of SEQ ID NO:400; or
(i) a VH having an amino acid sequence of SEQ ID NO:404; and (ii) a VL having an amino acid sequence of SEQ ID NO:408; or
(i) a VH having an amino acid sequence of SEQ ID NO:412; and (ii) a VL having an amino acid sequence of SEQ ID NO:416; or
(i) a VH having an amino acid sequence of SEQ ID NO:420; and (ii) a VL having an amino acid sequence of SEQ ID NO:424.

In some embodiments, one of the first binding domain or the second binding domain of the 1+1 Fab-scFv-Fc format antibody binds PSMA. In some embodiments, the PSMA binding domain is one of the following PSMA binding domains or a variant thereof: A10[PSMA], A10v2[PSMA], D01[PSMA], D01v2[PSMA], E07[PSMA], F02[PSMA], A11[PSMA], F07[PSMA], F07v2[PSMA], G02[PSMA], F01[PSMA], F01v2[PSMA], 011A11[PSMA], PSMB896 [PSMA], PSMA-H[PSMA], and D7[PSMA](FIGS. 25A-25E and 26A-26B).

In some embodiments of the 1+1 Fab-scFv-Fc format, the anti-PSMA ABD has a VH and VL domain selected from the following:
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:206; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:210; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:214; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:218; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:222; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:226; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:230; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:234; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:238; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:242; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:246; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:250; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:254; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:258; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:262; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:266; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:270; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:274; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:278; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:282; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:286; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:290; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:294; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:298; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:302; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:306; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:310; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:314; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:318; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:322; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:326; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:330; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:334; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:338.

In some embodiments of the 1+1 Fab-scFv-Fc format, the anti-PSMA ABD has a VH and VL domain selected from the following:

(i) a VH comprising a vhCDR1 having an amino acid sequence of SEQ ID NO:207; a vhCDR2 having an amino acid sequence of SEQ ID NO:208; and a vhCDR3 having an amino acid sequence of SEQ ID NO: 209; and (ii) a VL comprising a vlCDR1 having an amino acid sequence of SEQ ID NO:211, a vlCDR2 having an amino acid sequence of SEQ ID NO: 212, and a vlCDR3 having an amino acid sequence of SEQ ID NO:213; or (i) a VH comprising a vhCDR1 having an amino acid sequence of SEQ ID NO:215; a vhCDR2 having an amino acid sequence of SEQ ID NO:216; and a vhCDR3 having an amino acid sequence of SEQ ID NO:217; and (ii) a VL comprising a vlCDR1 having an amino acid sequence of SEQ ID NO:219, a vlCDR2 having an amino acid sequence of SEQ ID NO: 220, and a vlCDR3 having an amino acid sequence of SEQ ID NO:221;

(i) a VH comprising a vhCDR1 having an amino acid sequence of SEQ ID NO:223; a vhCDR2 having an amino acid sequence of SEQ ID NO:224; and a vhCDR3 having an amino acid sequence of SEQ ID NO:225; and (ii) a VL comprising a vlCDR1 having an amino acid sequence of SEQ ID NO:227, a vlCDR2 having an amino acid sequence of SEQ ID NO: 228, and a vlCDR3 having an amino acid sequence of SEQ ID NO:229; or (i) a VH comprising a vhCDR1 having an amino acid sequence of SEQ ID NO:231; a vhCDR2 having an amino acid sequence of SEQ ID NO:232; and a vhCDR3 having an amino acid sequence of SEQ ID NO:233; and (ii) a VL comprising a vlCDR1 having an amino acid sequence of SEQ ID NO:235, a vlCDR2 having an amino acid sequence of SEQ ID NO: 236, and a vlCDR3 having an amino acid sequence of SEQ ID NO:237; or (i) a VH comprising a vhCDR1 having an amino acid sequence of SEQ ID NO:239; a vhCDR2 having an amino acid sequence of SEQ ID NO:240; and a vhCDR3 having an amino acid sequence of SEQ ID NO:241; and (ii) a VL comprising a vlCDR1 having an amino acid sequence of SEQ ID NO:243, a vlCDR2 having an amino acid sequence of SEQ ID NO: 244, and a vlCDR3 having an amino acid sequence of SEQ ID NO:245; or (i) a VH comprising a vhCDR1 having an amino acid sequence of SEQ ID NO:247; a vhCDR2 having an amino acid sequence of SEQ ID NO:248; and a vhCDR3 having an amino acid sequence of SEQ ID NO:249; and (ii) a VL comprising a vlCDR1 having an amino acid sequence of SEQ ID NO:251, a vlCDR2 having an amino acid sequence of SEQ ID NO: 252, and a vlCDR3 having an amino acid sequence of SEQ ID NO:253; or (i) a VH comprising a vhCDR1 having an amino acid sequence of SEQ ID NO:255; a vhCDR2 having an amino acid sequence of SEQ ID NO:256; and a vhCDR3 having an amino acid sequence of SEQ ID NO:257; and (ii) a VL comprising a vlCDR1 having an amino acid sequence of SEQ ID NO:259, a vlCDR2 having an amino acid sequence of SEQ ID NO: 260, and a vlCDR3 having an amino acid sequence of SEQ ID NO:261; or (i) a VH comprising a vhCDR1 having an amino acid sequence of SEQ ID NO:263; a vhCDR2 having an amino acid sequence of SEQ ID NO:264; and a vhCDR3 having an amino acid sequence of SEQ ID NO:265; and (ii) a VL comprising a vlCDR1 having an amino acid sequence of SEQ ID NO:267, a vlCDR2 having an amino acid sequence of SEQ ID NO: 268, and a vlCDR3 having an amino acid sequence of SEQ ID NO:269; or
(i) a VH comprising a vhCDR1 having an amino acid sequence of SEQ ID NO:271; a vhCDR2 having an amino acid sequence of SEQ ID NO:212; and a vhCDR3 having an amino acid sequence of SEQ ID NO:273; and (ii) a VL comprising a vlCDR1 having an amino acid sequence of SEQ ID NO:275, a vlCDR2 having an amino acid sequence of SEQ ID NO: 276, and a vlCDR3 having an amino acid sequence of SEQ ID NO:277; or
(i) a VH comprising a vhCDR1 having an amino acid sequence of SEQ ID NO:279; a vhCDR2 having an amino acid sequence of SEQ ID NO:280; and a vhCDR3 having an amino acid sequence of SEQ ID NO:281; and (ii) a VL comprising a vlCDR1 having an amino acid sequence of SEQ ID NO:283, a vlCDR2 having an amino acid sequence of SEQ ID NO: 284, and a vlCDR3 having an amino acid sequence of SEQ ID NO:285; or
(i) a VH comprising a vhCDR1 having an amino acid sequence of SEQ ID NO:287; a vhCDR2 having an amino acid sequence of SEQ ID NO:288; and a vhCDR3 having an amino acid sequence of SEQ ID NO:289; and (ii) a VL comprising a vlCDR1 having an amino acid sequence of SEQ ID NO:291, a vlCDR2 having an amino acid sequence of SEQ ID NO: 292, and a vlCDR3 having an amino acid sequence of SEQ ID NO:293; or
(i) a VH comprising a vhCDR1 having an amino acid sequence of SEQ ID NO:295; a vhCDR2 having an amino acid sequence of SEQ ID NO:296; and a vhCDR3 having an amino acid sequence of SEQ ID NO:297; and (ii) a VL comprising a vlCDR1 having an amino acid sequence of SEQ ID NO:299, a vlCDR2 having an amino acid sequence of SEQ ID NO: 300, and a vlCDR3 having an amino acid sequence of SEQ ID NO:301; or
(i) a VH comprising a vhCDR1 having an amino acid sequence of SEQ ID NO:303; a vhCDR2 having an amino acid sequence of SEQ ID NO:304; and a vhCDR3 having an amino acid sequence of SEQ ID NO:305; and (ii) a VL comprising a vlCDR1 having an amino acid sequence of SEQ ID NO:307, a vlCDR2 having an amino acid sequence of SEQ ID NO: 308, and a vlCDR3 having an amino acid sequence of SEQ ID NO:309; or
(i) a VH comprising a vhCDR1 having an amino acid sequence of SEQ ID NO:311; a vhCDR2 having an amino acid sequence of SEQ ID NO:312; and a vhCDR3 having an amino acid sequence of SEQ ID NO:313; and (ii) a VL comprising a vlCDR1 having an amino acid sequence of SEQ ID NO: 315, a vlCDR2 having an amino acid sequence of SEQ ID NO: 316, and a vlCDR3 having an amino acid sequence of SEQ ID NO:317; or
(i) a VH comprising a vhCDR1 having an amino acid sequence of SEQ ID NO:319; a vhCDR2 having an amino acid sequence of SEQ ID NO:320; and a vhCDR3 having an amino acid sequence of SEQ ID NO:321; and (ii) a VL comprising a vlCDR1 having an amino acid sequence of SEQ ID NO: 323, a vlCDR2 having an amino acid sequence of SEQ ID NO: 324, and a vlCDR3 having an amino acid sequence of SEQ ID NO:325; or
(i) a VH comprising a vhCDR1 having an amino acid sequence of SEQ ID NO:327; a vhCDR2 having an amino acid sequence of SEQ ID NO:328; and a vhCDR3 having an amino acid sequence of SEQ ID NO:329; and (ii) a VL comprising a vlCDR1 having an amino acid sequence of SEQ ID NO:331, a vlCDR2 having an amino acid sequence of SEQ ID NO: 332, and a vlCDR3 having an amino acid sequence of SEQ ID NO:333; or
(i) a VH comprising a vhCDR1 having an amino acid sequence of SEQ ID NO:335; a vhCDR2 having an amino acid sequence of SEQ ID NO:336; and a vhCDR3 having an amino acid sequence of SEQ ID NO:337; and (ii) a VL comprising a vlCDR1 having an amino acid sequence of SEQ ID NO:339, a vlCDR2 having an amino acid sequence of SEQ ID NO: 340, and a vlCDR3 having an amino acid sequence of SEQ ID NO:341.

In some embodiments of the 1+1 Fab-scFv-Fc format, the anti-PSMA ABD has a VH and VL domain selected from the following:
(i) a VH having an amino acid sequence of SEQ ID NO:206; and (ii) a VL having an amino acid sequence of SEQ ID NO:210; or
(i) a VH having an amino acid sequence of SEQ ID NO:214; and (ii) a VL having an amino acid sequence of SEQ ID NO:218; or
(i) a VH having an amino acid sequence of SEQ ID NO:222; and (ii) a VL having an amino acid sequence of SEQ ID NO:226; or
(i) a VH having an amino acid sequence of SEQ ID NO:230; and (ii) a VL having an amino acid sequence of SEQ ID NO:234; or
(i) a VH having an amino acid sequence of SEQ ID NO:238; and (ii) a VL having an amino acid sequence of SEQ ID NO:242; or
(i) a VH having an amino acid sequence of SEQ ID NO:246; and (ii) a VL having an amino acid sequence of SEQ ID NO:250; or
(i) a VH having an amino acid sequence of SEQ ID NO:254; and (ii) a VL having an amino acid sequence of SEQ ID NO:258; or
(i) a VH having an amino acid sequence of SEQ ID NO:262; and (ii) a VL having an amino acid sequence of SEQ ID NO:266; or
(i) a VH having an amino acid sequence of SEQ ID NO:270; and (ii) a VL having an amino acid sequence of SEQ ID NO:274; or
(i) a VH having an amino acid sequence of SEQ ID NO:278; and (ii) a VL having an amino acid sequence of SEQ ID NO:282; or
(i) a VH having an amino acid sequence of SEQ ID NO:286; and (ii) a VL having an amino acid sequence of SEQ ID NO:290; or
(i) a VH having an amino acid sequence of SEQ ID NO:294; and (ii) a VL having an amino acid sequence of SEQ ID NO:298; or
(i) a VH having an amino acid sequence of SEQ ID NO:302; and (ii) a VL having an amino acid sequence of SEQ ID NO:306; or
(i) a VH having an amino acid sequence of SEQ ID NO:310; and (ii) a VL having an amino acid sequence of SEQ ID NO:314; or (i) a VH having an amino acid sequence of SEQ ID NO:318; and (ii) a VL having an amino acid sequence of SEQ ID NO:322; or (i) a VH having an amino acid sequence of SEQ ID NO:326; and (ii) a VL having an amino acid sequence of SEQ ID NO:330; or (i) a VH having an amino acid sequence of SEQ ID NO:334; and (ii) a VL having an amino acid sequence of SEQ ID NO:338.

In some embodiments, the anti-PSMAx anti-CD28 antibody includes a) a CD28 binding domain comprising:

i) a VH comprising a vhCDR1 having an amino acid sequence of SEQ ID NO:40; a vhCDR2 having an amino acid sequence of SEQ ID NO:41; and a vhCDR3 having an amino acid sequence of SEQ ID NO:42; and (ii) a VL comprising a vlCDR1 having an amino acid sequence of SEQ ID NO:44, a vlCDR2 having an amino acid sequence of SEQ ID NO: 45, and a vlCDR3 having an amino acid sequence of SEQ ID NO:46; and b) a PSMA binding domain comprising:

i) a VH comprising a vhCDR1 having an amino acid sequence of SEQ ID NO:215; a vhCDR2 having an amino acid sequence of SEQ ID NO:216; and a vhCDR3 having an amino acid sequence of SEQ ID NO:217; and (ii) a VL comprising a vlCDR1 having an amino acid sequence of SEQ ID NO:219, a vlCDR2 having an amino acid sequence of SEQ ID NO: 220, and a vlCDR3 having an amino acid sequence of SEQ ID NO:221.

FIGS. 10A-10E shows some exemplary Fc domain sequences that are useful in the 1+1 Fab-scFv-Fc format antibodies. The "monomer 1" sequences depicted in FIGS. 10A-10E typically refer to the Fc domain of the "Fab-Fc heavy chain" and the "monomer 2" sequences refer to the Fc domain of the "scFv-Fc heavy chain." In addition, FIGS. 12 and 13 provide exemplary CH1-hinge domains, CH1 domains, and hinge domains that can be included in the first or second monomer of the 1+1 Fab-scFv-Fc format. Further, FIG. 14 provides useful CL sequences that can be used with this format.

Exemplary subject anti-PSMAx anti-CD28 antibodies in the 1+1 Fab-scFv-Fc format are provided in FIGS. 29A-29RR and 30A-30L.

In some embodiments, the anti-PSMAx anti-CD28 antibody in the 1+1 Fab-scFv-Fc format is C28PB330 or a variant thereof (see FIGS. 30G and 30H). In some embodiments, the anti-PSMAx anti-CD28 antibody in the 1+1 Fab-scFv-Fc format includes: a) a first monomer having an amino acid sequence of SEQ ID NO:351; b) a second monomer having an amino acid sequence of SEQ ID NO:352; and c) a light chain having an amino acid sequence of SEQ ID NO:353.

In some embodiments, the C28PB330 variant includes a deletion of a C-terminal lysine (-K) or lysine and glycine (-GK) in the first monomer or second monomer. In some embodiments, the anti-PSMAx anti-CD28 antibody in the 1+1 Fab-scFv-Fc format includes: a) a first monomer having an amino acid sequence of SEQ ID NO:354; b) a second monomer having an amino acid sequence of SEQ ID NO:355; and c) a light chain having an amino acid sequence of SEQ ID NO:356. In some embodiments, the anti-PSMAx anti-CD28 antibody in the 1+1 Fab-scFv-Fc format includes: a) a first monomer having an amino acid sequence of SEQ ID NO:357; b) a second monomer having an amino acid sequence of SEQ ID NO:358; and c) a light chain having an amino acid sequence of SEQ ID NO:359.

In some embodiments, the anti-PSMAx anti-CD28 antibody in the 1+1 Fab-scFv-Fc format is C28PB397 or a variant thereof (see FIGS. 30D and 30E). In some embodiments, the anti-PSMAx anti-CD28 antibody in the 1+1 Fab-scFv-Fc format includes: a) a first monomer having an amino acid sequence of SEQ ID NO:342; b) a second monomer having an amino acid sequence of SEQ ID NO:343; and c) a light chain having an amino acid sequence of SEQ ID NO:344.

In some embodiments, the C28PB397 variant includes a deletion of a C-terminal lysine (-K) or lysine and glycine (-GK) in the first monomer or second monomer. In some embodiments, the anti-PSMAx anti-CD28 antibody in the 1+1 Fab-scFv-Fc format includes: a) a first monomer having an amino acid sequence of SEQ ID NO:345; b) a second monomer having an amino acid sequence of SEQ ID NO:346; and c) a light chain having an amino acid sequence of SEQ ID NO:347. In some embodiments, the anti-PSMAx anti-CD28 antibody in the 1+1 Fab-scFv-Fc format includes: a) a first monomer having an amino acid sequence of SEQ ID NO:348; b) a second monomer having an amino acid sequence of SEQ ID NO:349; and c) a light chain having an amino acid sequence of SEQ ID NO:350.

2. 2+1 Fab2-scFv-Fc Format

One heterodimeric antibody format that finds particular use in subject anti-CD28x anti-PSMA antibodies provided herein is the 2+1 $Fab_2$-scFv-Fc format (also referred to as "central-scFv format") shown in FIG. 24B. This antibody format includes three antigen binding domains: two Fab portions and an scFv that is inserted between the VH-CH1 and CH2-CH3 regions of one of the monomers. In some embodiments of this format, the Fab portions each bind PSMA and the "extra" scFv domain binds CD28. In some embodiments, the 2+1 $Fab_2$-scFv-Fc format antibody is a trivalent antibody.

In some embodiments of the 2+1 $Fab_2$-scFv-Fc format, a first monomer includes a standard heavy chain (i.e., VH1-CH1-hinge-CH2-CH3), wherein VH1 is a first variable heavy domain and CH2-CH3 is a first Fc domain. A second monomer includes another first variable heavy domain (VH1), a CH1 domain (and optional hinge), a second Fc domain, and an scFv that includes an scFv variable light domain (VL2), an scFv linker and a scFv variable heavy domain (VH2). The scFv is covalently attached between the C-terminus of the CH1 domain of the second monomer and the N-terminus of the second Fc domain using optional domain linkers (VH1-CH1-[optional linker]-VH2-scFv linker-VH2-[optional linker]-CH2-CH3, or the opposite orientation for the scFv, VH1-CH1-[optional linker]-VL2-scFv linker-VH2-[optional linker]-CH2-CH3). The optional linkers can be any suitable peptide linkers, including, for example, the domain linkers included in FIG. 7. This embodiment further utilizes a common light chain that includes a variable light domain (VL1) and a constant light domain (CL). The common light chain associates with the VH1-CH1 of the first and second monomers to form two identical Fabs. In some embodiments, the identical Fabs each bind PSMA. As for many of the embodiments herein, these constructs can include skew variants, pI variants, ablation variants, additional Fc variants, etc. as desired and described herein.

In some embodiments, the first and second Fc domains of the 2+1 $Fab_2$-scFv-Fc format antibody are variant Fc domains that include heterodimerization skew variants (e.g., a set of amino acid substitutions as shown in FIGS. 3A-3F and 9). Particularly useful heterodimerization skew variants include S364K/E357Q:L368D/K370S; L368D/K370S:

S364K; L368E/K370S:S364K; T411T/E360E/Q362E: D401K; L368D/K370S: S364K/E357L; K370S:S364K/ E357Q; T366S/L368A/Y407V:T366W and T366S/L368A/ Y407V/Y349C:T366W/S354C (EU numbering)). In exemplary embodiments, one of the first or second variant Fc domains includes heterodimerization skew variants L368D/K370S and the other of the first or second variant Fc domains includes heterodimerization skew variants S364K/ E357Q, wherein numbering is according to EU numbering. In exemplary embodiments, the first variant Fc domain includes heterodimerization skew variants L368D/K370S and the second variant Fc domain includes heterodimerization skew variants S364K/E357Q, wherein numbering is according to EU numbering.

In some embodiments, the variant Fc domains include ablation variants (including those shown in FIG. 5). In some embodiments, each of the first and second variant Fc domains include ablation variants E233P/L234V/L235A/ G236_/S267K, wherein numbering is according to EU numbering.

In some embodiments, the constant domain (CH1-hinge-CH2-CH3) of the first monomer includes pI variants (including those shown in FIG. 4). In exemplary embodiments, the constant domain (CH1-hinge-CH2-CH3) of the first monomer includes pI variants N208D/Q295E/N384D/Q418E/ N421D, wherein numbering is according to EU numbering.

In some embodiments, the scFv of the 2+1 Fab$_2$-scFv-Fc format antibody provided herein includes a charged scFv linker (including those shown in FIGS. 6A-6B). In some embodiments, the 2+1 Fab$_2$-scFv-Fc format antibody provided herein includes FcRn variants M428L/N434S, wherein numbering is according to EU numbering.

In exemplary embodiments 2+1 Fab$_2$-scFv-Fc format antibody with "Platform X" variants, the first variant Fc domain includes heterodimerization skew variants L368D/ K370S and the second variant Fc domain includes heterodimerization skew variants S364K/E357Q; each of the first and second variant Fc domains include ablation variants E233P/L234V/L235A/G236_/S267K; and the constant domain (CH1-hinge-CH2-CH3) of the first monomer includes pI variants N208D/Q295E/N384D/Q418E/N421D, wherein numbering is according to EU numbering. In some embodiments, the scFv of the 2+1 Fab2-scFv-Fc format antibody provided herein includes a (GKPGS)$_4$ charged scFv linker (SEQ ID NO:443). In some embodiments, the 2+1 Fab$_2$-scFv-Fc format antibody provided herein includes FcRn variants M428L/N434S, wherein numbering is according to EU numbering.

In some embodiments, the CH1-hinge-CH2-CH3 of the first monomer comprises amino acid variants L368D/ K370S/N208D/Q295E/N384D/Q418E/N421D/E233P/ L234V/L235A/G236del/S267 K, and the second Fc domain comprises amino acid variants S364K/E357Q/E233P/ L234V/L235A/G236del/S267K, wherein numbering is according to EU numbering.

In exemplary embodiments, the 2+1 Fab2-scFv-Fc format antibody include "Platform J" amino acid modifications as depicted in FIG. 8. In such embodiments, the first Fc domain comprises amino acid substitutions L234A/L235A/D265S/ T366S/L368A/Y407V/H435R/Y436F, and the first Fc domain comprises amino acid substitutions L234A/L235A/ D265S/LT366W, wherein numbering is according to EU numbering.

In exemplary embodiments of the 2+1 Fab$_2$-scFv-Fc format antibody with Platform J variants, the first Fc domain includes heterodimerization skew variants T366S/L368A/ Y407V and the second Fc domain includes heterodimerization skew variants T366W; each of the first and second variant Fc domains include ablation variants L234A/L235A/ D265S; and the second Fc domain includes purification variants H435R/Y436F, wherein numbering is according to EU numbering. In some embodiments, the scFv of the 1+1 Fab-scFv-Fc format antibody provided herein includes a (GKPGS)$_4$ charged scFv linker. In some embodiments, the 1+1 Fab-scFv-Fc format antibody provided herein includes FcRn variants M252Y/S254T/T256E, wherein numbering is according to EU numbering. In some embodiments, the scFv of the 2+1 Fab2-scFv-Fc Fc format antibody provided herein includes a charged scFv linker (including those shown in FIGS. 6A-6B).

In exemplary embodiments, the 2+1 Fab2-scFv-Fc format antibody with Platform J variants further includes a "stapled" scFv (e.g., a "stapled" anti-CD28 scFv). Stapled" scFvs that exhibit improved stability and/or reduced aggregation are further described in detail herein. Exemplary staple linkers that are useful for inclusion in such "stapled" scFvs are provided in FIGS. 6A-6B. In exemplary embodiments, the stapled linker is GGGSGGSGGCPPCGGSGG (SEQ ID NO:457).

In some embodiments, the scFv of the second monomer of the 2+1 Fab2-scFv-Fc format antibody is a CD28 binding and the VH1 of the first and second monomer and the VL1 of the common light chain each form binding domains that bind PSMA. Any suitable CD28 binding domain can be included in subject 2+1 Fab$_2$-scFv-Fc format antibody, including any of the CD28 binding domains provided herein. In some embodiments, the CD28 binding domain is one of the following CD28 binding domains or a variant thereof: 1A7[CD28]_H1L1, 1A7[CD28]_H1.1_L1, 1A7 [CD28]_H1_L1.71, 1A7[CD28]_H1.1_L1.71, 1A7[CD28] H1.14_L1, 1A7[CD28]_H1.14_L1.71, 1A7[CD28]_ H1sp_L1sp, 1A7[CD28]_H1.1sp_L1sp, 1A7[CD28] H1sp_L1.71sp, 1A7[CD28]_H1.1sp_L1.71sp, 1A7[CD28]_ H1.14sp_L1sp, 1A7[CD28]_H1.14sp_L1.71sp, CD28.3 [CD28]_H0L0, hCD28.3[CD28]_H1L1, 5.11A1[CD28]_ H0L0, TGN1412_H1L1, 341VL34[CD28]_H1L1, 341VL36[CD28]_H1L1, 281VL4[CD28]_H1L1, HuTN228 [CD28]_H1L1, PV1[CD28]H0L0, m9.3[CD28]_H0L0, hu9.3[CD28]_H1L1, 9G2[CD28]_H0L0, 9G2[CD28]_ H1L1, 2F10A3.140[CD28]_H1L1, and TN228[CD28]_ H4L2 (FIGS. 15-18C, 21A-21H, and 69A-69C).

In some embodiments of the 2+1 Fab$_2$-scFv-Fc format, the anti-CD28 ABD has a VH and VL domain selected from the following:
- (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:9; and
  (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:13; or
- (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:31; and
  (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:35; or
- (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:39; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:43; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:47; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:51; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:55; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:59; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:63; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:67; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:86; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:90; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:94; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:98; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 102; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:106; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:110; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:114; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:118; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:122; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 126; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:130; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 134; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:138; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 142; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:146; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 150; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:154; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 158; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:162; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 166; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:170; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 174; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:178; or
(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:182; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:186; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 190; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:194; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO: 198; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:202; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:380; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:384; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:388; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:392; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:396; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:400; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:404; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:408; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:412; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:416; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:420; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:424.

In some embodiments of the 2+1 Fab$_2$-scFv-Fc format, the anti-CD28 ABD has a VH and VL domain selected from the following:

(i) a VH comprising a vhCDR1 having an amino acid sequence of SEQ ID NO:10; a vhCDR2 having an amino acid sequence of SEQ ID NO:11; and a vhCDR3 having an amino acid sequence of SEQ ID NO: 12; and (ii) a VL comprising a vlCDR1 having an amino acid sequence of SEQ ID NO: 14, a vlCDR2 having an amino acid sequence of SEQ ID NO: 15, and a vlCDR3 having an amino acid sequence of SEQ ID NO:16; or (i) a VH comprising a vhCDR1 having an amino acid sequence of SEQ ID NO:32; a vhCDR2 having an amino acid sequence of SEQ ID NO:33; and a vhCDR3 having an amino acid sequence of SEQ ID NO:34; and (ii) a VL comprising a vlCDR1 having an amino acid sequence of SEQ ID NO:36, a vlCDR2 having an amino acid sequence of SEQ ID NO: 37, and a vlCDR3 having an amino acid sequence of SEQ ID NO:38; or i) a VH comprising a vhCDR1 having an amino acid sequence of SEQ ID NO:40; a vhCDR2 having an amino acid sequence of SEQ ID NO:41; and a vhCDR3 having an amino acid sequence of SEQ ID NO:42; and (ii) a VL comprising a vlCDR1 having an amino acid sequence of SEQ ID NO:44, a vlCDR2 having an amino acid sequence of SEQ ID NO: 45, and a vlCDR3 having an amino acid sequence of SEQ ID NO:46; or i) a VH comprising a vhCDR1 having an amino acid sequence of SEQ ID NO:48; a vhCDR2 having an amino acid sequence of SEQ ID NO:49; and a vhCDR3 having an amino acid sequence of SEQ ID NO:50; and (ii) a VL comprising a vlCDR1 having an amino acid sequence of SEQ ID NO: 52, a vlCDR2 having an amino acid sequence of SEQ ID NO: 53, and a vlCDR3 having an amino acid sequence of SEQ ID NO:54; or i) a VH comprising a vhCDR1 having an amino acid sequence of SEQ ID NO:56; a vhCDR2 having an amino acid sequence of SEQ ID NO:57; and a vhCDR3 having an amino acid sequence of SEQ ID NO:58; and (ii) a VL comprising a vlCDR1 having an amino acid sequence of SEQ ID NO:60, a vlCDR2 having an amino acid sequence of SEQ ID NO:61, and a vlCDR3 having an amino acid sequence of SEQ ID NO:62; or i) a VH comprising a vhCDR1 having an amino acid sequence of SEQ ID NO:64; a vhCDR2 having an amino acid sequence of SEQ ID NO:65; and a vhCDR3 having an amino acid sequence of SEQ ID NO:66; and (ii) a VL comprising a vlCDR1 having an amino acid sequence of SEQ ID NO:68, a vlCDR2 having an amino acid sequence of SEQ ID NO:69, and a vlCDR3 having an amino acid sequence of SEQ ID NO:70; or i) a VH comprising a vhCDR1 having an amino acid sequence of SEQ ID NO:87; a vhCDR2 having an amino acid sequence of SEQ ID NO:88; and a vhCDR3 having an amino acid sequence of SEQ ID NO:89; and (ii) a VL comprising a vlCDR1 having an amino acid sequence of SEQ ID NO:91, a vlCDR2 having an amino acid sequence of SEQ ID NO:92, and a vlCDR3 having an amino acid sequence of SEQ ID NO:93; or i) a VH comprising a vhCDR1 having an amino acid sequence of SEQ ID NO:95; a vhCDR2 having an amino acid sequence of SEQ ID NO:96; and a vhCDR3 having an amino acid sequence of SEQ ID NO:97; and (ii) a VL comprising a vlCDR1 having an amino acid sequence of SEQ ID NO: 99, a vlCDR2 having an amino acid sequence of SEQ ID NO:100, and a vlCDR3 having an amino acid sequence of SEQ ID NO:101; or i) a VH comprising a vhCDR1 having an amino acid sequence of SEQ ID NO:103; a vhCDR2 having an amino acid sequence of SEQ ID NO:104; and a vhCDR3 having an amino acid sequence of SEQ ID NO: 105; and (ii) a VL comprising a vlCDR1 having an amino acid sequence of SEQ ID NO:107, a vlCDR2 having an amino acid sequence of SEQ ID NO:108, and a vlCDR3 having an amino acid sequence of SEQ ID NO:109; or i) a VH comprising a vhCDR1 having an amino acid sequence of SEQ ID NO:111; a vhCDR2 having an amino acid sequence of SEQ ID NO:112; and a vhCDR3 having an amino acid sequence of SEQ ID NO:113; and (ii) a VL comprising a vlCDR1 having an amino acid sequence of SEQ ID NO: 115, a vlCDR2 having an amino acid sequence of SEQ ID NO:116, and a vlCDR3 having an amino acid sequence of SEQ ID NO:117; or i) a VH comprising a vhCDR1 having an amino acid sequence of SEQ ID NO:119; a vhCDR2 having an amino acid sequence of SEQ ID NO:120; and a vhCDR3 having an amino acid sequence of SEQ ID NO:121; and (ii) a VL comprising a vlCDR1 having an amino acid sequence of SEQ ID NO: 123, a vlCDR2 having an amino acid sequence of SEQ ID NO:124, and a vlCDR3 having an amino acid sequence of SEQ ID NO:125; or i) a VH comprising a vhCDR1 having an amino acid sequence of SEQ ID NO:127; a vhCDR2 having an amino acid sequence of SEQ ID NO:128; and a vhCDR3 having an amino acid sequence of SEQ ID NO:129; and (ii) a VL comprising a vlCDR1 having an amino acid sequence of SEQ ID NO:131, a vlCDR2 having an amino acid sequence of SEQ ID NO:132, and a vlCDR3 having an amino acid sequence of SEQ ID NO:133; or i) a VH comprising a vhCDR1 having an amino acid sequence of SEQ ID NO:135; a vhCDR2 having an amino acid sequence of SEQ ID NO:136; and a vhCDR3 having an amino acid sequence of SEQ ID NO:137; and (ii) a VL comprising a vlCDR1 having an amino acid sequence of SEQ ID NO: 139, a vlCDR2 having an amino acid sequence of SEQ ID NO:140, and a vlCDR3 having an amino acid sequence of SEQ ID NO:141; or i) a VH comprising a vhCDR1 having an amino acid sequence of SEQ ID NO:143; a vhCDR2 having an amino acid sequence of SEQ ID NO:144; and a vhCDR3 having an amino acid sequence of SEQ ID NO:115; and (ii) a VL comprising a vlCDR1 having an amino acid sequence of SEQ ID NO: 147, a vlCDR2 having an amino acid sequence of SEQ ID NO:149, and a vlCDR3 having an amino acid sequence of SEQ ID NO:149; or i) a VH comprising a vhCDR1 having an amino acid sequence of SEQ ID NO:151; a vhCDR2 having an amino acid sequence of SEQ ID NO:152; and a vhCDR3 having an amino acid sequence of SEQ ID NO:153; and (ii) a VL comprising a vlCDR1 having an amino acid sequence of SEQ ID NO: 155, a vlCDR2 having an amino acid sequence of SEQ ID NO:156, and a vlCDR3 having an amino acid sequence of SEQ ID NO:157; or i) a VH comprising a vhCDR1 having an amino acid sequence of SEQ ID NO:159; a vhCDR2 having an amino acid sequence of SEQ ID NO:160; and a vhCDR3 having an amino acid sequence of SEQ ID NO:161; and (ii) a VL comprising a vlCDR1 having an amino acid sequence of SEQ ID NO: 163, a vlCDR2 having an amino acid sequence of SEQ ID NO:164, and a vlCDR3 having an amino acid sequence of SEQ ID NO:165; or i) a VH comprising a vhCDR1 having an amino acid sequence of SEQ ID NO:167; a vhCDR2 having an amino acid sequence of SEQ ID NO:168; and a vhCDR3 having an amino acid sequence of SEQ ID NO:169; and (ii) a VL comprising a vlCDR1 having an amino acid sequence of SEQ ID NO:171, a vlCDR2 having an amino acid sequence of SEQ ID NO:172, and a vlCDR3 having an amino acid sequence of SEQ ID NO:173; or i) a VH comprising a vhCDR1 having an amino acid sequence of SEQ ID NO:175; a vhCDR2 having an amino acid sequence of SEQ ID NO:176; and a vhCDR3 having an amino acid sequence of SEQ ID NO:177; and (ii) a VL comprising a vlCDR1 having an amino acid sequence of SEQ ID NO: 179, a vlCDR2 having an amino acid sequence of SEQ ID NO:180, and a vlCDR3 having an amino acid sequence of SEQ ID NO:181; or i) a VH comprising a vhCDR1 having an amino acid sequence of SEQ ID NO:183; a vhCDR2 having an amino acid sequence of SEQ ID NO:184; and a vhCDR3 having an amino acid sequence of SEQ ID NO:185; and (ii) a VL comprising a vlCDR1 having an amino acid sequence of SEQ ID NO: 187, a vlCDR2 having an amino acid sequence of SEQ ID NO:188, and a vlCDR3 having an amino acid sequence of SEQ ID NO:189; or i) a VH comprising a vhCDR1 having an amino acid sequence of SEQ ID NO:191; a vhCDR2 having an amino acid sequence of SEQ ID NO:192; and a vhCDR3 having an amino acid sequence of SEQ ID NO:193; and (ii) a VL comprising a vlCDR1 having an amino acid sequence of SEQ ID NO: 195, a vlCDR2 having an amino acid sequence of SEQ ID NO:196, and a vlCDR3 having an amino acid sequence of SEQ ID NO:197; or i) a VH comprising a vhCDR1 having an amino acid sequence of SEQ ID NO:199; a vhCDR2 having an amino acid sequence of SEQ ID NO:200; and a vhCDR3 having an amino acid sequence of SEQ ID NO:201; and (ii) a VL comprising a vlCDR1 having an amino acid sequence of SEQ ID NO:203, a vlCDR2 having an amino acid sequence of SEQ ID NO:204, and a vlCDR3 having an amino acid sequence of SEQ ID NO:205; or i) a VH comprising a vhCDR1 having an amino acid sequence of SEQ ID NO:381; a vhCDR2 having an amino acid sequence of SEQ ID NO:382; and a vhCDR3 having an amino acid sequence of SEQ ID NO:383; and (ii) a VL comprising a vlCDR1 having an amino acid sequence of SEQ ID NO:385, a vlCDR2 having an amino acid sequence of SEQ ID NO:386, and a vlCDR3 having an amino acid sequence of SEQ ID NO:387; or i) a VH comprising a vhCDR1 having an amino acid sequence of SEQ ID NO:389; a vhCDR2 having an amino acid sequence of SEQ ID NO:390; and a vhCDR3 having an amino acid sequence of SEQ ID NO:391; and (ii) a VL comprising a vlCDR1 having an amino acid sequence of SEQ ID NO:393, a vlCDR2 having an amino acid sequence of SEQ ID NO:394, and a vlCDR3 having an amino acid sequence of SEQ ID NO:395; or i) a VH comprising a vhCDR1 having an amino acid sequence of SEQ ID NO:397; a vhCDR2 having an amino acid sequence of SEQ ID NO:398; and a vhCDR3 having an amino acid sequence of SEQ ID NO:399; and (ii) a VL comprising a vlCDR1 having an amino acid sequence of SEQ ID NO:401, a vlCDR2 having an amino acid sequence of SEQ ID NO:402, and a vlCDR3 having an amino acid sequence of SEQ ID NO:403; or i) a VH comprising a vhCDR1 having an amino acid sequence of SEQ ID NO:405; a vhCDR2 having an amino acid sequence of SEQ ID NO:406; and a vhCDR3 having an amino acid sequence of SEQ ID NO: 407; and (ii) a VL comprising a vlCDR1 having an amino acid sequence of SEQ ID NO:409, a vlCDR2 having an amino acid sequence of SEQ ID NO:410, and a vlCDR3 having an amino acid sequence of SEQ ID NO:411; or i) a VH comprising a vhCDR1 having an amino acid sequence of SEQ ID NO:413; a vhCDR2 having an amino acid sequence of SEQ ID NO:414; and a vhCDR3 having an amino acid sequence of SEQ ID NO:415; and (ii) a VL comprising a vlCDR1 having an amino acid sequence of SEQ ID NO:417, a vlCDR2 having an amino acid sequence of SEQ ID NO:418, and a vlCDR3 having an amino acid sequence of SEQ ID NO:419; or i) a VH comprising a vhCDR1 having an amino acid sequence of SEQ ID NO:421; a vhCDR2 having an amino acid sequence of SEQ ID NO:422; and a vhCDR3 having an amino acid sequence of SEQ ID NO:423; and (ii) a VL comprising a vlCDR1 having an amino acid sequence of SEQ ID NO:425, a vlCDR2 having an amino acid sequence of SEQ ID NO:426, and a vlCDR3 having an amino acid sequence of SEQ ID NO:427.

In some embodiments of the 2+1 Fab$_2$-scFv-Fc format, the anti-CD28 ABD has a VH and VL domain selected from the following:

(i) a VH having an amino acid sequence of SEQ ID NO:9; and (ii) a VL having an amino acid sequence of SEQ ID NO:13; or (i) a VH having an amino acid sequence of SEQ ID NO:31; and (ii) a VL having an amino acid sequence of SEQ ID NO:35; or (i) a VH having an amino acid sequence of SEQ ID NO:39; and (ii) a VL having an amino acid sequence of SEQ ID NO:43; or (i) a VH having an amino acid sequence of SEQ ID NO:47; and (ii) a VL having an amino acid sequence of SEQ ID NO:51; or (i) a VH having an amino acid sequence of SEQ ID NO:55; and (ii) a VL having an amino acid sequence of SEQ ID NO:59; or (i) a VH having an amino acid sequence of SEQ ID NO:63; and (ii) a VL having an amino acid sequence of SEQ ID NO:67; or (i) a VH having an amino acid sequence of SEQ ID NO:86; and (ii) a VL having an amino acid sequence of SEQ ID NO:90; or (i) a VH having an amino acid sequence of SEQ ID NO:94; and (ii) a VL having an amino acid sequence of SEQ ID NO:98; or (i) a VH having an amino acid sequence of SEQ ID NO:102; and (ii) a VL having an amino acid sequence of SEQ ID NO:106; or (i) a VH having an amino acid sequence of SEQ ID NO:110; and (ii) a VL having an amino acid sequence of SEQ ID NO:114; or (i) a VH having an amino acid sequence of SEQ ID NO:118; and (ii) a VL having an amino acid sequence of SEQ ID NO:122; or (i) a VH having an amino acid sequence of SEQ ID NO:126; and (ii) a VL having an amino acid sequence of SEQ ID NO:130; or (i) a VH having an amino acid sequence of SEQ ID NO:134; and (ii) a VL having an amino acid sequence of SEQ ID NO:138; or (i) a VH having an amino acid sequence of SEQ ID NO:142; and (ii) a VL having an amino acid sequence of SEQ ID NO:146; or (i) a VH having an amino acid sequence of SEQ ID NO:150; and (ii) a VL having an amino acid sequence of SEQ ID NO:154; or (i) a VH having an amino acid sequence of SEQ ID NO:158; and (ii) a VL having an amino acid sequence of SEQ ID NO:162; or (i) a VH having an amino acid sequence of SEQ ID NO:166; and (ii) a VL having an amino acid sequence of SEQ ID NO:170; or (i) a VH having an amino acid sequence of SEQ ID NO:174; and (ii) a VL having an amino acid sequence of SEQ ID NO:178; or (i) a VH having an amino acid sequence of SEQ ID NO:182; and (ii) a VL having an amino acid sequence of SEQ ID NO:186; or (i) a VH having an amino acid sequence of SEQ ID NO:190; and (ii) a VL having an amino acid sequence of SEQ ID NO:194; or (i) a VH having an amino acid sequence of SEQ ID NO:198; and (ii) a VL having an amino acid sequence of SEQ ID NO:202; or (i) a VH having an amino acid sequence of SEQ ID NO:380; and (ii) a VL having an amino acid sequence of SEQ ID NO:384; or (i) a VH having an amino acid sequence of SEQ ID NO:388; and (ii) a VL having an amino acid sequence of SEQ ID NO:392; or (i) a VH having an amino acid sequence of SEQ ID NO:396; and (ii) a VL having an amino acid sequence of SEQ ID NO:400; or (i) a VH having an amino acid sequence of SEQ ID NO:404; and (ii) a VL having an amino acid sequence of SEQ ID NO:408; or (i) a VH having an amino acid sequence of SEQ ID NO:412; and (ii) a VL having an amino acid sequence of SEQ ID NO:416; or (i) a VH having an amino acid sequence of SEQ ID NO:420; and (ii) a VL having an amino acid sequence of SEQ ID NO:424.

In some embodiments, the VH1 of the first and second monomer and the VL1 of the common light chain of the 2+1 Fab2-scFv-Fc format antibody each form a binding domain that binds PSMA. In some embodiments, the PSMA binding domain is one of the following PSMA binding domains or a variant thereof: A10[PSMA], A10v2[PSMA], D01[PSMA], D01v2[PSMA], E07[PSMA], F02[PSMA], A11[PSMA], F07[PSMA], F07v2[PSMA], G02[PSMA], F01[PSMA], F01v2[PSMA], 011A11[PSMA], PSMB896[PSMA], PSMA-H[PSMA], and D7[PSMA](FIGS. 25A-25E and 26A-26B).

In some embodiments of 2+1 Fab$_2$-scFv-Fc format, the anti-PSMA ABDs each include a VH and VL domain selected from the following:

(i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:206; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:210; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:214; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:218; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:222; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:226; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:230; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:234; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:238; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:242; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:246; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:250; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:254; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:258; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:262; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:266; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:270; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:274; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:278; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:282; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:286; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:290; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:294; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:298; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:302; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:306; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:310; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:314; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:318; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:322; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:326; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:330; or (i) a VH comprising a vhCDR1, a vhCDR2, and a vhCDR3 having an amino acid sequence of a vhCDR1, a vhCDR2, and a vhCDR3, respectively, of a VH having an amino acid sequence of SEQ ID NO:334; and (ii) a VL comprising a vlCDR1, a vlCDR2, and a vlCDR3 having an amino acid sequence of a vlCDR1, a vlCDR2, and a vlCDR3, respectively, of a VL having an amino acid sequence of SEQ ID NO:338.

In some embodiments of 2+1 Fab$_2$-scFv-Fc format, the anti-PSMA ABDs each include a VH and VL domain selected from the following:
- (i) a VH comprising a vhCDR1 having an amino acid sequence of SEQ ID NO:207; a vhCDR2 having an amino acid sequence of SEQ ID NO:208; and a vhCDR3 having an amino acid sequence of SEQ ID NO:209; and (ii) a VL comprising a vlCDR1 having an amino acid sequence of SEQ ID NO:211, a vlCDR2 having an amino acid sequence of SEQ ID NO: 212, and a vlCDR3 having an amino acid sequence of SEQ ID NO:213; or
- (i) a VH comprising a vhCDR1 having an amino acid sequence of SEQ ID NO:215; a vhCDR2 having an amino acid sequence of SEQ ID NO:216; and a vhCDR3 having an amino acid sequence of SEQ ID NO:217; and (ii) a VL comprising a vlCDR1 having an amino acid sequence of SEQ ID NO:219, a vlCDR2 having an amino acid sequence of SEQ ID NO: 220, and a vlCDR3 having an amino acid sequence of SEQ ID NO:221;
- (i) a VH comprising a vhCDR1 having an amino acid sequence of SEQ ID NO:223; a vhCDR2 having an amino acid sequence of SEQ ID NO:224; and a vhCDR3 having an amino acid sequence of SEQ ID NO:225; and (ii) a VL comprising a vlCDR1 having an amino acid sequence of SEQ ID NO:227, a vlCDR2 having an amino acid sequence of SEQ ID NO: 228, and a vlCDR3 having an amino acid sequence of SEQ ID NO:229; or
- (i) a VH comprising a vhCDR1 having an amino acid sequence of SEQ ID NO:231; a vhCDR2 having an amino acid sequence of SEQ ID NO:232; and a vhCDR3 having an amino acid sequence of SEQ ID NO:233; and (ii) a VL comprising a vlCDR1 having an amino acid sequence of SEQ ID NO:235, a vlCDR2 having an amino acid sequence of SEQ ID NO: 236, and a vlCDR3 having an amino acid sequence of SEQ ID NO:237; or
- (i) a VH comprising a vhCDR1 having an amino acid sequence of SEQ ID NO:239; a vhCDR2 having an amino acid sequence of SEQ ID NO:240; and a vhCDR3 having an amino acid sequence of SEQ ID NO:241; and (ii) a VL comprising a vlCDR1 having an amino acid sequence of SEQ ID NO:243, a vlCDR2 having an amino acid sequence of SEQ ID NO: 244, and a vlCDR3 having an amino acid sequence of SEQ ID NO:245; or
- (i) a VH comprising a vhCDR1 having an amino acid sequence of SEQ ID NO:247; a vhCDR2 having an amino acid sequence of SEQ ID NO:248; and a vhCDR3 having an amino acid sequence of SEQ ID NO:249; and (ii) a VL comprising a vlCDR1 having an amino acid sequence of SEQ ID NO:251, a vlCDR2 having an amino acid sequence of SEQ ID NO: 252, and a vlCDR3 having an amino acid sequence of SEQ ID NO:253; or
- (i) a VH comprising a vhCDR1 having an amino acid sequence of SEQ ID NO:255; a vhCDR2 having an amino acid sequence of SEQ ID NO:256; and a vhCDR3 having an amino acid sequence of SEQ ID NO:257; and (ii) a VL comprising a vlCDR1 having an amino acid sequence of SEQ ID NO:259, a vlCDR2 having an amino acid sequence of SEQ ID NO: 260, and a vlCDR3 having an amino acid sequence of SEQ ID NO:261; or
- (i) a VH comprising a vhCDR1 having an amino acid sequence of SEQ ID NO:263; a vhCDR2 having an amino acid sequence of SEQ ID NO:264; and a vhCDR3 having an amino acid sequence of SEQ ID NO:265; and (ii) a VL comprising a vlCDR1 having an amino acid sequence of SEQ ID NO:267, a vlCDR2 having an amino acid sequence of SEQ ID NO: 268, and a vlCDR3 having an amino acid sequence of SEQ ID NO:269; or
- (i) a VH comprising a vhCDR1 having an amino acid sequence of SEQ ID NO:271; a vhCDR2 having an amino acid sequence of SEQ ID NO:212; and a vhCDR3 having an amino acid sequence of SEQ ID NO:273; and (ii) a VL comprising a vlCDR1 having an amino acid sequence of SEQ ID NO:275, a vlCDR2 having an amino acid sequence of SEQ ID NO: 276, and a vlCDR3 having an amino acid sequence of SEQ ID NO:277; or
- (i) a VH comprising a vhCDR1 having an amino acid sequence of SEQ ID NO:279; a vhCDR2 having an amino acid sequence of SEQ ID NO:280; and a vhCDR3 having an amino acid sequence of SEQ ID NO:281; and (ii) a VL comprising a vlCDR1 having an amino acid sequence of SEQ ID NO:283, a vlCDR2 having an amino acid sequence of SEQ ID NO: 284, and a vlCDR3 having an amino acid sequence of SEQ ID NO:285; or
- (i) a VH comprising a vhCDR1 having an amino acid sequence of SEQ ID NO:287; a vhCDR2 having an amino acid sequence of SEQ ID NO:288; and a vhCDR3 having an amino acid sequence of SEQ ID NO:289; and (ii) a VL comprising a vlCDR1 having an amino acid sequence of SEQ ID NO:291, a vlCDR2 having an amino acid sequence of SEQ ID NO: 292, and a vlCDR3 having an amino acid sequence of SEQ ID NO:293; or
- (i) a VH comprising a vhCDR1 having an amino acid sequence of SEQ ID NO:295; a vhCDR2 having an amino acid sequence of SEQ ID NO:296; and a vhCDR3 having an amino acid sequence of SEQ ID NO:297; and (ii) a VL comprising a vlCDR1 having an amino acid sequence of SEQ ID NO:299, a vlCDR2 having an amino acid sequence of SEQ ID NO: 300, and a vlCDR3 having an amino acid sequence of SEQ ID NO:301; or
- (i) a VH comprising a vhCDR1 having an amino acid sequence of SEQ ID NO:303; a vhCDR2 having an amino acid sequence of SEQ ID NO:304; and a vhCDR3 having an amino acid sequence of SEQ ID NO:305; and (ii) a VL comprising a vlCDR1 having an amino acid sequence of SEQ ID NO:307, a vlCDR2 having an amino acid sequence of SEQ ID NO: 308, and a vlCDR3 having an amino acid sequence of SEQ ID NO:309; or
- (i) a VH comprising a vhCDR1 having an amino acid sequence of SEQ ID NO:311; a vhCDR2 having an amino acid sequence of SEQ ID NO:312; and a vhCDR3 having an amino acid sequence of SEQ ID NO:313; and (ii) a VL comprising a vlCDR1 having an amino acid sequence of SEQ ID NO: 315, a vlCDR2 having an amino acid sequence of SEQ ID NO: 316, and a vlCDR3 having an amino acid sequence of SEQ ID NO:317; or (i) a VH comprising a vhCDR1 having an amino acid sequence of SEQ ID NO:319; a vhCDR2 having an amino acid sequence of SEQ ID NO:320; and a vhCDR3 having an amino acid sequence of SEQ ID NO:321; and (ii) a VL comprising a vlCDR1 having an amino acid sequence of SEQ ID NO: 323, a vlCDR2 having an amino acid sequence of SEQ ID NO: 324, and a vlCDR3 having an amino acid sequence of SEQ ID NO:325; or (i) a VH comprising a vhCDR1 having an amino acid sequence of SEQ ID NO:327; a vhCDR2 having an amino acid sequence of SEQ ID NO:328; and a vhCDR3 having an amino acid sequence of SEQ ID NO:329; and (ii) a VL comprising a vlCDR1 having an amino acid sequence of SEQ ID NO:331, a vlCDR2 having an amino acid sequence of SEQ ID NO: 332, and a vlCDR3 having an amino acid sequence of SEQ ID NO:333; or (i) a VH comprising a vhCDR1 having an amino acid sequence of SEQ ID NO:335; a vhCDR2 having an amino acid sequence of SEQ ID NO:336; and a vhCDR3 having an amino acid sequence of SEQ ID NO:337; and (ii) a VL comprising a vlCDR1 having an amino acid sequence of SEQ ID NO: 339, a vlCDR2 having an amino acid sequence of SEQ ID NO: 340, and a vlCDR3 having an amino acid sequence of SEQ ID NO:341.

In some embodiments of 2+1 Fab$_2$-scFv-Fc format, the anti-PSMA ABDs each include a VH and VL domain selected from the following:

(i) a VH having an amino acid sequence of SEQ ID NO: 206; and (ii) a VL having an amino acid sequence of SEQ ID NO:210; or (i) a VH having an amino acid sequence of SEQ ID NO:214; and (ii) a VL having an amino acid sequence of SEQ ID NO:218; or (i) a VH having an amino acid sequence of SEQ ID NO:222; and (ii) a VL having an amino acid sequence of SEQ ID NO:226; or (i) a VH having an amino acid sequence of SEQ ID NO:230; and (ii) a VL having an amino acid sequence of SEQ ID NO:234; or (i) a VH having an amino acid sequence of SEQ ID NO:238; and (ii) a VL having an amino acid sequence of SEQ ID NO:242; or (i) a VH having an amino acid sequence of SEQ ID NO:246; and (ii) a VL having an amino acid sequence of SEQ ID NO:250; or (i) a VH having an amino acid sequence of SEQ ID NO:254; and (ii) a VL having an amino acid sequence of SEQ ID NO:258; or (i) a VH having an amino acid sequence of SEQ ID NO:262; and (ii) a VL having an amino acid sequence of SEQ ID NO:266; or (i) a VH having an amino acid sequence of SEQ ID NO:270; and (ii) a VL having an amino acid sequence of SEQ ID NO:274; or (i) a VH having an amino acid sequence of SEQ ID NO:278; and (ii) a VL having an amino acid sequence of SEQ ID NO:282; or (i) a VH having an amino acid sequence of SEQ ID NO:286; and (ii) a VL having an amino acid sequence of SEQ ID NO:290; or (i) a VH having an amino acid sequence of SEQ ID NO:294; and (ii) a VL having an amino acid sequence of SEQ ID NO:298; or (i) a VH having an amino acid sequence of SEQ ID NO:302; and (ii) a VL having an amino acid sequence of SEQ ID NO:306; or (i) a VH having an amino acid sequence of SEQ ID NO:310; and (ii) a VL having an amino acid sequence of SEQ ID NO:314; or (i) a VH having an amino acid sequence of SEQ ID NO:318; and (ii) a VL having an amino acid sequence of SEQ ID NO:322; or (i) a VH having an amino acid sequence of SEQ ID NO:326; and (ii) a VL having an amino acid sequence of SEQ ID NO:330; or (i) a VH having an amino acid sequence of SEQ ID NO:334; and (ii) a VL having an amino acid sequence of SEQ ID NO:338.

In some embodiments, the anti-PSMA× anti-CD28 antibody includes a) a CD28 binding domain comprising:

i) a VH comprising a vhCDR1 having an amino acid sequence of SEQ ID NO:40; a vhCDR2 having an amino acid sequence of SEQ ID NO:41; and a vhCDR3 having an amino acid sequence of SEQ ID NO:42; and (ii) a VL comprising a vlCDR1 having an amino acid sequence of SEQ ID NO:44, a vlCDR2 having an amino acid sequence of SEQ ID NO: 45, and a vlCDR3 having an amino acid sequence of SEQ ID NO:46; and b) two PSMA binding domains, each comprising:

i) a VH comprising a vhCDR1 having an amino acid sequence of SEQ ID NO:215; a vhCDR2 having an amino acid sequence of SEQ ID NO:216; and a vhCDR3 having an amino acid sequence of SEQ ID NO:217; and (ii) a VL comprising a vlCDR1 having an amino acid sequence of SEQ ID NO:219, a vlCDR2 having an amino acid sequence of SEQ ID NO: 220, and a vlCDR3 having an amino acid sequence of SEQ ID NO:221.

FIG. 11 shows some exemplary Fc domain sequences that are useful with the 2+1 Fab$_2$-scFv-Fc format. The "monomer 1" sequences depicted in FIG. 11 typically refer to the Fc domain of the "Fab-Fc heavy chain" and the "monomer 2" sequences refer to the Fc domain of the "Fab-scFv-Fc heavy chain." In addition, FIGS. 12 and 13 provide exemplary CH1-hinge domains, CH1 domains, and hinge domains that can be included in the first or second monomer of the 2+1 Fab$_2$-scFv-Fc format. Further, FIG. 14 provides useful CL sequences that can be used with this format.

3. 1+1 CLC Format

One heterodimeric antibody format that finds particular use in subject anti-CD28× anti-PSMA antibodies provided herein is the "1+1 Common Light Chain" or "1+1 CLC" format, which is depicted in FIG. 24C. The 1+1 CLC format antibody includes a first monomer that includes a VH1-CH1-hinge-CH2-CH3, wherein VH1 is a first variable heavy domain and CH2-CH3 is a first Fc domain; a second monomer that includes a VH2-CH1-hinge-CH2-CH3, wherein VH2 is a second variable heavy domain and CH2-C3 is a second Fc domain; and a third monomer "common light chain" comprising VL-CL, wherein VL is a common variable light domain and CL is a constant light domain. In such embodiments, the VL pairs with the VH1 to form a first binding domain with a first antigen binding specificity; and the VL pairs with the VH2 to form a second binding domain with a second antigen binding specificity. In some embodiments, the 1+1 CLC format antibody is a bivalent antibody.

In some embodiments, the first and second Fc domains of the 1+1 CLC format are variant Fc domains that include heterodimerization skew variants (e.g., a set of amino acid substitutions as shown in FIGS. 3A-3F and 9). Particularly useful heterodimerization skew variants include S364K/E357Q:L368D/K370S; L368D/K370S: S364K; L368E/K370S:S364K; T411T/E360E/Q362E:D401K; L368D/K370S: S364K/E357L; K370S:S364K/E357Q; T366S/L368A/Y407V:T366W and T366S/L368A/Y407V/Y349C: T366W/S354C (EU numbering). In exemplary embodiments, one of the first or second variant Fc domains includes heterodimerization skew variants L368D/K370S and the other of the first or second variant Fc domains includes heterodimerization skew variants S364K/E357Q, wherein numbering is according to EU numbering. In exemplary embodiments, the first variant Fc domain includes heterodimerization skew variants L368D/K370S and the second variant Fc domain includes heterodimerization skew variants S364K/E357Q, wherein numbering is according to EU numbering.

In some embodiments, the variant Fc domains include ablation variants (including those shown in FIG. 5). In some embodiments, each of the first and second variant Fc domains include ablation variants E233P/L234V/L235A/G236_/S267K, wherein numbering is according to EU numbering.

In some embodiments, the constant domain (CH1-hinge-CH2-CH3) of the first or second monomer includes pI variants (including those shown in FIG. 4). In exemplary embodiments, the constant domain (CH1-hinge-CH2-CH3) of the first or second monomer includes pI variants N208D/Q295E/N384D/Q418E/N421D, wherein numbering is according to EU numbering.

In some embodiments, the 1+1 CLC format antibody provided herein includes FcRn variants M428L/N434S, wherein numbering is according to EU numbering.

In exemplary embodiments, the first variant Fc domain includes heterodimerization skew variants L368D/K370S and the second variant Fc domain includes heterodimerization skew variants S364K/E357Q; each of the first and second variant Fc domains include ablation variants E233P/L234V/L235A/G236_/S267K; and the constant domain (CH1-hinge-CH2-CH3) of the first monomer includes pI variants N208D/Q295E/N384D/Q418E/N421D, wherein numbering is according to EU numbering.

In some embodiments, the CH1-hinge-CH2-CH3 of the first monomer comprises amino acid variants L368D/K370S/N208D/Q295E/N384D/Q418E/N421D/E233P/L234V/L235A/G236del/S267 K, and the second Fc domain comprises amino acid variants S364K/E357Q/E233P/L234V/L235A/G236del/S267K, wherein numbering is according to EU numbering.

In some embodiments, the 1+1 CLC format antibody provided herein further includes FcRn variants M428L/N434S, wherein numbering is according to EU numbering.

In some embodiments, one of the first binding domain or the second binding domain binds CD28 and the other binding domain binds PSMA. Any suitable CD28 binding domain and PSMA domain can be included in subject 1+1 CLC format antibody, including any of the CD28 binding domains and PSMA binding domains provided herein or a variant thereof (see, e.g., FIGS. 15-18C, 21A-21H, 25A-25E and 26A-26B).

4. 2+1 CLC Format

Another heterodimeric antibody format that finds particular use in subject CD28× anti-PSMA antibodies provided herein is the "2+1 Common Light Chain" or "2+1 CLC" format, which is depicted in FIG. 24D. The 2+1 CLC format includes a first monomer that includes a VH1-CH1-linker-VH1-CH1-hinge-CH2-CH3, wherein the VH1s are each a first variable heavy domain and CH2-CH3 is a first Fc domain; a second monomer that includes a VH2-CH1-hinge-CH2-CH3, wherein VH2 is a second variable heavy domain and CH2-CH3 is a second Fc domain; and a third monomer that includes a "common light chain" VL-CL, wherein VL is a common variable light domain and CL is a constant light domain. The VL pairs with each of the VH1s of the first monomer to form two first binding domains, each with a first antigen binding specificity; and the VL pairs with the VH2 to form a second binding domain with a second antigen binding specificity. The linker of the first monomer can be any suitable linker, including any one of the domain linkers or combinations thereof described in FIG. 7. In some embodiments, the linker is EPKSCGKPGSGKPGS (SEQ ID NO:483). In some embodiments, the 2+1 CLC format antibody is a trivalent antibody.

In some embodiments, the first and second Fc domains of the 2+1 CLC format are variant Fc domains that include heterodimerization skew variants (e.g., a set of amino acid substitutions as shown in FIGS. 3A-3F and 9). Particularly useful heterodimerization skew variants include S364K/E357Q:L368D/K370S; L368D/K370S: S364K; L368E/K370S:S364K; T411T/E360E/Q362E:D401K; L368D/K370S: S364K/E357L; K370S:S364K/E357Q; T366S/L368A/Y407V:T366W and T366S/L368A/Y407V/Y349C: T366W/S354C (EU numbering)). In exemplary embodiments, one of the first or second variant Fc domains includes heterodimerization skew variants L368D/K370S and the other of the first or second variant Fc domains includes heterodimerization skew variants S364K/E357Q, wherein numbering is according to EU numbering. In exemplary embodiments, the first variant Fc domain includes heterodimerization skew variants L368D/K370S and the second variant Fc domain includes heterodimerization skew variants S364K/E357Q, wherein numbering is according to EU numbering.

In some embodiments, the variant Fc domains include ablation variants (including those shown in FIG. 5). In some embodiments, each of the first and second variant Fc domains include ablation variants E233P/L234V/L235A/G236_/S267K, wherein numbering is according to EU numbering.

In some embodiments, the constant domain (CH1-hinge-CH2-CH3) of the first or second monomer includes pI variants (including those shown in FIG. 4). In exemplary embodiments, the constant domain (CH1-hinge-CH2-CH3) of the first or second monomer includes pI variants N208D/Q295E/N384D/Q418E/N421D, wherein numbering is according to EU numbering.

In some embodiments, the 2+1 CLC format antibody provided herein further includes FcRn variants M428L/N434S, wherein numbering is according to EU numbering.

In exemplary embodiments, the first variant Fc domain includes heterodimerization skew variants L368D/K370S and the second variant Fc domain includes heterodimerization skew variants S364K/E357Q; each of the first and second variant Fc domains include ablation variants E233P/L234V/L235A/G236_/S267K; and the constant domain (CH1-hinge-CH2-CH3) of the first monomer includes pI variants N208D/Q295E/N384D/Q418E/N421D, wherein numbering is according to EU numbering. In some embodiments, the 2+1 CLC format antibody provided herein further includes FcRn variants M428L/N434S, wherein numbering is according to EU numbering.

In some embodiments, the CH1-hinge-CH2-CH3 of the second monomer comprises amino acid variants L368D/K370S/N208D/Q295E/N384D/Q418E/N421D/E233P/L234V/L235A/G236del/S267 K, and the first Fc domain comprises amino acid variants S364K/E357Q/E233P/ L234V/L235A/G236del/S267K, wherein numbering is according to EU numbering.

In some embodiments, each of the two first binding domains binds a tumor PSMA and the second binding domain binds CD28 (see FIGS. 34A-34B). Any suitable CD28 binding domain and PSMA domain can be included in the subject 2+1 CLC format antibody, including any of the CD28 binding domains and PSMA binding domains provided herein or a variant thereof (see, e.g., FIGS. 15-18C, 21A-21H, 25A-25E and 26A-26B).

5. 2+1 mAb-scFv Format

One heterodimeric antibody format that finds particular use in the subject bispecific anti-CD28× anti-PSMA antibodies is the 2+1 mAb-scFv format shown in FIG. 24E. This antibody format includes three antigen binding domains: two Fab portions and an scFv that is attached to the C-terminal of one of the heavy chains. In some embodiments of this format, the Fab portions each bind PSMA, in this case, human PSMA and the "extra" scFv domain binds CD28. That is, this mAb-scFv format is a trivalent antibody.

In these embodiments, the first chain or monomer comprises, from N- to C-terminal, VH1-CH1-hinge-CH2-CH3, the second monomer comprises, from N- to C-terminal, VH1-CH1-hinge-CH2-CH3-domain linker-scFv domain, where the scFv domain comprises a second VH (VH2), a second VL (VL2) and a scFv linker. As for all the scFv domains herein, the scFv domain can be in either orientation, from N- to C-terminal, VH2-scFv linker-VL2 or VL2-scFv linker-VH2. Accordingly, the second monomer may comprise, from N- to C-terminal, VH1-CH1-hinge-CH2-CH3-domain linker-VH2-scFv linker-VL2 or VH1-CH1-hinge-CH2-CH3-domain linker-VL2-scFv linker-VH2. The composition also comprises a light chain, VL1-CL. In these embodiments, the VH1-VL1 each form a first ABD and the VH2-VL2 form a second ABD. In some embodiments, the first ABD binds to a tumor target antigen, including human PSMA, and the second ABD binds human CD28.

In some embodiments, the first and second Fc domains of the 2+1 mAb-scFv format antibody are variant Fc domains that include heterodimerization skew variants (e.g., a set of amino acid substitutions as shown in FIGS. 3A-3F and 9). Particularly useful heterodimerization skew variants include S364K/E357Q:L368D/K370S; L368D/K370S: S364K; L368E/K370S:S364K; T411T/E360E/Q362E:D401K; L368D/K370S: S364K/E357L; K370S:S364K/E357Q; T366S/L368A/Y407V:T366W and T366S/L368A/Y407V/Y349C:T366W/S354C (EU numbering)). In exemplary embodiments, one of the first or second variant Fc domains includes heterodimerization skew variants L368D/K370S and the other of the first or second variant Fc domains includes heterodimerization skew variants S364K/E357Q, wherein numbering is according to EU numbering. In exemplary embodiments, the first variant Fc domain includes heterodimerization skew variants L368D/K370S and the second variant Fc domain includes heterodimerization skew variants S364K/E357Q, wherein numbering is according to EU numbering.

In some embodiments, the variant Fc domains include ablation variants (including those shown in FIG. 5). In some embodiments, each of the first and second variant Fc domains include ablation variants E233P/L234V/L235A/G236_/S267K, wherein numbering is according to EU numbering.

In some embodiments, the constant domain (CH1-hinge-CH2-CH3) of the first monomer includes pI variants (including those shown in FIG. 4). In exemplary embodiments, the constant domain (CH1-hinge-CH2-CH3) of the first monomer includes pI variants N208D/Q295E/N384D/Q418E/N421D, wherein numbering is according to EU numbering.

In some embodiments, the scFv of the 2+1 mAb-scFv format antibody provided herein includes a charged scFv linker (including those shown in FIGS. 6A-6B). In some embodiments, the 2+1 mAb-scFv format antibody provided herein includes FcRn variants M428L/N434S, wherein numbering is according to EU numbering.

In exemplary embodiments, the first variant Fc domain includes heterodimerization skew variants L368D/K370S and the second variant Fc domain includes heterodimerization skew variants S364K/E357Q; each of the first and second variant Fc domains include ablation variants E233P/L234V/L235A/G236_/S267K; and the constant domain (CH1-hinge-CH2-CH3) of the first monomer includes pI variants N208D/Q295E/N384D/Q418E/N421D, wherein numbering is according to EU numbering. In some embodiments, the scFv of the 2+1 mAb-scFv format antibody provided herein includes a (GKPGS)$_4$ charged scFv linker (SEQ ID NO:443). In some embodiments, 2+1 mAb-scFv format antibody provided herein includes FcRn variants M428L/N434S, wherein numbering is according to EU numbering.

In some embodiments, the scFv of the second monomer of the 2+1 Fab$_2$-scFv-Fc format antibody is a CD28 binding and the VH1 of the first and second monomer and the VL1 of the common light chain each form binding domains that bind PSMA. Any suitable CD28 binding domain and PSMA binding domain can be included in the 2+1 mAb-scFv format antibody, including any of the CD28 binding domains and PSMA binding domains provided herein or a variant thereof (see, e.g., FIGS. 15-18C, 21A-21H, 25A-25E and 26A-26B).

6. Dual scFv Formats

Figure 24F:
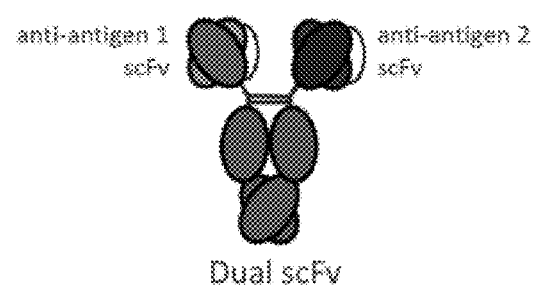

One heterodimeric antibody format that finds particular use in the subject bispecific anti-CD28× anti-PSMA antibodies is the dual scFv format, as are known in the art and shown in FIG. 24F. In this embodiment, the heterodimeric bispecific antibody is made up of two scFv-Fc monomers (both in either (vh-scFv linker-vl-[optional domain linker]-CH2-CH3) format or (vl-scFv linker-vh-[optional domain linker]-CH2-CH3) format, or with one monomer in one orientation and the other in the other orientation.

In this case, all ABDs are in the scFv format. Any suitable PSMA binding domain and CD28 binding domain can be included in anti-CD28× anti-PSMA antibody in the dual scFv format, including any of the PSMA binding domains and CD28 binding domains provided herein.

In addition, the Fc domains of the dual scFv format comprise skew variants (e.g. a set of amino acid substitutions as shown in FIG. 4, with particularly useful skew variants being selected from the group consisting of S364K/E357Q:L368D/K370S; L368D/K370S:S364K; L368E/K370S:S364K; T411T/E360E/Q362E:D401K; L368D/K370S:S364K/E357L, K370S:S364K/E357Q, T366S/L368A/Y407V:T366W and T366S/L368A/Y407V/Y349C:T366W/S354C), optionally ablation variants (including those shown in FIG. 5), optionally charged scFv linkers (including those shown in FIGS. 6A-6B) and the heavy chain comprises pI variants (including those shown in FIG. 4).

In some embodiments, the dual scFv format includes skew variants, pI variants, and ablation variants. Accordingly, some embodiments include formats that comprise: a) a first monomer that comprises the skew variants S364K/E357Q, the ablation variants E233P/L234V/L235A/

G236del/S267K, and a scFv that binds a first antigen (VH1-scFv linker-VL1-[optional domain linker]-CH2-CH3 or VL1-scFv linker-VH1-[optional domain linker]-CH2-CH3) and b) a first monomer that comprises the skew variants L368D/K370S, the ablation variants E233P/L234V/L235A/G236del/S267K, and a scFv that binds a second antigen (VH1-scFv linker-VL1-[optional domain linker]-CH2-CH3 or VL1-scFv linker-VH1-[optional domain linker]-CH2-CH3). pI variants can be as outlined herein, but most common will be charged scFv linkers of opposite charge for each monomer. FcRn variants, particularly 428L/434S, can optionally be included.

Any suitable PSMA binding domain and CD28 binding domain can be included in the dual scFv format, including any of the PSMA binding domains and CD28 binding domains provided herein or a variant thereof (see, e.g., FIGS. 15-18C, 21A-21H, 25A-25E and 26A-26B).

7. One-armed scFv-mAb Format

Figure 24G:
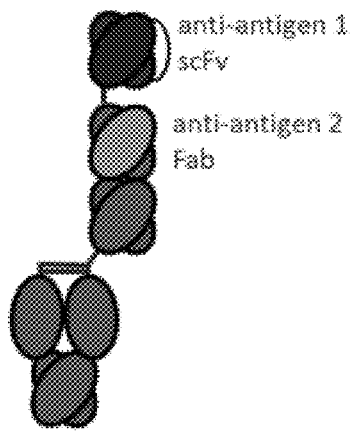

One heterodimeric antibody format that finds particular use in subject anti-CD28× anti-PSMA antibodies provided herein is the one-armed mAb-scFv format shown in FIG. 24G. This format includes: 1) a first monomer that comprises an "empty" Fc domain; 2) a second monomer that includes a first variable heavy domain (VH), a scFv domain (a second antigen binding domain) and an Fc domain, where the scFv domain is attached to the N-terminus of the first variable heavy domain; and 3) a light chain that includes a first variable light domain and a constant light domain. The first variable heavy domain and the first variable light domain form a first antigen binding domain and the scFv is a second antigen binding domain. In this format, one of the first antigen binding domain and second binding domain binds CD28, and the other antigen binding domain binds PSMA. As for many of the embodiments herein, these constructs include skew variants, pI variants, ablation variants, additional Fc variants, etc. as desired and described herein.

Any suitable PSMA binding domain and CD28 binding domain can be included in the one-armed scFv-mAb antibody format, including any of the PSMA binding domains and CD28 binding domains provided herein or a variant thereof (see, e.g., FIGS. 15-18C, 21A-21H, 25A-25E and 26A-26B).

8. scFv-mAb Format

Figure 24H:
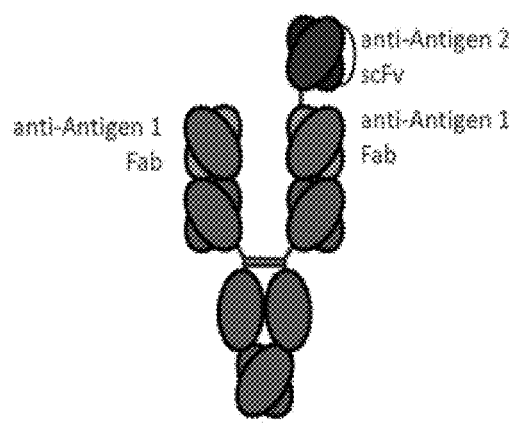

One heterodimeric antibody format that finds particular use in subject anti-CD28× anti-PSMA antibodies provided herein is the mAb-scFv format shown in FIG. 24H. In this embodiment, the format relies on the use of a N-terminal attachment of a scFv to one of the monomers, thus forming a third antigen binding domain, wherein the Fab portions of the two monomers each bind one target and the "extra" scFv domain binds a different target.

In this embodiment, the first monomer comprises a first heavy chain (comprising a variable heavy domain and a constant domain), with a N-terminally covalently attached scFv comprising a scFv variable light domain, an scFv linker and a scFv variable heavy domain in either orientation ((vh1-scFv linker-vl1-[optional domain linker]—vh2-CH1-hinge-CH2-CH3) or (with the scFv in the opposite orientation) ((vl1-scFv linker-vh1-[optional domain linker]-vh2-CH1-hinge-CH2-CH3)). The second monomer comprises a heavy chain VH2-CH1-hinge-CH2-CH3. This embodiment further utilizes a common light chain comprising a variable light domain and a constant light domain, that associates with the heavy chains to form two identical Fabs. As for many of the embodiments herein, these constructs include skew variants, pI variants, ablation variants, additional Fc variants, etc. as desired and described herein.

Any suitable PSMA binding domain and CD28 binding domain can be included in the scFv-mAb antibody format, including any of the PSMA binding domains and CD28 binding domains provided herein or a variant thereof (see, e.g., FIGS. 15-18C, 21A-21H, 25A-25E and 26A-26B).

9. Non-Heterodimeric Bispecific Antibodies

Figure 24I:
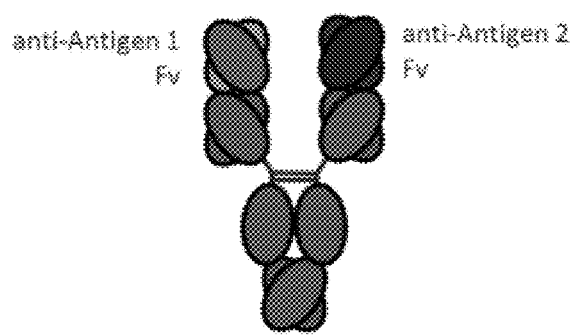

As will be appreciated by those in the art, the anti-CD28× anti-PSMA antibodies provided herein can also be included in non-heterodimeric bispecific formats (see FIG. 24I). In this format, the anti-CD28× anti-PSMA includes: 1) a first monomer comprising a VH1-CH1-hinge-CH2-CH3; 2) a second monomer comprising a VH2-CH1-hinge-CH2-CH3; 3) a first light chain comprising a VL1-CL; and 4) a second light chain comprising a VL2-CL. In such embodiments, the VH1 and VL1 form a first antigen binding domain and VH2 and VL2 form a second antigen binding domain. One of the first or second antigen binding domains binds CD28 and the other antigen binding domain binds PSMA.

Any suitable PSMA binding domain and CD28 binding domain can be included in anti-CD28× anti-PSMA antibody in the non-heterodimeric bispecific antibody format, including any of the PSMA binding domains and CD28 binding domains provided herein or a variant thereof (see, e.g., FIGS. 15-18C, 21A-21H, 25A-25E and 26A-26B).

10. One Armed Central-scFv

Figure 24J:
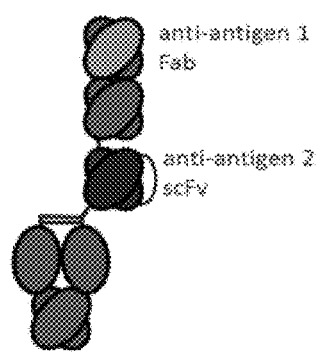

One heterodimeric antibody format that finds particular use in subject anti-CD28× anti-PSMA antibodies provided herein is the one armed central-scFv format shown in FIG. 24J. In this embodiment, one monomer comprises just an Fc domain, while the other monomer includes a Fab domain (a first antigen binding domain), a scFv domain (a second antigen binding domain) and an Fc domain, where the scFv domain is inserted between the Fc domain and the Fc domain.

In this embodiment, one monomer comprises a first heavy chain comprising a first variable heavy domain, a CH1 domain and Fc domain, with a scFv comprising a scFv variable light domain, an scFv linker and a scFv variable heavy domain. The scFv is covalently attached between the C-terminus of the CH1 domain of the heavy constant domain and the N-terminus of the first Fc domain using domain linkers, in either orientation, VH1-CH1-[optional domain linker]-VH2-scFv linker-VL2-[optional domain linker]-CH2-CH3 or VH1-CH1-[optional domain linker]-VL2-scFv linker-VH2-[optional domain linker]-CH2-CH3. The second monomer comprises an Fc domain (CH2-CH3). This embodiment further utilizes a light chain comprising a variable light domain and a constant light domain, that associates with the heavy chain to form a Fab. As for many of the embodiments herein, these constructs include skew variants, pI variants, ablation variants, additional Fc variants, etc. as desired and described herein.

Any suitable PSMA binding domain and CD28 binding domain can be included in the one armed central-scFv format, including any of the PSMA binding domains and CD28 binding domains provided herein.

11. mAb-Fv Format

Figure 24K:
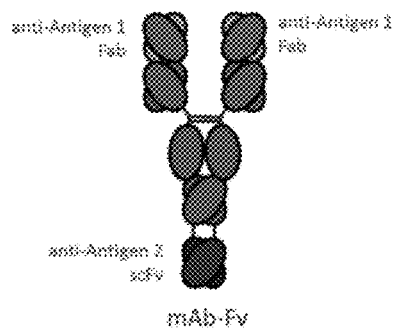

One heterodimeric antibody format that finds particular use in subject anti-CD28× anti-PSMA antibodies provided herein is the mAb-Fv format (FIG. 24K). In this embodiment, the format relies on the use of a C-terminal attachment of an "extra" variable heavy domain to one monomer and the C-terminal attachment of an "extra" variable light domain to the other monomer, thus forming a third antigen binding domain (i.e. an "extra" Fv domain), wherein the Fab portions of the two monomers bind CD28 and the "extra" Fv domain binds PSMA.

In this embodiment, the first monomer comprises a first heavy chain, comprising a first variable heavy domain and a first constant heavy domain comprising a first Fc domain, with a first variable light domain covalently attached to the C-terminus of the first Fc domain using a domain linker (vh1-CH1-hinge-CH2-CH3-[optional linker]-vl2). The second monomer comprises a second variable heavy domain, a second constant heavy domain comprising a second Fc domain, and a third variable heavy domain covalently attached to the C-terminus of the second Fc domain using a domain linker (vh1-CH1-hinge-CH2-CH3-[optional linker]-vh2. This embodiment further utilizes a common light chain comprising a variable light domain and a constant light domain, which associates with the heavy chains to form two identical Fabs that include two identical Fvs. The two C-terminally attached variable domains make up the "extra" third Fv. As for many of the embodiments herein, these constructs include skew variants, pI variants, ablation variants, additional Fc variants, etc. as desired and described herein.

In addition, the Fc domains of the mAb-Fv format comprise skew variants (e.g. a set of amino acid substitutions as shown in FIGS. 3A-3F, with particularly useful skew variants being selected from the group consisting of S364K/ E357Q:L368D/K370S; L368D/K370S:S364K; L368E/ K370S:S364K; T411T/E360E/Q362E:D401K; L368D/ K370S:S364K/E357L, K370S:S364K/E357Q, T366S/ L368A/Y407V:T366W and T366S/L368A/Y407V/Y349C: T366W/S354C), optionally ablation variants (including those shown in FIG. 5), optionally charged scFv linkers (including those shown in FIGS. 6A-6B) and the heavy chain comprises pI variants (including those shown in FIG. 4).

Any suitable PSMA binding domain and CD28 binding domain can be included in the mAb-Fv format, including any of the PSMA binding domains and CD28 binding domains provided herein or a variant thereof (see, e.g., FIGS. 15-18C, 21A-21H, 25A-25E and 26A-26B).

12. Central-Fv Format

Figure 24L:
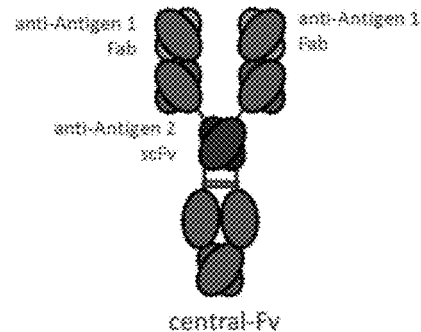

O One heterodimeric antibody format that finds particular use in subject anti-CD28× anti-PSMA antibodies provided herein is the central-Fv format shown in FIG. 24L. In this embodiment, the format relies on the use of an inserted Fv domain thus forming an "extra" third antigen binding domain, wherein the Fab portions of the two monomers bind PSMA and the "extra" central-Fv domain binds CD28. The Fv domain is inserted between the Fc domain and the CH1-Fv region of the monomers, thus providing a third antigen binding domain, wherein each monomer contains a component of the Fv (e.g. one monomer comprises a variable heavy domain and the other a variable light domain of the "extra" central Fv domain).

In this embodiment, one monomer comprises a first heavy chain comprising a first variable heavy domain, a CH1 domain, and Fc domain and an additional variable light domain. The additional variable light domain is covalently attached between the C-terminus of the CH1 domain of the heavy constant domain and the N-terminus of the first Fc domain using domain linkers (vh1-CH1-[optional linker]-vl2-hinge-CH2-CH3). The other monomer comprises a first heavy chain comprising a first variable heavy domain, a CH1 domain and Fc domain and an additional variable heavy domain (vh1-CH1-[optional linker]-vh2-hinge-CH2-CH3). The additional variable heavy domain is covalently attached between the C-terminus of the CH1 domain of the heavy constant domain and the N-terminus of the first Fc domain using domain linkers. This embodiment utilizes a common light chain comprising a variable light domain and a constant light domain, that associates with the heavy chains to form two identical Fabs that each bind PSMA. The additional variable heavy domain and additional variable light domain form an "extra" central Fv that binds CD28. As for many of the embodiments herein, these constructs include skew variants, pI variants, ablation variants, additional Fc variants, etc. as desired and described herein.

Any suitable PSMA binding domain and CD28 binding domain can be included in the central-Fv format, including any of the PSMA binding domains and CD28 binding domains provided herein or a variant thereof (see, e.g., FIGS. 15-18C, 21A-21H, 25A-25E and 26A-26B).

13. Trident Format

Figure 24M:
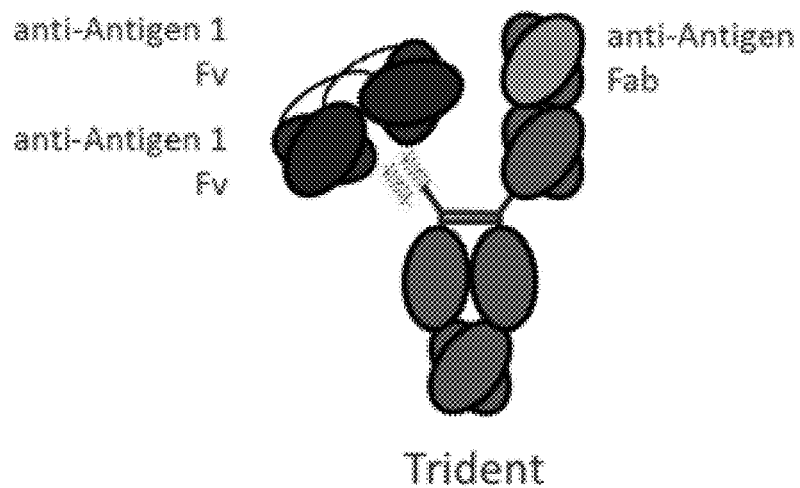

In some embodiments, the anti-CD28× anti-PSMA antibodies provided herein are in the "Trident" format as generally described in WO2015/184203, hereby expressly incorporated by reference in its entirety and in particular for the Figures, Legends, definitions and sequences of "Heterodimer-Promoting Domains" or "HPDs", including "K-coil" and "E-coil" sequences. Tridents rely on using two different HPDs that associate to form a heterodimeric structure as a component of the structure, see FIG. 24M. In this embodiment, the Trident format include a "traditional" heavy and light chain (e.g. VH1-CH1-hinge-CH2-CH3 and VL1-CL), a third chain comprising a first "diabody-type binding domain" or "DART®", VH2-(linker)-VL3-HPD1 and a fourth chain comprising a second DART®, VH3-(linker)-(linker)-VL2-HPD2. The VH1 and VL1 form a first ABD, the VH2 and VL2 form a second ABD, and the VH3 and VL3 form a third ABD. In some cases, as is shown in FIG. 24M, the second and third ABDs bind the same antigen.

Any suitable PSMA binding domain and CD28 binding domain can be included in the trident format, including any of the PSMA binding domains and CD28 binding domains provided herein or a variant thereof (see, e.g., FIGS. 15-18C, 21A-21H, 25A-25E and 26A-26B).

V. Nucleic Acids

In another aspect, provided herein are nucleic acid compositions encoding the anti-CD28× anti-PSMA antibodies provided herein. A nucleic acid composition may refer to one or multiple polynucleotides.

As will be appreciated by those in the art, the nucleic acid compositions will depend on the format and scaffold of the heterodimeric protein. Thus, for example, when the format requires three amino acid sequences, such as for the 1+1 Fab-scFv-Fc or 2+1 Fab2-scFv-Fc formats, three polynucleotides can be incorporated into one or more expression vectors for expression. In exemplary embodiments, each polynucleotide is incorporated into a different expression vector.

As is known in the art, the nucleic acids encoding the components of the binding domains and antibodies disclosed herein can be incorporated into expression vectors as is known in the art, and depending on the host cells used to produce the heterodimeric antibodies of the invention. Generally the nucleic acids are operably linked to any number of regulatory elements (promoters, origin of replication, selectable markers, ribosomal binding sites, inducers, etc.). The expression vectors can be extra-chromosomal or integrating vectors.

The polynucleotides and/or expression vectors of the invention are then transformed into any number of different types of host cells as is well known in the art, including mammalian, bacterial, yeast, insect and/or fungal cells, with mammalian cells (e.g., CHO cells), finding use in many embodiments.

In some embodiments, polynucleotides encoding each monomer are each contained within a single expression vector, generally under different or the same promoter controls. In embodiments of particular use in the present invention, each of these polynucleotides are contained on different expression vectors. As shown herein and in U.S. 62/025,931, hereby incorporated by reference, different vector ratios can be used to drive heterodimer formation. That is, surprisingly, while the proteins comprise first monomer: second monomer:light chains (in the case of many of the embodiments herein that have three polypeptides comprising the heterodimeric antibody) in a 1:1:2 ratio, these are not the ratios that give the best results.

The antibodies provided herein are made by culturing host cells comprising the expression vector(s) as is well known in the art. Once produced, traditional antibody purification steps are done, including an ion exchange chromatography step. As discussed herein, having the pIs of the two monomers differ by at least 0.5 can allow separation by ion exchange chromatography or isoelectric focusing, or other methods sensitive to isoelectric point. That is, the inclusion of pI substitutions that alter the isoelectric point (pI) of each monomer so that such that each monomer has a different pI and the heterodimer also has a distinct pI, thus facilitating isoelectric purification of the "1+1 Fab-scFv-Fc" heterodimer (e.g., anionic exchange columns, cationic exchange columns). These substitutions also aid in the determination and monitoring of any contaminating dual scFv-Fc and mAb homodimers post-purification (e.g., IEF gels, cIEF, and analytical IEX columns).

VI. Biological and Biochemical Functionality of the Anti-CD28× Anti-TAA Antibodies Generally the anti-CD28× anti-PSMA antibodies described herein are administered to patients with a PSMA-associated cancer (e.g., a prostate cancer), and efficacy is assessed, in a number of ways as described herein. Thus, while standard assays of efficacy can be run, such as cancer load, size of tumor, evaluation of presence or extent of metastasis, etc., immuno-oncology treatments can be assessed on the basis of immune status evaluations as well. This can be done in a number of ways, including both in vitro and in vivo assays.

A. Antibody Compositions for In Vivo Administration

Formulations of the anti-CD28× anti-PSMA antibodies described herein are prepared for storage by mixing an antibody having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

VII. Treatments

Once made, the compositions of the invention find use in a number of oncology applications, by treating cancer, generally by enhancing immune responses (e.g., T cell activation and proliferation), particularly when used with anti-cancer therapies such as anti-tumor bispecific antibodies. In some embodiments, the antibodies provided herein enhance immune responses (e.g., T cell activation and proliferation) by providing agonistic co-stimulation of T cells in the microenvironment of tumors expressing PSMA.

In some embodiments, the anti-CD28× anti-PSMA bispecific antibodies provided herein are administered with an anti-tumor therapy including, for example, anti-tumor-associated antigen (TAA) bispecific antibodies.

A. Anti-CD28× Anti-PSMA/Anti-PSMA Bispecific Antibody

In some embodiments, the anti-CD28× anti-PSMA antibodies provided herein are administered with an anti-PSMA bispecific antibody that is a T-cell engaging bispecific antibody, such as those that bind to human CD3.

In classic T cell/APC interaction, there is a first signal provided by TCR reactivity with peptide-MHC (Signal 1) and a second signal provided by CD28 crosslinking by CD80/CD86 being expressed on APCs (Signal 2) which together fully activate T cells (see FIG. 27A). In contrast, only the first signal is provided in treatment with CD3 bispecific antibodies that target a tumor-associated antigen (TAA)(i.e., anti-CD3× anti-PSMA bispecific antibodies).

Without being bound by any particular theory of operation, it is believed that the anti-CD28× anti-PSMA bispecific antibodies provided herein can enhance the anti-tumor response of an anti-CD3× anti-PSMA bispecific antibody by CD28 costimulation (see FIG. 27B). Thus, in one aspect, provided herein are methods of methods of treating a PSMA-associated cancer in a patient by administering the patient an anti-CD3× anti-PSMA bispecific antibody and an anti-CD28× anti-PSMA bispecific antibody provided herein.

Anti-CD3× anti-PSMA antibodies that are useful for providing "signal 1" in combination with the subject anti-CD28× anti-PSMA antibodies provided herein include, for example, those disclosed in FIGS. 28A-28C. Additional suitable anti-CD3× anti-PSMA antibodies for providing "signal 1" include, but are not limited to: Acapatamab (see, e.g., Kamat et al., Clin Cancer Res. 27(10:2675-2677 (2021)); DKTK CC-1 (see, e.g., EMBO Mol Med 13:e11902 (2021)), TNB-585 (see, e.g., J Immunother Cancer 9(6): e002488 (2021)); MOR209/ES414 (see, e.g., U.S. Pat. No. 9,782,478); REGN4338 (U.S. Pat. No. 10,179,819); JNJ-63898081 (see, e.g., WO2020/212947); CCW702 (see, e.g., WO2017/136659 and Lee et al., Sci Adv. 7(33):eabi8193 (2021)); HPN424 (see, e.g., WO2021/231434); and Pasotuxizumab (see, e.g., Hummel et al., Immunotherapy 13(2):125-141 (2021), all of the cited references are incorporate by reference herein in entirety and specifically for pertinent teachings relating to the enumerated exemplary anti-CD3× anti-PSMA antibodies and antibody sequences. In some embodiments, the anti-CD3× anti-PSMA antibody and the anti-CD28× anti-PSMA antibody used in combination bind to the same PSMA epitope. In some embodiments, the anti-CD3× anti-PSMA antibody and the anti-CD28× anti-PSMA antibody used in combination bind to different PSMA epitopes.

In addition to anti-CD3× anti-PSMA antibodies, the subject anti-CD28× anti-PSMA described herein can also be used as a "signal 2" in combination with an anti-CD3× anti-B7H3 antibody. See Examples 4, 5 and 7. Thus, in another aspect, provided herein are methods of treating a PSMA-associated cancer in a patient by administering the patient an anti-CD3× anti-B7H3 bispecific antibody and an anti-CD28× anti-PSMA bispecific antibody provided herein.

In other embodiments, the subject anti-CD28× anti-PSMA described herein can also be used as a "signal 2" in combination with a CD3 bispecific antibody that targets an alternative prostate antigen. Non-limiting examples of such "signal 1" bispecific antibodies include an anti-CD3× anti-hK2 bispecific antibody and an anti-CD3× anti-TMEFF2 bispecific antibody (e.g., as described in US 2021/0040210 and US 2019/0359711, respectively, which are incorporated by reference herein). Thus, in another aspect, provided herein are methods of treating a PSMA-associated cancer in a patient by administering the patient an anti-CD3× anti-hK2 bispecific antibody and an anti-CD28× anti-PSMA bispecific antibody provided herein. In another aspect, provided herein are methods of treating a PSMA-associated cancer in a patient by administering the patient an anti-CD3× anti-TMEFF2 bispecific antibody and an anti-CD28× anti-PSMA bispecific antibody provided herein.

B. Administrative Modalities

The antibodies provided herein administered to a subject, in accord with known methods, such as intravenous administration as a bolus or by continuous infusion over a period of time.

C. Treatment Modalities

In the methods of the invention, therapy is used to provide a positive therapeutic response with respect to a disease or condition.

By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the bispecific antibodies used in the present invention depend on the disease or condition to be treated and may be determined by the persons skilled in the art.

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

Examples

Examples are provided below to illustrate the present invention. These examples are not meant to constrain the present invention to any particular application or theory of operation. For all constant region positions discussed in the present invention, numbering is according to the EU index as in Kabat (Kabat et al., 1991, Sequences of Proteins of Immunological Interest, 5th Ed., United States Public Health Service, National Institutes of Health, Bethesda, entirely incorporated by reference). Those skilled in the art of antibodies will appreciate that this convention consists of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

General and specific scientific techniques are outlined in US Publications 2015/0307629, 2014/0288275 and WO2014/145806, all of which are expressly incorporated by reference in their entirety and particularly for the techniques outlined therein.

Example 1: CD28 Binding Domains

Sequences for human, mouse, and cynomolgus CD28 are depicted in FIGS. 1A-1B and are useful for the development of cross-reactive CD28 antigen binding domains for ease of clinical development.
1A: Novel CD28 Binding Domains An approach considered to avoid the superagonism associated with TGN1412 was to generate novel CD28 binding domains having lower affinity binding to CD28 and/or binding to a different CD28 epitope than TGN1412. In one campaign to generate such novel CD28 binding domains, in-house de novo phage libraries were panned against CD28.
1A(a): Phage-derived clone 1A7

It should be noted that this phage library utilized a human germline VL with diversity introduced into the LCDR3. The amino acid sequences for exemplary phage-derived clone 1A7 are depicted in FIG. 15.

The phage-derived clones were formatted as bivalent mAbs to investigate their binding characteristics. Plasmids containing the variable heavy and variable light domains of select clones were constructed by Gibson assembly and subcloned into a pTT5 expression vector containing the coding sequence for the IgG1 constant regions (with E233P/L234V/L235A/G236del/S67K ablation variants). DNA was transfected in HEK293E for expression and resulting bivalent mAbs were purified from the supernatant using protein A chromatography.

Affinity of the phage-derived bivalent mAbs for CD28 was screened using Octet, a BioLayer Interferometry (BLI)-based method. Experimental steps for Octet generally include the following: Immobilization (capture of ligand to a biosensor); Association (dipping of ligand-coated biosensors into wells containing the analyte); and Dissociation (returning of biosensors to well containing buffer). The resulting apparent dissociation constant ($K_{Dapp}$) are depicted in FIG. 23 for XENP28428 (based on clone 1A7) and additional phage-derived comparators.

Binding of the phage-derived bivalent mAbs to cell-surface CD28 was investigated. Human PBMCs were incubated with indicated concentrations of XENP28428 or comparator phage-derived mAbs for 1 hour at 4° C. Cells were then then stained with Alexa Fluor® 647 AffiniPure F(ab')$_2$ Fragment Goat Anti-Human IgG, Fcγ fragment specific secondary antibody (Jackson ImmunoResearch, West Grove, Penn.) for 1 hour at 4° C. and analyzed by flow cytometry. The data (FIG. 23) show that the phage-derived mAbs were able to bind human PBMCs, although with much weaker maximum binding than prior art anti-CD28 mAb HuTN228 (XENP27181, sequences for which are depicted in FIG. 22).

1A(b): 1A7 is not superagonistic

Potential superagonism of XENP34339 was assessed by air-drying per the Stebbings protocol (Stebbings R. et al. 2007). Air-drying of test articles was achieved by drying in a SpeedVac™ for 2 hours at room temperature. Human PBMCs were treated for 24 hours with 10 μg of air-dried XENP28428 (parental αCD28 mAb 1A7), and activity was compared to the superagonist TGN1412 (XENP29154; sequences for which are depicted in FIG. 22) or PBS control. Air-dried TGN1412 promoted IFNγ secretion from unstimulated human PBMC. In comparison, IFNγ level in PBMCs treated with air-dried XENP28428 remained similar to the negative control of PBS (data shown in FIG. 31). 1A(c): Engineering 1A7 affinity variants Towards optimization of PSMA×CD28 bsAbs as described in Example 5, numerous 1A7 affinity variants were developed by engineering VH variants (illustrative sequences as depicted in FIG. 16 and additional sequences depicted as SEQ ID NOs: 19-26), VL variants (illustrative sequences as depicted in FIG. 17 and additional sequences depicted as SEQ ID NOs: 27-30), consensus sequences for which are depicted in FIGS. 19A-19B, and combinations thereof (illustrative sequences for which are depicted in FIG. 18). Monovalent affinity of illustrative variants, in the context of scFvs, are depicted in FIG. 20.
1B: Additional CD28 Binding Domains Sequences for additional CD28 binding domains which may find use in the PSMA×CD28 bsAbs of the invention are depicted in FIG. 21A-21H.

Example 2: PSMA Binding Domains

Sequences for human, mouse, and cynomolgus PSMA are depicted in FIGS. 2A-2B and are useful for the development of cross-reactive PSMA antigen binding domains for ease of clinical development.
2A: Novel PSMA Binding Domains As will be described below, the PSMA×CD28 bsAbs of the invention were engineered with the aim to combine with PSMA×CD3 bsAbs. More specifically, they were anticipated to be combined with PSMA×CD3 bsAbs such as 1391 PSMA×CD3 and 1508 PSMA×CD3 (sequences for which are depicted in FIGS. 28A-28C). As will be described in Example 4C, PSMA×CD28 and PSMA×CD3 bsAbs having competing PSMA binding domains do not combine well at increasing concentrations. Therefore, novel PSMA binding domains were generated and selected based on binning to different epitope than 1391 and 1508, sequences for which are depicted in FIGS. 25A-25E. It should be noted that A10v2, D01v2, F07v2, G02v2, and F01v2 are respectively identical to A10, D01, F07, G02, and F01, except that degradation liabilities were removed.
2B: Additional PSMA Binding Domains Sequences for additional PSMA binding domains which may find use in the PSMA×CD28 bsAbs of the invention are depicted in FIGS. 26A-26B.

Example 3: Engineering PSMA×CD28 bsAbs

T cells require multiple signals for complete activation and differentiation. Signal 1, promoted by recognition of a peptide-MHC (pMHC) complex by the T cell receptor (TCR), is absolutely required for T cell activation. Signal 2, which synergizes with, and amplifies Signal 1, is typically provided by the interaction of the CD28 ligands CD80 and CD86 with CD28 itself. Although CD28 engagement alone is typically inert, when combined with Signal 1 activation, it promotes additional activation, survival, and proliferative signals, including IL2 secretion (see FIGS. 27A-27B). As CD80 and CD86 are only naturally expressed by professional antigen-presenting cells (APC), the extent of CD28 costimulation in the tumor setting can be highly variable. By creating this novel class of tumor-targeted CD28 bispecific antibodies, CD80/CD86 engagement of CD28 can be mimicked, providing an artificial source of Signal 2. Notably, signal can either be provided by the natural TCR:pMHC recognition of tumor cells, or it can be provided by combination of the CD28 bispecific with a CD3 bispecific (which can mimic Signal 1). As there are an increasing number of PSMA×CD3 undergoing clinical development for prostate cancer, it would be useful to develop PSMA×CD28 bsAbs to synergize with such molecules.

A number of formats are contemplated for use, schematics for which are outlined in FIG. 23. One exemplary format utilizing Fab domains and scFv is the 1+1 Fab-scFv-Fc format (depicted schematically in FIGS. 24A-24F) which comprises a first monomer comprising a single-chain Fv ("scFv") with a first antigen binding specificity covalently attached to a first heterodimeric Fc domain i.e., scFv-domain linker-CH2-CH3, a second monomer comprising a heavy chain i.e., VH-CH1-hinge-CH2-CH3, wherein the CH2-CH3 is a second heterodimeric Fc domain complementary to the first heterodimeric Fc domain, and a light chain (LC) transfected separately so that a Fab domain having a second antigen binding specificity is formed with the variable heavy domain. Any number of heterodimerization approaches as is known in the art could find use in this (and other) bispecific formats, in combination with any number of approaches for purifying heterodimers from contaminating homodimers, including those depicted in FIGS. 3A-3F. Regardless of bsAb format, the CD28 bispecific antibodies are monovalent for CD28 and incorporate Fc variants engineered to ablate FcγR binding to avoid potential superagonism. Such Fc variants include those depicted in FIG. 5. Any of the number of linkers as is known in the art may find use in linking the VH and VL domains of the scFv. Finally, it may be useful to maximize serum half-life of the bsAbs, and any of the number of half-life extending variants as is known in the art may find use in these bsAbs.

Two platforms based on the 1+1 Fab-scFv-Fc format were used, herein referred to as Platform X and Platform Y.
3A: Platform X Platform X (as described in FIG. 8) utilizes Backbones 1 or 11 in FIGS. 10A-10E. Specifically, this Platform utilizes the L368D/K370S (on the HC): S364K/E357Q (on the scFv-Fc) heterodimeric Fc variants. The Fab side further includes pI variants N208D/Q295E/N384D/Q418E/N421D to increase negative charge of the heavy chain. The scFv utilizes a positively charged (GKPGS)$_4$ linker (SEQ ID NO:443) between the VH and VL domains to increase positive charge of the scFv-Fc chain. Collectively, these two approaches enable easy purification of heterodimers from contaminating homodimers. The FcγR ablation variants utilized in this platform are the E233P/L234V/L235A/G236_/S267K substitutions on both the HC and the scFv-Fc monomers. In some cases, this platform includes the M428L/N434S half-life extension variants. Sequences for illustrative PSMA×CD28 bsAbs (based on binding domains as described in Examples 1 and 2) in the 1+1 Fab-scFv-Fc format and Platform X are depicted in FIGS. 29A-29RR.
3B: Platform J Platform J (as described in FIG. 8) utilizes Backbones 13 or 14 in FIGS. 10A-10E. Specifically, this Platform utilizes the T366S/L368A/Y407V (on the HC): T366W (on the scFv-Fc) heterodimeric Fc variants. The Fab side further includes H435R/Y436F to facilitate purification. The scFv may utilize a GGSEGKSSGSGSESKSTGGS (SEQ ID NO:456) (unstapled) or a GGGSGGSGGCPPCGGSGG (SEQ ID NO:457) (stapled) linker between the VH and VL domains. When using the latter stapled scFv linker, the VH and VL further include cysteine substitutions to form disulfide bridges with the linker. The FcγR ablation variants utilized in this platform are the L234A/L235A/D265S substitutions on both the HC and the scFv-Fc monomers. In some cases, this platform includes the M252Y/S254T/T256E half-life extension variants. Sequences for illustrative PSMA×CD28 bsAbs (based on binding domains as described in Examples 1 and 2) in the 1+1 Fab-scFv-Fc format and Platform J are depicted in FIGS. 30A-30L.

It should be noted that components from Platform X and Platform J can be mix and matched. For example, Platform J may utilize the (GKPGS)$_4$ linker (SEQ ID NO:443) of Platform X. Additionally, each of Platform X and Platform J may use alternative variants (e.g. alternative scFv linker, alternative half-life extension variants, alternative FcγR ablation variants, etc.).

Example 4: Prototype PSMA×CD28 bsAbs

Prototype PSMA×CD28 bsAbs were engineered and produced with high and low affinity 1A7 CD28 binding domains, respectively XENP37902 (1A7_H1.14_L1; 230 nM) and XENP37903 (1A7_H1.14_L1.71; 37 nM), sequences for which are depicted in FIGS. 29A-29RR.
4A: PSMA×CD28 bsAbs Combine Productively with CD3 bsAbs To investigate the combination of PSMA×CD28 bsAbs with CD3 bsAbs, the prototype PSMA×CD28 bsAbs were paired with an illustrative B7H3×CD3 bsAb or an illustrative PSMA×CD3.

In a first experiment, 2,500 C42B-NLR (PSMA$^{hi}$) and DU145-NLR (PSMA$^{lo}$) cancer cells were seeded. After 48 hours, CD3$^+$ T cells were added at an effector to target ratio of 1:1 along with 1 μg/mL B7H3×CD3 bsAb alone or in combination with 1 μg/mL XENP37902 or XENP37903. Data depicting induction of Redirected T Cell Cytotoxicity (RTCC) and T cell proliferation by the test articles are depicted in FIGS. 32 and 33A-33B. The data show that combination with PSMA×CD28 enhances both RTCC and T cell proliferation in the presence of PSMA$^{hi}$ C42B-NLR cancer cells. Notably, the low affinity 1A7_H1.14_L1 230 nM CD28 binding domain in XENP37902 was sufficient to enhance activity. Further, the data show that while the B7H3×CD3 bsAb alone induces RTCC and T cell proliferation in the presence of PSMA$^{null}$ DU145-NLR cancer cells, combination with the PSMA×CD28 bsAbs does not enhance activity indicating that PSMA×CD28 bsAbs only enhance activity in the presence of PSMA antigen.

In a second similar experiment, 2,500 C42B-NLR (PSMA$^{hi}$) and DU145-NLR (PSMA$^{lo}$) cancer cells were seeded. After 48 hours, CD3$^+$ T cells were added at an effector to target ratio of 1:1 along with 1 μg/mL PSMA×CD3 bsAb alone or in combination with 1 μg/mL XENP37902 or XENP37903. It should be noted that the PSMA×CD3 does not compete with the PSMA×CD28 bsAbs (i.e. their PSMA binding domains bind different epitopes). Data depicting induction of RTCC and T cell proliferation by the test articles are depicted in FIGS. 34A-34B and 35. Consistent with the above, the data show that combination with PSMA×CD28 enhances both RTCC and T cell proliferation in the presence of PSMA$^{hi}$ C42B-NLR cancer cells, but not in the presence of PSMA$^{lo}$ DU145-NLR cancer cells. 4B: PSMAxCD28 bsAbs are active on PSMA$^{hi}$ and PSMA$^{med}$ cells To further investigate the effect of PSMA antigen density on PSMAxCD28 activity, PC3 cell lines expressing varying PSMA antigen densities were generated. Cell-surface PSMA antigen density levels on the PSMA-transfected PC3 cell lines were estimated by FACS using fluorescently-labeled beads as advised by the QuickCal protocol (Bangs Laboratories, Inc., Fishers, IN). 50,000 cells per well and MESF beads were combined with A647-conjugated anti-PSMA mAb (J591) for 30 minutes at 4° C. Cells were then washed and fixed in 1% PFA. Flow cytometry was performed to determine antibody binding, and antigen density calculations were carried out using QuickCal® V.2.3. software (Bangs Laboratories, Inc., Fishers, IN). PSMA-transfected PC3 cell lines are hereon referred to by their PSMA density (i.e. PC3 (~100 k) has a MESF score of 100,000).

100,00 CD3$^+$ T cells were treated with a dose titration off XENP37902 or XENP37903 in the presence of 100,000 PC3 cancer cells (of varying PSMA densities) and constant 1 µg/mL non-competing PSMAxCD3 bsAb. 1 day post T cell seeding, IL-2 secretion was measured using MSD (Meso Scale Discovery, Rockville, Md.), data for which are depicted in FIG. 36. The data show that the PSMAxCD28 bsAb enhanced cytokine secretion in the presence of both PSMA$^{hi}$ and PSMA$^{med}$ cells, but not in the presence of PSMA$^{lo}$ cells.

4C: PSMAxCD28 bsAbs do not Combine Well with Competing PSMAxCD3 bsAbs

In the experiments above, a non-competing PSMAxCD3 bsAb was utilized. To investigate whether the PSMAxCD28 bsAbs combine productively with PSMAxCD3 bsAbs binding to the same epitope, additional competing PSMAxCD3 bsAb XENP32220 (sequences depicted in FIGS. 28A-28C) was utilized. 100,00 CD3$^+$ T cells were treated with a dose titration off XENP37902 or XENP37903 in the presence of 100,000 PC3 cancer cells (of varying PSMA densities) and constant 1 µg/mL XENP32220. 1 day post T cell seeding, IL-2 secretion was measured using MSD (Meso Scale Discovery, Rockville, Md.), data for which are depicted in FIG. 37. The data show that while the PSMAxCD28 bsAbs enhanced IL-2 secretion at lower concentration, there was a hooking effect and activity was diminished at higher concentrations. This suggests that it is useful for the PSMAxCD28 and PSMAxCD3 bsAbs to bind different epitopes, especially when higher concentration doses of PSMAxCD28 are expected.

Example 5: Characterizing PSMAxCD28 bsAbs Utilizing Novel PSMA Binding Domains

Additional PSMAxCD28 bsAbs were engineered in Platform X utilizing the novel PSMA binding domains as described in Example 2A. As noted above in Example 2A, the novel PSMA binding domains utilized in the PSMAxCD28 bsAbs were selected as they bind different PSMA epitope than selected PSMAxCD3 bsAb (1391 and 1508). Additionally for the investigation described in this section, medium CD28 affinity (1A7_H1_L1.71; 180 nM) binding domain was utilized to pull out differences on the PSMA side.

5A: PSMAxCD28 bsAbs Bound PSMAhi and PSMAmed Cell Lines

First, the ability of the PSMAxCD28 bsAbs to bind to PSMA$^+$ cell lines was investigated. 100,000 22Rv1 and C42B cancer cells were treated with a dose titration of the indicated PSMAxCD28 bsAbs at 37 degrees for 30 minutes. Cells were washed and then stained with anti-human-Ig-FITC for detecting bound bsAbs, data for which are depicted in FIG. 38. The data show that the PSMAxCD28 bsAbs bound the PSMA$^+$ cell lines with varying potencies. Notably, A10v2 demonstrated similar binding as A10; and D01v2 demonstrated similar binding as D01v2 indicating that the degradation liability fix did not negatively affect their binding. In an additional internalization experiment (data not shown), the bsAbs were found to internalize into C42B at different rates as well. While A11 bound well to PSMA$^+$ cell lines, it internalizes much quicker than the other PSMA binding domain. Additionally, while DOT and D01v2 demonstrated similar binding to the PSMA$^+$ cell lines, D01v2 internalizes more rapidly. PSMA binding domains having potent binding and low internalization rates were preferred.

5A: PSMAxCD28 bsAb Demonstrated In Vitro Activity Consistent with their PSMA Binding Next, the in vitro activity of the PSMAxCD28 bsAbs were investigated. In a first experiment, 10,000 22Rv1-NLR (PSMA$^{med}$) were seeded. The next day, T cells were added at an effector to target ratio of 1:1 with constant 1 µg/ml B7H3xCD3 bsAb and dose titration of PSMAxCD28 bsAbs. IL-2 was measured after 24 hours, data for which are depicted in FIG. 39. Next, a similar experiment was performed combining PSMAxCD28 bsAbs with PSMAxCD3 bsAbs 1391 or 1508. As before, IL-2 was measured after 24 hours, data for which are depicted in FIGS. 40 and 56. The data show a range of potencies consistent with cell binding. Notably as with binding, the degradation liability fixed A10v2 and D01v2 binding domains demonstrated similar activity as their parental counterparts.

Example 6: Tuning CD28 Binding Affinity

Based on observations associated with other T cell engagers (e.g. CD3 bsAbs), higher binding affinity for T cell antigen may negatively affect pharmacokinetic profile. Accordingly, preferred PSMA binding domains identified in Example 5 were paired with CD28 binding domains having varying CD28 binding affinities to identify the weakest CD28 binding domain that provides sufficient activity.

6A: Characterizing CD28 bsAb by Titrating PSMAxCD3 bsAb (Constant CD28 bsAb)

In a first set of experiment investigating the effect of varying CD28 binding affinities when paired with A10v2 or D01v2, constant 1 µg/mL dose of CD28 bsAbs were combined with a titration of PSMAxCD3 (1391 or 1508) in the presence of C42B-NLR (PSMA$^{hi}$), PC3-PSMA (~100K), 22Rv2-NLR (PSMA$^{med}$), and PC3-PSMA (~50K). Experiments were performed by seeding 10,000 cancer cells and incubating with T cells (1:1 E:T) and test articles after 24 hours. After a further 24 hour incubation, IL-2 secretion was measured, data for which are depicted in FIGS. 57 and 40 for A10v2 and FIGS. 42 and 58 for D01v2. The data show that most of the CD28 binding domains functioned well in the PSMAxCD28 bsAbs based on A10v2 and D01v2.

6B: Characterizing CD28 bsAb by Titrating PSMAxCD28 bsAb (Constant PSMAxCD3 bsAb)

In a further set of experiments investigating the effect of varying CD28 binding affinities when paired with A10v2 or D01v2, constant 1 µg/mL dose of PSMAxCD3 (1391 or 1508) were combined with a titration of PSMAxCD28 bsAbs in the presence of C42B-NLR (PSMA$^{hi}$), PC3-PSMA (~100K), 22Rv2-NLR (PSMA$^{med}$), and PC3-PSMA (~50K). Experiments were performed by seeding 10,000 cancer cells and incubating with T cells (1:1 E:T) and test articles after 24 hours. After a further 24 hour incubation, IL-2 secretion was measured, data for which are depicted in FIGS. 43 and 59 for A10v2 and FIGS. 44 and 60 for D01v2. Consistent with the above, the CD28 binding domains all functioned well in the PSMA×CD28 bsAbs based on A10v2 and D01v2.

Next, additional PSMA×CD28 bsAbs based on E07 paired with different CD28 binding affinities were investigated. Constant 1 µg/mL dose of PSMA×CD3 (1391 or 1508) were paired with dose titration of PSMA×CD28 bsAbs (based on A10v2, D01v2, and E07) in the presence of 22Rv1-NLR (PSMA$^{med}$) or PSMA-PC3 (~50K) cells. Experiments were performed by seeding 10,000 or 1,000 cancer cells and incubating with T cells (for 1:1 or 0.1:1 E:T ratio) and test articles after 24 hours. After a further 24 hour incubation, IL-2 secretion was measured, data for which are depicted in FIGS. 45-46 and 61-62. 5 days post incubation with test articles, T cell counts were analyzed using FACS, data for which are depicted in FIG. 47. Consistent with the foregoing, there is a ladder of potencies enabled by the use of the different PSMA binding domains (A10v2>D01v2>E07).

In another experiment, 1,250 22Rv1-NLR cancer cells were seeded. After 48 hours, T cells were added at an 1:1 E:T ratio with constant 1 µg/mL PSMA×CD28 bsAbs and 0.3 ng/mL, 1 ng/mL, 20 ng/mL, or 2.5 µg/mL 1391 PSMA× CD3. Incucyte recorded target cells over a period of 10 days (as an indicator off RTCC), as depicted in FIG. 48. At low 0.3 ng/mL concentration PSMA×CD3 bsAb, the CD28 bsAbs did not noticeably enhance RTCC activity. However at higher 1 ng/mL, 10 ng/mL, and 2.5 µg/mL PSMA×CD3 bsAb, the CD28 bsAbs noticeably enhanced RTCC activity. Notably, at 1 ng/mL PSMA×CD3 bsAbs with high affinity 37 nM and 96 nM CD28 binding domains lagged behind corresponding bsAbs with 180 nM and 230 nM CD28 binding domains. This trend is also observed in the combination with high concentration 2.5 µg/mL PSMA×CD3 bsAb.

6C: Investigating Lower CD28 Binding Affinities

In certain contexts (e.g. when targeting tumors with higher antigen density or combining with higher concentration CD3 bsAb), lower affinity CD28 binding domains may be preferred. In view of these observations, lower CD28 binding affinities were also investigated and XENP39231 and XENP40470 were produced pairing A10v2 with 1A7_H1.1_L1 600 nM and 1A7_H1L1 1000 nM CD28 binding domains. 10,000 PC3-PSMA (~100K) or 22Rv1-NLR (PSMA$^{med}$) cancer cells were seeded with T cells at a 1:1 E:T ratio in the presence of PSMA×CD3 (1391 or 1508) and dose titration of CD28 bsAbs. IL2 was assessed after 24 hours, data for which are shown in FIGS. 49 and 63. The data show that on PSMA$^{hi}$ cell lines, the lower affinity CD28 binding domains were still functional (although potency correlated to affinity). On the PSMA$^{med}$ cell line, the 600 nM CD28 binding domain was still functional.

Example 7: Further Characterization of PSMA×CD28 bsAbs

7A: PSMA×CD28 bsAbs in Combination with PSMA×CD3 is Only Active on PSMA Positive Cells Lines In combining CD3 and CD28 agonistic antibodies, it is especially important to ascertain that there are no off-target toxicities. To confirm this, activity of the PSMA×CD28 and PSMA×CD3 combination in the presence of PSMA$^{med}$ (PSMA-PC3 (~50K)), PSMA$^{lo}$ (PSMA-PC3 (~3K)), and PSMA$^{null}$ (DU145-NLR) cell lines were investigated. 10,000 cancer cells per well were seeded. After 24 hours, T cell were added at an effector to target ratio of 1:1 with 1 µg/mL 1391 PSMA×CD3 or 1508 PSMA×CD3 and dose titration off CD28 bsAbs. IL2 was measured after 24 hours, data for which are depicted in FIGS. 50 and 64. The data show that in fact the combination is only active on PSMA$^+$ cell lines.

7B: PSMA×CD28 bsAbs Produced on Platform X and Platform J Function Similarly

To investigate differences between Platform X and Platform J, XENP39234, XENP39233, and XENP38936 produced on Platform X were also produced on Platform J (i.e. grafting the variable regions). In a first experiment, binding of the bsAbs to C42B (PSMA$^{hi}$) cells was determined, data for which are depicted in FIG. 66. 10,000 PC3-PSMA (~50K) were seeded. After 24 hours, T cells were added at a 1:1 E:T ratio with 1 µg/mL PSMA×CD3 (1391 or 1508) and dose titration of CD28 bsAbs. IL2 was measured after 2 hours, data for which are depicted in FIGS. 51 and 65. The data show that molecules produced on Platform X and Platform J function similarly.

7C: PSMA×CD28 bsAbs Combine More Potently with Tumor Antigen Matched CD3 Bispecifics As previously noted, the PSMA×CD28 bsAbs of the invention were engineered with the aim to combine with certain PSMA×CD3 bsAbs. Nonetheless, it would be useful for the bsAbs to combine productively with other CD3 bsAbs. 10,000 PC3-PSMA (~100K) cancer cells were seeded. After 24 hours, T cells were added at 1:1 E:T ratio with 1 µg/mL B7H3×CD3 or PSMA×CD3 and dose titration of PSMA×CD28 bsAbs. IL2 and IFNγ secretion were measured after 1 day and RTCC was measured for 10 days, data for which are depicted in FIG. 52. The data show that the PSMA×CD28 bsAbs also combine productively with B7H3×CD3 bsAbs. Nonetheless, they combine more potently with tumor antigen matched CD3 bsAbs.

Example 8: In Vivo Anti-Tumor Activity

In a first experiment, NSG mice that were MHC EII-DKO (NSG-DKO) and thus resistant to GVHD were used. NSG-DKO mice (10 per group) were intradermally inoculated with 1×10$^6$ PC3-PSMA (~100K) cells on Day −13. Mice were then intraperitoneally injected with 5×10$^6$ human PBMCs and treated with the indicated test articles/test article combinations on Day 0, and further treated with the indicated test articles on Days 7 and 14. Tumor volumes were monitored by caliper measurements once to three times per week, data for which are shown (days post 1$^{st}$ dose) in FIGS. 53-54. Blood was drawn weekly and analyzed by flow cytometry to count expansion of human lymphocytes, data for which are shown in FIG. 55. The data show that each of the PSMA×CD28 bsAbs demonstrated anti-tumor activity as a single agent. This is likely by providing co-stimulation to alloreactivity between the human T cells and tumor cells. The PSMA×CD3 and B7H3×CD3 bsAbs as single agents also enhanced anti-tumor activity. Each of the PSMA×CD28 bsAbs further enhance anti-tumor activity when combined with the CD3 bsAbs (although more pronounced with a weaker Signal 1 e.g. in the case of lower dose PSMA×CD3). Notably, XENP39231 having a weak 1000 nM CD28 binding domain outperformed XENP38936 having a tighter 180 nM CD28 binding domain when combined with PSMA× CD3 bsAb.

Example 9: IL2 Production of Anti-PSMA×CD28 in Combination with PSMA×CD3 on Target Cells Using Human PBMCs C42B human prostate tumor cells were washed with DPBS and 0.05% trypsin was added to allow cells to detach.

Media was added to neutralize trypsin and the cells were transferred to a 15 mL conical with DPBS. The cells were centrifuged 1200 rpm for 3 minutes. DPBS was aspirated and cells were re-suspended in RPMI-10 complete medium. The cells were counted using the Vi-cell XR cell viability analyzer and were plated at 15K/well in 100 µL RPMI-10 complete medium. The plates were incubated at 37° C., 5% $CO_2$ overnight. Human PBMC Cells (Discovery Life Services) were thawed and transferred to a 15 mL conical with DPBS. The cells were centrifuged 1500 rpm for 3 minutes. DPBS was aspirated and cells were re-suspended in RPMI-10 complete medium. The cells were counted using the Vi-cell XR cell viability analyzer and were plated at an E:T of 1:1 (normalized to % CD3) in 50 µL of RPMI-10/well. PSMA×CD28 C28PB397 was prepared in a dilution block with a starting concentration of 40 nM, diluted 3-fold for a total of 10 dilution points including an untreated control. PSMA×CD28 C28PB397 was diluted in RPMI –10 or 1 nM of PSMA×CD3 1508. The molecules were added at 50 uL/well in RPMI-10 and plate was placed into an incubator at 37° C. overnight. Supernatant was collected after 24 hr of incubation. IL2 production was measured using IL2 AlphaLISA Kit(Perkinelmer). Data was graphed (GraphPad Prism) using a non-linear fit, log(agonist) vs. response—variable slope (4-parameters) (FIG. 72).

What is claimed is:

1. A heterodimeric antibody comprising:
   a) a first monomer comprising:
      i) a single chain variable fragment (scFv); and
      ii) a first Fc domain, wherein the scFv is covalently attached to the N-terminus of the first Fc domain using a domain linker;
   b) a second monomer comprising, from N-terminal to C-terminal, a VH1-CH1-hinge-CH2-CH3, wherein VH1 is a first variable heavy domain and CH2-CH3 is a second Fc domain; and
   c) a light chain comprising, from N-terminal to C-terminal, VL1-CL, wherein VL1 is a first variable light domain and CL is a constant light domain, wherein the scFv comprises a second VH domain (VH2), a scFv linker, and a second variable light domain (VL2),
   wherein the VH1 and the VL1 together form a first antigen binding domain (ABD) and the VH2 and the VL2 together form a second ABD, and
   wherein the first ABD binds Prostate Specific Membrane Antigen (PSMA) and the second ABD binds CD28, and
   wherein the VH1 has an amino acid sequence of SEQ ID NO: 214, the VH2 has an amino acid sequence of SEQ ID NO: 396, the VL1 has an amino acid of SEQ ID NO: 218, and the VL2 has an amino acid sequence of SEQ ID NO: 400.

* * * * *

```
                       SEQUENCE LISTING

Sequence total quantity: 1049
SEQ ID NO: 1           moltype = AA  length = 220
FEATURE                Location/Qualifiers
source                 1..220
                       mol_type = protein
                       organism = Homo sapiens
                       note = sp|0747:28_HUMAN T-cell-specific surface
                         glycoprotein CD28 OS=Homo sapiens OX=9606 GN=CD28 PE=1 SV=1
SEQUENCE: 1
MLRLLLALNL FPSIQVTGNK ILVKQSPMLV AYDNAVNLSC KYSYNLFSRE FRASLHKGLD   60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                        220

SEQ ID NO: 2           moltype = AA  length = 134
FEATURE                Location/Qualifiers
source                 1..134
                       mol_type = protein
                       organism = Homo sapiens
                       note = sp|0747[19]-152
SEQUENCE: 2
NKILVKQSPM LVAYDNAVNL SCKYSYNLFS REFRASLHKG LDSAVEVCVV YGNYSQQLQV   60
YSKTGFNCDG KLGNESVTFY LQNLYVNQTD IYFCKIEVMY PPPYLDNEKS NGTIIHVKGK  120
HLCPSPLFPG PSKP                                                    134

SEQ ID NO: 3           moltype = AA  length = 218
FEATURE                Location/Qualifiers
source                 1..218
                       mol_type = protein
                       organism = Mus musculus
                       note = sp[P3]1041:28_MOUSE T-cell-specific surface
                         glycoprotein CD28 OS=Mus musculus OX=10090 GN=Cd28 PE=1
                         SV=2
SEQUENCE: 3
MTLRLLLFLAL NFFSVQVTEN KILVKQSPLL VVDSNEVSLS CRYSYNLLAK EFRASLYKGV   60
NSDVEVCVGN GNFTYQPQFR SNAEFNCDGD FDNETVTFRL WNLHVNHTDI YFCKIEFMYP  120
PPYLDNERSN GTIIHIKEKH LCHTQSSPKL FWALVVVAGV LFCYGLLVTV ALCVIWTNSR  180
RNRLLQSDYM NMTPRRPGLT RKPYQPYAPA RDFAAYRP                          218

SEQ ID NO: 4           moltype = AA  length = 131
FEATURE                Location/Qualifiers
source                 1..131
                       mol_type = protein
                       organism = Mus musculus
                       note = sp[P3]1041[20]-150
SEQUENCE: 4
NKILVKQSPL LVVDSNEVSL SCRYSYNLLA KEFRASLYKG VNSDVEVCVG NGNFTYQPQF   60
RSNAEFNCDG DFDNETVTFR LWNLHVNHTD IYFCKIEFMY PPPYLDNERS NGTIIHIKEK  120
HLCHTQSSPK L                                                       131

SEQ ID NO: 5           moltype = AA  length = 220
FEATURE                Location/Qualifiers
source                 1..220
                       mol_type = protein
                       organism = Macaca fascicularis
                       note = trPDN3PDN3_MACFA CD28 OS=Macaca fascicularis
                         OX=9541 GN=CD28 PE=2 SV=1
SEQUENCE: 5
MLRLLLALNL LPSIQVTGNK ILVKQSPMLV AYDNAVNLSC KYSYNLFSRE FRASLHKGLD   60
SAVEVCVVYG NYSQQLQVYS KTGFNCDGKL GNESVTFYLQ NLYVNQTDIY FCKIEVMYPP  120
```

```
PYLDNEKSNG TIIHVKGKHL CPSPLFPGPS KPFWALVVVG GVLACYSLLV TVAFCIFWMR   180
SKRSRLLHSD YMNMTPRRPG PTRKHYQPYA PPRDFAAYRS                        220

SEQ ID NO: 6            moltype = AA  length = 134
FEATURE                 Location/Qualifiers
source                  1..134
                        mol_type = protein
                        organism = Macaca fascicularis
                        note = trPDN3[19]-152
SEQUENCE: 6
NKILVKQSPM LVAYDNAVNL SCKYSYNLFS REFRASLHKG LDSAVEVCVV YGNYSQQLQV   60
YSKTGFNCDG KLGNESVTFY LQNLYVNQTD IYFCKIEVMY PPPYLDNEKS NGTIIHVKGK   120
HLCPSPLFPG PSKP                                                    134

SEQ ID NO: 7            moltype = AA  length = 584
FEATURE                 Location/Qualifiers
source                  1..584
                        mol_type = protein
                        organism = Macaca fascicularis
                        note = XP_015308533.1 PREDICTED: CD276 antigen isoform X1
                        [Macaca fascicularis]
SEQUENCE: 7
MKLSSDHVFP LFRKLQWLPA AFRIQFTPVS PSAGAAFHHG EPSCQLPHSK MLHRRGSPGM   60
GVHVGAALGA LWFCLTGALE VQVPEDPVVA LVGTDATLRC SFSPEPGFSL AQLNLIWQLT   120
DTKQLVHSFT EGRDQGSAYA NRTALFLDLL AQGNASLRLQ RVRVADEGSF TCFVSIRDFG   180
SAAVSLQVAA PYSKPSMTLE PNKDLRPGDT VTITCSSYRG YPEAEVFWQD GQGAPLTGNV   240
TTSQMANEQG LFDVHSVLRV VLGANGTYSC LVRNPVLQQD AHGSITITPQ RSPTGAVEVQ   300
VPEDPVVALV GTDATLRCSF SPEPGFSLAQ LNLIWQLTDT KQLVHSFTEG RDQGSAYANR   360
TALFLDLLAQ GNASLRLQRV RVADEGSFTC FVSIRDFGSA AVSLQVAAPY SKPSMTLEPN   420
KDLRPGDTVT ITCSSYRGYP EAEVFWQDGQ GAPLTGNVTT SQMANEQGLF DVHSVLRVVL   480
GANGTYSCLV RNPVLQQDAH GSVTITGQPM TFPPEALWVT VGLSVCLVAL LVALAFVCWR   540
KIKQSCEEEN AGAEDQDGEG EGSKTALQPL KHSDSKEDDG QELA                   584

SEQ ID NO: 8            moltype = AA  length = 438
FEATURE                 Location/Qualifiers
source                  1..438
                        mol_type = protein
                        organism = Macaca fascicularis
                        note = XP_015308533.1[79]-516
SEQUENCE: 8
LEVQVPEDPV VALVGTDATL RCSFSPEPGF SLAQLNLIWQ LTDTKQLVHS FTEGRDQGSA   60
YANRTALFLD LLAQGNASLR LQRVRVADEG SFTCFVSIRD FGSAAVSLQV AAPYSKPSMT   120
LEPNKDLRPG DTVTITCSSY RGYPEAEVFW QDGQGAPLTG NVTTSQMANE QGLFDVHSVL   180
RVVLGANGTY SCLVRNPVLQ QDAHGSITIT PQRSPTGAVE VQVPEDPVVA LVGTDATLRC   240
SFSPEPGFSL AQLNLIWQLT DTKQLVHSFT EGRDQGSAYA NRTALFLDLL AQGNASLRLQ   300
RVRVADEGSF TCFVSIRDFG SAAVSLQVAA PYSKPSMTLE PNKDLRPGDT VTITCSSYRG   360
YPEAEVFWQD GQGAPLTGNV TTSQMANEQG LFDVHSVLRV VLGANGTYSC LVRNPVLQQD   420
AHGSVTITGQ PMTFPPEA                                                438

SEQ ID NO: 9            moltype = AA  length = 121
FEATURE                 Location/Qualifiers
source                  1..121
                        mol_type = protein
                        organism = synthetic construct
                        note = 1A7[CD28]_H1L1 Variable heavy (vh) domain
SEQUENCE: 9
EVQLLESGGG LVQPGGSLRL SCAASGFTFS SYAMSWVRQA PGKGLEWVST ISGSGDSTYY   60
ADSVKGRFTI SRDNSKNTLY LQMNSLRAED TAVYYCAKSG PGLRQVGFDY WGQGTLVTVS   120
S                                                                  121

SEQ ID NO: 10           moltype = AA  length = 5
FEATURE                 Location/Qualifiers
source                  1..5
                        mol_type = protein
                        organism = synthetic construct
                        note = 1A7[CD28]_H1L1 vhCDR1
SEQUENCE: 10
SYAMS                                                              5

SEQ ID NO: 11           moltype = AA  length = 17
FEATURE                 Location/Qualifiers
source                  1..17
                        mol_type = protein
                        organism = synthetic construct
                        note = 1A7[CD28]_H1L1 vhCDR2
SEQUENCE: 11
TISGSGDSTY YADSVKG                                                 17

SEQ ID NO: 12           moltype = AA  length = 12
```

```
FEATURE                 Location/Qualifiers
source                  1..12
                        mol_type = protein
                        organism = synthetic construct
                        note = 1A7[CD28]_H1L1 vhCDR3
SEQUENCE: 12
SGPGLRQVGF DY                                                          12

SEQ ID NO: 13           moltype = AA  length = 107
FEATURE                 Location/Qualifiers
source                  1..107
                        mol_type = protein
                        organism = synthetic construct
                        note = 1A7[CD28]_H1L1 Variable light (vl) domain
SEQUENCE: 13
DIQMTQSPSS LSASVGDRVT ITCRASQSIS SYLNWYQQKP GKAPKLLIYA ASSLQSGVPS        60
RFSGSGSGTD FTLTISSLQP EDFATYYCQQ SYSTPFTFGQ GTKLEIK                     107

SEQ ID NO: 14           moltype = AA  length = 11
FEATURE                 Location/Qualifiers
source                  1..11
                        mol_type = protein
                        organism = synthetic construct
                        note = 1A7[CD28]_H1L1 vlCDR1
SEQUENCE: 14
RASQSISSYL N                                                           11

SEQ ID NO: 15           moltype = AA  length = 7
FEATURE                 Location/Qualifiers
source                  1..7
                        mol_type = protein
                        organism = synthetic construct
                        note = 1A7[CD28]_H1L1 vlCDR2
SEQUENCE: 15
AASSLQS                                                                7

SEQ ID NO: 16           moltype = AA  length = 9
FEATURE                 Location/Qualifiers
source                  1..9
                        mol_type = protein
                        organism = synthetic construct
                        note = 1A7[CD28]_H1L1 vlCDR3
SEQUENCE: 16
QQSYSTPFT                                                              9

SEQ ID NO: 17           moltype = AA  length = 450
FEATURE                 Location/Qualifiers
source                  1..450
                        mol_type = protein
                        organism = synthetic construct
                        note = XENP28428 Heavy Chain
SEQUENCE: 17
EVQLLESGGG LVQPGGSLRL SCAASGFTFS SYAMSWVRQA PGKGLEWVST ISGSGDSTYY        60
ADSVKGRFTI SRDNSKNTLY LQMNSLRAED TAVYYCAKSG PGLRQVGFDY WGQGTLVTVS       120
SASTKGPSVF PLAPSSKSTS GGTAALGCLV KDYFPEPVTV SWNSGALTSG VHTFPAVLQS       180
SGLYSLSSVV TVPSSSLGTQ TYICNVNHKP SNTKVDKKVE PKSCDKTHTC PPCPAPPVAG       240
PSVFLFPPKP KDTLMISRTP EVTCVVVDVK HEDPEVKFNW YVDGVEVHNA KTKPREEQYN       300
STYRVVSVLT VLHQDWLNGK EYKCKVSNKA LPAPIEKTIS KAKGQPREPQ VYTLPPSREE       360
MTKNQVSLTC LVKGFYPSDI AVEWESNGQP ENNYKTTPPV LDSDGSFFLY SKLTVDKSRW       420
QQGNVFSCSV MHEALHNHYT QKSLSLSPGK                                       450

SEQ ID NO: 18           moltype = AA  length = 214
FEATURE                 Location/Qualifiers
source                  1..214
                        mol_type = protein
                        organism = synthetic construct
                        note = XENP28428 Light Chain
SEQUENCE: 18
DIQMTQSPSS LSASVGDRVT ITCRASQSIS SYLNWYQQKP GKAPKLLIYA ASSLQSGVPS        60
RFSGSGSGTD FTLTISSLQP EDFATYYCQQ SYSTPFTFGQ GTKLEIKRTV AAPSVFIFPP       120
SDEQLKSGTA SVVCLLNNFY PREAKVQWKV DNALQSGNSQ ESVTEQDSKD STYSLSSTLT       180
LSKADYEKHK VYACEVTHQG LSSPVTKSFN RGEC                                  214

SEQ ID NO: 19           moltype = AA  length = 121
FEATURE                 Location/Qualifiers
source                  1..121
                        mol_type = protein
                        organism = synthetic construct
                        note = 1A7_H1.1 Variable heavy (vh) domain
```

```
SEQUENCE: 19
EVQLLESGGG LVQPGGSLRL SCAASGFTFS SYYMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
S                                                                  121

SEQ ID NO: 20           moltype = AA  length = 5
FEATURE                 Location/Qualifiers
source                  1..5
                        mol_type = protein
                        organism = synthetic construct
                        note = 1A7_H1.1 vhCDR1
SEQUENCE: 20
SYYMS                                                                5

SEQ ID NO: 21           moltype = AA  length = 17
FEATURE                 Location/Qualifiers
source                  1..17
                        mol_type = protein
                        organism = synthetic construct
                        note = 1A7_H1.1 vhCDR2
SEQUENCE: 21
TISGSGDSTY YADSVKG                                                  17

SEQ ID NO: 22           moltype = AA  length = 12
FEATURE                 Location/Qualifiers
source                  1..12
                        mol_type = protein
                        organism = synthetic construct
                        note = 1A7_H1.1 vhCDR3
SEQUENCE: 22
SGPGLRQVGF DY                                                       12

SEQ ID NO: 23           moltype = AA  length = 121
FEATURE                 Location/Qualifiers
source                  1..121
                        mol_type = protein
                        organism = synthetic construct
                        note = 1A7_H1.14 Variable heavy (vh) domain
SEQUENCE: 23
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
S                                                                  121

SEQ ID NO: 24           moltype = AA  length = 5
FEATURE                 Location/Qualifiers
source                  1..5
                        mol_type = protein
                        organism = synthetic construct
                        note = 1A7_H1.14 vhCDR1
SEQUENCE: 24
SYYMS                                                                5

SEQ ID NO: 25           moltype = AA  length = 17
FEATURE                 Location/Qualifiers
source                  1..17
                        mol_type = protein
                        organism = synthetic construct
                        note = 1A7_H1.14 vhCDR2
SEQUENCE: 25
TISESGDSTY YADSVKG                                                  17

SEQ ID NO: 26           moltype = AA  length = 12
FEATURE                 Location/Qualifiers
source                  1..12
                        mol_type = protein
                        organism = synthetic construct
                        note = 1A7_H1.14 vhCDR3
SEQUENCE: 26
SGPGLRQVGF DY                                                       12

SEQ ID NO: 27           moltype = AA  length = 107
FEATURE                 Location/Qualifiers
source                  1..107
                        mol_type = protein
                        organism = synthetic construct
                        note = 1A7_L1.71 Variable light (vl) domain
SEQUENCE: 27
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ VYSTPFTFGQ GTKLEIK                 107
```

```
SEQ ID NO: 28            moltype = AA   length = 11
FEATURE                  Location/Qualifiers
source                   1..11
                         mol_type = protein
                         organism = synthetic construct
                         note = 1A7_L1.71 vlCDR1
SEQUENCE: 28
RASQSISSYL N                                                              11

SEQ ID NO: 29            moltype = AA   length = 7
FEATURE                  Location/Qualifiers
source                   1..7
                         mol_type = protein
                         organism = synthetic construct
                         note = 1A7_L1.71 vlCDR2
SEQUENCE: 29
AASSLQS                                                                    7

SEQ ID NO: 30            moltype = AA   length = 9
FEATURE                  Location/Qualifiers
source                   1..9
                         mol_type = protein
                         organism = synthetic construct
                         note = 1A7_L1.71 vlCDR3
SEQUENCE: 30
QQVYSTPFT                                                                  9

SEQ ID NO: 31            moltype = AA   length = 121
FEATURE                  Location/Qualifiers
source                   1..121
                         mol_type = protein
                         organism = synthetic construct
                         note = 1A7[CD28]_H1.1_L1 Variable Heavy (vh) Domain
SEQUENCE: 31
EVQLLESGGG LVQPGGSLRL SCAASGFTFS SYYMSWVRQA PGKGLEWVST ISGSGDSTYY           60
ADSVKGRFTI SRDNSKNTLY LQMNSLRAED TAVYYCAKSG PGLRQVGFDY WGQGTLVTVS          120
S                                                                        121

SEQ ID NO: 32            moltype = AA   length = 5
FEATURE                  Location/Qualifiers
source                   1..5
                         mol_type = protein
                         organism = synthetic construct
                         note = 1A7[CD28]_H1.1_L1 vhCDR1
SEQUENCE: 32
SYYMS                                                                      5

SEQ ID NO: 33            moltype = AA   length = 17
FEATURE                  Location/Qualifiers
source                   1..17
                         mol_type = protein
                         organism = synthetic construct
                         note = 1A7[CD28]_H1.1_L1 vhCDR2
SEQUENCE: 33
TISGSGDSTY YADSVKG                                                        17

SEQ ID NO: 34            moltype = AA   length = 12
FEATURE                  Location/Qualifiers
source                   1..12
                         mol_type = protein
                         organism = synthetic construct
                         note = 1A7[CD28]_H1.1_L1 vhCDR3
SEQUENCE: 34
SGPGLRQVGF DY                                                             12

SEQ ID NO: 35            moltype = AA   length = 107
FEATURE                  Location/Qualifiers
source                   1..107
                         mol_type = protein
                         organism = synthetic construct
                         note = 1A7[CD28]_H1.1_L1 Variable Light (vl) Domain
SEQUENCE: 35
DIQMTQSPSS LSASVGDRVT ITCRASQSIS SYLNWYQQKP GKAPKLLIYA ASSLQSGVPS          60
RFSGSGSGTD FTLTISSLQP EDFATYYCQQ SYSTPFTFGQ GTKLEIK                       107

SEQ ID NO: 36            moltype = AA   length = 11
FEATURE                  Location/Qualifiers
```

| | |
|---|---|
| source | 1..11<br>mol_type = protein<br>organism = synthetic construct<br>note = 1A7[CD28]_H1.1_L1 vlCDR1 |

SEQUENCE: 36
RASQSISSYL N                                                              11

| | |
|---|---|
| SEQ ID NO: 37<br>FEATURE<br>source | moltype = AA   length = 7<br>Location/Qualifiers<br>1..7<br>mol_type = protein<br>organism = synthetic construct<br>note = 1A7[CD28]_H1.1_L1 vlCDR2 |

SEQUENCE: 37
AASSLQS                                                                    7

| | |
|---|---|
| SEQ ID NO: 38<br>FEATURE<br>source | moltype = AA   length = 9<br>Location/Qualifiers<br>1..9<br>mol_type = protein<br>organism = synthetic construct<br>note = 1A7[CD28]_H1.1_L1 vlCDR3 |

SEQUENCE: 38
QQSYSTPFT                                                                  9

| | |
|---|---|
| SEQ ID NO: 39<br>FEATURE<br>source | moltype = AA   length = 121<br>Location/Qualifiers<br>1..121<br>mol_type = protein<br>organism = synthetic construct<br>note = 1A7[CD28]_H1_L1.71 Variable Heavy (vh) Domain |

SEQUENCE: 39
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS  120
S                                                                  121

| | |
|---|---|
| SEQ ID NO: 40<br>FEATURE<br>source | moltype = AA   length = 5<br>Location/Qualifiers<br>1..5<br>mol_type = protein<br>organism = synthetic construct<br>note = 1A7[CD28]_H1_L1.71 vhCDR1 |

SEQUENCE: 40
SYAMS                                                                      5

| | |
|---|---|
| SEQ ID NO: 41<br>FEATURE<br>source | moltype = AA   length = 17<br>Location/Qualifiers<br>1..17<br>mol_type = protein<br>organism = synthetic construct<br>note = 1A7[CD28]_H1_L1.71 vhCDR2 |

SEQUENCE: 41
TISGSGDSTY YADSVKG                                                        17

| | |
|---|---|
| SEQ ID NO: 42<br>FEATURE<br>source | moltype = AA   length = 12<br>Location/Qualifiers<br>1..12<br>mol_type = protein<br>organism = synthetic construct<br>note = 1A7[CD28]_H1_L1.71 vhCDR3 |

SEQUENCE: 42
SGPGLRQVGF DY                                                             12

| | |
|---|---|
| SEQ ID NO: 43<br>FEATURE<br>source | moltype = AA   length = 107<br>Location/Qualifiers<br>1..107<br>mol_type = protein<br>organism = synthetic construct<br>note = 1A7[CD28]_H1_L1.71 Variable Light (vl) Domain |

SEQUENCE: 43
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ VYSTPFTFGQ GTKLEIK                 107

| | |
|---|---|
| SEQ ID NO: 44<br>FEATURE<br>source | moltype = AA   length = 11<br>Location/Qualifiers<br>1..11<br>mol_type = protein<br>organism = synthetic construct<br>note = 1A7[CD28]_H1_L1.71 vlCDR1 |

-continued

```
SEQUENCE: 44
RASQSISSYL N                                                              11

SEQ ID NO: 45            moltype = AA  length = 7
FEATURE                  Location/Qualifiers
source                   1..7
                         mol_type = protein
                         organism = synthetic construct
                         note = 1A7[CD28]_H1_L1.71 vlCDR2
SEQUENCE: 45
AASSLQS                                                                    7

SEQ ID NO: 46            moltype = AA  length = 9
FEATURE                  Location/Qualifiers
source                   1..9
                         mol_type = protein
                         organism = synthetic construct
                         note = 1A7[CD28]_H1_L1.71 vlCDR3
SEQUENCE: 46
QQVYSTPFT                                                                  9

SEQ ID NO: 47            moltype = AA  length = 121
FEATURE                  Location/Qualifiers
source                   1..121
                         mol_type = protein
                         organism = synthetic construct
                         note = 1A7[CD28]_H1.1_L1.71 Variable Heavy (vh) Domain
SEQUENCE: 47
EVQLLESGGG LVQPGGSLRL SCAASGFTFS SYYMSWVRQA PGKGLEWVST ISGSGDSTYY          60
ADSVKGRFTI SRDNSKNTLY LQMNSLRAED TAVYYCAKSG PGLRQVGFDY WGQGTLVTVS        120
S                                                                        121

SEQ ID NO: 48            moltype = AA  length = 5
FEATURE                  Location/Qualifiers
source                   1..5
                         mol_type = protein
                         organism = synthetic construct
                         note = 1A7[CD28]_H1.1_L1.71 vhCDR1
SEQUENCE: 48
SYYMS                                                                      5

SEQ ID NO: 49            moltype = AA  length = 17
FEATURE                  Location/Qualifiers
source                   1..17
                         mol_type = protein
                         organism = synthetic construct
                         note = 1A7[CD28]_H1.1_L1.71 vhCDR2
SEQUENCE: 49
TISGSGDSTY YADSVKG                                                        17

SEQ ID NO: 50            moltype = AA  length = 12
FEATURE                  Location/Qualifiers
source                   1..12
                         mol_type = protein
                         organism = synthetic construct
                         note = 1A7[CD28]_H1.1_L1.71 vhCDR3
SEQUENCE: 50
SGPGLRQVGF DY                                                             12

SEQ ID NO: 51            moltype = AA  length = 107
FEATURE                  Location/Qualifiers
source                   1..107
                         mol_type = protein
                         organism = synthetic construct
                         note = 1A7[CD28]_H1.1_L1.71 Variable Light (vl) Domain
SEQUENCE: 51
DIQMTQSPSS LSASVGDRVT ITCRASQSIS SYLNWYQQKP GKAPKLLIYA ASSLQSGVPS         60
RFSGSGSGTD FTLTISSLQP EDFATYYCQQ VYSTPFTFGQ GTKLEIK                      107

SEQ ID NO: 52            moltype = AA  length = 11
FEATURE                  Location/Qualifiers
source                   1..11
                         mol_type = protein
                         organism = synthetic construct
                         note = 1A7[CD28]_H1.1_L1.71 vlCDR1
SEQUENCE: 52
RASQSISSYL N                                                              11

SEQ ID NO: 53            moltype = AA  length = 7
```

```
FEATURE                 Location/Qualifiers
source                  1..7
                        mol_type = protein
                        organism = synthetic construct
                        note = 1A7[CD28]_H1.1_L1.71 vlCDR2
SEQUENCE: 53
AASSLQS                                                                 7

SEQ ID NO: 54           moltype = AA  length = 9
FEATURE                 Location/Qualifiers
source                  1..9
                        mol_type = protein
                        organism = synthetic construct
                        note = 1A7[CD28]_H1.1_L1.71 vlCDR3
SEQUENCE: 54
QQVYSTPFT                                                               9

SEQ ID NO: 55           moltype = AA  length = 121
FEATURE                 Location/Qualifiers
source                  1..121
                        mol_type = protein
                        organism = synthetic construct
                        note = 1A7[CD28]_H1.14_L1 Variable Heavy (vh) Domain
SEQUENCE: 55
EVQLLESGGG LVQPGGSLRL SCAASGFTFS SYYMSWVRQA PGKGLEWVST ISESGDSTYY        60
ADSVKGRFTI SRDNSKNTLY LQMNSLRAED TAVYYCAKSG PGLRQVGFDY WGQGTLVTVS       120
S                                                                     121

SEQ ID NO: 56           moltype = AA  length = 5
FEATURE                 Location/Qualifiers
source                  1..5
                        mol_type = protein
                        organism = synthetic construct
                        note = 1A7[CD28]_H1.14_L1 vhCDR1
SEQUENCE: 56
SYYMS                                                                   5

SEQ ID NO: 57           moltype = AA  length = 17
FEATURE                 Location/Qualifiers
source                  1..17
                        mol_type = protein
                        organism = synthetic construct
                        note = 1A7[CD28]_H1.14_L1 vhCDR2
SEQUENCE: 57
TISESGDSTY YADSVKG                                                     17

SEQ ID NO: 58           moltype = AA  length = 12
FEATURE                 Location/Qualifiers
source                  1..12
                        mol_type = protein
                        organism = synthetic construct
                        note = 1A7[CD28]_H1.14_L1 vhCDR3
SEQUENCE: 58
SGPGLRQVGF DY                                                          12

SEQ ID NO: 59           moltype = AA  length = 107
FEATURE                 Location/Qualifiers
source                  1..107
                        mol_type = protein
                        organism = synthetic construct
                        note = 1A7[CD28]_H1.14_L1 Variable Light (vl) Domain
SEQUENCE: 59
DIQMTQSPSS LSASVGDRVT ITCRASQSIS SYLNWYQQKP GKAPKLLIYA ASSLQSGVPS        60
RFSGSGSGTD FTLTISSLQP EDFATYYCQQ SYSTPFTFGQ GTKLEIK                    107

SEQ ID NO: 60           moltype = AA  length = 11
FEATURE                 Location/Qualifiers
source                  1..11
                        mol_type = protein
                        organism = synthetic construct
                        note = 1A7[CD28]_H1.14_L1 vlCDR1
SEQUENCE: 60
RASQSISSYL N                                                           11

SEQ ID NO: 61           moltype = AA  length = 7
FEATURE                 Location/Qualifiers
```

```
source                       1..7
                             mol_type = protein
                             organism = synthetic construct
                             note = 1A7[CD28]_H1.14_L1 vlCDR2
SEQUENCE: 61
AASSLQS                                                                          7

SEQ ID NO: 62                moltype = AA   length = 9
FEATURE                      Location/Qualifiers
source                       1..9
                             mol_type = protein
                             organism = synthetic construct
                             note = 1A7[CD28]_H1.14_L1 vlCDR3
SEQUENCE: 62
QQSYSTPFT                                                                        9

SEQ ID NO: 63                moltype = AA   length = 121
FEATURE                      Location/Qualifiers
source                       1..121
                             mol_type = protein
                             organism = synthetic construct
                             note = 1A7[CD28]_H1.14_L1.71 Variable Heavy (vh) Domain
SEQUENCE: 63
EVQLLESGGG LVQPGGSLRL SCAASGFTFS SYYMSWVRQA PGKGLEWVST ISESGDSTYY                60
ADSVKGRFTI SRDNSKNTLY LQMNSLRAED TAVYYCAKSG PGLRQVGFDY WGQGTLVTVS               120
S                                                                              121

SEQ ID NO: 64                moltype = AA   length = 5
FEATURE                      Location/Qualifiers
source                       1..5
                             mol_type = protein
                             organism = synthetic construct
                             note = 1A7[CD28]_H1.14_L1.71 vhCDR1
SEQUENCE: 64
SYYMS                                                                            5

SEQ ID NO: 65                moltype = AA   length = 17
FEATURE                      Location/Qualifiers
source                       1..17
                             mol_type = protein
                             organism = synthetic construct
                             note = 1A7[CD28]_H1.14_L1.71 vhCDR2
SEQUENCE: 65
TISESGDSTY YADSVKG                                                              17

SEQ ID NO: 66                moltype = AA   length = 12
FEATURE                      Location/Qualifiers
source                       1..12
                             mol_type = protein
                             organism = synthetic construct
                             note = 1A7[CD28]_H1.14_L1.71 vhCDR3
SEQUENCE: 66
SGPGLRQVGF DY                                                                   12

SEQ ID NO: 67                moltype = AA   length = 107
FEATURE                      Location/Qualifiers
source                       1..107
                             mol_type = protein
                             organism = synthetic construct
                             note = 1A7[CD28]_H1.14_L1.71 Variable Light (vl) Domain
SEQUENCE: 67
DIQMTQSPSS LSASVGDRVT ITCRASQSIS SYLNWYQQKP GKAPKLLIYA ASSLQSGVPS                60
RFSGSGSGTD FTLTISSLQP EDFATYYCQQ VYSTPFTFGQ GTKLEIK                             107

SEQ ID NO: 68                moltype = AA   length = 11
FEATURE                      Location/Qualifiers
source                       1..11
                             mol_type = protein
                             organism = synthetic construct
                             note = 1A7[CD28]_H1.14_L1.71 vlCDR1
SEQUENCE: 68
RASQSISSYL N                                                                    11

SEQ ID NO: 69                moltype = AA   length = 7
FEATURE                      Location/Qualifiers
source                       1..7
                             mol_type = protein
                             organism = synthetic construct
                             note = 1A7[CD28]_H1.14_L1.71 vlCDR2
```

```
SEQUENCE: 69
AASSLQS                                                                   7

SEQ ID NO: 70           moltype = AA  length = 9
FEATURE                 Location/Qualifiers
source                  1..9
                        mol_type = protein
                        organism = synthetic construct
                        note = 1A7[CD28]_H1.14_L1.71 vlCDR3
SEQUENCE: 70
QQVYSTPFT                                                                 9

SEQ ID NO: 71           moltype = AA  length = 30
FEATURE                 Location/Qualifiers
source                  1..30
                        mol_type = protein
                        organism = synthetic construct
                        note = 1A7 VH HFR1
VARIANT                 28
                        note = T, S, or N
VARIANT                 29
                        note = F or L
VARIANT                 30
                        note = S, E, R, K, G, T, A, or N
SEQUENCE: 71
EVQLLESGGG LVQPGGSLRL SCAASGFXXX                                          30

SEQ ID NO: 72           moltype =    length =
SEQUENCE: 72
000

SEQ ID NO: 73           moltype = AA  length = 14
FEATURE                 Location/Qualifiers
source                  1..14
                        mol_type = protein
                        organism = synthetic construct
                        note = 1A7 VH HFR2
VARIANT                 14
                        note = S or A
SEQUENCE: 73
WVRQAPGKGL EWVX                                                           14

SEQ ID NO: 74           moltype = AA  length = 17
FEATURE                 Location/Qualifiers
source                  1..17
                        mol_type = protein
                        organism = synthetic construct
                        note = 1A7 VH HCDR2
VARIANT                 1
                        note = T or S
VARIANT                 3
                        note = S, D, E, Y, or T
VARIANT                 4
                        note = G, D, E, A, Y, S, N, or T
VARIANT                 5
                        note = S, D, N, or G
VARIANT                 6
                        note = D, T, Y, S, or A
VARIANT                 7
                        note = D, T, Y, S, or A
VARIANT                 8
                        note = S, Y, A, T, D, or N
SEQUENCE: 74
XIXXXXXXTY YADSVKG                                                        17

SEQ ID NO: 75           moltype = AA  length = 32
FEATURE                 Location/Qualifiers
source                  1..32
                        mol_type = protein
                        organism = synthetic construct
                        note = 1A7 VH HFR3
SEQUENCE: 75
RFTISRDNSK NTLYLQMNSL RAEDTAVYYC AK                                       32

SEQ ID NO: 76           moltype = AA  length = 12
FEATURE                 Location/Qualifiers
```

| | | |
|---|---|---|
| source | 1..12<br>mol_type = protein<br>organism = synthetic construct<br>note = 1A7 VH HCDR3 | |
| SEQUENCE: 76<br>SGPGLRQVGF DY | | 12 |
| SEQ ID NO: 77<br>FEATURE<br>source | moltype = AA length = 11<br>Location/Qualifiers<br>1..11<br>mol_type = protein<br>organism = synthetic construct<br>note = 1A7 VH HFR4 | |
| SEQUENCE: 77<br>WGQGTLVTVS S | | 11 |
| SEQ ID NO: 78<br>SEQUENCE: 78<br>000 | moltype = length = | |
| SEQ ID NO: 79<br>FEATURE<br>source | moltype = AA length = 23<br>Location/Qualifiers<br>1..23<br>mol_type = protein<br>organism = synthetic construct<br>note = 1A7 VL LFR1 | |
| SEQUENCE: 79<br>DIQMTQSPSS LSASVGDRVT ITC | | 23 |
| SEQ ID NO: 80<br>FEATURE<br>source<br><br>VARIANT<br><br>VARIANT<br><br>VARIANT | moltype = AA length = 11<br>Location/Qualifiers<br>1..11<br>mol_type = protein<br>organism = synthetic construct<br>note = 1A7 VL LCDR1<br>8<br>note = S, A, D, G, H, K, N, Q, T, V, or Y<br>9<br>note = Y, A, D, F, H, K, L, N, Q, S, or W<br>11<br>note = N, A, D, G, H, Q, S, T, or Y | |
| SEQUENCE: 80<br>RASQSISXXL X | | 11 |
| SEQ ID NO: 81<br>FEATURE<br>source | moltype = AA length = 15<br>Location/Qualifiers<br>1..15<br>mol_type = protein<br>organism = synthetic construct<br>note = 1A7 VL LFR2 | |
| SEQUENCE: 81<br>WYQQKPGKAP KLLIY | | 15 |
| SEQ ID NO: 82<br>SEQUENCE: 82<br>000 | moltype = length = | |
| SEQ ID NO: 83<br>FEATURE<br>source | moltype = AA length = 32<br>Location/Qualifiers<br>1..32<br>mol_type = protein<br>organism = synthetic construct<br>note = 1A7 VL LFR3 | |
| SEQUENCE: 83<br>GVPSRFSGSG SGTDFTLTIS SLQPEDFATY YC | | 32 |
| SEQ ID NO: 84<br>FEATURE<br>source<br><br>VARIANT<br><br>VARIANT<br><br>VARIANT | moltype = AA length = 9<br>Location/Qualifiers<br>1..9<br>mol_type = protein<br>organism = synthetic construct<br>note = 1A7 VL LCDR3<br>3<br>note = S, A, D, F, H, K, L, T, V, or Y<br>4<br>note = Y, A, D, F, H, K, L, Q, V, or W<br>5<br>note = S, A, D, G, H, K, N, Q, T, V, or Y | |

```
VARIANT                  6
                         note = T, A, D, F, I, K, L, Q, S, V, or Y
VARIANT                  8
                         note = F, I, L, or W
SEQUENCE: 84
QQXXXXPXT                                                             9

SEQ ID NO: 85            moltype = AA  length = 10
FEATURE                  Location/Qualifiers
source                   1..10
                         mol_type = protein
                         organism = synthetic construct
                         note = 1A7 VL LFR4
SEQUENCE: 85
FGQGTKLEIK                                                            10

SEQ ID NO: 86            moltype = AA  length = 121
FEATURE                  Location/Qualifiers
source                   1..121
                         mol_type = protein
                         organism = synthetic construct
                         note = CD28.3[CD28]_H0L0 Variable heavy (vh) domain
SEQUENCE: 86
EVKLQQSGAE LVKPGASVRL SCKASGYTFT EYIIHWIKLR SGQGLEWIGW FYPGSNDIQY      60
NAKFKGKATL TADKSSSTVY MELTGLTSED SAVYFCARRD DFSGYDALPY WGQGTMVTVS     120
S                                                                    121

SEQ ID NO: 87            moltype = AA  length = 5
FEATURE                  Location/Qualifiers
source                   1..5
                         mol_type = protein
                         organism = synthetic construct
                         note = CD28.3[CD28]_H0L0 vhCDR1
SEQUENCE: 87
EYIIH                                                                 5

SEQ ID NO: 88            moltype = AA  length = 17
FEATURE                  Location/Qualifiers
source                   1..17
                         mol_type = protein
                         organism = synthetic construct
                         note = CD28.3[CD28]_H0L0 vhCDR2
SEQUENCE: 88
WFYPGSNDIQ YNAKFKG                                                    17

SEQ ID NO: 89            moltype = AA  length = 12
FEATURE                  Location/Qualifiers
source                   1..12
                         mol_type = protein
                         organism = synthetic construct
                         note = CD28.3[CD28]_H0L0 vhCDR3
SEQUENCE: 89
RDDFSGYDAL PY                                                         12

SEQ ID NO: 90            moltype = AA  length = 107
FEATURE                  Location/Qualifiers
source                   1..107
                         mol_type = protein
                         organism = synthetic construct
                         note = CD28.3[CD28]_H0L0 Variable light (vl) domain
SEQUENCE: 90
DIQMTQSPAS LSVSVGETVT ITCRTNENIY SNLAWYQQKQ GKSPQLLIYA ATHLVEGVPS      60
RFSGSGSGTQ YSLKITSLQS EDFGNYYCQH FWGTPCTFGG GTKLEIK                   107

SEQ ID NO: 91            moltype = AA  length = 11
FEATURE                  Location/Qualifiers
source                   1..11
                         mol_type = protein
                         organism = synthetic construct
                         note = CD28.3[CD28]_H0L0 vlCDR1
SEQUENCE: 91
RTNENIYSNL A                                                          11

SEQ ID NO: 92            moltype = AA  length = 7
FEATURE                  Location/Qualifiers
source                   1..7
                         mol_type = protein
                         organism = synthetic construct
                         note = CD28.3[CD28]_H0L0 vlCDR2
```

```
SEQUENCE: 92
AATHLVE                                                                    7

SEQ ID NO: 93           moltype = AA   length = 9
FEATURE                 Location/Qualifiers
source                  1..9
                        mol_type = protein
                        organism = synthetic construct
                        note = CD28.3[CD28]_H0L0 vlCDR3
SEQUENCE: 93
QHFWGTPCT                                                                  9

SEQ ID NO: 94           moltype = AA   length = 121
FEATURE                 Location/Qualifiers
source                  1..121
                        mol_type = protein
                        organism = synthetic construct
                        note = hCD28.3[CD28]_H1L1 Variable heavy (vh) domain
SEQUENCE: 94
QVQLQQSGAE LKKPGASVKV SCKASGYTFT EYIIHWIKLR SGQGLEWIGW FYPGSNDIQY          60
NAQFKGKATL TADKSSSTVY MELTGLTPED SAVYFCARRD DFSGYDALPY WGQGTLVTVS         120
A                                                                        121

SEQ ID NO: 95           moltype = AA   length = 5
FEATURE                 Location/Qualifiers
source                  1..5
                        mol_type = protein
                        organism = synthetic construct
                        note = hCD28.3[CD28]_H1L1 vhCDR1
SEQUENCE: 95
EYIIH                                                                      5

SEQ ID NO: 96           moltype = AA   length = 17
FEATURE                 Location/Qualifiers
source                  1..17
                        mol_type = protein
                        organism = synthetic construct
                        note = hCD28.3[CD28]_H1L1 vhCDR2
SEQUENCE: 96
WFYPGSNDIQ YNAQFKG                                                        17

SEQ ID NO: 97           moltype = AA   length = 12
FEATURE                 Location/Qualifiers
source                  1..12
                        mol_type = protein
                        organism = synthetic construct
                        note = hCD28.3[CD28]_H1L1 vhCDR3
SEQUENCE: 97
RDDFSGYDAL PY                                                             12

SEQ ID NO: 98           moltype = AA   length = 107
FEATURE                 Location/Qualifiers
source                  1..107
                        mol_type = protein
                        organism = synthetic construct
                        note = hCD28.3[CD28]_H1L1 Variable light (vl) domain
SEQUENCE: 98
DIQMTQSPSS LSASVGDRVT ITCKTNENIY SNLAWYQQKD GKSPQLLIYA ATHLVEGVPS         60
RFSGSGSGTQ YSLTISSLQP EDFGNYYCQH FWGTPCTFGG GTKLEIK                      107

SEQ ID NO: 99           moltype = AA   length = 11
FEATURE                 Location/Qualifiers
source                  1..11
                        mol_type = protein
                        organism = synthetic construct
                        note = hCD28.3[CD28]_H1L1 vlCDR1
SEQUENCE: 99
KTNENIYSNL A                                                              11

SEQ ID NO: 100          moltype = AA   length = 7
FEATURE                 Location/Qualifiers
source                  1..7
                        mol_type = protein
                        organism = synthetic construct
                        note = hCD28.3[CD28]_H1L1 vlCDR2
SEQUENCE: 100
AATHLVE                                                                    7

SEQ ID NO: 101          moltype = AA   length = 9
```

```
FEATURE                 Location/Qualifiers
source                  1..9
                        mol_type = protein
                        organism = synthetic construct
                        note = hCD28.3[CD28]_H1L1 vlCDR3
SEQUENCE: 101
QHFWGTPCT                                                                  9

SEQ ID NO: 102          moltype = AA  length = 120
FEATURE                 Location/Qualifiers
source                  1..120
                        mol_type = protein
                        organism = synthetic construct
                        note = 5.11A1[CD28]_H0L0 Variable heavy (vh) domain
SEQUENCE: 102
QVQLQQSGPE LVKPGTSVRI SCEASGYTFT SYYIHWVKQR PGQGLEWIGC IYPGNVNTNY    60
NEKFKDKATL IVDTSSNTAY MQLSRMTSED SAVYFCTRSH YGLDWNFDVW GAGTTVTVSS   120

SEQ ID NO: 103          moltype = AA  length = 5
FEATURE                 Location/Qualifiers
source                  1..5
                        mol_type = protein
                        organism = synthetic construct
                        note = 5.11A1[CD28]_H0L0 vhCDR1
SEQUENCE: 103
SYYIH                                                                      5

SEQ ID NO: 104          moltype = AA  length = 17
FEATURE                 Location/Qualifiers
source                  1..17
                        mol_type = protein
                        organism = synthetic construct
                        note = 5.11A1[CD28]_H0L0 vhCDR2
SEQUENCE: 104
CIYPGNVNTN YNEKFKD                                                        17

SEQ ID NO: 105          moltype = AA  length = 11
FEATURE                 Location/Qualifiers
source                  1..11
                        mol_type = protein
                        organism = synthetic construct
                        note = 5.11A1[CD28]_H0L0 vhCDR3
SEQUENCE: 105
SHYGLDWNFD V                                                              11

SEQ ID NO: 106          moltype = AA  length = 107
FEATURE                 Location/Qualifiers
source                  1..107
                        mol_type = protein
                        organism = synthetic construct
                        note = 5.11A1[CD28]_H0L0 Variable light (vl) domain
SEQUENCE: 106
DIQMNQSPSS LSASLGDTIT ITCHASQNIY VWLNWYQQKP GNIPKLLIYK ASNLHTGVPS    60
RFSGSGSGTG FTLTISSLQP EDIATYYCQQ GQTYPYTFGG GTKLEIK                 107

SEQ ID NO: 107          moltype = AA  length = 11
FEATURE                 Location/Qualifiers
source                  1..11
                        mol_type = protein
                        organism = synthetic construct
                        note = 5.11A1[CD28]_H0L0 vlCDR1
SEQUENCE: 107
HASQNIYVWL N                                                              11

SEQ ID NO: 108          moltype = AA  length = 7
FEATURE                 Location/Qualifiers
source                  1..7
                        mol_type = protein
                        organism = synthetic construct
                        note = 5.11A1[CD28]_H0L0 vlCDR2
SEQUENCE: 108
KASNLHT                                                                    7

SEQ ID NO: 109          moltype = AA  length = 9
FEATURE                 Location/Qualifiers
source                  1..9
                        mol_type = protein
                        organism = synthetic construct
                        note = 5.11A1[CD28]_H0L0 vlCDR3
```

```
SEQUENCE: 109
QQGQTYPYT                                                                9

SEQ ID NO: 110          moltype = AA   length = 120
FEATURE                 Location/Qualifiers
source                  1..120
                        mol_type = protein
                        organism = synthetic construct
                        note = TGN1412_H1L1 Variable heavy (vh) domain
SEQUENCE: 110
QVQLVQSGAE VKKPGASVKV SCKASGYTFT SYYIHWVRQA PGQGLEWIGC IYPGNVNTNY         60
NEKFKDRATL TVDTSISTAY MELSRLRSDD TAVYFCTRSH YGLDWNFDVW GQGTTVTVSS        120

SEQ ID NO: 111          moltype = AA   length = 5
FEATURE                 Location/Qualifiers
source                  1..5
                        mol_type = protein
                        organism = synthetic construct
                        note = TGN1412_H1L1 vhCDR1
SEQUENCE: 111
SYYIH                                                                    5

SEQ ID NO: 112          moltype = AA   length = 17
FEATURE                 Location/Qualifiers
source                  1..17
                        mol_type = protein
                        organism = synthetic construct
                        note = TGN1412_H1L1 vhCDR2
SEQUENCE: 112
CIYPGNVNTN YNEKFKD                                                       17

SEQ ID NO: 113          moltype = AA   length = 11
FEATURE                 Location/Qualifiers
source                  1..11
                        mol_type = protein
                        organism = synthetic construct
                        note = TGN1412_H1L1 vhCDR3
SEQUENCE: 113
SHYGLDWNFD V                                                             11

SEQ ID NO: 114          moltype = AA   length = 107
FEATURE                 Location/Qualifiers
source                  1..107
                        mol_type = protein
                        organism = synthetic construct
                        note = TGN1412_H1L1 Variable light (vl) domain
SEQUENCE: 114
DIQMTQSPSS LSASVGDRVT ITCHASQNIY VWLNWYQQKP GKAPKLLIYK ASNLHTGVPS         60
RFSGSGSGTD FTLTISSLQP EDFATYYCQQ GQTYPYTFGG GTKVEIK                      107

SEQ ID NO: 115          moltype = AA   length = 11
FEATURE                 Location/Qualifiers
source                  1..11
                        mol_type = protein
                        organism = synthetic construct
                        note = TGN1412_H1L1 vlCDR1
SEQUENCE: 115
HASQNIYVWL N                                                             11

SEQ ID NO: 116          moltype = AA   length = 7
FEATURE                 Location/Qualifiers
source                  1..7
                        mol_type = protein
                        organism = synthetic construct
                        note = TGN1412_H1L1 vlCDR2
SEQUENCE: 116
KASNLHT                                                                  7

SEQ ID NO: 117          moltype = AA   length = 9
FEATURE                 Location/Qualifiers
source                  1..9
                        mol_type = protein
                        organism = synthetic construct
                        note = TGN1412_H1L1 vlCDR3
SEQUENCE: 117
QQGQTYPYT                                                                9

SEQ ID NO: 118          moltype = AA   length = 127
FEATURE                 Location/Qualifiers
```

```
source                     1..127
                           mol_type = protein
                           organism = synthetic construct
                           note = 341VL34[CD28]_H1L1 Variable heavy (vh) domain
SEQUENCE: 118
EVQLVESGGG LVKPGGSLRL SCGGSGFTFN NAWMNWVRQA PGKGLEWVGR IKGKTDGGTA    60
DYAAPVKGRF TISRDYSKNT LYLQMNSLTT EDTAVYYCNT DLPYYYGSGR YSGMDVWGQG   120
TTVTVSS                                                            127

SEQ ID NO: 119             moltype = AA  length = 5
FEATURE                    Location/Qualifiers
source                     1..5
                           mol_type = protein
                           organism = synthetic construct
                           note = 341VL34[CD28]_H1L1 vhCDR1
SEQUENCE: 119
NAWMN                                                                5

SEQ ID NO: 120             moltype = AA  length = 19
FEATURE                    Location/Qualifiers
source                     1..19
                           mol_type = protein
                           organism = synthetic construct
                           note = 341VL34[CD28]_H1L1 vhCDR2
SEQUENCE: 120
RIKGKTDGGT ADYAAPVKG                                                19

SEQ ID NO: 121             moltype = AA  length = 16
FEATURE                    Location/Qualifiers
source                     1..16
                           mol_type = protein
                           organism = synthetic construct
                           note = 341VL34[CD28]_H1L1 vhCDR3
SEQUENCE: 121
DLPYYYGSGR YSGMDV                                                   16

SEQ ID NO: 122             moltype = AA  length = 104
FEATURE                    Location/Qualifiers
source                     1..104
                           mol_type = protein
                           organism = synthetic construct
                           note = 341VL34[CD28]_H1L1 Variable light (vl) domain
SEQUENCE: 122
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNTFGPGTK VDIK                   104

SEQ ID NO: 123             moltype = AA  length = 11
FEATURE                    Location/Qualifiers
source                     1..11
                           mol_type = protein
                           organism = synthetic construct
                           note = 341VL34[CD28]_H1L1 vlCDR1
SEQUENCE: 123
RASQSVSSYL A                                                        11

SEQ ID NO: 124             moltype = AA  length = 7
FEATURE                    Location/Qualifiers
source                     1..7
                           mol_type = protein
                           organism = synthetic construct
                           note = 341VL34[CD28]_H1L1 vlCDR2
SEQUENCE: 124
DASNRAT                                                              7

SEQ ID NO: 125             moltype = AA  length = 6
FEATURE                    Location/Qualifiers
source                     1..6
                           mol_type = protein
                           organism = synthetic construct
                           note = 341VL34[CD28]_H1L1 vlCDR3
SEQUENCE: 125
QQRSNT                                                               6

SEQ ID NO: 126             moltype = AA  length = 127
FEATURE                    Location/Qualifiers
source                     1..127
                           mol_type = protein
                           organism = synthetic construct
                           note = 341VL36[CD28]_H1L1 Variable heavy (vh) domain
```

```
SEQUENCE: 126
EVQLVESGGG LVKPGGSLRL SCGGSGFTFN NAWMNWVRQA PGKGLEWVGR IKGKTDGGTA    60
DYAAPVKGRF TISRDYSKNT LYLQMNSLKT EDTGVYYCTT YLPYYYGSER WSGMDVWGQG   120
TTVTVSS                                                            127

SEQ ID NO: 127          moltype = AA   length = 5
FEATURE                 Location/Qualifiers
source                  1..5
                        mol_type = protein
                        organism = synthetic construct
                        note = 341VL36[CD28]_H1L1 vhCDR1
SEQUENCE: 127
NAWMN                                                                5

SEQ ID NO: 128          moltype = AA   length = 19
FEATURE                 Location/Qualifiers
source                  1..19
                        mol_type = protein
                        organism = synthetic construct
                        note = 341VL36[CD28]_H1L1 vhCDR2
SEQUENCE: 128
RIKGKTDGGT ADYAAPVKG                                                19

SEQ ID NO: 129          moltype = AA   length = 16
FEATURE                 Location/Qualifiers
source                  1..16
                        mol_type = protein
                        organism = synthetic construct
                        note = 341VL36[CD28]_H1L1 vhCDR3
SEQUENCE: 129
YLPYYYGSER WSGMDV                                                   16

SEQ ID NO: 130          moltype = AA   length = 104
FEATURE                 Location/Qualifiers
source                  1..104
                        mol_type = protein
                        organism = synthetic construct
                        note = 341VL36[CD28]_H1L1 Variable light (vl) domain
SEQUENCE: 130
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNTFGPGTK VDIK                    104

SEQ ID NO: 131          moltype = AA   length = 11
FEATURE                 Location/Qualifiers
source                  1..11
                        mol_type = protein
                        organism = synthetic construct
                        note = 341VL36[CD28]_H1L1 vlCDR1
SEQUENCE: 131
RASQSVSSYL A                                                        11

SEQ ID NO: 132          moltype = AA   length = 7
FEATURE                 Location/Qualifiers
source                  1..7
                        mol_type = protein
                        organism = synthetic construct
                        note = 341VL36[CD28]_H1L1 vlCDR2
SEQUENCE: 132
DASNRAT                                                              7

SEQ ID NO: 133          moltype = AA   length = 6
FEATURE                 Location/Qualifiers
source                  1..6
                        mol_type = protein
                        organism = synthetic construct
                        note = 341VL36[CD28]_H1L1 vlCDR3
SEQUENCE: 133
QQRSNT                                                               6

SEQ ID NO: 134          moltype = AA   length = 126
FEATURE                 Location/Qualifiers
source                  1..126
                        mol_type = protein
                        organism = synthetic construct
                        note = 281VL4[CD28]_H1L1 Variable heavy (vh) domain
SEQUENCE: 134
EVQLVQSGSE LKKPGSSVKV SCKASGGTSR SFAISWVRQA PGQGLEWMGG IIPIFGPANY    60
AQKFQGRVTI TADESTSTAY MELSSLRSED TAVYYCARHA IAMGWGVITT NYFDSWGQGT   120
MVTVSS                                                             126
```

```
SEQ ID NO: 135            moltype = AA   length = 5
FEATURE                   Location/Qualifiers
source                    1..5
                          mol_type = protein
                          organism = synthetic construct
                          note = 281VL4[CD28]_H1L1 vhCDR1
SEQUENCE: 135
SFAIS                                                                5

SEQ ID NO: 136            moltype = AA   length = 17
FEATURE                   Location/Qualifiers
source                    1..17
                          mol_type = protein
                          organism = synthetic construct
                          note = 281VL4[CD28]_H1L1 vhCDR2
SEQUENCE: 136
GIIPIFGPAN YAQKFQG                                                  17

SEQ ID NO: 137            moltype = AA   length = 17
FEATURE                   Location/Qualifiers
source                    1..17
                          mol_type = protein
                          organism = synthetic construct
                          note = 281VL4[CD28]_H1L1 vhCDR3
SEQUENCE: 137
HAIAMGWGVI TTNYFDS                                                  17

SEQ ID NO: 138            moltype = AA   length = 108
FEATURE                   Location/Qualifiers
source                    1..108
                          mol_type = protein
                          organism = synthetic construct
                          note = 281VL4[CD28]_H1L1 Variable light (vl) domain
SEQUENCE: 138
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPITFG QGTRLEIK                108

SEQ ID NO: 139            moltype = AA   length = 12
FEATURE                   Location/Qualifiers
source                    1..12
                          mol_type = protein
                          organism = synthetic construct
                          note = 281VL4[CD28]_H1L1 vlCDR1
SEQUENCE: 139
RASQSVSSSY LA                                                       12

SEQ ID NO: 140            moltype = AA   length = 7
FEATURE                   Location/Qualifiers
source                    1..7
                          mol_type = protein
                          organism = synthetic construct
                          note = 281VL4[CD28]_H1L1 vlCDR2
SEQUENCE: 140
GASSRAT                                                              7

SEQ ID NO: 141            moltype = AA   length = 9
FEATURE                   Location/Qualifiers
source                    1..9
                          mol_type = protein
                          organism = synthetic construct
                          note = 281VL4[CD28]_H1L1 vlCDR3
SEQUENCE: 141
QQYGSSPIT                                                            9

SEQ ID NO: 142            moltype = AA   length = 121
FEATURE                   Location/Qualifiers
source                    1..121
                          mol_type = protein
                          organism = synthetic construct
                          note = HuTN228[CD28]_H1L1 Variable heavy (vh) domain
SEQUENCE: 142
QVQLQESGPG LVKPSETLSL TCAVSGFSLT SYGVHWIRQP PGKGLEWLGV IWPGGGTNFN    60
SALMSRLTIS EDTSKNQVSL KLSSVTAADT AVYYCARDRA YGNYLYAMDY WGQGTLVTVS   120
S                                                                  121

SEQ ID NO: 143            moltype = AA   length = 5
FEATURE                   Location/Qualifiers
```

```
                            source          1..5
                                            mol_type = protein
                                            organism = synthetic construct
                                            note = HuTN228[CD28]_H1L1 vhCDR1
SEQUENCE: 143
SYGVH                                                                             5

SEQ ID NO: 144          moltype = AA  length = 16
FEATURE                 Location/Qualifiers
source                  1..16
                        mol_type = protein
                        organism = synthetic construct
                        note = HuTN228[CD28]_H1L1 vhCDR2
SEQUENCE: 144
VIWPGGGTNF NSALMS                                                                16

SEQ ID NO: 145          moltype = AA  length = 13
FEATURE                 Location/Qualifiers
source                  1..13
                        mol_type = protein
                        organism = synthetic construct
                        note = HuTN228[CD28]_H1L1 vhCDR3
SEQUENCE: 145
DRAYGNYLYA MDY                                                                   13

SEQ ID NO: 146          moltype = AA  length = 111
FEATURE                 Location/Qualifiers
source                  1..111
                        mol_type = protein
                        organism = synthetic construct
                        note = HuTN228[CD28]_H1L1 Variable light (vl) domain
SEQUENCE: 146
DIQMTQSPSS LSASVGDRVT ITCRASESVE YYVTSLMQWY QQKPGKAPKL LIYAASNVDS                60
GVPSRFSGSG SGTDFTLTIS SLQPEDIATY YCQQSRKVPF TFGGGTKVEI K                        111

SEQ ID NO: 147          moltype = AA  length = 15
FEATURE                 Location/Qualifiers
source                  1..15
                        mol_type = protein
                        organism = synthetic construct
                        note = HuTN228[CD28]_H1L1 vlCDR1
SEQUENCE: 147
RASESVEYYV TSLMQ                                                                 15

SEQ ID NO: 148          moltype = AA  length = 7
FEATURE                 Location/Qualifiers
source                  1..7
                        mol_type = protein
                        organism = synthetic construct
                        note = HuTN228[CD28]_H1L1 vlCDR2
SEQUENCE: 148
AASNVDS                                                                           7

SEQ ID NO: 149          moltype = AA  length = 9
FEATURE                 Location/Qualifiers
source                  1..9
                        mol_type = protein
                        organism = synthetic construct
                        note = HuTN228[CD28]_H1L1 vlCDR3
SEQUENCE: 149
QQSRKVPFT                                                                         9

SEQ ID NO: 150          moltype = AA  length = 124
FEATURE                 Location/Qualifiers
source                  1..124
                        mol_type = protein
                        organism = synthetic construct
                        note = PV1[CD28]_H0L0 Variable heavy (vh) domain
SEQUENCE: 150
QVQLKQSGAE LVKPGASVKI SCKTSGYTFT DGYMNWVEQK PGQGLEWIGR IDPDSGNTRY                60
NQKFQGKATL TRDKSSSTVY MDLRSLTSED SAVYYCARDG TFYGTYGYWY FDFWGQGTQV               120
TVSS                                                                            124

SEQ ID NO: 151          moltype = AA  length = 5
FEATURE                 Location/Qualifiers
source                  1..5
                        mol_type = protein
                        organism = synthetic construct
                        note = PV1[CD28]_H0L0 vhCDR1
```

```
SEQUENCE: 151
DGYMN                                                                      5

SEQ ID NO: 152         moltype = AA  length = 17
FEATURE                Location/Qualifiers
source                 1..17
                       mol_type = protein
                       organism = synthetic construct
                       note = PV1[CD28]_H0L0 vhCDR2
SEQUENCE: 152
RIDPDSGNTR YNQKFQG                                                        17

SEQ ID NO: 153         moltype = AA  length = 15
FEATURE                Location/Qualifiers
source                 1..15
                       mol_type = protein
                       organism = synthetic construct
                       note = PV1[CD28]_H0L0 vhCDR3
SEQUENCE: 153
DGTFYGTYGY WYFDF                                                          15

SEQ ID NO: 154         moltype = AA  length = 113
FEATURE                Location/Qualifiers
source                 1..113
                       mol_type = protein
                       organism = synthetic construct
                       note = PV1[CD28]_H0L0 Variable light (vl) domain
SEQUENCE: 154
DIVMTQSPYS LAVSAGEKVT MSCRSSQSLY YSGIKKNLLA WYQQKPGQSP KLLIYFTSTR         60
LPGVPDRFTG SGSGTDYTLT ITSVQAEDMG HYFCQQGIST PLTFGDGTKL EIR               113

SEQ ID NO: 155         moltype = AA  length = 17
FEATURE                Location/Qualifiers
source                 1..17
                       mol_type = protein
                       organism = synthetic construct
                       note = PV1[CD28]_H0L0 vlCDR1
SEQUENCE: 155
RSSQSLYYSG IKKNLLA                                                        17

SEQ ID NO: 156         moltype = AA  length = 7
FEATURE                Location/Qualifiers
source                 1..7
                       mol_type = protein
                       organism = synthetic construct
                       note = PV1[CD28]_H0L0 vlCDR2
SEQUENCE: 156
FTSTRLP                                                                    7

SEQ ID NO: 157         moltype = AA  length = 9
FEATURE                Location/Qualifiers
source                 1..9
                       mol_type = protein
                       organism = synthetic construct
                       note = PV1[CD28]_H0L0 vlCDR3
SEQUENCE: 157
QQGISTPLT                                                                  9

SEQ ID NO: 158         moltype = AA  length = 120
FEATURE                Location/Qualifiers
source                 1..120
                       mol_type = protein
                       organism = synthetic construct
                       note = m9.3[CD28]_H0L0 Variable heavy (vh) domain
SEQUENCE: 158
EVKLQQSGPG LVTPSQSLSI TCTVSGFSLS DYGVHWVRQS PGQGLEWLGV IWAGGGTNYN         60
SALMSRKSIS KDNSKSQVFL KMNSLQADDT AVYYCARDKG YSYYYSMDYW GQGTSVTVSS        120

SEQ ID NO: 159         moltype = AA  length = 5
FEATURE                Location/Qualifiers
source                 1..5
                       mol_type = protein
                       organism = synthetic construct
                       note = m9.3[CD28]_H0L0 vhCDR1
SEQUENCE: 159
DYGVH                                                                      5

SEQ ID NO: 160         moltype = AA  length = 16
FEATURE                Location/Qualifiers
```

```
source                      1..16
                            mol_type = protein
                            organism = synthetic construct
                            note = m9.3[CD28]_H0L0 vhCDR2
SEQUENCE: 160
VIWAGGGTNY NSALMS                                                          16

SEQ ID NO: 161              moltype = AA  length = 12
FEATURE                     Location/Qualifiers
source                      1..12
                            mol_type = protein
                            organism = synthetic construct
                            note = m9.3[CD28]_H0L0 vhCDR3
SEQUENCE: 161
DKGYSYYYSM DY                                                              12

SEQ ID NO: 162              moltype = AA  length = 111
FEATURE                     Location/Qualifiers
source                      1..111
                            mol_type = protein
                            organism = synthetic construct
                            note = m9.3[CD28]_H0L0 Variable light (vl) domain
SEQUENCE: 162
DIELTQSPAS LAVSLGQRAT ISCRASESVE YYVTSLMQWY QQKPGQPPKL LIFAASNVES           60
GVPARFSGSG SGTNFSLNIH PVDEDDVAMY FCQQSRKVPY TFGGGTKLEI K                  111

SEQ ID NO: 163              moltype = AA  length = 15
FEATURE                     Location/Qualifiers
source                      1..15
                            mol_type = protein
                            organism = synthetic construct
                            note = m9.3[CD28]_H0L0 vlCDR1
SEQUENCE: 163
RASESVEYYV TSLMQ                                                           15

SEQ ID NO: 164              moltype = AA  length = 7
FEATURE                     Location/Qualifiers
source                      1..7
                            mol_type = protein
                            organism = synthetic construct
                            note = m9.3[CD28]_H0L0 vlCDR2
SEQUENCE: 164
AASNVES                                                                     7

SEQ ID NO: 165              moltype = AA  length = 9
FEATURE                     Location/Qualifiers
source                      1..9
                            mol_type = protein
                            organism = synthetic construct
                            note = m9.3[CD28]_H0L0 vlCDR3
SEQUENCE: 165
QQSRKVPYT                                                                   9

SEQ ID NO: 166              moltype = AA  length = 120
FEATURE                     Location/Qualifiers
source                      1..120
                            mol_type = protein
                            organism = synthetic construct
                            note = hu9.3[CD28]_H1L1 Variable heavy (vh) domain
SEQUENCE: 166
EVQLVQSGGG LVQPGGSLRL SCAGSGFTFS DYGVHWVRQA PGKGLEWVSA IWAGGGTNYA           60
SSVMGRFTIS RDNAKNSLYL QMNSLRAEDM AVYYCARDKG YSYYYSMDYW GQGTLVTSS          120

SEQ ID NO: 167              moltype = AA  length = 5
FEATURE                     Location/Qualifiers
source                      1..5
                            mol_type = protein
                            organism = synthetic construct
                            note = hu9.3[CD28]_H1L1 vhCDR1
SEQUENCE: 167
DYGVH                                                                       5

SEQ ID NO: 168              moltype = AA  length = 16
FEATURE                     Location/Qualifiers
source                      1..16
                            mol_type = protein
                            organism = synthetic construct
                            note = hu9.3[CD28]_H1L1 vhCDR2
```

```
SEQUENCE: 168
AIWAGGGTNY ASSVMG                                                       16

SEQ ID NO: 169          moltype = AA  length = 12
FEATURE                 Location/Qualifiers
source                  1..12
                        mol_type = protein
                        organism = synthetic construct
                        note = hu9.3[CD28]_H1L1 vhCDR3
SEQUENCE: 169
DKGYSYYYSM DY                                                           12

SEQ ID NO: 170          moltype = AA  length = 111
FEATURE                 Location/Qualifiers
source                  1..111
                        mol_type = protein
                        organism = synthetic construct
                        note = hu9.3[CD28]_H1L1 Variable light (vl) domain
SEQUENCE: 170
DIVMTQSPDS LAVSLGERAT INCRASESVE YYVTSLMAWY QQKPGQPPKL LIYAASNVES        60
GVPDRFSGSG SGTNFSLTIS SLQAEDVAVY YCQQSRKVPY TFGQGTKLEI K                111

SEQ ID NO: 171          moltype = AA  length = 15
FEATURE                 Location/Qualifiers
source                  1..15
                        mol_type = protein
                        organism = synthetic construct
                        note = hu9.3[CD28]_H1L1 vlCDR1
SEQUENCE: 171
RASESVEYYV TSLMA                                                        15

SEQ ID NO: 172          moltype = AA  length = 7
FEATURE                 Location/Qualifiers
source                  1..7
                        mol_type = protein
                        organism = synthetic construct
                        note = hu9.3[CD28]_H1L1 vlCDR2
SEQUENCE: 172
AASNVES                                                                 7

SEQ ID NO: 173          moltype = AA  length = 9
FEATURE                 Location/Qualifiers
source                  1..9
                        mol_type = protein
                        organism = synthetic construct
                        note = hu9.3[CD28]_H1L1 vlCDR3
SEQUENCE: 173
QQSRKVPYT                                                               9

SEQ ID NO: 174          moltype = AA  length = 127
FEATURE                 Location/Qualifiers
source                  1..127
                        mol_type = protein
                        organism = synthetic construct
                        note = 9G2[CD28]_H0L0 Variable heavy (vh) domain
SEQUENCE: 174
EVQLVESGGG LVQPGRSLKL SCAASGFTFS NYYMAWVRQA PTKGLEWVAS ITNTGGSTYY        60
RDSVKGRFTI SRDNAKSTLY LQMDSLRSED TATYYCTRGL IYYYDGRNYY DYVMDAWGQG       120
ASVTVSS                                                                127

SEQ ID NO: 175          moltype = AA  length = 5
FEATURE                 Location/Qualifiers
source                  1..5
                        mol_type = protein
                        organism = synthetic construct
                        note = 9G2[CD28]_H0L0 vhCDR1
SEQUENCE: 175
NYYMA                                                                   5

SEQ ID NO: 176          moltype = AA  length = 17
FEATURE                 Location/Qualifiers
source                  1..17
                        mol_type = protein
                        organism = synthetic construct
                        note = 9G2[CD28]_H0L0 vhCDR2
SEQUENCE: 176
SITNTGGSTY YRDSVKG                                                      17

SEQ ID NO: 177          moltype = AA  length = 18
```

```
FEATURE                 Location/Qualifiers
source                  1..18
                        mol_type = protein
                        organism = synthetic construct
                        note = 9G2[CD28]_H0L0 vhCDR3
SEQUENCE: 177
GLIYYYDGRN YYDYVMDA                                                  18

SEQ ID NO: 178          moltype = AA  length = 107
FEATURE                 Location/Qualifiers
source                  1..107
                        mol_type = protein
                        organism = synthetic construct
                        note = 9G2[CD28]_H0L0 Variable light (vl) domain
SEQUENCE: 178
DIQMTQSPAS LSASLGETVS IECLASEGIS NSLAWYQQKP GKSPQLLIYG ASSLQDGVPS     60
RFSGSGSGTQ YSLKISGMQP EDEGVYYCQQ GYKYPLTFGS GTKLEIK                 107

SEQ ID NO: 179          moltype = AA  length = 11
FEATURE                 Location/Qualifiers
source                  1..11
                        mol_type = protein
                        organism = synthetic construct
                        note = 9G2[CD28]_H0L0 vlCDR1
SEQUENCE: 179
LASEGISNSL A                                                         11

SEQ ID NO: 180          moltype = AA  length = 7
FEATURE                 Location/Qualifiers
source                  1..7
                        mol_type = protein
                        organism = synthetic construct
                        note = 9G2[CD28]_H0L0 vlCDR2
SEQUENCE: 180
GASSLQD                                                               7

SEQ ID NO: 181          moltype = AA  length = 9
FEATURE                 Location/Qualifiers
source                  1..9
                        mol_type = protein
                        organism = synthetic construct
                        note = 9G2[CD28]_H0L0 vlCDR3
SEQUENCE: 181
QQGYKYPLT                                                             9

SEQ ID NO: 182          moltype = AA  length = 127
FEATURE                 Location/Qualifiers
source                  1..127
                        mol_type = protein
                        organism = synthetic construct
                        note = 9G2[CD28]_H1L1 Variable heavy (vh) domain
SEQUENCE: 182
EVQLLESGGG LVQPGGSLRL SCAASGFTFS NYYMAWVRQA PGKGLEWVSS ITNTGGSTYY     60
RDSVKGRFTI SRDNSKSTLY LQMNSLRAED TAVYYCTRGL IYYYDGRNYY DYVMDAWGQG    120
TTVTVSS                                                             127

SEQ ID NO: 183          moltype = AA  length = 5
FEATURE                 Location/Qualifiers
source                  1..5
                        mol_type = protein
                        organism = synthetic construct
                        note = 9G2[CD28]_H1L1 vhCDR1
SEQUENCE: 183
NYYMA                                                                 5

SEQ ID NO: 184          moltype = AA  length = 17
FEATURE                 Location/Qualifiers
source                  1..17
                        mol_type = protein
                        organism = synthetic construct
                        note = 9G2[CD28]_H1L1 vhCDR2
SEQUENCE: 184
SITNTGGSTY YRDSVKG                                                   17

SEQ ID NO: 185          moltype = AA  length = 18
FEATURE                 Location/Qualifiers
```

```
source                   1..18
                         mol_type = protein
                         organism = synthetic construct
                         note = 9G2[CD28]_H1L1 vhCDR3
SEQUENCE: 185
GLIYYYDGRN YYDYVMDA                                                      18

SEQ ID NO: 186           moltype = AA   length = 107
FEATURE                  Location/Qualifiers
source                   1..107
                         mol_type = protein
                         organism = synthetic construct
                         note = 9G2[CD28]_H1L1 Variable light (vl) domain
SEQUENCE: 186
DIQMTQSPSS LSASVGDRVT ITCRASEGIS NSLAWYQQKP GKSPKLLIYG ASSLQDGVPS         60
RFSGSGSGTD YTLTISSLQP EDFATYYCQQ GYKYPLTFGS GTKVEIK                      107

SEQ ID NO: 187           moltype = AA   length = 11
FEATURE                  Location/Qualifiers
source                   1..11
                         mol_type = protein
                         organism = synthetic construct
                         note = 9G2[CD28]_H1L1 vlCDR1
SEQUENCE: 187
RASEGISNSL A                                                             11

SEQ ID NO: 188           moltype = AA   length = 7
FEATURE                  Location/Qualifiers
source                   1..7
                         mol_type = protein
                         organism = synthetic construct
                         note = 9G2[CD28]_H1L1 vlCDR2
SEQUENCE: 188
GASSLQD                                                                  7

SEQ ID NO: 189           moltype = AA   length = 9
FEATURE                  Location/Qualifiers
source                   1..9
                         mol_type = protein
                         organism = synthetic construct
                         note = 9G2[CD28]_H1L1 vlCDR3
SEQUENCE: 189
QQGYKYPLT                                                                9

SEQ ID NO: 190           moltype = AA   length = 121
FEATURE                  Location/Qualifiers
source                   1..121
                         mol_type = protein
                         organism = synthetic construct
                         note = 2F10A3.140[CD28]_H1L1 Variable heavy (vh) domain
SEQUENCE: 190
EVQLLESGGG LVQPGGSLRL SCAASGFSFG GNSMSWVRQA PGKGLEWVAT ISDNSYSTYY         60
ADSVKGRFTI SRDNSKNTLY LQMNSLRAED TAVYYCAKSG PGLRQVGFDY WGQGTLVTVS         120
S                                                                        121

SEQ ID NO: 191           moltype = AA   length = 5
FEATURE                  Location/Qualifiers
source                   1..5
                         mol_type = protein
                         organism = synthetic construct
                         note = 2F10A3.140[CD28]_H1L1 vhCDR1
SEQUENCE: 191
GNSMS                                                                    5

SEQ ID NO: 192           moltype = AA   length = 17
FEATURE                  Location/Qualifiers
source                   1..17
                         mol_type = protein
                         organism = synthetic construct
                         note = 2F10A3.140[CD28]_H1L1 vhCDR2
SEQUENCE: 192
TISDNSYSTY YADSVKG                                                       17

SEQ ID NO: 193           moltype = AA   length = 12
FEATURE                  Location/Qualifiers
source                   1..12
                         mol_type = protein
                         organism = synthetic construct
                         note = 2F10A3.140[CD28]_H1L1 vhCDR3
```

-continued

| | | |
|---|---|---|
| SEQUENCE: 193 | | |
| SGPGLRQVGF DY | | 12 |
| | | |
| SEQ ID NO: 194 | moltype = AA  length = 107 | |
| FEATURE | Location/Qualifiers | |
| source | 1..107 | |
| | mol_type = protein | |
| | organism = synthetic construct | |
| | note = 2F10A3.140[CD28]_H1L1 Variable light (vl) domain | |
| SEQUENCE: 194 | | |
| DIQMTQSPSS LSASVGDRVT ITCRASQSIS SYLNWYQQKP GKAPKLLIYA ASSLQSGVPS | | 60 |
| RFSGSGSGTD FTLTISSLQP EDFATYYCQQ SYSTPFTFGQ GTKLEIK | | 107 |
| | | |
| SEQ ID NO: 195 | moltype = AA  length = 11 | |
| FEATURE | Location/Qualifiers | |
| source | 1..11 | |
| | mol_type = protein | |
| | organism = synthetic construct | |
| | note = 2F10A3.140[CD28]_H1L1 vlCDR1 | |
| SEQUENCE: 195 | | |
| RASQSISSYL N | | 11 |
| | | |
| SEQ ID NO: 196 | moltype = AA  length = 7 | |
| FEATURE | Location/Qualifiers | |
| source | 1..7 | |
| | mol_type = protein | |
| | organism = synthetic construct | |
| | note = 2F10A3.140[CD28]_H1L1 vlCDR2 | |
| SEQUENCE: 196 | | |
| AASSLQS | | 7 |
| | | |
| SEQ ID NO: 197 | moltype = AA  length = 9 | |
| FEATURE | Location/Qualifiers | |
| source | 1..9 | |
| | mol_type = protein | |
| | organism = synthetic construct | |
| | note = 2F10A3.140[CD28]_H1L1 vlCDR3 | |
| SEQUENCE: 197 | | |
| QQSYSTPFT | | 9 |
| | | |
| SEQ ID NO: 198 | moltype = AA  length = 121 | |
| FEATURE | Location/Qualifiers | |
| source | 1..121 | |
| | mol_type = protein | |
| | organism = synthetic construct | |
| | note = TN228[CD28]_H4L2 Variable heavy (vh) domain | |
| SEQUENCE: 198 | | |
| QVQLQESGPG LVKPSETLSL TCTVSGFSLT SYGVHWVRQP PGKGLEWIGV IWPGGGTNYN | | 60 |
| SALKSRVTIS EDTSKSQVSL KLSSVTAADT AVYYCARDRA YGNYLYAMDY WGQGTLVTVS | | 120 |
| S | | 121 |
| | | |
| SEQ ID NO: 199 | moltype = AA  length = 5 | |
| FEATURE | Location/Qualifiers | |
| source | 1..5 | |
| | mol_type = protein | |
| | organism = synthetic construct | |
| | note = TN228[CD28]_H4L2 vhCDR1 | |
| SEQUENCE: 199 | | |
| SYGVH | | 5 |
| | | |
| SEQ ID NO: 200 | moltype = AA  length = 16 | |
| FEATURE | Location/Qualifiers | |
| source | 1..16 | |
| | mol_type = protein | |
| | organism = synthetic construct | |
| | note = TN228[CD28]_H4L2 vhCDR2 | |
| SEQUENCE: 200 | | |
| VIWPGGGTNY NSALKS | | 16 |
| | | |
| SEQ ID NO: 201 | moltype = AA  length = 13 | |
| FEATURE | Location/Qualifiers | |
| source | 1..13 | |
| | mol_type = protein | |
| | organism = synthetic construct | |
| | note = TN228[CD28]_H4L2 vhCDR3 | |
| SEQUENCE: 201 | | |
| DRAYGNYLYA MDY | | 13 |
| | | |
| SEQ ID NO: 202 | moltype = AA  length = 111 | |

```
FEATURE                 Location/Qualifiers
source                  1..111
                        mol_type = protein
                        organism = synthetic construct
                        note = TN228[CD28]_H4L2 Variable light (vl) domain
SEQUENCE: 202
EIVLTQSPAT LSLSPGERAT LSCRASESVE YYVTSLMQWY QQKPGQAPRL LIYAASNVDS     60
GVPARFSGSG SGTDFTLTIS SLEPEDFAVY YCQQSRKVPF TFGGGTKVEI K             111

SEQ ID NO: 203          moltype = AA  length = 15
FEATURE                 Location/Qualifiers
source                  1..15
                        mol_type = protein
                        organism = synthetic construct
                        note = TN228[CD28]_H4L2 vlCDR1
SEQUENCE: 203
RASESVEYYV TSLMQ                                                      15

SEQ ID NO: 204          moltype = AA  length = 7
FEATURE                 Location/Qualifiers
source                  1..7
                        mol_type = protein
                        organism = synthetic construct
                        note = TN228[CD28]_H4L2 vlCDR2
SEQUENCE: 204
AASNVDS                                                                7

SEQ ID NO: 205          moltype = AA  length = 9
FEATURE                 Location/Qualifiers
source                  1..9
                        mol_type = protein
                        organism = synthetic construct
                        note = TN228[CD28]_H4L2 vlCDR3
SEQUENCE: 205
QQSRKVPFT                                                              9

SEQ ID NO: 206          moltype = AA  length = 120
FEATURE                 Location/Qualifiers
source                  1..120
                        mol_type = protein
                        organism = synthetic construct
                        note = A10[PSMA] Variable Heavy (vh) Domain
SEQUENCE: 206
QVQLVESGGG VVQPGRSLRL SCAASGFTFS SYNMNWVRQA PGKGLEWVAI IYYDGSNKYY     60
ADSVKGRFTI SRDISKNTLY LQMNSLRAED TAVYYCARER GRDYYGMDVW GQGTTVTVSS    120

SEQ ID NO: 207          moltype = AA  length = 5
FEATURE                 Location/Qualifiers
source                  1..5
                        mol_type = protein
                        organism = synthetic construct
                        note = A10[PSMA] vhCDR1
SEQUENCE: 207
SYNMN                                                                  5

SEQ ID NO: 208          moltype = AA  length = 17
FEATURE                 Location/Qualifiers
source                  1..17
                        mol_type = protein
                        organism = synthetic construct
                        note = A10[PSMA] vhCDR2
SEQUENCE: 208
IIYYDGSNKY YADSVKG                                                    17

SEQ ID NO: 209          moltype = AA  length = 11
FEATURE                 Location/Qualifiers
source                  1..11
                        mol_type = protein
                        organism = synthetic construct
                        note = A10[PSMA] vhCDR3
SEQUENCE: 209
ERGRDYYGMD V                                                          11

SEQ ID NO: 210          moltype = AA  length = 107
FEATURE                 Location/Qualifiers
source                  1..107
                        mol_type = protein
                        organism = synthetic construct
                        note = A10[PSMA] Variable Light (vl) Domain
```

```
SEQUENCE: 210
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVL                 107

SEQ ID NO: 211          moltype = AA  length = 11
FEATURE                 Location/Qualifiers
source                  1..11
                        mol_type = protein
                        organism = synthetic construct
                        note = A10[PSMA] vlCDR1
SEQUENCE: 211
SGDALPKQYA Y                                                        11

SEQ ID NO: 212          moltype = AA  length = 7
FEATURE                 Location/Qualifiers
source                  1..7
                        mol_type = protein
                        organism = synthetic construct
                        note = A10[PSMA] vlCDR2
SEQUENCE: 212
KDSERPS                                                             7

SEQ ID NO: 213          moltype = AA  length = 10
FEATURE                 Location/Qualifiers
source                  1..10
                        mol_type = protein
                        organism = synthetic construct
                        note = A10[PSMA] vlCDR3
SEQUENCE: 213
QSADSSGTYV                                                          10

SEQ ID NO: 214          moltype = AA  length = 120
FEATURE                 Location/Qualifiers
source                  1..120
                        mol_type = protein
                        organism = synthetic construct
                        note = A10v2[PSMA] Variable Heavy (vh) Domain
SEQUENCE: 214
QVQLVESGGG VVQPGRSLRL SCAASGFTFS SYNMNWVRQA PGKGLEWVAI IYYDESNKYY    60
ADSVKGRFTI SRDISKNTLY LQMNSLRAED TAVYYCARER GRDYYGMDVW GQGTTVTVSS   120

SEQ ID NO: 215          moltype = AA  length = 5
FEATURE                 Location/Qualifiers
source                  1..5
                        mol_type = protein
                        organism = synthetic construct
                        note = A10v2[PSMA] vhCDR1
SEQUENCE: 215
SYNMN                                                               5

SEQ ID NO: 216          moltype = AA  length = 17
FEATURE                 Location/Qualifiers
source                  1..17
                        mol_type = protein
                        organism = synthetic construct
                        note = A10v2[PSMA] vhCDR2
SEQUENCE: 216
IIYYDESNKY YADSVKG                                                  17

SEQ ID NO: 217          moltype = AA  length = 11
FEATURE                 Location/Qualifiers
source                  1..11
                        mol_type = protein
                        organism = synthetic construct
                        note = A10v2[PSMA] vhCDR3
SEQUENCE: 217
ERGRDYYGMD V                                                        11

SEQ ID NO: 218          moltype = AA  length = 107
FEATURE                 Location/Qualifiers
source                  1..107
                        mol_type = protein
                        organism = synthetic construct
                        note = A10v2[PSMA] Variable Light (vl) Domain
SEQUENCE: 218
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVL                 107

SEQ ID NO: 219          moltype = AA  length = 11
```

| FEATURE | Location/Qualifiers |
|---|---|
| source | 1..11<br>mol_type = protein<br>organism = synthetic construct<br>note = A10v2[PSMA] vlCDR1 |

SEQUENCE: 219
SGDALPKQYA Y                                                                    11

| SEQ ID NO: 220 | moltype = AA length = 7 |
|---|---|
| FEATURE | Location/Qualifiers |
| source | 1..7<br>mol_type = protein<br>organism = synthetic construct<br>note = A10v2[PSMA] vlCDR2 |

SEQUENCE: 220
KDSERPS                                                                         7

| SEQ ID NO: 221 | moltype = AA length = 10 |
|---|---|
| FEATURE | Location/Qualifiers |
| source | 1..10<br>mol_type = protein<br>organism = synthetic construct<br>note = A10v2[PSMA] vlCDR3 |

SEQUENCE: 221
QSADSSGTYV                                                                      10

| SEQ ID NO: 222 | moltype = AA length = 126 |
|---|---|
| FEATURE | Location/Qualifiers |
| source | 1..126<br>mol_type = protein<br>organism = synthetic construct<br>note = D01[PSMA] Variable Heavy (vh) Domain |

SEQUENCE: 222
EVQLVESGGD LVQPGGSLRL SCAASGFTFN NYNMNWVRQA PGKGLEWVSH ISTSSSNKYY      60
ADSVKGRFSI SRDIAKNSMY LQMNSLRDED TAVYYCARDG VGADYGDYYY YGMDVWGQGT     120
TVTVSS                                                               126

| SEQ ID NO: 223 | moltype = AA length = 5 |
|---|---|
| FEATURE | Location/Qualifiers |
| source | 1..5<br>mol_type = protein<br>organism = synthetic construct<br>note = D01[PSMA] vhCDR1 |

SEQUENCE: 223
NYNMN                                                                           5

| SEQ ID NO: 224 | moltype = AA length = 17 |
|---|---|
| FEATURE | Location/Qualifiers |
| source | 1..17<br>mol_type = protein<br>organism = synthetic construct<br>note = D01[PSMA] vhCDR2 |

SEQUENCE: 224
HISTSSSNKY YADSVKG                                                              17

| SEQ ID NO: 225 | moltype = AA length = 17 |
|---|---|
| FEATURE | Location/Qualifiers |
| source | 1..17<br>mol_type = protein<br>organism = synthetic construct<br>note = D01[PSMA] vhCDR3 |

SEQUENCE: 225
DGVGADYGDY YYYGMDV                                                              17

| SEQ ID NO: 226 | moltype = AA length = 110 |
|---|---|
| FEATURE | Location/Qualifiers |
| source | 1..110<br>mol_type = protein<br>organism = synthetic construct<br>note = D01[PSMA] Variable Light (vl) Domain |

SEQUENCE: 226
QSVLTQPASV SGSPGQSITI SCTGTSSDVG GYNYVSWYQQ HPGKAPKLMI YEVSNRPSGV      60
SNRFSGSKSG NTASLTISGL QAEDEADYYC SSYTSSYTYV FGTGTKLTVL                110

| SEQ ID NO: 227 | moltype = AA length = 14 |
|---|---|
| FEATURE | Location/Qualifiers |

```
source                     1..14
                           mol_type = protein
                           organism = synthetic construct
                           note = D01[PSMA] vlCDR1
SEQUENCE: 227
TGTSSDVGGY NYVS                                                            14

SEQ ID NO: 228             moltype = AA   length = 7
FEATURE                    Location/Qualifiers
source                     1..7
                           mol_type = protein
                           organism = synthetic construct
                           note = D01[PSMA] vlCDR2
SEQUENCE: 228
EVSNRPS                                                                     7

SEQ ID NO: 229             moltype = AA   length = 10
FEATURE                    Location/Qualifiers
source                     1..10
                           mol_type = protein
                           organism = synthetic construct
                           note = D01[PSMA] vlCDR3
SEQUENCE: 229
SSYTSSYTYV                                                                 10

SEQ ID NO: 230             moltype = AA   length = 126
FEATURE                    Location/Qualifiers
source                     1..126
                           mol_type = protein
                           organism = synthetic construct
                           note = D01v2[PSMA] Variable Heavy (vh) Domain
SEQUENCE: 230
EVQLVESGGD LVQPGGSLRL SCAASGFTFN NYNMNWVRQA PGKGLEWVSH ISTSSSNKYY           60
ADSVKGRFSI SRDIAKNSMY LQMNSLRDED TAVYYCAREG VGADYGDYYY YGMDVWGQGT          120
TVTVSS                                                                    126

SEQ ID NO: 231             moltype = AA   length = 5
FEATURE                    Location/Qualifiers
source                     1..5
                           mol_type = protein
                           organism = synthetic construct
                           note = D01v2[PSMA] vhCDR1
SEQUENCE: 231
NYNMN                                                                       5

SEQ ID NO: 232             moltype = AA   length = 17
FEATURE                    Location/Qualifiers
source                     1..17
                           mol_type = protein
                           organism = synthetic construct
                           note = D01v2[PSMA] vhCDR2
SEQUENCE: 232
HISTSSSNKY YADSVKG                                                         17

SEQ ID NO: 233             moltype = AA   length = 17
FEATURE                    Location/Qualifiers
source                     1..17
                           mol_type = protein
                           organism = synthetic construct
                           note = D01v2[PSMA] vhCDR3
SEQUENCE: 233
EGVGADYGDY YYYGMDV                                                         17

SEQ ID NO: 234             moltype = AA   length = 110
FEATURE                    Location/Qualifiers
source                     1..110
                           mol_type = protein
                           organism = synthetic construct
                           note = D01v2[PSMA] Variable Light (vl) Domain
SEQUENCE: 234
QSVLTQPASV SGSPGQSITI SCTGTSSDVG GYNYVSWYQQ HPGKAPKLMI YEVSNRPSGV           60
SNRFSGSKSG NTASLTISGL QAEDEADYYC SSYTSSYTYV FGTGTKLTVL                     110

SEQ ID NO: 235             moltype = AA   length = 14
FEATURE                    Location/Qualifiers
source                     1..14
                           mol_type = protein
                           organism = synthetic construct
                           note = D01v2[PSMA] vlCDR1
```

```
SEQUENCE: 235
TGTSSDVGGY NYVS                                                       14

SEQ ID NO: 236           moltype = AA  length = 7
FEATURE                  Location/Qualifiers
source                   1..7
                         mol_type = protein
                         organism = synthetic construct
                         note = D01v2[PSMA] vlCDR2
SEQUENCE: 236
EVSNRPS                                                                7

SEQ ID NO: 237           moltype = AA  length = 10
FEATURE                  Location/Qualifiers
source                   1..10
                         mol_type = protein
                         organism = synthetic construct
                         note = D01v2[PSMA] vlCDR3
SEQUENCE: 237
SSYTSSYTYV                                                            10

SEQ ID NO: 238           moltype = AA  length = 125
FEATURE                  Location/Qualifiers
source                   1..125
                         mol_type = protein
                         organism = synthetic construct
                         note = E07[PSMA] Variable Heavy (vh) Domain
SEQUENCE: 238
EVQLVESGGG VVQPGRSLRL SCAASGFTFI TYGMHWVRQA PGKGLEWVAV VSFDESNKYY      60
ADSVKGRFTI SRDNSKNTLY LQMNSLRAED TAVYYCARAL RDGNNWDYFN GMDVWGQGTT     120
VTVSS                                                                125

SEQ ID NO: 239           moltype = AA  length = 5
FEATURE                  Location/Qualifiers
source                   1..5
                         mol_type = protein
                         organism = synthetic construct
                         note = E07[PSMA] vhCDR1
SEQUENCE: 239
TYGMH                                                                  5

SEQ ID NO: 240           moltype = AA  length = 17
FEATURE                  Location/Qualifiers
source                   1..17
                         mol_type = protein
                         organism = synthetic construct
                         note = E07[PSMA] vhCDR2
SEQUENCE: 240
VVSFDESNKY YADSVKG                                                    17

SEQ ID NO: 241           moltype = AA  length = 16
FEATURE                  Location/Qualifiers
source                   1..16
                         mol_type = protein
                         organism = synthetic construct
                         note = E07[PSMA] vhCDR3
SEQUENCE: 241
ALRDGNNWDY FNGMDV                                                     16

SEQ ID NO: 242           moltype = AA  length = 110
FEATURE                  Location/Qualifiers
source                   1..110
                         mol_type = protein
                         organism = synthetic construct
                         note = E07[PSMA] Variable Light (vl) Domain
SEQUENCE: 242
QSVLTQPPSA SGTPGQGVTI SCSGSSSNIG SNTVNWFQQL PGTAPKLLIY SDNQRPSGVP      60
DRFSGSKSGT SASLAISGLQ SEDEADYYCA AWDDSLNGYV FGTGTKVTVL                110

SEQ ID NO: 243           moltype = AA  length = 13
FEATURE                  Location/Qualifiers
source                   1..13
                         mol_type = protein
                         organism = synthetic construct
                         note = E07[PSMA] vlCDR1
SEQUENCE: 243
SGSSSNIGSN TVN                                                        13

SEQ ID NO: 244           moltype = AA  length = 7
```

```
FEATURE                 Location/Qualifiers
source                  1..7
                        mol_type = protein
                        organism = synthetic construct
                        note = E07[PSMA] vlCDR2
SEQUENCE: 244
SDNQRPS                                                                 7

SEQ ID NO: 245          moltype = AA  length = 11
FEATURE                 Location/Qualifiers
source                  1..11
                        mol_type = protein
                        organism = synthetic construct
                        note = E07[PSMA] vlCDR3
SEQUENCE: 245
AAWDDSLNGY V                                                           11

SEQ ID NO: 246          moltype = AA  length = 118
FEATURE                 Location/Qualifiers
source                  1..118
                        mol_type = protein
                        organism = synthetic construct
                        note = F02[PSMA] Variable Heavy (vh) Domain
SEQUENCE: 246
EVQLLESGPG LVKPSETLSL TCTVSGGSII SYYWSWIRQP AGKGLEWIGR IYSSGSTNYN       60
PSLKSRVTMS VDTSKNQFSL KLSSVTAADT AVYYCAKVGV WPGAFDIWGQ GTMVTVSS        118

SEQ ID NO: 247          moltype = AA  length = 5
FEATURE                 Location/Qualifiers
source                  1..5
                        mol_type = protein
                        organism = synthetic construct
                        note = F02[PSMA] vhCDR1
SEQUENCE: 247
SYYWS                                                                   5

SEQ ID NO: 248          moltype = AA  length = 16
FEATURE                 Location/Qualifiers
source                  1..16
                        mol_type = protein
                        organism = synthetic construct
                        note = F02[PSMA] vhCDR2
SEQUENCE: 248
RIYSSGSTNY NPSLKS                                                      16

SEQ ID NO: 249          moltype = AA  length = 10
FEATURE                 Location/Qualifiers
source                  1..10
                        mol_type = protein
                        organism = synthetic construct
                        note = F02[PSMA] vhCDR3
SEQUENCE: 249
VGVWPGAFDI                                                             10

SEQ ID NO: 250          moltype = AA  length = 110
FEATURE                 Location/Qualifiers
source                  1..110
                        mol_type = protein
                        organism = synthetic construct
                        note = F02[PSMA] Variable Light (vl) Domain
SEQUENCE: 250
QSVLTQPPSA SGTPGQRVTI SCSGSSSNIG SNTVNWYQQL PGTAPKLLIY SSNQRPSGVP       60
DRFSGSKSGT SASLAISGLQ SEDEADYYCA AWDDSLNGVV FGGGTKLTVL                 110

SEQ ID NO: 251          moltype = AA  length = 13
FEATURE                 Location/Qualifiers
source                  1..13
                        mol_type = protein
                        organism = synthetic construct
                        note = F02[PSMA] vlCDR1
SEQUENCE: 251
SGSSSNIGSN TVN                                                         13

SEQ ID NO: 252          moltype = AA  length = 7
FEATURE                 Location/Qualifiers
source                  1..7
                        mol_type = protein
                        organism = synthetic construct
                        note = F02[PSMA] vlCDR2
```

```
SEQUENCE: 252
SSNQRPS                                                                    7

SEQ ID NO: 253          moltype = AA   length = 11
FEATURE                 Location/Qualifiers
source                  1..11
                        mol_type = protein
                        organism = synthetic construct
                        note = F02[PSMA] vlCDR3
SEQUENCE: 253
AAWDDSLNGV V                                                              11

SEQ ID NO: 254          moltype = AA   length = 122
FEATURE                 Location/Qualifiers
source                  1..122
                        mol_type = protein
                        organism = synthetic construct
                        note = A11[PSMA] Variable Heavy (vh) Domain
SEQUENCE: 254
QVQLQESGGD VVQPGRSLRL SCAASGFSFS GYGLHWVRQA PGRGLEWVTL ISYDGSNKYY          60
ADSVKGRFTI SRDNSKNTLY LQMNSLRAED TAVYYCAKTT VSDPYYYGMD VWGQGTTVTV        120
SS                                                                       122

SEQ ID NO: 255          moltype = AA   length = 5
FEATURE                 Location/Qualifiers
source                  1..5
                        mol_type = protein
                        organism = synthetic construct
                        note = A11[PSMA] vhCDR1
SEQUENCE: 255
GYGLH                                                                      5

SEQ ID NO: 256          moltype = AA   length = 17
FEATURE                 Location/Qualifiers
source                  1..17
                        mol_type = protein
                        organism = synthetic construct
                        note = A11[PSMA] vhCDR2
SEQUENCE: 256
LISYDGSNKY YADSVKG                                                        17

SEQ ID NO: 257          moltype = AA   length = 13
FEATURE                 Location/Qualifiers
source                  1..13
                        mol_type = protein
                        organism = synthetic construct
                        note = A11[PSMA] vhCDR3
SEQUENCE: 257
TTVSDPYYYG MDV                                                            13

SEQ ID NO: 258          moltype = AA   length = 108
FEATURE                 Location/Qualifiers
source                  1..108
                        mol_type = protein
                        organism = synthetic construct
                        note = A11[PSMA] Variable Light (vl) Domain
SEQUENCE: 258
SYELTQPPSV SVAPGQTARI TCGGNNIGSK SVHWYQQKPG QAPVLVVYDD SDRPSGIPER          60
FSGTNSGNTA TLTISRAEAG DEADYYCQVW DSSSDHVVFG GGTKLTVL                     108

SEQ ID NO: 259          moltype = AA   length = 11
FEATURE                 Location/Qualifiers
source                  1..11
                        mol_type = protein
                        organism = synthetic construct
                        note = A11[PSMA] vlCDR1
SEQUENCE: 259
GGNNIGSKSV H                                                              11

SEQ ID NO: 260          moltype = AA   length = 7
FEATURE                 Location/Qualifiers
source                  1..7
                        mol_type = protein
                        organism = synthetic construct
                        note = A11[PSMA] vlCDR2
SEQUENCE: 260
DDSDRPS                                                                    7

SEQ ID NO: 261          moltype = AA   length = 11
```

```
FEATURE                 Location/Qualifiers
source                  1..11
                        mol_type = protein
                        organism = synthetic construct
                        note = A11[PSMA] vlCDR3
SEQUENCE: 261
QVWDSSSDHV V                                                              11

SEQ ID NO: 262          moltype = AA   length = 122
FEATURE                 Location/Qualifiers
source                  1..122
                        mol_type = protein
                        organism = synthetic construct
                        note = F07[PSMA] Variable Heavy (vh) Domain
SEQUENCE: 262
EVQLVESGGG VVQPGRSLRL SCAASGFTFS SYGMNWVRQA PGKGLEWVAV TSYDGSNKYY          60
ADSVKGRFTI SRDISKNTLY LQMSSLRAED TAVYYCARDP YSSSWNGAFD IWGPGTMVTV        120
SS                                                                       122

SEQ ID NO: 263          moltype = AA   length = 5
FEATURE                 Location/Qualifiers
source                  1..5
                        mol_type = protein
                        organism = synthetic construct
                        note = F07[PSMA] vhCDR1
SEQUENCE: 263
SYGMN                                                                      5

SEQ ID NO: 264          moltype = AA   length = 17
FEATURE                 Location/Qualifiers
source                  1..17
                        mol_type = protein
                        organism = synthetic construct
                        note = F07[PSMA] vhCDR2
SEQUENCE: 264
VTSYDGSNKY YADSVKG                                                        17

SEQ ID NO: 265          moltype = AA   length = 13
FEATURE                 Location/Qualifiers
source                  1..13
                        mol_type = protein
                        organism = synthetic construct
                        note = F07[PSMA] vhCDR3
SEQUENCE: 265
DPYSSSWNGA FDI                                                            13

SEQ ID NO: 266          moltype = AA   length = 108
FEATURE                 Location/Qualifiers
source                  1..108
                        mol_type = protein
                        organism = synthetic construct
                        note = F07[PSMA] Variable Light (vl) Domain
SEQUENCE: 266
SYELTQPPSV SVAPGQTARI TCGGNNIGSK SVHWYQQKPG QAPVLVVYDD SDRPSGIPER          60
FSGSNSGNTA TLTISRVEAG DEADYYCQVW DSSTDHVVFG GGTKLTVL                      108

SEQ ID NO: 267          moltype = AA   length = 11
FEATURE                 Location/Qualifiers
source                  1..11
                        mol_type = protein
                        organism = synthetic construct
                        note = F07[PSMA] vlCDR1
SEQUENCE: 267
GGNNIGSKSV H                                                              11

SEQ ID NO: 268          moltype = AA   length = 7
FEATURE                 Location/Qualifiers
source                  1..7
                        mol_type = protein
                        organism = synthetic construct
                        note = F07[PSMA] vlCDR2
SEQUENCE: 268
DDSDRPS                                                                    7

SEQ ID NO: 269          moltype = AA   length = 11
FEATURE                 Location/Qualifiers
```

| | | |
|---|---|---|
| source | 1..11<br>mol_type = protein<br>organism = synthetic construct<br>note = F07[PSMA] vlCDR3 | |
| SEQUENCE: 269<br>QVWDSSTDHV V | | 11 |
| SEQ ID NO: 270<br>FEATURE<br>source | moltype = AA  length = 122<br>Location/Qualifiers<br>1..122<br>mol_type = protein<br>organism = synthetic construct<br>note = F07v2[PSMA] Variable Heavy (vh) Domain | |
| SEQUENCE: 270<br>EVQLVESGGG VVQPGRSLRL SCAASGFTFS SYGMNWVRQA PGKGLEWVAV TSYDESNKYY<br>ADSVKGRFTI SRDISKNTLY LQMSSLRAED TAVYYCARDP YSSSWNGAFD IWGPGTMVTV<br>SS | | 60<br>120<br>122 |
| SEQ ID NO: 271<br>FEATURE<br>source | moltype = AA  length = 5<br>Location/Qualifiers<br>1..5<br>mol_type = protein<br>organism = synthetic construct<br>note = F07v2[PSMA] vhCDR1 | |
| SEQUENCE: 271<br>SYGMN | | 5 |
| SEQ ID NO: 272<br>FEATURE<br>source | moltype = AA  length = 17<br>Location/Qualifiers<br>1..17<br>mol_type = protein<br>organism = synthetic construct<br>note = F07v2[PSMA] vhCDR2 | |
| SEQUENCE: 272<br>VTSYDESNKY YADSVKG | | 17 |
| SEQ ID NO: 273<br>FEATURE<br>source | moltype = AA  length = 13<br>Location/Qualifiers<br>1..13<br>mol_type = protein<br>organism = synthetic construct<br>note = F07v2[PSMA] vhCDR3 | |
| SEQUENCE: 273<br>DPYSSSWNGA FDI | | 13 |
| SEQ ID NO: 274<br>FEATURE<br>source | moltype = AA  length = 108<br>Location/Qualifiers<br>1..108<br>mol_type = protein<br>organism = synthetic construct<br>note = F07v2[PSMA] Variable Light (vl) Domain | |
| SEQUENCE: 274<br>SYELTQPPSV SVAPGQTARI TCGGNNIGSK SVHWYQQKPG QAPVLVVYDD SDRPSGIPER<br>FSGSNSGNTA TLTISRVEAG DEADYYCQVW DSSTDHVVFG GGTKLTVL | | 60<br>108 |
| SEQ ID NO: 275<br>FEATURE<br>source | moltype = AA  length = 11<br>Location/Qualifiers<br>1..11<br>mol_type = protein<br>organism = synthetic construct<br>note = F07v2[PSMA] vlCDR1 | |
| SEQUENCE: 275<br>GGNNIGSKSV H | | 11 |
| SEQ ID NO: 276<br>FEATURE<br>source | moltype = AA  length = 7<br>Location/Qualifiers<br>1..7<br>mol_type = protein<br>organism = synthetic construct<br>note = F07v2[PSMA] vlCDR2 | |
| SEQUENCE: 276<br>DDSDRPS | | 7 |
| SEQ ID NO: 277<br>FEATURE<br>source | moltype = AA  length = 11<br>Location/Qualifiers<br>1..11<br>mol_type = protein<br>organism = synthetic construct<br>note = F07v2[PSMA] vlCDR3 | |

```
SEQUENCE: 277
QVWDSSTDHV V                                                                    11

SEQ ID NO: 278          moltype = AA   length = 124
FEATURE                 Location/Qualifiers
source                  1..124
                        mol_type = protein
                        organism = synthetic construct
                        note = G02[PSMA] Variable Heavy (vh) Domain
SEQUENCE: 278
EVQLVESGGG VVQPGRSLRL SCAASGFSFS GYGMHWVRQA PGKGLEWVAV ISYDGSNKYY               60
ADSVKGRFTI SRDNSKNTLY LQMNSLRVED TAVYYCARDR IWGSRGYYYG MDVWGQGTTV              120
TVSS                                                                           124

SEQ ID NO: 279          moltype = AA   length = 5
FEATURE                 Location/Qualifiers
source                  1..5
                        mol_type = protein
                        organism = synthetic construct
                        note = G02[PSMA] vhCDR1
SEQUENCE: 279
GYGMH                                                                           5

SEQ ID NO: 280          moltype = AA   length = 17
FEATURE                 Location/Qualifiers
source                  1..17
                        mol_type = protein
                        organism = synthetic construct
                        note = G02[PSMA] vhCDR2
SEQUENCE: 280
VISYDGSNKY YADSVKG                                                              17

SEQ ID NO: 281          moltype = AA   length = 15
FEATURE                 Location/Qualifiers
source                  1..15
                        mol_type = protein
                        organism = synthetic construct
                        note = G02[PSMA] vhCDR3
SEQUENCE: 281
DRIWGSRGYY YGMDV                                                                15

SEQ ID NO: 282          moltype = AA   length = 110
FEATURE                 Location/Qualifiers
source                  1..110
                        mol_type = protein
                        organism = synthetic construct
                        note = G02[PSMA] Variable Light (vl) Domain
SEQUENCE: 282
QSALTQPASV SGSPGQSITI SCTGASSDVG GYNYVSWYQQ HPGKAPKLMI YEVSNRPSGV               60
SNRFSGSKSG NTASLTISGL QAEDEADYYC SSYTITSTLV FGGGTKLTVL                         110

SEQ ID NO: 283          moltype = AA   length = 14
FEATURE                 Location/Qualifiers
source                  1..14
                        mol_type = protein
                        organism = synthetic construct
                        note = G02[PSMA] vlCDR1
SEQUENCE: 283
TGASSDVGGY NYVS                                                                 14

SEQ ID NO: 284          moltype = AA   length = 7
FEATURE                 Location/Qualifiers
source                  1..7
                        mol_type = protein
                        organism = synthetic construct
                        note = G02[PSMA] vlCDR2
SEQUENCE: 284
EVSNRPS                                                                         7

SEQ ID NO: 285          moltype = AA   length = 10
FEATURE                 Location/Qualifiers
source                  1..10
                        mol_type = protein
                        organism = synthetic construct
                        note = G02[PSMA] vlCDR3
SEQUENCE: 285
SSYTITSTLV                                                                      10

SEQ ID NO: 286          moltype = AA   length = 124
```

```
FEATURE                 Location/Qualifiers
source                  1..124
                        mol_type = protein
                        organism = synthetic construct
                        note = G02v2[PSMA] Variable Heavy (vh) Domain
SEQUENCE: 286
EVQLVESGGG VVQPGRSLRL SCAASGFSFS GYGMHWVRQA PGKGLEWVAV ISYDESNKYY     60
ADSVKGRFTI SRDNSKNTLY LQMNSLRVED TAVYYCARDR IWGSRGYYYG MDVWGQGTTV    120
TVSS                                                                 124

SEQ ID NO: 287          moltype = AA  length = 5
FEATURE                 Location/Qualifiers
source                  1..5
                        mol_type = protein
                        organism = synthetic construct
                        note = G02v2[PSMA] vhCDR1
SEQUENCE: 287
GYGMH                                                                  5

SEQ ID NO: 288          moltype = AA  length = 17
FEATURE                 Location/Qualifiers
source                  1..17
                        mol_type = protein
                        organism = synthetic construct
                        note = G02v2[PSMA] vhCDR2
SEQUENCE: 288
VISYDESNKY YADSVKG                                                    17

SEQ ID NO: 289          moltype = AA  length = 15
FEATURE                 Location/Qualifiers
source                  1..15
                        mol_type = protein
                        organism = synthetic construct
                        note = G02v2[PSMA] vhCDR3
SEQUENCE: 289
DRIWGSRGYY YGMDV                                                      15

SEQ ID NO: 290          moltype = AA  length = 110
FEATURE                 Location/Qualifiers
source                  1..110
                        mol_type = protein
                        organism = synthetic construct
                        note = G02v2[PSMA] Variable Light (vl) Domain
SEQUENCE: 290
QSALTQPASV SGSPGQSITI SCTGASSDVG GYNYVSWYQQ HPGKAPKLMI YEVSNRPSGV     60
SNRFSGSKSG NTASLTISGL QAEDEADYYC SSYTITSTLV FGGGTKLTVL               110

SEQ ID NO: 291          moltype = AA  length = 14
FEATURE                 Location/Qualifiers
source                  1..14
                        mol_type = protein
                        organism = synthetic construct
                        note = G02v2[PSMA] vlCDR1
SEQUENCE: 291
TGASSDVGGY NYVS                                                       14

SEQ ID NO: 292          moltype = AA  length = 7
FEATURE                 Location/Qualifiers
source                  1..7
                        mol_type = protein
                        organism = synthetic construct
                        note = G02v2[PSMA] vlCDR2
SEQUENCE: 292
EVSNRPS                                                                7

SEQ ID NO: 293          moltype = AA  length = 10
FEATURE                 Location/Qualifiers
source                  1..10
                        mol_type = protein
                        organism = synthetic construct
                        note = G02v2[PSMA] vlCDR3
SEQUENCE: 293
SSYTITSTLV                                                            10

SEQ ID NO: 294          moltype = AA  length = 122
FEATURE                 Location/Qualifiers
```

```
source                      1..122
                            mol_type = protein
                            organism = synthetic construct
                            note = F01[PSMA] Variable Heavy (vh) Domain
SEQUENCE: 294
QVQLQESGGG VVQPGRSLRL SCAASGFTFS TYGMHWVRQA PGKGLEWVAF ISYDGSNKYY    60
ADSVKGRFTI SRDNSKHTLY LQMNSLRAED TAVYYCAGRD NLRFLEWFMD VWGQGTTVTV   120
SS                                                                 122

SEQ ID NO: 295              moltype = AA  length = 5
FEATURE                     Location/Qualifiers
source                      1..5
                            mol_type = protein
                            organism = synthetic construct
                            note = F01[PSMA] vhCDR1
SEQUENCE: 295
TYGMH                                                                5

SEQ ID NO: 296              moltype = AA  length = 17
FEATURE                     Location/Qualifiers
source                      1..17
                            mol_type = protein
                            organism = synthetic construct
                            note = F01[PSMA] vhCDR2
SEQUENCE: 296
FISYDGSNKY YADSVKG                                                  17

SEQ ID NO: 297              moltype = AA  length = 13
FEATURE                     Location/Qualifiers
source                      1..13
                            mol_type = protein
                            organism = synthetic construct
                            note = F01[PSMA] vhCDR3
SEQUENCE: 297
RDNLRFLEWF MDV                                                      13

SEQ ID NO: 298              moltype = AA  length = 108
FEATURE                     Location/Qualifiers
source                      1..108
                            mol_type = protein
                            organism = synthetic construct
                            note = F01[PSMA] Variable Light (vl) Domain
SEQUENCE: 298
EIVLTQSPGT LSVSPGERAT LSCRASQSVR SNLAWYQQKP GQAPRLLIYG ASTRATGIPA   60
RFSGSGSGTE FTLTISSLQS EDFAVYYCHQ YNDWPPYTFG QGTKLEIK               108

SEQ ID NO: 299              moltype = AA  length = 11
FEATURE                     Location/Qualifiers
source                      1..11
                            mol_type = protein
                            organism = synthetic construct
                            note = F01[PSMA] vlCDR1
SEQUENCE: 299
RASQSVRSNL A                                                        11

SEQ ID NO: 300              moltype = AA  length = 7
FEATURE                     Location/Qualifiers
source                      1..7
                            mol_type = protein
                            organism = synthetic construct
                            note = F01[PSMA] vlCDR2
SEQUENCE: 300
GASTRAT                                                              7

SEQ ID NO: 301              moltype = AA  length = 10
FEATURE                     Location/Qualifiers
source                      1..10
                            mol_type = protein
                            organism = synthetic construct
                            note = F01[PSMA] vlCDR3
SEQUENCE: 301
HQYNDWPPYT                                                          10

SEQ ID NO: 302              moltype = AA  length = 122
FEATURE                     Location/Qualifiers
source                      1..122
                            mol_type = protein
                            organism = synthetic construct
                            note = F01v2[PSMA] Variable Heavy (vh) Domain
```

```
SEQUENCE: 302
QVQLQESGGG VVQPGRSLRL SCAASGFTFS TYGMHWVRQA PGKGLEWVAF ISYDESNKYY    60
ADSVKGRFTI SRDNSKHTLY LQMNSLRAED TAVYYCAGRD NLRFLEWFMD VWGQGTTVTV   120
SS                                                                 122

SEQ ID NO: 303           moltype = AA  length = 5
FEATURE                  Location/Qualifiers
source                   1..5
                         mol_type = protein
                         organism = synthetic construct
                         note = F01v2[PSMA] vhCDR1
SEQUENCE: 303
TYGMH                                                                5

SEQ ID NO: 304           moltype = AA  length = 17
FEATURE                  Location/Qualifiers
source                   1..17
                         mol_type = protein
                         organism = synthetic construct
                         note = F01v2[PSMA] vhCDR2
SEQUENCE: 304
FISYDESNKY YADSVKG                                                  17

SEQ ID NO: 305           moltype = AA  length = 13
FEATURE                  Location/Qualifiers
source                   1..13
                         mol_type = protein
                         organism = synthetic construct
                         note = F01v2[PSMA] vhCDR3
SEQUENCE: 305
RDNLRFLEWF MDV                                                      13

SEQ ID NO: 306           moltype = AA  length = 108
FEATURE                  Location/Qualifiers
source                   1..108
                         mol_type = protein
                         organism = synthetic construct
                         note = F01v2[PSMA] Variable Light (vl) Domain
SEQUENCE: 306
EIVLTQSPGT LSVSPGERAT LSCRASQSVR SNLAWYQQKP GQAPRLLIYG ASTRATGIPA    60
RFSGSGSGTE FTLTISSLQS EDFAVYYCHQ YNDWPPYTFG QGTKLEIK                108

SEQ ID NO: 307           moltype = AA  length = 11
FEATURE                  Location/Qualifiers
source                   1..11
                         mol_type = protein
                         organism = synthetic construct
                         note = F01v2[PSMA] vlCDR1
SEQUENCE: 307
RASQSVRSNL A                                                        11

SEQ ID NO: 308           moltype = AA  length = 7
FEATURE                  Location/Qualifiers
source                   1..7
                         mol_type = protein
                         organism = synthetic construct
                         note = F01v2[PSMA] vlCDR2
SEQUENCE: 308
GASTRAT                                                              7

SEQ ID NO: 309           moltype = AA  length = 10
FEATURE                  Location/Qualifiers
source                   1..10
                         mol_type = protein
                         organism = synthetic construct
                         note = F01v2[PSMA] vlCDR3
SEQUENCE: 309
HQYNDWPPYT                                                          10

SEQ ID NO: 310           moltype = AA  length = 120
FEATURE                  Location/Qualifiers
source                   1..120
                         mol_type = protein
                         organism = synthetic construct
                         note = 011A11[PSMA] Variable Heavy (vh) Domain
SEQUENCE: 310
EVQLVESGGG LVKPGGSLRL SCVASGFTFS FYSMNWVRQA PGKGLDWVSS ISSSGNYIYY    60
ADSVKGRFTI SRDNAKNSLH LHMNSLKAED TAMYFCARSY SGSYDAFDFW GQGTMVTVSS   120
```

-continued

```
SEQ ID NO: 311           moltype = AA  length = 5
FEATURE                  Location/Qualifiers
source                   1..5
                         mol_type = protein
                         organism = synthetic construct
                         note = 011A11[PSMA] vhCDR1
SEQUENCE: 311
FYSMN                                                                    5

SEQ ID NO: 312           moltype = AA  length = 17
FEATURE                  Location/Qualifiers
source                   1..17
                         mol_type = protein
                         organism = synthetic construct
                         note = 011A11[PSMA] vhCDR2
SEQUENCE: 312
SISSSGNYIY YADSVKG                                                       17

SEQ ID NO: 313           moltype = AA  length = 11
FEATURE                  Location/Qualifiers
source                   1..11
                         mol_type = protein
                         organism = synthetic construct
                         note = 011A11[PSMA] vhCDR3
SEQUENCE: 313
SYSGSYDAFD F                                                             11

SEQ ID NO: 314           moltype = AA  length = 108
FEATURE                  Location/Qualifiers
source                   1..108
                         mol_type = protein
                         organism = synthetic construct
                         note = 011A11[PSMA] Variable Light (vl) Domain
SEQUENCE: 314
EIVMTQSPGT LSLSPGERAT LSCRASQSVS SSFLAWYQQK PGQAPRLLIS GASSRATGIP         60
DRFSVSGSGT DFTLTISRLE PEDFAVYYCQ QYGVSPWTFG QGTKVEIK                     108

SEQ ID NO: 315           moltype = AA  length = 12
FEATURE                  Location/Qualifiers
source                   1..12
                         mol_type = protein
                         organism = synthetic construct
                         note = 011A11[PSMA] vlCDR1
SEQUENCE: 315
RASQSVSSSF LA                                                            12

SEQ ID NO: 316           moltype = AA  length = 7
FEATURE                  Location/Qualifiers
source                   1..7
                         mol_type = protein
                         organism = synthetic construct
                         note = 011A11[PSMA] vlCDR2
SEQUENCE: 316
GASSRAT                                                                  7

SEQ ID NO: 317           moltype = AA  length = 9
FEATURE                  Location/Qualifiers
source                   1..9
                         mol_type = protein
                         organism = synthetic construct
                         note = 011A11[PSMA] vlCDR3
SEQUENCE: 317
QQYGVSPWT                                                                9

SEQ ID NO: 318           moltype = AA  length = 121
FEATURE                  Location/Qualifiers
source                   1..121
                         mol_type = protein
                         organism = synthetic construct
                         note = PSMB896[PSMA] Variable Heavy (vh) Domain
SEQUENCE: 318
EVQLVESGGG LVQPGGSLRL SCAASGFTFS SYAMSWVRQA PGKGLEWVSA ISGGIGSTYY         60
ADSVKGRFTI SRDNSKNTLW LQMNSLRAED TAVYYCAKDA VGATPYYFDY WGQGTLVTVS        120
S                                                                       121

SEQ ID NO: 319           moltype = AA  length = 5
FEATURE                  Location/Qualifiers
source                   1..5
                         mol_type = protein
```

```
                        organism = synthetic construct
                        note = PSMB896[PSMA] vhCDR1
SEQUENCE: 319
SYAMS                                                                   5

SEQ ID NO: 320          moltype = AA   length = 17
FEATURE                 Location/Qualifiers
source                  1..17
                        mol_type = protein
                        organism = synthetic construct
                        note = PSMB896[PSMA] vhCDR2
SEQUENCE: 320
AISGGIGSTY YADSVKG                                                     17

SEQ ID NO: 321          moltype = AA   length = 12
FEATURE                 Location/Qualifiers
source                  1..12
                        mol_type = protein
                        organism = synthetic construct
                        note = PSMB896[PSMA] vhCDR3
SEQUENCE: 321
DAVGATPYYF DY                                                          12

SEQ ID NO: 322          moltype = AA   length = 110
FEATURE                 Location/Qualifiers
source                  1..110
                        mol_type = protein
                        organism = synthetic construct
                        note = PSMB896[PSMA] Variable Light (vl) Domain
SEQUENCE: 322
QSVLTQPPSV SAAPGQKVTI SCSGSSSNIG INYVSWYQQL PGTAPKLLIY DNNKRPSGIP       60
DRFSGSKSGT SATLGITGLQ TGDEADYYCG TWDSSLSAVV FGGGTKLTVL                 110

SEQ ID NO: 323          moltype = AA   length = 13
FEATURE                 Location/Qualifiers
source                  1..13
                        mol_type = protein
                        organism = synthetic construct
                        note = PSMB896[PSMA] vlCDR1
SEQUENCE: 323
SGSSSNIGIN YVS                                                         13

SEQ ID NO: 324          moltype = AA   length = 7
FEATURE                 Location/Qualifiers
source                  1..7
                        mol_type = protein
                        organism = synthetic construct
                        note = PSMB896[PSMA] vlCDR2
SEQUENCE: 324
DNNKRPS                                                                 7

SEQ ID NO: 325          moltype = AA   length = 11
FEATURE                 Location/Qualifiers
source                  1..11
                        mol_type = protein
                        organism = synthetic construct
                        note = PSMB896[PSMA] vlCDR3
SEQUENCE: 325
GTWDSSLSAV V                                                           11

SEQ ID NO: 326          moltype = AA   length = 115
FEATURE                 Location/Qualifiers
source                  1..115
                        mol_type = protein
                        organism = synthetic construct
                        note = PSMA-H[PSMA] Variable Heavy (vh) Domain
SEQUENCE: 326
EVQLVQSGAE VKKPGASVKV SCKTSGYTFT EYTIHWVRQA PGQSLEWMGN INPNNGGTTY       60
NQKFQGRVTI TVDKSTSTAY MELSSLRSED TAVYYCAAGW NFDYWGQGTL VTVSS           115

SEQ ID NO: 327          moltype = AA   length = 5
FEATURE                 Location/Qualifiers
source                  1..5
                        mol_type = protein
                        organism = synthetic construct
                        note = PSMA-H[PSMA] vhCDR1
SEQUENCE: 327
EYTIH                                                                   5
```

```
SEQ ID NO: 328          moltype = AA  length = 17
FEATURE                 Location/Qualifiers
source                  1..17
                        mol_type = protein
                        organism = synthetic construct
                        note = PSMA-H[PSMA] vhCDR2
SEQUENCE: 328
NINPNNGGTT YNQKFQG                                                    17

SEQ ID NO: 329          moltype = AA  length = 6
FEATURE                 Location/Qualifiers
source                  1..6
                        mol_type = protein
                        organism = synthetic construct
                        note = PSMA-H[PSMA] vhCDR3
SEQUENCE: 329
GWNFDY                                                                 6

SEQ ID NO: 330          moltype = AA  length = 107
FEATURE                 Location/Qualifiers
source                  1..107
                        mol_type = protein
                        organism = synthetic construct
                        note = PSMA-H[PSMA] Variable Light (vl) Domain
SEQUENCE: 330
DIVMTQSPDS LAVSLGERAT LSCRASQDVG TAVDWYQQKP DQSPKLLIYW ASTRHTGVPD      60
RFTGSGSGTD FTLTISSLQA EDVAVYFCQQ YNSYPLTFGA GTKVEIK                  107

SEQ ID NO: 331          moltype = AA  length = 11
FEATURE                 Location/Qualifiers
source                  1..11
                        mol_type = protein
                        organism = synthetic construct
                        note = PSMA-H[PSMA] vlCDR1
SEQUENCE: 331
RASQDVGTAV D                                                          11

SEQ ID NO: 332          moltype = AA  length = 7
FEATURE                 Location/Qualifiers
source                  1..7
                        mol_type = protein
                        organism = synthetic construct
                        note = PSMA-H[PSMA] vlCDR2
SEQUENCE: 332
WASTRHT                                                                7

SEQ ID NO: 333          moltype = AA  length = 9
FEATURE                 Location/Qualifiers
source                  1..9
                        mol_type = protein
                        organism = synthetic construct
                        note = PSMA-H[PSMA] vlCDR3
SEQUENCE: 333
QQYNSYPLT                                                              9

SEQ ID NO: 334          moltype = AA  length = 120
FEATURE                 Location/Qualifiers
source                  1..120
                        mol_type = protein
                        organism = synthetic construct
                        note = D7[PSMA] Variable Heavy (vh) Domain
SEQUENCE: 334
QVQLQQSGAE LVEPGASVKL SCKASGYTFT YFDINWLRQR PEQGLEWIGG ISPGDGNTNY      60
NENFKGKATL TIDKSSTTAY IQLSRLTSED SAVYFCARDG NFPYYAMDSW GQGTSVTVSS    120

SEQ ID NO: 335          moltype = AA  length = 5
FEATURE                 Location/Qualifiers
source                  1..5
                        mol_type = protein
                        organism = synthetic construct
                        note = D7[PSMA] vhCDR1
SEQUENCE: 335
YFDIN                                                                  5

SEQ ID NO: 336          moltype = AA  length = 17
FEATURE                 Location/Qualifiers
```

```
source                  1..17
                        mol_type = protein
                        organism = synthetic construct
                        note = D7[PSMA] vhCDR2
SEQUENCE: 336
GISPGDGNTN YNENFKG                                                   17

SEQ ID NO: 337          moltype = AA   length = 11
FEATURE                 Location/Qualifiers
source                  1..11
                        mol_type = protein
                        organism = synthetic construct
                        note = D7[PSMA] vhCDR3
SEQUENCE: 337
DGNFPYYAMD S                                                         11

SEQ ID NO: 338          moltype = AA   length = 111
FEATURE                 Location/Qualifiers
source                  1..111
                        mol_type = protein
                        organism = synthetic construct
                        note = D7[PSMA] Variable Light (vl) Domain
SEQUENCE: 338
DIELTQSPLS LPVILGDQAS ISCRSSQSLV HSNGNTYLHW FLQKPGQSPK LLIYTVSNRF     60
SGVPDRFSGS GSGTDFTLKI SRVEAEDLGV YFCSQSTHVP TFGGGTKLEI K             111

SEQ ID NO: 339          moltype = AA   length = 16
FEATURE                 Location/Qualifiers
source                  1..16
                        mol_type = protein
                        organism = synthetic construct
                        note = D7[PSMA] vlCDR1
SEQUENCE: 339
RSSQSLVHSN GNTYLH                                                    16

SEQ ID NO: 340          moltype = AA   length = 7
FEATURE                 Location/Qualifiers
source                  1..7
                        mol_type = protein
                        organism = synthetic construct
                        note = D7[PSMA] vlCDR2
SEQUENCE: 340
TVSNRFS                                                              7

SEQ ID NO: 341          moltype = AA   length = 8
FEATURE                 Location/Qualifiers
source                  1..8
                        mol_type = protein
                        organism = synthetic construct
                        note = D7[PSMA] vlCDR3
SEQUENCE: 341
SQSTHVPT                                                             8

SEQ ID NO: 342          moltype = AA   length = 478
FEATURE                 Location/Qualifiers
source                  1..478
                        mol_type = protein
                        organism = synthetic construct
                        note = C28PB397 Chain 1 - 1A7[CD28]_H1_L1.71 spFv
SEQUENCE: 342
EVQLLESGGG LVQPGGSLRL SCAASGFTFS SYAMSWVRQA PGCGLEWVST ISGSGDSTYY     60
ADSVKGRFTI SRDNSKNTLY LQMNSLRAED TAVYYCAKSG PGLRQVGFDY WGQGTLVTVS     120
SGGGSGGSGG CPPCGGSGGD IQMTQSPSSL SASVGDRVTI TCRASQSISS YLNWYQQKPG     180
KAPKLLIYAA SSLQSGVPSR FSGSGSGTDF TLTISSLQPE DFATYYCQQV YSTPFTFGCG     240
TKLEIKEPKS SDKTHTCPPC PAPEAAGGPS VFLFPPKPKD TLMISRTPEV TCVVVSVSHE     300
DPEVKFNWYV DGVEVHNAKT KPREEQYNST YRVVSVLTVL HQDWLNGKEY KCKVSNKALP     360
APIEKTISKA KGQPREPQVY TLPPSREEMT KNQVSLWCLV KGFYPSDIAV EWESNGQPEN     420
NYKTTPPVLD SDGSFFLYSK LTVDKSRWQQ GNVFSCSVMH EALHNHYTQK SLSLSPGK      478

SEQ ID NO: 343          moltype = AA   length = 450
FEATURE                 Location/Qualifiers
source                  1..450
                        mol_type = protein
                        organism = synthetic construct
                        note = C28PB397 Chain 2 - HC1 (hole3 RF): PSMA_P72_A10V2
SEQUENCE: 343
QVQLVESGGG VVQPGRSLRL SCAASGFTFS SYNMNWVRQA PGKGLEWVAI IYYDESNKYY     60
ADSVKGRFTI SRDISKNTLY LQMNSLRAED TAVYYCARER GRDYYGMDVW GQGTTVTVSS    120
ASTKGPSVFP LAPSSKSTSG GTAALGCLVK DYFPEPVTVS WNSGALTSGV HTFPAVLQSS    180
```

```
GLYSLSSVVT VPSSSLGTQT YICNVNHKPS NTKVDKKVEP KSCDKTHTCP PCPAPEAAGG    240
PSVFLFPPKP KDTLMISRTP EVTCVVVSVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLSC AVKGFYPSDI AVEWESNGQP ENNYKTTPPV LDSDGSFFLV SKLTVDKSRW    420
QQGNVFSCSV MHEALHNRFT QKSLSLSPGK                                     450

SEQ ID NO: 344           moltype = AA   length = 213
FEATURE                  Location/Qualifiers
source                   1..213
                         mol_type = protein
                         organism = synthetic construct
                         note = C28PB397 Chain 3 - LC: PSMA_P72_A10V2
SEQUENCE: 344
SYELMQPPSV SVSPGQTARI TCSGDALPKQ YAYWYQQKPG QAPVLVIYKD SERPSGIPVR     60
FSGSSSGTTV TLTITGVQAE DEADYYCQSA DSSGTYVFGT GTKVTVLGQP KAAPSVTLFP    120
PSSEELQANK ATLVCLISDF YPGAVTVAWK ADSSPVKAGV ETTTPSKQSN NKYAASSYLS    180
LTPEQWKSHR SYSCQVTHEG STVEKTVAPT ECS                                 213

SEQ ID NO: 345           moltype = AA   length = 477
FEATURE                  Location/Qualifiers
source                   1..477
                         mol_type = protein
                         organism = synthetic construct
                         note = C28PB397[(K447del)] Chain 1 - 1A7[CD28]_H1_L1.71
                            spFv (K447del)
SEQUENCE: 345
EVQLLESGGG LVQPGGSLRL SCAASGFTFS SYAMSWVRQA PGCGLEWVST ISGSGDSTYY     60
ADSVKGRFTI SRDNSKNTLY LQMNSLRAED TAVYYCAKSG PGLRQVGFDY WGQGTLVTVS    120
SGGGSGGSGG CPPCGGSGGD IQMTQSPSSL SASVGDRVTI TCRASQSISS YLNWYQQKPG    180
KAPKLLIYAA SSLQSGVPSR FSGSGSGTDF TLTISSLQPE DFATYYCQQV YSTPFTFGCG    240
TKLEIKEPKS SDKTHTCPPC PAPEAAGGPS VFLFPPKPKD TLMISRTPEV TCVVVSVSHE    300
DPEVKFNWYV DGVEVHNAKT KPREEQYNST YRVVSVLTVL HQDWLNGKEY KCKVSNKALP    360
APIEKTISKA KGQPREPQVY TLPPSREEMT KNQVSLWCLV KGFYPSDIAV EWESNGQPEN    420
NYKTTPPVLD SDGSFFLYSK LTVDKSRWQQ GNVFSCSVMH EALHNHYTQK SLSLSPG       477

SEQ ID NO: 346           moltype = AA   length = 449
FEATURE                  Location/Qualifiers
source                   1..449
                         mol_type = protein
                         organism = synthetic construct
                         note = C28PB397[(K447del)] Chain 2 - HC1 (hole3 RF):
                            PSMA_P72_A10V2 (K447del)
SEQUENCE: 346
QVQLVESGGG VVQPGRSLRL SCAASGFTFS SYNMNWVRQA PGKGLEWVAI IYYDESNKYY     60
ADSVKGRFTI SRDISKNTLY LQMNSLRAED TAVYYCARER GRDYYGMDVW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPEAAGG    240
PSVFLFPPKP KDTLMISRTP EVTCVVVSVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLSC AVKGFYPSDI AVEWESNGQP ENNYKTTPPV LDSDGSFFLV SKLTVDKSRW    420
QQGNVFSCSV MHEALHNRFT QKSLSLSPG                                      449

SEQ ID NO: 347           moltype = AA   length = 213
FEATURE                  Location/Qualifiers
source                   1..213
                         mol_type = protein
                         organism = synthetic construct
                         note = C28PB397[(K447del)] Chain 3 - LC: PSMA_P72_A10V2
SEQUENCE: 347
SYELMQPPSV SVSPGQTARI TCSGDALPKQ YAYWYQQKPG QAPVLVIYKD SERPSGIPVR     60
FSGSSSGTTV TLTITGVQAE DEADYYCQSA DSSGTYVFGT GTKVTVLGQP KAAPSVTLFP    120
PSSEELQANK ATLVCLISDF YPGAVTVAWK ADSSPVKAGV ETTTPSKQSN NKYAASSYLS    180
LTPEQWKSHR SYSCQVTHEG STVEKTVAPT ECS                                 213

SEQ ID NO: 348           moltype = AA   length = 476
FEATURE                  Location/Qualifiers
source                   1..476
                         mol_type = protein
                         organism = synthetic construct
                         note = C28PB397[(G446del/K447del)] Chain 1 -
                            1A7[CD28]_H1_L1.71 spFv (G446del/K447del)
SEQUENCE: 348
EVQLLESGGG LVQPGGSLRL SCAASGFTFS SYAMSWVRQA PGCGLEWVST ISGSGDSTYY     60
ADSVKGRFTI SRDNSKNTLY LQMNSLRAED TAVYYCAKSG PGLRQVGFDY WGQGTLVTVS    120
SGGGSGGSGG CPPCGGSGGD IQMTQSPSSL SASVGDRVTI TCRASQSISS YLNWYQQKPG    180
KAPKLLIYAA SSLQSGVPSR FSGSGSGTDF TLTISSLQPE DFATYYCQQV YSTPFTFGCG    240
TKLEIKEPKS SDKTHTCPPC PAPEAAGGPS VFLFPPKPKD TLMISRTPEV TCVVVSVSHE    300
DPEVKFNWYV DGVEVHNAKT KPREEQYNST YRVVSVLTVL HQDWLNGKEY KCKVSNKALP    360
```

```
APIEKTISKA KGQPREPQVY TLPPSREEMT KNQVSLWCLV KGFYPSDIAV EWESNGQPEN   420
NYKTTPPVLD SDGSFFLYSK LTVDKSRWQQ GNVFSCSVMH EALHNHYTQK SLSLSP       476

SEQ ID NO: 349           moltype = AA  length = 448
FEATURE                  Location/Qualifiers
source                   1..448
                         mol_type = protein
                         organism = synthetic construct
                         note = C28PB397[(G446del/K447del)] Chain 2 - HC1 (hole3
                          RF): PSMA_P72_A10V2 (G446del/K447del)
SEQUENCE: 349
QVQLVESGGG VVQPGRSLRL SCAASGFTFS SYNMNWVRQA PGKGLEWVAI IYYDESNKYY   60
ADSVKGRFTI SRDISKNTLY LQMNSLRAED TAVYYCARER GRDYYGMDVW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVSVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLSC AVKGFYPSDI AVEWESNGQP ENNYKTTPPV LDSDGSFFLV SKLTVDKSRW   420
QQGNVFSCSV MHEALHNRFT QKSLSLSP                                     448

SEQ ID NO: 350           moltype = AA  length = 213
FEATURE                  Location/Qualifiers
source                   1..213
                         mol_type = protein
                         organism = synthetic construct
                         note = C28PB397[(G446del/K447del)] Chain 3 - LC:
                          PSMA_P72_A10V2
SEQUENCE: 350
SYELMQPPSV SVSPGQTARI TCSGDALPKQ YAYWYQQKPG QAPVLVIYKD SERPSGIPVR   60
FSGSSSGTTV TLTITGVQAE DEADYYCQSA DSSGTYVFGT GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                               213

SEQ ID NO: 351           moltype = AA  length = 480
FEATURE                  Location/Qualifiers
source                   1..480
                         mol_type = protein
                         organism = synthetic construct
                         note = C28PB330 Chain 1 - 1A7[CD28]_H1_L1.71-HL-scFv
SEQUENCE: 351
EVQLLESGGG LVQPGGSLRL SCAASGFTFS SYAMSWVRQA PGKGLEWVST ISGSGDSTYY   60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPEAAGG PSVFLFPPKP KDTLMISRTP EVTCVVVSVS   300
HEDPEVKFNW YVDGVEVHNA KTKPREEQYN STYRVVSVLT VLHQDWLNGK EYKCKVSNKA   360
LPAPIEKTIS KAKGQPREPQ VYTLPPSREE MTKNQVSLWC LVKGFYPSDI AVEWESNGQP   420
ENNYKTTPPV LDSDGSFFLY SKLTVDKSRW QQGNVFSCSV MHEALHNHYT QKSLSLSPGK   480

SEQ ID NO: 352           moltype = AA  length = 450
FEATURE                  Location/Qualifiers
source                   1..450
                         mol_type = protein
                         organism = synthetic construct
                         note = C28PB330 Chain 2 - HC1 (knob): PSMA_P72_A10V2
SEQUENCE: 352
QVQLVESGGG VVQPGRSLRL SCAASGFTFS SYNMNWVRQA PGKGLEWVAI IYYDESNKYY   60
ADSVKGRFTI SRDISKNTLY LQMNSLRAED TAVYYCARER GRDYYGMDVW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVSVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLSC AVKGFYPSDI AVEWESNGQP ENNYKTTPPV LDSDGSFFLV SKLTVDKSRW   420
QQGNVFSCSV MHEALHNRFT QKSLSLSPGK                                   450

SEQ ID NO: 353           moltype = AA  length = 213
FEATURE                  Location/Qualifiers
source                   1..213
                         mol_type = protein
                         organism = synthetic construct
                         note = C28PB330 Chain 3 - LC: PSMA_P72_A10V2
SEQUENCE: 353
SYELMQPPSV SVSPGQTARI TCSGDALPKQ YAYWYQQKPG QAPVLVIYKD SERPSGIPVR   60
FSGSSSGTTV TLTITGVQAE DEADYYCQSA DSSGTYVFGT GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                               213

SEQ ID NO: 354           moltype = AA  length = 479
FEATURE                  Location/Qualifiers
```

```
source                  1..479
                        mol_type = protein
                        organism = synthetic construct
                        note = C28PB330[(K447del)] Chain 1 -
                        1A7[CD28]_H1_L1.71-HL-scFv (K447del)
SEQUENCE: 354
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPEAAGG PSVFLFPPKP KDTLMISRTP EVTCVVVSVS   300
HEDPEVKFNW YVDGVEVHNA KTKPREEQYN STYRVVSVLT VLHQDWLNGK EYKCKVSNKA   360
LPAPIEKTIS KAKGQPREPQ VYTLPPSREE MTKNQVSLWC LVKGFYPSDI AVEWESNGQP   420
ENNYKTTPPV LDSDGSFFLY SKLTVDKSRW QQGNVFSCSV MHEALHNHYT QKSLSLSPG    479

SEQ ID NO: 355          moltype = AA  length = 449
FEATURE                 Location/Qualifiers
source                  1..449
                        mol_type = protein
                        organism = synthetic construct
                        note = C28PB330[(K447del)] Chain 2 - HC1 (knob):  PSMA_P72_A
                        10V2 (K447del)
SEQUENCE: 355
QVQLVESGGG VVQPGRSLRL SCAASGFTFS SYNMNWVRQA PGKGLEWVAI IYYDESNKYY    60
ADSVKGRFTI SRDISKNTLY LQMNSLRAED TAVYYCARER GRDYYGMDVW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVSVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLSC AVKGFYPSDI AVEWESNGQP ENNYKTTPPV LDSDGSFFLV SKLTVDKSRW   420
QQGNVFSCSV MHEALHNRFT QKSLSLSPG                                    449

SEQ ID NO: 356          moltype = AA  length = 213
FEATURE                 Location/Qualifiers
source                  1..213
                        mol_type = protein
                        organism = synthetic construct
                        note = C28PB330[(K447del)] Chain 3 - LC:  PSMA_P72_A10V2
SEQUENCE: 356
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                                213

SEQ ID NO: 357          moltype = AA  length = 478
FEATURE                 Location/Qualifiers
source                  1..478
                        mol_type = protein
                        organism = synthetic construct
                        note = C28PB330[(G446del/K447del)] Chain 1 -
                        1A7[CD28]_H1_L1.71-HL-scFv (G446del/K447del)
SEQUENCE: 357
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPEAAGG PSVFLFPPKP KDTLMISRTP EVTCVVVSVS   300
HEDPEVKFNW YVDGVEVHNA KTKPREEQYN STYRVVSVLT VLHQDWLNGK EYKCKVSNKA   360
LPAPIEKTIS KAKGQPREPQ VYTLPPSREE MTKNQVSLWC LVKGFYPSDI AVEWESNGQP   420
ENNYKTTPPV LDSDGSFFLY SKLTVDKSRW QQGNVFSCSV MHEALHNHYT QKSLSLSP     478

SEQ ID NO: 358          moltype = AA  length = 448
FEATURE                 Location/Qualifiers
source                  1..448
                        mol_type = protein
                        organism = synthetic construct
                        note = C28PB330[(G446del/K447del)] Chain 2 - HC1 (knob):  PS
                        MA_P72_A10V2 (G446del/K447del)
SEQUENCE: 358
QVQLVESGGG VVQPGRSLRL SCAASGFTFS SYNMNWVRQA PGKGLEWVAI IYYDESNKYY    60
ADSVKGRFTI SRDISKNTLY LQMNSLRAED TAVYYCARER GRDYYGMDVW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVSVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLSC AVKGFYPSDI AVEWESNGQP ENNYKTTPPV LDSDGSFFLV SKLTVDKSRW   420
QQGNVFSCSV MHEALHNRFT QKSLSLSP                                     448

SEQ ID NO: 359          moltype = AA  length = 213
```

```
FEATURE                 Location/Qualifiers
source                  1..213
                        mol_type = protein
                        organism = synthetic construct
                        note = C28PB330[(G446del/K447del)] Chain 3 - LC:  PSMA_P72_A
                           10V2
SEQUENCE: 359
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                                213

SEQ ID NO: 360          moltype = AA   length = 121
FEATURE                 Location/Qualifiers
source                  1..121
                        mol_type = protein
                        organism = synthetic construct
                        note = 1A7_H1sp Variable heavy (vh) domain
SEQUENCE: 360
EVQLLESGGG LVQPGGSLRL SCAASGFTFS SYAMSWVRQA PGCGLEWVST ISGSGDSTYY    60
ADSVKGRFTI SRDNSKNTLY LQMNSLRAED TAVYYCAKSG PGLRQVGFDY WGQGTLVTVS   120
S                                                                   121

SEQ ID NO: 361          moltype = AA   length = 5
FEATURE                 Location/Qualifiers
source                  1..5
                        mol_type = protein
                        organism = synthetic construct
                        note = 1A7_H1sp vhCDR1
SEQUENCE: 361
SYAMS                                                                 5

SEQ ID NO: 362          moltype = AA   length = 17
FEATURE                 Location/Qualifiers
source                  1..17
                        mol_type = protein
                        organism = synthetic construct
                        note = 1A7_H1sp vhCDR2
SEQUENCE: 362
TISGSGDSTY YADSVKG                                                   17

SEQ ID NO: 363          moltype = AA   length = 12
FEATURE                 Location/Qualifiers
source                  1..12
                        mol_type = protein
                        organism = synthetic construct
                        note = 1A7_H1sp vhCDR3
SEQUENCE: 363
SGPGLRQVGF DY                                                        12

SEQ ID NO: 364          moltype = AA   length = 121
FEATURE                 Location/Qualifiers
source                  1..121
                        mol_type = protein
                        organism = synthetic construct
                        note = 1A7_H1.1sp Variable heavy (vh) domain
SEQUENCE: 364
EVQLLESGGG LVQPGGSLRL SCAASGFTFS SYYMSWVRQA PGCGLEWVST ISGSGDSTYY    60
ADSVKGRFTI SRDNSKNTLY LQMNSLRAED TAVYYCAKSG PGLRQVGFDY WGQGTLVTVS   120
S                                                                   121

SEQ ID NO: 365          moltype = AA   length = 5
FEATURE                 Location/Qualifiers
source                  1..5
                        mol_type = protein
                        organism = synthetic construct
                        note = 1A7_H1.1sp vhCDR1
SEQUENCE: 365
SYYMS                                                                 5

SEQ ID NO: 366          moltype = AA   length = 17
FEATURE                 Location/Qualifiers
source                  1..17
                        mol_type = protein
                        organism = synthetic construct
                        note = 1A7_H1.1sp vhCDR2
SEQUENCE: 366
TISGSGDSTY YADSVKG                                                   17
```

| | | |
|---|---|---|
| SEQ ID NO: 367 | moltype = AA   length = 12 | |
| FEATURE | Location/Qualifiers | |
| source | 1..12<br>mol_type = protein<br>organism = synthetic construct<br>note = 1A7_H1.1sp vhCDR3 | |
| SEQUENCE: 367 | | |
| SGPGLRQVGF DY | | 12 |
| | | |
| SEQ ID NO: 368 | moltype = AA   length = 121 | |
| FEATURE | Location/Qualifiers | |
| source | 1..121<br>mol_type = protein<br>organism = synthetic construct<br>note = 1A7_H1.14sp Variable heavy (vh) domain | |
| SEQUENCE: 368 | | |
| EVQLLESGGG LVQPGGSLRL SCAASGFTFS SYYMSWVRQA PGCGLEWVST ISESGDSTYY | | 60 |
| ADSVKGRFTI SRDNSKNTLY LQMNSLRAED TAVYYCAKSG PGLRQVGFDY WGQGTLVTVS | | 120 |
| S | | 121 |
| | | |
| SEQ ID NO: 369 | moltype = AA   length = 5 | |
| FEATURE | Location/Qualifiers | |
| source | 1..5<br>mol_type = protein<br>organism = synthetic construct<br>note = 1A7_H1.14sp vhCDR1 | |
| SEQUENCE: 369 | | |
| SYYMS | | 5 |
| | | |
| SEQ ID NO: 370 | moltype = AA   length = 17 | |
| FEATURE | Location/Qualifiers | |
| source | 1..17<br>mol_type = protein<br>organism = synthetic construct<br>note = 1A7_H1.14sp vhCDR2 | |
| SEQUENCE: 370 | | |
| TISESGDSTY YADSVKG | | 17 |
| | | |
| SEQ ID NO: 371 | moltype = AA   length = 12 | |
| FEATURE | Location/Qualifiers | |
| source | 1..12<br>mol_type = protein<br>organism = synthetic construct<br>note = 1A7_H1.14sp vhCDR3 | |
| SEQUENCE: 371 | | |
| SGPGLRQVGF DY | | 12 |
| | | |
| SEQ ID NO: 372 | moltype = AA   length = 107 | |
| FEATURE | Location/Qualifiers | |
| source | 1..107<br>mol_type = protein<br>organism = synthetic construct<br>note = 1A7_L1sp Variable light (vl) domain | |
| SEQUENCE: 372 | | |
| DIQMTQSPSS LSASVGDRVT ITCRASQSIS SYLNWYQQKP GKAPKLLIYA ASSLQSGVPS | | 60 |
| RFSGSGSGTD FTLTISSLQP EDFATYYCQQ SYSTPFTFGC GTKLEIK | | 107 |
| | | |
| SEQ ID NO: 373 | moltype = AA   length = 11 | |
| FEATURE | Location/Qualifiers | |
| source | 1..11<br>mol_type = protein<br>organism = synthetic construct<br>note = 1A7_L1sp vlCDR1 | |
| SEQUENCE: 373 | | |
| RASQSISSYL N | | 11 |
| | | |
| SEQ ID NO: 374 | moltype = AA   length = 7 | |
| FEATURE | Location/Qualifiers | |
| source | 1..7<br>mol_type = protein<br>organism = synthetic construct<br>note = 1A7_L1sp vlCDR2 | |
| SEQUENCE: 374 | | |
| AASSLQS | | 7 |
| | | |
| SEQ ID NO: 375 | moltype = AA   length = 9 | |
| FEATURE | Location/Qualifiers | |
| source | 1..9<br>mol_type = protein | |

|   |   |   |
|---|---|---|
|   | organism = synthetic construct<br>note = 1A7_L1sp vlCDR3 |   |
| SEQUENCE: 375<br>QQSYSTPFT |   | 9 |
| SEQ ID NO: 376<br>FEATURE<br>source | moltype = AA  length = 107<br>Location/Qualifiers<br>1..107<br>mol_type = protein<br>organism = synthetic construct<br>note = 1A7_L1.71sp Variable light (vl) domain |   |
| SEQUENCE: 376<br>DIQMTQSPSS LSASVGDRVT ITCRASQSIS SYLNWYQQKP GKAPKLLIYA ASSLQSGVPS<br>RFSGSGSGTD FTLTISSLQP EDFATYYCQQ VYSTPFTFGC GTKLEIK | | 60<br>107 |
| SEQ ID NO: 377<br>FEATURE<br>source | moltype = AA  length = 11<br>Location/Qualifiers<br>1..11<br>mol_type = protein<br>organism = synthetic construct<br>note = 1A7_L1.71sp vlCDR1 |   |
| SEQUENCE: 377<br>RASQSISSYL N |   | 11 |
| SEQ ID NO: 378<br>FEATURE<br>source | moltype = AA  length = 7<br>Location/Qualifiers<br>1..7<br>mol_type = protein<br>organism = synthetic construct<br>note = 1A7_L1.71sp vlCDR2 |   |
| SEQUENCE: 378<br>AASSLQS |   | 7 |
| SEQ ID NO: 379<br>FEATURE<br>source | moltype = AA  length = 9<br>Location/Qualifiers<br>1..9<br>mol_type = protein<br>organism = synthetic construct<br>note = 1A7_L1.71sp vlCDR3 |   |
| SEQUENCE: 379<br>QQVYSTPFT |   | 9 |
| SEQ ID NO: 380<br>FEATURE<br>source | moltype = AA  length = 121<br>Location/Qualifiers<br>1..121<br>mol_type = protein<br>organism = synthetic construct<br>note = 1A7[CD28]_H1sp_L1sp Variable Heavy (vh) Domain |   |
| SEQUENCE: 380<br>EVQLLESGGG LVQPGGSLRL SCAASGFTFS SYAMSWVRQA PGCGLEWVST ISGSGDSTYY<br>ADSVKGRFTI SRDNSKNTLY LQMNSLRAED TAVYYCAKSG PGLRQVGFDY WGQGTLVTVS<br>S | | 60<br>120<br>121 |
| SEQ ID NO: 381<br>FEATURE<br>source | moltype = AA  length = 5<br>Location/Qualifiers<br>1..5<br>mol_type = protein<br>organism = synthetic construct<br>note = 1A7[CD28]_H1sp_L1sp vhCDR1 |   |
| SEQUENCE: 381<br>SYAMS |   | 5 |
| SEQ ID NO: 382<br>FEATURE<br>source | moltype = AA  length = 17<br>Location/Qualifiers<br>1..17<br>mol_type = protein<br>organism = synthetic construct<br>note = 1A7[CD28]_H1sp_L1sp vhCDR2 |   |
| SEQUENCE: 382<br>TISGSGDSTY YADSVKG |   | 17 |
| SEQ ID NO: 383<br>FEATURE<br>source | moltype = AA  length = 12<br>Location/Qualifiers<br>1..12<br>mol_type = protein<br>organism = synthetic construct<br>note = 1A7[CD28]_H1sp_L1sp vhCDR3 |   |
| SEQUENCE: 383<br>SGPGLRQVGF DY |   | 12 |

```
SEQ ID NO: 384          moltype = AA   length = 107
FEATURE                 Location/Qualifiers
source                  1..107
                        mol_type = protein
                        organism = synthetic construct
                        note = 1A7[CD28]_H1sp_L1sp Variable Light (vl) Domain
SEQUENCE: 384
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPFTFGC GTKLEIK                107

SEQ ID NO: 385          moltype = AA   length = 11
FEATURE                 Location/Qualifiers
source                  1..11
                        mol_type = protein
                        organism = synthetic construct
                        note = 1A7[CD28]_H1sp_L1sp vlCDR1
SEQUENCE: 385
RASQSISSYL N                                                       11

SEQ ID NO: 386          moltype = AA   length = 7
FEATURE                 Location/Qualifiers
source                  1..7
                        mol_type = protein
                        organism = synthetic construct
                        note = 1A7[CD28]_H1sp_L1sp vlCDR2
SEQUENCE: 386
AASSLQS                                                            7

SEQ ID NO: 387          moltype = AA   length = 9
FEATURE                 Location/Qualifiers
source                  1..9
                        mol_type = protein
                        organism = synthetic construct
                        note = 1A7[CD28]_H1sp_L1sp vlCDR3
SEQUENCE: 387
QQSYSTPFT                                                          9

SEQ ID NO: 388          moltype = AA   length = 121
FEATURE                 Location/Qualifiers
source                  1..121
                        mol_type = protein
                        organism = synthetic construct
                        note = 1A7[CD28]_H1.1sp_L1sp Variable Heavy (vh) Domain
SEQUENCE: 388
EVQLLESGGG LVQPGGSLRL SCAASGFTFS SYYMSWVRQA PGCGLEWVST ISGSGDSTYY   60
ADSVKGRFTI SRDNSKNTLY LQMNSLRAED TAVYYCAKSG PGLRQVGFDY WGQGTLVTVS  120
S                                                                 121

SEQ ID NO: 389          moltype = AA   length = 5
FEATURE                 Location/Qualifiers
source                  1..5
                        mol_type = protein
                        organism = synthetic construct
                        note = 1A7[CD28]_H1.1sp_L1sp vhCDR1
SEQUENCE: 389
SYYMS                                                              5

SEQ ID NO: 390          moltype = AA   length = 17
FEATURE                 Location/Qualifiers
source                  1..17
                        mol_type = protein
                        organism = synthetic construct
                        note = 1A7[CD28]_H1.1sp_L1sp vhCDR2
SEQUENCE: 390
TISGSGDSTY YADSVKG                                                 17

SEQ ID NO: 391          moltype = AA   length = 12
FEATURE                 Location/Qualifiers
source                  1..12
                        mol_type = protein
                        organism = synthetic construct
                        note = 1A7[CD28]_H1.1sp_L1sp vhCDR3
SEQUENCE: 391
SGPGLRQVGF DY                                                      12

SEQ ID NO: 392          moltype = AA   length = 107
FEATURE                 Location/Qualifiers
source                  1..107
```

```
                        mol_type = protein
                        organism = synthetic construct
                        note = 1A7[CD28]_H1.1sp_L1sp Variable Light (vl) Domain
SEQUENCE: 392
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPFTFGC GTKLEIK                 107

SEQ ID NO: 393          moltype = AA  length = 11
FEATURE                 Location/Qualifiers
source                  1..11
                        mol_type = protein
                        organism = synthetic construct
                        note = 1A7[CD28]_H1.1sp_L1sp vlCDR1
SEQUENCE: 393
RASQSISSYL N                                                         11

SEQ ID NO: 394          moltype = AA  length = 7
FEATURE                 Location/Qualifiers
source                  1..7
                        mol_type = protein
                        organism = synthetic construct
                        note = 1A7[CD28]_H1.1sp_L1sp vlCDR2
SEQUENCE: 394
AASSLQS                                                               7

SEQ ID NO: 395          moltype = AA  length = 9
FEATURE                 Location/Qualifiers
source                  1..9
                        mol_type = protein
                        organism = synthetic construct
                        note = 1A7[CD28]_H1.1sp_L1sp vlCDR3
SEQUENCE: 395
QQSYSTPFT                                                             9

SEQ ID NO: 396          moltype = AA  length = 121
FEATURE                 Location/Qualifiers
source                  1..121
                        mol_type = protein
                        organism = synthetic construct
                        note = 1A7[CD28]_H1sp_L1.71sp Variable Heavy (vh) Domain
SEQUENCE: 396
EVQLLESGGG LVQPGGSLRL SCAASGFTFS SYAMSWVRQA PGCGLEWVST ISGSGDSTYY    60
ADSVKGRFTI SRDNSKNTLY LQMNSLRAED TAVYYCAKSG PGLRQVGFDY WGQGTLVTVS   120
S                                                                  121

SEQ ID NO: 397          moltype = AA  length = 5
FEATURE                 Location/Qualifiers
source                  1..5
                        mol_type = protein
                        organism = synthetic construct
                        note = 1A7[CD28]_H1sp_L1.71sp vhCDR1
SEQUENCE: 397
SYAMS                                                                 5

SEQ ID NO: 398          moltype = AA  length = 17
FEATURE                 Location/Qualifiers
source                  1..17
                        mol_type = protein
                        organism = synthetic construct
                        note = 1A7[CD28]_H1sp_L1.71sp vhCDR2
SEQUENCE: 398
TISGSGDSTY YADSVKG                                                   17

SEQ ID NO: 399          moltype = AA  length = 12
FEATURE                 Location/Qualifiers
source                  1..12
                        mol_type = protein
                        organism = synthetic construct
                        note = 1A7[CD28]_H1sp_L1.71sp vhCDR3
SEQUENCE: 399
SGPGLRQVGF DY                                                        12

SEQ ID NO: 400          moltype = AA  length = 107
FEATURE                 Location/Qualifiers
source                  1..107
                        mol_type = protein
                        organism = synthetic construct
                        note = 1A7[CD28]_H1sp_L1.71sp Variable Light (vl) Domain
```

```
SEQUENCE: 400
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ VYSTPFTFGC GTKLEIK                 107

SEQ ID NO: 401          moltype = AA  length = 11
FEATURE                 Location/Qualifiers
source                  1..11
                        mol_type = protein
                        organism = synthetic construct
                        note = 1A7[CD28]_H1sp_L1.71sp vlCDR1
SEQUENCE: 401
RASQSISSYL N                                                         11

SEQ ID NO: 402          moltype = AA  length = 7
FEATURE                 Location/Qualifiers
source                  1..7
                        mol_type = protein
                        organism = synthetic construct
                        note = 1A7[CD28]_H1sp_L1.71sp vlCDR2
SEQUENCE: 402
AASSLQS                                                               7

SEQ ID NO: 403          moltype = AA  length = 9
FEATURE                 Location/Qualifiers
source                  1..9
                        mol_type = protein
                        organism = synthetic construct
                        note = 1A7[CD28]_H1sp_L1.71sp vlCDR3
SEQUENCE: 403
QQVYSTPFT                                                             9

SEQ ID NO: 404          moltype = AA  length = 121
FEATURE                 Location/Qualifiers
source                  1..121
                        mol_type = protein
                        organism = synthetic construct
                        note = 1A7[CD28]_H1.1sp_L1.71sp Variable Heavy (vh) Domain
SEQUENCE: 404
EVQLLESGGG LVQPGGSLRL SCAASGFTFS SYYMSWVRQA PGCGLEWVST ISGSGDSTYY    60
ADSVKGRFTI SRDNSKNTLY LQMNSLRAED TAVYYCAKSG PGLRQVGFDY WGQGTLVTVS   120
S                                                                   121

SEQ ID NO: 405          moltype = AA  length = 5
FEATURE                 Location/Qualifiers
source                  1..5
                        mol_type = protein
                        organism = synthetic construct
                        note = 1A7[CD28]_H1.1sp_L1.71sp vhCDR1
SEQUENCE: 405
SYYMS                                                                 5

SEQ ID NO: 406          moltype = AA  length = 17
FEATURE                 Location/Qualifiers
source                  1..17
                        mol_type = protein
                        organism = synthetic construct
                        note = 1A7[CD28]_H1.1sp_L1.71sp vhCDR2
SEQUENCE: 406
TISGSGDSTY YADSVKG                                                   17

SEQ ID NO: 407          moltype = AA  length = 12
FEATURE                 Location/Qualifiers
source                  1..12
                        mol_type = protein
                        organism = synthetic construct
                        note = 1A7[CD28]_H1.1sp_L1.71sp vhCDR3
SEQUENCE: 407
SGPGLRQVGF DY                                                        12

SEQ ID NO: 408          moltype = AA  length = 107
FEATURE                 Location/Qualifiers
source                  1..107
                        mol_type = protein
                        organism = synthetic construct
                        note = 1A7[CD28]_H1.1sp_L1.71sp Variable Light (vl) Domain
SEQUENCE: 408
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ VYSTPFTFGC GTKLEIK                 107
```

-continued

| | | |
|---|---|---|
| SEQ ID NO: 409<br>FEATURE<br>source | moltype = AA   length = 11<br>Location/Qualifiers<br>1..11<br>mol_type = protein<br>organism = synthetic construct<br>note = 1A7[CD28]_H1.1sp_L1.71sp vlCDR1 | |
| SEQUENCE: 409<br>RASQSISSYL N | | 11 |
| SEQ ID NO: 410<br>FEATURE<br>source | moltype = AA   length = 7<br>Location/Qualifiers<br>1..7<br>mol_type = protein<br>organism = synthetic construct<br>note = 1A7[CD28]_H1.1sp_L1.71sp vlCDR2 | |
| SEQUENCE: 410<br>AASSLQS | | 7 |
| SEQ ID NO: 411<br>FEATURE<br>source | moltype = AA   length = 9<br>Location/Qualifiers<br>1..9<br>mol_type = protein<br>organism = synthetic construct<br>note = 1A7[CD28]_H1.1sp_L1.71sp vlCDR3 | |
| SEQUENCE: 411<br>QQVYSTPFT | | 9 |
| SEQ ID NO: 412<br>FEATURE<br>source | moltype = AA   length = 121<br>Location/Qualifiers<br>1..121<br>mol_type = protein<br>organism = synthetic construct<br>note = 1A7[CD28]_H1.14sp_L1sp Variable Heavy (vh) Domain | |
| SEQUENCE: 412<br>EVQLLESGGG LVQPGGSLRL SCAASGFTFS SYYMSWVRQA PGCGLEWVST ISESGDSTYY<br>ADSVKGRFTI SRDNSKNTLY LQMNSLRAED TAVYYCAKSG PGLRQVGFDY WGQGTLVTVS<br>S | | 60<br>120<br>121 |
| SEQ ID NO: 413<br>FEATURE<br>source | moltype = AA   length = 5<br>Location/Qualifiers<br>1..5<br>mol_type = protein<br>organism = synthetic construct<br>note = 1A7[CD28]_H1.14sp_L1sp vhCDR1 | |
| SEQUENCE: 413<br>SYYMS | | 5 |
| SEQ ID NO: 414<br>FEATURE<br>source | moltype = AA   length = 17<br>Location/Qualifiers<br>1..17<br>mol_type = protein<br>organism = synthetic construct<br>note = 1A7[CD28]_H1.14sp_L1sp vhCDR2 | |
| SEQUENCE: 414<br>TISESGDSTY YADSVKG | | 17 |
| SEQ ID NO: 415<br>FEATURE<br>source | moltype = AA   length = 12<br>Location/Qualifiers<br>1..12<br>mol_type = protein<br>organism = synthetic construct<br>note = 1A7[CD28]_H1.14sp_L1sp vhCDR3 | |
| SEQUENCE: 415<br>SGPGLRQVGF DY | | 12 |
| SEQ ID NO: 416<br>FEATURE<br>source | moltype = AA   length = 107<br>Location/Qualifiers<br>1..107<br>mol_type = protein<br>organism = synthetic construct<br>note = 1A7[CD28]_H1.14sp_L1sp Variable Light (vl) Domain | |
| SEQUENCE: 416<br>DIQMTQSPSS LSASVGDRVT ITCRASQSIS SYLNWYQQKP GKAPKLLIYA ASSLQSGVPS<br>RFSGSGSGTD FTLTISSLQP EDFATYYCQQ SYSTPFTFGC GTKLEIK | | 60<br>107 |
| SEQ ID NO: 417<br>FEATURE<br>source | moltype = AA   length = 11<br>Location/Qualifiers<br>1..11<br>mol_type = protein | |

```
                            organism = synthetic construct
                            note = 1A7[CD28]_H1.14sp_L1sp vlCDR1
SEQUENCE: 417
RASQSISSYL N                                                             11

SEQ ID NO: 418              moltype = AA   length = 7
FEATURE                     Location/Qualifiers
source                      1..7
                            mol_type = protein
                            organism = synthetic construct
                            note = 1A7[CD28]_H1.14sp_L1sp vlCDR2
SEQUENCE: 418
AASSLQS                                                                  7

SEQ ID NO: 419              moltype = AA   length = 9
FEATURE                     Location/Qualifiers
source                      1..9
                            mol_type = protein
                            organism = synthetic construct
                            note = 1A7[CD28]_H1.14sp_L1sp vlCDR3
SEQUENCE: 419
QQSYSTPFT                                                                9

SEQ ID NO: 420              moltype = AA   length = 121
FEATURE                     Location/Qualifiers
source                      1..121
                            mol_type = protein
                            organism = synthetic construct
                            note = 1A7[CD28]_H1.14sp_L1.71sp Variable Heavy (vh) Domain
SEQUENCE: 420
EVQLLESGGG LVQPGGSLRL SCAASGFTFS SYYMSWVRQA PGCGLEWVST ISESGDSTYY         60
ADSVKGRFTI SRDNSKNTLY LQMNSLRAED TAVYYCAKSG PGLRQVGFDY WGQGTLVTVS        120
S                                                                       121

SEQ ID NO: 421              moltype = AA   length = 5
FEATURE                     Location/Qualifiers
source                      1..5
                            mol_type = protein
                            organism = synthetic construct
                            note = 1A7[CD28]_H1.14sp_L1.71sp vhCDR1
SEQUENCE: 421
SYYMS                                                                    5

SEQ ID NO: 422              moltype = AA   length = 17
FEATURE                     Location/Qualifiers
source                      1..17
                            mol_type = protein
                            organism = synthetic construct
                            note = 1A7[CD28]_H1.14sp_L1.71sp vhCDR2
SEQUENCE: 422
TISESGDSTY YADSVKG                                                       17

SEQ ID NO: 423              moltype = AA   length = 12
FEATURE                     Location/Qualifiers
source                      1..12
                            mol_type = protein
                            organism = synthetic construct
                            note = 1A7[CD28]_H1.14sp_L1.71sp vhCDR3
SEQUENCE: 423
SGPGLRQVGF DY                                                            12

SEQ ID NO: 424              moltype = AA   length = 107
FEATURE                     Location/Qualifiers
source                      1..107
                            mol_type = protein
                            organism = synthetic construct
                            note = 1A7[CD28]_H1.14sp_L1.71sp Variable Light (vl) Domain
SEQUENCE: 424
DIQMTQSPSS LSASVGDRVT ITCRASQSIS SYLNWYQQKP GKAPKLLIYA ASSLQSGVPS         60
RFSGSGSGTD FTLTISSLQP EDFATYYCQQ VYSTPFTFGC GTKLEIK                      107

SEQ ID NO: 425              moltype = AA   length = 11
FEATURE                     Location/Qualifiers
source                      1..11
                            mol_type = protein
                            organism = synthetic construct
                            note = 1A7[CD28]_H1.14sp_L1.71sp vlCDR1
SEQUENCE: 425
RASQSISSYL N                                                             11
```

```
SEQ ID NO: 426           moltype = AA   length = 7
FEATURE                  Location/Qualifiers
source                   1..7
                         mol_type = protein
                         organism = synthetic construct
                         note = 1A7[CD28]_H1.14sp_L1.71sp vlCDR2
SEQUENCE: 426
AASSLQS                                                                    7

SEQ ID NO: 427           moltype = AA   length = 9
FEATURE                  Location/Qualifiers
source                   1..9
                         mol_type = protein
                         organism = synthetic construct
                         note = 1A7[CD28]_H1.14sp_L1.71sp vlCDR3
SEQUENCE: 427
QQVYSTPFT                                                                  9

SEQ ID NO: 428           moltype = AA   length = 750
FEATURE                  Location/Qualifiers
source                   1..750
                         mol_type = protein
                         organism = Homo sapiens
                         note = sp4609
SEQUENCE: 428
MWNLLHETDS AVATARRPRW LCAGALVLAG GFFLLGFLFG WFIKSSNEAT NITPKHNMKA    60
FLDELKAENI KKFLYNFTQI PHLAGTEQNF QLAKQIQSQW KEFGLDSVEL AHYDVLLSYP   120
NKTHPNYISI INEDGNEIFN TSLFEPPPPG YENVSDIVPP FSAFSPQGMP EGDLVYVNYA   180
RTEDFFKLER DMKINCSGKI VIARYGKVFR GNKVKNAQLA GAKGVILYSD PADYFAPGVK   240
SYPDGWNLPG GGVQRGNILN LNGAGDPLTG YPANEYAYR RGIAEAVGLP SIPVHPIGYY    300
DAQKLLEKMG GSAPPDSSWR GSLKVPYNVG PGFTGNFSTQ KVKMHIHSTN EVTRIYNVIG   360
TLRGAVEPDR YVILGGHRDS WVFGGIDPQS GAAVVHEIVR SFGTLKKEGW RPRRTILFAS   420
WDAEEFGLLG STEWAEENSR LLQERGVAYI NADSSIEGNY TLRVDCTPLM YSLVHNLTKE   480
LKSPDEGFEG KSLYESWTKK SPSPEFSGMP RISKLGSGND FEVFFQRLGI ASGRARYTKN   540
WETNKFSGYP LYHSVYETYE LVEKFYDPMF KYHLTVAQVR GGMVFELANS IVLPFDCRDY   600
AVVLRKYADK IYSISMKHPQ EMKTYSVSFD SLFSAVKNFT EIASKFSERL QDFDKSNPIV   660
LRMMNDQLMF LERAFIDPLG LPDRPFYRHV IYAPSSHNKY AGESFPGIYD ALFDIESKVD   720
PSKAWGEVKR QIYVAAFTVQ AAAETLSEVA                                     750

SEQ ID NO: 429           moltype = AA   length = 707
FEATURE                  Location/Qualifiers
source                   1..707
                         mol_type = protein
                         organism = Homo sapiens
                         note = sp4609[44]-750
SEQUENCE: 429
KSSNEATNIT PKHNMKAFLD ELKAENIKKF LYNFTQIPHL AGTEQNFQLA KQIQSQWKEF    60
GLDSVELAHY DVLLSYPNKT HPNYISIINE DGNEIFNTSL FEPPPPGYEN VSDIVPPFSA   120
FSPQGMPEGD LVYVNYARTE DFFKLERDMK INCSGKIVIA RYGKVFRGNK VKNAQLAGAK   180
GVILYSDPAD YFAPGVKSYP DGWNLPGGGV QRGNILNLNG AGDPLTGYP ANEYAYRRGI    240
AEAVGLPSIP VHPIGYYDAQ KLLEKMGGSA PPDSSWRGSL KVPYNVGPGF TGNFSTQKVK   300
MHIHSTNEVT RIYNVIGTLR GAVEPDRYVI LGGHRDSWVF GGIDPQSGAA VVHEIVRSFG   360
TLKKEGWRPR RTILFASWDA EEFGLLGSTE WAEENSRLLQ ERGVAYINAD SSIEGNYTLR   420
VDCTPLMYSL VHNLTKELKS PDEGFEGKSL YESWTKKSPS PEFSGMPRIS KLGSGNDFEV   480
FFQRLGIASG RARYTKNWET NKFSGYPLYH SVYETYELVE KFYDPMFKYH LTVAQVRGGM   540
VFELANSIVL PFDCRDYAVV LRKYADKIYS ISMKHPQEMK TYSVSFDSLF SAVKNFTEIA   600
SKFSERLQDF DKSNPIVLRM MNDQLMFLER AFIDPLGLPD RPFYRHVIYA PSSHNKYAGE   660
SFPGIYDALF DIESKVDPSK AWGEVKRQIY VAAFTVQAAA ETLSEVA                  707

SEQ ID NO: 430           moltype = AA   length = 752
FEATURE                  Location/Qualifiers
source                   1..752
                         mol_type = protein
                         organism = Mus musculus
                         note = sp5409
SEQUENCE: 430
MWNALQDRDS AEVLGHRQRW LRVGTLVLAL TGTFLIGFLF GWFIKPSNEA TGNVSHSGMK    60
KEFLHELKAE NIKKFLYNFT RTPHLAGTQN NFELAKQIHD QWKEFGLDLV ELSHYDVLLS   120
YPNKTHPNYI SIINEDGNEI FKTSLSEQPP PGYENISDVV PPYSAFSPQG TPEGDLVYVN   180
YARTEDFFKL EREMKISCSG KIVIARYGKV FRGNMVKNAQ LAGAKGMILY SDPADYFVPA   240
VKSYPDGWNL PGGGVQRGNV LNLNGAGDPL TPGYPANEHA YRHELTNAVG LPSIPVHPIG   300
YDDAQKLLEH MGGPAPPDSS WKGGLKVPYN VGPGFAGNFS TQKVKMHIHS YTKVTRIYNV   360
IGTLKGALEP DRYVILGGHR DAWVFGGIDP QSGAAVVHEI VRSFGTLKKK GRRPRRTILF   420
ASWDAEEFGL LGSTEWAEEH SRLLQERGVA YINADSSIEG NYTLRVDCTP LMYSLVHNLT   480
KELQSPDEGF EGKSLYDSWK EKSPSPEFIG MPRISKLGSG NDFEVFFQRL GIASGRARYT   540
KNWKTNKVSS YPLHSVYET YELVVKFYDP TFKYHLTVAQ VRGAMVFELA NSIVLPFDCQ    600
SYAVALKKYA DTIYNISMKH PQEMKAYMIS FDSLFSAVNN FTDVASKFNQ RLQELDKSNP   660
```

```
ILLRIMNDQL MYLERAFIDP LGLPGRPFYR HIIYAPSSHN KYAGESFPGI YDALFDISSK    720
VNASKAWNEV KRQISIATFT VQAAAETLRE VA                                 752

SEQ ID NO: 431              moltype = AA  length = 708
FEATURE                     Location/Qualifiers
source                      1..708
                            mol_type = protein
                            organism = Mus musculus
                            note = sp5409[45]-752
SEQUENCE: 431
KPSNEATGNV SHSGMKKEFL HELKAENIKK FLYNFTRTPH LAGTQNNFEL AKQIHDQWKE    60
FGLDLVELSH YDVLLSYPNK THPNYISIIN EDGNEIFKTS LSEQPPPGYE NISDVVPPYS    120
AFSPQGTPEG DLVYVNYART EDFFKLEREM KISCSGKIVI ARYGKVFRGN MVKNAQLAGA    180
KGMILYSDPA DYFVPAVKSY PDGWNLPGGG VQRGNVLNLN GAGDPLTPGY PANEHAYRHE    240
LTNAVGLPSI PVHPIGYDDA QKLLEHMGGP APPDSSWKGG LKVPYNVGPG FAGNFSTQKV    300
KMHIHSYTKV TRIYNVIGTL KGALEPDRYV ILGGHRDAWV FGGIDPQSGA AVVHEIVRSF    360
GTLKKKGRRP RRTILFASWD AEEFGLLGST EWAEEHSRLL QERGVAYINA DSSIEGNYTL    420
RVDCTPLMYS LVYNLTKELQ SPDEGFEGKS LYDSWKEKSP SPEFIGMPRI SKLGSGNDFE    480
VFFQRLGIAS GRARYTKNWK TNKVSSYPLY HSVYETYELV VKFYDPTFKY HLTVAQVRGA    540
MVFELANSIV LPFDCQSYAV ALKKYADTIY NISMKHPQEM KAYMISFDSL FSAVNNFTDV    600
ASKFNQRLQE LDKSNPILLR IMNDQLMYLE RAFIDPLGLP GRPFYRHIIY APSSHNKYAG    660
ESFPGIYDAL FDISSKVNAS KAWNEVKRQI SIATFTVQAA AETLREVA                708

SEQ ID NO: 432              moltype = AA  length = 750
FEATURE                     Location/Qualifiers
source                      1..750
                            mol_type = protein
                            organism = Macaca fascicularis
                            note = trPNF
SEQUENCE: 432
MWNLLHETDS AVATARRPRW LCAGALVLAG GFFLLGFLFG WFIKSSSEAT NITPKHNMKA    60
FLDELKAENI KKFLHNFTQI PHLAGTEQNF QLAKQIQSQW KEFGLDSVEL THYDVLLSYP    120
NKTHPNYISI INEDGNEIFN TSLFEPPPAG YENVSDIVPP FSAFSPQGMP EGDLVYVNYA    180
RTEDFFKLER DMKINCSGKI VIARYGKVFR GNKVKNAQLA GATGVILYSD PDDYFAPGVK    240
SYPDGWNLPG GGVQRGNILN LNGAGDPLTP GYPANEYAYR RGMAEAVGLP SIPVHPIGYY    300
DAQKLLEKMG GSASPDSSWR GSLKVPYNVG PGFTGNFSTQ KVKMHIHSTS EVTRIYNVIG    360
TLRGAVEPDR YVILGGHRDS WVFGGIDPQS GAAVVHEIVR SFGMLKKEGW RPRRTILFAS    420
WDAEEFGLLG STEWAEENSR LLQERGVAYI NADSSIEGNY TLRVDCTPLM YSLVYNLTKK    480
LESPDEGFEG KSLYESWTKK SPSPEFSGMP RISKLGSGND FEVFFQRLGI ASGRARYTKN    540
WETNKFSSYP LYHSVYETYE LVEKFYDPMF KYHLTVAQVR GGMVFELANS VVLPFDCRDY    600
AVVLRKYADK IYNISMKHPQ EMKTYSVSFD SLFSAVKNFT EIASKFSERL RDFDKSNPIL    660
LRMMNDQLMF LERAFIDPLG LPDRPFYRHV IYAPSSHNKY AGESFPGIYD ALFDIESKVD    720
PSQAWGEVKR QISIATFTVQ AAAETLSEVA                                    750

SEQ ID NO: 433              moltype = AA  length = 707
FEATURE                     Location/Qualifiers
source                      1..707
                            mol_type = protein
                            organism = Macaca fascicularis
                            note = trPNF[44]-750
SEQUENCE: 433
KSSSEATNIT PKHNMKAFLD ELKAENIKKF LHNFTQIPHL AGTEQNFQLA KQIQSQWKEF    60
GLDSVELTHY DVLLSYPNKT HPNYISIINE DGNEIFNTSL FEPPPAGYEN VSDIVPPFSA    120
FSPQGMPEGD LVYVNYARTE DFFKLERDMK INCSGKIVIA RYGKVFRGNK VKNAQLAGAT    180
GVILYSDPDD YFAPGVKSYP DGWNLPGGGV QRGNILNLNG AGDPLTPGYP ANEYAYRRGM    240
AEAVGLPSIP VHPIGYYDAQ KLLEKMGGSA SPDSSWRGSL KVPYNVGPGF TGNFSTQKVK    300
MHIHSTSEVT RIYNVIGTLR GAVEPDRYVI LGGHRDSWVF GGIDPQSGAA VVHEIVRSFG    360
MLKKEGWRPR RTILFASWDA EEFGLLGSTE WAEENSRLLQ ERGVAYINAD SSIEGNYTLR    420
VDCTPLMYSL VYNLTKELES PDEGFEGKSL YESWTKKSPS PEFSGMPRIS KLGSGNDFEV    480
FFQRLGIASG RARYTKNWET NKFSSYPLYH SVYETYELVE KFYDPMFKYH LTVAQVRGGM    540
VFELANSVVL PFDCRDYAVV LRKYADKIYN ISMKHPQEMK TYSVSFDSLF SAVKNFTEIA    600
SKFSERLRDF DKSNPILLRM MNDQLMFLER AFIDPLGLPD RPFYRHVIYA PSSHNKYAGE    660
SFPGIYDALF DIESKVDPSQ AWGEVKRQIS IATFTVQAAA ETLSEVA                 707

SEQ ID NO: 434              moltype = AA  length = 15
FEATURE                     Location/Qualifiers
source                      1..15
                            mol_type = protein
                            organism = synthetic construct
SEQUENCE: 434
GGGGSGGGGS GGGGS                                                    15

SEQ ID NO: 435              moltype = AA  length = 18
FEATURE                     Location/Qualifiers
source                      1..18
                            mol_type = protein
                            organism = synthetic construct
SEQUENCE: 435
GSTSGSGKPG SGEGSTKG                                                 18
```

```
SEQ ID NO: 436           moltype = AA  length = 14
FEATURE                  Location/Qualifiers
source                   1..14
                         mol_type = protein
                         organism = synthetic construct
SEQUENCE: 436
IRPRAIGGSK PRVA                                                           14

SEQ ID NO: 437           moltype = AA  length = 15
FEATURE                  Location/Qualifiers
source                   1..15
                         mol_type = protein
                         organism = synthetic construct
SEQUENCE: 437
GKGGSGKGGS GKGGS                                                          15

SEQ ID NO: 438           moltype = AA  length = 15
FEATURE                  Location/Qualifiers
source                   1..15
                         mol_type = protein
                         organism = synthetic construct
SEQUENCE: 438
GGKGSGGKGS GGKGS                                                          15

SEQ ID NO: 439           moltype = AA  length = 15
FEATURE                  Location/Qualifiers
source                   1..15
                         mol_type = protein
                         organism = synthetic construct
SEQUENCE: 439
GGGKSGGGKS GGGKS                                                          15

SEQ ID NO: 440           moltype = AA  length = 15
FEATURE                  Location/Qualifiers
source                   1..15
                         mol_type = protein
                         organism = synthetic construct
SEQUENCE: 440
GKGKSGKGKS GKGKS                                                          15

SEQ ID NO: 441           moltype = AA  length = 15
FEATURE                  Location/Qualifiers
source                   1..15
                         mol_type = protein
                         organism = synthetic construct
SEQUENCE: 441
GGGKSGGKGS GKGGS                                                          15

SEQ ID NO: 442           moltype = AA  length = 15
FEATURE                  Location/Qualifiers
source                   1..15
                         mol_type = protein
                         organism = synthetic construct
SEQUENCE: 442
GKPGSGKPGS GKPGS                                                          15

SEQ ID NO: 443           moltype = AA  length = 20
FEATURE                  Location/Qualifiers
source                   1..20
                         mol_type = protein
                         organism = synthetic construct
SEQUENCE: 443
GKPGSGKPGS GKPGSGKPGS                                                     20

SEQ ID NO: 444           moltype = AA  length = 20
FEATURE                  Location/Qualifiers
source                   1..20
                         mol_type = protein
                         organism = synthetic construct
SEQUENCE: 444
GKGKSGKGKS GKGKSGKGKS                                                     20

SEQ ID NO: 445           moltype = AA  length = 20
FEATURE                  Location/Qualifiers
source                   1..20
                         mol_type = protein
                         organism = synthetic construct
```

```
SEQUENCE: 445
GGGGSGGGGS GGGGSGGGGS                                                        20

SEQ ID NO: 446           moltype = AA   length = 14
FEATURE                  Location/Qualifiers
source                   1..14
                         mol_type = protein
                         organism = synthetic construct
SEQUENCE: 446
STAGDTHLGG EDFD                                                              14

SEQ ID NO: 447           moltype = AA   length = 15
FEATURE                  Location/Qualifiers
source                   1..15
                         mol_type = protein
                         organism = synthetic construct
SEQUENCE: 447
GEGGSGEGGS GEGGS                                                             15

SEQ ID NO: 448           moltype = AA   length = 15
FEATURE                  Location/Qualifiers
source                   1..15
                         mol_type = protein
                         organism = synthetic construct
SEQUENCE: 448
GGEGSGGEGS GGEGS                                                             15

SEQ ID NO: 449           moltype = AA   length = 15
FEATURE                  Location/Qualifiers
source                   1..15
                         mol_type = protein
                         organism = synthetic construct
SEQUENCE: 449
GGGESGGGES GGGES                                                             15

SEQ ID NO: 450           moltype = AA   length = 15
FEATURE                  Location/Qualifiers
source                   1..15
                         mol_type = protein
                         organism = synthetic construct
SEQUENCE: 450
GEGESGEGES GEGES                                                             15

SEQ ID NO: 451           moltype = AA   length = 15
FEATURE                  Location/Qualifiers
source                   1..15
                         mol_type = protein
                         organism = synthetic construct
SEQUENCE: 451
GGGESGGEGS GEGGS                                                             15

SEQ ID NO: 452           moltype = AA   length = 20
FEATURE                  Location/Qualifiers
source                   1..20
                         mol_type = protein
                         organism = synthetic construct
SEQUENCE: 452
GEGESGEGES GEGESGEGES                                                        20

SEQ ID NO: 453           moltype = AA   length = 19
FEATURE                  Location/Qualifiers
source                   1..19
                         mol_type = protein
                         organism = synthetic construct
SEQUENCE: 453
PRGASKSGSA SQTGSAPGS                                                         19

SEQ ID NO: 454           moltype = AA   length = 19
FEATURE                  Location/Qualifiers
source                   1..19
                         mol_type = protein
                         organism = synthetic construct
SEQUENCE: 454
GTAAAGAGAA GGAAAGAAG                                                         19

SEQ ID NO: 455           moltype = AA   length = 19
FEATURE                  Location/Qualifiers
```

```
                                   -continued
source                 1..19
                       mol_type = protein
                       organism = synthetic construct
SEQUENCE: 455
GTSGSSGSGS GGSGSGGGG                                              19

SEQ ID NO: 456         moltype = AA   length = 20
FEATURE                Location/Qualifiers
source                 1..20
                       mol_type = protein
                       organism = synthetic construct
SEQUENCE: 456
GGSEGKSSGS GSESKSTGGS                                             20

SEQ ID NO: 457         moltype = AA   length = 18
FEATURE                Location/Qualifiers
source                 1..18
                       mol_type = protein
                       organism = synthetic construct
SEQUENCE: 457
GGGSGGSGGC PPCGGSGG                                               18

SEQ ID NO: 458         moltype = AA   length = 5
FEATURE                Location/Qualifiers
source                 1..5
                       mol_type = protein
                       organism = synthetic construct
SEQUENCE: 458
GGGGS                                                              5

SEQ ID NO: 459         moltype = AA   length = 10
FEATURE                Location/Qualifiers
source                 1..10
                       mol_type = protein
                       organism = synthetic construct
SEQUENCE: 459
GGGGSGGGGS                                                        10

SEQ ID NO: 460         moltype = AA   length = 25
FEATURE                Location/Qualifiers
source                 1..25
                       mol_type = protein
                       organism = synthetic construct
SEQUENCE: 460
GGGGSGGGGS GGGGSGGGGS GGGGS                                       25

SEQ ID NO: 461         moltype = AA   length = 30
FEATURE                Location/Qualifiers
source                 1..30
                       mol_type = protein
                       organism = synthetic construct
SEQUENCE: 461
GGGGSGGGGS GGGGSGGGGS GGGGSGGGGS                                  30

SEQ ID NO: 462         moltype = AA   length = 35
FEATURE                Location/Qualifiers
source                 1..35
                       mol_type = protein
                       organism = synthetic construct
SEQUENCE: 462
GGGGSGGGGS GGGGSGGGGS GGGGSGGGGS GGGGS                            35

SEQ ID NO: 463         moltype = AA   length = 5
FEATURE                Location/Qualifiers
source                 1..5
                       mol_type = protein
                       organism = synthetic construct
SEQUENCE: 463
GGGGA                                                              5

SEQ ID NO: 464         moltype = AA   length = 10
FEATURE                Location/Qualifiers
source                 1..10
                       mol_type = protein
                       organism = synthetic construct
SEQUENCE: 464
GGGGAGGGGA                                                        10

SEQ ID NO: 465         moltype = AA   length = 15
```

```
FEATURE              Location/Qualifiers
source               1..15
                     mol_type = protein
                     organism = synthetic construct
SEQUENCE: 465
GGGGAGGGGA GGGGA                                                          15

SEQ ID NO: 466       moltype = AA  length = 20
FEATURE              Location/Qualifiers
source               1..20
                     mol_type = protein
                     organism = synthetic construct
SEQUENCE: 466
GGGGAGGGGA GGGGAGGGGA                                                     20

SEQ ID NO: 467       moltype = AA  length = 25
FEATURE              Location/Qualifiers
source               1..25
                     mol_type = protein
                     organism = synthetic construct
SEQUENCE: 467
GGGGAGGGGA GGGGAGGGGA GGGGA                                               25

SEQ ID NO: 468       moltype = AA  length = 30
FEATURE              Location/Qualifiers
source               1..30
                     mol_type = protein
                     organism = synthetic construct
SEQUENCE: 468
GGGGAGGGGA GGGGAGGGGA GGGGAGGGGA                                          30

SEQ ID NO: 469       moltype = AA  length = 35
FEATURE              Location/Qualifiers
source               1..35
                     mol_type = protein
                     organism = synthetic construct
SEQUENCE: 469
GGGGAGGGGA GGGGAGGGGA GGGGAGGGGA GGGGA                                    35

SEQ ID NO: 470       moltype = AA  length = 30
FEATURE              Location/Qualifiers
source               1..30
                     mol_type = protein
                     organism = synthetic construct
SEQUENCE: 470
DPALVHQRPA PPGGGSGGG GSGGGGSGGG                                           30

SEQ ID NO: 471       moltype = AA  length = 5
FEATURE              Location/Qualifiers
source               1..5
                     mol_type = protein
                     organism = synthetic construct
SEQUENCE: 471
GKPGS                                                                     5

SEQ ID NO: 472       moltype = AA  length = 25
FEATURE              Location/Qualifiers
source               1..25
                     mol_type = protein
                     organism = synthetic construct
SEQUENCE: 472
GKPGSGKPGS GKPGSGKPGS GKPGS                                               25

SEQ ID NO: 473       moltype = AA  length = 30
FEATURE              Location/Qualifiers
source               1..30
                     mol_type = protein
                     organism = synthetic construct
SEQUENCE: 473
GKPGSGKPGS GKPGSGKPGS GKPGSGKPGS                                          30

SEQ ID NO: 474       moltype = AA  length = 5
FEATURE              Location/Qualifiers
source               1..5
                     mol_type = protein
                     organism = synthetic construct
SEQUENCE: 474
GGGES                                                                     5
```

```
SEQ ID NO: 475          moltype = AA   length = 15
FEATURE                 Location/Qualifiers
source                  1..15
                        mol_type = protein
                        organism = synthetic construct
SEQUENCE: 475
EPKSCDKTHT CPPCP                                                        15

SEQ ID NO: 476          moltype = AA   length = 9
FEATURE                 Location/Qualifiers
source                  1..9
                        mol_type = protein
                        organism = synthetic construct
SEQUENCE: 476
KTHTCPPCP                                                                9

SEQ ID NO: 477          moltype = AA   length = 15
FEATURE                 Location/Qualifiers
source                  1..15
                        mol_type = protein
                        organism = synthetic construct
SEQUENCE: 477
EPKSSDKTHT CPPCP                                                        15

SEQ ID NO: 478          moltype = AA   length = 19
FEATURE                 Location/Qualifiers
source                  1..19
                        mol_type = protein
                        organism = synthetic construct
SEQUENCE: 478
GGGGSGGGGS KTHTCPPCP                                                    19

SEQ ID NO: 479          moltype = AA   length = 19
FEATURE                 Location/Qualifiers
source                  1..19
                        mol_type = protein
                        organism = synthetic construct
SEQUENCE: 479
GKPGSGKPGS KTHTCPPCP                                                    19

SEQ ID NO: 480          moltype = AA   length = 14
FEATURE                 Location/Qualifiers
source                  1..14
                        mol_type = protein
                        organism = synthetic construct
SEQUENCE: 480
GKPGSKTHTC PPCP                                                         14

SEQ ID NO: 481          moltype = AA   length = 5
FEATURE                 Location/Qualifiers
source                  1..5
                        mol_type = protein
                        organism = synthetic construct
SEQUENCE: 481
EPKSC                                                                    5

SEQ ID NO: 482          moltype = AA   length = 15
FEATURE                 Location/Qualifiers
source                  1..15
                        mol_type = protein
                        organism = synthetic construct
SEQUENCE: 482
EPKSCGGGGS GGGGS                                                        15

SEQ ID NO: 483          moltype = AA   length = 15
FEATURE                 Location/Qualifiers
source                  1..15
                        mol_type = protein
                        organism = synthetic construct
SEQUENCE: 483
EPKSCGKPGS GKPGS                                                        15

SEQ ID NO: 484          moltype = AA   length = 10
FEATURE                 Location/Qualifiers
source                  1..10
                        mol_type = protein
                        organism = synthetic construct
SEQUENCE: 484
EPKSCGKPGS                                                              10
```

```
SEQ ID NO: 485          moltype = AA  length = 216
FEATURE                 Location/Qualifiers
source                  1..216
                        mol_type = protein
                        organism = synthetic construct
                        note = Heterodimeric Fc Backbone 1 monomer 1 (-)
SEQUENCE: 485
APPVAGPSVF LFPPKPKDTL MISRTPEVTC VVVDVKHEDP EVKFNWYVDG VEVHNAKTKP    60
REEEYNSTYR VVSVLTVLHQ DWLNGKEYKC KVSNKALPAP IEKTISKAKG QPREPQVYTL   120
PPSREEMTKN QVSLTCDVSG FYPSDIAVEW ESDGQPENNY KTTPPVLDSD GSFFLYSKLT   180
VDKSRWEQGD VFSCSVMHEA LHNHYTQKSL SLSPGK                             216

SEQ ID NO: 486          moltype = AA  length = 216
FEATURE                 Location/Qualifiers
source                  1..216
                        mol_type = protein
                        organism = synthetic construct
                        note = Heterodimeric Fc Backbone 1 monomer 2 (+)
SEQUENCE: 486
APPVAGPSVF LFPPKPKDTL MISRTPEVTC VVVDVKHEDP EVKFNWYVDG VEVHNAKTKP    60
REEQYNSTYR VVSVLTVLHQ DWLNGKEYKC KVSNKALPAP IEKTISKAKG QPREPQVYTL   120
PPSREQMTKN QVKLTCLVKG FYPSDIAVEW ESNGQPENNY KTTPPVLDSD GSFFLYSKLT   180
VDKSRWQQGN VFSCSVMHEA LHNHYTQKSL SLSPGK                             216

SEQ ID NO: 487          moltype = AA  length = 216
FEATURE                 Location/Qualifiers
source                  1..216
                        mol_type = protein
                        organism = synthetic construct
                        note = Heterodimeric Fc Backbone 2 monomer 1 (-)
SEQUENCE: 487
APPVAGPSVF LFPPKPKDTL MISRTPEVTC VVVDVKHEDP EVKFNWYVDG VEVHNAKTKP    60
REEEYNSTYR VVSVLTVLHQ DWLNGKEYKC KVSNKALPAP IEKTISKAKG QPREPQVYTL   120
PPSREEMTKN QVSLTCDVSG FYPSDIAVEW ESDGQPENNY KTTPPVLDSD GSFFLYSKLT   180
VDKSRWEQGD VFSCSVMHEA LHNHYTQKSL SLSPGK                             216

SEQ ID NO: 488          moltype = AA  length = 216
FEATURE                 Location/Qualifiers
source                  1..216
                        mol_type = protein
                        organism = synthetic construct
                        note = Heterodimeric Fc Backbone monomer 2 (+)
SEQUENCE: 488
APPVAGPSVF LFPPKPKDTL MISRTPEVTC VVVDVKHEDP EVKFNWYVDG VEVHNAKTKP    60
REEQYNSTYR VVSVLTVLHQ DWLNGKEYKC KVSNKALPAP IEKTISKAKG QPREPQVYTL   120
PPSREEMTKN QVKLTCLVKG FYPSDIAVEW ESNGQPENNY KTTPPVLDSD GSFFLYSKLT   180
VDKSRWQQGN VFSCSVMHEA LHNHYTQKSL SLSPGK                             216

SEQ ID NO: 489          moltype = AA  length = 216
FEATURE                 Location/Qualifiers
source                  1..216
                        mol_type = protein
                        organism = synthetic construct
                        note = Heterodimeric Fc Backbone 3 monomer 1 (-)
SEQUENCE: 489
APPVAGPSVF LFPPKPKDTL MISRTPEVTC VVVDVKHEDP EVKFNWYVDG VEVHNAKTKP    60
REEEYNSTYR VVSVLTVLHQ DWLNGKEYKC KVSNKALPAP IEKTISKAKG QPREPQVYTL   120
PPSREEMTKN QVSLTCEVSG FYPSDIAVEW ESDGQPENNY KTTPPVLDSD GSFFLYSKLT   180
VDKSRWEQGD VFSCSVMHEA LHNHYTQKSL SLSPGK                             216

SEQ ID NO: 490          moltype = AA  length = 216
FEATURE                 Location/Qualifiers
source                  1..216
                        mol_type = protein
                        organism = synthetic construct
                        note = Heterodimeric Fc Backbone 3 monomer 2 (+)
SEQUENCE: 490
APPVAGPSVF LFPPKPKDTL MISRTPEVTC VVVDVKHEDP EVKFNWYVDG VEVHNAKTKP    60
REEQYNSTYR VVSVLTVLHQ DWLNGKEYKC KVSNKALPAP IEKTISKAKG QPREPQVYTL   120
PPSREQMTKN QVKLTCLVKG FYPSDIAVEW ESNGQPENNY KTTPPVLDSD GSFFLYSKLT   180
VDKSRWQQGN VFSCSVMHEA LHNHYTQKSL SLSPGK                             216

SEQ ID NO: 491          moltype = AA  length = 216
FEATURE                 Location/Qualifiers
source                  1..216
                        mol_type = protein
                        organism = synthetic construct
                        note = Heterodimeric Fc Backbone 4 monomer 1 (-)
```

```
SEQUENCE: 491
APPVAGPSVF LFPPKPKDTL MISRTPEVTC VVVDVKHEDP EVKFNWYVDG VEVHNAKTKP    60
REEEYNSTYR VVSVLTVLHQ DWLNGKEYKC KVSNKALPAP IEKTISKAKG QPREPQVYTL   120
PPSREEMTEN EVSLTCLVKG FYPSDIAVEW ESDGQPENNY KTTPPVLDSD GSFFLYSKLE   180
VDKSRWEQGD VFSCSVMHEA LHNHYTQKSL SLSPGK                             216

SEQ ID NO: 492          moltype = AA  length = 216
FEATURE                 Location/Qualifiers
source                  1..216
                        mol_type = protein
                        organism = synthetic construct
                        note = Heterodimeric Fc Backbone 4 monomer 2 (+)
SEQUENCE: 492
APPVAGPSVF LFPPKPKDTL MISRTPEVTC VVVDVKHEDP EVKFNWYVDG VEVHNAKTKP    60
REEQYNSTYR VVSVLTVLHQ DWLNGKEYKC KVSNKALPAP IEKTISKAKG QPREPQVYTL   120
PPSREEMTKN QVSLTCLVKG FYPSDIAVEW ESNGQPENNY KTTPPVLDSK GSFFLYSKLT   180
VDKSRWQQGN VFSCSVMHEA LHNHYTQKSL SLSPGK                             216

SEQ ID NO: 493          moltype = AA  length = 216
FEATURE                 Location/Qualifiers
source                  1..216
                        mol_type = protein
                        organism = synthetic construct
                        note = Heterodimeric Fc Backbone 5 monomer 1 (-)
SEQUENCE: 493
APPVAGPSVF LFPPKPKDTL MISRTPEVTC VVVDVKHEDP EVKFNWYVDG VEVHNAKTKP    60
REEEYNSTYR VVSVLTVLHQ DWLNGKEYKC KVSNKALPAP IEKTISKAKG QPREPQVYTL   120
PPSRDELTKN QVSLTCDVSG FYPSDIAVEW ESDGQPENNY KTTPPVLDSD GSFFLYSKLT   180
VDKSRWEQGD VFSCSVMHEA LHNHYTQKSL SLSPGK                             216

SEQ ID NO: 494          moltype = AA  length = 216
FEATURE                 Location/Qualifiers
source                  1..216
                        mol_type = protein
                        organism = synthetic construct
                        note = Heterodimeric Fc Backbone 5 monomer 2 (+)
SEQUENCE: 494
APPVAGPSVF LFPPKPKDTL MISRTPEVTC VVVDVKHEDP EVKFNWYVDG VEVHNAKTKP    60
REEQYNSTYR VVSVLTVLHQ DWLNGKEYKC KVSNKALPAP IEKTISKAKG QPREPQVYTL   120
PPSRDQLTKN QVKLTCLVKG FYPSDIAVEW ESNGQPENNY KTTPPVLDSD GSFFLYSKLT   180
VDKSRWQQGN VFSCSVMHEA LHNHYTQKSL SLSPGK                             216

SEQ ID NO: 495          moltype = AA  length = 216
FEATURE                 Location/Qualifiers
source                  1..216
                        mol_type = protein
                        organism = synthetic construct
                        note = Heterodimeric Fc Backbone 6 monomer 1 (-)
SEQUENCE: 495
APPVAGPSVF LFPPKPKDTL MISRTPEVTC VVVDVKHEDP EVKFNWYVDG VEVHNAKTKP    60
REEEYASTYR VVSVLTVLHQ DWLNGKEYKC KVSNKALPAP IEKTISKAKG QPREPQVYTL   120
PPSREEMTKN QVSLTCDVSG FYPSDIAVEW ESDGQPENNY KTTPPVLDSD GSFFLYSKLT   180
VDKSRWEQGD VFSCSVMHEA LHNHYTQKSL SLSPGK                             216

SEQ ID NO: 496          moltype = AA  length = 216
FEATURE                 Location/Qualifiers
source                  1..216
                        mol_type = protein
                        organism = synthetic construct
                        note = Heterodimeric Fc Backbone 6 monomer 2 (+)
SEQUENCE: 496
APPVAGPSVF LFPPKPKDTL MISRTPEVTC VVVDVKHEDP EVKFNWYVDG VEVHNAKTKP    60
REEQYASTYR VVSVLTVLHQ DWLNGKEYKC KVSNKALPAP IEKTISKAKG QPREPQVYTL   120
PPSREQMTKN QVKLTCLVKG FYPSDIAVEW ESNGQPENNY KTTPPVLDSD GSFFLYSKLT   180
VDKSRWQQGN VFSCSVMHEA LHNHYTQKSL SLSPGK                             216

SEQ ID NO: 497          moltype = AA  length = 216
FEATURE                 Location/Qualifiers
source                  1..216
                        mol_type = protein
                        organism = synthetic construct
                        note = Heterodimeric Fc Backbone 7 monomer 1 (-)
SEQUENCE: 497
APPVAGPSVF LFPPKPKDTL MISRTPEVTC VVVDVKHEDP EVKFNWYVDG VEVHNAKTKP    60
REEEYSSTYR VVSVLTVLHQ DWLNGKEYKC KVSNKALPAP IEKTISKAKG QPREPQVYTL   120
PPSREEMTKN QVSLTCDVSG FYPSDIAVEW ESDGQPENNY KTTPPVLDSD GSFFLYSKLT   180
VDKSRWEQGD VFSCSVMHEA LHNHYTQKSL SLSPGK                             216

SEQ ID NO: 498          moltype = AA  length = 216
```

```
FEATURE                 Location/Qualifiers
source                  1..216
                        mol_type = protein
                        organism = synthetic construct
                        note = Heterodimeric Fc Backbone 7 monomer 2 (+)
SEQUENCE: 498
APPVAGPSVF LFPPKPKDTL MISRTPEVTC VVVDVKHEDP EVKFNWYVDG VEVHNAKTKP    60
REEQYSSTYR VVSVLTVLHQ DWLNGKEYKC KVSNKALPAP IEKTISKAKG QPREPQVYTL   120
PPSREQMTKN QVKLTCLVKG FYPSDIAVEW ESNGQPENNY KTTPPVLDSD GSFFLYSKLT   180
VDKSRWQQGN VFSCSVMHEA LHNHYTQKSL SLSPGK                             216

SEQ ID NO: 499          moltype = AA  length = 217
FEATURE                 Location/Qualifiers
source                  1..217
                        mol_type = protein
                        organism = synthetic construct
                        note = Heterodimeric Fc Backbone 8 monomer 1 (-)
SEQUENCE: 499
APEFLGGPSV FLFPPKPKDT LMISRTPEVT CVVVDVSQED PEVQFNWYVD GVEVHNAKTK    60
PREEEFNSTY RVVSVLTVLH QDWLNGKEYK CKVSNKGLPS SIEKTISKAK GQPREPQVYT   120
LPPSQEEMTK NQVSLTCDVS GFYPSDIAVE WESDGQPENN YKTTPPVLDS DGSFFLYSRL   180
TVDKSRWEEG DVFSCSVMHE ALHNHYTQKS LSLSLGK                            217

SEQ ID NO: 500          moltype = AA  length = 217
FEATURE                 Location/Qualifiers
source                  1..217
                        mol_type = protein
                        organism = synthetic construct
                        note = Heterodimeric Fc Backbone 8 monomer 2 (+)
SEQUENCE: 500
APEFLGGPSV FLFPPKPKDT LMISRTPEVT CVVVDVSQED PEVQFNWYVD GVEVHNAKTK    60
PREEQFNSTY RVVSVLTVLH QDWLNGKEYK CKVSNKGLPS SIEKTISKAK GQPREPQVYT   120
LPPSQEQMTK NQVKLTCLVK GFYPSDIAVE WESNGQPENN YKTTPPVLDS DGSFFLYSRL   180
TVDKSRWQEG NVFSCSVMHE ALHNHYTQKS LSLSLGK                            217

SEQ ID NO: 501          moltype = AA  length = 216
FEATURE                 Location/Qualifiers
source                  1..216
                        mol_type = protein
                        organism = synthetic construct
                        note = Heterodimeric Fc Backbone 9 monomer 1 (-)
SEQUENCE: 501
APPVAGPSVF LFPPKPKDTL MISRTPEVTC VVVDVSHEDP EVQFNWYVDG VEVHNAKTKP    60
REEEFNSTFR VVSVLTVVHQ DWLNGKEYKC KVSNKGLPAP IEKTISKTKG QPREPQVYTL   120
PPSREEMTKN QVSLTCDVSG FYPSDIAVEW ESDGQPENNY KTTPPMLDSD GSFFLYSKLT   180
VDKSRWEQGD VFSCSVMHEA LHNHYTQKSL SLSPGK                             216

SEQ ID NO: 502          moltype = AA  length = 216
FEATURE                 Location/Qualifiers
source                  1..216
                        mol_type = protein
                        organism = synthetic construct
                        note = Heterodimeric Fc Backbone 9 monomer 2 (+)
SEQUENCE: 502
APPVAGPSVF LFPPKPKDTL MISRTPEVTC VVVDVSHEDP EVQFNWYVDG VEVHNAKTKP    60
REEQFNSTFR VVSVLTVVHQ DWLNGKEYKC KVSNKGLPAP IEKTISKTKG QPREPQVYTL   120
PPSREQMTKN QVKLTCLVKG FYPSDIAVEW ESNGQPENNY KTTPPMLDSD GSFFLYSKLT   180
VDKSRWQQGN VFSCSVMHEA LHNHYTQKSL SLSPGK                             216

SEQ ID NO: 503          moltype = AA  length = 216
FEATURE                 Location/Qualifiers
source                  1..216
                        mol_type = protein
                        organism = synthetic construct
                        note = Heterodimeric Fc Backbone 10 monomer 1 (-)
SEQUENCE: 503
APPVAGPSVF LFPPKPKDTL MISRTPEVTC VVVDVKHEDP EVQFNWYVDG VEVHNAKTKP    60
REEEFNSTFR VVSVLTVVHQ DWLNGKEYKC KVSNKGLPAP IEKTISKTKG QPREPQVYTL   120
PPSREEMTKN QVSLTCDVSG FYPSDIAVEW ESDGQPENNY KTTPPMLDSD GSFFLYSKLT   180
VDKSRWEQGD VFSCSVMHEA LHNHYTQKSL SLSPGK                             216

SEQ ID NO: 504          moltype = AA  length = 216
FEATURE                 Location/Qualifiers
source                  1..216
                        mol_type = protein
                        organism = synthetic construct
                        note = Heterodimeric Fc Backbone 10 monomer 2 (+)
```

```
SEQUENCE: 504
APPVAGPSVF LFPPKPKDTL MISRTPEVTC VVVDVKHEDP EVQFNWYVDG VEVHNAKTKP    60
REEQFNSTFR VVSVLTVVHQ DWLNGKEYKC KVSNKGLPAP IEKTISKTKG QPREPQVYTL   120
PPSREQMTKN QVKLTCLVKG FYPSDIAVEW ESNGQPENNY KTTPPMLDSD GSFFLYSKLT   180
VDKSRWQQGN VFSCSVMHEA LHNHYTQKSL SLSPGK                            216

SEQ ID NO: 505          moltype = AA   length = 216
FEATURE                 Location/Qualifiers
source                  1..216
                        mol_type = protein
                        organism = synthetic construct
                        note = Heterodimeric Fc Backbone 11 monomer 1 (-)
SEQUENCE: 505
APPVAGPSVF LFPPKPKDTL MISRTPEVTC VVVDVKHEDP EVKFNWYVDG VEVHNAKTKP    60
REEEYNSTYR VVSVLTVLHQ DWLNGKEYKC KVSNKALPAP IEKTISKAKG QPREPQVYTL   120
PPSREEMTKN QVSLTCDVSG FYPSDIAVEW ESDGQPENNY KTTPPVLDSD GSFFLYSKLT   180
VDKSRWEQGD VFSCSVLHEA LHSHYTQKSL SLSPGK                            216

SEQ ID NO: 506          moltype = AA   length = 216
FEATURE                 Location/Qualifiers
source                  1..216
                        mol_type = protein
                        organism = synthetic construct
                        note = Heterodimeric Fc Backbone 11 monomer 2 (+)
SEQUENCE: 506
APPVAGPSVF LFPPKPKDTL MISRTPEVTC VVVDVKHEDP EVKFNWYVDG VEVHNAKTKP    60
REEQYNSTYR VVSVLTVLHQ DWLNGKEYKC KVSNKALPAP IEKTISKAKG QPREPQVYTL   120
PPSREQMTKN QVKLTCLVKG FYPSDIAVEW ESNGQPENNY KTTPPVLDSD GSFFLYSKLT   180
VDKSRWQQGN VFSCSVLHEA LHSHYTQKSL SLSPGK                            216

SEQ ID NO: 507          moltype = AA   length = 216
FEATURE                 Location/Qualifiers
source                  1..216
                        mol_type = protein
                        organism = synthetic construct
                        note = Heterodimeric Fc Backbone 12 monomer 1 (-)
SEQUENCE: 507
APPVAGPSVF LFPPKPKDTL MISRTPEVTC VVVDVKHEDP EVKFKWYVDG VEVHNAKTKP    60
REEQYNSTYR VVSVLTVLHQ DWLNGKEYKC KVSNKALPAP IEKTISKAKG QPREPQVYTL   120
PPSREQMTKN QVKLTCLVKG FYPSDIAVEW ESNGQPENNY KTTPPVLDSD GSFFLYSKLT   180
VDKSRWQQGN VFSCSVMHEA LHNHYTQKSL SLSPGK                            216

SEQ ID NO: 508          moltype = AA   length = 216
FEATURE                 Location/Qualifiers
source                  1..216
                        mol_type = protein
                        organism = synthetic construct
                        note = Heterodimeric Fc Backbone 12 monomer 2 (+)
SEQUENCE: 508
APPVAGPSVF LFPPKPKDTL MISRTPEVTC VVVDVKHEDP EVKFNWYVDG VEVHNAKTKP    60
REEEYNSTYR VVSVLTVLHQ DWLNGKEYKC KVSNKALPAP IEKTISKAKG QPREPQVYT   120
PPSREEMTKN QVSLTCDVSG FYPSDIAVEW ESDGQPENNY KTTPPVLDSD GSFFLYSKLT   180
VDKSRWEQGD VFSCSVMHEA LHNHYTQKSL SLSPGK                            216

SEQ ID NO: 509          moltype = AA   length = 217
FEATURE                 Location/Qualifiers
source                  1..217
                        mol_type = protein
                        organism = synthetic construct
                        note = Heterodimeric Fc Backbone 13 monomer 1
SEQUENCE: 509
APEAAGGPSV FLFPPKPKDT LMISRTPEVT CVVVSVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSREEMTK NQVSLWCLVK GFYPSDIAVE WESNGQPENN YKTTPPVLDS DGSFFLYSKL   180
TVDKSRWQQG NVFSCSVMHE ALHNHYTQKS LSLSPGK                           217

SEQ ID NO: 510          moltype = AA   length = 217
FEATURE                 Location/Qualifiers
source                  1..217
                        mol_type = protein
                        organism = synthetic construct
                        note = Heterodimeric Fc Backbone 13 monomer 2
SEQUENCE: 510
APEAAGGPSV FLFPPKPKDT LMISRTPEVT CVVVSVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSREEMTK NQVSLSCAVK GFYPSDIAVE WESNGQPENN YKTTPPVLDS DGSFFLVSKL   180
TVDKSRWQQG NVFSCSVMHE ALHNRFTQKS LSLSPGK                           217

SEQ ID NO: 511          moltype = AA   length = 217
```

```
FEATURE                 Location/Qualifiers
source                  1..217
                        mol_type = protein
                        organism = synthetic construct
                        note = Heterodimeric Fc Backbone 14 monomer 1
SEQUENCE: 511
APEAAGGPSV FLFPPKPKDT LYITREPEVT CVVVSVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSREEMTK NQVSLWCLVK GFYPSDIAVE WESNGQPENN YKTTPPVLDS DGSFFLYSKL   180
TVDKSRWQQG NVFSCSVMHE ALHNHYTQKS LSLSPGK                            217

SEQ ID NO: 512          moltype = AA   length = 217
FEATURE                 Location/Qualifiers
source                  1..217
                        mol_type = protein
                        organism = synthetic construct
                        note = Heterodimeric Fc Backbone 14 monomer 2
SEQUENCE: 512
APEAAGGPSV FLFPPKPKDT LYITREPEVT CVVVSVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSREEMTK NQVSLSCAVK GFYPSDIAVE WESNGQPENN YKTTPPVLDS DGSFFLVSKL   180
TVDKSRWQQG NVFSCSVMHE ALHNRFTQKS LSLSPGK                            217

SEQ ID NO: 513          moltype = AA   length = 216
FEATURE                 Location/Qualifiers
source                  1..216
                        mol_type = protein
                        organism = synthetic construct
                        note = Heterodimeric Fc Backbone 15 monomer 1
SEQUENCE: 513
APPVAGPSVF LFPPKPKDTL MISRTPEVTC VVVDVKHEDP EVKFNWYVDG VEVHNAKTKP    60
REEEYNSTYR VVSVLTVLHQ DWLNGKEYKC KVSNKALPAP IEKTISKAKG QPREPQVYTL   120
PPSRDELTKN QVSLTCDVSG FYPSDIAVEW ESDGQPENNY KTTPPVLDSD GSFFLYSKLT   180
VDKSRWEQGD VFSCSVLHEA LHSHYTQKSL SLSPGK                             216

SEQ ID NO: 514          moltype = AA   length = 216
FEATURE                 Location/Qualifiers
source                  1..216
                        mol_type = protein
                        organism = synthetic construct
                        note = Heterodimeric Fc Backbone 15 monomer 2
SEQUENCE: 514
APPVAGPSVF LFPPKPKDTL MISRTPEVTC VVVDVKHEDP EVKFNWYVDG VEVHNAKTKP    60
REEQYNSTYR VVSVLTVLHQ DWLNGKEYKC KVSNKALPAP IEKTISKAKG QPREPQVYTL   120
PPSRDQLTKN QVKLTCLVKG FYPSDIAVEW ESNGQPENNY KTTPPVLDSD GSFFLYSKLT   180
VDKSRWQQGN VFSCSVLHEA LHSHYTQKSL SLSPGK                             216

SEQ ID NO: 515          moltype = AA   length = 216
FEATURE                 Location/Qualifiers
source                  1..216
                        mol_type = protein
                        organism = synthetic construct
                        note = Heterodimeric Fc Backbone 16 monomer 1
SEQUENCE: 515
APPVAGPSVF LFPPKPKDTL MISRTPEVTC VVVDVKHEDP EVKFNWYVDG VEVHNAKTKP    60
REEEYNSTYR VVSVLTVLHQ DWLNGKEYKC KVSNKALPAP IEKTISKAKG QPREPQVYTL   120
PPSREEMTKN QVSLTCDVSG FYPSDIAVEW ESDGQPENNY KTTPPVLDSD GSFFLYSKLT   180
VDKSRWEQGD VFSCSVLHEA LHAHYTQKSL SLSPGK                             216

SEQ ID NO: 516          moltype = AA   length = 216
FEATURE                 Location/Qualifiers
source                  1..216
                        mol_type = protein
                        organism = synthetic construct
                        note = Heterodimeric Fc Backbone 16 monomer 2
SEQUENCE: 516
APPVAGPSVF LFPPKPKDTL MISRTPEVTC VVVDVKHEDP EVKFNWYVDG VEVHNAKTKP    60
REEQYNSTYR VVSVLTVLHQ DWLNGKEYKC KVSNKALPAP IEKTISKAKG QPREPQVYTL   120
PPSREQMTKN QVKLTCLVKG FYPSDIAVEW ESNGQPENNY KTTPPVLDSD GSFFLYSKLT   180
VDKSRWQQGN VFSCSVLHEA LHAHYTQKSL SLSPGK                             216

SEQ ID NO: 517          moltype = AA   length = 216
FEATURE                 Location/Qualifiers
source                  1..216
                        mol_type = protein
                        organism = synthetic construct
                        note = Heterodimeric Fc Backbone 17 monomer 1
```

```
SEQUENCE: 517
APPVAGPSVF LFPPKPKDTL MISRTPEVTC VVVDVKHEDP EVKFNWYVDG VEVHNAKTKP    60
REEEYNSTYR VVSVLTVLHQ DWLNGKEYKC KVSNKALPAP IEKTISKAKG QPREPQVYTL   120
PPSRDELTKN QVSLTCDVSG FYPSDIAVEW ESDGQPENNY KTTPPVLDSD GSFFLYSKLT   180
VDKSRWEQGD VFSCSVLHEA LHAHYTQKSL SLSPGK                             216

SEQ ID NO: 518           moltype = AA  length = 216
FEATURE                  Location/Qualifiers
source                   1..216
                         mol_type = protein
                         organism = synthetic construct
                         note = Heterodimeric Fc Backbone 17 monomer 2
SEQUENCE: 518
APPVAGPSVF LFPPKPKDTL MISRTPEVTC VVVDVKHEDP EVKFNWYVDG VEVHNAKTKP    60
REEQYNSTYR VVSVLTVLHQ DWLNGKEYKC KVSNKALPAP IEKTISKAKG QPREPQVYTL   120
PPSRDQLTKN QVKLTCLVKG FYPSDIAVEW ESNGQPENNY KTTPPVLDSD GSFFLYSKLT   180
VDKSRWQQGN VFSCSVLHEA LHAHYTQKSL SLSPGK                             216

SEQ ID NO: 519           moltype = AA  length = 216
FEATURE                  Location/Qualifiers
source                   1..216
                         mol_type = protein
                         organism = synthetic construct
                         note = 2 + 1 mAb-scFv Heterodimeric Fc Backbone monomer 1
SEQUENCE: 519
APPVAGPSVF LFPPKPKDTL MISRTPEVTC VVVDVKHEDP EVKFNWYVDG VEVHNAKTKP    60
REEEYNSTYR VVSVLTVLHQ DWLNGKEYKC KVSNKALPAP IEKTISKAKG QPREPQVYTL   120
PPSREEMTKN QVSLTCDVSG FYPSDIAVEW ESDGQPENNY KTTPPVLDSD GSFFLYSKLT   180
VDKSRWEQGD VFSCSVMHEA LHNHYTQKSL SLSPGK                             216

SEQ ID NO: 520           moltype = AA  length = 215
FEATURE                  Location/Qualifiers
source                   1..215
                         mol_type = protein
                         organism = synthetic construct
                         note = 2 + 1 mAb-scFv Heterodimeric Fc Backbone monomer 2
SEQUENCE: 520
APPVAGPSVF LFPPKPKDTL MISRTPEVTC VVVDVKHEDP EVKFNWYVDG VEVHNAKTKP    60
REEQYNSTYR VVSVLTVLHQ DWLNGKEYKC KVSNKALPAP IEKTISKAKG QPREPQVYTL   120
PPSREQMTKN QVKLTCLVKG FYPSDIAVEW ESNGQPENNY KTTPPVLDSD GSFFLYSKLT   180
VDKSRWQQGN VFSCSVMHEA LHNHYTQKSL SLSPG                              215

SEQ ID NO: 521           moltype = AA  length = 217
FEATURE                  Location/Qualifiers
source                   1..217
                         mol_type = protein
                         organism = synthetic construct
                         note = 2 + 1 mAb-scFv Heterodimeric Fc Backbone monomer 1
SEQUENCE: 521
APEAAGGPSV FLFPPKPKDT LMISRTPEVT CVVVSVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSREEMTK NQVSLWCLVK GFYPSDIAVE WESNGQPENN YKTTPPVLDS DGSFFLYSKL   180
TVDKSRWQQG NVFSCSVMHE ALHNYTQKS LSLSPGK                             217

SEQ ID NO: 522           moltype = AA  length = 216
FEATURE                  Location/Qualifiers
source                   1..216
                         mol_type = protein
                         organism = synthetic construct
                         note = 2 + 1 mAb-scFv Heterodimeric Fc Backbone monomer 2
SEQUENCE: 522
APEAAGGPSV FLFPPKPKDT LMISRTPEVT CVVVSVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSREEMTK NQVSLSCAVK GFYPSDIAVE WESNGQPENN YKTTPPVLDS DGSFFLVSKL   180
TVDKSRWQQG NVFSCSVMHE ALHNRFTQKS LSLSPG                             216

SEQ ID NO: 523           moltype = AA  length = 98
FEATURE                  Location/Qualifiers
source                   1..98
                         mol_type = protein
                         organism = synthetic construct
                         note = IgG1 CH1(+)
SEQUENCE: 523
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKV                           98

SEQ ID NO: 524           moltype = AA  length = 98
FEATURE                  Location/Qualifiers
source                   1..98
```

```
                        mol_type = protein
                        organism = synthetic construct
                        note = IgG1 CH1(-)
SEQUENCE: 524
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS DTKVDKKV                            98

SEQ ID NO: 525          moltype = AA  length = 98
FEATURE                 Location/Qualifiers
source                  1..98
                        mol_type = protein
                        organism = synthetic construct
                        note = IgG2 CH1(+)
SEQUENCE: 525
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTV                            98

SEQ ID NO: 526          moltype = AA  length = 98
FEATURE                 Location/Qualifiers
source                  1..98
                        mol_type = protein
                        organism = synthetic construct
                        note = IgG2 CH1(-)
SEQUENCE: 526
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS DTKVDKTV                            98

SEQ ID NO: 527          moltype = AA  length = 98
FEATURE                 Location/Qualifiers
source                  1..98
                        mol_type = protein
                        organism = synthetic construct
                        note = IgG4 CH1(+)
SEQUENCE: 527
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRV                            98

SEQ ID NO: 528          moltype = AA  length = 98
FEATURE                 Location/Qualifiers
source                  1..98
                        mol_type = protein
                        organism = synthetic construct
                        note = IgG4 CH1(-)
SEQUENCE: 528
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS DTKVDKRV                            98

SEQ ID NO: 529          moltype = AA  length = 15
FEATURE                 Location/Qualifiers
source                  1..15
                        mol_type = protein
                        organism = synthetic construct
                        note = IgG1 hinge
SEQUENCE: 529
EPKSCDKTHT CPPCP                                                     15

SEQ ID NO: 530          moltype = AA  length = 12
FEATURE                 Location/Qualifiers
source                  1..12
                        mol_type = protein
                        organism = synthetic construct
                        note = IgG2 hinge
SEQUENCE: 530
ERKCCVECPP CP                                                        12

SEQ ID NO: 531          moltype = AA  length = 12
FEATURE                 Location/Qualifiers
source                  1..12
                        mol_type = protein
                        organism = synthetic construct
                        note = IgG4 hinge
SEQUENCE: 531
ESKYGPPCPS CP                                                        12

SEQ ID NO: 532          moltype = AA  length = 107
FEATURE                 Location/Qualifiers
```

-continued

```
source                  1..107
                        mol_type = protein
                        organism = synthetic construct
                        note = Light Chain Constant Domain - Kappa
SEQUENCE: 532
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                  107

SEQ ID NO: 533          moltype = AA   length = 106
FEATURE                 Location/Qualifiers
source                  1..106
                        mol_type = protein
                        organism = synthetic construct
                        note = Light Chain Constant Domain - Lambda
SEQUENCE: 533
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                   106

SEQ ID NO: 534          moltype = AA   length = 450
FEATURE                 Location/Qualifiers
source                  1..450
                        mol_type = protein
                        organism = synthetic construct
                        note = XENP27181 Heavy Chain
SEQUENCE: 534
QVQLQESGPG LVKPSETLSL TCAVSGFSLT SYGVHWIRQP PGKGLEWLGV IWPGGGTNFN    60
SALMSRLTIS EDTSKNQVSL KLSSVTAADT AVYYCARDRA YGNYLYAMDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPPVAG    240
PSVFLFPPKP KDTLMISRTP EVTCVVVDVK HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                     450

SEQ ID NO: 535          moltype = AA   length = 218
FEATURE                 Location/Qualifiers
source                  1..218
                        mol_type = protein
                        organism = synthetic construct
                        note = XENP27181 Light Chain
SEQUENCE: 535
DIQMTQSPSS LSASVGDRVT ITCRASESVE YYVTSLMQWY QQKPGKAPKL LIYAASNVDS    60
GVPSRFSGSG SGTDFTLTIS SLQPEDIATY YCQQSRKVPF TFGGGTKVEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 536          moltype = AA   length = 446
FEATURE                 Location/Qualifiers
source                  1..446
                        mol_type = protein
                        organism = synthetic construct
                        note = XENP29154 Heavy Chain - TGN1412 HC
SEQUENCE: 536
QVQLVQSGAE VKKPGASVKV SCKASGYTFT SYYIHWVRQA PGQGLEWIGC IYPGNVNTNY    60
NEKFKDRATL TVDTSISTAY MELSRLRSDD TAVYFCTRSH YGLDWNFDVW GQGTTVTVSS    120
ASTKGPSVFP LAPCSRSTSE STAALGCLVK DYFPEPVTVS WNSGALTSGV HTFPAVLQSS    180
GLYSLSSVVT VPSSSLGTKT YTCNVDHKPS NTKVDKRVES KYGPPCPSCP APEFLGGPSV    240
FLFPPKPKDT LMISRTPEVT CVVVDVSQED PEVQFNWYVD GVEVHNAKTK PREEQFNSTY    300
RVVSVLTVLH QDWLNGKEYK CKVSNKGLPS SIEKTISKAK GQPREPQVYT LPPSQEEMTK    360
NQVSLTCLVK GFYPSDIAVE WESNGQPENN YKTTPPVLDS DGSFFLYSRL TVDKSRWQEG    420
NVFSCSVMHE ALHNHYTQKS LSLSLG                                         446

SEQ ID NO: 537          moltype = AA   length = 214
FEATURE                 Location/Qualifiers
source                  1..214
                        mol_type = protein
                        organism = synthetic construct
                        note = XENP29154 Light Chain - TGN1412 LC
SEQUENCE: 537
DIQMTQSPSS LSASVGDRVT ITCHASQNIY VWLNWYQQKP GKAPKLLIYK ASNLHTGVPS    60
RFSGSGSGTD FTLTISSLQP EDFATYYCQQ GQTYPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 538          moltype = AA   length = 449
FEATURE                 Location/Qualifiers
```

```
source                  1..449
                        mol_type = protein
                        organism = synthetic construct
                        note = XENP31600 Chain 1 -
                        D7[PSMA]_H0_IgG1_pI(-)_Isosteric_A_/PVA_/S267K/L368D/K370S
SEQUENCE: 538
QVQLQQSGAE LVEPGASVKL SCKASGYTFT YFDINWLRQR PEQGLEWIGG ISPGDGNTNY    60
NENFKGKATL TIDKSSTTAY IQLSRLTSED SAVYFCARDG NFPYYAMDSW GQGTSVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                   449

SEQ ID NO: 539          moltype = AA   length = 485
FEATURE                 Location/Qualifiers
source                  1..485
                        mol_type = protein
                        organism = synthetic construct
                        note = XENP31600 Chain 2 -
                        [CD3]_H1.30_L1.47_scFv(GKPGS)4_Fc(222)_IgG1_C220S/PVA_/S267
                        K/S364K/E357Q
SEQUENCE: 539
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVSHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                             485

SEQ ID NO: 540          moltype = AA   length = 218
FEATURE                 Location/Qualifiers
source                  1..218
                        mol_type = protein
                        organism = synthetic construct
                        note = XENP31600 Chain 3 - D7_L0 Light Chain
SEQUENCE: 540
DIELTQSPLS LPVILGDQAS ISCRSSQSLV HSNGNTYLHW FLQKPGQSPK LLIYTVSNRF    60
SGVPDRFSGS GSGTDFTLKI SRVEAEDLGV YFCSQSTHVP TFGGGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                         218

SEQ ID NO: 541          moltype = AA   length = 444
FEATURE                 Location/Qualifiers
source                  1..444
                        mol_type = protein
                        organism = synthetic construct
                        note = XENP32220 Chain 1 -
                        PSMA-H_H1_IgG1_pI(-)_Isosteric_A_/PVA_/S267K/L368D/K370S
SEQUENCE: 541
EVQLVQSGAE VKKPGASVKV SCKTSGYTFT EYTIHWVRQA PGQSLEWMGN INPNNGGTTY    60
NQKFQGRVTI TVDKSTSTAY MELSSLRSED TAVYYCAAGW NFDYWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSDTKVD KKVEPKSCDK THTCPPCPAP PVAGPSVFLF   240
PPKPKDTLMI SRTPEVTCVV VDVKHEDPEV KFNWYVDGVE VHNAKTKPRE EQYNSTYRVV   300
SVLTVLHQDW LNGKEYKCKV SNKALPAPIE KTISKAKGQP REPQVYTLPP SREEMTKNQV   360
SLTCDVSGFY PSDIAVEWES DGQPENNYKT TPPVLDSDGS FFLYSKLTVD KSRWEQGDVF   420
SCSVMHEALH NHYTQKSLSL SPGK                                        444

SEQ ID NO: 542          moltype = AA   length = 717
FEATURE                 Location/Qualifiers
source                  1..717
                        mol_type = protein
                        organism = synthetic construct
                        note = XENP32220 Chain 2 -
                        PSMA-H_H1_(G4S)_[CD3]_L1.47_H1.32_scFv(GKPGS)4_Fc(222)_IgG1
                        _C220S/PVA_/S267K/S364K/E357Q
SEQUENCE: 542
EVQLVQSGAE VKKPGASVKV SCKTSGYTFT EYTIHWVRQA PGQSLEWMGN INPNNGGTTY    60
NQKFQGRVTI TVDKSTSTAY MELSSLRSED TAVYYCAAGW NFDYWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCGG GGSGGGGSQA VVTQEPSLTV   240
SPGGTVTLTC GSSTGAVTTS NYANWVQQKP GKSPRGLIGG TNKRAPGVPA RFSGSLLGGK   300
AALTISGAQP EDEADYYCAL WYSNHWVFGG GTKLTVLGKP GSGKPGSGKP GSGKPGSEVQ   360
LVESGGGLVQ PGGSLRLSCA ASGFTFSTYA MNWVRQAPGK GLEWVGRIRS KANNYATYYA   420
```

```
DSVKGRFTIS RDDSKNTLYL QMNSLRAEDT AVYYCVRHGN FGDSYVSWFA YWGQGTLVTV   480
SSGGGGSGGG GSKTHTCPPC PAPPVAGPSV FLFPPKPKDT LMISRTPEVT CVVVDVKHED   540
PEVKFNWYVD GVEVHNAKTK PREEQYNSTY RVVSVLTVLH QDWLNGKEYK CKVSNKALPA   600
PIEKTISKAK GQPREPQVYT LPPSREQMTK NQVKLTCLVK GFYPSDIAVE WESNGQPENN   660
YKTTPPVLDS DGSFFLYSKL TVDKSRWQQG NVFSCSVMHE ALHNHYTQKS LSLSPGK     717

SEQ ID NO: 543              moltype = AA  length = 214
FEATURE                     Location/Qualifiers
source                      1..214
                            mol_type = protein
                            organism = synthetic construct
                            note = XENP32220 Chain 3 - PSMA-H_L1.24 Light Chain
SEQUENCE: 543
DIVMTQSPDS LAVSLGERAT LSCRASQDVG TAVDWYQQKP DQSPKLLIYY ASTRHTGVPD   60
RFTGSGSGTD FTLTISSLQA EDVAVYFCQQ YNSYPLTFGA GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 544              moltype = AA  length = 444
FEATURE                     Location/Qualifiers
source                      1..444
                            mol_type = protein
                            organism = synthetic construct
                            note = XENP33063 Chain 1 -
                            PSMA-H_H1_IgG1_pI(-)_Isosteric_A_/PVA_/S267K/L368D/K370S
SEQUENCE: 544
EVQLVQSGAE VKKPGASVKV SCKTSGYTFT EYTIHWVRQA PGQSLEWMGN INPNNGGTTY   60
NQKFQGRVTI TVDKSTSTAY MELSSLRSED TAVYYCAAGW NFDYWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSDTKVD KKVEPKSCDK THTCPPCPAP PVAGPSVFLF   240
PPKPKDTLMI SRTPEVTCVV VDVKHEDPEV KFNWYVDGVE VHNAKTKPRE EEYNSTYRVV   300
SVLTVLHQDW LNGKEYKCKV SNKALPAPIE KTISKAKGQP REPQVYTLPP SREEMTKNQV   360
SLTCDVSGFY PSDIAVEWES DGQPENNYKT TPPVLDSDGS FFLYSKLTVD KSRWEQGDVF   420
SCSVMHEALH NHYTQKSLSL SPGK                                         444

SEQ ID NO: 545              moltype = AA  length = 713
FEATURE                     Location/Qualifiers
source                      1..713
                            mol_type = protein
                            organism = synthetic construct
                            note = XENP33063 Chain 2 -
                            PSMA-H_H1_(G4S)_[CD3]_L1.47_H1.89_scFv(GKPGS)4_Fc(216)_IgG1
                            _C220S/PVA_/S267K/S364K/E357Q
SEQUENCE: 545
EVQLVQSGAE VKKPGASVKV SCKTSGYTFT EYTIHWVRQA PGQSLEWMGN INPNNGGTTY   60
NQKFQGRVTI TVDKSTSTAY MELSSLRSED TAVYYCAAGW NFDYWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCGG GGSGGGGSQA VVTQEPSLTV   240
SPGGTVTLTC GSSTGAVTTS NYANWVQQKP GKSPRGLIGG TNKRAPGVPA RFSGSLLGGK   300
AALTLISGAQP EDEADYYCAL WYSNHWVFGG GTKLTVLGKP GSGKPGSGKP GSGKPGSEVQ   360
LVESGGGLVQ PGGSLRLSCA ASGFTFSTYA MNWVRQAPGK GLEWVGRIRS KYNNYATYYA   420
DSVKGRFTIS RDDSKNTLYL QMNSLRAEDT AVYYCVRHGN FGDEYVSWFA YWGQGTLVTV   480
SSEPKSSDKT HTCPPCPAPP VAGPSVFLFP PKPKDTLMIS RTPEVTCVVV DVKHEDPEVK   540
FNWYVDGVEV HNAKTKPREE QYNSTYRVVS VLTVLHQDWL NGKEYKCKVS NKALPAPIEK   600
TISKAKGQPR EPQVYTLPPS REQMTKNQVK LTCLVKGFYP SDIAVEWESN GQPENNYKTT   660
PPVLDSDGSF FLYSKLTVDK SRWQQGNVFS CSVMHEALHN HYTQKSLSLS PGK          713

SEQ ID NO: 546              moltype = AA  length = 214
FEATURE                     Location/Qualifiers
source                      1..214
                            mol_type = protein
                            organism = synthetic construct
                            note = XENP33063 Chain 3 - PSMA-H_L1.58 Light Chain
SEQUENCE: 546
DIVMTQSPDS LAVSLGERAT LSCRASQDVG TAVDWYQQKP DQSPKLLIYW ASTRHTGVPD   60
RFTGSGSGTD FTLTISSLQA EDVAVYFCQQ YQSYPLTFGA GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 547              moltype = AA  length = 479
FEATURE                     Location/Qualifiers
source                      1..479
                            mol_type = protein
                            organism = synthetic construct
                            note = 1391 PSMA x CD3 Chain 1
SEQUENCE: 547
EIVLTQSPAT LSASPGERVT LSCSASSSVS YMNWYQQKPG QAPRRWIYDS SKLASGVPAR   60
FSGSGSGRDY TLTISSLEPE DFAVYYCQQW SRNPPTFGGG TKVEIKGGSE GKSSGSGSES   120
KSTGGSQVQL VQSGAEVKKP GSSVKVSCKA SGYTFTRSTM HWVKQAPGQG LEWIGYINPS   180
```

```
SAYTNYNQKF QGRVTLTADK STSTAYMELS SLRSEDTAVY YCASPQVHYD YAGFPYWGQG    240
TLVTVSSEPK SSDKTHTCPP CPAPEAAGGP SVFLFPPKPK DTLMISRTPE VTCVVVSVSH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREEM TKNQVSLWCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 548          moltype = AA  length = 450
FEATURE                 Location/Qualifiers
source                  1..450
                        mol_type = protein
                        organism = synthetic construct
                        note = 1391 PSMA x CD3 Chain 2
SEQUENCE: 548
EVQLVESGGG LVKPGGSLRL SCVASGFTFS FYSMNWVRQA PGKGLDWVSS ISSSGNYIYY     60
ADSVKGRFTI SRDNAKNSLH LHMNSLKAED TAMYFCARSY SGSYDAFDFW GQGTMVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPEAAGG    240
PSVFLFPPKP KDTLMISRTP EVTCVVVSVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLSC AVKGFYPSDI AVEWESNGQP ENNYKTTPPV LDSDGSFFLV SKLTVDKSRW    420
QQGNVFSCSV MHEALHNRFT QKSLSLSPGK                                    450

SEQ ID NO: 549          moltype = AA  length = 215
FEATURE                 Location/Qualifiers
source                  1..215
                        mol_type = protein
                        organism = synthetic construct
                        note = 1391 PSMA x CD3 Chain 3
SEQUENCE: 549
EIVMTQSPGT LSLSPGERAT LSCRASQSVS SSFLAWYQQK PGQAPRLLIS GASSRATGIP     60
DRFSVSGSGT DFTLTISRLE PEDFAVYYCQ QYGVSPWTFG QGTKVEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                              215

SEQ ID NO: 550          moltype = AA  length = 475
FEATURE                 Location/Qualifiers
source                  1..475
                        mol_type = protein
                        organism = synthetic construct
                        note = 1508 PSMA x CD3 Chain 1
SEQUENCE: 550
DIQMTQSPSS LSASVGDRVT ITCRARQSIG TAIHWYQQKP GKAPKLLIKY ASESISGVPS     60
RFSGSGSGTD FTLTISSLQP EDFATYYCQQ SGSWPYTFGQ GTKLEIKGGS EGKSSGSGSE    120
SKSTGGSEVQ LVESGGGLVK PGGSLRLSCA ASGFTFSRYN MNWVRQAPGK GLEWVSSIST    180
SSNYIYYADS VKGRFTFSRD NAKNSLDLQM SGLRAEDTAI YYCTRGWGPF DYWGQGTLVT    240
VSSEPKSSDK THTCPPCPAP EAAGGPSVFL FPPKPKDTLM ISRTPEVTCV VVSVSHEDPE    300
VKFNWYVDGV EVHNAKTKPR EEQYNSTYRV VSVLTVLHQD WLNGKEYKCK VSNKALPAPI    360
EKTISKAKGQ PREPQVYTLP PSREEMTKNQ VSLWCLVKGF YPSDIAVEWE SNGQPENNYK    420
TTPPVLDSDG SFFLYSKLTV DKSRWQQGNV FSCSVMHEAL HNHYTQKSLS LSPGK         475

SEQ ID NO: 551          moltype = AA  length = 451
FEATURE                 Location/Qualifiers
source                  1..451
                        mol_type = protein
                        organism = synthetic construct
                        note = 1508 PSMA x CD3 Chain 2
SEQUENCE: 551
EVQLVESGGG LVQPGGSLRL SCAASGFTFS SYAMSWVRQA PGKGLEWVSA ISGGIGSTYY     60
ADSVKGRFTI SRDNSKNTLW LQMNSLRAED TAVYYCAKDA VGATPYYFDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPEAAG    240
GPSVFLFPPK PKDTLMISRT PEVTCVVVSV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRE    360
EMTKNQVSLS CAVKGFYPSD IAVEWESNGQ PENNYKTTPP VLDSDGSFFL VSKLTVDKSR    420
WQQGNVFSCS VMHEALHNRF TQKSLSLSPG K                                  451

SEQ ID NO: 552          moltype = AA  length = 216
FEATURE                 Location/Qualifiers
source                  1..216
                        mol_type = protein
                        organism = synthetic construct
                        note = 1508 PSMA x CD3 Chain 3
SEQUENCE: 552
QSVLTQPPSV SAAPGQKVTI SCSGSSSNIG INYVSWYQQL PGTAPKLLIY DNNKRPSGIP     60
DRFSGSKSGT SATLGITGLQ TGDEADYYCG TWDSSLSAVV FGGGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                             216

SEQ ID NO: 553          moltype = AA  length = 449
```

```
FEATURE                  Location/Qualifiers
source                   1..449
                         mol_type = protein
                         organism = synthetic construct
                         note = XENP37900 Chain 1 -
                             D7[PSMA]_H0_IgG1_pI(-)_Isosteric_A_/PVA_/S267K/L368D/K370S
SEQUENCE: 553
QVQLQQSGAE LVEPGASVKL SCKASGYTFT YFDINWLRQR PEQGLEWIGG ISPGDGNTNY    60
NENFKGKATL TIDKSSTTAY IQLSRLTSED SAVYFCARDG NFPYYAMDSW GQGTSVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                    449

SEQ ID NO: 554           moltype = AA   length = 479
FEATURE                  Location/Qualifiers
source                   1..479
                         mol_type = protein
                         organism = synthetic construct
                         note = XENP37900 Chain 2 -
                             1A7[CD28]_H1.14_L1_scFv(GKPGS)4_Fc(216)_IgG1_C220S/PVA_/S26
                             7K/S364K/E357Q
SEQUENCE: 554
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 555           moltype = AA   length = 218
FEATURE                  Location/Qualifiers
source                   1..218
                         mol_type = protein
                         organism = synthetic construct
                         note = XENP37900 Chain 3 - D7[PSMA]_L0 Light Chain
SEQUENCE: 555
DIELTQSPLS LPVILGDQAS ISCRSSQSLV HSNGNTYLHW FLQKPGQSPK LLIYTVSNRF    60
SGVPDRFSGS GSGTDFTLKI SRVEAEDLGV YFCSQSTHVP TFGGGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                          218

SEQ ID NO: 556           moltype = AA   length = 449
FEATURE                  Location/Qualifiers
source                   1..449
                         mol_type = protein
                         organism = synthetic construct
                         note = XENP37901 Chain 1 -
                             D7[PSMA]_H0_IgG1_pI(-)_Isosteric_A_/PVA_/S267K/L368D/K370S
SEQUENCE: 556
QVQLQQSGAE LVEPGASVKL SCKASGYTFT YFDINWLRQR PEQGLEWIGG ISPGDGNTNY    60
NENFKGKATL TIDKSSTTAY IQLSRLTSED SAVYFCARDG NFPYYAMDSW GQGTSVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                    449

SEQ ID NO: 557           moltype = AA   length = 479
FEATURE                  Location/Qualifiers
source                   1..479
                         mol_type = protein
                         organism = synthetic construct
                         note = XENP37901 Chain 2 -
                             1A7[CD28]_H1.14_L1.71_scFv(GKPGS)4_Fc(216)_IgG1_C220S/PVA_/
                             S267K/S364K/E357Q
SEQUENCE: 557
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
```

```
EDPEVKFNWY VDGVEVHNAK TKPREEQYNS TYRVVSVLTV LHQDWLNGKE YKCKVSNKAL  360
PAPIEKTISK AKGQPREPQV YTLPPSREQM TKNQVKLTCL VKGFYPSDIA VEWESNGQPE  420
NNYKTTPPVL DSDGSFFLYS KLTVDKSRWQ QGNVFSCSVM HEALHNHYTQ KSLSLSPGK   479

SEQ ID NO: 558          moltype = AA   length = 218
FEATURE                 Location/Qualifiers
source                  1..218
                        mol_type = protein
                        organism = synthetic construct
                        note = XENP37901 Chain 3 - D7[PSMA]_L0 Light Chain
SEQUENCE: 558
DIELTQSPLS LPVILGDQAS ISCRSSQSLV HSNGNTYLHW FLQKPGQSPK LLIYTVSNRF  60
SGVPDRFSGS GSGTDFTLKI SRVEAEDLGV YFCSQSTHVP TFGGGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 559          moltype = AA   length = 444
FEATURE                 Location/Qualifiers
source                  1..444
                        mol_type = protein
                        organism = synthetic construct
                        note = XENP37902 Chain 1 -
                        PSMA-H[PSMA]_H1_IgG1_pI(-)_Isosteric_A_/PVA_/S267K/L368D/K3
                        70S
SEQUENCE: 559
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSDTKVD KKVEPKSCDK THTCPPCPAP PVAGPSVFLF  240
PPKPKDTLMI SRTPEVTCVV VDVKHEDPEV KFNWYVDGVE VHNAKTKPRE EEYNSTYRVV  300
SVLTVLHQDW LNGKEYKCKV SNKALPAPIE KTISKAKGQP REPQVYTLPP SREEMTKNQV  360
SLTCDVSGFY PSDIAVEWES DGQPENNYKT TPPVLDSDGS FFLYSKLTVD KSRWEQGDVF  420
SCSVMHEALH NHYTQKSLSL SPGK                                         444

SEQ ID NO: 560          moltype = AA   length = 214
FEATURE                 Location/Qualifiers
source                  1..214
                        mol_type = protein
                        organism = synthetic construct
                        note = XENP37902 Chain 3 - PSMA-H[PSMA]_L1 Light Chain
SEQUENCE: 560
DIVMTQSPDS LAVSLGERAT LSCRASQDVG TAVDWYQQKP DQSPKLLIYW ASTRHTGVPD  60
RFTGSGSGTD FTLTISSLQA EDVAVYFCQQ YNSYPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 561          moltype = AA   length = 444
FEATURE                 Location/Qualifiers
source                  1..444
                        mol_type = protein
                        organism = synthetic construct
                        note = XENP37903 Chain 1 -
                        PSMA-H[PSMA]_H1_IgG1_pI(-)_Isosteric_A_/PVA_/S267K/L368D/K3
                        70S
SEQUENCE: 561
EVQLVQSGAE VKKPGASVKV SCKTSGYTFT EYTIHWVRQA PGQSLEWMGN INPNNGGTTY  60
NQKFQGRVTI TVDKSTSTAY MELSSLRSED TAVYYCAAGW NFDYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSDTKVD KKVEPKSCDK THTCPPCPAP PVAGPSVFLF  240
PPKPKDTLMI SRTPEVTCVV VDVKHEDPEV KFNWYVDGVE VHNAKTKPRE EEYNSTYRVV  300
SVLTVLHQDW LNGKEYKCKV SNKALPAPIE KTISKAKGQP REPQVYTLPP SREEMTKNQV  360
SLTCDVSGFY PSDIAVEWES DGQPENNYKT TPPVLDSDGS FFLYSKLTVD KSRWEQGDVF  420
SCSVMHEALH NHYTQKSLSL SPGK                                         444

SEQ ID NO: 562          moltype = AA   length = 214
FEATURE                 Location/Qualifiers
source                  1..214
                        mol_type = protein
                        organism = synthetic construct
                        note = XENP37903 Chain 3 - PSMA-H[PSMA]_L1 Light Chain
SEQUENCE: 562
DIVMTQSPDS LAVSLGERAT LSCRASQDVG TAVDWYQQKP DQSPKLLIYW ASTRHTGVPD  60
RFTGSGSGTD FTLTISSLQA EDVAVYFCQQ YNSYPLTFGA GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 563          moltype = AA   length = 449
FEATURE                 Location/Qualifiers
```

```
source                  1..449
                        mol_type = protein
                        organism = synthetic construct
                        note = XENP38931 Chain 1 -
                            P72_A10[PSMA]_H0_IgG1_pI(-)_Isosteric_A_/PVA_/S267K/L368D/K
                            370S
SEQUENCE: 563
QVQLVESGGG VVQPGRSLRL SCAASGFTFS SYNMNWVRQA PGKGLEWVAI IYYDGSNKYY    60
ADSVKGRFTI SRDISKNTLY LQMNSLRAED TAVYYCARER GRDYYGMDVW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                    449

SEQ ID NO: 564          moltype = AA   length = 479
FEATURE                 Location/Qualifiers
source                  1..479
                        mol_type = protein
                        organism = synthetic construct
                        note = XENP38931 Chain 2 -
                            1A7[CD28]_H1_L1.71_scFv(GKPGS)4_Fc(216)_IgG1_C220S/PVA_/S26
                            7K/S364K/E357Q
SEQUENCE: 564
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK   479

SEQ ID NO: 565          moltype = AA   length = 213
FEATURE                 Location/Qualifiers
source                  1..213
                        mol_type = protein
                        organism = synthetic construct
                        note = XENP38931 Chain 3 - P72_A10[PSMA]_L0 Light Chain
SEQUENCE: 565
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                              213

SEQ ID NO: 566          moltype = AA   length = 455
FEATURE                 Location/Qualifiers
source                  1..455
                        mol_type = protein
                        organism = synthetic construct
                        note = XENP38932 Chain 1 -
                            P72_D01[PSMA]_H0_IgG1_pI(-)_Isosteric_A_/PVA_/S267K/L368D/K
                            370S
SEQUENCE: 566
EVQLVESGGD LVQPGGSLRL SCAASGFTFN NYNMNWVRQA PGKGLEWVSH ISTSSSNKYY    60
ADSVKGRFSI SRDIAKNSMY LQMNSLRDED TAVYYCARDG VGADYGDYYY YGMDVWGQGT   120
TVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSDTKV DKKVEPKSCD KTHTCPPCPA   240
PPVAGPSVFL FPPKPKDTLM ISRTPEVTCV VVDVKHEDPE VKFNWYVDGV EVHNAKTKPR   300
EEEYNSTYRV VSVLTVLHQD WLNGKEYKCK VSNKALPAPI EKTISKAKGQ PREPQVYTLP   360
PSREEMTKNQ VSLTCDVSGF YPSDIAVEWE SDGQPENNYK TTPPVLDSDG SFFLYSKLTV   420
DKSRWEQGDV FSCSVMHEAL HNHYTQKSLS LSPGK                            455

SEQ ID NO: 567          moltype = AA   length = 479
FEATURE                 Location/Qualifiers
source                  1..479
                        mol_type = protein
                        organism = synthetic construct
                        note = XENP38932 Chain 2 -
                            1A7[CD28]_H1_L1.71_scFv(GKPGS)4_Fc(216)_IgG1_C220S/PVA_/S26
                            7K/S364K/E357Q
SEQUENCE: 567
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
```

PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 568          moltype = AA  length = 216
FEATURE                 Location/Qualifiers
source                  1..216
                        mol_type = protein
                        organism = synthetic construct
                        note = XENP38932 Chain 3 - P72_D01[PSMA]_L0 Light Chain
SEQUENCE: 568
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSYTYV FGTGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 569          moltype = AA  length = 454
FEATURE                 Location/Qualifiers
source                  1..454
                        mol_type = protein
                        organism = synthetic construct
                        note = XENP38933 Chain 1 -
                        P72_E07[PSMA]_H0_IgG1_pI(-)_Isosteric_A_/PVA_/S267K/L368D/K
                        370S
SEQUENCE: 569
EVQLVESGGG VVQPGRSLRL SCAASGFTFI TYGMHWVRQA PGKGLEWVAV VSFDESNKYY    60
ADSVKGRFTI SRDNSKNTLY LQMNSLRAED TAVYYCARAL RDGNNWDYFN GMDVWGQGTT    120
VTVSSASTKG PSVFPLAPSS KSTSGGTAAL GCLVKDYFPE PVTVSWNSGA LTSGVHTFPA    180
VLQSSGLYSL SSVVTVPSSS LGTQTYICNV NHKPSDTKVD KKVEPKSCDK THTCPPCPAP    240
PVAGPSVFLF PPKPKDTLMI SRTPEVTCVV VDVKHEDPEV KFNWYVDGVE VHNAKTKPRE    300
EEYNSTYRVV SVLTVLHQDW LNGKEYKCKV SNKALPAPIE KTISKAKGQP REPQVYTLPP    360
SREEMTKNQV SLTCDVSGFY PSDIAVEWES DGQPENNYKT TPPVLDSDGS FFLYSKLTVD    420
KSRWEQGDVF SCSVMHEALH NHYTQKSLSL SPGK                                454

SEQ ID NO: 570          moltype = AA  length = 479
FEATURE                 Location/Qualifiers
source                  1..479
                        mol_type = protein
                        organism = synthetic construct
                        note = XENP38933 Chain 2 -
                        1A7[CD28]_H1_L1.71_scFv(GKPGS)4_Fc(216)_IgG1_C220S/PVA_/S26
                        7K/S364K/E357Q
SEQUENCE: 570
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 571          moltype = AA  length = 216
FEATURE                 Location/Qualifiers
source                  1..216
                        mol_type = protein
                        organism = synthetic construct
                        note = XENP38933 Chain 3 - P72_E07[PSMA]_L0 Light Chain
SEQUENCE: 571
QSVLTQPPSA SGTPGQGVTI SCSGSSSNIG SNTVNWFQQL PGTAPKLLIY SDNQRPSGVP    60
DRFSGSKSGT SASLAISGLQ SEDEADYYCA AWDDSLNGYV FGTGTKVTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 572          moltype = AA  length = 447
FEATURE                 Location/Qualifiers
source                  1..447
                        mol_type = protein
                        organism = synthetic construct
                        note = XENP38934 Chain 1 -
                        P70_F02[PSMA]_H0_IgG1_pI(-)_Isosteric_A_/PVA_/S267K/L368D/K
                        370S
SEQUENCE: 572
EVQLLESGPG LVKPSETLSL TCTVSGGSII SYYWSWIRQP AGKGLEWIGR IYSSGSTNYN    60
PSLKSRVTMS VDTSKNQFSL KLSSVTAADT AVYYCAKVGV WPGAFDIWGQ GTMVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSDT KVDKKVEPKS CDKTHTCPPC PAPPVAGPSV    240
FLFPPKPKDT LMISRTPEVT CVVVDVKHED PEVKFNWYVD GVEVHNAKTK PREEEYNSTY    300

```
RVVSVLTVLH  QDWLNGKEYK  CKVSNKALPA  PIEKTISKAK  GQPREPQVYT  LPPSREEMTK   360
NQVSLTCDVS  GFYPSDIAVE  WESDGQPENN  YKTTPPVLDS  DGSFFLYSKL  TVDKSRWEQG   420
DVFSCSVMHE  ALHNHYTQKS  LSLSPGK                                          447

SEQ ID NO: 573              moltype = AA  length = 479
FEATURE                     Location/Qualifiers
source                      1..479
                            mol_type = protein
                            organism = synthetic construct
                            note = XENP38934 Chain 2 -
                            1A7[CD28]_H1_L1.71_scFv(GKPGS)4_Fc(216)_IgG1_C220S/PVA_/S26
                            7K/S364K/E357Q
SEQUENCE: 573
EVQLLESGGG  LVQPGGSLRL  SCAASGFTFS  SYAMSWVRQA  PGKGLEWVST  ISGSGDSTYY    60
ADSVKGRFTI  SRDNSKNTLY  LQMNSLRAED  TAVYYCAKSG  PGLRQVGFDY  WGQGTLVTVS   120
SGKPGSGKPG  SGKPGSGKPG  SDIQMTQSPS  SLSASVGDRV  TITCRASQSI  SSYLNWYQQK   180
PGKAPKLLIY  AASSLQSGVP  SRFSGSGSGT  DFTLTISSLQ  PEDFATYYCQ  QVYSTPFTFG   240
QGTKLEIKEP  KSSDKTHTCP  PCPAPPVAGP  SVFLFPPKPK  DTLMISRTPE  VTCVVVDVKH   300
EDPEVKFNWY  VDGVEVHNAK  TKPREEQYNS  TYRVVSVLTV  LHQDWLNGKE  YKCKVSNKAL   360
PAPIEKTISK  AKGQPREPQV  YTLPPSREQM  TKNQVKLTCL  VKGFYPSDIA  VEWESNGQPE   420
NNYKTTPPVL  DSDGSFFLYS  KLTVDKSRWQ  QGNVFSCSVM  HEALHNHYTQ  KSLSLSPGK    479

SEQ ID NO: 574              moltype = AA  length = 216
FEATURE                     Location/Qualifiers
source                      1..216
                            mol_type = protein
                            organism = synthetic construct
                            note = XENP38934 Chain 3 - P70_F02[PSMA]_L0 Light Chain
SEQUENCE: 574
QSVLTQPPSA  SGTPGQRVTI  SCSGSSSNIG  SNTVNWYQQL  PGTAPKLLIY  SSNQRPSGVP    60
DRFSGSKSGT  SASLAISGLQ  SEDEADYYCA  AWDDSLNGVV  FGGGTKLTVL  GQPKAAPSVT   120
LFPPSSEELQ  ANKATLVCLI  SDFYPGAVTV  AWKADSSPVK  AGVETTTPSK  QSNNKYAASS   180
YLSLTPEQWK  SHRSYSCQVT  HEGSTVEKTV  APTECS                               216

SEQ ID NO: 575              moltype = AA  length = 451
FEATURE                     Location/Qualifiers
source                      1..451
                            mol_type = protein
                            organism = synthetic construct
                            note = XENP38935 Chain 1 -
                            P72_A11[PSMA]_H0_IgG1_pI(-)_Isosteric_A_/PVA_/S267K/L368D/K
                            370S
SEQUENCE: 575
QVQLQESGGD  VVQPGRSLRL  SCAASGFSFS  GYGLHWVRQA  PGRGLEWVTL  ISYDGSNKYY    60
ADSVKGRFTI  SRDNSKNTLY  LQMNSLRAED  TAVYYCAKTT  VSDPYYYGMD  VWGQGTTVTV   120
SSASTKGPSV  FPLAPSSKST  SGGTAALGCL  VKDYFPEPVT  VSWNSGALTS  GVHTFPAVLQ   180
SSGLYSLSSV  VTVPSSSLGT  QTYICNVNHK  PSDTKVDKKV  EPKSCDKTHT  CPPCPAPPVA   240
GPSVFLFPPK  PKDTLMISRT  PEVTCVVVDV  KHEDPEVKFN  WYVDGVEVHN  AKTKPREEEY   300
NSTYRVVSVL  TVLHQDWLNG  KEYKCKVSNK  ALPAPIEKTI  SKAKGQPREP  QVYTLPPSRE   360
EMTKNQVSLT  CDVSGFYPSD  IAVEWESDGQ  PENNYKTTPP  VLDSDGSFFL  YSKLTVDKSR   420
WEQGDVFSCS  VMHEALHNHY  TQKSLSLSPG  K                                    451

SEQ ID NO: 576              moltype = AA  length = 479
FEATURE                     Location/Qualifiers
source                      1..479
                            mol_type = protein
                            organism = synthetic construct
                            note = XENP38935 Chain 2 -
                            1A7[CD28]_H1_L1.71_scFv(GKPGS)4_Fc(216)_IgG1_C220S/PVA_/S26
                            7K/S364K/E357Q
SEQUENCE: 576
EVQLLESGGG  LVQPGGSLRL  SCAASGFTFS  SYAMSWVRQA  PGKGLEWVST  ISGSGDSTYY    60
ADSVKGRFTI  SRDNSKNTLY  LQMNSLRAED  TAVYYCAKSG  PGLRQVGFDY  WGQGTLVTVS   120
SGKPGSGKPG  SGKPGSGKPG  SDIQMTQSPS  SLSASVGDRV  TITCRASQSI  SSYLNWYQQK   180
PGKAPKLLIY  AASSLQSGVP  SRFSGSGSGT  DFTLTISSLQ  PEDFATYYCQ  QVYSTPFTFG   240
QGTKLEIKEP  KSSDKTHTCP  PCPAPPVAGP  SVFLFPPKPK  DTLMISRTPE  VTCVVVDVKH   300
EDPEVKFNWY  VDGVEVHNAK  TKPREEQYNS  TYRVVSVLTV  LHQDWLNGKE  YKCKVSNKAL   360
PAPIEKTISK  AKGQPREPQV  YTLPPSREQM  TKNQVKLTCL  VKGFYPSDIA  VEWESNGQPE   420
NNYKTTPPVL  DSDGSFFLYS  KLTVDKSRWQ  QGNVFSCSVM  HEALHNHYTQ  KSLSLSPGK    479

SEQ ID NO: 577              moltype = AA  length = 214
FEATURE                     Location/Qualifiers
source                      1..214
                            mol_type = protein
                            organism = synthetic construct
                            note = XENP38935 Chain 3 - P72_A11[PSMA]_L0 Light Chain
SEQUENCE: 577
SYELTQPPSV  SVAPGQTARI  TCGGNNIGSK  SVHWYQQKPG  QAPVLVVYDD  SDRPSGIPER    60
FSGTNSGNTA  TLTISRAEAG  DEADYYCQVW  DSSSDHVVFG  GGTKLTVLGQ  PKAAPSVTLF   120
```

```
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECS                                214

SEQ ID NO: 578          moltype = AA  length = 449
FEATURE                 Location/Qualifiers
source                  1..449
                        mol_type = protein
                        organism = synthetic construct
                        note = XENP38936 Chain 1 -
                          P72_A10V2[PSMA]_H0_IgG1_pI(-)_Isosteric_A_/PVA_/S267K/L368D
                          /K370S
SEQUENCE: 578
QVQLVESGGG VVQPGRSLRL SCAASGFTFS SYNMNWVRQA PGKGLEWVAI IYYDESNKYY     60
ADSVKGRFTI SRDISKNTLY LQMNSLRAED TAVYYCARER GRDYYGMDVW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS DTKVDKKVEP KSCDKTHTCP PCPAPPVAGP    240
SVFLFPPKPK DTLMISRTPE VTCVVVDVKH EDPEVKFNWY VDGVEVHNAK TKPREEEYNS    300
TYRVVSVLTV LHQDWLNGKE YKCKVSNKAL PAPIEKTISK AKGQPREPQV YTLPPSREEM    360
TKNQVSLTCD VSGFYPSDIA VEWESDGQPE NNYKTTPPVL DSDGSFFLYS KLTVDKSRWE    420
QGDVFSCSVM HEALHNHYTQ KSLSLSPGK                                      449

SEQ ID NO: 579          moltype = AA  length = 479
FEATURE                 Location/Qualifiers
source                  1..479
                        mol_type = protein
                        organism = synthetic construct
                        note = XENP38936 Chain 2 -
                          1A7[CD28]_H1_L1.71_scFv(GKPGS)4_Fc(216)_IgG1_C220S/PVA_/S26
                          7K/S364K/E357Q
SEQUENCE: 579
EVQLLESGGG LVQPGGSLRL SCAASGFTFS SYAMSWVRQA PGKGLEWVST ISGSGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 580          moltype = AA  length = 213
FEATURE                 Location/Qualifiers
source                  1..213
                        mol_type = protein
                        organism = synthetic construct
                        note = XENP38936 Chain 3 - P72_A10V2[PSMA]_L0 Light Chain
SEQUENCE: 580
SYELMQPPSV SVSPGQTARI TCSGDALPKQ YAYWYQQKPG QAPVLVIYKD SERPSGIPVR     60
FSGSSSGTTV TLTITGVQAE DEADYYCQSA DSSGTYVFGT GTKVTVLGQP KAAPSVTLFP    120
PSSEELQANK ATLVCLISDF YPGAVTVAWK ADSSPVKAGV ETTTPSKQSN NKYAASSYLS    180
LTPEQWKSHR SYSCQVTHEG STVEKTVAPT ECS                                 213

SEQ ID NO: 581          moltype = AA  length = 455
FEATURE                 Location/Qualifiers
source                  1..455
                        mol_type = protein
                        organism = synthetic construct
                        note = XENP38937 Chain 1 -
                          P72_D01V2[PSMA]_H0_IgG1_pI(-)_Isosteric_A_/PVA_/S267K/L368D
                          /K370S
SEQUENCE: 581
EVQLVESGGD LVQPGGSLRL SCAASGFTFN NYNMNWVRQA PGKGLEWVSH ISTSSSNKYY     60
ADSVKGRFSI SRDIAKNSMY LQMNSLRDED TAVYYCAREG VGADYGDYYY YGMDVWGQGT    120
TVTVSSASTK GPSVFPLAPS SKSTSGGTAA LGCLVKDYFP EPVTVSWNSG ALTSGVHTFP    180
AVLQSSGLYS LSSVVTVPSS SLGTQTYICN VNHKPSDTKV DKVEPKSCD KTHTCPPCPA     240
PPVAGPSVFL FPPKPKDTLM ISRTPEVTCV VVDVKHEDPE VKFNWYVDGV EVHNAKTKPR    300
EEEYNSTYRV VSVLTVLHQD WLNGKEYKCK VSNKALPAPI EKTISKAKGQ PREPQVYTLP    360
PSREEMTKNQ VSLTCDVSGF YPSDIAVEWE SDGQPENNYK TTPPVLDSDG SFFLYSKLTV    420
DKSRWEQGDV FSCSVMHEAL HNHYTQKSLS LSPGK                               455

SEQ ID NO: 582          moltype = AA  length = 479
FEATURE                 Location/Qualifiers
source                  1..479
                        mol_type = protein
                        organism = synthetic construct
                        note = XENP38937 Chain 2 -
                          1A7[CD28]_H1_L1.71_scFv(GKPGS)4_Fc(216)_IgG1_C220S/PVA_/S26
                          7K/S364K/E357Q
```

```
SEQUENCE: 582
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 583          moltype = AA  length = 216
FEATURE                 Location/Qualifiers
source                  1..216
                        mol_type = protein
                        organism = synthetic construct
                        note = XENP38937 Chain 3 - P72_D01V2[PSMA]_L0 Light Chain
SEQUENCE: 583
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSYTYV FGTGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 584          moltype = AA  length = 451
FEATURE                 Location/Qualifiers
source                  1..451
                        mol_type = protein
                        organism = synthetic construct
                        note = XENP38938 Chain 1 -
                        P72_F07[PSMA]_H0_IgG1_pI(-)_Isosteric_A_/PVA_/S267K/L368D/K
                        370S
SEQUENCE: 584
EVQLVESGGG VVQPGRSLRL SCAASGFTFS SYGMNWVRQA PGKGLEWVAV TSYDGSNKYY    60
ADSVKGRFTI SRDISKNTLY LQMSSLRAED TAVYYCARDP YSSSWNGAFD IWGPGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSDTKVDKKV EPKSCDKTHT CPPCPAPPVA   240
GPSVFLFPPK PKDTLMISRT PEVTCVVVDV KHEDPEVKFN WYVDGVEVHN AKTKPREEEY   300
NSTYRVVSVL TVLHQDWLNG KEYKCKVSNK ALPAPIEKTI SKAKGQPREP QVYTLPPSRE   360
EMTKNQVSLT CDVSGFYPSD IAVEWESDGQ PENNYKTTPP VLDSDGSFFL YSKLTVDKSR   420
WEQGDVFSCS VMHEALHNHY TQKSLSLSPG K                                 451

SEQ ID NO: 585          moltype = AA  length = 479
FEATURE                 Location/Qualifiers
source                  1..479
                        mol_type = protein
                        organism = synthetic construct
                        note = XENP38938 Chain 2 -
                        1A7[CD28]_H1_L1.71_scFv(GKPGS)4_Fc(216)_IgG1_C220S/PVA_/S26
                        7K/S364K/E357Q
SEQUENCE: 585
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 586          moltype = AA  length = 214
FEATURE                 Location/Qualifiers
source                  1..214
                        mol_type = protein
                        organism = synthetic construct
                        note = XENP38938 Chain 3 - P72_F07[PSMA]_L0 Light Chain
SEQUENCE: 586
SYELTQPPSV SVAPGQTARI TCGGNNIGSK SVHWYQQKPG QAPVLVVYDD SDRPSGIPER    60
FSGSNSGNTA TLTISRVEAG DEADYYCQVW DSSTDHVVPG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                              214

SEQ ID NO: 587          moltype = AA  length = 453
FEATURE                 Location/Qualifiers
source                  1..453
                        mol_type = protein
                        organism = synthetic construct
                        note = XENP38939 Chain 1 -
                        P72_G02[PSMA]_H0_IgG1_pI(-)_Isosteric_A_/PVA_/S267K/L368D/K
                        370S
```

-continued

```
SEQUENCE: 587
EVQLVESGGG VVQPGRSLRL SCAASGFSFS GYGMHWVRQA PGKGLEWVAV ISYDGSNKYY    60
ADSVKGRFTI SRDNSKNTLY LQMNSLRVED TAVYYCARDR IWGSRGYYYG MDVWGQGTTV   120
TVSSASTKGP SVFPLAPSSK STSGGTAALG CLVKDYFPEP VTVSWNSGAL TSGVHTPPAV   180
LQSSGLYSLS SVVTVPSSSL GTQTYICNVN HKPSDTKVDK KVEPKSCDKT HTCPPCPAPP   240
VAGPSVFLFP PKPKDTLMIS RTPEVTCVVV DVKHEDPEVK FNWYVDGVEV HNAKTKPREE   300
EYNSTYRVVS VLTVLHQDWL NGKEYKCKVS NKALPAPIEK TISKAKGQPR EPQVYTLPPS   360
REEMTKNQVS LTCDVSGFYP SDIAVEWESD GQPENNYKTT PPVLDSDGSF FLYSKLTVDK   420
SRWEQGDVFS CSVMHEALHN HYTQKSLSLS PGK                                453

SEQ ID NO: 588           moltype = AA   length = 479
FEATURE                  Location/Qualifiers
source                   1..479
                         mol_type = protein
                         organism = synthetic construct
                         note = XENP38939 Chain 2 -
                         1A7[CD28]_H1_L1.71_scFv(GKPGS)4_Fc(216)_IgG1_C220S/PVA_/S26
                         7K/S364K/E357Q
SEQUENCE: 588
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 589           moltype = AA   length = 216
FEATURE                  Location/Qualifiers
source                   1..216
                         mol_type = protein
                         organism = synthetic construct
                         note = XENP38939 Chain 3 - P72_G02[PSMA]_L0 Light Chain
SEQUENCE: 589
QSALTQPASV SGSPGQSITI SCTGASSDVG GYNYVSWYQQ HPGKAPKLMI YEVSNRPSGV    60
SNRFSGSKSG NTASLTISGL QAEDEADYYC SSYTITSTLV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 590           moltype = AA   length = 451
FEATURE                  Location/Qualifiers
source                   1..451
                         mol_type = protein
                         organism = synthetic construct
                         note = XENP38940 Chain 1 -
                         P75_F01[PSMA]_H0_IgG1_pI(-)_Isosteric_A_/PVA_/S267K/L368D/K
                         370S
SEQUENCE: 590
QVQLQESGGG VVQPGRSLRL SCAASGFTFS TYGMHWVRQA PGKGLEWVAF ISYDGSNKYY    60
ADSVKGRFTI SRDNSKHTLY LQMNSLRAED TAVYYCAGRD NLRFLEWFMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSDTKVDKKV EPKSCDKTHT CPPCPAPPVA   240
GPSVFLFPPK PKDTLMISRT PEVTCVVVDV KHEDPEVKFN WYVDGVEVHN AKTKPREEEY   300
NSTYRVVSVL TVLHQDWLNG KEYKCKVSNK ALPAPIEKTI SKAKGQPREP QVYTLPPSRE   360
EMTKNQVSLT CDVSGFYPSD IAVEWESDGQ PENNYKTTPP VLDSDGSFFL YSKLTVDKSR   420
WEQGDVFSCS VMHEALHNHY TQKSLSLSPG K                                  451

SEQ ID NO: 591           moltype = AA   length = 479
FEATURE                  Location/Qualifiers
source                   1..479
                         mol_type = protein
                         organism = synthetic construct
                         note = XENP38940 Chain 2 -
                         1A7[CD28]_H1_L1.71_scFv(GKPGS)4_Fc(216)_IgG1_C220S/PVA_/S26
                         7K/S364K/E357Q
SEQUENCE: 591
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479
```

```
SEQ ID NO: 592           moltype = AA  length = 215
FEATURE                  Location/Qualifiers
source                   1..215
                         mol_type = protein
                         organism = synthetic construct
                         note = XENP38940 Chain 3 - P75_F01[PSMA]_L0 Light Chain
SEQUENCE: 592
EIVLTQSPGT LSVSPGERAT LSCRASQSVR SNLAWYQQKP GQAPRLLIYG ASTRATGIPA     60
RFSGSGSGTE FTLTISSLQS EDFAVYYCHQ YNDWPPYTFG QGTKLEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                              215

SEQ ID NO: 593           moltype = AA  length = 451
FEATURE                  Location/Qualifiers
source                   1..451
                         mol_type = protein
                         organism = synthetic construct
                         note = XENP38941 Chain 1 -
                         P72_F07V2[PSMA]_H0_IgG1_pI(-)_Isosteric_A_/PVA_/S267K/L368D
                         /K370S
SEQUENCE: 593
EVQLVESGGG VVQPGRSLRL SCAASGFTFS SYGMNWVRQA PGKGLEWVAV TSYDESNKYY     60
ADSVKGRFTI SRDISKNTLY LQMSSLRAED TAVYYCARDP YSSSWNGAFD IWGPGTMVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSDTKVDKKV EPKSCDKTHT CPPCPAPPVA    240
GPSVFLFPPK PKDTLMISRT PEVTCVVVDV KHEDPEVKFN WYVDGVEVHN AKTKPREEEY    300
NSTYRVVSVL TVLHQDWLNG KEYKCKVSNK ALPAPIEKTI SKAKGQPREP QVYTLPPSRE    360
EMTKNQVSLT CDVSGFYPSD IAVEWESDGQ PENNYKTTPP VLDSDGSFFL YSKLTVDKSR    420
WEQGDVFSCS VMHEALHNHY TQKSLSLSPG K                                  451

SEQ ID NO: 594           moltype = AA  length = 479
FEATURE                  Location/Qualifiers
source                   1..479
                         mol_type = protein
                         organism = synthetic construct
                         note = XENP38941 Chain 2 -
                         1A7[CD28]_H1_L1.71_scFv(GKPGS)4_Fc(216)_IgG1_C220S/PVA_/S26
                         7K/S364K/E357Q
SEQUENCE: 594
EVQLLESGGG LVQPGGSLRL SCAASGFTFS SYAMSWVRQA PGKGLEWVST ISGSGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPPFTG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 595           moltype = AA  length = 214
FEATURE                  Location/Qualifiers
source                   1..214
                         mol_type = protein
                         organism = synthetic construct
                         note = XENP38941 Chain 3 - P72_F07V2[PSMA]_L0 Light Chain
SEQUENCE: 595
SYELTQPPSV SVAPGQTARI TCGGNNIGSK SVHWYQQKPG QAPVLVVYDD SDRPSGIPER     60
FSGSNSGNTA TLTISRVEAG DEADYYCQVW DSSTDHVVFG GGTKLTVLGQ PKAAPSVTLF    120
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECS                               214

SEQ ID NO: 596           moltype = AA  length = 453
FEATURE                  Location/Qualifiers
source                   1..453
                         mol_type = protein
                         organism = synthetic construct
                         note = XENP38942 Chain 1 -
                         P72_G02V2[PSMA]_H0_IgG1_pI(-)_Isosteric_A_/PVA_/S267K/L368D
                         /K370S
SEQUENCE: 596
EVQLVESGGG VVQPGRSLRL SCAASGFSFS GYGMHWVRQA PGKGLEWVAV ISYDESNKYY     60
ADSVKGRFTI SRDNSKNTLY LQMNSLRVED TAVYYCARDR IWGSRGYYYG MDVWGQGTTV    120
TVSSASTKGP SVFPLAPSSK STSGGTAALG CLVKDYFPEP VTVSWNSGAL TSGVHTFPAV    180
LQSSGLYSLS SVVTVPSSSL GTQTYICNVN HKPSDTKVDK KVEPKSCDKT HTCPPCPAPP    240
VAGPSVFLFP PKPKDTLMIS RTPEVTCVVV DVKHEDPEVK FNWYVDGVEV HNAKTKPREE    300
EYNSTYRVVS VLTVLHQDWL NGKEYKCKVS NKALPAPIEK TISKAKGQPR EPQVYTLPPS    360
REEMTKNQVS LTCDVSGFYP SDIAVEWESD GQPENNYKTT PPVLDSDGSF FLYSKLTVDK    420
SRWEQGDVFS CSVMHEALHN HYTQKSLSLS PGK                                453
```

-continued

```
SEQ ID NO: 597            moltype = AA   length = 479
FEATURE                   Location/Qualifiers
source                    1..479
                          mol_type = protein
                          organism = synthetic construct
                          note = XENP38942 Chain 2 -
                          1A7[CD28]_H1_L1.71_scFv(GKPGS)4_Fc(216)_IgG1_C220S/PVA_/S26
                          7K/S364K/E357Q
SEQUENCE: 597
EVQLLESGGG LVQPGGSLRL SCAASGFTFS SYAMSWVRQA PGKGLEWVST ISGSGDSTYY   60
ADSVKGRFTI SRDNSKNTLY LQMNSLRAED TAVYYCAKSG PGLRQVGFDY WGQGTLVTVS  120
SGKPGSGKPG SGKPGSGKPG SDIQMTQSPS SLSASVGDRV TITCRASQSI SSYLNWYQQK  180
PGKAPKLLIY AASSLQSGVP SRFSGSGSGT DFTLTISSLQ PEDFATYYCQ QVYSTPFTFG  240
QGTKLEIKEP KSSDKTHTCP PCPAPPVAGP SVFLFPPKPK DTLMISRTPE VTCVVVDVKH  300
EDPEVKFNWY VDGVEVHNAK TKPREEQYNS TYRVVSVLTV LHQDWLNGKE YKCKVSNKAL  360
PAPIEKTISK AKGQPREPQV YTLPPSREQM TKNQVKLTCL VKGFYPSDIA VEWESNGQPE  420
NNYKTTPPVL DSDGSFFLYS KLTVDKSRWQ QGNVFSCSVM HEALHNHYTQ KSLSLSPGK   479

SEQ ID NO: 598            moltype = AA   length = 216
FEATURE                   Location/Qualifiers
source                    1..216
                          mol_type = protein
                          organism = synthetic construct
                          note = XENP38942 Chain 3 - P72_G02V2[PSMA]_L0 Light Chain
SEQUENCE: 598
QSALTQPASV SGSPGQSITI SCTGASSDVG GYNYVSWYQQ HPGKAPKLMI YEVSNRPSGV   60
SNRFSGSKSG NTASLTISGL QAEDEADYYC SSYTITSTLV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                            216

SEQ ID NO: 599            moltype = AA   length = 451
FEATURE                   Location/Qualifiers
source                    1..451
                          mol_type = protein
                          organism = synthetic construct
                          note = XENP38943 Chain 1 -
                          P75_F01V2[PSMA]_H0_IgG1_pI(-)_Isosteric_A_/PVA_/S267K/L368D
                          /K370S
SEQUENCE: 599
QVQLQESGGG VVQPGRSLRL SCAASGFTFS TYGMHWVRQA PGKGLEWVAF ISYDESNKYY   60
ADSVKGRFTI SRDNSKHTLY LQMNSLRAED TAVYYCAGRD NLRFLEWFMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSDTKVDKKV EPKSCDKTHT CPPCPAPPVA  240
GPSVFLPPPK PKDTLMISRT PEVTCVVVDV KHEDPEVKFN WYVDGVEVHN AKTKPREEEY  300
NSTYRVVSVL TVLHQDWLNG KEYKCKVSNK ALPAPIEKTI SKAKGQPREP QVYTLPPSRE  360
EMTKNQVSLT CDVSGFYPSD IAVEWESDGQ PENNYKTTPP VLDSDGSFFL YSKLTVDKSR  420
WEQGDVFSCS VMHEALHNHY TQKSLSLSPG K                                 451

SEQ ID NO: 600            moltype = AA   length = 479
FEATURE                   Location/Qualifiers
source                    1..479
                          mol_type = protein
                          organism = synthetic construct
                          note = XENP38943 Chain 2 -
                          1A7[CD28]_H1_L1.71_scFv(GKPGS)4_Fc(216)_IgG1_C220S/PVA_/S26
                          7K/S364K/E357Q
SEQUENCE: 600
EVQLLESGGG LVQPGGSLRL SCAASGFTFS SYAMSWVRQA PGKGLEWVST ISGSGDSTYY   60
ADSVKGRFTI SRDNSKNTLY LQMNSLRAED TAVYYCAKSG PGLRQVGFDY WGQGTLVTVS  120
SGKPGSGKPG SGKPGSGKPG SDIQMTQSPS SLSASVGDRV TITCRASQSI SSYLNWYQQK  180
PGKAPKLLIY AASSLQSGVP SRFSGSGSGT DFTLTISSLQ PEDFATYYCQ QVYSTPFTFG  240
QGTKLEIKEP KSSDKTHTCP PCPAPPVAGP SVFLFPPKPK DTLMISRTPE VTCVVVDVKH  300
EDPEVKFNWY VDGVEVHNAK TKPREEQYNS TYRVVSVLTV LHQDWLNGKE YKCKVSNKAL  360
PAPIEKTISK AKGQPREPQV YTLPPSREQM TKNQVKLTCL VKGFYPSDIA VEWESNGQPE  420
NNYKTTPPVL DSDGSFFLYS KLTVDKSRWQ QGNVFSCSVM HEALHNHYTQ KSLSLSPGK   479

SEQ ID NO: 601            moltype = AA   length = 215
FEATURE                   Location/Qualifiers
source                    1..215
                          mol_type = protein
                          organism = synthetic construct
                          note = XENP38943 Chain 3 - P75_F01V2[PSMA]_L0 Light Chain
SEQUENCE: 601
EIVLTQSPGT LSVSPGERAT LSCRASQSVR SNLAWYQQKP GQAPRLLIYG ASTRATGIPA   60
RFSGSGSGTE FTLTISSLQS EDFAVYYCHQ YNDWPPYTFG QGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 602            moltype = AA   length = 450
```

```
FEATURE                 Location/Qualifiers
source                  1..450
                        mol_type = protein
                        organism = synthetic construct
                        note = XENP38944 Chain 1 -
                        PSMB896-HC-G100A[PSMA]_H0_IgG1_pI(-)_Isosteric_A_/PVA_/S267
                        K/L368D/K370S
SEQUENCE: 602
EVQLVESGGG LVQPGGSLRL SCAASGFTFS SYAMSWVRQA PGKGLEWVSA ISGGIGSTYY     60
ADSVKGRFTI SRDNSKNTLW LQMNSLRAED TAVYYCAKDA VGATPYYFDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SDTKVDKKVE PKSCDKTHTC PPCPAPPVAG    240
PSVFLFPPKP KDTLMISRTP EVTCVVVDVK HEDPEVKFNW YVDGVEVHNA KTKPREEEYN    300
STYRVVSVLT VLHQDWLNGK EYKCKVSNKA LPAPIEKTIS KAKGQPREPQ VYTLPPSREE    360
MTKNQVSLTC DVSGFYPSDI AVEWESDGQP ENNYKTTPPV LDSDGSFFLY SKLTVDKSRW    420
EQGDVFSCSV MHEALHNHYT QKSLSLSPGK                                    450

SEQ ID NO: 603          moltype = AA  length = 479
FEATURE                 Location/Qualifiers
source                  1..479
                        mol_type = protein
                        organism = synthetic construct
                        note = XENP38944 Chain 2 -
                        1A7[CD28]_H1_L1.71_scFv(GKPGS)4_Fc(216)_IgG1_C220S/PVA_/S26
                        7K/S364K/E357Q
SEQUENCE: 603
EVQLLESGGG LVQPGGSLRL SCAASGFTFS SYAMSWVRQA PGKGLEWVST ISGSGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK    479

SEQ ID NO: 604          moltype = AA  length = 216
FEATURE                 Location/Qualifiers
source                  1..216
                        mol_type = protein
                        organism = synthetic construct
                        note = XENP38944 Chain 3 - PSMB896-HC-G100A[PSMA]_L0 Light
                        Chain
SEQUENCE: 604
QSVLTQPPSV SAAPGQKVTI SCSGSSSNIG INYVSWYQQL PGTAPKLLIY DNNKRPSGIP     60
DRFSGSKSGT SATLGITGLQ TGDEADYYCG TWDSSLSAVV FGGGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                             216

SEQ ID NO: 605          moltype = AA  length = 449
FEATURE                 Location/Qualifiers
source                  1..449
                        mol_type = protein
                        organism = synthetic construct
                        note = XENP38945 Chain 1 -
                        011A11[PSMA]_H0_IgG1_pI(-)_Isosteric_A_/PVA_/S267K/L368D/K3
                        70S
SEQUENCE: 605
EVQLVESGGG LVKPGGSLRL SCVASGFTFS FYSMNWVRQA PGKGLDWVSS ISSSGNYIYY     60
ADSVKGRFTI SRDNAKNSLH LHMNSLKAED TAMYFCARSY SGSYDAFDFW GQGTMVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS DTKVDKKVEP KSCDKTHTCP PCPAPPVAGP    240
SVFLFPPKPK DTLMISRTPE VTCVVVDVKH EDPEVKFNWY VDGVEVHNAK TKPREEEYNS    300
TYRVVSVLTV LHQDWLNGKE YKCKVSNKAL PAPIEKTISK AKGQPREPQV YTLPPSREEM    360
TKNQVSLTCD VSGFYPSDIA VEWESDGQPE NNYKTTPPVL DSDGSFFLYS KLTVDKSRWE    420
QGDVFSCSVM HEALHNHYTQ KSLSLSPGK                                     449

SEQ ID NO: 606          moltype = AA  length = 479
FEATURE                 Location/Qualifiers
source                  1..479
                        mol_type = protein
                        organism = synthetic construct
                        note = XENP38945 Chain 2 -
                        1A7[CD28]_H1_L1.71_scFv(GKPGS)4_Fc(216)_IgG1_C220S/PVA_/S26
                        7K/S364K/E357Q
SEQUENCE: 606
EVQLLESGGG LVQPGGSLRL SCAASGFTFS SYAMSWVRQA PGKGLEWVST ISGSGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
```

```
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 607            moltype = AA  length = 215
FEATURE                   Location/Qualifiers
source                    1..215
                          mol_type = protein
                          organism = synthetic construct
                          note = XENP38945 Chain 3 - 011A11[PSMA]_L0 Light Chain
SEQUENCE: 607
EIVMTQSPGT LSLSPGERAT LSCRASQSVS SSFLAWYQQK PGQAPRLLIS GASSRATGIP   60
DRFSVSGSGT DFTLTISRLE PEDFAVYYCQ QYGVSPWTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 608            moltype = AA  length = 449
FEATURE                   Location/Qualifiers
source                    1..449
                          mol_type = protein
                          organism = synthetic construct
                          note = XENP39211 Chain 1 -
                          P72_A10[PSMA]_H0_IgG1_pI(-)_Isosteric_A_/PVA_/S267K/L368D/K
                          370S
SEQUENCE: 608
QVQLVESGGG VVQPGRSLRL SCAASGFTFS SYNMNWVRQA PGKGLEWVAI IYYDGSNKYY   60
ADSVKGRFTI SRDISKNTLY LQMNSLRAED TAVYYCARER GRDYYGMDVW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEYNS    300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                    449

SEQ ID NO: 609            moltype = AA  length = 479
FEATURE                   Location/Qualifiers
source                    1..479
                          mol_type = protein
                          organism = synthetic construct
                          note = XENP39211 Chain 2 -
                          1A7[CD28]_H1L1_scFv(GKPGS)4_Fc(216)_IgG1_C220S/PVA_/S267K/S
                          364K/E357Q
SEQUENCE: 609
EVQLLESGGG LVQPGGSLRL SCAASGFTFS SYAMSWVRQA PGKGLEWVST ISGSGDSTYY   60
ADSVKGRFTI SRDNSKNTLY LQMNSLRAED TAVYYCAKSG PGLRQVGFDY WGQGTLVTVS   120
SGKPGSGGKP GSGKPGSGGK PGSDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 610            moltype = AA  length = 213
FEATURE                   Location/Qualifiers
source                    1..213
                          mol_type = protein
                          organism = synthetic construct
                          note = XENP39211 Chain 3 - P72_A10[PSMA]_L0 Light Chain
SEQUENCE: 610
SYELMQPPSV SVSPGQTARI TCSGDALPKQ YAYWYQQKPG QAPVLVIYKD SERPSGIPVR   60
FSGSSSGTTV TLTITGVQAE DEADYYCQSA DSSGTYVFGT GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                               213

SEQ ID NO: 611            moltype = AA  length = 449
FEATURE                   Location/Qualifiers
source                    1..449
                          mol_type = protein
                          organism = synthetic construct
                          note = XENP39212 Chain 1 -
                          P72_A10[PSMA]_H0_IgG1_pI(-)_Isosteric_A_/PVA_/S267K/L368D/K
                          370S
SEQUENCE: 611
QVQLVESGGG VVQPGRSLRL SCAASGFTFS SYNMNWVRQA PGKGLEWVAI IYYDGSNKYY   60
ADSVKGRFTI SRDISKNTLY LQMNSLRAED TAVYYCARER GRDYYGMDVW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEYNS    300
```

```
TYRVVSVLTV LHQDWLNGKE YKCKVSNKAL PAPIEKTISK AKGQPREPQV YTLPPSREEM    360
TKNQVSLTCD VSGFYPSDIA VEWESDGQPE NNYKTTPPVL DSDGSFFLYS KLTVDKSRWE    420
QGDVFSCSVM HEALHNHYTQ KSLSLSPGK                                      449

SEQ ID NO: 612              moltype = AA   length = 479
FEATURE                     Location/Qualifiers
source                      1..479
                            mol_type = protein
                            organism = synthetic construct
                            note = XENP39212 Chain 2 -
                            1A7[CD28]_H1.14_L1_scFv(GKPGS)4_Fc(216)_IgG1_C220S/PVA_/S26
                            7K/S364K/E357Q
SEQUENCE: 612
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QSYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK    479

SEQ ID NO: 613              moltype = AA   length = 213
FEATURE                     Location/Qualifiers
source                      1..213
                            mol_type = protein
                            organism = synthetic construct
                            note = XENP39212 Chain 3 - P72_A10[PSMA]_L0 Light Chain
SEQUENCE: 613
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVLGQP KAAPSVTLFP    120
PSSEELQANK ATLVCLISDF YPGAVTVAWK ADSSPVKAGV ETTTPSKQSN NKYAASSYLS    180
LTPEQWKSHR SYSCQVTHEG STVEKTVAPT ECS                                 213

SEQ ID NO: 614              moltype = AA   length = 449
FEATURE                     Location/Qualifiers
source                      1..449
                            mol_type = protein
                            organism = synthetic construct
                            note = XENP39213 Chain 1 -
                            P72_A10[PSMA]_H0_IgG1_pI(-)_Isosteric_A_/PVA_/S267K/L368D/K
                            370S
SEQUENCE: 614
QVQLVESGGG VVQPGRSLRL SCAASGFTFS SYNMNWVRQA PGKGLEWVAI IYYDGSNKYY    60
ADSVKGRFTI SRDISKNTLY LQMNSLRAED TAVYYCARER GRDYYGMDVW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS DTKVDKKVEP KSCDKTHTCP PCPAPPVAGP    240
SVFLFPPKPK DTLMISRTPE VTCVVVDVKH EDPEVKFNWY VDGVEVHNAK TKPREEEYNS    300
TYRVVSVLTV LHQDWLNGKE YKCKVSNKAL PAPIEKTISK AKGQPREPQV YTLPPSREEM    360
TKNQVSLTCD VSGFYPSDIA VEWESDGQPE NNYKTTPPVL DSDGSFFLYS KLTVDKSRWE    420
QGDVFSCSVM HEALHNHYTQ KSLSLSPGK                                      449

SEQ ID NO: 615              moltype = AA   length = 479
FEATURE                     Location/Qualifiers
source                      1..479
                            mol_type = protein
                            organism = synthetic construct
                            note = XENP39213 Chain 2 -
                            1A7[CD28]_H1.1_L1.71_scFv(GKPGS)4_Fc(216)_IgG1_C220S/PVA_/S
                            267K/S364K/E357Q
SEQUENCE: 615
EVQLLESGGG LVQPGGSLRL SCAASGFTFS SYYMSWVRQA PGKGLEWVST ISGSGDSTYY    60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK    479

SEQ ID NO: 616              moltype = AA   length = 213
FEATURE                     Location/Qualifiers
source                      1..213
                            mol_type = protein
                            organism = synthetic construct
                            note = XENP39213 Chain 3 - P72_A10[PSMA]_L0 Light Chain
SEQUENCE: 616
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVLGQP KAAPSVTLFP    120
```

```
PSSEELQANK ATLVCLISDF YPGAVTVAWK ADSSPVKAGV ETTTPSKQSN NKYAASSYLS    180
LTPEQWKSHR SYSCQVTHEG STVEKTVAPT ECS                                 213

SEQ ID NO: 617           moltype = AA  length = 449
FEATURE                  Location/Qualifiers
source                   1..449
                         mol_type = protein
                         organism = synthetic construct
                         note = XENP39214 Chain 1 -
                           P72_A10[PSMA]_H0_IgG1_pI(-)_Isosteric_A_/PVA_/S267K/L368D/K
                           370S
SEQUENCE: 617
QVQLVESGGG VVQPGRSLRL SCAASGFTFS SYNMNWVRQA PGKGLEWVAI IYYDGSNKYY    60
ADSVKGRFTI SRDISKNTLY LQMNSLRAED TAVYYCARER GRDYYGMDVW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS DTKVDKKVEP KSCDKTHTCP PCPAPPVAGP    240
SVFLFPPKPK DTLMISRTPE VTCVVVDVKH EDPEVKFNWY VDGVEVHNAK TKPREEEYNS    300
TYRVVSVLTV LHQDWLNGKE YKCKVSNKAL PAPIEKTISK AKGQPREPQV YTLPPSREEM    360
TKNQVSLTCD VSGFYPSDIA VEWESDGQPE NNYKTTPPVL DSDGSFFLYS KLTVDKSRWE    420
QGDVFSCSVM HEALHNHYTQ KSLSLSPGK                                      449

SEQ ID NO: 618           moltype = AA  length = 479
FEATURE                  Location/Qualifiers
source                   1..479
                         mol_type = protein
                         organism = synthetic construct
                         note = XENP39214 Chain 2 -
                           1A7[CD28]_H1.14_L1.71_scFv(GKPGS)4_Fc(216)_IgG1_C220S/PVA_/
                           S267K/S364K/E357Q
SEQUENCE: 618
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 619           moltype = AA  length = 213
FEATURE                  Location/Qualifiers
source                   1..213
                         mol_type = protein
                         organism = synthetic construct
                         note = XENP39214 Chain 3 - P72_A10[PSMA]_L0 Light Chain
SEQUENCE: 619
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVLGQP KAAPSVTLFP    120
PSSEELQANK ATLVCLISDF YPGAVTVAWK ADSSPVKAGV ETTTPSKQSN NKYAASSYLS    180
LTPEQWKSHR SYSCQVTHEG STVEKTVAPT ECS                                 213

SEQ ID NO: 620           moltype = AA  length = 455
FEATURE                  Location/Qualifiers
source                   1..455
                         mol_type = protein
                         organism = synthetic construct
                         note = XENP39215 Chain 1 -
                           P72_D01[PSMA]_H0_IgG1_pI(-)_Isosteric_A_/PVA_/S267K/L368D/K
                           370S
SEQUENCE: 620
EVQLVESGGD LVQPGGSLRL SCAASGFTFN NYNMNWVRQA PGKGLEWVSH ISTSSSNKYY    60
ADSVKGRFSI SRDIAKNSMY LQMNSLRDED TAVYYCARDG VGADYGDYYY YGMDVWGQGT    120
TVTVSSASTK GPSVFPLAPS SKSTSGGTAA LGCLVKDYFP EPVTVSWNSG ALTSGVHTFP    180
AVLQSSGLYS LSSVVTVPSS SLGTQTYICN VNHKPSDTKV DKKVEPKSCD KTHTCPPCPA    240
PPVAGPSVFL FPPKPKDTLM ISRTPEVTCV VVDVKHEDPE VKFNWYVDGV EVHNAKTKPR    300
EEEYNSTYRV VSVLTVLHQD WLNGKEYKCK VSNKALPAPI EKTISKAKGQ PREPQVYTLP    360
PSREEMTKNQ VSLTCDVSGF YPSDIAVEWE SDGQPENNYK TTPPVLDSDG SFFLYSKLTV    420
DKSRWEQGDV FSCSVMHEAL HNHYTQKSLS LSPGK                               455

SEQ ID NO: 621           moltype = AA  length = 479
FEATURE                  Location/Qualifiers
source                   1..479
                         mol_type = protein
                         organism = synthetic construct
                         note = XENP39215 Chain 2 -
                           1A7[CD28]_H1L1_scFv(GKPGS)4_Fc(216)_IgG1_C220S/PVA_/S267K/S
                           364K/E357Q
```

```
SEQUENCE: 621
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 622            moltype = AA  length = 216
FEATURE                   Location/Qualifiers
source                    1..216
                          mol_type = protein
                          organism = synthetic construct
                          note = XENP39215 Chain 3 - P72_D01[PSMA]_L0 Light Chain
SEQUENCE: 622
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSSYTYV FGTGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                            216

SEQ ID NO: 623            moltype = AA  length = 455
FEATURE                   Location/Qualifiers
source                    1..455
                          mol_type = protein
                          organism = synthetic construct
                          note = XENP39216 Chain 1 -
                          P72_D01[PSMA]_H0_IgG1_pI(-)_Isosteric_A_/PVA_/S267K/L368D/K
                          370S
SEQUENCE: 623
EVQLVESGGD LVQPGGSLRL SCAASGFTFN NYNMNWVRQA PGKGLEWVSH ISTSSSNKYY    60
ADSVKGRFSI SRDIAKNSMY LQMNSLRDED TAVYYCARDG VGADYGDYYY YGMDVWGQGT   120
TVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSDTKV DKKVEPKSCD KTHTCPPCPA   240
PPVAGPSVFL FPPKPKDTLM ISRTPEVTCV VVDVKHEDPE VKFNWYVDGV EVHNAKTKPR   300
EEEYNSTYRV VSVLTVLHQD WLNGKEYKCK VSNKALPAPI EKTISKAKGQ PREPQVYTLP   360
PSREEMTKNQ VSLTCDVSGF YPSDIAVEWE SDGQPENNYK TTPPVLDSDG SFFLYSKLTV   420
DKSRWEQGDV FSCSVMHEAL HNHYTQKSLS LSPGK                             455

SEQ ID NO: 624            moltype = AA  length = 479
FEATURE                   Location/Qualifiers
source                    1..479
                          mol_type = protein
                          organism = synthetic construct
                          note = XENP39216 Chain 2 -
                          1A7[CD28]_H1.14_L1_scFv(GKPGS)4_Fc(216)_IgG1_C220S/PVA_/S26
                          7K/S364K/E357Q
SEQUENCE: 624
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 625            moltype = AA  length = 216
FEATURE                   Location/Qualifiers
source                    1..216
                          mol_type = protein
                          organism = synthetic construct
                          note = XENP39216 Chain 3 - P72_D01[PSMA]_L0 Light Chain
SEQUENCE: 625
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSSYTYV FGTGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                            216

SEQ ID NO: 626            moltype = AA  length = 455
FEATURE                   Location/Qualifiers
source                    1..455
                          mol_type = protein
                          organism = synthetic construct
                          note = XENP39217 Chain 1 -
                          P72_D01[PSMA]_H0_IgG1_pI(-)_Isosteric_A_/PVA_/S267K/L368D/K
                          370S
```

```
SEQUENCE: 626
EVQLVESGGD LVQPGGSLRL SCAASGFTFN NYNMNWVRQA PGKGLEWVSH ISTSSSNKYY    60
ADSVKGRFSI SRDIAKNSMY LQMNSLRDED TAVYYCARDG VGADYGDYYY YGMDVWGQGT   120
TVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSDTKV DKKVEPKSCD KTHTCPPCPA   240
PPVAGPSVFL FPPKPKDTLM ISRTPEVTCV VVDVKHEDPE VKFNWYVDGV EVHNAKTKPR   300
EEEYNSTYRV VSVLTVLHQD WLNGKEYKCK VSNKALPAPI EKTISKAKGQ PREPQVYTLP   360
PSREEMTKNQ VSLTCDVSGF YPSDIAVEWE SDGQPENNYK TTPPVLDSDG SFFLYSKLTV   420
DKSRWEQGDV FSCSVMHEAL HNHYTQKSLS LSPGK                              455

SEQ ID NO: 627          moltype = AA   length = 479
FEATURE                 Location/Qualifiers
source                  1..479
                        mol_type = protein
                        organism = synthetic construct
                        note = XENP39217 Chain 2 -
                        1A7[CD28]_H1.1_L1.71_scFv(GKPGS)4_Fc(216)_IgG1_C220S/PVA_/S
                        267K/S364K/E357Q
SEQUENCE: 627
EVQLLESGGG LVQPGGSLRL SCAASGFTFS SYYMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 628          moltype = AA   length = 216
FEATURE                 Location/Qualifiers
source                  1..216
                        mol_type = protein
                        organism = synthetic construct
                        note = XENP39217 Chain 3 - P72_D01[PSMA]_L0 Light Chain
SEQUENCE: 628
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSYTYV FGTGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 629          moltype = AA   length = 455
FEATURE                 Location/Qualifiers
source                  1..455
                        mol_type = protein
                        organism = synthetic construct
                        note = XENP39218 Chain 1 -
                        P72_D01[PSMA]_H0_IgG1_pI(-)_Isosteric_A_/PVA_/S267K/L368D/K
                        370S
SEQUENCE: 629
EVQLVESGGD LVQPGGSLRL SCAASGFTFN NYNMNWVRQA PGKGLEWVSH ISTSSSNKYY    60
ADSVKGRFSI SRDIAKNSMY LQMNSLRDED TAVYYCARDG VGADYGDYYY YGMDVWGQGT   120
TVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSDTKV DKKVEPKSCD KTHTCPPCPA   240
PPVAGPSVFL FPPKPKDTLM ISRTPEVTCV VVDVKHEDPE VKFNWYVDGV EVHNAKTKPR   300
EEEYNSTYRV VSVLTVLHQD WLNGKEYKCK VSNKALPAPI EKTISKAKGQ PREPQVYTLP   360
PSREEMTKNQ VSLTCDVSGF YPSDIAVEWE SDGQPENNYK TTPPVLDSDG SFFLYSKLTV   420
DKSRWEQGDV FSCSVMHEAL HNHYTQKSLS LSPGK                              455

SEQ ID NO: 630          moltype = AA   length = 479
FEATURE                 Location/Qualifiers
source                  1..479
                        mol_type = protein
                        organism = synthetic construct
                        note = XENP39218 Chain 2 -
                        1A7[CD28]_H1.14_L1.71_scFv(GKPGS)4_Fc(216)_IgG1_C220S/PVA_/
                        S267K/S364K/E357Q
SEQUENCE: 630
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 631          moltype = AA   length = 216
FEATURE                 Location/Qualifiers
source                  1..216
```

```
                         mol_type = protein
                         organism = synthetic construct
                         note = XENP39218 Chain 3 - P72_D01[PSMA]_L0 Light Chain
SEQUENCE: 631
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSYTYV FGTGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 632          moltype = AA   length = 454
FEATURE                 Location/Qualifiers
source                  1..454
                        mol_type = protein
                        organism = synthetic construct
                        note = XENP39219 Chain 1 -
                        P72_E07[PSMA]_H0_IgG1_pI(-)_Isosteric_A_/PVA_/S267K/L368D/K
                        370S
SEQUENCE: 632
EVQLVESGGG VVQPGRSLRL SCAASGFTFI TYGMHWVRQA PGKGLEWVAV VSFDESNKYY    60
ADSVKGRFTI SRDNSKNTLY LQMNSLRAED TAVYYCARAL RDGNNWDYFN GMDVWGQGTT   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSDTKVD KKVEPKSCDK THTCPPCPAP   240
PVAGPSVFLF PPKPKDTLMI SRTPEVTCVV VDVKHEDPEV KFNWYVDGVE VHNAKTKPRE   300
EEYNSTYRVV SVLTVLHQDW LNGKEYKCKV SNKALPAPIE KTISKAKGQP REPQVYTLPP   360
SREEMTKNQV SLTCDVSGFY PSDIAVEWES DGQPENNYKT TPPVLDSDGS FFLYSKLTVD   420
KSRWEQGDVF SCSVMHEALH NHYTQKSLSL SPGK                              454

SEQ ID NO: 633          moltype = AA   length = 479
FEATURE                 Location/Qualifiers
source                  1..479
                        mol_type = protein
                        organism = synthetic construct
                        note = XENP39219 Chain 2 -
                        1A7[CD28]_H1L1_scFv(GKPGS)4_Fc(216)_IgG1_C220S/PVA_/S267K/S
                        364K/E357Q
SEQUENCE: 633
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 634          moltype = AA   length = 216
FEATURE                 Location/Qualifiers
source                  1..216
                        mol_type = protein
                        organism = synthetic construct
                        note = XENP39219 Chain 3 - P72_E07[PSMA]_L0 Light Chain
SEQUENCE: 634
QSVLTQPPSA SGTPGQGVTI SCSGSSSNIG SNTVNWFQQL PGTAPKLLIY SDNQRPSGVP    60
DRFSGSKSGT SASLAISGLQ SEDEADYYCA AWDDSLNGYV FGTGTKVTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 635          moltype = AA   length = 454
FEATURE                 Location/Qualifiers
source                  1..454
                        mol_type = protein
                        organism = synthetic construct
                        note = XENP39220 Chain 1 -
                        P72_E07[PSMA]_H0_IgG1_pI(-)_Isosteric_A_/PVA_/S267K/L368D/K
                        370S
SEQUENCE: 635
EVQLVESGGG VVQPGRSLRL SCAASGFTFI TYGMHWVRQA PGKGLEWVAV VSFDESNKYY    60
ADSVKGRFTI SRDNSKNTLY LQMNSLRAED TAVYYCARAL RDGNNWDYFN GMDVWGQGTT   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSDTKVD KKVEPKSCDK THTCPPCPAP   240
PVAGPSVFLF PPKPKDTLMI SRTPEVTCVV VDVKHEDPEV KFNWYVDGVE VHNAKTKPRE   300
EEYNSTYRVV SVLTVLHQDW LNGKEYKCKV SNKALPAPIE KTISKAKGQP REPQVYTLPP   360
SREEMTKNQV SLTCDVSGFY PSDIAVEWES DGQPENNYKT TPPVLDSDGS FFLYSKLTVD   420
KSRWEQGDVF SCSVMHEALH NHYTQKSLSL SPGK                              454

SEQ ID NO: 636          moltype = AA   length = 479
FEATURE                 Location/Qualifiers
source                  1..479
                        mol_type = protein
```

```
                            organism = synthetic construct
                            note = XENP39220 Chain 2 -
                                1A7[CD28]_H1.14_L1_scFv(GKPGS)4_Fc(216)_IgG1_C220S/PVA_/S26
                                7K/S364K/E357Q
SEQUENCE: 636
EVQLLESGGG LVQPGGSLRL SCAASGFTFS SYYMSWVRQA PGKGLEWVST ISESGDSTYY        60
ADSVKGRFTI SRDNSKNTLY LQMNSLRAED TAVYYCAKSG PGLRQVGFDY WGQGTLVTVS       120
SGKPGSGKPG SGKPGSGKPG SDIQMTQSPS SLSASVGDRV TITCRASQSI SSYLNWYQQK       180
PGKAPKLLIY AASSLQSGVP SRFSGSGSGT DFTLTISSLQ PEDFATYYCQ QSYSTPFTFG       240
QGTKLEIKEP KSSDKTHTCP PCPAPPVAGP SVFLFPPKPK DTLMISRTPE VTCVVVDVKH       300
EDPEVKFNWY VDGVEVHNAK TKPREEQYNS TYRVVSVLTV LHQDWLNGKE YKCKVSNKAL       360
PAPIEKTISK AKGQPREPQV YTLPPSREQM TKNQVKLTCL VKGFYPSDIA VEWESNGQPE       420
NNYKTTPPVL DSDGSFFLYS KLTVDKSRWQ QGNVFSCSVM HEALHNHYTQ KSLSLSPGK        479

SEQ ID NO: 637              moltype = AA   length = 216
FEATURE                     Location/Qualifiers
source                      1..216
                            mol_type = protein
                            organism = synthetic construct
                            note = XENP39220 Chain 3 - P72_E07[PSMA]_L0 Light Chain
SEQUENCE: 637
QSVLTQPPSA SGTPGQGVTI SCSGSSSNIG SNTVNWFQQL PGTAPKLLIY SDNQRPSGVP        60
DRFSGSKSGT SASLAISGLQ SEDEADYYCA AWDDSLNGYV FGTGTKVTVL GQPKAAPSVT       120
LFPPSSEELQ ANKATLVCLI SDFYPGAVTV AWKADSSPVK AGVETTTPSK QSNNKYAASS       180
YLSLTPEQWK SHRSYSCQVT HEGSTVEKTV APTECS                                 216

SEQ ID NO: 638              moltype = AA   length = 454
FEATURE                     Location/Qualifiers
source                      1..454
                            mol_type = protein
                            organism = synthetic construct
                            note = XENP39221 Chain 1 -
                                P72_E07[PSMA]_H0_IgG1_pI(-)_Isosteric_A_/PVA_/S267K/L368D/K
                                370S
SEQUENCE: 638
EVQLVESGGG VVQPGRSLRL SCAASGFTFI TYGMHWVRQA PGKGLEWVAV VSFDESNKYY        60
ADSVKGRFTI SRDNSKNTLY LQMNSLRAED TAVYYCARAL RDGNNWDYFN GMDVWGQGTT       120
VTVSSASTKG PSVFPLAPSS KSTSGGTAAL GCLVKDYFPE PVTVSWNSGA LTSGVHTFPA       180
VLQSSGLYSL SSVVTVPSSS LGTQTYICNV NHKPSDTKVD KKVEPKSCDK THTCPPCPAP       240
PVAGPSVFLF PPKPKDTLMI SRTPEVTCVV VDVKHEDPEV KFNWYVDGVE VHNAKTKPRE       300
EEYNSTYRVV SVLTVLHQDW LNGKEYKCKV SNKALPAPIE KTISKAKGQP REPQVYTLPP       360
SREEMTKNQV SLTCDVSGFY PSDIAVEWES DGQPENNYKT TPPVLDSDGS FFLYSKLTVD       420
KSRWEQGDVF SCSVMHEALH NHYTQKSLSL SPGK                                  454

SEQ ID NO: 639              moltype = AA   length = 479
FEATURE                     Location/Qualifiers
source                      1..479
                            mol_type = protein
                            organism = synthetic construct
                            note = XENP39221 Chain 2 -
                                1A7[CD28]_H1.1_L1.71_scFv(GKPGS)4_Fc(216)_IgG1_C220S/PVA_/S
                                267K/S364K/E357Q
SEQUENCE: 639
EVQLLESGGG LVQPGGSLRL SCAASGFTFS SYYMSWVRQA PGKGLEWVST ISGSGDSTYY        60
ADSVKGRFTI SRDNSKNTLY LQMNSLRAED TAVYYCAKSG PGLRQVGFDY WGQGTLVTVS       120
SGKPGSGKPG SGKPGSGKPG SDIQMTQSPS SLSASVGDRV TITCRASQSI SSYLNWYQQK       180
PGKAPKLLIY AASSLQSGVP SRFSGSGSGT DFTLTISSLQ PEDFATYYCQ QVYSTPFTFG       240
QGTKLEIKEP KSSDKTHTCP PCPAPPVAGP SVFLFPPKPK DTLMISRTPE VTCVVVDVKH       300
EDPEVKFNWY VDGVEVHNAK TKPREEQYNS TYRVVSVLTV LHQDWLNGKE YKCKVSNKAL       360
PAPIEKTISK AKGQPREPQV YTLPPSREQM TKNQVKLTCL VKGFYPSDIA VEWESNGQPE       420
NNYKTTPPVL DSDGSFFLYS KLTVDKSRWQ QGNVFSCSVM HEALHNHYTQ KSLSLSPGK        479

SEQ ID NO: 640              moltype = AA   length = 216
FEATURE                     Location/Qualifiers
source                      1..216
                            mol_type = protein
                            organism = synthetic construct
                            note = XENP39221 Chain 3 - P72_E07[PSMA]_L0 Light Chain
SEQUENCE: 640
QSVLTQPPSA SGTPGQGVTI SCSGSSSNIG SNTVNWFQQL PGTAPKLLIY SDNQRPSGVP        60
DRFSGSKSGT SASLAISGLQ SEDEADYYCA AWDDSLNGYV FGTGTKVTVL GQPKAAPSVT       120
LFPPSSEELQ ANKATLVCLI SDFYPGAVTV AWKADSSPVK AGVETTTPSK QSNNKYAASS       180
YLSLTPEQWK SHRSYSCQVT HEGSTVEKTV APTECS                                 216

SEQ ID NO: 641              moltype = AA   length = 454
FEATURE                     Location/Qualifiers
source                      1..454
                            mol_type = protein
                            organism = synthetic construct
```

-continued

```
                          note = XENP39222 Chain 1 -
                              P72_E07[PSMA]_H0_IgG1_pI(-)_Isosteric_A_/PVA_/S267K/L368D/K
                              370S
SEQUENCE: 641
EVQLVESGGG VVQPGRSLRL SCAASGFTFI TYGMHWVRQA PGKGLEWVAV VSFDESNKYY    60
ADSVKGRFTI SRDNSKNTLY LQMNSLRAED TAVYYCARAL RDGNNWDYFN GMDVWGQGTT   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSDTKVD KKVEPKSCDK THTCPPCPAP   240
PVAGPSVFLF PPKPKDTLMI SRTPEVTCVV VDVKHEDPEV KFNWYVDGVE VHNAKTKPRE   300
EEYNSTYRVV SVLTVLHQDW LNGKEYKCKV SNKALPAPIE KTISKAKGQP REPQVYTLPP   360
SREEMTKNQV SLTCDVSGFY PSDIAVEWES DGQPENNYKT TPPVLDSDGS FFLYSKLTVD   420
KSRWEQGDVF SCSVMHEALH NHYTQKSLSL SPGK                               454

SEQ ID NO: 642            moltype = AA   length = 479
FEATURE                   Location/Qualifiers
source                    1..479
                          mol_type = protein
                          organism = synthetic construct
                          note = XENP39222 Chain 2 -
                              1A7[CD28]_H1.14_L1.71_scFv(GKPGS)4_Fc(216)_IgG1_C220S/PVA_/
                              S267K/S364K/E357Q
SEQUENCE: 642
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QYSTPFTFG    240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 643            moltype = AA   length = 216
FEATURE                   Location/Qualifiers
source                    1..216
                          mol_type = protein
                          organism = synthetic construct
                          note = XENP39222 Chain 3 - P72_E07[PSMA]_L0 Light Chain
SEQUENCE: 643
QSVLTQPPSA SGTPGQGVTI SCSGSSSNIG SNTVNWFQQL PGTAPKLLIY SDNQRPSGVP    60
DRFSGSKSGT SASLAISGLQ SEDEADYYCA AWDDSLNGYV FGTGTKVTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 644            moltype = AA   length = 447
FEATURE                   Location/Qualifiers
source                    1..447
                          mol_type = protein
                          organism = synthetic construct
                          note = XENP39223 Chain 1 -
                              P70_F02[PSMA]_H0_IgG1_pI(-)_Isosteric_A_/PVA_/S267K/L368D/K
                              370S
SEQUENCE: 644
EVQLLESGPG LVKPSETLSL TCTVSGGSII SYYWSWIRQP AGKGLEWIGR IYSSGSTNYN    60
PSLKSRVTMS VDTSKNQFSL KLSSVTAADT AVYYCAKVGV WPGAFDIWGQ GTMVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSDT KVDKKVEPKS CDKTHTCPPC PAPPVAGPSV   240
FLFPPKPKDT LMISRTPEVT CVVVDVKHED PEVKFNWYVD GVEVHNAKTK PREEEYNSTY   300
RVVSVLTVLH QDWLNGKEYK CKVSNKALPA PIEKTISKAK GQPREPQVYT LPPSREEMTK   360
NQVSLTCDVS GFYPSDIAVE WESDGQPENN YKTTPPVLDS DGSFFLYSKL TVDKSRWEQG   420
DVFSCSVMHE ALHNHYTQKS LSLSPGK                                       447

SEQ ID NO: 645            moltype = AA   length = 479
FEATURE                   Location/Qualifiers
source                    1..479
                          mol_type = protein
                          organism = synthetic construct
                          note = XENP39223 Chain 2 -
                              1A7[CD28]_H1L1_scFv(GKPGS)4_Fc(216)_IgG1_C220S/PVA_/S267K/S
                              364K/E357Q
SEQUENCE: 645
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479
```

-continued

```
SEQ ID NO: 646           moltype = AA  length = 216
FEATURE                  Location/Qualifiers
source                   1..216
                         mol_type = protein
                         organism = synthetic construct
                         note = XENP39223 Chain 3 - P70_F02[PSMA]_L0 Light Chain
SEQUENCE: 646
QSVLTQPPSA SGTPGQRVTI SCSGSSSNIG SNTVNWYQQL PGTAPKLLIY SSNQRPSGVP    60
DRFSGSKSGT SASLAISGLQ SEDEADYYCA AWDDSLNGVV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 647           moltype = AA  length = 447
FEATURE                  Location/Qualifiers
source                   1..447
                         mol_type = protein
                         organism = synthetic construct
                         note = XENP39224 Chain 1 -
                         P70_F02[PSMA]_H0_IgG1_pI(-)_Isosteric_A_/PVA_/S267K/L368D/K
                         370S
SEQUENCE: 647
EVQLLESGPG LVKPSETLSL TCTVSGGSII SYYWSWIRQP AGKGLEWIGR IYSSGSTNYN    60
PSLKSRVTMS VDTSKNQFSL KLSSVTAADT AVYYCAKVGV WPGAFDIWGQ GTMVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSDT KVDKKVEPKS CDKTHTCPPC PAPPVAGPSV   240
FLFPPKPKDT LMISRTPEVT CVVVDVKHED PEVKFNWYVD GVEVHNAKTK PREEEYNSTY   300
RVVSVLTVLH QDWLNGKEYK CKVSNKALPA PIEKTISKAK GQPREPQVYT LPPSREEMTK   360
NQVSLTCDVS GFYPSDIAVE WESDGQPENN YKTTPPVLDS DGSFFLYSKL TVDKSRWEQG   420
DVFSCSVMHE ALHNHYTQKS LSLSPGK                                      447

SEQ ID NO: 648           moltype = AA  length = 479
FEATURE                  Location/Qualifiers
source                   1..479
                         mol_type = protein
                         organism = synthetic construct
                         note = XENP39224 Chain 2 -
                         1A7[CD28]_H1.14_L1_scFv(GKPGS)4_Fc(216)_IgG1_C220S/PVA_/S26
                         7K/S364K/E357Q
SEQUENCE: 648
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 649           moltype = AA  length = 216
FEATURE                  Location/Qualifiers
source                   1..216
                         mol_type = protein
                         organism = synthetic construct
                         note = XENP39224 Chain 3 - P70_F02[PSMA]_L0 Light Chain
SEQUENCE: 649
QSVLTQPPSA SGTPGQRVTI SCSGSSSNIG SNTVNWYQQL PGTAPKLLIY SSNQRPSGVP    60
DRFSGSKSGT SASLAISGLQ SEDEADYYCA AWDDSLNGVV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 650           moltype = AA  length = 447
FEATURE                  Location/Qualifiers
source                   1..447
                         mol_type = protein
                         organism = synthetic construct
                         note = XENP39225 Chain 1 -
                         P70_F02[PSMA]_H0_IgG1_pI(-)_Isosteric_A_/PVA_/S267K/L368D/K
                         370S
SEQUENCE: 650
EVQLLESGPG LVKPSETLSL TCTVSGGSII SYYWSWIRQP AGKGLEWIGR IYSSGSTNYN    60
PSLKSRVTMS VDTSKNQFSL KLSSVTAADT AVYYCAKVGV WPGAFDIWGQ GTMVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSDT KVDKKVEPKS CDKTHTCPPC PAPPVAGPSV   240
FLFPPKPKDT LMISRTPEVT CVVVDVKHED PEVKFNWYVD GVEVHNAKTK PREEEYNSTY   300
RVVSVLTVLH QDWLNGKEYK CKVSNKALPA PIEKTISKAK GQPREPQVYT LPPSREEMTK   360
NQVSLTCDVS GFYPSDIAVE WESDGQPENN YKTTPPVLDS DGSFFLYSKL TVDKSRWEQG   420
DVFSCSVMHE ALHNHYTQKS LSLSPGK                                      447

SEQ ID NO: 651           moltype = AA  length = 479
```

```
FEATURE                 Location/Qualifiers
source                  1..479
                        mol_type = protein
                        organism = synthetic construct
                        note = XENP39225 Chain 2 -
                        1A7[CD28]_H1.1_L1.71_scFv(GKPGS)4_Fc(216)_IgG1_C220S/PVA_/S
                        267K/S364K/E357Q
SEQUENCE: 651
EVQLLESGGG LVQPGGSLRL SCAASGFTFS SYYMSWVRQA PGKGLEWVST ISGSGDSTYY      60
ADSVKGRFTI SRDNSKNTLY LQMNSLRAED TAVYYCAKSG PGLRQVGFDY WGQGTLVTVS     120
SGKPGSGKPG SGKPGSGKPG SDIQMTQSPS SLSASVGDRV TITCRASQSI SSYLNWYQQK     180
PGKAPKLLIY AASSLQSGVP SRFSGSGSGT DFTLTISSLQ PEDFATYYCQ QVYSTPFTFG     240
QGTKLEIKEP KSSDKTHTCP PCPAPPVAGP SVFLFPPKPK DTLMISRTPE VTCVVVDVKH     300
EDPEVKFNWY VDGVEVHNAK TKPREEQYNS TYRVVSVLTV LHQDWLNGKE YKCKVSNKAL     360
PAPIEKTISK AKGQPREPQV YTLPPSREQM TKNQVKLTCL VKGFYPSDIA VEWESNGQPE     420
NNYKTTPPVL DSDGSFFLYS KLTVDKSRWQ QGNVFSCSVM HEALHNHYTQ KSLSLSPGK     479

SEQ ID NO: 652          moltype = AA  length = 216
FEATURE                 Location/Qualifiers
source                  1..216
                        mol_type = protein
                        organism = synthetic construct
                        note = XENP39225 Chain 3 - P70_F02[PSMA]_L0 Light Chain
SEQUENCE: 652
QSVLTQPPSA SGTPGQRVTI SCSGSSSNIG SNTVNWYQQL PGTAPKLLIY SSNQRPSGVP      60
DRFSGSKSGT SASLAISGLQ SEDEADYYCA AWDDSLNGVV FGGGTKLTVL GQPKAAPSVT     120
LFPPSSEELQ ANKATLVCLI SDFYPGAVTV AWKADSSPVK AGVETTTPSK QSNNKYAASS     180
YLSLTPEQWK SHRSYSCQVT HEGSTVEKTV APTECS                               216

SEQ ID NO: 653          moltype = AA  length = 447
FEATURE                 Location/Qualifiers
source                  1..447
                        mol_type = protein
                        organism = synthetic construct
                        note = XENP39226 Chain 1 -
                        P70_F02[PSMA]_H0_IgG1_pI(-)_Isosteric_A_/PVA_/S267K/L368D/K
                        370S
SEQUENCE: 653
EVQLLESGPG LVKPSETLSL TCTVSGGSII SYYWSWIRQP AGKGLEWIGR IYSSGSTNYN      60
PSLKSRVTMS VDTSKNQFSL KLSSVTAADT AVYYCAKVGV WPGAFDIWGQ GTMVTVSSAS     120
TKGPSVFPLA PSSKSTSGGT AALGCLVKDY FPEPVTVSWN SGALTSGVHT FPAVLQSSGL     180
YSLSSVVTVP SSSLGTQTYI CNVNHKPSDT KVDKKVEPKS CDKTHTCPPC PAPPVAGPSV     240
FLFPPKPKDT LMISRTPEVT CVVVDVKHED PEVKFNWYVD GVEVHNAKTK PREEEYNSTY     300
RVVSVLTVLH QDWLNGKEYK CKVSNKALPA PIEKTISKAK GQPREPQVYT LPPSREEMTK     360
NQVSLTCDVS GFYPSDIAVE WESDGQPENN YKTTPPVLDS DGSFFLYSKL TVDKSRWEQG     420
DVFSCSVMHE ALHNHYTQKS LSLSPGK                                         447

SEQ ID NO: 654          moltype = AA  length = 479
FEATURE                 Location/Qualifiers
source                  1..479
                        mol_type = protein
                        organism = synthetic construct
                        note = XENP39226 Chain 2 -
                        1A7[CD28]_H1.14_L1.71_scFv(GKPGS)4_Fc(216)_IgG1_C220S/PVA_/
                        S267K/S364K/E357Q
SEQUENCE: 654
EVQLLESGGG LVQPGGSLRL SCAASGFTFS SYYMSWVRQA PGKGLEWVST ISESGDSTYY      60
ADSVKGRFTI SRDNSKNTLY LQMNSLRAED TAVYYCAKSG PGLRQVGFDY WGQGTLVTVS     120
SGKPGSGKPG SGKPGSGKPG SDIQMTQSPS SLSASVGDRV TITCRASQSI SSYLNWYQQK     180
PGKAPKLLIY AASSLQSGVP SRFSGSGSGT DFTLTISSLQ PEDFATYYCQ QVYSTPFTFG     240
QGTKLEIKEP KSSDKTHTCP PCPAPPVAGP SVFLFPPKPK DTLMISRTPE VTCVVVDVKH     300
EDPEVKFNWY VDGVEVHNAK TKPREEQYNS TYRVVSVLTV LHQDWLNGKE YKCKVSNKAL     360
PAPIEKTISK AKGQPREPQV YTLPPSREQM TKNQVKLTCL VKGFYPSDIA VEWESNGQPE     420
NNYKTTPPVL DSDGSFFLYS KLTVDKSRWQ QGNVFSCSVM HEALHNHYTQ KSLSLSPGK     479

SEQ ID NO: 655          moltype = AA  length = 216
FEATURE                 Location/Qualifiers
source                  1..216
                        mol_type = protein
                        organism = synthetic construct
                        note = XENP39226 Chain 3 - P70_F02[PSMA]_L0 Light Chain
SEQUENCE: 655
QSVLTQPPSA SGTPGQRVTI SCSGSSSNIG SNTVNWYQQL PGTAPKLLIY SSNQRPSGVP      60
DRFSGSKSGT SASLAISGLQ SEDEADYYCA AWDDSLNGVV FGGGTKLTVL GQPKAAPSVT     120
LFPPSSEELQ ANKATLVCLI SDFYPGAVTV AWKADSSPVK AGVETTTPSK QSNNKYAASS     180
YLSLTPEQWK SHRSYSCQVT HEGSTVEKTV APTECS                               216

SEQ ID NO: 656          moltype = AA  length = 451
FEATURE                 Location/Qualifiers
```

```
source                  1..451
                        mol_type = protein
                        organism = synthetic construct
                        note = XENP39227 Chain 1 -
                        P72_A11[PSMA]_H0_IgG1_pI(-)_Isosteric_A_/PVA_/S267K/L368D/K
                        370S
SEQUENCE: 656
QVQLQESGGD VVQPGRSLRL SCAASGFSFS GYGLHWVRQA PGRGLEWVTL ISYDGSNKYY    60
ADSVKGRFTI SRDNSKNTLY LQMNSLRAED TAVYYCAKTT VSDPYYYGMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSDKTVDKKV EPKSCDKTHT CPPCPAPPVA   240
GPSVFLFPPK PKDTLMISRT PEVTCVVVDV KHEDPEVKFN WYVDGVEVHN AKTKPREEEY   300
NSTYRVVSVL TVLHQDWLNG KEYKCKVSNK ALPAPIEKTI SKAKGQPREP QVYTLPPSRE   360
EMTKNQVSLT CDVSGFYPSD IAVEWESDGQ PENNYKTTPP VLDSDGSFFL YSKLTVDKSR   420
WEQGDVFSCS VMHEALHNHY TQKSLSLSPG K                                  451

SEQ ID NO: 657          moltype = AA  length = 479
FEATURE                 Location/Qualifiers
source                  1..479
                        mol_type = protein
                        organism = synthetic construct
                        note = XENP39227 Chain 2 -
                        1A7[CD28]_H1L1_scFv(GKPGS)4_Fc(216)_IgG1_C220S/PVA_/S267K/S
                        364K/E357Q
SEQUENCE: 657
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 658          moltype = AA  length = 214
FEATURE                 Location/Qualifiers
source                  1..214
                        mol_type = protein
                        organism = synthetic construct
                        note = XENP39227 Chain 3 - P72_A11[PSMA]_L0 Light Chain
SEQUENCE: 658
SYELTQPPSV SVAPGQTARI TCGGNNIGSK SVHWYQQKPG QAPVLVVYDD SDRPSGIPER    60
FSGTNSGNTA TLTISRAEAG DEADYYCQVW DSSSDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 659          moltype = AA  length = 451
FEATURE                 Location/Qualifiers
source                  1..451
                        mol_type = protein
                        organism = synthetic construct
                        note = XENP39228 Chain 1 -
                        P72_A11[PSMA]_H0_IgG1_pI(-)_Isosteric_A_/PVA_/S267K/L368D/K
                        370S
SEQUENCE: 659
QVQLQESGGD VVQPGRSLRL SCAASGFSFS GYGLHWVRQA PGRGLEWVTL ISYDGSNKYY    60
ADSVKGRFTI SRDNSKNTLY LQMNSLRAED TAVYYCAKTT VSDPYYYGMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSDKTVDKKV EPKSCDKTHT CPPCPAPPVA   240
GPSVFLFPPK PKDTLMISRT PEVTCVVVDV KHEDPEVKFN WYVDGVEVHN AKTKPREEEY   300
NSTYRVVSVL TVLHQDWLNG KEYKCKVSNK ALPAPIEKTI SKAKGQPREP QVYTLPPSRE   360
EMTKNQVSLT CDVSGFYPSD IAVEWESDGQ PENNYKTTPP VLDSDGSFFL YSKLTVDKSR   420
WEQGDVFSCS VMHEALHNHY TQKSLSLSPG K                                  451

SEQ ID NO: 660          moltype = AA  length = 479
FEATURE                 Location/Qualifiers
source                  1..479
                        mol_type = protein
                        organism = synthetic construct
                        note = XENP39228 Chain 2 -
                        1A7[CD28]_H1.14_L1_scFv(GKPGS)4_Fc(216)_IgG1_C220S/PVA_/S26
                        7K/S364K/E357Q
SEQUENCE: 660
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
```

```
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 661          moltype = AA  length = 214
FEATURE                 Location/Qualifiers
source                  1..214
                        mol_type = protein
                        organism = synthetic construct
                        note = XENP39228 Chain 3 - P72_A11[PSMA]_L0 Light Chain
SEQUENCE: 661
SYELTQPPSV SVAPGQTARI TCGGNNIGSK SVHWYQQKPG QAPVLVVYDD SDRPSGIPER    60
FSGTNSGNTA TLTISRAEAG DEADYYCQVW DSSSDHVVFG GGTKLTVLGQ PKAAPSVTLF    120
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECS                                214

SEQ ID NO: 662          moltype = AA  length = 451
FEATURE                 Location/Qualifiers
source                  1..451
                        mol_type = protein
                        organism = synthetic construct
                        note = XENP39229 Chain 1 -
                         P72_A11[PSMA]_H0_IgG1_pI(-)_Isosteric_A_/PVA_/S267K/L368D/K
                         370S
SEQUENCE: 662
QVQLQESGGD VVQPGRSLRL SCAASGFSFS GYGLHWVRQA PGRGLEWVTL ISYDGSNKYY    60
ADSVKGRFTI SRDNSKNTLY LQMNSLRAED TAVYYCAKTT VSDPYYYGMD VWGQGTTVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSDTKVDKKV EPKSCDKTHT CPPCPAPPVA    240
GPSVFLFPPK PKDTLMISRT PEVTCVVVDV KHEDPEVKFN WYVDGVEVHN AKTKPREEEY    300
NSTYRVVSVL TVLHQDWLNG KEYKCKVSNK ALPAPIEKTI SKAKGQPREP QVYTLPPSRE    360
EMTKNQVSLT CDVSGFYPSD IAVEWESDGQ PENNYKTTPP VLDSDGSFFL YSKLTVDKSR    420
WEQGDVFSCS VMHEALHNHY TQKSLSLSPG K                                   451

SEQ ID NO: 663          moltype = AA  length = 479
FEATURE                 Location/Qualifiers
source                  1..479
                        mol_type = protein
                        organism = synthetic construct
                        note = XENP39229 Chain 2 -
                         1A7[CD28]_H1.1_L1.71_scFv(GKPGS)4_Fc(216)_IgG1_C220S/PVA_/S
                         267K/S364K/E357Q
SEQUENCE: 663
EVQLLESGGG LVQPGGSLRL SCAASGFTFS SYYMSWVRQA PGKGLEWVST ISGSGDSTYY    60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 664          moltype = AA  length = 214
FEATURE                 Location/Qualifiers
source                  1..214
                        mol_type = protein
                        organism = synthetic construct
                        note = XENP39229 Chain 3 - P72_A11[PSMA]_L0 Light Chain
SEQUENCE: 664
SYELTQPPSV SVAPGQTARI TCGGNNIGSK SVHWYQQKPG QAPVLVVYDD SDRPSGIPER    60
FSGTNSGNTA TLTISRAEAG DEADYYCQVW DSSSDHVVFG GGTKLTVLGQ PKAAPSVTLF    120
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECS                                214

SEQ ID NO: 665          moltype = AA  length = 451
FEATURE                 Location/Qualifiers
source                  1..451
                        mol_type = protein
                        organism = synthetic construct
                        note = XENP39230 Chain 1 -
                         P72_A11[PSMA]_H0_IgG1_pI(-)_Isosteric_A_/PVA_/S267K/L368D/K
                         370S
SEQUENCE: 665
QVQLQESGGD VVQPGRSLRL SCAASGFSFS GYGLHWVRQA PGRGLEWVTL ISYDGSNKYY    60
ADSVKGRFTI SRDNSKNTLY LQMNSLRAED TAVYYCAKTT VSDPYYYGMD VWGQGTTVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSDTKVDKKV EPKSCDKTHT CPPCPAPPVA    240
```

```
GPSVFLFPPK PKDTLMISRT PEVTCVVVDV KHEDPEVKFN WYVDGVEVHN AKTKPREEEY    300
NSTYRVVSVL TVLHQDWLNG KEYKCKVSNK ALPAPIEKTI SKAKGQPREP QVYTLPPSRE    360
EMTKNQVSLT CDVSGFYPSD IAVEWESDGQ PENNYKTTPP VLDSDGSFFL YSKLTVDKSR    420
WEQGDVFSCS VMHEALHNHY TQKSLSLSPG K                                  451

SEQ ID NO: 666          moltype = AA   length = 479
FEATURE                 Location/Qualifiers
source                  1..479
                        mol_type = protein
                        organism = synthetic construct
                        note = XENP39230 Chain 2 -
                          1A7[CD28]_H1.14_L1.71_scFv(GKPGS)4_Fc(216)_IgG1_C220S/PVA_/
                          S267K/S364K/E357Q
SEQUENCE: 666
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK    479

SEQ ID NO: 667          moltype = AA   length = 214
FEATURE                 Location/Qualifiers
source                  1..214
                        mol_type = protein
                        organism = synthetic construct
                        note = XENP39230 Chain 3 - P72_A11[PSMA]_L0 Light Chain
SEQUENCE: 667
SYELTQPPSV SVAPGQTARI TCGGNNIGSK SVHWYQQKPG QAPVLVVYDD SDRPSGIPER    60
FSGTNSGNTA TLTISRAEAG DEADYYCQVW DSSSDHVVFG GGTKLTVLGQ PKAAPSVTLF    120
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECS                               214

SEQ ID NO: 668          moltype = AA   length = 449
FEATURE                 Location/Qualifiers
source                  1..449
                        mol_type = protein
                        organism = synthetic construct
                        note = XENP39231 Chain 1 -
                          P72_A10V2[PSMA]_H0_IgG1_pI(-)_Isosteric_A_/PVA_/S267K/L368D
                          /K370S
SEQUENCE: 668
QVQLVESGGG VVQPGRSLRL SCAASGFTFS SYNMNWVRQA PGKGLEWVAI IYYDESNKYY    60
ADSVKGRFTI SRDISKNTLY LQMNSLRAED TAVYYCARER GRDYYGMDVW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS DTKVDKKVEP KSCDKTHTCP PCPAPPVAGP    240
SVFLFPPKPK DTLMISRTPE VTCVVVDVKH EDPEVKFNWY VDGVEVHNAK TKPREEEYNS    300
TYRVVSVLTV LHQDWLNGKE YKCKVSNKAL PAPIEKTISK AKGQPREPQV YTLPPSREEM    360
TKNQVSLTCD VSGFYPSDIA VEWESDGQPE NNYKTTPPVL DSDGSFFLYS KLTVDKSRWE    420
QGDVFSCSVM HEALHNHYTQ KSLSLSPGK                                      449

SEQ ID NO: 669          moltype = AA   length = 479
FEATURE                 Location/Qualifiers
source                  1..479
                        mol_type = protein
                        organism = synthetic construct
                        note = XENP39231 Chain 2 -
                          1A7[CD28]_H1L1_scFv(GKPGS)4_Fc(216)_IgG1_C220S/PVA_/S
                          364K/E357Q
SEQUENCE: 669
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QSYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK    479

SEQ ID NO: 670          moltype = AA   length = 213
FEATURE                 Location/Qualifiers
source                  1..213
                        mol_type = protein
                        organism = synthetic construct
                        note = XENP39231 Chain 3 - P72_A10V2[PSMA]_L0 Light Chain
```

```
SEQUENCE: 670
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                                213

SEQ ID NO: 671          moltype = AA  length = 449
FEATURE                 Location/Qualifiers
source                  1..449
                        mol_type = protein
                        organism = synthetic construct
                        note = XENP39232 Chain 1 -
                        P72_A10V2[PSMA]_H0_IgG1_pI(-)_Isosteric_A_/PVA_/S267K/L368D
                        /K370S
SEQUENCE: 671
QVQLVESGGG VVQPGRSLRL SCAASGFTFS SYNMNWVRQA PGKGLEWVAI IYYDESNKYY    60
ADSVKGRFTI SRDISKNTLY LQMNSLRAED TAVYYCARER GRDYYGMDVW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449

SEQ ID NO: 672          moltype = AA  length = 479
FEATURE                 Location/Qualifiers
source                  1..479
                        mol_type = protein
                        organism = synthetic construct
                        note = XENP39232 Chain 2 -
                        1A7[CD28]_H1.14_L1_scFv(GKPGS)4_Fc(216)_IgG1_C220S/PVA_/S26
                        7K/S364K/E357Q
SEQUENCE: 672
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 673          moltype = AA  length = 213
FEATURE                 Location/Qualifiers
source                  1..213
                        mol_type = protein
                        organism = synthetic construct
                        note = XENP39232 Chain 3 - P72_A10V2[PSMA]_L0 Light Chain
SEQUENCE: 673
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                                213

SEQ ID NO: 674          moltype = AA  length = 449
FEATURE                 Location/Qualifiers
source                  1..449
                        mol_type = protein
                        organism = synthetic construct
                        note = XENP39233 Chain 1 -
                        P72_A10V2[PSMA]_H0_IgG1_pI(-)_Isosteric_A_/PVA_/S267K/L368D
                        /K370S
SEQUENCE: 674
QVQLVESGGG VVQPGRSLRL SCAASGFTFS SYNMNWVRQA PGKGLEWVAI IYYDESNKYY    60
ADSVKGRFTI SRDISKNTLY LQMNSLRAED TAVYYCARER GRDYYGMDVW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449

SEQ ID NO: 675          moltype = AA  length = 479
FEATURE                 Location/Qualifiers
source                  1..479
                        mol_type = protein
                        organism = synthetic construct
                        note = XENP39233 Chain 2 -
                        1A7[CD28]_H1.1_L1.71_scFv(GKPGS)4_Fc(216)_IgG1_C220S/PVA_/S
```

267K/S364K/E357Q
SEQUENCE: 675
EVQLLESGGG LVQPGGSLRL SCAASGFTFS SYYMSWVRQA PGKGLEWVST ISGSGDSTYY   60
ADSVKGRFTI SRDNSKNTLY LQMNSLRAED TAVYYCAKSG PGLRQVGFDY WGQGTLVTVS  120
SGKPGSGKPG SGKPGSGKPG SDIQMTQSPS SLSASVGDRV TITCRASQSI SSYLNWYQQK  180
PGKAPKLLIY AASSLQSGVP SRFSGSGSGT DFTLTISSLQ PEDFATYYCQ QVYSTPFTFG  240
QGTKLEIKEP KSSDKTHTCP PCPAPPVAGP SVFLFPPKPK DTLMISRTPE VTCVVVDVKH  300
EDPEVKFNWY VDGVEVHNAK TKPREEQYNS TYRVVSVLTV LHQDWLNGKE YKCKVSNKAL  360
PAPIEKTISK AKGQPREPQV YTLPPSREQM TKNQVKLTCL VKGFYPSDIA VEWESNGQPE  420
NNYKTTPPVL DSDGSFFLYS KLTVDKSRWQ QGNVFSCSVM HEALHNHYTQ KSLSLSPGK   479

SEQ ID NO: 676           moltype = AA  length = 213
FEATURE                  Location/Qualifiers
source                   1..213
                         mol_type = protein
                         organism = synthetic construct
                         note = XENP39233 Chain 3 - P72_A10V2[PSMA]_L0 Light Chain
SEQUENCE: 676
SYELMQPPSV SVSPGQTARI TCSGDALPKQ YAYWYQQKPG QAPVLVIYKD SERPSGIPVR   60
FSGSSSGTTV TLTITGVQAE DEADYYCQSA DSSGTYVFGT GTKVTVLGQP KAAPSVTLFP  120
PSSEELQANK ATLVCLISDF YPGAVTVAWK ADSSPVKAGV ETTTPSKQSN NKYAASSYLS  180
LTPEQWKSHR SYSCQVTHEG STVEKTVAPT ECS                               213

SEQ ID NO: 677           moltype = AA  length = 449
FEATURE                  Location/Qualifiers
source                   1..449
                         mol_type = protein
                         organism = synthetic construct
                         note = XENP39234 Chain 1 -
                         P72_A10V2[PSMA]_H0_IgG1_pI(-)_Isosteric_A_/PVA_/S267K/L368D
                         /K370S
SEQUENCE: 677
QVQLVESGGG VVQPGRSLRL SCAASGFTFS SYNMNWVRQA PGKGLEWVAI IYYDESNKYY   60
ADSVKGRFTI SRDISKNTLY LQMNSLRAED TAVYYCARER GRDYYGMDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 678           moltype = AA  length = 479
FEATURE                  Location/Qualifiers
source                   1..479
                         mol_type = protein
                         organism = synthetic construct
                         note = XENP39234 Chain 2 -
                         1A7[CD28]_H1.14_L1.71_scFv(GKPGS)4_Fc(216)_IgG1_C220S/PVA_/
                         S267K/S364K/E357Q
SEQUENCE: 678
EVQLLESGGG LVQPGGSLRL SCAASGFTFS SYYMSWVRQA PGKGLEWVST ISESGDSTYY   60
ADSVKGRFTI SRDNSKNTLY LQMNSLRAED TAVYYCAKSG PGLRQVGFDY WGQGTLVTVS  120
SGKPGSGKPG SGKPGSGKPG SDIQMTQSPS SLSASVGDRV TITCRASQSI SSYLNWYQQK  180
PGKAPKLLIY AASSLQSGVP SRFSGSGSGT DFTLTISSLQ PEDFATYYCQ QVYSTPFTFG  240
QGTKLEIKEP KSSDKTHTCP PCPAPPVAGP SVFLFPPKPK DTLMISRTPE VTCVVVDVKH  300
EDPEVKFNWY VDGVEVHNAK TKPREEQYNS TYRVVSVLTV LHQDWLNGKE YKCKVSNKAL  360
PAPIEKTISK AKGQPREPQV YTLPPSREQM TKNQVKLTCL VKGFYPSDIA VEWESNGQPE  420
NNYKTTPPVL DSDGSFFLYS KLTVDKSRWQ QGNVFSCSVM HEALHNHYTQ KSLSLSPGK   479

SEQ ID NO: 679           moltype = AA  length = 213
FEATURE                  Location/Qualifiers
source                   1..213
                         mol_type = protein
                         organism = synthetic construct
                         note = XENP39234 Chain 3 - P72_A10V2[PSMA]_L0 Light Chain
SEQUENCE: 679
SYELMQPPSV SVSPGQTARI TCSGDALPKQ YAYWYQQKPG QAPVLVIYKD SERPSGIPVR   60
FSGSSSGTTV TLTITGVQAE DEADYYCQSA DSSGTYVFGT GTKVTVLGQP KAAPSVTLFP  120
PSSEELQANK ATLVCLISDF YPGAVTVAWK ADSSPVKAGV ETTTPSKQSN NKYAASSYLS  180
LTPEQWKSHR SYSCQVTHEG STVEKTVAPT ECS                               213

SEQ ID NO: 680           moltype = AA  length = 455
FEATURE                  Location/Qualifiers
source                   1..455
                         mol_type = protein
                         organism = synthetic construct
                         note = XENP39235 Chain 1 -
                         P72_D01V2[PSMA]_H0_IgG1_pI(-)_Isosteric_A_/PVA_/S267K/L368D
                         /K370S

```
SEQUENCE: 680
EVQLVESGGD LVQPGGSRRL SCAASGFTFN NYMNWVRQA PGKGLEWVSH ISTSSSNKYY    60
ADSVKGRFSI SRDIAKNSMY LQMNSLRDED TAVYYCAREG VGADYGDYYY YGMDVWGQGT   120
TVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSDTKV DKKVEPKSCD KTHTCPPCPA   240
PPVAGPSVFL FPPKPKDTLM ISRTPEVTCV VVDVSHEDPE VKFNWYVDGV EVHNAKTKPR   300
EEEYNSTYRV VSVLTVLHQD WLNGKEYKCK VSNKALPAPI EKTISKAKGQ PREPQVYTLP   360
PSREEMTKNQ VSLTCDVSGF YPSDIAVEWE SDGQPENNYK TTPPVLDSDG SFFLYSKLTV   420
DKSRWEQGDV FSCSVMHEAL HNHYTQKSLS LSPGK                              455

SEQ ID NO: 681          moltype = AA  length = 479
FEATURE                 Location/Qualifiers
source                  1..479
                        mol_type = protein
                        organism = synthetic construct
                        note = XENP39235 Chain 2 -
                        1A7[CD28]_H1L1_scFv(GKPGS)4_Fc(216)_IgG1_C220S/PVA_/S267K/S
                        364K/E357Q
SEQUENCE: 681
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 682          moltype = AA  length = 216
FEATURE                 Location/Qualifiers
source                  1..216
                        mol_type = protein
                        organism = synthetic construct
                        note = XENP39235 Chain 3 - P72_D01V2[PSMA]_L0 Light Chain
SEQUENCE: 682
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSYTYV FGTGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 683          moltype = AA  length = 455
FEATURE                 Location/Qualifiers
source                  1..455
                        mol_type = protein
                        organism = synthetic construct
                        note = XENP39236 Chain 1 -
                        P72_D01V2[PSMA]_H0_IgG1_pI(-)_Isosteric_A_/PVA_/S267K/L368D
                        /K370S
SEQUENCE: 683
EVQLVESGGD LVQPGGSRRL SCAASGFTFN NYMNWVRQA PGKGLEWVSH ISTSSSNKYY    60
ADSVKGRFSI SRDIAKNSMY LQMNSLRDED TAVYYCAREG VGADYGDYYY YGMDVWGQGT   120
TVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSDTKV DKKVEPKSCD KTHTCPPCPA   240
PPVAGPSVFL FPPKPKDTLM ISRTPEVTCV VVDVSHEDPE VKFNWYVDGV EVHNAKTKPR   300
EEEYNSTYRV VSVLTVLHQD WLNGKEYKCK VSNKALPAPI EKTISKAKGQ PREPQVYTLP   360
PSREEMTKNQ VSLTCDVSGF YPSDIAVEWE SDGQPENNYK TTPPVLDSDG SFFLYSKLTV   420
DKSRWEQGDV FSCSVMHEAL HNHYTQKSLS LSPGK                              455

SEQ ID NO: 684          moltype = AA  length = 479
FEATURE                 Location/Qualifiers
source                  1..479
                        mol_type = protein
                        organism = synthetic construct
                        note = XENP39236 Chain 2 -
                        1A7[CD28]_H1.14_L1_scFv(GKPGS)4_Fc(216)_IgG1_C220S/PVA_/S26
                        7K/S364K/E357Q
SEQUENCE: 684
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 685          moltype = AA  length = 216
FEATURE                 Location/Qualifiers
source                  1..216
```

```
                             mol_type = protein
                             organism = synthetic construct
                             note = XENP39236 Chain 3 - P72_D01V2[PSMA]_L0 Light Chain
SEQUENCE: 685
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSYTYV FGTGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 686               moltype = AA  length = 455
FEATURE                      Location/Qualifiers
source                       1..455
                             mol_type = protein
                             organism = synthetic construct
                             note = XENP39237 Chain 1 -
                               P72_D01V2[PSMA]_H0_IgG1_pI(-)_Isosteric_A_/PVA_/S267K/L368D
                               /K370S
SEQUENCE: 686
EVQLVESGGD LVQPGGSLRL SCAASGFTFN NYNMNWVRQA PGKGLEWVSH ISTSSSNKYY    60
ADSVKGRFSI SRDIAKNSMY LQMNSLRDED TAVYYCAREG VGADYGDYYY YGMDVWGQGT   120
TVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSDTKV DKKVEPKSCD KTHTCPPCPA   240
PPVAGPSVFL FPPKPKDTLM ISRTPEVTCV VVDVKHEDPE VKFNWYVDGV EVHNAKTKPR   300
EEEYNSTYRV VSVLTVLHQD WLNGKEYKCK VSNKALPAPI EKTISKAKGQ PREPQVYTLP   360
PSREEMTKNQ VSLTCDVSGF YPSDIAVEWE SDGQPENNYK TTPPVLDSDG SFFLYSKLTV   420
DKSRWEQGDV FSCSVMHEAL HNHYTQKSLS LSPGK                              455

SEQ ID NO: 687               moltype = AA  length = 479
FEATURE                      Location/Qualifiers
source                       1..479
                             mol_type = protein
                             organism = synthetic construct
                             note = XENP39237 Chain 2 -
                               1A7[CD28]_H1.1_L1.71_scFv(GKPGS)4_Fc(216)_IgG1_C220S/PVA_/S
                               267K/S364K/E357Q
SEQUENCE: 687
EVQLLESGGG LVQPGGSLRL SCAASGFTFS SYYMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 688               moltype = AA  length = 216
FEATURE                      Location/Qualifiers
source                       1..216
                             mol_type = protein
                             organism = synthetic construct
                             note = XENP39237 Chain 3 - P72_D01V2[PSMA]_L0 Light Chain
SEQUENCE: 688
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSYTYV FGTGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 689               moltype = AA  length = 455
FEATURE                      Location/Qualifiers
source                       1..455
                             mol_type = protein
                             organism = synthetic construct
                             note = XENP39238 Chain 1 -
                               P72_D01V2[PSMA]_H0_IgG1_pI(-)_Isosteric_A_/PVA_/S267K/L368D
                               /K370S
SEQUENCE: 689
EVQLVESGGD LVQPGGSLRL SCAASGFTFN NYNMNWVRQA PGKGLEWVSH ISTSSSNKYY    60
ADSVKGRFSI SRDIAKNSMY LQMNSLRDED TAVYYCAREG VGADYGDYYY YGMDVWGQGT   120
TVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSDTKV DKKVEPKSCD KTHTCPPCPA   240
PPVAGPSVFL FPPKPKDTLM ISRTPEVTCV VVDVKHEDPE VKFNWYVDGV EVHNAKTKPR   300
EEEYNSTYRV VSVLTVLHQD WLNGKEYKCK VSNKALPAPI EKTISKAKGQ PREPQVYTLP   360
PSREEMTKNQ VSLTCDVSGF YPSDIAVEWE SDGQPENNYK TTPPVLDSDG SFFLYSKLTV   420
DKSRWEQGDV FSCSVMHEAL HNHYTQKSLS LSPGK                              455

SEQ ID NO: 690               moltype = AA  length = 479
FEATURE                      Location/Qualifiers
source                       1..479
                             mol_type = protein
```

```
                            organism = synthetic construct
                            note = XENP39238 Chain 2 -
                                1A7[CD28]_H1.14_L1.71_scFv(GKPGS)4_Fc(216)_IgG1_C220S/PVA_/
                                S267K/S364K/E357Q
SEQUENCE: 690
EVQLLESGGG LVQPGGSLRL SCAASGFTFS SYYMSWVRQA PGKGLEWVST ISESGDSTYY      60
ADSVKGRFTI SRDNSKNTLY LQMNSLRAED TAVYYCAKSG PGLRQVGFDY WGQGTLVTVS     120
SGKPGSGKPG SGKPGSGKPG SDIQMTQSPS SLSASVGDRV TITCRASQSI SSYLNWYQQK     180
PGKAPKLLIY AASSLQSGVP SRFSGSGSGT DFTLTISSLQ PEDFATYYCQ QVYSTPFTFG     240
QGTKLEIKEP KSSDKTHTCP PCPAPPVAGP SVFLFPPKPK DTLMISRTPE VTCVVVDVKH     300
EDPEVKFNWY VDGVEVHNAK TKPREEQYNS TYRVVSVLTV LHQDWLNGKE YKCKVSNKAL     360
PAPIEKTISK AKGQPREPQV YTLPPSREQM TKNQVKLTCL VKGFYPSDIA VEWESNGQPE     420
NNYKTTPPVL DSDGSFFLYS KLTVDKSRWQ QGNVFSCSVM HEALHNHYTQ KSLSLSPGK      479

SEQ ID NO: 691              moltype = AA  length = 216
FEATURE                     Location/Qualifiers
source                      1..216
                            mol_type = protein
                            organism = synthetic construct
                            note = XENP39238 Chain 3 - P72_D01V2[PSMA]_L0 Light Chain
SEQUENCE: 691
QSVLTQPASV SGSPGQSITI SCTGTSSDVG GYNYVSWYQQ HPGKAPKLMI YEVSNRPSGV      60
SNRFSGSKSG NTASLTISGL QAEDEADYYC SSYTSSYTYV FGTGTKLTVL GQPKAAPSVT     120
LFPPSSEELQ ANKATLVCLI SDFYPGAVTV AWKADSSPVK AGVETTTPSK QSNNKYAASS     180
YLSLTPEQWK SHRSYSCQVT HEGSTVEKTV APTECS                               216

SEQ ID NO: 692              moltype = AA  length = 451
FEATURE                     Location/Qualifiers
source                      1..451
                            mol_type = protein
                            organism = synthetic construct
                            note = XENP39239 Chain 1 -
                                P72_F07[PSMA]_H0_IgG1_pI(-)_Isosteric_A_/PVA_/S267K/L368D/K
                                370S
SEQUENCE: 692
EVQLVESGGG VVQPGRSLRL SCAASGFTFS SYGMNWVRQA PGKGLEWVAV TSYDGSNKYY      60
ADSVKGRFTI SRDISKNTLY LQMSSLRAED TAVYYCARDP YSSSWNGAFD IWGPGTMVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSDTKVDKKV EPKSCDKTHT CPPCPAPPVA     240
GPSVFLPPPK PKDTLMISRT PEVTCVVVDV KHEDPEVKFN WYVDGVEVHN AKTKPREEEY     300
NSTYRVVSVL TVLHQDWLNG KEYKCKVSNK ALPAPIEKTI SKAKGQPREP QVYTLPPSRE     360
EMTKNQVSLT CDVSGFYPSD IAVEWESDGQ PENNYKTTPP VLDSDGSFFL YSKLTVDKSR     420
WEQGDVFSCS VMHEALHNHY TQKSLSLSPG K                                    451

SEQ ID NO: 693              moltype = AA  length = 479
FEATURE                     Location/Qualifiers
source                      1..479
                            mol_type = protein
                            organism = synthetic construct
                            note = XENP39239 Chain 2 -
                                1A7[CD28]_H1L1_scFv(GKPGS)4_Fc(216)_IgG1_C220S/PVA_/S267K/S
                                364K/E357Q
SEQUENCE: 693
EVQLLESGGG LVQPGGSLRL SCAASGFTFS SYAMSWVRQA PGKGLEWVST ISGSGDSTYY      60
ADSVKGRFTI SRDNSKNTLY LQMNSLRAED TAVYYCAKSG PGLRQVGFDY WGQGTLVTVS     120
SGKPGSGKPG SGKPGSGKPG SDIQMTQSPS SLSASVGDRV TITCRASQSI SSYLNWYQQK     180
PGKAPKLLIY AASSLQSGVP SRFSGSGSGT DFTLTISSLQ PEDFATYYCQ QSYSTPFTFG     240
QGTKLEIKEP KSSDKTHTCP PCPAPPVAGP SVFLFPPKPK DTLMISRTPE VTCVVVDVKH     300
EDPEVKFNWY VDGVEVHNAK TKPREEQYNS TYRVVSVLTV LHQDWLNGKE YKCKVSNKAL     360
PAPIEKTISK AKGQPREPQV YTLPPSREQM TKNQVKLTCL VKGFYPSDIA VEWESNGQPE     420
NNYKTTPPVL DSDGSFFLYS KLTVDKSRWQ QGNVFSCSVM HEALHNHYTQ KSLSLSPGK      479

SEQ ID NO: 694              moltype = AA  length = 214
FEATURE                     Location/Qualifiers
source                      1..214
                            mol_type = protein
                            organism = synthetic construct
                            note = XENP39239 Chain 3 - P72_F07[PSMA]_L0 Light Chain
SEQUENCE: 694
SYELTQPPSV SVAPGQTARI TCGGNNIGSK SVHWYQQKPG QAPVLVVYDD SDRPSGIPER      60
FSGSNSGNTA TLTISRVEAG DEADYYCQVW DSSTDHVVFG GGTKLTVLGQ PKAAPSVTLF     120
PPSSEELQAN KATLVCLISD FYPGAVTVAW KADSSPVKAG VETTTPSKQS NNKYAASSYL     180
SLTPEQWKSH RSYSCQVTHE GSTVEKTVAP TECS                                 214

SEQ ID NO: 695              moltype = AA  length = 451
FEATURE                     Location/Qualifiers
source                      1..451
                            mol_type = protein
                            organism = synthetic construct
```

```
                        note = XENP39240 Chain 1 -
                        P72_F07[PSMA]_H0_IgG1_pI(-)_Isosteric_A_/PVA_/S267K/L368D/K
                        370S
SEQUENCE: 695
EVQLVESGGG VVQPGRSLRL SCAASGFTFS SYGMNWVRQA PGKGLEWVAV TSYDGSNKYY    60
ADSVKGRFTI SRDISKNTLY LQMSSLRAED TAVYYCARDP YSSSWNGAFD IWGPGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSDTKVDKKV EPKSCDKTHT CPPCPAPPVA   240
GPSVFLFPPK PKDTLMISRT PEVTCVVVDV KHEDPEVKFN WYVDGVEVHN AKTKPREEEY   300
NSTYRVVSVL TVLHQDWLNG KEYKCKVSNK ALPAPIEKTI SKAKGQPREP QVYTLPPSRE   360
EMTKNQVSLT CDVSGFYPSD IAVEWESDGQ PENNYKTTPP VLDSDGSFFL YSKLTVDKSR   420
WEQGDVFSCS VMHEALHNHY TQKSLSLSPG K                                 451

SEQ ID NO: 696          moltype = AA  length = 479
FEATURE                 Location/Qualifiers
source                  1..479
                        mol_type = protein
                        organism = synthetic construct
                        note = XENP39240 Chain 2 -
                        1A7[CD28]_H1.14_L1_scFv(GKPGS)4_Fc(216)_IgG1_C220S/PVA_/S26
                        7K/S364K/E357Q
SEQUENCE: 696
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK   479

SEQ ID NO: 697          moltype = AA  length = 214
FEATURE                 Location/Qualifiers
source                  1..214
                        mol_type = protein
                        organism = synthetic construct
                        note = XENP39240 Chain 3 - P72_F07[PSMA]_L0 Light Chain
SEQUENCE: 697
SYELTQPPSV SVAPGQTARI TCGGNNIGSK SVHWYQQKPG QAPVLVVYDD SDRPSGIPER    60
FSGSNSGNTA TLTISRVEAG DEADYYCQVW DSSTDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                              214

SEQ ID NO: 698          moltype = AA  length = 451
FEATURE                 Location/Qualifiers
source                  1..451
                        mol_type = protein
                        organism = synthetic construct
                        note = XENP39241 Chain 1 -
                        P72_F07[PSMA]_H0_IgG1_pI(-)_Isosteric_A_/PVA_/S267K/L368D/K
                        370S
SEQUENCE: 698
EVQLVESGGG VVQPGRSLRL SCAASGFTFS SYGMNWVRQA PGKGLEWVAV TSYDGSNKYY    60
ADSVKGRFTI SRDISKNTLY LQMSSLRAED TAVYYCARDP YSSSWNGAFD IWGPGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSDTKVDKKV EPKSCDKTHT CPPCPAPPVA   240
GPSVFLFPPK PKDTLMISRT PEVTCVVVDV KHEDPEVKFN WYVDGVEVHN AKTKPREEEY   300
NSTYRVVSVL TVLHQDWLNG KEYKCKVSNK ALPAPIEKTI SKAKGQPREP QVYTLPPSRE   360
EMTKNQVSLT CDVSGFYPSD IAVEWESDGQ PENNYKTTPP VLDSDGSFFL YSKLTVDKSR   420
WEQGDVFSCS VMHEALHNHY TQKSLSLSPG K                                 451

SEQ ID NO: 699          moltype = AA  length = 479
FEATURE                 Location/Qualifiers
source                  1..479
                        mol_type = protein
                        organism = synthetic construct
                        note = XENP39241 Chain 2 -
                        1A7[CD28]_H1.1_L1.71_scFv(GKPGS)4_Fc(216)_IgG1_C220S/PVA_/S
                        267K/S364K/E357Q
SEQUENCE: 699
EVQLLESGGG LVQPGGSLRL SCAASGFTFS SYYMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK   479
```

```
SEQ ID NO: 700             moltype = AA  length = 214
FEATURE                    Location/Qualifiers
source                     1..214
                           mol_type = protein
                           organism = synthetic construct
                           note = XENP39241 Chain 3 - P72_F07[PSMA]_L0 Light Chain
SEQUENCE: 700
SYELTQPPSV SVAPGQTARI TCGGNNIGSK SVHWYQQKPG QAPVLVVYDD SDRPSGIPER    60
FSGSNSGNTA TLTISRVEAG DEADYYCQVW DSSTDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 701             moltype = AA  length = 451
FEATURE                    Location/Qualifiers
source                     1..451
                           mol_type = protein
                           organism = synthetic construct
                           note = XENP39242 Chain 1 -
                           P72_F07[PSMA]_H0_IgG1_pI(-)_Isosteric_A_/PVA_/S267K/L368D/K
                           370S
SEQUENCE: 701
EVQLVESGGG VVQPGRSLRL SCAASGFTFS SYGMNWVRQA PGKGLEWVAV TSYDGSNKYY    60
ADSVKGRFTI SRDISKNTLY LQMSSLRAED TAVYYCARDP YSSSWNGAFD IWGPGTMVTV   120
SSSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSDTKVDKKV EPKSCDKTHT CPPCPAPPVA   240
GPSVFLFPPK PKDTLMISRT PEVTCVVVDV KHEDPEVKFN WYVDGVEVHN AKTKPREEEY   300
NSTYRVVSVL TVLHQDWLNG KEYKCKVSNK ALPAPIEKTI SKAKGQPREP QVYTLPPSRE   360
EMTKNQVSLT CDVSGFYPSD IAVEWESDGQ PENNYKTTPP VLDSDGSFFL YSKLTVDKSR   420
WEQGDVFSCS VMHEALHNHY TQKSLSLSPG K                                  451

SEQ ID NO: 702             moltype = AA  length = 479
FEATURE                    Location/Qualifiers
source                     1..479
                           mol_type = protein
                           organism = synthetic construct
                           note = XENP39242 Chain 2 -
                           1A7[CD28]_H1.14_L1.71_scFv(GKPGS)4_Fc(216)_IgG1_C220S/PVA_/
                           S267K/S364K/E357Q
SEQUENCE: 702
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QYSTPFTFG    240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 703             moltype = AA  length = 214
FEATURE                    Location/Qualifiers
source                     1..214
                           mol_type = protein
                           organism = synthetic construct
                           note = XENP39242 Chain 3 - P72_F07[PSMA]_L0 Light Chain
SEQUENCE: 703
SYELTQPPSV SVAPGQTARI TCGGNNIGSK SVHWYQQKPG QAPVLVVYDD SDRPSGIPER    60
FSGSNSGNTA TLTISRVEAG DEADYYCQVW DSSTDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 704             moltype = AA  length = 453
FEATURE                    Location/Qualifiers
source                     1..453
                           mol_type = protein
                           organism = synthetic construct
                           note = XENP39243 Chain 1 -
                           P72_G02[PSMA]_H0_IgG1_pI(-)_Isosteric_A_/PVA_/S267K/L368D/K
                           370S
SEQUENCE: 704
EVQLVESGGG VVQPGRSLRL SCAASGFSFS GYGMHWVRQA PGKGLEWVAV ISYDGSNKYY    60
ADSVKGRFTI SRDNSKNTLY LQMNSLRVED TAVYYCARDR IWGSRGYYYG MDVWGQGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSDTKVDK KVEPKSCDKT HTCPPCPAPP   240
VAGPSVFLFP PKPKDTLMIS RTPEVTCVVV DVKHEDPEVK FNWYVDGVEV HNAKTKPREE   300
EYNSTYRVVS VLTVLHQDWL NGKEYKCKVS NKALPAPIEK TISKAKGQPR EPQVYTLPPS   360
REEMTKNQVS LTCDVSGFYP SDIAVEWESD GQPENNYKTT PPVLDSDGSF FLYSKLTVDK   420
SRWEQGDVFS CSVMHEALHN HYTQKSLSLS PGK                                453

SEQ ID NO: 705             moltype = AA  length = 479
```

```
FEATURE                 Location/Qualifiers
source                  1..479
                        mol_type = protein
                        organism = synthetic construct
                        note = XENP39243 Chain 2 -
                          1A7[CD28]_H1L1_scFv(GKPGS)4_Fc(216)_IgG1_C220S/PVA_/S267K/S
                          364K/E357Q
SEQUENCE: 705
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 706          moltype = AA  length = 216
FEATURE                 Location/Qualifiers
source                  1..216
                        mol_type = protein
                        organism = synthetic construct
                        note = XENP39243 Chain 3 - P72_G02[PSMA]_L0 Light Chain
SEQUENCE: 706
QSALTQPASV SGSPGQSITI SCTGASSDVG GYNYVSWYQQ HPGKAPKLMI YEVSNRPSGV    60
SNRFSGSKSG NTASLTISGL QAEDEADYYC SSYTITSTLV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 707          moltype = AA  length = 453
FEATURE                 Location/Qualifiers
source                  1..453
                        mol_type = protein
                        organism = synthetic construct
                        note = XENP39244 Chain 1 -
                          P72_G02[PSMA]_H0_IgG1_pI(-)_Isosteric_A_/PVA_/S267K/L368D/K
                          370S
SEQUENCE: 707
EVQLVESGGG VVQPGRSLRL SCAASGFSFS GYGMHWVRQA PGKGLEWVAV ISYDGSNKYY    60
ADSVKGRFTI SRDNSKNTLY LQMNSLRVED TAVYYCARDR IWGSRGYYYG MDVWGQGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSDTKVDK KVEPKSCDKT HTCPPCPAPP   240
VAGPSVFLFP PKPKDTLMIS RTPEVTCVVV DVKHEDPEVK FNWYVDGVEV HNAKTKPREE   300
EYNSTYRVVS VLTVLHQDWL NGKEYKCKVS NKALPAPIEK TISKAKGQPR EPQVYTLPPS   360
REEMTKNQVS LTCDVSGFYP SDIAVEWESD GQPENNYKTT PPVLDSDGSF FLYSKLTVDK   420
SRWEQGDVFS CSVMHEALHN HYTQKSLSLS PGK                               453

SEQ ID NO: 708          moltype = AA  length = 479
FEATURE                 Location/Qualifiers
source                  1..479
                        mol_type = protein
                        organism = synthetic construct
                        note = XENP39244 Chain 2 -
                          1A7[CD28]_H1.14_L1_scFv(GKPGS)4_Fc(216)_IgG1_C220S/PVA_/S26
                          7K/S364K/E357Q
SEQUENCE: 708
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 709          moltype = AA  length = 216
FEATURE                 Location/Qualifiers
source                  1..216
                        mol_type = protein
                        organism = synthetic construct
                        note = XENP39244 Chain 3 - P72_G02[PSMA]_L0 Light Chain
SEQUENCE: 709
QSALTQPASV SGSPGQSITI SCTGASSDVG GYNYVSWYQQ HPGKAPKLMI YEVSNRPSGV    60
SNRFSGSKSG NTASLTISGL QAEDEADYYC SSYTITSTLV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 710          moltype = AA  length = 453
FEATURE                 Location/Qualifiers
```

| | | |
|---|---|---|
| source | 1..453<br>mol_type = protein<br>organism = synthetic construct<br>note = XENP39245 Chain 1 -<br>P72_G02[PSMA]_H0_IgG1_pI(-)_Isosteric_A_/PVA_/S267K/L368D/K<br>370S | |

SEQUENCE: 710
```
EVQLVESGGG VVQPGRSLRL SCAASGFSFS GYGMHWVRQA PGKGLEWVAV ISYDGSNKYY   60
ADSVKGRFTI SRDNSKNTLY LQMNSLRVED TAVYYCARDR IWGSRGYYYG MDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSDTKVDK KVEPKSCDKT HTCPPCPAPP  240
VAGPSVFLFP PKPKDTLMIS RTPEVTCVVV DVKHEDPEVK FNWYVDGVEV HNAKTKPREE  300
EYNSTYRVVS VLTVLHQDWL NGKEYKCKVS NKALPAPIEK TISKAKGQPR EPQVYTLPPS  360
REEMTKNQVS LTCDVSGFYP SDIAVEWESD GQPENNYKTT PPVLDSDGSF FLYSKLTVDK  420
SRWEQGDVFS CSVMHEALHN HYTQKSLSLS PGK                             453
```

| | | |
|---|---|---|
| SEQ ID NO: 711<br>FEATURE<br>source | moltype = AA   length = 479<br>Location/Qualifiers<br>1..479<br>mol_type = protein<br>organism = synthetic construct<br>note = XENP39245 Chain 2 -<br>1A7[CD28]_H1.1_L1.71_scFv(GKPGS)4_Fc(216)_IgG1_C220S/PVA_/S<br>267K/S364K/E357Q | |

SEQUENCE: 711
```
EVQLLESGGG LVQPGGSLRL SCAASGFTFS SYYMSWVRQA PGKGLEWVST ISGSGDSTYY   60
ADSVKGRFTI SRDNSKNTLY LQMNSLRAED TAVYYCAKSG PGLRQVGFDY WGQGTLVTVS  120
SGKPGSGKPG SGKPGSGKPG SDIQMTQSPS SLSASVGDRV TITCRASQSI SSYLNWYQQK  180
PGKAPKLLIY AASSLQSGVP SRFSGSGSGT DFTLTISSLQ PEDFATYYCQ QVYSTPFTFG  240
QGTKLEIKEP KSSDKTHTCP PCPAPPVAGP SVFLFPPKPK DTLMISRTPE VTCVVVDVKH  300
EDPEVKFNWY VDGVEVHNAK TKPREEQYNS TYRVVSVLTV LHQDWLNGKE YKCKVSNKAL  360
PAPIEKTISK AKGQPREPQV YTLPPSREQM TKNQVSLTCL VKGFYPSDIA VEWESNGQPE  420
NNYKTTPPVL DSDGSFFLYS KLTVDKSRWQ QGNVFSCSVM HEALHNHYTQ KSLSLSPGK   479
```

| | | |
|---|---|---|
| SEQ ID NO: 712<br>FEATURE<br>source | moltype = AA   length = 216<br>Location/Qualifiers<br>1..216<br>mol_type = protein<br>organism = synthetic construct<br>note = XENP39245 Chain 3 - P72_G02[PSMA]_L0 Light Chain | |

SEQUENCE: 712
```
QSALTQPASV SGSPGQSITI SCTGASSDVG GYNYVSWYQQ HPGKAPKLMI YEVSNRPSGV   60
SNRFSGSKSG NTASLTISGL QAEDEADYYC SSYTITSTLV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                          216
```

| | | |
|---|---|---|
| SEQ ID NO: 713<br>FEATURE<br>source | moltype = AA   length = 453<br>Location/Qualifiers<br>1..453<br>mol_type = protein<br>organism = synthetic construct<br>note = XENP39246 Chain 1 -<br>P72_G02[PSMA]_H0_IgG1_pI(-)_Isosteric_A_/PVA_/S267K/L368D/K<br>370S | |

SEQUENCE: 713
```
EVQLVESGGG VVQPGRSLRL SCAASGFSFS GYGMHWVRQA PGKGLEWVAV ISYDGSNKYY   60
ADSVKGRFTI SRDNSKNTLY LQMNSLRVED TAVYYCARDR IWGSRGYYYG MDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSDTKVDK KVEPKSCDKT HTCPPCPAPP  240
VAGPSVFLFP PKPKDTLMIS RTPEVTCVVV DVKHEDPEVK FNWYVDGVEV HNAKTKPREE  300
EYNSTYRVVS VLTVLHQDWL NGKEYKCKVS NKALPAPIEK TISKAKGQPR EPQVYTLPPS  360
REEMTKNQVS LTCDVSGFYP SDIAVEWESD GQPENNYKTT PPVLDSDGSF FLYSKLTVDK  420
SRWEQGDVFS CSVMHEALHN HYTQKSLSLS PGK                             453
```

| | | |
|---|---|---|
| SEQ ID NO: 714<br>FEATURE<br>source | moltype = AA   length = 479<br>Location/Qualifiers<br>1..479<br>mol_type = protein<br>organism = synthetic construct<br>note = XENP39246 Chain 2 -<br>1A7[CD28]_H1.14_L1.71_scFv(GKPGS)4_Fc(216)_IgG1_C220S/PVA_/<br>S267K/S364K/E357Q | |

SEQUENCE: 714
```
EVQLLESGGG LVQPGGSLRL SCAASGFTFS SYYMSWVRQA PGKGLEWVST ISESGDSTYY   60
ADSVKGRFTI SRDNSKNTLY LQMNSLRAED TAVYYCAKSG PGLRQVGFDY WGQGTLVTVS  120
SGKPGSGKPG SGKPGSGKPG SDIQMTQSPS SLSASVGDRV TITCRASQSI SSYLNWYQQK  180
PGKAPKLLIY AASSLQSGVP SRFSGSGSGT DFTLTISSLQ PEDFATYYCQ QVYSTPFTFG  240
QGTKLEIKEP KSSDKTHTCP PCPAPPVAGP SVFLFPPKPK DTLMISRTPE VTCVVVDVKH  300
EDPEVKFNWY VDGVEVHNAK TKPREEQYNS TYRVVSVLTV LHQDWLNGKE YKCKVSNKAL  360
```

```
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 715              moltype = AA  length = 216
FEATURE                     Location/Qualifiers
source                      1..216
                            mol_type = protein
                            organism = synthetic construct
                            note = XENP39246 Chain 3 - P72_G02[PSMA]_L0 Light Chain
SEQUENCE: 715
QSALTQPASV SGSPGQSITI SCTGASSDVG GYNYVSWYQQ HPGKAPKLMI YEVSNRPSGV    60
SNRFSGSKSG NTASLTISGL QAEDEADYYC SSYTITSTLV FGGGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                             216

SEQ ID NO: 716              moltype = AA  length = 451
FEATURE                     Location/Qualifiers
source                      1..451
                            mol_type = protein
                            organism = synthetic construct
                            note = XENP39247 Chain 1 -
                            P75_F01[PSMA]_H0_IgG1_pI(-)_Isosteric_A_/PVA_/S267K/L368D/K
                            370S
SEQUENCE: 716
QVQLQESGGG VVQPGRSLRL SCAASGFTFS TYGMHWVRQA PGKGLEWVAF ISYDGSNKYY    60
ADSVKGRFTI SRDNSKHTLY LQMNSLRAED TAVYYCAGRD NLRFLEWFMD VWGQGTTVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSDTKVDKKV EPKSCDKTHT CPPCPAPPVA    240
GPSVFLFPPK PKDTLMISRT PEVTCVVVDV KHEDPEVKFN WYVDGVEVHN AKTKPREEEY    300
NSTYRVVSVL TVLHQDWLNG KEYKCKVSNK ALPAPIEKTI SKAKGQPREP QVYTLPPSRE    360
EMTKNQVSLT CDVSGFYPSD IAVEWESDGQ PENNYKTTPP VLDSDGSFFL YSKLTVDKSR    420
WQEGDVFSCS VMHEALHNHY TQKSLSLSPG K                                  451

SEQ ID NO: 717              moltype = AA  length = 479
FEATURE                     Location/Qualifiers
source                      1..479
                            mol_type = protein
                            organism = synthetic construct
                            note = XENP39247 Chain 2 -
                            1A7[CD28]_H1L1_scFv(GKPGS)4_Fc(216)_IgG1_C220S/PVA_/S267K/S
                            364K/E357Q
SEQUENCE: 717
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QSYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 718              moltype = AA  length = 215
FEATURE                     Location/Qualifiers
source                      1..215
                            mol_type = protein
                            organism = synthetic construct
                            note = XENP39247 Chain 3 - P75_F01[PSMA]_L0 Light Chain
SEQUENCE: 718
EIVLTQSPGT LSVSPGERAT LSCRASQSVR SNLAWYQQKP GQAPRLLIYG ASTRATGIPA    60
RFSGSGSGTE FTLTISSLQS EDFAVYYCHQ YNDWPPYTFG QGTKLEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                              215

SEQ ID NO: 719              moltype = AA  length = 451
FEATURE                     Location/Qualifiers
source                      1..451
                            mol_type = protein
                            organism = synthetic construct
                            note = XENP39248 Chain 1 -
                            P75_F01[PSMA]_H0_IgG1_pI(-)_Isosteric_A_/PVA_/S267K/L368D/K
                            370S
SEQUENCE: 719
QVQLQESGGG VVQPGRSLRL SCAASGFTFS TYGMHWVRQA PGKGLEWVAF ISYDGSNKYY    60
ADSVKGRFTI SRDNSKHTLY LQMNSLRAED TAVYYCAGRD NLRFLEWFMD VWGQGTTVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSDTKVDKKV EPKSCDKTHT CPPCPAPPVA    240
GPSVFLFPPK PKDTLMISRT PEVTCVVVDV KHEDPEVKFN WYVDGVEVHN AKTKPREEEY    300
```

```
NSTYRVVSVL TVLHQDWLNG KEYKCKVSNK ALPAPIEKTI SKAKGQPREP QVYTLPPSRE    360
EMTKNQVSLT CDVSGFYPSD IAVEWESDGQ PENNYKTTPP VLDSDGSFFL YSKLTVDKSR    420
WEQGDVFSCS VMHEALHNHY TQKSLSLSPG K                                   451

SEQ ID NO: 720             moltype = AA   length = 479
FEATURE                    Location/Qualifiers
source                     1..479
                           mol_type = protein
                           organism = synthetic construct
                           note = XENP39248 Chain 2 -
                           1A7[CD28]_H1.14_L1_scFv(GKPGS)4_Fc(216)_IgG1_C220S/PVA_/S26
                           7K/S364K/E357Q
SEQUENCE: 720
EVQLLESGGG LVQPGGSLRL SCAASGFTFS SYYMSWVRQA PGKGLEWVST ISESGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QSYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 721             moltype = AA   length = 215
FEATURE                    Location/Qualifiers
source                     1..215
                           mol_type = protein
                           organism = synthetic construct
                           note = XENP39248 Chain 3 - P75_F01[PSMA]_L0 Light Chain
SEQUENCE: 721
EIVLTQSPGT LSVSPGERAT LSCRASQSVR SNLAWYQQKP GQAPRLLIYG ASTRATGIPA     60
RFSGSGSGTE FTLTISSLQS EDFAVYYCHQ YNDWPPYTFG QGTKLEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                               215

SEQ ID NO: 722             moltype = AA   length = 451
FEATURE                    Location/Qualifiers
source                     1..451
                           mol_type = protein
                           organism = synthetic construct
                           note = XENP39249 Chain 1 -
                           P75_F01[PSMA]_H0_IgG1_pI(-)_Isosteric_A_/PVA_/S267K/L368D/K
                           370S
SEQUENCE: 722
QVQLQESGGG VVQPGRSLRL SCAASGFTFS TYGMHWVRQA PGKGLEWVAF ISYDGSNKYY     60
ADSVKGRFTI SRDNSKHTLY LQMNSLRAED TAVYYCAGRD NLRFLEWFMD VWGQGTTVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSDTKVDKKV EPKSCDKTHT CPPCPAPPVA    240
GPSVFLFPPK PKDTLMISRT PEVTCVVVDV KHEDPEVKFN WYVDGVEVHN AKTKPREEEY    300
NSTYRVVSVL TVLHQDWLNG KEYKCKVSNK ALPAPIEKTI SKAKGQPREP QVYTLPPSRE    360
EMTKNQVSLT CDVSGFYPSD IAVEWESDGQ PENNYKTTPP VLDSDGSFFL YSKLTVDKSR    420
WEQGDVFSCS VMHEALHNHY TQKSLSLSPG K                                   451

SEQ ID NO: 723             moltype = AA   length = 479
FEATURE                    Location/Qualifiers
source                     1..479
                           mol_type = protein
                           organism = synthetic construct
                           note = XENP39249 Chain 2 -
                           1A7[CD28]_H1.1_L1.71_scFv(GKPGS)4_Fc(216)_IgG1_C220S/PVA_/S
                           267K/S364K/E357Q
SEQUENCE: 723
EVQLLESGGG LVQPGGSLRL SCAASGFTFS SYYMSWVRQA PGKGLEWVST ISGSGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 724             moltype = AA   length = 215
FEATURE                    Location/Qualifiers
source                     1..215
                           mol_type = protein
                           organism = synthetic construct
                           note = XENP39249 Chain 3 - P75_F01[PSMA]_L0 Light Chain
SEQUENCE: 724
EIVLTQSPGT LSVSPGERAT LSCRASQSVR SNLAWYQQKP GQAPRLLIYG ASTRATGIPA     60
RFSGSGSGTE FTLTISSLQS EDFAVYYCHQ YNDWPPYTFG QGTKLEIKRT VAAPSVFIFP    120
```

```
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                              215

SEQ ID NO: 725              moltype = AA  length = 451
FEATURE                     Location/Qualifiers
source                      1..451
                            mol_type = protein
                            organism = synthetic construct
                            note = XENP39250 Chain 1 -
                              P75_F01[PSMA]_H0_IgG1_pI(-)_Isosteric_A_/PVA_/S267K/L368D/K
                              370S
SEQUENCE: 725
QVQLQESGGG VVQPGRSLRL SCAASGFTFS TYGMHWVRQA PGKGLEWVAF ISYDGSNKYY    60
ADSVKGRFTI SRDNSKHTLY LQMNSLRAED TAVYYCAGRD NLRFLEWFMD VWGQGTTVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSDTKVDKKV EPKSCDKTHT CPPCPAPPVA    240
GPSVFLFPPK PKDTLMISRT PEVTCVVVDV KHEDPEVKFN WYVDGVEVHN AKTKPREEEY    300
NSTYRVVSVL TVLHQDWLNG KEYKCKVSNK ALPAPIEKTI SKAKGQPREP QVYTLPPSRE    360
EMTKNQVSLT CDVSGFYPSD IAVEWESDGQ PENNYKTTPP VLDSDGSFFL YSKLTVDKSR    420
WEQGDVFSCS VMHEALHNHY TQKSLSLSPG K                                  451

SEQ ID NO: 726              moltype = AA  length = 479
FEATURE                     Location/Qualifiers
source                      1..479
                            mol_type = protein
                            organism = synthetic construct
                            note = XENP39250 Chain 2 -
                              1A7[CD28]_H1.14_L1.71_scFv(GKPGS)4_Fc(216)_IgG1_C220S/PVA_/
                              S267K/S364K/E357Q
SEQUENCE: 726
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK    479

SEQ ID NO: 727              moltype = AA  length = 215
FEATURE                     Location/Qualifiers
source                      1..215
                            mol_type = protein
                            organism = synthetic construct
                            note = XENP39250 Chain 3 - P75_F01[PSMA]_L0 Light Chain
SEQUENCE: 727
EIVLTQSPGT LSVSPGERAT LSCRASQSVR SNLAWYQQKP GQAPRLLIYG ASTRATGIPA    60
RFSGSGSGTE FTLTISSLQS EDFAVYYCHQ YNDWPPYTFG QGTKLEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                              215

SEQ ID NO: 728              moltype = AA  length = 451
FEATURE                     Location/Qualifiers
source                      1..451
                            mol_type = protein
                            organism = synthetic construct
                            note = XENP39251 Chain 1 -
                              P72_F07V2[PSMA]_H0_IgG1_pI(-)_Isosteric_A_/PVA_/S267K/L368D
                              /K370S
SEQUENCE: 728
EVQLVESGGG VVQPGRSLRL SCAASGFTFS SYGMNWVRQA PGKGLEWVAV TSYDESNKYY    60
ADSVKGRFTI SRDISKNTLY LQMSSLRAED TAVYYCARDP YSSSWNGAFD IWGPGTMVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSDTKVDKKV EPKSCDKTHT CPPCPAPPVA    240
GPSVFLFPPK PKDTLMISRT PEVTCVVVDV KHEDPEVKFN WYVDGVEVHN AKTKPREEEY    300
NSTYRVVSVL TVLHQDWLNG KEYKCKVSNK ALPAPIEKTI SKAKGQPREP QVYTLPPSRE    360
EMTKNQVSLT CDVSGFYPSD IAVEWESDGQ PENNYKTTPP VLDSDGSFFL YSKLTVDKSR    420
WEQGDVFSCS VMHEALHNHY TQKSLSLSPG K                                  451

SEQ ID NO: 729              moltype = AA  length = 479
FEATURE                     Location/Qualifiers
source                      1..479
                            mol_type = protein
                            organism = synthetic construct
                            note = XENP39251 Chain 2 -
                              1A7[CD28]_H1L1_scFv(GKPGS)4_Fc(216)_IgG1_C220S/PVA_/S267K/S
                              364K/E357Q
```

```
SEQUENCE: 729
EVQLLESGGG LVQPGGSLRL SCAASGFTFS SYAMSWVRQA PGKGLEWVST ISGSGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QSYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK    479

SEQ ID NO: 730          moltype = AA  length = 214
FEATURE                 Location/Qualifiers
source                  1..214
                        mol_type = protein
                        organism = synthetic construct
                        note = XENP39251 Chain 3 - P72_F07V2[PSMA]_L0 Light Chain
SEQUENCE: 730
SYELTQPPSV SVAPGQTARI TCGGNNIGSK SVHWYQQKPG QAPVLVVYDD SDRPSGIPER     60
FSGSNSGNTA TLTISRVEAG DEADYYCQVW DSSTDHVVFG GGTKLTVLGQ PKAAPSVTLF    120
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECS                                214

SEQ ID NO: 731          moltype = AA  length = 451
FEATURE                 Location/Qualifiers
source                  1..451
                        mol_type = protein
                        organism = synthetic construct
                        note = XENP39252 Chain 1 -
                           P72_F07V2[PSMA]_H0_IgG1_pI(-)_Isosteric_A_/PVA_/S267K/L368D
                           /K370S
SEQUENCE: 731
EVQLVESGGG VVQPGRSLRL SCAASGFTFS SYGMNWVRQA PGKGLEWVAV TSYDESNKYY     60
ADSVKGRFTI SRDISKNTLY LQMSSLRAED TAVYYCARDP YSSSWNGAFD IWGPGTMVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSDTKVDKKV EPKSCDKTHT CPPCPAPPVA    240
GPSVFLPPPK PKDTLMISRT PEVTCVVVDV KHEDPEVKFN WYVDGVEVHN AKTKPREEEY    300
NSTYRVVSVL TVLHQDWLNG KEYKCKVSNK ALPAPIEKTI SKAKGQPREP QVYTLPPSRE    360
EMTKNQVSLT CDVSGFYPSD IAVEWESDGQ PENNYKTTPP VLDSDGSFFL YSKLTVDKSR    420
WEQGDVFSCS VMHEALHNHY TQKSLSLSPG K                                   451

SEQ ID NO: 732          moltype = AA  length = 479
FEATURE                 Location/Qualifiers
source                  1..479
                        mol_type = protein
                        organism = synthetic construct
                        note = XENP39252 Chain 2 -
                           1A7[CD28]_H1.14_L1_scFv(GKPGS)4_Fc(216)_IgG1_C220S/PVA_/S26
                           7K/S364K/E357Q
SEQUENCE: 732
EVQLLESGGG LVQPGGSLRL SCAASGFTFS SYYMSWVRQA PGKGLEWVST ISESGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QSYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK    479

SEQ ID NO: 733          moltype = AA  length = 214
FEATURE                 Location/Qualifiers
source                  1..214
                        mol_type = protein
                        organism = synthetic construct
                        note = XENP39252 Chain 3 - P72_F07V2[PSMA]_L0 Light Chain
SEQUENCE: 733
SYELTQPPSV SVAPGQTARI TCGGNNIGSK SVHWYQQKPG QAPVLVVYDD SDRPSGIPER     60
FSGSNSGNTA TLTISRVEAG DEADYYCQVW DSSTDHVVFG GGTKLTVLGQ PKAAPSVTLF    120
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECS                                214

SEQ ID NO: 734          moltype = AA  length = 451
FEATURE                 Location/Qualifiers
source                  1..451
                        mol_type = protein
                        organism = synthetic construct
                        note = XENP39253 Chain 1 -
                           P72_F07V2[PSMA]_H0_IgG1_pI(-)_Isosteric_A_/PVA_/S267K/L368D
                           /K370S
```

```
SEQUENCE: 734
EVQLVESGGG VVQPGRSLRL SCAASGFTFS SYGMNWVRQA PGKGLEWVAV TSYDESNKYY    60
ADSVKGRFTI SRDISKNTLY LQMSSLRAED TAVYYCARDP YSSSWNGAFD IWGPGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSDTKVDKKV EPKSCDKTHT CPPCPAPPVA   240
GPSVFLFPPK PKDTLMISRT PEVTCVVVDV KHEDPEVKFN WYVDGVEVHN AKTKPREEEY   300
NSTYRVVSVL TVLHQDWLNG KEYKCKVSNK ALPAPIEKTI SKAKGQPREP QVYTLPPSRE   360
EMTKNQVSLT CDVSGFYPSD IAVEWESDGQ PENNYKTTPP VLDSDGSFFL YSKLTVDKSR   420
WEQGDVFSCS VMHEALHNHY TQKSLSLSPG K                                 451

SEQ ID NO: 735         moltype = AA  length = 479
FEATURE                Location/Qualifiers
source                 1..479
                       mol_type = protein
                       organism = synthetic construct
                       note = XENP39253 Chain 2 -
                       1A7[CD28]_H1.1_L1.71_scFv(GKPGS)4_Fc(216)_IgG1_C220S/PVA_/S
                       267K/S364K/E357Q
SEQUENCE: 735
EVQLLESGGG LVQPGGSLRL SCAASGFTFS SYYMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 736         moltype = AA  length = 214
FEATURE                Location/Qualifiers
source                 1..214
                       mol_type = protein
                       organism = synthetic construct
                       note = XENP39253 Chain 3 - P72_F07V2[PSMA]_L0 Light Chain
SEQUENCE: 736
SYELTQPPSV SVAPGQTARI TCGGNNIGSK SVHWYQQKPG QAPVLVVYDD SDRPSGIPER    60
FSGSNSGNTA TLTISRVEAG DEADYYCQVW DSSTDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 737         moltype = AA  length = 451
FEATURE                Location/Qualifiers
source                 1..451
                       mol_type = protein
                       organism = synthetic construct
                       note = XENP39254 Chain 1 -
                       P72_F07V2[PSMA]_H0_IgG1_pI(-)_Isosteric_A_/PVA_/S267K/L368D
                       /K370S
SEQUENCE: 737
EVQLVESGGG VVQPGRSLRL SCAASGFTFS SYGMNWVRQA PGKGLEWVAV TSYDESNKYY    60
ADSVKGRFTI SRDISKNTLY LQMSSLRAED TAVYYCARDP YSSSWNGAFD IWGPGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSDTKVDKKV EPKSCDKTHT CPPCPAPPVA   240
GPSVFLFPPK PKDTLMISRT PEVTCVVVDV KHEDPEVKFN WYVDGVEVHN AKTKPREEEY   300
NSTYRVVSVL TVLHQDWLNG KEYKCKVSNK ALPAPIEKTI SKAKGQPREP QVYTLPPSRE   360
EMTKNQVSLT CDVSGFYPSD IAVEWESDGQ PENNYKTTPP VLDSDGSFFL YSKLTVDKSR   420
WEQGDVFSCS VMHEALHNHY TQKSLSLSPG K                                 451

SEQ ID NO: 738         moltype = AA  length = 479
FEATURE                Location/Qualifiers
source                 1..479
                       mol_type = protein
                       organism = synthetic construct
                       note = XENP39254 Chain 2 -
                       1A7[CD28]_H1.14_L1.71_scFv(GKPGS)4_Fc(216)_IgG1_C220S/PVA_/
                       S267K/S364K/E357Q
SEQUENCE: 738
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 739         moltype = AA  length = 214
FEATURE                Location/Qualifiers
source                 1..214
```

-continued

```
                               mol_type = protein
                               organism = synthetic construct
                               note = XENP39254 Chain 3 - P72_F07V2[PSMA]_L0 Light Chain
SEQUENCE: 739
SYELTQPPSV SVAPGQTARI TCGGNNIGSK SVHWYQQKPG QAPVLVVYDD SDRPSGIPER    60
FSGSNSGNTA TLTISRVEAG DEADYYCQVW DSSTDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 740               moltype = AA  length = 453
FEATURE                      Location/Qualifiers
source                       1..453
                             mol_type = protein
                             organism = synthetic construct
                             note = XENP39255 Chain 1 -
                                P72_G02V2[PSMA]_H0_IgG1_pI(-)_Isosteric_A_/PVA_/S267K/L368D
                                /K370S
SEQUENCE: 740
EVQLVESGGG VVQPGRSLRL SCAASGFSFS GYGMHWVRQA PGKGLEWVAV ISYDESNKYY    60
ADSVKGRFTI SRDNSKNTLY LQMNSLRVED TAVYYCARDR IWGSRGYYYG MDVWGQGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSDTKVDK KVEPKSCDKT HTCPPCPAPP   240
VAGPSVFLFP PKPKDTLMIS RTPEVTCVVV DVKHEDPEVK FNWYVDGVEV HNAKTKPREE   300
EYNSTYRVVS VLTVLHQDWL NGKEYKCKVS NKALPAPIEK TISKAKGQPR EPQVYTLPPS   360
REEMTKNQVS LTCDVSGFYP SDIAVEWESD GQPENNYKTT PPVLDSDGSF FLYSKLTVDK   420
SRWEQGDVFS CSVMHEALHN HYTQKSLSLS PGK                                453

SEQ ID NO: 741               moltype = AA  length = 479
FEATURE                      Location/Qualifiers
source                       1..479
                             mol_type = protein
                             organism = synthetic construct
                             note = XENP39255 Chain 2 -
                                1A7[CD28]_H1L1_scFv(GKPGS)4_Fc(216)_IgG1_C220S/PVA_/S267K/S
                                364K/E357Q
SEQUENCE: 741
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 742               moltype = AA  length = 216
FEATURE                      Location/Qualifiers
source                       1..216
                             mol_type = protein
                             organism = synthetic construct
                             note = XENP39255 Chain 3 - P72_G02V2[PSMA]_L0 Light Chain
SEQUENCE: 742
QSALTQPASV SGSPGQSITI SCTGASSDVG GYNYVSWYQQ HPGKAPKLMI YEVSNRPSGV    60
SNRFSGSKSG NTASLTISGL QAEDEADYYC SSYTITSTLV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 743               moltype = AA  length = 453
FEATURE                      Location/Qualifiers
source                       1..453
                             mol_type = protein
                             organism = synthetic construct
                             note = XENP39256 Chain 1 -
                                P72_G02V2[PSMA]_H0_IgG1_pI(-)_Isosteric_A_/PVA_/S267K/L368D
                                /K370S
SEQUENCE: 743
EVQLVESGGG VVQPGRSLRL SCAASGFSFS GYGMHWVRQA PGKGLEWVAV ISYDESNKYY    60
ADSVKGRFTI SRDNSKNTLY LQMNSLRVED TAVYYCARDR IWGSRGYYYG MDVWGQGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSDTKVDK KVEPKSCDKT HTCPPCPAPP   240
VAGPSVFLFP PKPKDTLMIS RTPEVTCVVV DVKHEDPEVK FNWYVDGVEV HNAKTKPREE   300
EYNSTYRVVS VLTVLHQDWL NGKEYKCKVS NKALPAPIEK TISKAKGQPR EPQVYTLPPS   360
REEMTKNQVS LTCDVSGFYP SDIAVEWESD GQPENNYKTT PPVLDSDGSF FLYSKLTVDK   420
SRWEQGDVFS CSVMHEALHN HYTQKSLSLS PGK                                453

SEQ ID NO: 744               moltype = AA  length = 479
FEATURE                      Location/Qualifiers
source                       1..479
                             mol_type = protein
```

```
                            organism = synthetic construct
                            note = XENP39256 Chain 2 -
                              1A7[CD28]_H1.14_L1_scFv(GKPGS)4_Fc(216)_IgG1_C220S/PVA_/S26
                              7K/S364K/E357Q
SEQUENCE: 744
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 745          moltype = AA  length = 216
FEATURE                 Location/Qualifiers
source                  1..216
                        mol_type = protein
                        organism = synthetic construct
                        note = XENP39256 Chain 3 - P72_G02V2[PSMA]_L0 Light Chain
SEQUENCE: 745
QSALTQPASV SGSPGQSITI SCTGASSDVG GYNYVSWYQQ HPGKAPKLMI YEVSNRPSGV    60
SNRFSGSKSG NTASLTISGL QAEDEADYYC SSYTITSTLV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 746          moltype = AA  length = 453
FEATURE                 Location/Qualifiers
source                  1..453
                        mol_type = protein
                        organism = synthetic construct
                        note = XENP39257 Chain 1 -
                          P72_G02V2[PSMA]_H0_IgG1_pI(-)_Isosteric_A_/PVA_/S267K/L368D
                          /K370S
SEQUENCE: 746
EVQLVESGGG VVQPGRSLRL SCAASGFSFS GYGMHWVRQA PGKGLEWVAV ISYDESNKYY    60
ADSVKGRFTI SRDNSKNTLY LQMNSLRVED TAVYYCARDR IWGSRGYYYG MDVWGQTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSDTKVDK KVEPKSCDKT HTCPPCPAPP   240
VAGPSVFLFP PKPKDTLMIS RTPEVTCVVV DVKHEDPEVK FNWYVDGVEV HNAKTKPREE   300
EYNSTYRVVS VLTVLHQDWL NGKEYKCKVS NKALPAPIEK TISKAKGQPR EPQVYTLPPS   360
REEMTKNQVS LTCDVSGFYP SDIAVEWESD GQPENNYKTT PPVLDSDGSF FLYSKLTVDK   420
SRWEQGDVFS CSVMHEALHN HYTQKSLSLS PGK                                453

SEQ ID NO: 747          moltype = AA  length = 479
FEATURE                 Location/Qualifiers
source                  1..479
                        mol_type = protein
                        organism = synthetic construct
                        note = XENP39257 Chain 2 -
                          1A7[CD28]_H1.1_L1.71_scFv(GKPGS)4_Fc(216)_IgG1_C220S/PVA_/S
                          267K/S364K/E357Q
SEQUENCE: 747
EVQLLESGGG LVQPGGSLRL SCAASGFTFS SYYMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 748          moltype = AA  length = 216
FEATURE                 Location/Qualifiers
source                  1..216
                        mol_type = protein
                        organism = synthetic construct
                        note = XENP39257 Chain 3 - P72_G02V2[PSMA]_L0 Light Chain
SEQUENCE: 748
QSALTQPASV SGSPGQSITI SCTGASSDVG GYNYVSWYQQ HPGKAPKLMI YEVSNRPSGV    60
SNRFSGSKSG NTASLTISGL QAEDEADYYC SSYTITSTLV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 749          moltype = AA  length = 453
FEATURE                 Location/Qualifiers
source                  1..453
                        mol_type = protein
                        organism = synthetic construct
```

```
                                     note = XENP39258 Chain 1 -
                                     P72_G02V2[PSMA]_H0_IgG1_pI(-)_Isosteric_A_/PVA_/S267K/L368D
                                     /K370S
SEQUENCE: 749
EVQLVESGGG VVQPGRSLRL SCAASGFSFS GYGMHWVRQA PGKGLEWVAV ISYDESNKYY     60
ADSVKGRFTI SRDNSKNTLY LQMNSLRVED TAVYYCARDR IWGSRGYYYG MDVWGQGTTV    120
TVSSASTKGP SVFPLAPSSK STSGGTAALG CLVKDYFPEP VTVSWNSGAL TSGVHTFPAV    180
LQSSGLYSLS SVVTVPSSSL GTQTYICNVN HKPSDTKVDK KVEPKSCDKT HTCPPCPAPP    240
VAGPSVFLFP PKPKDTLMIS RTPEVTCVVV DVKHEDPEVK FNWYVDGVEV HNAKTKPREE    300
EYNSTYRVVS VLTVLHQDWL NGKEYKCKVS NKALPAPIEK TISKAKGQPR EPQVYTLPPS    360
REEMTKNQVS LTCDVSGFYP SDIAVEWESD GQPENNYKTT PPVLDSDGSF FLYSKLTVDK    420
SRWEQGDVFS CSVMHEALHN HYTQKSLSLS PGK                                 453

SEQ ID NO: 750            moltype = AA  length = 479
FEATURE                   Location/Qualifiers
source                    1..479
                          mol_type = protein
                          organism = synthetic construct
                          note = XENP39258 Chain 2 -
                          1A7[CD28]_H1.14_L1.71_scFv(GKPGS)4_Fc(216)_IgG1_C220S/PVA_/
                          S267K/S364K/E357Q
SEQUENCE: 750
EVQLLESGGG LVQPGGSLRL SCAASGFTFS SYYMSWVRQA PGKGLEWVST ISESGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 751            moltype = AA  length = 216
FEATURE                   Location/Qualifiers
source                    1..216
                          mol_type = protein
                          organism = synthetic construct
                          note = XENP39258 Chain 3 - P72_G02V2[PSMA]_L0 Light Chain
SEQUENCE: 751
QSALTQPASV SGSPGQSITI SCTGASSDVG GYNYVSWYQQ HPGKAPKLMI YEVSNRPSGV     60
SNRFSGSKSG NTASLTISGL QAEDEADYYC SSYTITSTLV FGGGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 752            moltype = AA  length = 451
FEATURE                   Location/Qualifiers
source                    1..451
                          mol_type = protein
                          organism = synthetic construct
                          note = XENP39259 Chain 1 -
                          P75_F01V2[PSMA]_H0_IgG1_pI(-)_Isosteric_A_/PVA_/S267K/L368D
                          /K370S
SEQUENCE: 752
QVQLQESGGG VVQPGRSLRL SCAASGFTFS TYGMHWVRQA PGKGLEWVAF ISYDESNKYY     60
ADSVKGRFTI SRDNSKHTLY LQMNSLRAED TAVYYCAGRD NLRFLEWFMD VWGQGTTVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSDTKVDKKV EPKSCDKTHT CPPCPAPPVA    240
GPSVFLFPPK PKDTLMISRT PEVTCVVVDV KHEDPEVKFN WYVDGVEVHN AKTKPREEEY    300
NSTYRVVSVL TVLHQDWLNG KEYKCKVSNK ALPAPIEKTI SKAKGQPREP QVYTLPPSRE    360
EMTKNQVSLT CDVSGFYPSD IAVEWESDGQ PENNYKTTPP VLDSDGSFFL YSKLTVDKSR    420
WEQGDVFSCS VMHEALHNHY TQKSLSLSPG K                                   451

SEQ ID NO: 753            moltype = AA  length = 479
FEATURE                   Location/Qualifiers
source                    1..479
                          mol_type = protein
                          organism = synthetic construct
                          note = XENP39259 Chain 2 -
                          1A7[CD28]_H1L1_scFv(GKPGS)4_Fc(216)_IgG1_C220S/PVA_/S267K/S
                          364K/E357Q
SEQUENCE: 753
EVQLLESGGG LVQPGGSLRL SCAASGFTFS SYAMSWVRQA PGKGLEWVST ISGSGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QSYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479
```

```
SEQ ID NO: 754           moltype = AA   length = 215
FEATURE                  Location/Qualifiers
source                   1..215
                         mol_type = protein
                         organism = synthetic construct
                         note = XENP39259 Chain 3 - P75_F01V2[PSMA]_L0 Light Chain
SEQUENCE: 754
EIVLTQSPGT LSVSPGERAT LSCRASQSVR SNLAWYQQKP GQAPRLLIYG ASTRATGIPA    60
RFSGSGSGTE FTLTISSLQS EDFAVYYCHQ YNDWPPYTFG QGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 755           moltype = AA   length = 451
FEATURE                  Location/Qualifiers
source                   1..451
                         mol_type = protein
                         organism = synthetic construct
                         note = XENP39260 Chain 1 -
                         P75_F01V2[PSMA]_H0_IgG1_pI(-)_Isosteric_A_/PVA_/S267K/L368D
                         /K370S
SEQUENCE: 755
QVQLQESGGG VVQPGRSLRL SCAASGFTFS TYGMHWVRQA PGKGLEWVAF ISYDESNKYY    60
ADSVKGRFTI SRDNSKHTLY LQMNSLRAED TAVYYCAGRD NLRFLEWFMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSDTKVDKKV EPKSCDKTHT CPPCPAPPVA   240
GPSVFLFPPK PKDTLMISRT PEVTCVVVDV KHEDPEVKFN WYVDGVEVHN AKTKPREEEY   300
NSTYRVVSVL TVLHQDWLNG KEYKCKVSNK ALPAPIEKTI SKAKGQPREP QVYTLPPSRE   360
EMTKNQVSLT CDVSGFYPSD IAVEWESDGQ PENNYKTTPP VLDSDGSFFL YSKLTVDKSR   420
WEQGDVFSCS VMHEALHNHY TQKSLSLSPG K                                  451

SEQ ID NO: 756           moltype = AA   length = 479
FEATURE                  Location/Qualifiers
source                   1..479
                         mol_type = protein
                         organism = synthetic construct
                         note = XENP39260 Chain 2 -
                         1A7[CD28]_H1.14_L1_scFv(GKPGS)4_Fc(216)_IgG1_C220S/PVA_/S26
                         7K/S364K/E357Q
SEQUENCE: 756
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 757           moltype = AA   length = 215
FEATURE                  Location/Qualifiers
source                   1..215
                         mol_type = protein
                         organism = synthetic construct
                         note = XENP39260 Chain 3 - P75_F01V2[PSMA]_L0 Light Chain
SEQUENCE: 757
EIVLTQSPGT LSVSPGERAT LSCRASQSVR SNLAWYQQKP GQAPRLLIYG ASTRATGIPA    60
RFSGSGSGTE FTLTISSLQS EDFAVYYCHQ YNDWPPYTFG QGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 758           moltype = AA   length = 451
FEATURE                  Location/Qualifiers
source                   1..451
                         mol_type = protein
                         organism = synthetic construct
                         note = XENP39261 Chain 1 -
                         P75_F01V2[PSMA]_H0_IgG1_pI(-)_Isosteric_A_/PVA_/S267K/L368D
                         /K370S
SEQUENCE: 758
QVQLQESGGG VVQPGRSLRL SCAASGFTFS TYGMHWVRQA PGKGLEWVAF ISYDESNKYY    60
ADSVKGRFTI SRDNSKHTLY LQMNSLRAED TAVYYCAGRD NLRFLEWFMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSDTKVDKKV EPKSCDKTHT CPPCPAPPVA   240
GPSVFLFPPK PKDTLMISRT PEVTCVVVDV KHEDPEVKFN WYVDGVEVHN AKTKPREEEY   300
NSTYRVVSVL TVLHQDWLNG KEYKCKVSNK ALPAPIEKTI SKAKGQPREP QVYTLPPSRE   360
EMTKNQVSLT CDVSGFYPSD IAVEWESDGQ PENNYKTTPP VLDSDGSFFL YSKLTVDKSR   420
WEQGDVFSCS VMHEALHNHY TQKSLSLSPG K                                  451

SEQ ID NO: 759           moltype = AA   length = 479
```

```
FEATURE                     Location/Qualifiers
source                      1..479
                            mol_type = protein
                            organism = synthetic construct
                            note = XENP39261 Chain 2 -
                                1A7[CD28]_H1.1_L1.71_scFv(GKPGS)4_Fc(216)_IgG1_C220S/PVA_/S
                                267K/S364K/E357Q
SEQUENCE: 759
EVQLLESGGG LVQPGGSLRL SCAASGFTFS SYYMSWVRQA PGKGLEWVST ISGSGDSTYY      60
ADSVKGRFTI SRDNSKNTLY LQMNSLRAED TAVYYCAKSG PGLRQVGFDY WGQGTLVTVS     120
SGKPGSGKPG SGKPGSGKPG SDIQMTQSPS SLSASVGDRV TITCRASQSI SSYLNWYQQK     180
PGKAPKLLIY AASSLQSGVP SRFSGSGSGT DFTLTISSLQ PEDFATYYCQ QVYSTPFTFG     240
QGTKLEIKEP KSSDKTHTCP PCPAPPVAGP SVFLFPPKPK DTLMISRTPE VTCVVVDVKH     300
EDPEVKFNWY VDGVEVHNAK TKPREEQYNS TYRVVSVLTV LHQDWLNGKE YKCKVSNKAL     360
PAPIEKTISK AKGQPREPQV YTLPPSREQM TKNQVKLTCL VKGFYPSDIA VEWESNGQPE     420
NNYKTTPPVL DSDGSFFLYS KLTVDKSRWQ QGNVFSCSVM HEALHNHYTQ KSLSLSPGK      479

SEQ ID NO: 760              moltype = AA  length = 215
FEATURE                     Location/Qualifiers
source                      1..215
                            mol_type = protein
                            organism = synthetic construct
                            note = XENP39261 Chain 3 - P75_F01V2[PSMA]_L0 Light Chain
SEQUENCE: 760
EIVLTQSPGT LSVSPGERAT LSCRASQSVR SNLAWYQQKP GQAPRLLIYG ASTRATGIPA      60
RFSGSGSGTE FTLTISSLQS EDFAVYYCHQ YNDWPPYTFG QGTKLEIKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPVTKSF NRGEC                                215

SEQ ID NO: 761              moltype = AA  length = 451
FEATURE                     Location/Qualifiers
source                      1..451
                            mol_type = protein
                            organism = synthetic construct
                            note = XENP39262 Chain 1 -
                                P75_F01V2[PSMA]_H0_IgG1_pI(-)_Isosteric_A_/PVA_/S267K/L368D
                                /K370S
SEQUENCE: 761
QVQLQESGGG VVQPGRSLRL SCAASGFTFS TYGMHWVRQA PGKGLEWVAF ISYDESNKYY      60
ADSVKGRFTI SRDNSKHTLY LQMNSLRAED TAVYYCAGRD NLRFLEWFMD VWGQGTTVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSDTKVDKKV EPKSCDKTHT CPPCPAPPVA     240
GPSVFLFPPK PKDTLMISRT PEVTCVVVDV KHEDPEVKFN WYVDGVEVHN AKTKPREEEY     300
NSTYRVVSVL TVLHQDWLNG KEYKCKVSNK ALPAPIEKTI SKAKGQPREP QVYTLPPSRE     360
EMTKNQVSLT CDVSGFYPSD IAVEWESDGQ PENNYKTTPP VLDSDGSFFL YSKLTVDKSR     420
WEQGDVFSCS VMHEALHNHY TQKSLSLSPG K                                    451

SEQ ID NO: 762              moltype = AA  length = 479
FEATURE                     Location/Qualifiers
source                      1..479
                            mol_type = protein
                            organism = synthetic construct
                            note = XENP39262 Chain 2 -
                                1A7[CD28]_H1.14_L1.71_scFv(GKPGS)4_Fc(216)_IgG1_C220S/PVA_/
                                S267K/S364K/E357Q
SEQUENCE: 762
EVQLLESGGG LVQPGGSLRL SCAASGFTFS SYYMSWVRQA PGKGLEWVST ISESGDSTYY      60
ADSVKGRFTI SRDNSKNTLY LQMNSLRAED TAVYYCAKSG PGLRQVGFDY WGQGTLVTVS     120
SGKPGSGKPG SGKPGSGKPG SDIQMTQSPS SLSASVGDRV TITCRASQSI SSYLNWYQQK     180
PGKAPKLLIY AASSLQSGVP SRFSGSGSGT DFTLTISSLQ PEDFATYYCQ QVYSTPFTFG     240
QGTKLEIKEP KSSDKTHTCP PCPAPPVAGP SVFLFPPKPK DTLMISRTPE VTCVVVDVKH     300
EDPEVKFNWY VDGVEVHNAK TKPREEQYNS TYRVVSVLTV LHQDWLNGKE YKCKVSNKAL     360
PAPIEKTISK AKGQPREPQV YTLPPSREQM TKNQVKLTCL VKGFYPSDIA VEWESNGQPE     420
NNYKTTPPVL DSDGSFFLYS KLTVDKSRWQ QGNVFSCSVM HEALHNHYTQ KSLSLSPGK      479

SEQ ID NO: 763              moltype = AA  length = 215
FEATURE                     Location/Qualifiers
source                      1..215
                            mol_type = protein
                            organism = synthetic construct
                            note = XENP39262 Chain 3 - P75_F01V2[PSMA]_L0 Light Chain
SEQUENCE: 763
EIVLTQSPGT LSVSPGERAT LSCRASQSVR SNLAWYQQKP GQAPRLLIYG ASTRATGIPA      60
RFSGSGSGTE FTLTISSLQS EDFAVYYCHQ YNDWPPYTFG QGTKLEIKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPVTKSF NRGEC                                215

SEQ ID NO: 764              moltype = AA  length = 450
FEATURE                     Location/Qualifiers
```

```
source                    1..450
                          mol_type = protein
                          organism = synthetic construct
                          note = XENP39263 Chain 1 -
                          PSMB896-HC-G100A[PSMA]_H0_IgG1_pI(-)_Isosteric_A_/PVA_/S267
                          K/L368D/K370S
SEQUENCE: 764
EVQLVESGGG LVQPGGSLRL SCAASGFTFS SYAMSWVRQA PGKGLEWVSA ISGGIGSTYY    60
ADSVKGRFTI SRDNSKNTLW LQMNSLRAED TAVYYCAKDA VGATPYYFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SDTKVDKKVE PKSCDKTHTC PPCPAPPVAG   240
PSVFLFPPKP KDTLMISRTP EVTCVVVDVK HEDPEVKFNW YVDGVEVHNA KTKPREEEYN   300
STYRVVSVLT VLHQDWLNGK EYKCKVSNKA LPAPIEKTIS KAKGQPREPQ VYTLPPSREE   360
MTKNQVSLTC DVSGFYPSDI AVEWESDGQP ENNYKTTPPV LDSDGSFFLY SKLTVDKSRW   420
EQGDVFSCSV MHEALHNHYT QKSLSLSPGK                                   450

SEQ ID NO: 765            moltype = AA   length = 479
FEATURE                   Location/Qualifiers
source                    1..479
                          mol_type = protein
                          organism = synthetic construct
                          note = XENP39263 Chain 2 -
                          1A7[CD28]_H1L1_scFv(GKPGS)4_Fc(216)_IgG1_C220S/PVA_/S267K/S
                          364K/E357Q
SEQUENCE: 765
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 766            moltype = AA   length = 216
FEATURE                   Location/Qualifiers
source                    1..216
                          mol_type = protein
                          organism = synthetic construct
                          note = XENP39263 Chain 3 - PSMB896-HC-G100A[PSMA]_L0 Light
                          Chain
SEQUENCE: 766
QSVLTQPPSV SAAPGQKVTI SCSGSSSNIG INYVSWYQQL PGTAPKLLIY DNNKRPSGIP    60
DRFSGSKSGT SATLGITGLQ TGDEADYYCG TWDSSLSAVV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 767            moltype = AA   length = 450
FEATURE                   Location/Qualifiers
source                    1..450
                          mol_type = protein
                          organism = synthetic construct
                          note = XENP39264 Chain 1 -
                          PSMB896-HC-G100A[PSMA]_H0_IgG1_pI(-)_Isosteric_A_/PVA_/S267
                          K/L368D/K370S
SEQUENCE: 767
EVQLVESGGG LVQPGGSLRL SCAASGFTFS SYAMSWVRQA PGKGLEWVSA ISGGIGSTYY    60
ADSVKGRFTI SRDNSKNTLW LQMNSLRAED TAVYYCAKDA VGATPYYFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SDTKVDKKVE PKSCDKTHTC PPCPAPPVAG   240
PSVFLFPPKP KDTLMISRTP EVTCVVVDVK HEDPEVKFNW YVDGVEVHNA KTKPREEEYN   300
STYRVVSVLT VLHQDWLNGK EYKCKVSNKA LPAPIEKTIS KAKGQPREPQ VYTLPPSREE   360
MTKNQVSLTC DVSGFYPSDI AVEWESDGQP ENNYKTTPPV LDSDGSFFLY SKLTVDKSRW   420
EQGDVFSCSV MHEALHNHYT QKSLSLSPGK                                   450

SEQ ID NO: 768            moltype = AA   length = 479
FEATURE                   Location/Qualifiers
source                    1..479
                          mol_type = protein
                          organism = synthetic construct
                          note = XENP39264 Chain 2 -
                          1A7[CD28]_H1.14_L1_scFv(GKPGS)4_Fc(216)_IgG1_C220S/PVA_/S26
                          7K/S364K/E357Q
SEQUENCE: 768
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
```

```
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 769            moltype = AA   length = 216
FEATURE                   Location/Qualifiers
source                    1..216
                          mol_type = protein
                          organism = synthetic construct
                          note = XENP39264 Chain 3 - PSMB896-HC-G100A[PSMA]_L0 Light
                            Chain
SEQUENCE: 769
QSVLTQPPSV SAAPGQKVTI SCSGSSSNIG INYVSWYQQL PGTAPKLLIY DNNKRPSGIP    60
DRFSGSKSGT SATLGITGLQ TGDEADYYCG TWDSSLSAVV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 770            moltype = AA   length = 450
FEATURE                   Location/Qualifiers
source                    1..450
                          mol_type = protein
                          organism = synthetic construct
                          note = XENP39265 Chain 1 -
                            PSMB896-HC-G100A[PSMA]_H0_IgG1_pI(-)_Isosteric_A_/PVA_/S267
                            K/L368D/K370S
SEQUENCE: 770
EVQLVESGGG LVQPGGSLRL SCAASGFTFS SYAMSWVRQA PGKGLEWVSA ISGGIGSTYY    60
ADSVKGRFTI SRDNSKNTLW LQMNSLRAED TAVYYCAKDA VGATPYYFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SDTKVDKKVE PKSCDKTHTC PPCPAPPVAG   240
PSVFLFPPKP KDTLMISRTP EVTCVVVDVK HEDPEVKFNW YVDGVEVHNA KTKPREEEYN   300
STYRVVSVLT VLHQDWLNGK EYKCKVSNKA LPAPIEKTIS KAKGQPREPQ VYTLPPSREE   360
MTKNQVSLTC DVSGFYPSDI AVEWESDGQP ENNYKTTPPV LDSDGSFFLY SKLTVDKSRW   420
EQGDVFSCSV MHEALHNHYT QKSLSLSPGK                                   450

SEQ ID NO: 771            moltype = AA   length = 479
FEATURE                   Location/Qualifiers
source                    1..479
                          mol_type = protein
                          organism = synthetic construct
                          note = XENP39265 Chain 2 -
                            1A7[CD28]_H1.1_L1.71_scFv(GKPGS)4_Fc(216)_IgG1_C220S/PVA_/S
                            267K/S364K/E357Q
SEQUENCE: 771
EVQLLESGGG LVQPGGSLRL SCAASGFTFS SYYMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 772            moltype = AA   length = 216
FEATURE                   Location/Qualifiers
source                    1..216
                          mol_type = protein
                          organism = synthetic construct
                          note = XENP39265 Chain 3 - PSMB896-HC-G100A[PSMA]_L0 Light
                            Chain
SEQUENCE: 772
QSVLTQPPSV SAAPGQKVTI SCSGSSSNIG INYVSWYQQL PGTAPKLLIY DNNKRPSGIP    60
DRFSGSKSGT SATLGITGLQ TGDEADYYCG TWDSSLSAVV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 773            moltype = AA   length = 450
FEATURE                   Location/Qualifiers
source                    1..450
                          mol_type = protein
                          organism = synthetic construct
                          note = XENP39266 Chain 1 -
                            PSMB896-HC-G100A[PSMA]_H0_IgG1_pI(-)_Isosteric_A_/PVA_/S267
                            K/L368D/K370S
SEQUENCE: 773
EVQLVESGGG LVQPGGSLRL SCAASGFTFS SYAMSWVRQA PGKGLEWVSA ISGGIGSTYY    60
ADSVKGRFTI SRDNSKNTLW LQMNSLRAED TAVYYCAKDA VGATPYYFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SDTKVDKKVE PKSCDKTHTC PPCPAPPVAG   240
```

```
PSVFLPPPKP KDTLMISRTP EVTCVVVDVK HEDPEVKFNW YVDGVEVHNA KTKPREEEYN   300
STYRVVSVLT VLHQDWLNGK EYKCKVSNKA LPAPIEKTIS KAKGQPREPQ VYTLPPSREE   360
MTKNQVSLTC DVSGFYPSDI AVEWESDGQP ENNYKTTPPV LDSDGSFFLY SKLTVDKSRW   420
EQGDVFSCSV MHEALHNHYT QKSLSLSPGK                                   450

SEQ ID NO: 774          moltype = AA   length = 479
FEATURE                 Location/Qualifiers
source                  1..479
                        mol_type = protein
                        organism = synthetic construct
                        note = XENP39266 Chain 2 -
                            1A7[CD28]_H1.14_L1.71_scFv(GKPGS)4_Fc(216)_IgG1_C220S/PVA_/
                            S267K/S364K/E357Q
SEQUENCE: 774
EVQLLESGGG LVQPGGSLRL SCAASGFTFS SYYMSWVRQA PGKGLEWVST ISESGDSTYY   60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 775          moltype = AA   length = 216
FEATURE                 Location/Qualifiers
source                  1..216
                        mol_type = protein
                        organism = synthetic construct
                        note = XENP39266 Chain 3 - PSMB896-HC-G100A[PSMA]_L0 Light
                            Chain
SEQUENCE: 775
QSVLTQPPSV SAAPGQKVTI SCSGSSSNIG INYVSWYQQL PGTAPKLLIY DNNKRPSGIP   60
DRFSGSKSGT SATLGITGLQ TGDEADYYCG TWDSSLSAVV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 776          moltype = AA   length = 449
FEATURE                 Location/Qualifiers
source                  1..449
                        mol_type = protein
                        organism = synthetic construct
                        note = XENP39267 Chain 1 -
                            011A11[PSMA]_H0_IgG1_pI(-)_Isosteric_A_/PVA_/S267K/L368D/K3
                            70S
SEQUENCE: 776
EVQLVESGGG LVKPGGSLRL SCVASGFTFS FYSMNWVRQA PGKGLDWVSS ISSSGNYIYY   60
ADSVKGRFTI SRDNAKNSLH LHMNSLKAED TAMYFCARSY SGSYDAFDFW GQGTMVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                    449

SEQ ID NO: 777          moltype = AA   length = 479
FEATURE                 Location/Qualifiers
source                  1..479
                        mol_type = protein
                        organism = synthetic construct
                        note = XENP39267 Chain 2 -
                            1A7[CD28]_H1L1_scFv(GKPGS)4_Fc(216)_IgG1_C220S/PVA_/S267K/S
                            364K/E357Q
SEQUENCE: 777
EVQLLESGGG LVQPGGSLRL SCAASGFTFS SYAMSWVRQA PGKGLEWVST ISGSGDSTYY   60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QYSTPFTFG    240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 778          moltype = AA   length = 215
FEATURE                 Location/Qualifiers
source                  1..215
                        mol_type = protein
                        organism = synthetic construct
                        note = XENP39267 Chain 3 - 011A11[PSMA]_L0 Light Chain
```

```
SEQUENCE: 778
EIVMTQSPGT LSLSPGERAT LSCRASQSVS SSFLAWYQQK PGQAPRLLIS GASSRATGIP    60
DRFSVSGSGT DFTLTISRLE PEDFAVYYCQ QYGVSPWTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 779           moltype = AA  length = 449
FEATURE                  Location/Qualifiers
source                   1..449
                         mol_type = protein
                         organism = synthetic construct
                         note = XENP39268 Chain 1 -
                           011A11[PSMA]_H0_IgG1_pI(-)_Isosteric_A_/PVA_/S267K/L368D/K3
                           70S
SEQUENCE: 779
EVQLVESGGG LVKPGGSLRL SCVASGFTFS FYSMNWVRQA PGKGLDWVSS ISSSGNYIYY    60
ADSVKGRFTI SRDNAKNSLH LHMNSLKAED TAMYFCARSY SGSYDAFDFW GQGTMVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449

SEQ ID NO: 780           moltype = AA  length = 479
FEATURE                  Location/Qualifiers
source                   1..479
                         mol_type = protein
                         organism = synthetic construct
                         note = XENP39268 Chain 2 -
                           1A7[CD28]_H1.14_L1_scFv(GKPGS)4_Fc(216)_IgG1_C220S/PVA_/S26
                           7K/S364K/E357Q
SEQUENCE: 780
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK   479

SEQ ID NO: 781           moltype = AA  length = 215
FEATURE                  Location/Qualifiers
source                   1..215
                         mol_type = protein
                         organism = synthetic construct
                         note = XENP39268 Chain 3 - 011A11[PSMA]_L0 Light Chain
SEQUENCE: 781
EIVMTQSPGT LSLSPGERAT LSCRASQSVS SSFLAWYQQK PGQAPRLLIS GASSRATGIP    60
DRFSVSGSGT DFTLTISRLE PEDFAVYYCQ QYGVSPWTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 782           moltype = AA  length = 449
FEATURE                  Location/Qualifiers
source                   1..449
                         mol_type = protein
                         organism = synthetic construct
                         note = XENP39269 Chain 1 -
                           011A11[PSMA]_H0_IgG1_pI(-)_Isosteric_A_/PVA_/S267K/L368D/K3
                           70S
SEQUENCE: 782
EVQLVESGGG LVKPGGSLRL SCVASGFTFS FYSMNWVRQA PGKGLDWVSS ISSSGNYIYY    60
ADSVKGRFTI SRDNAKNSLH LHMNSLKAED TAMYFCARSY SGSYDAFDFW GQGTMVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449

SEQ ID NO: 783           moltype = AA  length = 479
FEATURE                  Location/Qualifiers
source                   1..479
                         mol_type = protein
                         organism = synthetic construct
```

|  | note = XENP39269 Chain 2 -<br>1A7[CD28]_H1.1_L1.71_scFv(GKPGS)4_Fc(216)_IgG1_C220S/PVA_/S<br>267K/S364K/E357Q |  |
|---|---|---|
| SEQUENCE: 783 | | |
| EVQLLESGGG | LVQPGGSLRL SCAASGFTFS SYYMSWVRQA PGKGLEWVST ISGSGDSTYY | 60 |
| ADSVKGRFTI | SRDNSKNTLY LQMNSLRAED TAVYYCAKSG PGLRQVGFDY WGQGTLVTVS | 120 |
| SGKPGSGKPG | SGKPGSGKPG SDIQMTQSPS SLSASVGDRV TITCRASQSI SSYLNWYQQK | 180 |
| PGKAPKLLIY | AASSLQSGVP SRFSGSGSGT DFTLTISSLQ PEDFATYYCQ QVYSTPFTFG | 240 |
| QGTKLEIKEP | KSSDKTHTCP PCPAPPVAGP SVFLFPPKPK DTLMISRTPE VTCVVVDVKH | 300 |
| EDPEVKFNWY | VDGVEVHNAK TKPREEQYNS TYRVVSVLTV LHQDWLNGKE YKCKVSNKAL | 360 |
| PAPIEKTISK | AKGQPREPQV YTLPPSREQM TKNQVKLTCL VKGFYPSDIA VEWESNGQPE | 420 |
| NNYKTTPPVL | DSDGSFFLYS KLTVDKSRWQ QGNVFSCSVM HEALHNHYTQ KSLSLSPGK | 479 |

| SEQ ID NO: 784<br>FEATURE<br>source | moltype = AA length = 215<br>Location/Qualifiers<br>1..215<br>mol_type = protein<br>organism = synthetic construct<br>note = XENP39269 Chain 3 - 011A11[PSMA]_L0 Light Chain |  |
|---|---|---|
| SEQUENCE: 784 | | |
| EIVMTQSPGT | LSLSPGERAT LSCRASQSVS SSFLAWYQQK PGQAPRLLIS GASSRATGIP | 60 |
| DRFSVSGSGT | DFTLTISRLE PEDFAVYYCQ QYGVSPWTFG QGTKVEIKRT VAAPSVFIFP | 120 |
| PSDEQLKSGT | ASVVCLLNNF YPREAKVQWK VDNALQSGNS QESVTEQDSK DSTYSLSSTL | 180 |
| TLSKADYEKH | KVYACEVTHQ GLSSPVTKSF NRGEC | 215 |

| SEQ ID NO: 785<br>FEATURE<br>source | moltype = AA length = 449<br>Location/Qualifiers<br>1..449<br>mol_type = protein<br>organism = synthetic construct<br>note = XENP39270 Chain 1 -<br>011A11[PSMA]_H0_IgG1_pI(-)_Isosteric_A_/PVA_/S267K/L368D/K3<br>70S |  |
|---|---|---|
| SEQUENCE: 785 | | |
| EVQLVESGGG | LVKPGGSLRL SCVASGFTFS FYSMNWVRQA PGKGLDWVSS ISSSGNYIYY | 60 |
| ADSVKGRFTI | SRDNAKNSLH LHMNSLKAED TAMYFCARSY SGSYDAFDFW GQGTMVTVSS | 120 |
| ASTKGPSVFP | LAPSSKSTSG GTAALGCLVK DYFPEPVTVS WNSGALTSGV HTFPAVLQSS | 180 |
| GLYSLSSVVT | VPSSSLGTQT YICNVNHKPS DTKVDKKVEP KSCDKTHTCP PCPAPPVAGP | 240 |
| SVFLFPPKPK | DTLMISRTPE VTCVVVDVKH EDPEVKFNWY VDGVEVHNAK TKPREEEYNS | 300 |
| TYRVVSVLTV | LHQDWLNGKE YKCKVSNKAL PAPIEKTISK AKGQPREPQV YTLPPSREEM | 360 |
| TKNQVSLTCD | VSGFYPSDIA VEWESDGQPE NNYKTTPPVL DSDGSFFLYS KLTVDKSRWE | 420 |
| QGDVFSCSVM | HEALHNHYTQ KSLSLSPGK | 449 |

| SEQ ID NO: 786<br>FEATURE<br>source | moltype = AA length = 479<br>Location/Qualifiers<br>1..479<br>mol_type = protein<br>organism = synthetic construct<br>note = XENP39270 Chain 2 -<br>1A7[CD28]_H1.14_L1.71_scFv(GKPGS)4_Fc(216)_IgG1_C220S/PVA_/<br>S267K/S364K/E357Q |  |
|---|---|---|
| SEQUENCE: 786 | | |
| EVQLLESGGG | LVQPGGSLRL SCAASGFTFS SYYMSWVRQA PGKGLEWVST ISESGDSTYY | 60 |
| ADSVKGRFTI | SRDNSKNTLY LQMNSLRAED TAVYYCAKSG PGLRQVGFDY WGQGTLVTVS | 120 |
| SGKPGSGKPG | SGKPGSGKPG SDIQMTQSPS SLSASVGDRV TITCRASQSI SSYLNWYQQK | 180 |
| PGKAPKLLIY | AASSLQSGVP SRFSGSGSGT DFTLTISSLQ PEDFATYYCQ QVYSTPFTFG | 240 |
| QGTKLEIKEP | KSSDKTHTCP PCPAPPVAGP SVFLFPPKPK DTLMISRTPE VTCVVVDVKH | 300 |
| EDPEVKFNWY | VDGVEVHNAK TKPREEQYNS TYRVVSVLTV LHQDWLNGKE YKCKVSNKAL | 360 |
| PAPIEKTISK | AKGQPREPQV YTLPPSREQM TKNQVKLTCL VKGFYPSDIA VEWESNGQPE | 420 |
| NNYKTTPPVL | DSDGSFFLYS KLTVDKSRWQ QGNVFSCSVM HEALHNHYTQ KSLSLSPGK | 479 |

| SEQ ID NO: 787<br>FEATURE<br>source | moltype = AA length = 215<br>Location/Qualifiers<br>1..215<br>mol_type = protein<br>organism = synthetic construct<br>note = XENP39270 Chain 3 - 011A11[PSMA]_L0 Light Chain |  |
|---|---|---|
| SEQUENCE: 787 | | |
| EIVMTQSPGT | LSLSPGERAT LSCRASQSVS SSFLAWYQQK PGQAPRLLIS GASSRATGIP | 60 |
| DRFSVSGSGT | DFTLTISRLE PEDFAVYYCQ QYGVSPWTFG QGTKVEIKRT VAAPSVFIFP | 120 |
| PSDEQLKSGT | ASVVCLLNNF YPREAKVQWK VDNALQSGNS QESVTEQDSK DSTYSLSSTL | 180 |
| TLSKADYEKH | KVYACEVTHQ GLSSPVTKSF NRGEC | 215 |

| SEQ ID NO: 788<br>FEATURE<br>source | moltype = AA length = 449<br>Location/Qualifiers<br>1..449<br>mol_type = protein<br>organism = synthetic construct<br>note = XENP39274 Chain 1 - |  |
|---|---|---|

```
                              P72_A10V2[PSMA]_H0_IgG1_pI(-)_Isosteric_A_/PVA_/S267K/L368D
                              /K370S
SEQUENCE: 788
QVQLVESGGG  VVQPGRSLRL  SCAASGFTFS  SYNMNWVRQA  PGKGLEWVAI  IYYDESNKYY   60
ADSVKGRFTI  SRDISKNTLY  LQMNSLRAED  TAVYYCARER  GRDYYGMDVW  GQGTTVTVSS  120
ASTKGPSVFP  LAPSSKSTSG  GTAALGCLVK  DYFPEPVTVS  WNSGALTSGV  HTFPAVLQSS  180
GLYSLSSVVT  VPSSSLGTQT  YICNVNHKPS  DTKVDKKVEP  KSCDKTHTCP  PCPAPPVAGP  240
SVFLFPPKPK  DTLMISRTPE  VTCVVVDVKH  EDPEVKFNWY  VDGVEVHNAK  TKPREEEYNS  300
TYRVVSVLTV  LHQDWLNGKE  YKCKVSNKAL  PAPIEKTISK  AKGQPREPQV  YTLPPSREEM  360
TKNQVSLTCD  VSGFYPSDIA  VEWESDGQPE  NNYKTTPPVL  DSDGSFFLYS  KLTVDKSRWE  420
QGDVFSCSVM  HEALHNHYTQ  KSLSLSPGK                                      449

SEQ ID NO: 789              moltype = AA   length = 479
FEATURE                     Location/Qualifiers
source                      1..479
                            mol_type = protein
                            organism = synthetic construct
                            note = XENP39274 Chain 2 -
                            1A7[CD28]_L1_H1.14_scFv(GKPGS)4_Fc(216)_IgG1_C220S/PVA_/S26
                            7K/S364K/E357Q
SEQUENCE: 789
DIQMTQSPSS  LSASVGDRVT  ITCRASQSIS  SYLNWYQQKP  GKAPKLLIYA  ASSLQSGVPS   60
RFSGSGSGTD  FTLTISSLQP  EDFATYYCQQ  SYSTPFTFGQ  GTKLEIKGKP  GSGKPGSGKP  120
GSGKPGSEVQ  LLESGGGLVQ  PGGSLRLSCA  ASGFTFSSYY  MSWVRQAPGK  GLEWVSTISE  180
SGDSTYYADS  VKGRFTISRD  NSKNTLYLQM  NSLRAEDTAV  YYCAKSGPGL  RQVGFDYWGQ  240
GTLVTVSSEP  KSSDKTHTCP  PCPAPPVAGP  SVFLFPPKPK  DTLMISRTPE  VTCVVVDVKH  300
EDPEVKFNWY  VDGVEVHNAK  TKPREEQYNS  TYRVVSVLTV  LHQDWLNGKE  YKCKVSNKAL  360
PAPIEKTISK  AKGQPREPQV  YTLPPSREQM  TKNQVKLTCL  VKGFYPSDIA  VEWESNGQPE  420
NNYKTTPPVL  DSDGSFFLYS  KLTVDKSRWQ  QGNVFSCSVM  HEALHNHYTQ  KSLSLSPGK   479

SEQ ID NO: 790              moltype = AA   length = 213
FEATURE                     Location/Qualifiers
source                      1..213
                            mol_type = protein
                            organism = synthetic construct
                            note = XENP39274 Chain 3 - P72_A10V2[PSMA]_L0 Light Chain
SEQUENCE: 790
SYELMQPPSV  SVSPGQTARI  TCSGDALPKQ  YAYWYQQKPG  QAPVLVIYKD  SERPSGIPVR   60
FSGSSSGTTV  TLTITGVQAE  DEADYYCQSA  DSSGTYVFGT  GTKVTVLGQP  KAAPSVTLFP  120
PSSEELQANK  ATLVCLISDF  YPGAVTVAWK  ADSSPVKAGV  ETTTPSKQSN  NKYAASSYLS  180
LTPEQWKSHR  SYSCQVTHEG  STVEKTVAPT  ECS                                 213

SEQ ID NO: 791              moltype = AA   length = 455
FEATURE                     Location/Qualifiers
source                      1..455
                            mol_type = protein
                            organism = synthetic construct
                            note = XENP39275 Chain 1 -
                            P72_D01V2[PSMA]_H0_IgG1_pI(-)_Isosteric_A_/PVA_/S267K/L368D
                            /K370S
SEQUENCE: 791
EVQLVESGGD  LVQPGGSLRL  SCAASGFTFN  NYNMNWVRQA  PGKGLEWVSH  ISTSSSNKYY   60
ADSVKGRFSI  SRDIAKNSMY  LQMNSLRDED  TAVYYCAREG  VGADYGDYYY  YGMDVWGQGT  120
TVTVSSASTK  GPSVFPLAPS  SKSTSGGTAA  LGCLVKDYFP  EPVTVSWNSG  ALTSGVHTFP  180
AVLQSSGLYS  LSSVVTVPSS  SLGTQTYICN  VNHKPSDTKV  DKKVEPKSCD  KTHTCPPCPA  240
PPVAGPSVFL  FPPKPKDTLM  ISRTPEVTCV  VVDVKHEDPE  VKFNWYVDGV  EVHNAKTKPR  300
EEEYNSTYRV  VSVLTVLHQD  WLNGKEYKCK  VSNKALPAPI  EKTISKAKGQ  PREPQVYTLP  360
PSREEMTKNQ  VSLTCDVSGF  YPSDIAVEWE  SDGQPENNYK  TTPPVLDSDG  SFFLYSKLTV  420
DKSRWEQGDV  FSCSVMHEAL  HNHYTQKSLS  LSPGK                               455

SEQ ID NO: 792              moltype = AA   length = 479
FEATURE                     Location/Qualifiers
source                      1..479
                            mol_type = protein
                            organism = synthetic construct
                            note = XENP39275 Chain 2 -
                            1A7[CD28]_L1_H1.14_scFv(GKPGS)4_Fc(216)_IgG1_C220S/PVA_/S26
                            7K/S364K/E357Q
SEQUENCE: 792
DIQMTQSPSS  LSASVGDRVT  ITCRASQSIS  SYLNWYQQKP  GKAPKLLIYA  ASSLQSGVPS   60
RFSGSGSGTD  FTLTISSLQP  EDFATYYCQQ  SYSTPFTFGQ  GTKLEIKGKP  GSGKPGSGKP  120
GSGKPGSEVQ  LLESGGGLVQ  PGGSLRLSCA  ASGFTFSSYY  MSWVRQAPGK  GLEWVSTISE  180
SGDSTYYADS  VKGRFTISRD  NSKNTLYLQM  NSLRAEDTAV  YYCAKSGPGL  RQVGFDYWGQ  240
GTLVTVSSEP  KSSDKTHTCP  PCPAPPVAGP  SVFLFPPKPK  DTLMISRTPE  VTCVVVDVKH  300
EDPEVKFNWY  VDGVEVHNAK  TKPREEQYNS  TYRVVSVLTV  LHQDWLNGKE  YKCKVSNKAL  360
PAPIEKTISK  AKGQPREPQV  YTLPPSREQM  TKNQVKLTCL  VKGFYPSDIA  VEWESNGQPE  420
NNYKTTPPVL  DSDGSFFLYS  KLTVDKSRWQ  QGNVFSCSVM  HEALHNHYTQ  KSLSLSPGK   479

SEQ ID NO: 793              moltype = AA   length = 216
```

```
FEATURE                 Location/Qualifiers
source                  1..216
                        mol_type = protein
                        organism = synthetic construct
                        note = XENP39275 Chain 3 - P72_D01V2[PSMA]_L0 Light Chain
SEQUENCE: 793
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSYTYV FGTGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 794          moltype = AA  length = 451
FEATURE                 Location/Qualifiers
source                  1..451
                        mol_type = protein
                        organism = synthetic construct
                        note = XENP39276 Chain 1 -
                        P72_F07[PSMA]_H0_IgG1_pI(-)_Isosteric_A_/PVA_/S267K/L368D/K
                        370S
SEQUENCE: 794
EVQLVESGGG VVQPGRSLRL SCAASGFTFS SYGMNWVRQA PGKGLEWVAV TSYDGSNKYY    60
ADSVKGRFTI SRDISKNTLY LQMSSLRAED TAVYYCARDP YSSSWNGAFD IWGPGTMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSDTKVDKKV EPKSCDKTHT CPPCPAPPVA   240
GPSVFLFPPK PKDTLMISRT PEVTCVVVDV KHEDPEVKFN WYVDGVEVHN AKTKPREEEY   300
NSTYRVVSVL TVLHQDWLNG KEYKCKVSNK ALPAPIEKTI SKAKGQPREP QVYTLPPSRE   360
EMTKNQVSLT CDVSGFYPSD IAVEWESDGQ PENNYKTTPP VLDSDGSFFL YSKLTVDKSR   420
WEQGDVFSCS VMHEALHNHY TQKSLSLSPG K                                  451

SEQ ID NO: 795          moltype = AA  length = 479
FEATURE                 Location/Qualifiers
source                  1..479
                        mol_type = protein
                        organism = synthetic construct
                        note = XENP39276 Chain 2 -
                        1A7[CD28]_L1_H1.14_scFv(GKPGS)4_Fc(216)_IgG1_C220S/PVA_/S26
                        7K/S364K/E357Q
SEQUENCE: 795
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPFTFGQ GTKLEIKGKP GSGKPGSGKP   120
GSGKPGSEVQ LLESGGGLVQ PGGSLRLSCA ASGFTFSSYY MSWVRQAPGK GLEWVSTISE   180
SGDSTYYADS VKGRFTISRD NSKNTLYLQM NSLRAEDTAV YYCAKSGPGL RQVGFDYWGQ   240
GTLVTVSSEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 796          moltype = AA  length = 214
FEATURE                 Location/Qualifiers
source                  1..214
                        mol_type = protein
                        organism = synthetic construct
                        note = XENP39276 Chain 3 - P72_F07[PSMA]_L0 Light Chain
SEQUENCE: 796
SYELTQPPSV SVAPGQTARI TCGGNNIGSK SVHWYQQKPG QAPVLVVYDD SDRPSGIPER    60
FSGSNSGNTA TLTISRVEAG DEADYYCQVW DSSTDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 797          moltype = AA  length = 449
FEATURE                 Location/Qualifiers
source                  1..449
                        mol_type = protein
                        organism = synthetic construct
                        note = XENP39277 Chain 1 -
                        P72_A10V2[PSMA]_H0_IgG1_pI(-)_Isosteric_A_/PVA_/S267K/L368D
                        /K370S
SEQUENCE: 797
QVQLVESGGG VVQPGRSLRL SCAASGFTFS SYNMNWVRQA PGKGLEWVAI IYYDESNKYY    60
ADSVKGRFTI SRDISKNTLY LQMNSLRAED TAVYYCARER GRDYYGMDVW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449

SEQ ID NO: 798          moltype = AA  length = 479
FEATURE                 Location/Qualifiers
```

```
source                    1..479
                          mol_type = protein
                          organism = synthetic construct
                          note = XENP39277 Chain 2 -
                          1A7[CD28]_L1.71_H1.14_scFv(GKPGS)4_Fc(216)_IgG1_C220S/PVA_/
                          S267K/S364K/E357Q
SEQUENCE: 798
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ VYSTPFTFGQ GTKLEIKGKP GSGKPGSGKP   120
GSGKPGSEVQ LLESGGGLVQ PGGSLRLSCA ASGFTSSYY  MSWVRQAPGK GLEWVSTISE   180
SGDSTYYADS VKGRFTISRD NSKNTLYLQM NSLRAEDTAV YYCAKSGPGL RQVGFDYWGQ   240
GTLVTVSSEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 799            moltype = AA  length = 213
FEATURE                   Location/Qualifiers
source                    1..213
                          mol_type = protein
                          organism = synthetic construct
                          note = XENP39277 Chain 3 - P72_A10V2[PSMA]_L0 Light Chain
SEQUENCE: 799
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                                213

SEQ ID NO: 800            moltype = AA  length = 455
FEATURE                   Location/Qualifiers
source                    1..455
                          mol_type = protein
                          organism = synthetic construct
                          note = XENP39278 Chain 1 -
                          P72_D01V2[PSMA]_H0_IgG1_pI(-)_Isosteric_A_/PVA_/S267K/L368D
                          /K370S
SEQUENCE: 800
EVQLVESGGD LVQPGGSLRL SCAASGFTFN NYNMNWVRQA PGKGLEWVSH ISTSSSNKYY    60
ADSVKGRFSI SRDIAKNSMY LQMNSLRDED TAVYYCAREG VGADYGDYYY YGMDVWGQGT   120
TVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSDTKV DKKVEPKSCD KTHTCPPCPA   240
PPVAGPSVFL FPPKPKDTLM ISRTPEVTCV VVDVKHEDPE VKFNWYVDGV EVHNAKTKPR   300
EEEYNSTYRV VSVLTVLHQD WLNGKEYKCK VSNKALPAPI EKTISKAKGQ PREPQVYTLP   360
PSREEMTKNQ VSLTCDVSGF YPSDIAVEWE SDGQPENNYK TTPPVLDSDG SFFLYSKLTV   420
DKSRWEQGDV FSCSVMHEAL HNHYTQKSLS LSPGK                              455

SEQ ID NO: 801            moltype = AA  length = 479
FEATURE                   Location/Qualifiers
source                    1..479
                          mol_type = protein
                          organism = synthetic construct
                          note = XENP39278 Chain 2 -
                          1A7[CD28]_L1.71_H1.14_scFv(GKPGS)4_Fc(216)_IgG1_C220S/PVA_/
                          S267K/S364K/E357Q
SEQUENCE: 801
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ VYSTPFTFGQ GTKLEIKGKP GSGKPGSGKP   120
GSGKPGSEVQ LLESGGGLVQ PGGSLRLSCA ASGFTSSYY  MSWVRQAPGK GLEWVSTISE   180
SGDSTYYADS VKGRFTISRD NSKNTLYLQM NSLRAEDTAV YYCAKSGPGL RQVGFDYWGQ   240
GTLVTVSSEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 802            moltype = AA  length = 216
FEATURE                   Location/Qualifiers
source                    1..216
                          mol_type = protein
                          organism = synthetic construct
                          note = XENP39278 Chain 3 - P72_D01V2[PSMA]_L0 Light Chain
SEQUENCE: 802
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSYTYV FGTGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 803            moltype = AA  length = 451
FEATURE                   Location/Qualifiers
```

| | | |
|---|---|---|
| source | 1..451<br>mol_type = protein<br>organism = synthetic construct<br>note = XENP39279 Chain 1 -<br>P72_F07[PSMA]_H0_IgG1_pI(-)_Isosteric_A_/PVA_/S267K/L368D/K<br>370S | |
| SEQUENCE: 803 | | |
| EVQLVESGGG | VVQPGRSLRL SCAASGFTFS SYGMNWVRQA PGKGLEWVAV TSYDGSNKYY | 60 |
| ADSVKGRFTI | SRDISKNTLY LQMSSLRAED TAVYYCARDP YSSSWNGAFD IWGPGTMVTV | 120 |
| SSASTKGPSV | FPLAPSSKST SGGTAALGCL VKDYFPEPVT VSWNSGALTS GVHTFPAVLQ | 180 |
| SSGLYSLSSV | VTVPSSSLGT QTYICNVNHK PSDKTVDKKV EPKSCDKTHT CPPCPAPPVA | 240 |
| GPSVFLFPPK | PKDTLMISRT PEVTCVVVDV KHEDPEVKFN WYVDGVEVHN AKTKPREEEY | 300 |
| NSTYRVVSVL | TVLHQDWLNG KEYKCKVSNK ALPAPIEKTI SKAKGQPREP QVYTLPPSRE | 360 |
| EMTKNQVSLT | CDVSGFYPSD IAVEWESDGQ PENNYKTTPP VLDSDGSFFL YSKLTVDKSR | 420 |
| WEQGDVFSCS | VMHEALHNHY TQKSLSLSPG K | 451 |
| | | |
| SEQ ID NO: 804 | moltype = AA length = 479 | |
| FEATURE | Location/Qualifiers | |
| source | 1..479<br>mol_type = protein<br>organism = synthetic construct<br>note = XENP39279 Chain 2 -<br>1A7[CD28]_L1.71_H1.14_scFv(GKPGS)4_Fc(216)_IgG1_C220S/PVA_/<br>S267K/S364K/E357Q | |
| SEQUENCE: 804 | | |
| DIQMTQSPSS | LSASVGDRVT ITCRASQSIS SYLNWYQQKP GKAPKLLIYA ASSLQSGVPS | 60 |
| RFSGSGSGTD | FTLTISSLQP EDFATYYCQQ VYSTPFTFGQ GTKLEIKGKP GSGKPGSGKP | 120 |
| GSGKPGSEVQ | LLESGGGLVQ PGGSLRLSCA ASGFTFSSYY MSWVRQAPGK GLEWVSTISE | 180 |
| SGDSTYYADS | VKGRFTISRD NSKNTLYLQM NSLRAEDTAV YYCAKSGPGL RQVGFDYWGQ | 240 |
| GTLVTVSSEP | KSSDKTHTCP PCPAPPVAGP SVFLFPPKPK DTLMISRTPE VTCVVVDVKH | 300 |
| EDPEVKFNWY | VDGVEVHNAK TKPREEQYNS TYRVVSVLTV LHQDWLNGKE YKCKVSNKAL | 360 |
| PAPIEKTISK | AKGQPREPQV YTLPPSREQM TKNQVKLTCL VKGFYPSDIA VEWESNGQPE | 420 |
| NNYKTTPPVL | DSDGSFFLYS KLTVDKSRWQ QGNVFSCSVM HEALHNHYTQ KSLSLSPGK | 479 |
| | | |
| SEQ ID NO: 805 | moltype = AA length = 214 | |
| FEATURE | Location/Qualifiers | |
| source | 1..214<br>mol_type = protein<br>organism = synthetic construct<br>note = XENP39279 Chain 3 - P72_F07[PSMA]_L0 Light Chain | |
| SEQUENCE: 805 | | |
| SYELTQPPSV | SVAPGQTARI TCGGNNIGSK SVHWYQQKPG QAPVLVVYDD SDRPSGIPER | 60 |
| FSGSNSGNTA | TLTISRVEAG DEADYYCQVW DSSTDHVVFG GGTKLTVLGQ PKAAPSVTLF | 120 |
| PPSSEELQAN | KATLVCLISD FYPGAVTVAW KADSSPVKAG VETTTPSKQS NNKYAASSYL | 180 |
| SLTPEQWKSH | RSYSCQVTHE GSTVEKTVAP TECS | 214 |
| | | |
| SEQ ID NO: 806 | moltype = AA length = 449 | |
| FEATURE | Location/Qualifiers | |
| source | 1..449<br>mol_type = protein<br>organism = synthetic construct<br>note = XENP40470 Chain 1 -<br>P72_A10V2[PSMA]_H0_IgG1_pI(-)_Isosteric_A_/PVA_/S267K/L368D<br>/K370S | |
| SEQUENCE: 806 | | |
| QVQLVESGGG | VVQPGRSLRL SCAASGFTFS SYNMNWVRQA PGKGLEWVAI IYYDESNKYY | 60 |
| ADSVKGRFTI | SRDISKNTLY LQMNSLRAED TAVYYCARER GRDYYGMDVW GQGTTVTVSS | 120 |
| ASTKGPSVFP | LAPSSKSTSG GTAALGCLVK DYFPEPVTVS WNSGALTSGV HTFPAVLQSS | 180 |
| GLYSLSSVVT | VPSSSLGTQT YICNVNHKPS DKTVDKKVEP KSCDKTHTCP PCPAPPVAGP | 240 |
| SVFLFPPKPK | DTLMISRTPE VTCVVVDVKH EDPEVKFNWY VDGVEVHNAK TKPREEEYNS | 300 |
| TYRVVSVLTV | LHQDWLNGKE YKCKVSNKAL PAPIEKTISK AKGQPREPQV YTLPPSREEM | 360 |
| TKNQVSLTCD | VSGFYPSDIA VEWESDGQPE NNYKTTPPVL DSDGSFFLYS KLTVDKSRWE | 420 |
| QGDVFSCSVM | HEALHNHYTQ KSLSLSPGK | 449 |
| | | |
| SEQ ID NO: 807 | moltype = AA length = 479 | |
| FEATURE | Location/Qualifiers | |
| source | 1..479<br>mol_type = protein<br>organism = synthetic construct<br>note = XENP40470 Chain 2 -<br>1A7[CD28]_H1.1_L1_scFv(GKPGS)4_Fc(216)_IgG1_C220S/PVA_/S267<br>K/S364K/E357Q | |
| SEQUENCE: 807 | | |
| EVQLLESGGG | LVQPGGSLRL SCAASGFTFS SYYMSWVRQA PGKGLEWVST ISGSGDSTYY | 60 |
| ADSVKGRFTI | SRDNSKNTLY LQMNSLRAED TAVYYCAKSG PGLRQVGFDY WGQGTLVTVS | 120 |
| SGKPGSGKPG | SGKPGSGKPG SDIQMTQSPS SLSASVGDRV TITCRASQSI SSYLNWYQQK | 180 |
| PGKAPKLLIY | AASSLQSGVP SRFSGSGSGT DFTLTISSLQ PEDFATYYCQ QSYSTPFTFG | 240 |
| QGTKLEIKEP | KSSDKTHTCP PCPAPPVAGP SVFLFPPKPK DTLMISRTPE VTCVVVDVKH | 300 |
| EDPEVKFNWY | VDGVEVHNAK TKPREEQYNS TYRVVSVLTV LHQDWLNGKE YKCKVSNKAL | 360 |

```
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 808          moltype = AA  length = 213
FEATURE                 Location/Qualifiers
source                  1..213
                        mol_type = protein
                        organism = synthetic construct
                        note = XENP40470 Chain 3 - P72_A10V2[PSMA]_L0 Light Chain
SEQUENCE: 808
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVLGQP KAAPSVTLFP    120
PSSEELQANK ATLVCLISDF YPGAVTVAWK ADSSPVKAGV ETTTPSKQSN NKYAASSYLS    180
LTPEQWKSHR SYSCQVTHEG STVEKTVAPT ECS                                213

SEQ ID NO: 809          moltype = AA  length = 455
FEATURE                 Location/Qualifiers
source                  1..455
                        mol_type = protein
                        organism = synthetic construct
                        note = XENP41406 Chain 1 -
                        P72_D01[PSMA]_H0_IgG1_pI(-)_Isosteric_A_/PVA_/S267K/L368D/K
                        370S
SEQUENCE: 809
EVQLVESGGD LVQPGGSLRL SCAASGFTFN NYNMNWVRQA PGKGLEWVSH ISTSSSNKYY    60
ADSVKGRFSI SRDIAKNSMY LQMNSLRDED TAVYYCARDG VGADYGDYYY YGMDVWGQGT    120
TVTVSSASTK GPSVFPLAPS SKSTSGGTAA LGCLVKDYFP EPVTVSWNSG ALTSGVHTFP    180
AVLQSSGLYS LSSVVTVPSS SLGTQTYICN VNHKPSDTKV DKKVEPKSCD KTHTCPPCPA    240
PPVAGPSVFL FPPKPKDTLM ISRTPEVTCV VVDVKHEDPE VKFNWYVDGV EVHNAKTKPR    300
EEEYNSTYRV VSVLTVLHQD WLNGKEYKCK VSNKALPAPI EKTISKAKGQ PREPQVYTLP    360
PSREEMTKNQ VSLTCDVSGF YPSDIAVEWE SDGQPENNYK TTPPVLDSDG SFFLYSKLTV    420
DKSRWEQGDV FSCSVMHEAL HNHYTQKSLS LSPGK                              455

SEQ ID NO: 810          moltype = AA  length = 479
FEATURE                 Location/Qualifiers
source                  1..479
                        mol_type = protein
                        organism = synthetic construct
                        note = XENP41406 Chain 2 -
                        1A7[CD28]_L1.71_H1_scFv(GKPGS)4_Fc(216)_IgG1_C220S/PVA_/S26
                        7K/S364K/E357Q
SEQUENCE: 810
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ VYSTPFTFGQ GTKLEIKGKP GSGKPGSGKP    120
GSGKPGSGEV QLLESGGGLV QPGGSLRLSCA ASGFTFSSYA MSWVRQAPGK GLEWVSTISG    180
SGDSTYYADS VKGRFTISRD NSKNTLYLQM NSLRAEDTAV YYCAKSGPGL RQVGFDYWGQ    240
GTLVTVSSEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 811          moltype = AA  length = 216
FEATURE                 Location/Qualifiers
source                  1..216
                        mol_type = protein
                        organism = synthetic construct
                        note = XENP41406 Chain 3 - P72_D01[PSMA]_L0 Light Chain
SEQUENCE: 811
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSYTYV FGTGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                             216

SEQ ID NO: 812          moltype = AA  length = 450
FEATURE                 Location/Qualifiers
source                  1..450
                        mol_type = protein
                        organism = synthetic construct
                        note = XENP42268 Chain 1 - C28PB247
                        (PSMB896-HC-G100A[PSMA]_H0_IgG1_pI(-)_Isosteric_A_/S26
                        7K/L368D/K370S
SEQUENCE: 812
EVQLVESGGG LVQPGGSLRL SCAASGFTFS SYAMSWVRQA PGKGLEWVSA ISGGIGSTYY    60
ADSVKGRFTI SRDNSKNTLW LQMNSLRAED TAVYYCAKDA VGATPYYFDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SDTKVDKKVE PKSCDKTHTC PPCPAPPVAG    240
PSVFLFPPKP KDTLMISRTP EVTCVVVDVK HEDPEVKFNW YVDGVEVHNA KTKPREEEYN    300
```

```
STYRVVSVLT VLHQDWLNGK EYKCKVSNKA LPAPIEKTIS KAKGQPREPQ VYTLPPSREE    360
MTKNQVSLTC DVSGFYPSDI AVEWESDGQP ENNYKTTPPV LDSDGSFFLY SKLTVDKSRW    420
EQGDVFSCSV MHEALHNHYT QKSLSLSPGK                                    450

SEQ ID NO: 813          moltype = AA   length = 479
FEATURE                 Location/Qualifiers
source                  1..479
                        mol_type = protein
                        organism = synthetic construct
                        note = XENP42268 Chain 2 -
                        1A7[CD28]_H1_L1.71_scFv(GKPGS)4_Fc(216)_IgG1_C220S/PVA_/S26
                        7K/S364K/E357Q)
SEQUENCE: 813
EVQLLESGGG LVQPGGSLRL SCAASGFTFS SYAMSWVRQA PGKGLEWVST ISGSGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPPVAGP SVFLFPPKPK DTLMISRTPE VTCVVVDVKH    300
EDPEVKFNWY VDGVEVHNAK TKPREEQYNS TYRVVSVLTV LHQDWLNGKE YKCKVSNKAL    360
PAPIEKTISK AKGQPREPQV YTLPPSREQM TKNQVKLTCL VKGFYPSDIA VEWESNGQPE    420
NNYKTTPPVL DSDGSFFLYS KLTVDKSRWQ QGNVFSCSVM HEALHNHYTQ KSLSLSPGK     479

SEQ ID NO: 814          moltype = AA   length = 216
FEATURE                 Location/Qualifiers
source                  1..216
                        mol_type = protein
                        organism = synthetic construct
                        note = XENP42268 Chain 3 - PSMB896-HC-G100A[PSMA]_L0 Light
                         Chain
SEQUENCE: 814
QSVLTQPPSV SAAPGQKVTI SCSGSSSNIG INYVSWYQQL PGTAPKLLIY DNNKRPSGIP     60
DRFSGSKSGT SATLGITGLQ TGDEADYYCG TWDSSLSAVV FGGGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                             216

SEQ ID NO: 815          moltype = AA   length = 478
FEATURE                 Location/Qualifiers
source                  1..478
                        mol_type = protein
                        organism = synthetic construct
                        note = C28PB405 Chain 1 - 1A7[CD28]_h1.14_l1-spFv
SEQUENCE: 815
EVQLLESGGG LVQPGGSLRL SCAASGFTFS SYAMSWVRQA PGCGLEWVST ISGSGDSTYY     60
ADSVKGRFTI SRDNSKNTLY LQMNSLRAED TAVYYCAKSG PGLRQVGFDY WGQGTLVTVS    120
SGGGSGGSGG CPPCGGSGGD IQMTQSPSSL SASVGDRVTI TCRASQSISS YLNWYQQKPG    180
KAPKLLIYAA SSLQSGVPSR FSGSGSGTDF TLTISSLQPE DFATYYCQQS YSTPFTFGCG    240
TKLEIKEPKS SDKTHTCPPC PAPEAAGGPS VFLFPPKPKD TLMISRTPEV TCVVVSVSHE    300
DPEVKFNWYV DGVEVHNAKT KPREEQYNST YRVVSVLTVL HQDWLNGKEY KCKVSNKALP    360
APIEKTISKA KGQPREPQVY TLPPSREEMT KNQVSLWCLV KGFYPSDIAV EWESNGQPEN    420
NYKTTPPVLD SDGSFFLYSK LTVDKSRWQQ GNVFSCSVMH EALHNHYTQK SLSLSPGK      478

SEQ ID NO: 816          moltype = AA   length = 450
FEATURE                 Location/Qualifiers
source                  1..450
                        mol_type = protein
                        organism = synthetic construct
                        note = C28PB405 Chain 2 - HC1 (AAS_knob3): P72_A10V2
SEQUENCE: 816
QVQLVESGGG VVQPGRSLRL SCAASGFTFS SYNMNWVRQA PGKGLEWVAI IYYDESNKYY     60
ADSVKGRFTI SRDISKNTLY LQMNSLRAED TAVYYCARER GRDYYGMDVW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPEAAGG    240
PSVFLFPPKP KDTLMISRTP EVTCVVVSVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLSC AVKGFYPSDI AVEWESNGQP ENNYKTTPPV LDSDGSFFLV SKLTVDKSRW    420
QQGNVFSCSV MHEALHNRFT QKSLSLSPGK                                    450

SEQ ID NO: 817          moltype = AA   length = 213
FEATURE                 Location/Qualifiers
source                  1..213
                        mol_type = protein
                        organism = synthetic construct
                        note = C28PB405 Chain 3 - LC: P72_A10V2
SEQUENCE: 817
SYELMQPPSV SVSPGQTARI TCSGDALPKQ YAYWYQQKPG QAPVLVIYKD SERPSGIPVR     60
FSGSSSGTTV TLTITGVQAE DEADYYCQSA DSSGTYVFGT GTKVTVLGQP KAAPSVTLFP    120
PSSEELQANK ATLVCLISDF YPGAVTVAWK ADSSPVKAGV ETTTPSKQSN NKYAASSYLS    180
LTPEQWKSHR SYSCQVTHEG STVEKTVAPT ECS                                213
```

| | | |
|---|---|---|
| SEQ ID NO: 818 | moltype = AA length = 478 | |
| FEATURE | Location/Qualifiers | |
| source | 1..478 | |
| | mol_type = protein | |
| | organism = synthetic construct | |
| | note = C28PB404 Chain 1 - 1A7[CD28]_h1.14_l1-spFv | |
| SEQUENCE: 818 | | |
| EVQLLESGGG LVQPGGSLRL SCAASGFTFS SYAMSWVRQA PGCGLEWVST ISGSGDSTYY | | 60 |
| ADSVKGRFTI SRDNSKNTLY LQMNSLRAED TAVYYCAKSG PGLRQVGFDY WGQGTLVTVS | | 120 |
| SGGGSGGSGG CPPCGGSGGD IQMTQSPSSL SASVGDRVTI TCRASQSISS YLNWYQQKPG | | 180 |
| KAPKLLIYAA SSLQSGVPSR FSGSGSGTDF TLTISSLQPE DFATYYCQQS YSTPFTFGCG | | 240 |
| TKLEIKEPKS SDKTHTCPPC PAPEAAGGPS VFLFPPKPKD TLMISRTPEV TCVVVSVSHE | | 300 |
| DPEVKFNWYV DGVEVHNAKT KPREEQYNST YRVVSVLTVL HQDWLNGKEY KCKVSNKALP | | 360 |
| APIEKTISKA KGQPREPQVY TLPPSREEMT KNQVSLWCLV KGFYPSDIAV EWESNGQPEN | | 420 |
| NYKTTPPVLD SDGSFFLYSK LTVDKSRWQQ GNVFSCSVMH EALHNHYTQK SLSLSPGK | | 478 |
| | | |
| SEQ ID NO: 819 | moltype = AA length = 451 | |
| FEATURE | Location/Qualifiers | |
| source | 1..451 | |
| | mol_type = protein | |
| | organism = synthetic construct | |
| | note = C28PB404 Chain 2 - HC1 (AAS_knob3): PSMB896-G100A | |
| SEQUENCE: 819 | | |
| EVQLVESGGG LVQPGGSLRL SCAASGFTFS SYAMSWVRQA PGKGLEWVSA ISGGIGSTYY | | 60 |
| ADSVKGRFTI SRDNSKNTLW LQMNSLRAED TAVYYCAKDA VGATPYYFDY WGQGTLVTVS | | 120 |
| SASTKGPSVF PLAPSSKSTS GGTAALGCLV KDYFPEPVTV SWNSGALTSG VHTFPAVLQS | | 180 |
| SGLYSLSSVV TVPSSSLGTQ TYICNVNHKP SNTKVDKKVE PKSCDKTHTC PPCPAPEAAG | | 240 |
| GPSVFLFPPK PKDTLMISRT PEVTCVVVSV SHEDPEVKFN WYVDGVEVHN AKTKPREEQY | | 300 |
| NSTYRVVSVL TVLHQDWLNG KEYKCKVSNK ALPAPIEKTI SKAKGQPREP QVYTLPPSRE | | 360 |
| EMTKNQVSLS CAVKGFYPSD IAVEWESNGQ PENNYKTTPP VLDSDGSFFL VSKLTVDKSR | | 420 |
| WQQGNVFSCS VMHEALHNRF TQKSLSLSPG K | | 451 |
| | | |
| SEQ ID NO: 820 | moltype = AA length = 216 | |
| FEATURE | Location/Qualifiers | |
| source | 1..216 | |
| | mol_type = protein | |
| | organism = synthetic construct | |
| | note = C28PB404 Chain 3 - LC: PSMB896-G100A | |
| SEQUENCE: 820 | | |
| QSVLTQPPSV SAAPGQKVTI SCSGSSSNIG INYVSWYQQL PGTAPKLLIY DNNKRPSGIP | | 60 |
| DRFSGSKSGT SATLGITGLQ TGDEADYYCG TWDSSLSAVV FGGGTKLTVL GQPKAAPSVT | | 120 |
| LFPPSSEELQ ANKATLVCLI SDFYPGAVTV AWKADSSPVK AGVETTTPSK QSNNKYAASS | | 180 |
| YLSLTPEQWK SHRSYSCQVT HEGSTVEKTV APTECS | | 216 |
| | | |
| SEQ ID NO: 821 | moltype = AA length = 478 | |
| FEATURE | Location/Qualifiers | |
| source | 1..478 | |
| | mol_type = protein | |
| | organism = synthetic construct | |
| | note = C28PB403 Chain 1 - 1A7_H1.1_L1-spFv | |
| SEQUENCE: 821 | | |
| EVQLLESGGG LVQPGGSLRL SCAASGFTFS SYYMSWVRQA PGCGLEWVST ISGSGDSTYY | | 60 |
| ADSVKGRFTI SRDNSKNTLY LQMNSLRAED TAVYYCAKSG PGLRQVGFDY WGQGTLVTVS | | 120 |
| SGGGSGGSGG CPPCGGSGGD IQMTQSPSSL SASVGDRVTI TCRASQSISS YLNWYQQKPG | | 180 |
| KAPKLLIYAA SSLQSGVPSR FSGSGSGTDF TLTISSLQPE DFATYYCQQS YSTPFTFGCG | | 240 |
| TKLEIKEPKS SDKTHTCPPC PAPEAAGGPS VFLFPPKPKD TLMISRTPEV TCVVVSVSHE | | 300 |
| DPEVKFNWYV DGVEVHNAKT KPREEQYNST YRVVSVLTVL HQDWLNGKEY KCKVSNKALP | | 360 |
| APIEKTISKA KGQPREPQVY TLPPSREEMT KNQVSLWCLV KGFYPSDIAV EWESNGQPEN | | 420 |
| NYKTTPPVLD SDGSFFLYSK LTVDKSRWQQ GNVFSCSVMH EALHNHYTQK SLSLSPGK | | 478 |
| | | |
| SEQ ID NO: 822 | moltype = AA length = 450 | |
| FEATURE | Location/Qualifiers | |
| source | 1..450 | |
| | mol_type = protein | |
| | organism = synthetic construct | |
| | note = C28PB403 Chain 2 - HC1 (AAS_knob3): P72_A10V2 | |
| SEQUENCE: 822 | | |
| QVQLVESGGG VVQPGRSLRL SCAASGFTFS SYNMNWVRQA PGKGLEWVAI IYYDESNKYY | | 60 |
| ADSVKGRFTI SRDISKNTLY LQMNSLRAED TAVYYCARER GRDYYGMDVW GQGTTVTVSS | | 120 |
| ASTKGPSVFP LAPSSKSTSG GTAALGCLVK DYFPEPVTVS WNSGALTSGV HTFPAVLQSS | | 180 |
| GLYSLSSVVT VPSSSLGTQT YICNVNHKPS NTKVDKKVEP KSCDKTHTCP PCPAPEAAGG | | 240 |
| PSVFLFPPKP KDTLMISRTP EVTCVVVSVS HEDPEVKFNW YVDGVEVHNA KTKPREEQYN | | 300 |
| STYRVVSVLT VLHQDWLNGK EYKCKVSNKA LPAPIEKTIS KAKGQPREPQ VYTLPPSREE | | 360 |
| MTKNQVSLSC AVKGFYPSDI AVEWESNGQP ENNYKTTPPV LDSDGSFFLV SKLTVDKSRW | | 420 |
| QQGNVFSCSV MHEALHNRFT QKSLSLSPGK | | 450 |
| | | |
| SEQ ID NO: 823 | moltype = AA length = 213 | |
| FEATURE | Location/Qualifiers | |

```
source                  1..213
                        mol_type = protein
                        organism = synthetic construct
                        note = C28PB403 Chain 3 - LC:  P72_A10V2
SEQUENCE: 823
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                                213

SEQ ID NO: 824          moltype = AA  length = 478
FEATURE                 Location/Qualifiers
source                  1..478
                        mol_type = protein
                        organism = synthetic construct
                        note = C28PB402 Chain 1 - 1A7_H1.1_L1-spFv
SEQUENCE: 824
EVQLLESGGG LVQPGGSLRL SCAASGFTFS SYYMSWVRQA PGCGLEWVST ISGSGDSTYY    60
ADSVKGRFTI SRDNSKNTLY LQMNSLRAED TAVYYCAKSG PGLRQVGFDY WGQGTLVTVS   120
SGGGSGGSGG CPPCGGSGGD IQMTQSPSSL SASVGDRVTI TCRASQSISS YLNWYQQKPG   180
KAPKLLIYAA SSLQSGVPSR FSGSGSGTDF TLTISSLQPE DFATYYCQQS YSTPFTFGCG   240
TKLEIKEPKS SDKTHTCPPC PAPEAAGGPS VFLFPPKPKD TLMISRTPEV TCVVVSVSHE   300
DPEVKFNWYV DGVEVHNAKT KPREEQYNST YRVVSVLTVL HQDWLNGKEY KCKVSNKALP   360
APIEKTISKA KGQPREPQVY TLPPSREEMT KNQVSLWCLV KGFYPSDIAV EWESNGQPEN   420
NYKTTPPVLD SDGSFFLYSK LTVDKSRWQQ GNVFSCSVMH EALHNHYTQK SLSLSPGK     478

SEQ ID NO: 825          moltype = AA  length = 451
FEATURE                 Location/Qualifiers
source                  1..451
                        mol_type = protein
                        organism = synthetic construct
                        note = C28PB402 Chain 2 - HC1 (AAS_knob3): PSMB896-G100A
SEQUENCE: 825
EVQLVESGGG LVQPGGSLRL SCAASGFTFS SYAMSWVRQA PGKGLEWVSA ISGGIGSTYY    60
ADSVKGRFTI SRDNSKNTLW LQMNSLRAED TAVYYCAKDA VGATPYYFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVSV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLS CAVKGFYPSD IAVEWESNGQ PENNYKTTPP VLDSDGSFFL VSKLTVDKSR   420
WQQGNVFSCS VMHEALHNRF TQKSLSLSPG K                                  451

SEQ ID NO: 826          moltype = AA  length = 216
FEATURE                 Location/Qualifiers
source                  1..216
                        mol_type = protein
                        organism = synthetic construct
                        note = C28PB402 Chain 3 - LC: PSMB896-G100A
SEQUENCE: 826
QSVLTQPPSV SAAPGQKVTI SCSGSSSNIG INYVSWYQQL PGTAPKLLIY DNNKRPSGIP    60
DRFSGSKSGT SATLGITGLQ TGDEADYYCG TWDSSLSAVV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 827          moltype = AA  length = 478
FEATURE                 Location/Qualifiers
source                  1..478
                        mol_type = protein
                        organism = synthetic construct
                        note = C28PB401 Chain 1 - 1A7[CD28]_h1.14_l1-spFv
SEQUENCE: 827
EVQLLESGGG LVQPGGSLRL SCAASGFTFS SYYMSWVRQA PGCGLEWVST ISESGDSTYY    60
ADSVKGRFTI SRDNSKNTLY LQMNSLRAED TAVYYCAKSG PGLRQVGFDY WGQGTLVTVS   120
SGGGSGGSGG CPPCGGSGGD IQMTQSPSSL SASVGDRVTI TCRASQSISS YLNWYQQKPG   180
KAPKLLIYAA SSLQSGVPSR FSGSGSGTDF TLTISSLQPE DFATYYCQQS YSTPFTFGCG   240
TKLEIKEPKS SDKTHTCPPC PAPEAAGGPS VFLFPPKPKD TLMISRTPEV TCVVVSVSHE   300
DPEVKFNWYV DGVEVHNAKT KPREEQYNST YRVVSVLTVL HQDWLNGKEY KCKVSNKALP   360
APIEKTISKA KGQPREPQVY TLPPSREEMT KNQVSLWCLV KGFYPSDIAV EWESNGQPEN   420
NYKTTPPVLD SDGSFFLYSK LTVDKSRWQQ GNVFSCSVMH EALHNHYTQK SLSLSPGK     478

SEQ ID NO: 828          moltype = AA  length = 450
FEATURE                 Location/Qualifiers
source                  1..450
                        mol_type = protein
                        organism = synthetic construct
                        note = C28PB401 Chain 2 - HC1 (AAS_knob3): P72_A10V2
SEQUENCE: 828
QVQLVESGGG VVQPGRSLRL SCAASGFTFS SYNMWVRQA PGKGLEWVAI IYYDESNKYY     60
ADSVKGRFTI SRDISKNTLY LQMNSLRAED TAVYYCARER GRDYYGMDVW GQGTTVTVSS   120
```

```
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVSVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLSC AVKGFYPSDI AVEWESNGQP ENNYKTTPPV LDSDGSFFLV SKLTVDKSRW   420
QQGNVFSCSV MHEALHNRFT QKSLSLSPGK                                   450

SEQ ID NO: 829         moltype = AA  length = 213
FEATURE                Location/Qualifiers
source                 1..213
                       mol_type = protein
                       organism = synthetic construct
                       note = C28PB401 Chain 3 - LC: P72_A10V2
SEQUENCE: 829
SYELMQPPSV SVSPGQTARI TCSGDALPKQ YAYWYQQKPG QAPVLVIYKD SERPSGIPVR   60
FSGSSSGTTV TLTITGVQAE DEADYYCQSA DSSGTYVFGT GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                               213

SEQ ID NO: 830         moltype = AA  length = 478
FEATURE                Location/Qualifiers
source                 1..478
                       mol_type = protein
                       organism = synthetic construct
                       note = C28PB400 Chain 1 - 1A7[CD28]_H1_L1.71-spFv
SEQUENCE: 830
EVQLLESGGG LVQPGGSLRL SCAASGFTFS SYAMSWVRQA PGCGLEWVST ISGSGDSTYY   60
ADSVKGRFTI SRDNSKNTLY LQMNSLRAED TAVYYCAKSG PGLRQVGFDY WGQGTLVTVS   120
SGGGGSGGSG CPPCGGSGGD IQMTQSPSSL SASVGDRVTI TCRASQSISS YLNWYQQKPG   180
KAPKLLIYAA SSLQSGVPSR FSGSGSGTDF TLTISSLQPE DFATYYCQQV YSTPFTFGCG   240
TKLEIKEPKS SDKTHTCPPC PAPEAAGPS VFLFPPKPKD TLMISRTPEV TCVVVSVSHE   300
DPEVKFNWYV DGVEVHNAKT KPREEQYNST YRVVSVLTVL HQDWLNGKEY KCKVSNKALP   360
APIEKTISKA KGQPREPQVY TLPPSREEMT KNQVSLWCLV KGFYPSDIAV EWESNGQPEN   420
NYKTTPPVLD SDGSFFLYSK LTVDKSRWQQ GNVFSCSVMH EALHNHYTQK SLSLSPGK    478

SEQ ID NO: 831         moltype = AA  length = 451
FEATURE                Location/Qualifiers
source                 1..451
                       mol_type = protein
                       organism = synthetic construct
                       note = C28PB400 Chain 2 - HC1 (AAS_knob3): PSMB896-G100A
SEQUENCE: 831
EVQLVESGGG LVQPGGSLRL SCAASGFTFS SYAMSWVRQA PGKGLEWVSA ISGGIGSTYY   60
ADSVKGRFTI SRDNSKNTLW LQMNSLRAED TAVYYCAKDA VGATPYYFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVSV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLS CAVKGFYPSD IAVEWESNGQ PENNYKTTPP VLDSDGSFFL VSKLTVDKSR   420
WQQGNVFSCS VMHEALHNRF TQKSLSLSPG K                                 451

SEQ ID NO: 832         moltype = AA  length = 216
FEATURE                Location/Qualifiers
source                 1..216
                       mol_type = protein
                       organism = synthetic construct
                       note = C28PB400 Chain 3 - LC: PSMB896-G100A
SEQUENCE: 832
QSVLTQPPSV SAAPGQKVTI SCSGSSSNIG INYVSWYQQL PGTAPKLLIY DNNKRPSGIP   60
DRFSGSKSGT SATLGITGLQ TGDEADYYCG TWDSSLSAVV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 833         moltype = AA  length = 480
FEATURE                Location/Qualifiers
source                 1..480
                       mol_type = protein
                       organism = synthetic construct
                       note = C28PB343 Chain 1 - 1A7[CD28]_H1L1-HL-scFv
SEQUENCE: 833
EVQLLESGGG LVQPGGSLRL SCAASGFTFS SYAMSWVRQA PGKGLEWVST ISGSGDSTYY   60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QYSTPFTFG    240
QGTKLEIKEP KSSDKTHTCP PCPAPEAAGG PSVFLFPPKP KDTLMISRTP EVTCVVVSVS   300
HEDPEVKFNW YVDGVEVHNA KTKPREEQYS TYRVVSVLT VLHQDWLNGK EYKCKVSNKA   360
LPAPIEKTIS KAKGQPREPQ VYTLPPSREE MTKNQVSLWC LVKGFYPSDI AVEWESNGQP   420
ENNYKTTPPV LDSDGSFFLY SKLTVDKSRW QQGNVFSCSV MHEALHNHYT QKSLSLSPGK   480
```

```
SEQ ID NO: 834          moltype = AA  length = 456
FEATURE                 Location/Qualifiers
source                  1..456
                        mol_type = protein
                        organism = synthetic construct
                        note = C28PB343 Chain 2 - HC1 (knob):  PSMA_P72_D01V2
SEQUENCE: 834
EVQLVESGGD LVQPGGSLRL SCAASGFTFN NYNMNWVRQA PGKGLEWVSH ISTSSSNKYY  60
ADSVKGRFSI SRDIAKNSMY LQMNSLRDED TAVYYCAREG VGADYGDYYY YGMDVWGQGT 120
TVTVSSASTK GPSVFPLAPS SKSTSGGTAA LGCLVKDYFP EPVTVSWNSG ALTSGVHTFP 180
AVLQSSGLYS LSSVVTVPSS SLGTQTYICN VNHKPSNTKV DKKVEPKSCD KTHTCPPCPA 240
PEAAGGPSVF LFPPKPKDTL MISRTPEVTC VVVSVSHEDP EVKFNWYVDG VEVHNAKTKP 300
REEQYNSTYR VVSVLTVLHQ DWLNGKEYKC KVSNKALPAP IEKTISKAKG QPREPQVYTL 360
PPSREEMTKN QVSLSCAVKG FYPSDIAVEW ESNGQPENNY KTTPPVLDSD GSFFLVSKLT 420
VDKSRWQQGN VFSCSVMHEA LHNRFTQKSL SLSPGK                           456

SEQ ID NO: 835          moltype = AA  length = 216
FEATURE                 Location/Qualifiers
source                  1..216
                        mol_type = protein
                        organism = synthetic construct
                        note = C28PB343 Chain 3 - LC:  PSMA_P72_D01V2
SEQUENCE: 835
QSVLTQPASV SGSPGQSITI SCTGTSSDVG GYNYVSWYQQ HPGKAPKLMI YEVSNRPSGV  60
SNRFSGSKSG NTASLTISGL QAEDEADYYC SSYTSSYTYV FGTGTKLTVL GQPKAAPSVT 120
LFPPSSEELQ ANKATLVCLI SDFYPGAVTV AWKADSSPVK AGVETTTPSK QSNNKYAASS 180
YLSLTPEQWK SHRSYSCQVT HEGSTVEKTV APTECS                           216

SEQ ID NO: 836          moltype = AA  length = 480
FEATURE                 Location/Qualifiers
source                  1..480
                        mol_type = protein
                        organism = synthetic construct
                        note = C28PB342 Chain 1 - 1A7[CD28]_H1L1-HL-scFv
SEQUENCE: 836
EVQLLESGGG LVQPGGSLRL SCAASGFTFS SYAMSWVRQA PGKGLEWVST ISGSGDSTYY  60
ADSVKGRFTI SRDNSKNTLY LQMNSLRAED TAVYYCAKSG PGLRQVGFDY WGQGTLVTVS 120
SGKPGSGKPG SGKPGSGKPG SDIQMTQSPS SLSASVGDRV TITCRASQSI SSYLNWYQQK 180
PGKAPKLLIY AASSLQSGVP SRFSGSGSGT DFTLTISSLQ PEDFATYYCQ QSYSTPFTFG 240
QGTKLEIKEP KSSDKTHTCP PCPAPEAAGG PSVFLFPPKP KDTLMISRTP EVTCVVVSVS 300
HEDPEVKFNW YVDGVEVHNA KTKPREEQYN STYRVVSVLT VLHQDWLNGK EYKCKVSNKA 360
LPAPIEKTIS KAKGQPREPQ VYTLPPSREE MTKNQVSLWC LVKGFYPSDI AVEWESNGQP 420
ENNYKTTPPV LDSDGSFFLY SKLTVDKSRW QQGNVFSCSV MHEALHNHYT QKSLSLSPGK 480

SEQ ID NO: 837          moltype = AA  length = 450
FEATURE                 Location/Qualifiers
source                  1..450
                        mol_type = protein
                        organism = synthetic construct
                        note = C28PB342 Chain 2 - HC1 (knob):  PSMA_P72_A10V2
SEQUENCE: 837
QVQLVESGGG VVQPGRSLRL SCAASGFTFS SYNMNWVRQA PGKGLEWVAI IYYDESNKYY  60
ADSVKGRFTI SRDISKNTLY LQMNSLRAED TAVYYCARER GRDYYGMDVW GQGTTVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS NTKVDKKVEP KSCDKTHTCP PCPAPEAAGG 240
PSVFLFPPKP KDTLMISRTP EVTCVVVSVS HEDPEVKFNW YVDGVEVHNA KTKPREEQYN 300
STYRVVSVLT VLHQDWLNGK EYKCKVSNKA LPAPIEKTIS KAKGQPREPQ VYTLPPSREE 360
MTKNQVSLSC AVKGFYPSDI AVEWESNGQP ENNYKTTPPV LDSDGSFFLV SKLTVDKSRW 420
QQGNVFSCSV MHEALHNRFT QKSLSLSPGK                                  450

SEQ ID NO: 838          moltype = AA  length = 213
FEATURE                 Location/Qualifiers
source                  1..213
                        mol_type = protein
                        organism = synthetic construct
                        note = C28PB342 Chain 3 - LC:  PSMA_P72_A10V2
SEQUENCE: 838
SYELMQPPSV SVSPGQTARI TCSGDALPKQ YAYWYQQKPG QAPVLVIYKD SERPSGIPVR  60
FSGSSSGTTV TLTITGVQAE DEADYYCQSA DSSGTYVFGT GTKVTVLGQP KAAPSVTLFP 120
PSSEELQANK ATLVCLISDF YPGAVTVAWK ADSSPVKAGV ETTTPSKQSN NKYAASSYLS 180
LTPEQWKSHR SYSCQVTHEG STVEKTVAPT ECS                              213

SEQ ID NO: 839          moltype = AA  length = 480
FEATURE                 Location/Qualifiers
source                  1..480
                        mol_type = protein
                        organism = synthetic construct
                        note = C28PB341 Chain 1 - 1A7[CD28]_H1L1-HL-scFv
```

```
SEQUENCE: 839
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPEAAGG PSVFLFPPKP KDTLMISRTP EVTCVVVSVS   300
HEDPEVKFNW YVDGVEVHNA KTKPREEQYN STYRVVSVLT VLHQDWLNGK EYKCKVSNKA   360
LPAPIEKTIS KAKGQPREPQ VYTLPPSREE MTKNQVSLWC LVKGFYPSDI AVEWESNGQP   420
ENNYKTTPPV LDSDGSFFLY SKLTVDKSRW QQGNVFSCSV MHEALHNHYT QKSLSLSPGK   480

SEQ ID NO: 840           moltype = AA  length = 451
FEATURE                  Location/Qualifiers
source                   1..451
                         mol_type = protein
                         organism = synthetic construct
                         note = C28PB341 Chain 2 - HC1 (knob):  PSMB896-HC-G100A
SEQUENCE: 840
EVQLVESGGG LVQPGGSLRL SCAASGFTFS SYAMSWVRQA PGKGLEWVSA ISGGIGSTYY    60
ADSVKGRFTI SRDNSKNTLW LQMNSLRAED TAVYYCAKDA VGATPYYFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVSN KSHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLS CAVKGFYPSD IAVEWESNGQ PENNYKTTPP VLDSDGSFFL VSKLTVDKSR   420
WQQGNVFSCS VMHEALHNRF TQKSLSLSPG K                                  451

SEQ ID NO: 841           moltype = AA  length = 216
FEATURE                  Location/Qualifiers
source                   1..216
                         mol_type = protein
                         organism = synthetic construct
                         note = C28PB341 Chain 3 - LC:  PSMB896-HC-G100A
SEQUENCE: 841
QSVLTQPPSV SAAPGQKVTI SCSGSSSNIG INYVSWYQQL PGTAPKLLIY DNNKRPSGIP    60
DRFSGSKSGT SATLGITGLQ TGDEADYYCG TWDSSLSAVV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 842           moltype = AA  length = 480
FEATURE                  Location/Qualifiers
source                   1..480
                         mol_type = protein
                         organism = synthetic construct
                         note = C28PB331 Chain 1 - 1A7[CD28]_H1_L1.71-HL-scFv
SEQUENCE: 842
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPEAAGG PSVFLFPPKP KDTLMISRTP EVTCVVVSVS   300
HEDPEVKFNW YVDGVEVHNA KTKPREEQYN STYRVVSVLT VLHQDWLNGK EYKCKVSNKA   360
LPAPIEKTIS KAKGQPREPQ VYTLPPSREE MTKNQVSLWC LVKGFYPSDI AVEWESNGQP   420
ENNYKTTPPV LDSDGSFFLY SKLTVDKSRW QQGNVFSCSV MHEALHNHYT QKSLSLSPGK   480

SEQ ID NO: 843           moltype = AA  length = 456
FEATURE                  Location/Qualifiers
source                   1..456
                         mol_type = protein
                         organism = synthetic construct
                         note = C28PB331 Chain 2 - HC1 (knob):  PSMA_P72_D01V2
SEQUENCE: 843
EVQLVESGGD LVQPGGSLRL SCAASGFTFN NYNMNWVRQA PGKGLEWVSH ISTSSSNKYY    60
ADSVKGRFSI SRDIAKNSMY LQMNSLRDED TAVYYCAREG VGADYGDYYY YGMDVWGQGT   120
TVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKKVEPKSCD KTHTCPPCPA   240
PEAAGGPSVF LFPPKPKDTL MISRTPEVTC VVVSVSHEDP EVKFNWYVDG VEVHNAKTKP   300
REEQYNSTYR VVSVLTVLHQ DWLNGKEYKC KVSNKALPAP IEKTISKAKG QPREPQVYTL   360
PPSREEMTKN QVSLSCAVKG FYPSDIAVEW ESNGQPENNY KTTPPVLDSD GSFFLVSKLT   420
VDKSRWQQGN VFSCSVMHEA LHNRFTQKSL SLSPGK                             456

SEQ ID NO: 844           moltype = AA  length = 216
FEATURE                  Location/Qualifiers
source                   1..216
                         mol_type = protein
                         organism = synthetic construct
                         note = C28PB331 Chain 3 - LC:  PSMA_P72_D01V2
SEQUENCE: 844
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSYTYV FGTGTKLTVL GQPKAAPSVT   120
```

```
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 845              moltype = AA  length = 480
FEATURE                     Location/Qualifiers
source                      1..480
                            mol_type = protein
                            organism = synthetic construct
                            note = C28PB329 Chain 1 - 1A7[CD28]_H1_L1.71-HL-scFv
SEQUENCE: 845
EVQLLESGGG LVQPGGSLRL SCAASGFTFS SYAMSWVRQA PGKGLEWVST ISGSGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPEAAGG PSVFLFPPKP KDTLMISRTP EVTCVVVSVS    300
HEDPEVKFNW YVDGVEVHNA KTKPREEQYN STYRVVSVLT VLHQDWLNGK EYKCKVSNKA    360
LPAPIEKTIS KAKGQPREPQ VYTLPPSREE MTKNQVSLWC LVKGFYPSDI AVEWESNGQP    420
ENNYKTTPPV LDSDGSFFLY SKLTVDKSRW QQGNVFSCSV MHEALHNHYT QKSLSLSPGK    480

SEQ ID NO: 846              moltype = AA  length = 451
FEATURE                     Location/Qualifiers
source                      1..451
                            mol_type = protein
                            organism = synthetic construct
                            note = C28PB329 Chain 2 - HC1 (knob): PSMB896-HC-G100A
SEQUENCE: 846
EVQLVESGGG LVQPGGSLRL SCAASGFTFS SYAMSWVRQA PGKGLEWVSA ISGGIGSTYY     60
ADSVKGRFTI SRDNSKNTLW LQMNSLRAED TAVYYCAKDA VGATPYYFDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPEAAG    240
GPSVFLFPPK PKDTLMISRT PEVTCVVVSV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRE    360
EMTKNQVSLS CAVKGFYPSD IAVEWESNGQ PENNYKTTPP VLDSDGSFFL VSKLTVDKSR    420
WQQGNVFSCS VMHEALHNRF TQKSLSLSPG K                                   451

SEQ ID NO: 847              moltype = AA  length = 216
FEATURE                     Location/Qualifiers
source                      1..216
                            mol_type = protein
                            organism = synthetic construct
                            note = C28PB329 Chain 3 - LC: PSMB896-HC-G100A
SEQUENCE: 847
QSVLTQPPSV SAAPGQKVTI SCSGSSSNIG INYVSWYQQL PGTAPKLLIY DNNKRPSGIP     60
DRFSGSKSGT SATLGITGLQ TGDEADYYCG TWDSSLSAVV FGGGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 848              moltype = AA  length = 480
FEATURE                     Location/Qualifiers
source                      1..480
                            mol_type = protein
                            organism = synthetic construct
                            note = C28PB319 Chain 1 - 1A7[CD28]_H1.1_L1.71-HL-scFv
SEQUENCE: 848
EVQLLESGGG LVQPGGSLRL SCAASGFTFS SYYMSWVRQA PGKGLEWVST ISGSGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPEAAGG PSVFLFPPKP KDTLMISRTP EVTCVVVSVS    300
HEDPEVKFNW YVDGVEVHNA KTKPREEQYN STYRVVSVLT VLHQDWLNGK EYKCKVSNKA    360
LPAPIEKTIS KAKGQPREPQ VYTLPPSREE MTKNQVSLWC LVKGFYPSDI AVEWESNGQP    420
ENNYKTTPPV LDSDGSFFLY SKLTVDKSRW QQGNVFSCSV MHEALHNHYT QKSLSLSPGK    480

SEQ ID NO: 849              moltype = AA  length = 456
FEATURE                     Location/Qualifiers
source                      1..456
                            mol_type = protein
                            organism = synthetic construct
                            note = C28PB319 Chain 2 - HC1 (knob): PSMA_P72_D01V2
SEQUENCE: 849
EVQLVESGGD LVQPGGSLRL SCAASGFTFN NYNMNWVRQA PGKGLEWVSH ISTSSSNKYY     60
ADSVKGRFSI SRDIAKNSMY LQMNSLRDED TAVYYCAREG VGADYGDYYY YGMDVWGQGT    120
TVTVSSASTK GPSVFPLAPS SKSTSGGTAA LGCLVKDYFP EPVTVSWNSG ALTSGVHTFP    180
AVLQSSGLYS LSSVVTVPSS SLGTQTYICN VNHKPSNTKV DKKVEPKSCD KTHTCPPCPA    240
PEAAGGPSVF LFPPKPKDTL MISRTPEVTC VVVSVSHEDP EVKFNWYVDG VEVHNAKTKP    300
REEQYNSTYR VVSVLTVLHQ DWLNGKEYKC KVSNKALPAP IEKTISKAKG QPREPQVYTL    360
PPSREEMTKN QVSLSCAVKG FYPSDIAVEW ESNGQPENNY KTTPPVLDSD GSFFLVSKLT    420
VDKSRWQQGN VFSCSVMHEA LHNRFTQKSL SLSPGK                              456
```

| | | |
|---|---|---|
| SEQ ID NO: 850 | moltype = AA  length = 216 | |
| FEATURE | Location/Qualifiers | |
| source | 1..216 | |
| | mol_type = protein | |
| | organism = synthetic construct | |
| | note = C28PB319 Chain 3 - LC:  PSMA_P72_D01V2 | |

SEQUENCE: 850
```
QSVLTQPASV SGSPGQSITI SCTGTSSDVG GYNYVSWYQQ HPGKAPKLMI YEVSNRPSGV   60
SNRFSGSKSG NTASLTISGL QAEDEADYYC SSYTSSYTYV FGTGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                          216
```

| | | |
|---|---|---|
| SEQ ID NO: 851 | moltype = AA  length = 480 | |
| FEATURE | Location/Qualifiers | |
| source | 1..480 | |
| | mol_type = protein | |
| | organism = synthetic construct | |
| | note = C28PB318 Chain 1 - 1A7[CD28]_H1.1_L1.71-HL-scFv | |

SEQUENCE: 851
```
EVQLLESGGG LVQPGGSLRL SCAASGFTFS SYYMSWVRQA PGKGLEWVST ISGSGDSTYY   60
ADSVKGRFTI SRDNSKNTLY LQMNSLRAED TAVYYCAKSG PGLRQVGFDY WGQGTLVTVS  120
SGKPGSGKPG SGKPGSGKPG SDIQMTQSPS SLSASVGDRV TITCRASQSI SSYLNWYQQK  180
PGKAPKLLIY AASSLQSGVP SRFSGSGSGT DFTLTISSLQ PEDFATYYCQ QVYSTPFTFG  240
QGTKLEIKEP KSSDKTHTCP PCPAPEAAGG PSVFLFPPKP KDTLMISRTP EVTCVVVSVS  300
HEDPEVKFNW YVDGVEVHNA KTKPREEQYN STYRVVSVLT VLHQDWLNGK EYKCKVSNKA  360
LPAPIEKTIS KAKGQPREPQ VYTLPPSREE MTKNQVSLWC LVKGFYPSDI AVEWESNGQP  420
ENNYKTTPPV LDSDGSFFLY SKLTVDKSRW QQGNVFSCSV MHEALHNHYT QKSLSLSPGK  480
```

| | | |
|---|---|---|
| SEQ ID NO: 852 | moltype = AA  length = 450 | |
| FEATURE | Location/Qualifiers | |
| source | 1..450 | |
| | mol_type = protein | |
| | organism = synthetic construct | |
| | note = C28PB318 Chain 2 - HC1 (knob):  PSMA_P72_A10V2 | |

SEQUENCE: 852
```
QVQLVESGGG VVQPGRSLRL SCAASGFTFS SYNMNWVRQA PGKGLEWVAI IYYDESNKYY   60
ADSVKGRFTI SRDISKNTLY LQMNSLRAED TAVYYCARER GRDYYGMDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVSVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLSC AVKGFYPSDI AVEWESNGQP ENNYKTTPPV LDSDGSFFLV SKLTVDKSRW  420
QQGNVFSCSV MHEALHNRFT QKSLSLSPGK                                 450
```

| | | |
|---|---|---|
| SEQ ID NO: 853 | moltype = AA  length = 213 | |
| FEATURE | Location/Qualifiers | |
| source | 1..213 | |
| | mol_type = protein | |
| | organism = synthetic construct | |
| | note = C28PB318 Chain 3 - LC:  PSMA_P72_A10V2 | |

SEQUENCE: 853
```
SYELMQPPSV SVSPGQTARI TCSGDALPKQ YAYWYQQKPG QAPVLVIYKD SERPSGIPVR   60
FSGSSSGTTV TLTITGVQAE DEADYYCQSA DSSGTYVFGT GTKVTVLGQP KAAPSVTLFP  120
PSSEELQANK ATLVCLISDF YPGAVTVAWK ADSSPVKAGV ETTTPSKQSN NKYAASSYLS  180
LTPEQWKSHR SYSCQVTHEG STVEKTVAPT ECS                              213
```

| | | |
|---|---|---|
| SEQ ID NO: 854 | moltype = AA  length = 480 | |
| FEATURE | Location/Qualifiers | |
| source | 1..480 | |
| | mol_type = protein | |
| | organism = synthetic construct | |
| | note = C28PB307 Chain 1 - 1A7[CD28]_H1.14_L1-HL-scFv | |

SEQUENCE: 854
```
EVQLLESGGG LVQPGGSLRL SCAASGFTFS SYYMSWVRQA PGKGLEWVST ISESGDSTYY   60
ADSVKGRFTI SRDNSKNTLY LQMNSLRAED TAVYYCAKSG PGLRQVGFDY WGQGTLVTVS  120
SGKPGSGKPG SGKPGSGKPG SDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPFTFG  240
QGTKLEIKEP KSSDKTHTCP PCPAPEAAGG PSVFLFPPKP KDTLMISRTP EVTCVVVSVS  300
HEDPEVKFNW YVDGVEVHNA KTKPREEQYN STYRVVSVLT VLHQDWLNGK EYKCKVSNKA  360
LPAPIEKTIS KAKGQPREPQ VYTLPPSREE MTKNQVSLWC LVKGFYPSDI AVEWESNGQP  420
ENNYKTTPPV LDSDGSFFLY SKLTVDKSRW QQGNVFSCSV MHEALHNHYT QKSLSLSPGK  480
```

| | | |
|---|---|---|
| SEQ ID NO: 855 | moltype = AA  length = 456 | |
| FEATURE | Location/Qualifiers | |
| source | 1..456 | |
| | mol_type = protein | |
| | organism = synthetic construct | |
| | note = C28PB307 Chain 2 - HC1 (knob):  PSMA_P72_D01V2 | |

```
SEQUENCE: 855
EVQLVESGGD LVQPGGSLRL SCAASGFTFN NYNMNWVRQA PGKGLEWVSH ISTSSSNKYY    60
ADSVKGRFSI SRDIAKNSMY LQMNSLRDED TAVYYCAREG VGADYGDYYY YGMDVWGQGT   120
TVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKKVEPKSCD KTHTCPPCPA   240
PEAAGGPSVF LFPPKPKDTL MISRTPEVTC VVVSVSHEDP EVKFNWYVDG VEVHNAKTKP   300
REEQYNSTYR VVSVLTVLHQ DWLNGKEYKC KVSNKALPAP IEKTISKAKG QPREPQVYTL   360
PPSREEMTKN QVSLSCAVKG FYPSDIAVEW ESNGQPENNY KTTPPVLDSD GSFFLVSKLT   420
VDKSRWQQGN VFSCSVMHEA LHNRFTQKSL SLSPGK                             456

SEQ ID NO: 856         moltype = AA  length = 216
FEATURE                Location/Qualifiers
source                 1..216
                       mol_type = protein
                       organism = synthetic construct
                       note = C28PB307 Chain 3 - LC:  PSMA_P72_D01V2
SEQUENCE: 856
QSVLTQPASV SGSPGQSITI SCTGTSSDVG GYNYVSWYQQ HPGKAPKLMI YEVSNRPSGV    60
SNRFSGSKSG NTASLTISGL QAEDEADYYC SSYTSSYTYV FGTGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 857         moltype = AA  length = 480
FEATURE                Location/Qualifiers
source                 1..480
                       mol_type = protein
                       organism = synthetic construct
                       note = C28PB306 Chain 1 - 1A7[CD28]_H1.14_L1-HL-scFv
SEQUENCE: 857
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPEAAGG PSVFLFPPKP KDTLMISRTP EVTCVVVSVS   300
HEDPEVKFNW YVDGVEVHNA KTKPREEQYN STYRVVSVLT VLHQDWLNGK EYKCKVSNKA   360
LPAPIEKTIS KAKGQPREPQ VYTLPPSREE MTKNQVSLWC LVKGFYPSDI AVEWESNGQP   420
ENNYKTTPPV LDSDGSFFLY SKLTVDKSRW QQGNVFSCSV MHEALHNHYT QKSLSLSPGK   480

SEQ ID NO: 858         moltype = AA  length = 450
FEATURE                Location/Qualifiers
source                 1..450
                       mol_type = protein
                       organism = synthetic construct
                       note = C28PB306 Chain 2 - HC1 (knob):  PSMA_P72_A10V2
SEQUENCE: 858
QVQLVESGGG VVQPGRSLRL SCAASGFTFS SYNMNWVRQA PGKGLEWVAI IYYDESNKYY    60
ADSVKGRFTI SRDISKNTLY LQMNSLRAED TAVYYCARER GRDYYGMDVW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVSVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLSC AVKGFYPSDI AVEWESNGQP ENNYKTTPPV LDSDGSFFLV SKLTVDKSRW   420
QQGNVFSCSV MHEALHNRFT QKSLSLSPGK                                    450

SEQ ID NO: 859         moltype = AA  length = 213
FEATURE                Location/Qualifiers
source                 1..213
                       mol_type = protein
                       organism = synthetic construct
                       note = C28PB306 Chain 3 - LC:  PSMA_P72_A10V2
SEQUENCE: 859
SYELMQPPSV SVSPGQTARI TCSGDALPKQ YAYWYQQKPG QAPVLVIYKD SERPSGIPVR    60
FSGSSSGTTV TLTITGVQAE DEADYYCQSA DSSGTYVFGT GTKVTVLGQP KAAPSVTLFP   120
PSSEELQANK ATLVCLISDF YPGAVTVAWK ADSSPVKAGV ETTTPSKQSN NKYAASSYLS   180
LTPEQWKSHR SYSCQVTHEG STVEKTVAPT ECS                                213

SEQ ID NO: 860         moltype = AA  length = 480
FEATURE                Location/Qualifiers
source                 1..480
                       mol_type = protein
                       organism = synthetic construct
                       note = C28PB295 Chain 1 - 1A7[CD28]_H1.14_L1.71-HL-scFv
SEQUENCE: 860
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPEAAGG PSVFLFPPKP KDTLMISRTP EVTCVVVSVS   300
HEDPEVKFNW YVDGVEVHNA KTKPREEQYN STYRVVSVLT VLHQDWLNGK EYKCKVSNKA   360
```

```
LPAPIEKTIS KAKGQPREPQ VYTLPPSREE MTKNQVSLWC LVKGFYPSDI AVEWESNGQP    420
ENNYKTTPPV LDSDGSFFLY SKLTVDKSRW QQGNVFSCSV MHEALHNHYT QKSLSLSPGK    480

SEQ ID NO: 861           moltype = AA  length = 456
FEATURE                  Location/Qualifiers
source                   1..456
                         mol_type = protein
                         organism = synthetic construct
                         note = C28PB295 Chain 2 - HC1 (knob):  PSMA_P72_D01V2
SEQUENCE: 861
EVQLVESGGD LVQPGGSLRL SCAASGFTFN NYNMNWVRQA PGKGLEWVSH ISTSSSNKYY     60
ADSVKGRFSI SRDIAKNSMY LQMNSLRDED TAVYYCAREG VGADYGDYYY YGMDVWGQGT    120
TVTVSSASTK GPSVFPLAPS SKSTSGGTAA LGCLVKDYFP EPVTVSWNSG ALTSGVHTFP    180
AVLQSSGLYS LSSVVTVPSS SLGTQTYICN VNHKPSNTKV DKKVEPKSCD KTHTCPPCPA    240
PEAAGGPSVF LFPPKPKDTL MISRTPEVTC VVVSVSHEDP EVKFNWYVDG VEVHNAKTKP    300
REEQYNSTYR VVSVLTVLHQ DWLNGKEYKC KVSNKALPAP IEKTISKAKG QPREPQVYTL    360
PPSREEMTKN QVSLSCAVKG FYPSDIAVEW ESNGQPENNY KTTPPVLDSD GSFFLVSKLT    420
VDKSRWQQGN VFSCSVMHEA LHNRFTQKSL SLSPGK                              456

SEQ ID NO: 862           moltype = AA  length = 216
FEATURE                  Location/Qualifiers
source                   1..216
                         mol_type = protein
                         organism = synthetic construct
                         note = C28PB295 Chain 3 - LC:  PSMA_P72_D01V2
SEQUENCE: 862
QSVLTQPASV SGSPGQSITI SCTGTSSDVG GYNYVSWYQQ HPGKAPKLMI YEVSNRPSGV     60
SNRFSGSKSG NTASLTISGL QAEDEADYYC SSYTSSYTYV FGTGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 863           moltype = AA  length = 480
FEATURE                  Location/Qualifiers
source                   1..480
                         mol_type = protein
                         organism = synthetic construct
                         note = C28PB294 Chain 1 - 1A7[CD28]_H1.14_L1.71-HL-scFv
SEQUENCE: 863
EVQLLESGGG LVQPGGSLRL SCAASGFTFS SYYMSWVRQA PGKGLEWVST ISESGDSTYY     60
ADSVKGRFTI SRDNSKNTLY LQMNSLRAED TAVYYCAKSG PGLRQVGFDY WGQGTLVTVS    120
SGKPGSGKPG SGKPGSGKPG SDIQMTQSPS SLSASVGDRV TITCRASQSI SSYLNWYQQK    180
PGKAPKLLIY AASSLQSGVP SRFSGSGSGT DFTLTISSLQ PEDFATYYCQ QVYSTPFTFG    240
QGTKLEIKEP KSSDKTHTCP PCPAPEAAGG PSVFLFPPKP KDTLMISRTP EVTCVVVSVS    300
HEDPEVKFNW YVDGVEVHNA KTKPREEQYN STYRVVSVLT VLHQDWLNGK EYKCKVSNKA    360
LPAPIEKTIS KAKGQPREPQ VYTLPPSREE MTKNQVSLWC LVKGFYPSDI AVEWESNGQP    420
ENNYKTTPPV LDSDGSFFLY SKLTVDKSRW QQGNVFSCSV MHEALHNHYT QKSLSLSPGK    480

SEQ ID NO: 864           moltype = AA  length = 450
FEATURE                  Location/Qualifiers
source                   1..450
                         mol_type = protein
                         organism = synthetic construct
                         note = C28PB294 Chain 2 - HC1 (knob):  PSMA_P72_A10V2
SEQUENCE: 864
QVQLVESGGG VVQPGRSLRL SCAASGFTFS SYNMNWVRQA PGKGLEWVAI IYYDESNKYY     60
ADSVKGRFTI SRDISKNTLY LQMNSLRAED TAVYYCARER GRDYYGMDVW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPEAAGG    240
PSVFLFPPKP KDTLMISRTP EVTCVVVSVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLSC AVKGFYPSDI AVEWESNGQP ENNYKTTPPV LDSDGSFFLV SKLTVDKSRW    420
QQGNVFSCSV MHEALHNRFT QKSLSLSPGK                                     450

SEQ ID NO: 865           moltype = AA  length = 213
FEATURE                  Location/Qualifiers
source                   1..213
                         mol_type = protein
                         organism = synthetic construct
                         note = C28PB294 Chain 3 - LC:  PSMA_P72_A10V2
SEQUENCE: 865
SYELMQPPSV SVSPGQTARI TCSGDALPKQ YAYWYQQKPG QAPVLVIYKD SERPSGIPVR     60
FSGSSSGTTV TLTITGVQAE DEADYYCQSA DSSGTYVFGT GTKVTVLGQP KAAPSVTLFP    120
PSSEELQANK ATLVCLISDF YPGAVTVAWK ADSSPVKAGV ETTTPSKQSN NKYAASSYLS    180
LTPEQWKSHR SYSCQVTHEG STVEKTVAPT ECS                                 213

SEQ ID NO: 866           moltype = AA  length = 451
FEATURE                  Location/Qualifiers
source                   1..451
                         mol_type = protein
```

```
                            organism = synthetic construct
                            note = C28PB329 Chain 1 -
                                PSMB896-HC-G100A[PSMA]_H0_IgG1_L234A/L235A/D265S/T366S/L368
                                A/Y407V/H435R/Y436F
SEQUENCE: 866
EVQLVESGGG LVQPGGSLRL SCAASGFTFS SYAMSWVRQA PGKGLEWVSA ISGGIGSTYY    60
ADSVKGRFTI SRDNSKNTLW LQMNSLRAED TAVYYCAKDA VGATPYYFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVSV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLS CAVKGFYPSD IAVEWESNGQ PENNYKTTPP VLDSDGSFFL VSKLTVDKSR   420
WQQGNVFSCS VMHEALHNRF TQKSLSLSPG K                                  451

SEQ ID NO: 867              moltype = AA   length = 480
FEATURE                     Location/Qualifiers
source                      1..480
                            mol_type = protein
                            organism = synthetic construct
                            note = C28PB329 Chain 2 -
                                1A7[CD28]_H1_L1.71_scFv(GKPGS)4_Fc(216)_IgG1_C220S/L234A/L2
                                35A/D265S/T366W
SEQUENCE: 867
EVQLLESGGG LVQPGGSLRL SCAASGFTFS SYAMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPEAAGG PSVFLFPPKP KDTLMISRTP EVTCVVVSVS   300
HEDPEVKFNW YVDGVEVHNA KTKPREEQYN STYRVVSVLT VLHQDWLNGK EYKCKVSNKA   360
LPAPIEKTIS KAKGQPREPQ VYTLPPSREE MTKNQVSLWC LVKGFYPSDI AVEWESNGQP   420
ENNYKTTPPV LDSDGSFFLY SKLTVDKSRW QQGNVFSCSV MHEALHNHYT QKSLSLSPGK   480

SEQ ID NO: 868              moltype = AA   length = 216
FEATURE                     Location/Qualifiers
source                      1..216
                            mol_type = protein
                            organism = synthetic construct
                            note = C28PB329 Chain 3 - PSMB896-HC-G100A[PSMA]_L0 Light
                                Chain
SEQUENCE: 868
QSVLTQPPSV SAAPGQKVTI SCSGSSSNIG INYVSWYQQL PGTAPKLLIY DNNKRPSGIP    60
DRFSGSKSGT SATLGITGLQ TGDEADYYCG TWDSSLSAVV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 869              moltype = AA   length = 121
FEATURE                     Location/Qualifiers
source                      1..121
                            mol_type = protein
                            organism = synthetic construct
                            note = 1A7[CD28]_H1.1
SEQUENCE: 869
EVQLLESGGG LVQPGGSLRL SCAASGFTFS SYYMSWVRQA PGKGLEWVST ISGSGDSTYY    60
ADSVKGRFTI SRDNSKNTLY LQMNSLRAED TAVYYCAKSG PGLRQVGFDY WGQGTLVTVS   120
S                                                                   121

SEQ ID NO: 870              moltype = AA   length = 121
FEATURE                     Location/Qualifiers
source                      1..121
                            mol_type = protein
                            organism = synthetic construct
                            note = 1A7[CD28]_H1.2
SEQUENCE: 870
EVQLLESGGG LVQPGGSLRL SCAASGFTFS SYAMSWVRQA PGKGLEWVST IDGSGDSTYY    60
ADSVKGRFTI SRDNSKNTLY LQMNSLRAED TAVYYCAKSG PGLRQVGFDY WGQGTLVTVS   120
S                                                                   121

SEQ ID NO: 871              moltype = AA   length = 121
FEATURE                     Location/Qualifiers
source                      1..121
                            mol_type = protein
                            organism = synthetic construct
                            note = 1A7[CD28]_H1.3
SEQUENCE: 871
EVQLLESGGG LVQPGGSLRL SCAASGFTFS SYAMSWVRQA PGKGLEWVST IEGSGDSTYY    60
ADSVKGRFTI SRDNSKNTLY LQMNSLRAED TAVYYCAKSG PGLRQVGFDY WGQGTLVTVS   120
S                                                                   121

SEQ ID NO: 872              moltype = AA   length = 121
```

```
FEATURE                 Location/Qualifiers
source                  1..121
                        mol_type = protein
                        organism = synthetic construct
                        note = 1A7[CD28]_H1.4
SEQUENCE: 872
EVQLLESGGG LVQPGGSLRL SCAASGFTFS SYAMSWVRQA PGKGLEWVST IYGSGDSTYY   60
ADSVKGRFTI SRDNSKNTLY LQMNSLRAED TAVYYCAKSG PGLRQVGFDY WGQGTLVTVS  120
S                                                                  121

SEQ ID NO: 873          moltype = AA  length = 121
FEATURE                 Location/Qualifiers
source                  1..121
                        mol_type = protein
                        organism = synthetic construct
                        note = 1A7[CD28]_H1.5
SEQUENCE: 873
EVQLLESGGG LVQPGGSLRL SCAASGFTFS SYAMSWVRQA PGKGLEWVST ISDSGDSTYY   60
ADSVKGRFTI SRDNSKNTLY LQMNSLRAED TAVYYCAKSG PGLRQVGFDY WGQGTLVTVS  120
S                                                                  121

SEQ ID NO: 874          moltype = AA  length = 121
FEATURE                 Location/Qualifiers
source                  1..121
                        mol_type = protein
                        organism = synthetic construct
                        note = 1A7[CD28]_H1.6
SEQUENCE: 874
EVQLLESGGG LVQPGGSLRL SCAASGFTFS SYAMSWVRQA PGKGLEWVST ISESGDSTYY   60
ADSVKGRFTI SRDNSKNTLY LQMNSLRAED TAVYYCAKSG PGLRQVGFDY WGQGTLVTVS  120
S                                                                  121

SEQ ID NO: 875          moltype = AA  length = 121
FEATURE                 Location/Qualifiers
source                  1..121
                        mol_type = protein
                        organism = synthetic construct
                        note = 1A7[CD28]_H1.7
SEQUENCE: 875
EVQLLESGGG LVQPGGSLRL SCAASGFTFS SYAMSWVRQA PGKGLEWVST ISGSGTSTYY   60
ADSVKGRFTI SRDNSKNTLY LQMNSLRAED TAVYYCAKSG PGLRQVGFDY WGQGTLVTVS  120
S                                                                  121

SEQ ID NO: 876          moltype = AA  length = 121
FEATURE                 Location/Qualifiers
source                  1..121
                        mol_type = protein
                        organism = synthetic construct
                        note = 1A7[CD28]_H1.8
SEQUENCE: 876
EVQLLESGGG LVQPGGSLRL SCAASGFTFS SYAMSWVRQA PGKGLEWVST ISGSGYSTYY   60
ADSVKGRFTI SRDNSKNTLY LQMNSLRAED TAVYYCAKSG PGLRQVGFDY WGQGTLVTVS  120
S                                                                  121

SEQ ID NO: 877          moltype = AA  length = 121
FEATURE                 Location/Qualifiers
source                  1..121
                        mol_type = protein
                        organism = synthetic construct
                        note = 1A7[CD28]_H1.9
SEQUENCE: 877
EVQLLESGGG LVQPGGSLRL SCAASGFTFS SYAMSWVRQA PGKGLEWVST ISGSGDYTYY   60
ADSVKGRFTI SRDNSKNTLY LQMNSLRAED TAVYYCAKSG PGLRQVGFDY WGQGTLVTVS  120
S                                                                  121

SEQ ID NO: 878          moltype = AA  length = 121
FEATURE                 Location/Qualifiers
source                  1..121
                        mol_type = protein
                        organism = synthetic construct
                        note = 1A7[CD28]_H1.10
SEQUENCE: 878
EVQLLESGGG LVQPGGSLRL SCAASGFTFS SYYMSWVRQA PGKGLEWVST IDGSGDSTYY   60
ADSVKGRFTI SRDNSKNTLY LQMNSLRAED TAVYYCAKSG PGLRQVGFDY WGQGTLVTVS  120
S                                                                  121

SEQ ID NO: 879          moltype = AA  length = 121
FEATURE                 Location/Qualifiers
```

```
source                  1..121
                        mol_type = protein
                        organism = synthetic construct
                        note = 1A7[CD28]_H1.11
SEQUENCE: 879
EVQLLESGGG LVQPGGSLRL SCAASGFTFS SYYMSWVRQA PGKGLEWVST IEGSGDSTYY    60
ADSVKGRFTI SRDNSKNTLY LQMNSLRAED TAVYYCAKSG PGLRQVGFDY WGQGTLVTVS   120
S                                                                  121

SEQ ID NO: 880          moltype = AA  length = 121
FEATURE                 Location/Qualifiers
source                  1..121
                        mol_type = protein
                        organism = synthetic construct
                        note = 1A7[CD28]_H1.12
SEQUENCE: 880
EVQLLESGGG LVQPGGSLRL SCAASGFTFS SYYMSWVRQA PGKGLEWVST IYGSGDSTYY    60
ADSVKGRFTI SRDNSKNTLY LQMNSLRAED TAVYYCAKSG PGLRQVGFDY WGQGTLVTVS   120
S                                                                  121

SEQ ID NO: 881          moltype = AA  length = 121
FEATURE                 Location/Qualifiers
source                  1..121
                        mol_type = protein
                        organism = synthetic construct
                        note = 1A7[CD28]_H1.13
SEQUENCE: 881
EVQLLESGGG LVQPGGSLRL SCAASGFTFS SYYMSWVRQA PGKGLEWVST ISDSGDSTYY    60
ADSVKGRFTI SRDNSKNTLY LQMNSLRAED TAVYYCAKSG PGLRQVGFDY WGQGTLVTVS   120
S                                                                  121

SEQ ID NO: 882          moltype = AA  length = 121
FEATURE                 Location/Qualifiers
source                  1..121
                        mol_type = protein
                        organism = synthetic construct
                        note = 1A7[CD28]_H1.14
SEQUENCE: 882
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
S                                                                  121

SEQ ID NO: 883          moltype = AA  length = 121
FEATURE                 Location/Qualifiers
source                  1..121
                        mol_type = protein
                        organism = synthetic construct
                        note = 1A7[CD28]_H1.15
SEQUENCE: 883
EVQLLESGGG LVQPGGSLRL SCAASGFTFS SYYMSWVRQA PGKGLEWVST ISGSGTSTYY    60
ADSVKGRFTI SRDNSKNTLY LQMNSLRAED TAVYYCAKSG PGLRQVGFDY WGQGTLVTVS   120
S                                                                  121

SEQ ID NO: 884          moltype = AA  length = 121
FEATURE                 Location/Qualifiers
source                  1..121
                        mol_type = protein
                        organism = synthetic construct
                        note = 1A7[CD28]_H1.16
SEQUENCE: 884
EVQLLESGGG LVQPGGSLRL SCAASGFTFS SYYMSWVRQA PGKGLEWVST ISGSGYSTYY    60
ADSVKGRFTI SRDNSKNTLY LQMNSLRAED TAVYYCAKSG PGLRQVGFDY WGQGTLVTVS   120
S                                                                  121

SEQ ID NO: 885          moltype = AA  length = 121
FEATURE                 Location/Qualifiers
source                  1..121
                        mol_type = protein
                        organism = synthetic construct
                        note = 1A7[CD28]_H1.17
SEQUENCE: 885
EVQLLESGGG LVQPGGSLRL SCAASGFTFS SYYMSWVRQA PGKGLEWVST ISGSGDYTYY    60
ADSVKGRFTI SRDNSKNTLY LQMNSLRAED TAVYYCAKSG PGLRQVGFDY WGQGTLVTVS   120
S                                                                  121

SEQ ID NO: 886          moltype = AA  length = 121
FEATURE                 Location/Qualifiers
source                  1..121
                        mol_type = protein
```

```
                        organism = synthetic construct
                        note = 1A7[CD28]_H1.18
SEQUENCE: 886
EVQLLESGGG LVQPGGSLRL SCAASGFTFS SYAMSWVRQA PGKGLEWVST IDDSGDSTYY     60
ADSVKGRFTI SRDNSKNTLY LQMNSLRAED TAVYYCAKSG PGLRQVGFDY WGQGTLVTVS    120
S                                                                   121

SEQ ID NO: 887          moltype = AA   length = 121
FEATURE                 Location/Qualifiers
source                  1..121
                        mol_type = protein
                        organism = synthetic construct
                        note = 1A7[CD28]_H1.19
SEQUENCE: 887
EVQLLESGGG LVQPGGSLRL SCAASGFTFS SYAMSWVRQA PGKGLEWVST IDESGDSTYY     60
ADSVKGRFTI SRDNSKNTLY LQMNSLRAED TAVYYCAKSG PGLRQVGFDY WGQGTLVTVS    120
S                                                                   121

SEQ ID NO: 888          moltype = AA   length = 121
FEATURE                 Location/Qualifiers
source                  1..121
                        mol_type = protein
                        organism = synthetic construct
                        note = 1A7[CD28]_H1.20
SEQUENCE: 888
EVQLLESGGG LVQPGGSLRL SCAASGFTFS SYAMSWVRQA PGKGLEWVST IDGSGTSTYY     60
ADSVKGRFTI SRDNSKNTLY LQMNSLRAED TAVYYCAKSG PGLRQVGFDY WGQGTLVTVS    120
S                                                                   121

SEQ ID NO: 889          moltype = AA   length = 121
FEATURE                 Location/Qualifiers
source                  1..121
                        mol_type = protein
                        organism = synthetic construct
                        note = 1A7[CD28]_H1.21
SEQUENCE: 889
EVQLLESGGG LVQPGGSLRL SCAASGFTFS SYAMSWVRQA PGKGLEWVST IDGSGYSTYY     60
ADSVKGRFTI SRDNSKNTLY LQMNSLRAED TAVYYCAKSG PGLRQVGFDY WGQGTLVTVS    120
S                                                                   121

SEQ ID NO: 890          moltype = AA   length = 121
FEATURE                 Location/Qualifiers
source                  1..121
                        mol_type = protein
                        organism = synthetic construct
                        note = 1A7[CD28]_H1.22
SEQUENCE: 890
EVQLLESGGG LVQPGGSLRL SCAASGFTFS SYAMSWVRQA PGKGLEWVST IDGSGDYTYY     60
ADSVKGRFTI SRDNSKNTLY LQMNSLRAED TAVYYCAKSG PGLRQVGFDY WGQGTLVTVS    120
S                                                                   121

SEQ ID NO: 891          moltype = AA   length = 121
FEATURE                 Location/Qualifiers
source                  1..121
                        mol_type = protein
                        organism = synthetic construct
                        note = 1A7[CD28]_H1.23
SEQUENCE: 891
EVQLLESGGG LVQPGGSLRL SCAASGFTFS SYAMSWVRQA PGKGLEWVST IEDSGDSTYY     60
ADSVKGRFTI SRDNSKNTLY LQMNSLRAED TAVYYCAKSG PGLRQVGFDY WGQGTLVTVS    120
S                                                                   121

SEQ ID NO: 892          moltype = AA   length = 121
FEATURE                 Location/Qualifiers
source                  1..121
                        mol_type = protein
                        organism = synthetic construct
                        note = 1A7[CD28]_H1.24
SEQUENCE: 892
EVQLLESGGG LVQPGGSLRL SCAASGFTFS SYAMSWVRQA PGKGLEWVST IEESGDSTYY     60
ADSVKGRFTI SRDNSKNTLY LQMNSLRAED TAVYYCAKSG PGLRQVGFDY WGQGTLVTVS    120
S                                                                   121

SEQ ID NO: 893          moltype = AA   length = 121
FEATURE                 Location/Qualifiers
source                  1..121
                        mol_type = protein
                        organism = synthetic construct
                        note = 1A7[CD28]_H1.25
```

```
SEQUENCE: 893
EVQLLESGGG LVQPGGSLRL SCAASGFTFS SYAMSWVRQA PGKGLEWVST IEGSGTSTYY    60
ADSVKGRFTI SRDNSKNTLY LQMNSLRAED TAVYYCAKSG PGLRQVGFDY WGQGTLVTVS   120
S                                                                  121

SEQ ID NO: 894          moltype = AA   length = 121
FEATURE                 Location/Qualifiers
source                  1..121
                        mol_type = protein
                        organism = synthetic construct
                        note = 1A7[CD28]_H1.26
SEQUENCE: 894
EVQLLESGGG LVQPGGSLRL SCAASGFTFS SYAMSWVRQA PGKGLEWVST IEGSGYSTYY    60
ADSVKGRFTI SRDNSKNTLY LQMNSLRAED TAVYYCAKSG PGLRQVGFDY WGQGTLVTVS   120
S                                                                  121

SEQ ID NO: 895          moltype = AA   length = 121
FEATURE                 Location/Qualifiers
source                  1..121
                        mol_type = protein
                        organism = synthetic construct
                        note = 1A7[CD28]_H1.27
SEQUENCE: 895
EVQLLESGGG LVQPGGSLRL SCAASGFTFS SYAMSWVRQA PGKGLEWVST IEGSGDYTYY    60
ADSVKGRFTI SRDNSKNTLY LQMNSLRAED TAVYYCAKSG PGLRQVGFDY WGQGTLVTVS   120
S                                                                  121

SEQ ID NO: 896          moltype = AA   length = 121
FEATURE                 Location/Qualifiers
source                  1..121
                        mol_type = protein
                        organism = synthetic construct
                        note = 1A7[CD28]_H1.28
SEQUENCE: 896
EVQLLESGGG LVQPGGSLRL SCAASGFTFS SYAMSWVRQA PGKGLEWVST IYDSGDSTYY    60
ADSVKGRFTI SRDNSKNTLY LQMNSLRAED TAVYYCAKSG PGLRQVGFDY WGQGTLVTVS   120
S                                                                  121

SEQ ID NO: 897          moltype = AA   length = 121
FEATURE                 Location/Qualifiers
source                  1..121
                        mol_type = protein
                        organism = synthetic construct
                        note = 1A7[CD28]_H1.29
SEQUENCE: 897
EVQLLESGGG LVQPGGSLRL SCAASGFTFS SYAMSWVRQA PGKGLEWVST IYESGDSTYY    60
ADSVKGRFTI SRDNSKNTLY LQMNSLRAED TAVYYCAKSG PGLRQVGFDY WGQGTLVTVS   120
S                                                                  121

SEQ ID NO: 898          moltype = AA   length = 121
FEATURE                 Location/Qualifiers
source                  1..121
                        mol_type = protein
                        organism = synthetic construct
                        note = 1A7[CD28]_H1.30
SEQUENCE: 898
EVQLLESGGG LVQPGGSLRL SCAASGFTFS SYAMSWVRQA PGKGLEWVST IYGSGTSTYY    60
ADSVKGRFTI SRDNSKNTLY LQMNSLRAED TAVYYCAKSG PGLRQVGFDY WGQGTLVTVS   120
S                                                                  121

SEQ ID NO: 899          moltype = AA   length = 121
FEATURE                 Location/Qualifiers
source                  1..121
                        mol_type = protein
                        organism = synthetic construct
                        note = 1A7[CD28]_H1.31
SEQUENCE: 899
EVQLLESGGG LVQPGGSLRL SCAASGFTFS SYAMSWVRQA PGKGLEWVST IYGSGYSTYY    60
ADSVKGRFTI SRDNSKNTLY LQMNSLRAED TAVYYCAKSG PGLRQVGFDY WGQGTLVTVS   120
S                                                                  121

SEQ ID NO: 900          moltype = AA   length = 121
FEATURE                 Location/Qualifiers
source                  1..121
                        mol_type = protein
                        organism = synthetic construct
                        note = 1A7[CD28]_H1.32
```

```
SEQUENCE: 900
EVQLLESGGG LVQPGGSLRL SCAASGFTFS SYAMSWVRQA PGKGLEWVST IYGSGDYTYY    60
ADSVKGRFTI SRDNSKNTLY LQMNSLRAED TAVYYCAKSG PGLRQVGFDY WGQGTLVTVS   120
S                                                                  121

SEQ ID NO: 901            moltype = AA  length = 121
FEATURE                   Location/Qualifiers
source                    1..121
                          mol_type = protein
                          organism = synthetic construct
                          note = 1A7[CD28]_H1.33
SEQUENCE: 901
EVQLLESGGG LVQPGGSLRL SCAASGFTFS SYAMSWVRQA PGKGLEWVST ISDSGTSTYY    60
ADSVKGRFTI SRDNSKNTLY LQMNSLRAED TAVYYCAKSG PGLRQVGFDY WGQGTLVTVS   120
S                                                                  121

SEQ ID NO: 902            moltype = AA  length = 121
FEATURE                   Location/Qualifiers
source                    1..121
                          mol_type = protein
                          organism = synthetic construct
                          note = 1A7[CD28]_H1.34
SEQUENCE: 902
EVQLLESGGG LVQPGGSLRL SCAASGFTFS SYAMSWVRQA PGKGLEWVST ISDSGYSTYY    60
ADSVKGRFTI SRDNSKNTLY LQMNSLRAED TAVYYCAKSG PGLRQVGFDY WGQGTLVTVS   120
S                                                                  121

SEQ ID NO: 903            moltype = AA  length = 121
FEATURE                   Location/Qualifiers
source                    1..121
                          mol_type = protein
                          organism = synthetic construct
                          note = 1A7[CD28]_H1.35
SEQUENCE: 903
EVQLLESGGG LVQPGGSLRL SCAASGFTFS SYAMSWVRQA PGKGLEWVST ISDSGDYTYY    60
ADSVKGRFTI SRDNSKNTLY LQMNSLRAED TAVYYCAKSG PGLRQVGFDY WGQGTLVTVS   120
S                                                                  121

SEQ ID NO: 904            moltype = AA  length = 121
FEATURE                   Location/Qualifiers
source                    1..121
                          mol_type = protein
                          organism = synthetic construct
                          note = 1A7[CD28]_H1.36
SEQUENCE: 904
EVQLLESGGG LVQPGGSLRL SCAASGFTFS SYAMSWVRQA PGKGLEWVST ISESGTSTYY    60
ADSVKGRFTI SRDNSKNTLY LQMNSLRAED TAVYYCAKSG PGLRQVGFDY WGQGTLVTVS   120
S                                                                  121

SEQ ID NO: 905            moltype = AA  length = 121
FEATURE                   Location/Qualifiers
source                    1..121
                          mol_type = protein
                          organism = synthetic construct
                          note = 1A7[CD28]_H1.37
SEQUENCE: 905
EVQLLESGGG LVQPGGSLRL SCAASGFTFS SYAMSWVRQA PGKGLEWVST ISESGYSTYY    60
ADSVKGRFTI SRDNSKNTLY LQMNSLRAED TAVYYCAKSG PGLRQVGFDY WGQGTLVTVS   120
S                                                                  121

SEQ ID NO: 906            moltype = AA  length = 121
FEATURE                   Location/Qualifiers
source                    1..121
                          mol_type = protein
                          organism = synthetic construct
                          note = 1A7[CD28]_H1.38
SEQUENCE: 906
EVQLLESGGG LVQPGGSLRL SCAASGFTFS SYAMSWVRQA PGKGLEWVST ISESGDYTYY    60
ADSVKGRFTI SRDNSKNTLY LQMNSLRAED TAVYYCAKSG PGLRQVGFDY WGQGTLVTVS   120
S                                                                  121

SEQ ID NO: 907            moltype = AA  length = 121
FEATURE                   Location/Qualifiers
source                    1..121
                          mol_type = protein
                          organism = synthetic construct
                          note = 1A7[CD28]_H1.39
```

```
SEQUENCE: 907
EVQLLESGGG LVQPGGSLRL SCAASGFTFS SYAMSWVRQA PGKGLEWVST ISGSGTYTYY    60
ADSVKGRFTI SRDNSKNTLY LQMNSLRAED TAVYYCAKSG PGLRQVGFDY WGQGTLVTVS   120
S                                                                  121

SEQ ID NO: 908          moltype = AA   length = 121
FEATURE                 Location/Qualifiers
source                  1..121
                        mol_type = protein
                        organism = synthetic construct
                        note = 1A7[CD28]_H1.40
SEQUENCE: 908
EVQLLESGGG LVQPGGSLRL SCAASGFTFS SYAMSWVRQA PGKGLEWVST ISGSGYYTYY    60
ADSVKGRFTI SRDNSKNTLY LQMNSLRAED TAVYYCAKSG PGLRQVGFDY WGQGTLVTVS   120
S                                                                  121

SEQ ID NO: 909          moltype = AA   length = 121
FEATURE                 Location/Qualifiers
source                  1..121
                        mol_type = protein
                        organism = synthetic construct
                        note = 1A7[CD28]_H1.41
SEQUENCE: 909
EVQLLESGGG LVQPGGSLRL SCAASGFTFS SYYMSWVRQA PGKGLEWVST IEGSGDYTYY    60
ADSVKGRFTI SRDNSKNTLY LQMNSLRAED TAVYYCAKSG PGLRQVGFDY WGQGTLVTVS   120
S                                                                  121

SEQ ID NO: 910          moltype = AA   length = 121
FEATURE                 Location/Qualifiers
source                  1..121
                        mol_type = protein
                        organism = synthetic construct
                        note = 1A7[CD28]_H1.42
SEQUENCE: 910
EVQLLESGGG LVQPGGSLRL SCAASGFTFS SYYMSWVRQA PGKGLEWVST ISESGDYTYY    60
ADSVKGRFTI SRDNSKNTLY LQMNSLRAED TAVYYCAKSG PGLRQVGFDY WGQGTLVTVS   120
S                                                                  121

SEQ ID NO: 911          moltype = AA   length = 121
FEATURE                 Location/Qualifiers
source                  1..121
                        mol_type = protein
                        organism = synthetic construct
                        note = 1A7[CD28]_H1.43
SEQUENCE: 911
EVQLLESGGG LVQPGGSLRL SCAASGFSFS GNYMTWVRQA PGKGLEWVAT ITADSDATYY    60
ADSVKGRFTI SRDNSKNTLY LQMNSLRAED TAVYYCAKSG PGLRQVGFDY WGQGTLVTVS   120
S                                                                  121

SEQ ID NO: 912          moltype = AA   length = 121
FEATURE                 Location/Qualifiers
source                  1..121
                        mol_type = protein
                        organism = synthetic construct
                        note = 1A7[CD28]_H1.44
SEQUENCE: 912
EVQLLESGGG LVQPGGSLRL SCAASGFTFS GYSMNWVRQA PGKGLEWVAT IYANGSYTYY    60
ADSVKGRFTI SRDNSKNTLY LQMNSLRAED TAVYYCAKSG PGLRQVGFDY WGQGTLVTVS   120
S                                                                  121

SEQ ID NO: 913          moltype = AA   length = 121
FEATURE                 Location/Qualifiers
source                  1..121
                        mol_type = protein
                        organism = synthetic construct
                        note = 1A7[CD28]_H1.45
SEQUENCE: 913
EVQLLESGGG LVQPGGSLRL SCAASGFNFE EYSMNWVRQA PGKGLEWVAT ITYNGDYTYY    60
ADSVKGRFTI SRDNSKNTLY LQMNSLRAED TAVYYCAKSG PGLRQVGFDY WGQGTLVTVS   120
S                                                                  121

SEQ ID NO: 914          moltype = AA   length = 121
FEATURE                 Location/Qualifiers
source                  1..121
                        mol_type = protein
                        organism = synthetic construct
                        note = 1A7[CD28]_H1.46
```

```
SEQUENCE: 914
EVQLLESGGG LVQPGGSLRL SCAASGFSFR TYYMTWVRQA PGKGLEWVAT ITSDGDYTYY    60
ADSVKGRFTI SRDNSKNTLY LQMNSLRAED TAVYYCAKSG PGLRQVGFDY WGQGTLVTVS   120
S                                                                  121

SEQ ID NO: 915          moltype = AA   length = 121
FEATURE                 Location/Qualifiers
source                  1..121
                        mol_type = protein
                        organism = synthetic construct
                        note = 1A7[CD28]_H1.47
SEQUENCE: 915
EVQLLESGGG LVQPGGSLRL SCAASGFSFK GYSMNWVRQA PGKGLEWVAT IYASSDSTYY    60
ADSVKGRFTI SRDNSKNTLY LQMNSLRAED TAVYYCAKSG PGLRQVGFDY WGQGTLVTVS   120
S                                                                  121

SEQ ID NO: 916          moltype = AA   length = 121
FEATURE                 Location/Qualifiers
source                  1..121
                        mol_type = protein
                        organism = synthetic construct
                        note = 1A7[CD28]_H1.48
SEQUENCE: 916
EVQLLESGGG LVQPGGSLRL SCAASGFSFG EYSMNWVRQA PGKGLEWVST IYADGDYTYY    60
ADSVKGRFTI SRDNSKNTLY LQMNSLRAED TAVYYCAKSG PGLRQVGFDY WGQGTLVTVS   120
S                                                                  121

SEQ ID NO: 917          moltype = AA   length = 121
FEATURE                 Location/Qualifiers
source                  1..121
                        mol_type = protein
                        organism = synthetic construct
                        note = 1A7[CD28]_H1.49
SEQUENCE: 917
EVQLLESGGG LVQPGGSLRL SCAASGFTFT DYSMNWVRQA PGKGLEWVAT IYADSSSTYY    60
ADSVKGRFTI SRDNSKNTLY LQMNSLRAED TAVYYCAKSG PGLRQVGFDY WGQGTLVTVS   120
S                                                                  121

SEQ ID NO: 918          moltype = AA   length = 121
FEATURE                 Location/Qualifiers
source                  1..121
                        mol_type = protein
                        organism = synthetic construct
                        note = 1A7[CD28]_H1.50
SEQUENCE: 918
EVQLLESGGG LVQPGGSLRL SCAASGFTFG GYSMNWVRQA PGKGLEWVAT IYYDSTTTYY    60
ADSVKGRFTI SRDNSKNTLY LQMNSLRAED TAVYYCAKSG PGLRQVGFDY WGQGTLVTVS   120
S                                                                  121

SEQ ID NO: 919          moltype = AA   length = 121
FEATURE                 Location/Qualifiers
source                  1..121
                        mol_type = protein
                        organism = synthetic construct
                        note = 1A7[CD28]_H1.51
SEQUENCE: 919
EVQLLESGGG LVQPGGSLRL SCAASGFTFG AYSMNWVRQA PGKGLEWVST IYNDGATTYY    60
ADSVKGRFTI SRDNSKNTLY LQMNSLRAED TAVYYCAKSG PGLRQVGFDY WGQGTLVTVS   120
S                                                                  121

SEQ ID NO: 920          moltype = AA   length = 121
FEATURE                 Location/Qualifiers
source                  1..121
                        mol_type = protein
                        organism = synthetic construct
                        note = 1A7[CD28]_H1.52
SEQUENCE: 920
EVQLLESGGG LVQPGGSLRL SCAASGFSFE AYSMNWVRQA PGKGLEWVAT IYYDSSYTYY    60
ADSVKGRFTI SRDNSKNTLY LQMNSLRAED TAVYYCAKSG PGLRQVGFDY WGQGTLVTVS   120
S                                                                  121

SEQ ID NO: 921          moltype = AA   length = 121
FEATURE                 Location/Qualifiers
source                  1..121
                        mol_type = protein
                        organism = synthetic construct
                        note = 1A7[CD28]_H1.53
```

```
SEQUENCE: 921
EVQLLESGGG LVQPGGSLRL SCAASGFSFG SYYMSWVRQA PGKGLEWVAS IYYGGYDTYY    60
ADSVKGRFTI SRDNSKNTLY LQMNSLRAED TAVYYCAKSG PGLRQVGFDY WGQGTLVTVS   120
S                                                                  121

SEQ ID NO: 922          moltype = AA   length = 121
FEATURE                 Location/Qualifiers
source                  1..121
                        mol_type = protein
                        organism = synthetic construct
                        note = 1A7[CD28]_H1.54
SEQUENCE: 922
EVQLLESGGG LVQPGGSLRL SCAASGFNFA EYSMSWVRQA PGKGLEWVAT IYAGSDYTYY    60
ADSVKGRFTI SRDNSKNTLY LQMNSLRAED TAVYYCAKSG PGLRQVGFDY WGQGTLVTVS   120
S                                                                  121

SEQ ID NO: 923          moltype = AA   length = 121
FEATURE                 Location/Qualifiers
source                  1..121
                        mol_type = protein
                        organism = synthetic construct
                        note = 1A7[CD28]_H1.55
SEQUENCE: 923
EVQLLESGGG LVQPGGSLRL SCAASGFTFG AYSINWVRQA PGKGLEWVAT IYYDGSYTYY    60
ADSVKGRFTI SRDNSKNTLY LQMNSLRAED TAVYYCAKSG PGLRQVGFDY WGQGTLVTVS   120
S                                                                  121

SEQ ID NO: 924          moltype = AA   length = 121
FEATURE                 Location/Qualifiers
source                  1..121
                        mol_type = protein
                        organism = synthetic construct
                        note = 1A7[CD28]_H1.56
SEQUENCE: 924
EVQLLESGGG LVQPGGSLRL SCAASGFTFS RYYINWVRQA PGKGLEWVAS IYDGGADTYY    60
ADSVKGRFTI SRDNSKNTLY LQMNSLRAED TAVYYCAKSG PGLRQVGFDY WGQGTLVTVS   120
S                                                                  121

SEQ ID NO: 925          moltype = AA   length = 121
FEATURE                 Location/Qualifiers
source                  1..121
                        mol_type = protein
                        organism = synthetic construct
                        note = 1A7[CD28]_H1.57
SEQUENCE: 925
EVQLLESGGG LVQPGGSLRL SCAASGFSFG TYSINWVRQA PGKGLEWVST IYYDGASTYY    60
ADSVKGRFTI SRDNSKNTLY LQMNSLRAED TAVYYCAKSG PGLRQVGFDY WGQGTLVTVS   120
S                                                                  121

SEQ ID NO: 926          moltype = AA   length = 121
FEATURE                 Location/Qualifiers
source                  1..121
                        mol_type = protein
                        organism = synthetic construct
                        note = 1A7[CD28]_H1.58
SEQUENCE: 926
EVQLLESGGG LVQPGGSLRL SCAASGFTFG KYSISWVRQA PGKGLEWVAT IYNDGYYTYY    60
ADSVKGRFTI SRDNSKNTLY LQMNSLRAED TAVYYCAKSG PGLRQVGFDY WGQGTLVTVS   120
S                                                                  121

SEQ ID NO: 927          moltype = AA   length = 121
FEATURE                 Location/Qualifiers
source                  1..121
                        mol_type = protein
                        organism = synthetic construct
                        note = 1A7[CD28]_H1.59
SEQUENCE: 927
EVQLLESGGG LVQPGGSLRL SCAASGFSFE KYYISWVRQA PGKGLEWVAS IYDGSYDTYY    60
ADSVKGRFTI SRDNSKNTLY LQMNSLRAED TAVYYCAKSG PGLRQVGFDY WGQGTLVTVS   120
S                                                                  121

SEQ ID NO: 928          moltype = AA   length = 121
FEATURE                 Location/Qualifiers
source                  1..121
                        mol_type = protein
                        organism = synthetic construct
                        note = 1A7[CD28]_H1.60
```

SEQUENCE: 928
EVQLLESGGG LVQPGGSLRL SCAASGFSFG TYSMNWVRQA PGKGLEWVAT IDYDGSNTYY    60
ADSVKGRFTI SRDNSKNTLY LQMNSLRAED TAVYYCAKSG PGLRQVGFDY WGQGTLVTVS   120
S                                                                  121

SEQ ID NO: 929          moltype = AA   length = 121
FEATURE                 Location/Qualifiers
source                  1..121
                        mol_type = protein
                        organism = synthetic construct
                        note = 1A7[CD28]_H1.61
SEQUENCE: 929
EVQLLESGGG LVQPGGSLRL SCAASGFSFA AYSMSWVRQA PGKGLEWVAT IYAGSDYTYY    60
ADSVKGRFTI SRDNSKNTLY LQMNSLRAED TAVYYCAKSG PGLRQVGFDY WGQGTLVTVS   120
S                                                                  121

SEQ ID NO: 930          moltype = AA   length = 121
FEATURE                 Location/Qualifiers
source                  1..121
                        mol_type = protein
                        organism = synthetic construct
                        note = 1A7[CD28]_H1.62
SEQUENCE: 930
EVQLLESGGG LVQPGGSLRL SCAASGFTFT TYSMTWVRQA PGKGLEWVAT IYNDGYYTYY    60
ADSVKGRFTI SRDNSKNTLY LQMNSLRAED TAVYYCAKSG PGLRQVGFDY WGQGTLVTVS   120
S                                                                  121

SEQ ID NO: 931          moltype = AA   length = 121
FEATURE                 Location/Qualifiers
source                  1..121
                        mol_type = protein
                        organism = synthetic construct
                        note = 1A7[CD28]_H1.63
SEQUENCE: 931
EVQLLESGGG LVQPGGSLRL SCAASGFSFK DYSMNWVRQA PGKGLEWVAT IYYDGTYTYY    60
ADSVKGRFTI SRDNSKNTLY LQMNSLRAED TAVYYCAKSG PGLRQVGFDY WGQGTLVTVS   120
S                                                                  121

SEQ ID NO: 932          moltype = AA   length = 121
FEATURE                 Location/Qualifiers
source                  1..121
                        mol_type = protein
                        organism = synthetic construct
                        note = 1A7[CD28]_H1.64
SEQUENCE: 932
EVQLLESGGG LVQPGGSLRL SCAASGFSFA AYSMNWVRQA PGKGLEWVAT IYAGGAYTYY    60
ADSVKGRFTI SRDNSKNTLY LQMNSLRAED TAVYYCAKSG PGLRQVGFDY WGQGTLVTVS   120
S                                                                  121

SEQ ID NO: 933          moltype = AA   length = 121
FEATURE                 Location/Qualifiers
source                  1..121
                        mol_type = protein
                        organism = synthetic construct
                        note = 1A7[CD28]_H1.65
SEQUENCE: 933
EVQLLESGGG LVQPGGSLRL SCAASGFNFA EYYISWVRQA PGKGLEWVAS IYNGGSDTYY    60
ADSVKGRFTI SRDNSKNTLY LQMNSLRAED TAVYYCAKSG PGLRQVGFDY WGQGTLVTVS   120
S                                                                  121

SEQ ID NO: 934          moltype = AA   length = 121
FEATURE                 Location/Qualifiers
source                  1..121
                        mol_type = protein
                        organism = synthetic construct
                        note = 1A7[CD28]_H1.66
SEQUENCE: 934
EVQLLESGGG LVQPGGSLRL SCAASGFSLG EYYMNWVRQA PGKGLEWVST IDYDGTYTYY    60
ADSVKGRFTI SRDNSKNTLY LQMNSLRAED TAVYYCAKSG PGLRQVGFDY WGQGTLVTVS   120
S                                                                  121

SEQ ID NO: 935          moltype = AA   length = 121
FEATURE                 Location/Qualifiers
source                  1..121
                        mol_type = protein
                        organism = synthetic construct
                        note = 1A7[CD28]_H1.67

```
SEQUENCE: 935
EVQLLESGGG LVQPGGSLRL SCAASGFTFN EYYITWVRQA PGKGLEWVSS IYSSSYDTYY    60
ADSVKGRFTI SRDNSKNTLY LQMNSLRAED TAVYYCAKSG PGLRQVGFDY WGQGTLVTVS   120
S                                                                  121

SEQ ID NO: 936          moltype = AA   length = 121
FEATURE                 Location/Qualifiers
source                  1..121
                        mol_type = protein
                        organism = synthetic construct
                        note = 1A7[CD28]_H1.68
SEQUENCE: 936
EVQLLESGGG LVQPGGSLRL SCAASGFTFK DYYITWVRQA PGKGLEWVSS IYTSGYDTYY    60
ADSVKGRFTI SRDNSKNTLY LQMNSLRAED TAVYYCAKSG PGLRQVGFDY WGQGTLVTVS   120
S                                                                  121

SEQ ID NO: 937          moltype = AA   length = 121
FEATURE                 Location/Qualifiers
source                  1..121
                        mol_type = protein
                        organism = synthetic construct
                        note = 1A7[CD28]_H1.69
SEQUENCE: 937
EVQLLESGGG LVQPGGSLRL SCAASGFSFG KYSINWVRQA PGKGLEWVAT IYSDGTDTYY    60
ADSVKGRFTI SRDNSKNTLY LQMNSLRAED TAVYYCAKSG PGLRQVGFDY WGQGTLVTVS   120
S                                                                  121

SEQ ID NO: 938          moltype = AA   length = 107
FEATURE                 Location/Qualifiers
source                  1..107
                        mol_type = protein
                        organism = synthetic construct
                        note = 1A7[CD28]_L1.1
SEQUENCE: 938
DIQMTQSPSS LSASVGDRVT ITCRASQSIS AYLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 939          moltype = AA   length = 107
FEATURE                 Location/Qualifiers
source                  1..107
                        mol_type = protein
                        organism = synthetic construct
                        note = 1A7[CD28]_L1.2
SEQUENCE: 939
DIQMTQSPSS LSASVGDRVT ITCRASQSIS DYLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 940          moltype = AA   length = 107
FEATURE                 Location/Qualifiers
source                  1..107
                        mol_type = protein
                        organism = synthetic construct
                        note = 1A7[CD28]_L1.3
SEQUENCE: 940
DIQMTQSPSS LSASVGDRVT ITCRASQSIS GYLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 941          moltype = AA   length = 107
FEATURE                 Location/Qualifiers
source                  1..107
                        mol_type = protein
                        organism = synthetic construct
                        note = 1A7[CD28]_L1.4
SEQUENCE: 941
DIQMTQSPSS LSASVGDRVT ITCRASQSIS HYLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 942          moltype = AA   length = 107
FEATURE                 Location/Qualifiers
source                  1..107
                        mol_type = protein
                        organism = synthetic construct
                        note = 1A7[CD28]_L1.5
SEQUENCE: 942
DIQMTQSPSS LSASVGDRVT ITCRASQSIS KYLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 943          moltype = AA   length = 107
FEATURE                 Location/Qualifiers
```

```
source                        1..107
                              mol_type = protein
                              organism = synthetic construct
                              note = 1A7[CD28]_L1.6
SEQUENCE: 943
DIQMTQSPSS LSASVGDRVT ITCRASQSIS NYLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 944                moltype = AA  length = 107
FEATURE                       Location/Qualifiers
source                        1..107
                              mol_type = protein
                              organism = synthetic construct
                              note = 1A7[CD28]_L1.7
SEQUENCE: 944
DIQMTQSPSS LSASVGDRVT ITCRASQSIS QYLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 945                moltype = AA  length = 107
FEATURE                       Location/Qualifiers
source                        1..107
                              mol_type = protein
                              organism = synthetic construct
                              note = 1A7[CD28]_L1.8
SEQUENCE: 945
DIQMTQSPSS LSASVGDRVT ITCRASQSIS TYLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 946                moltype = AA  length = 107
FEATURE                       Location/Qualifiers
source                        1..107
                              mol_type = protein
                              organism = synthetic construct
                              note = 1A7[CD28]_L1.9
SEQUENCE: 946
DIQMTQSPSS LSASVGDRVT ITCRASQSIS VYLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 947                moltype = AA  length = 107
FEATURE                       Location/Qualifiers
source                        1..107
                              mol_type = protein
                              organism = synthetic construct
                              note = 1A7[CD28]_L1.10
SEQUENCE: 947
DIQMTQSPSS LSASVGDRVT ITCRASQSIS YYLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 948                moltype = AA  length = 107
FEATURE                       Location/Qualifiers
source                        1..107
                              mol_type = protein
                              organism = synthetic construct
                              note = 1A7[CD28]_L1.11
SEQUENCE: 948
DIQMTQSPSS LSASVGDRVT ITCRASQSIS SALNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 949                moltype = AA  length = 107
FEATURE                       Location/Qualifiers
source                        1..107
                              mol_type = protein
                              organism = synthetic construct
                              note = 1A7[CD28]_L1.12
SEQUENCE: 949
DIQMTQSPSS LSASVGDRVT ITCRASQSIS SDLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 950                moltype = AA  length = 107
FEATURE                       Location/Qualifiers
source                        1..107
                              mol_type = protein
                              organism = synthetic construct
                              note = 1A7[CD28]_L1.13
SEQUENCE: 950
DIQMTQSPSS LSASVGDRVT ITCRASQSIS SFLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 951                moltype = AA  length = 107
```

```
FEATURE                 Location/Qualifiers
source                  1..107
                        mol_type = protein
                        organism = synthetic construct
                        note = 1A7[CD28]_L1.14
SEQUENCE: 951
DIQMTQSPSS LSASVGDRVT ITCRASQSIS SHLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 952          moltype = AA   length = 107
FEATURE                 Location/Qualifiers
source                  1..107
                        mol_type = protein
                        organism = synthetic construct
                        note = 1A7[CD28]_L1.15
SEQUENCE: 952
DIQMTQSPSS LSASVGDRVT ITCRASQSIS SKLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 953          moltype = AA   length = 107
FEATURE                 Location/Qualifiers
source                  1..107
                        mol_type = protein
                        organism = synthetic construct
                        note = 1A7[CD28]_L1.16
SEQUENCE: 953
DIQMTQSPSS LSASVGDRVT ITCRASQSIS SLLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 954          moltype = AA   length = 107
FEATURE                 Location/Qualifiers
source                  1..107
                        mol_type = protein
                        organism = synthetic construct
                        note = 1A7[CD28]_L1.17
SEQUENCE: 954
DIQMTQSPSS LSASVGDRVT ITCRASQSIS SNLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 955          moltype = AA   length = 107
FEATURE                 Location/Qualifiers
source                  1..107
                        mol_type = protein
                        organism = synthetic construct
                        note = 1A7[CD28]_L1.18
SEQUENCE: 955
DIQMTQSPSS LSASVGDRVT ITCRASQSIS SQLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 956          moltype = AA   length = 107
FEATURE                 Location/Qualifiers
source                  1..107
                        mol_type = protein
                        organism = synthetic construct
                        note = 1A7[CD28]_L1.19
SEQUENCE: 956
DIQMTQSPSS LSASVGDRVT ITCRASQSIS SSLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 957          moltype = AA   length = 107
FEATURE                 Location/Qualifiers
source                  1..107
                        mol_type = protein
                        organism = synthetic construct
                        note = 1A7[CD28]_L1.20
SEQUENCE: 957
DIQMTQSPSS LSASVGDRVT ITCRASQSIS SWLNWYQQKP GKAPKLLIYA ASSLQSGVPS    60
RFSGSGSGTD FTLTISSLQP EDFATYYCQQ SYSTPFTFGQ GTKLEIK                 107

SEQ ID NO: 958          moltype = AA   length = 107
FEATURE                 Location/Qualifiers
source                  1..107
                        mol_type = protein
                        organism = synthetic construct
                        note = 1A7[CD28]_L1.21
SEQUENCE: 958
DIQMTQSPSS LSASVGDRVT ITCRASQSIS SYLAWYQQKP GKAPKLLIYA ASSLQSGVPS    60
RFSGSGSGTD FTLTISSLQP EDFATYYCQQ SYSTPFTFGQ GTKLEIK                 107
```

```
SEQ ID NO: 959         moltype = AA  length = 107
FEATURE                Location/Qualifiers
source                 1..107
                       mol_type = protein
                       organism = synthetic construct
                       note = 1A7[CD28]_L1.22
SEQUENCE: 959
DIQMTQSPSS LSASVGDRVT ITCRASQSIS SYLDWYQQKP GKAPKLLIYA ASSLQSGVPS    60
RFSGSGSGTD FTLTISSLQP EDFATYYCQQ SYSTPFTFGQ GTKLEIK                  107

SEQ ID NO: 960         moltype = AA  length = 107
FEATURE                Location/Qualifiers
source                 1..107
                       mol_type = protein
                       organism = synthetic construct
                       note = 1A7[CD28]_L1.23
SEQUENCE: 960
DIQMTQSPSS LSASVGDRVT ITCRASQSIS SYLGWYQQKP GKAPKLLIYA ASSLQSGVPS    60
RFSGSGSGTD FTLTISSLQP EDFATYYCQQ SYSTPFTFGQ GTKLEIK                  107

SEQ ID NO: 961         moltype = AA  length = 107
FEATURE                Location/Qualifiers
source                 1..107
                       mol_type = protein
                       organism = synthetic construct
                       note = 1A7[CD28]_L1.24
SEQUENCE: 961
DIQMTQSPSS LSASVGDRVT ITCRASQSIS SYLHWYQQKP GKAPKLLIYA ASSLQSGVPS    60
RFSGSGSGTD FTLTISSLQP EDFATYYCQQ SYSTPFTFGQ GTKLEIK                  107

SEQ ID NO: 962         moltype = AA  length = 107
FEATURE                Location/Qualifiers
source                 1..107
                       mol_type = protein
                       organism = synthetic construct
                       note = 1A7[CD28]_L1.25
SEQUENCE: 962
DIQMTQSPSS LSASVGDRVT ITCRASQSIS SYLQWYQQKP GKAPKLLIYA ASSLQSGVPS    60
RFSGSGSGTD FTLTISSLQP EDFATYYCQQ SYSTPFTFGQ GTKLEIK                  107

SEQ ID NO: 963         moltype = AA  length = 107
FEATURE                Location/Qualifiers
source                 1..107
                       mol_type = protein
                       organism = synthetic construct
                       note = 1A7[CD28]_L1.26
SEQUENCE: 963
DIQMTQSPSS LSASVGDRVT ITCRASQSIS SYLSWYQQKP GKAPKLLIYA ASSLQSGVPS    60
RFSGSGSGTD FTLTISSLQP EDFATYYCQQ SYSTPFTFGQ GTKLEIK                  107

SEQ ID NO: 964         moltype = AA  length = 107
FEATURE                Location/Qualifiers
source                 1..107
                       mol_type = protein
                       organism = synthetic construct
                       note = 1A7[CD28]_L1.27
SEQUENCE: 964
DIQMTQSPSS LSASVGDRVT ITCRASQSIS SYLTWYQQKP GKAPKLLIYA ASSLQSGVPS    60
RFSGSGSGTD FTLTISSLQP EDFATYYCQQ SYSTPFTFGQ GTKLEIK                  107

SEQ ID NO: 965         moltype = AA  length = 107
FEATURE                Location/Qualifiers
source                 1..107
                       mol_type = protein
                       organism = synthetic construct
                       note = 1A7[CD28]_L1.28
SEQUENCE: 965
DIQMTQSPSS LSASVGDRVT ITCRASQSIS SYLYWYQQKP GKAPKLLIYA ASSLQSGVPS    60
RFSGSGSGTD FTLTISSLQP EDFATYYCQQ SYSTPFTFGQ GTKLEIK                  107

SEQ ID NO: 966         moltype = AA  length = 107
FEATURE                Location/Qualifiers
source                 1..107
                       mol_type = protein
                       organism = synthetic construct
                       note = 1A7[CD28]_L1.29
SEQUENCE: 966
DIQMTQSPSS LSASVGDRVT ITCRASQSIS SYLNWYQQKP GKAPKLLIYD ASSLQSGVPS    60
RFSGSGSGTD FTLTISSLQP EDFATYYCQQ SYSTPFTFGQ GTKLEIK                  107
```

```
SEQ ID NO: 967          moltype = AA  length = 107
FEATURE                 Location/Qualifiers
source                  1..107
                        mol_type = protein
                        organism = synthetic construct
                        note = 1A7[CD28]_L1.30
SEQUENCE: 967
DIQMTQSPSS LSASVGDRVT ITCRASQSIS SYLNWYQQKP GKAPKLLIYG ASSLQSGVPS    60
RFSGSGSGTD FTLTISSLQP EDFATYYCQQ SYSTPFTFGQ GTKLEIK                 107

SEQ ID NO: 968          moltype = AA  length = 107
FEATURE                 Location/Qualifiers
source                  1..107
                        mol_type = protein
                        organism = synthetic construct
                        note = 1A7[CD28]_L1.31
SEQUENCE: 968
DIQMTQSPSS LSASVGDRVT ITCRASQSIS SYLNWYQQKP GKAPKLLIYK ASSLQSGVPS    60
RFSGSGSGTD FTLTISSLQP EDFATYYCQQ SYSTPFTFGQ GTKLEIK                 107

SEQ ID NO: 969          moltype = AA  length = 107
FEATURE                 Location/Qualifiers
source                  1..107
                        mol_type = protein
                        organism = synthetic construct
                        note = 1A7[CD28]_L1.32
SEQUENCE: 969
DIQMTQSPSS LSASVGDRVT ITCRASQSIS SYLNWYQQKP GKAPKLLIYL ASSLQSGVPS    60
RFSGSGSGTD FTLTISSLQP EDFATYYCQQ SYSTPFTFGQ GTKLEIK                 107

SEQ ID NO: 970          moltype = AA  length = 107
FEATURE                 Location/Qualifiers
source                  1..107
                        mol_type = protein
                        organism = synthetic construct
                        note = 1A7[CD28]_L1.33
SEQUENCE: 970
DIQMTQSPSS LSASVGDRVT ITCRASQSIS SYLNWYQQKP GKAPKLLIYQ ASSLQSGVPS    60
RFSGSGSGTD FTLTISSLQP EDFATYYCQQ SYSTPFTFGQ GTKLEIK                 107

SEQ ID NO: 971          moltype = AA  length = 107
FEATURE                 Location/Qualifiers
source                  1..107
                        mol_type = protein
                        organism = synthetic construct
                        note = 1A7[CD28]_L1.34
SEQUENCE: 971
DIQMTQSPSS LSASVGDRVT ITCRASQSIS SYLNWYQQKP GKAPKLLIYS ASSLQSGVPS    60
RFSGSGSGTD FTLTISSLQP EDFATYYCQQ SYSTPFTFGQ GTKLEIK                 107

SEQ ID NO: 972          moltype = AA  length = 107
FEATURE                 Location/Qualifiers
source                  1..107
                        mol_type = protein
                        organism = synthetic construct
                        note = 1A7[CD28]_L1.35
SEQUENCE: 972
DIQMTQSPSS LSASVGDRVT ITCRASQSIS SYLNWYQQKP GKAPKLLIYT ASSLQSGVPS    60
RFSGSGSGTD FTLTISSLQP EDFATYYCQQ SYSTPFTFGQ GTKLEIK                 107

SEQ ID NO: 973          moltype = AA  length = 107
FEATURE                 Location/Qualifiers
source                  1..107
                        mol_type = protein
                        organism = synthetic construct
                        note = 1A7[CD28]_L1.36
SEQUENCE: 973
DIQMTQSPSS LSASVGDRVT ITCRASQSIS SYLNWYQQKP GKAPKLLIYW ASSLQSGVPS    60
RFSGSGSGTD FTLTISSLQP EDFATYYCQQ SYSTPFTFGQ GTKLEIK                 107

SEQ ID NO: 974          moltype = AA  length = 107
FEATURE                 Location/Qualifiers
source                  1..107
                        mol_type = protein
                        organism = synthetic construct
                        note = 1A7[CD28]_L1.37
```

SEQUENCE: 974
DIQMTQSPSS LSASVGDRVT ITCRASQSIS SYLNWYQQKP GKAPKLLIYY ASSLQSGVPS    60
RFSGSGSGTD FTLTISSLQP EDFATYYCQQ SYSTPFTFGQ GTKLEIK                 107

SEQ ID NO: 975           moltype = AA   length = 107
FEATURE                  Location/Qualifiers
source                   1..107
                         mol_type = protein
                         organism = synthetic construct
                         note = 1A7[CD28]_L1.38
SEQUENCE: 975
DIQMTQSPSS LSASVGDRVT ITCRASQSIS SYLNWYQQKP GKAPKLLIYA ASALQSGVPS    60
RFSGSGSGTD FTLTISSLQP EDFATYYCQQ SYSTPFTFGQ GTKLEIK                 107

SEQ ID NO: 976           moltype = AA   length = 107
FEATURE                  Location/Qualifiers
source                   1..107
                         mol_type = protein
                         organism = synthetic construct
                         note = 1A7[CD28]_L1.39
SEQUENCE: 976
DIQMTQSPSS LSASVGDRVT ITCRASQSIS SYLNWYQQKP GKAPKLLIYA ASDLQSGVPS    60
RFSGSGSGTD FTLTISSLQP EDFATYYCQQ SYSTPFTFGQ GTKLEIK                 107

SEQ ID NO: 977           moltype = AA   length = 107
FEATURE                  Location/Qualifiers
source                   1..107
                         mol_type = protein
                         organism = synthetic construct
                         note = 1A7[CD28]_L1.40
SEQUENCE: 977
DIQMTQSPSS LSASVGDRVT ITCRASQSIS SYLNWYQQKP GKAPKLLIYA ASKLQSGVPS    60
RFSGSGSGTD FTLTISSLQP EDFATYYCQQ SYSTPFTFGQ GTKLEIK                 107

SEQ ID NO: 978           moltype = AA   length = 107
FEATURE                  Location/Qualifiers
source                   1..107
                         mol_type = protein
                         organism = synthetic construct
                         note = 1A7[CD28]_L1.41
SEQUENCE: 978
DIQMTQSPSS LSASVGDRVT ITCRASQSIS SYLNWYQQKP GKAPKLLIYA ASNLQSGVPS    60
RFSGSGSGTD FTLTISSLQP EDFATYYCQQ SYSTPFTFGQ GTKLEIK                 107

SEQ ID NO: 979           moltype = AA   length = 107
FEATURE                  Location/Qualifiers
source                   1..107
                         mol_type = protein
                         organism = synthetic construct
                         note = 1A7[CD28]_L1.42
SEQUENCE: 979
DIQMTQSPSS LSASVGDRVT ITCRASQSIS SYLNWYQQKP GKAPKLLIYA ASQLQSGVPS    60
RFSGSGSGTD FTLTISSLQP EDFATYYCQQ SYSTPFTFGQ GTKLEIK                 107

SEQ ID NO: 980           moltype = AA   length = 107
FEATURE                  Location/Qualifiers
source                   1..107
                         mol_type = protein
                         organism = synthetic construct
                         note = 1A7[CD28]_L1.43
SEQUENCE: 980
DIQMTQSPSS LSASVGDRVT ITCRASQSIS SYLNWYQQKP GKAPKLLIYA ASTLQSGVPS    60
RFSGSGSGTD FTLTISSLQP EDFATYYCQQ SYSTPFTFGQ GTKLEIK                 107

SEQ ID NO: 981           moltype = AA   length = 107
FEATURE                  Location/Qualifiers
source                   1..107
                         mol_type = protein
                         organism = synthetic construct
                         note = 1A7[CD28]_L1.44
SEQUENCE: 981
DIQMTQSPSS LSASVGDRVT ITCRASQSIS SYLNWYQQKP GKAPKLLIYA ASYLQSGVPS    60
RFSGSGSGTD FTLTISSLQP EDFATYYCQQ SYSTPFTFGQ GTKLEIK                 107

SEQ ID NO: 982           moltype = AA   length = 107
FEATURE                  Location/Qualifiers

```
source                       1..107
                             mol_type = protein
                             organism = synthetic construct
                             note = 1A7[CD28]_L1.45
SEQUENCE: 982
DIQMTQSPSS LSASVGDRVT ITCRASQSIS SYLNWYQQKP GKAPKLLIYA ASSLASGVPS    60
RFSGSGSGTD FTLTISSLQP EDFATYYCQQ SYSTPFTFGQ GTKLEIK                 107

SEQ ID NO: 983               moltype = AA  length = 107
FEATURE                      Location/Qualifiers
source                       1..107
                             mol_type = protein
                             organism = synthetic construct
                             note = 1A7[CD28]_L1.46
SEQUENCE: 983
DIQMTQSPSS LSASVGDRVT ITCRASQSIS SYLNWYQQKP GKAPKLLIYA ASSLESGVPS    60
RFSGSGSGTD FTLTISSLQP EDFATYYCQQ SYSTPFTFGQ GTKLEIK                 107

SEQ ID NO: 984               moltype = AA  length = 107
FEATURE                      Location/Qualifiers
source                       1..107
                             mol_type = protein
                             organism = synthetic construct
                             note = 1A7[CD28]_L1.47
SEQUENCE: 984
DIQMTQSPSS LSASVGDRVT ITCRASQSIS SYLNWYQQKP GKAPKLLIYA ASSLFSGVPS    60
RFSGSGSGTD FTLTISSLQP EDFATYYCQQ SYSTPFTFGQ GTKLEIK                 107

SEQ ID NO: 985               moltype = AA  length = 107
FEATURE                      Location/Qualifiers
source                       1..107
                             mol_type = protein
                             organism = synthetic construct
                             note = 1A7[CD28]_L1.48
SEQUENCE: 985
DIQMTQSPSS LSASVGDRVT ITCRASQSIS SYLNWYQQKP GKAPKLLIYA ASSLHSGVPS    60
RFSGSGSGTD FTLTISSLQP EDFATYYCQQ SYSTPFTFGQ GTKLEIK                 107

SEQ ID NO: 986               moltype = AA  length = 107
FEATURE                      Location/Qualifiers
source                       1..107
                             mol_type = protein
                             organism = synthetic construct
                             note = 1A7[CD28]_L1.49
SEQUENCE: 986
DIQMTQSPSS LSASVGDRVT ITCRASQSIS SYLNWYQQKP GKAPKLLIYA ASSLISGVPS    60
RFSGSGSGTD FTLTISSLQP EDFATYYCQQ SYSTPFTFGQ GTKLEIK                 107

SEQ ID NO: 987               moltype = AA  length = 107
FEATURE                      Location/Qualifiers
source                       1..107
                             mol_type = protein
                             organism = synthetic construct
                             note = 1A7[CD28]_L1.50
SEQUENCE: 987
DIQMTQSPSS LSASVGDRVT ITCRASQSIS SYLNWYQQKP GKAPKLLIYA ASSLKSGVPS    60
RFSGSGSGTD FTLTISSLQP EDFATYYCQQ SYSTPFTFGQ GTKLEIK                 107

SEQ ID NO: 988               moltype = AA  length = 107
FEATURE                      Location/Qualifiers
source                       1..107
                             mol_type = protein
                             organism = synthetic construct
                             note = 1A7[CD28]_L1.51
SEQUENCE: 988
DIQMTQSPSS LSASVGDRVT ITCRASQSIS SYLNWYQQKP GKAPKLLIYA ASSLNSGVPS    60
RFSGSGSGTD FTLTISSLQP EDFATYYCQQ SYSTPFTFGQ GTKLEIK                 107

SEQ ID NO: 989               moltype = AA  length = 107
FEATURE                      Location/Qualifiers
source                       1..107
                             mol_type = protein
                             organism = synthetic construct
                             note = 1A7[CD28]_L1.52
SEQUENCE: 989
DIQMTQSPSS LSASVGDRVT ITCRASQSIS SYLNWYQQKP GKAPKLLIYA ASSLSSGVPS    60
RFSGSGSGTD FTLTISSLQP EDFATYYCQQ SYSTPFTFGQ GTKLEIK                 107

SEQ ID NO: 990               moltype = AA  length = 107
```

```
FEATURE                 Location/Qualifiers
source                  1..107
                        mol_type = protein
                        organism = synthetic construct
                        note = 1A7[CD28]_L1.53
SEQUENCE: 990
DIQMTQSPSS LSASVGDRVT ITCRASQSIS SYLNWYQQKP GKAPKLLIYA ASSLVSGVPS    60
RFSGSGSGTD FTLTISSLQP EDFATYYCQQ SYSTPFTFGQ GTKLEIK                 107

SEQ ID NO: 991          moltype = AA  length = 107
FEATURE                 Location/Qualifiers
source                  1..107
                        mol_type = protein
                        organism = synthetic construct
                        note = 1A7[CD28]_L1.54
SEQUENCE: 991
DIQMTQSPSS LSASVGDRVT ITCRASQSIS SYLNWYQQKP GKAPKLLIYA ASSLYSGVPS    60
RFSGSGSGTD FTLTISSLQP EDFATYYCQQ SYSTPFTFGQ GTKLEIK                 107

SEQ ID NO: 992          moltype = AA  length = 107
FEATURE                 Location/Qualifiers
source                  1..107
                        mol_type = protein
                        organism = synthetic construct
                        note = 1A7[CD28]_L1.55
SEQUENCE: 992
DIQMTQSPSS LSASVGDRVT ITCRASQSIS SYLNWYQQKP GKAPKLLIYA ASSLQAGVPS    60
RFSGSGSGTD FTLTISSLQP EDFATYYCQQ SYSTPFTFGQ GTKLEIK                 107

SEQ ID NO: 993          moltype = AA  length = 107
FEATURE                 Location/Qualifiers
source                  1..107
                        mol_type = protein
                        organism = synthetic construct
                        note = 1A7[CD28]_L1.56
SEQUENCE: 993
DIQMTQSPSS LSASVGDRVT ITCRASQSIS SYLNWYQQKP GKAPKLLIYA ASSLQDGVPS    60
RFSGSGSGTD FTLTISSLQP EDFATYYCQQ SYSTPFTFGQ GTKLEIK                 107

SEQ ID NO: 994          moltype = AA  length = 107
FEATURE                 Location/Qualifiers
source                  1..107
                        mol_type = protein
                        organism = synthetic construct
                        note = 1A7[CD28]_L1.57
SEQUENCE: 994
DIQMTQSPSS LSASVGDRVT ITCRASQSIS SYLNWYQQKP GKAPKLLIYA ASSLQGGVPS    60
RFSGSGSGTD FTLTISSLQP EDFATYYCQQ SYSTPFTFGQ GTKLEIK                 107

SEQ ID NO: 995          moltype = AA  length = 107
FEATURE                 Location/Qualifiers
source                  1..107
                        mol_type = protein
                        organism = synthetic construct
                        note = 1A7[CD28]_L1.58
SEQUENCE: 995
DIQMTQSPSS LSASVGDRVT ITCRASQSIS SYLNWYQQKP GKAPKLLIYA ASSLQHGVPS    60
RFSGSGSGTD FTLTISSLQP EDFATYYCQQ SYSTPFTFGQ GTKLEIK                 107

SEQ ID NO: 996          moltype = AA  length = 107
FEATURE                 Location/Qualifiers
source                  1..107
                        mol_type = protein
                        organism = synthetic construct
                        note = 1A7[CD28]_L1.59
SEQUENCE: 996
DIQMTQSPSS LSASVGDRVT ITCRASQSIS SYLNWYQQKP GKAPKLLIYA ASSLQKGVPS    60
RFSGSGSGTD FTLTISSLQP EDFATYYCQQ SYSTPFTFGQ GTKLEIK                 107

SEQ ID NO: 997          moltype = AA  length = 107
FEATURE                 Location/Qualifiers
source                  1..107
                        mol_type = protein
                        organism = synthetic construct
                        note = 1A7[CD28]_L1.60
SEQUENCE: 997
DIQMTQSPSS LSASVGDRVT ITCRASQSIS SYLNWYQQKP GKAPKLLIYA ASSLQQGVPS    60
RFSGSGSGTD FTLTISSLQP EDFATYYCQQ SYSTPFTFGQ GTKLEIK                 107
```

| | |
|---|---|
| SEQ ID NO: 998 | moltype = AA   length = 107 |
| FEATURE | Location/Qualifiers |
| source | 1..107 |
| | mol_type = protein |
| | organism = synthetic construct |
| | note = 1A7[CD28]_L1.61 |

SEQUENCE: 998
DIQMTQSPSS LSASVGDRVT ITCRASQSIS SYLNWYQQKP GKAPKLLIYA ASSLQTGVPS 60
RFSGSGSGTD FTLTISSLQP EDFATYYCQQ SYSTPFTFGQ GTKLEIK 107

| | |
|---|---|
| SEQ ID NO: 999 | moltype = AA   length = 107 |
| FEATURE | Location/Qualifiers |
| source | 1..107 |
| | mol_type = protein |
| | organism = synthetic construct |
| | note = 1A7[CD28]_L1.62 |

SEQUENCE: 999
DIQMTQSPSS LSASVGDRVT ITCRASQSIS SYLNWYQQKP GKAPKLLIYA ASSLQVGVPS 60
RFSGSGSGTD FTLTISSLQP EDFATYYCQQ SYSTPFTFGQ GTKLEIK 107

| | |
|---|---|
| SEQ ID NO: 1000 | moltype = AA   length = 107 |
| FEATURE | Location/Qualifiers |
| source | 1..107 |
| | mol_type = protein |
| | organism = synthetic construct |
| | note = 1A7[CD28]_L1.63 |

SEQUENCE: 1000
DIQMTQSPSS LSASVGDRVT ITCRASQSIS SYLNWYQQKP GKAPKLLIYA ASSLQYGVPS 60
RFSGSGSGTD FTLTISSLQP EDFATYYCQQ SYSTPFTFGQ GTKLEIK 107

| | |
|---|---|
| SEQ ID NO: 1001 | moltype = AA   length = 107 |
| FEATURE | Location/Qualifiers |
| source | 1..107 |
| | mol_type = protein |
| | organism = synthetic construct |
| | note = 1A7[CD28]_L1.64 |

SEQUENCE: 1001
DIQMTQSPSS LSASVGDRVT ITCRASQSIS SYLNWYQQKP GKAPKLLIYA ASSLQSGVPS 60
RFSGSGSGTD FTLTISSLQP EDFATYYCQQ AYSTPFTFGQ GTKLEIK 107

| | |
|---|---|
| SEQ ID NO: 1002 | moltype = AA   length = 107 |
| FEATURE | Location/Qualifiers |
| source | 1..107 |
| | mol_type = protein |
| | organism = synthetic construct |
| | note = 1A7[CD28]_L1.65 |

SEQUENCE: 1002
DIQMTQSPSS LSASVGDRVT ITCRASQSIS SYLNWYQQKP GKAPKLLIYA ASSLQSGVPS 60
RFSGSGSGTD FTLTISSLQP EDFATYYCQQ DYSTPFTFGQ GTKLEIK 107

| | |
|---|---|
| SEQ ID NO: 1003 | moltype = AA   length = 107 |
| FEATURE | Location/Qualifiers |
| source | 1..107 |
| | mol_type = protein |
| | organism = synthetic construct |
| | note = 1A7[CD28]_L1.66 |

SEQUENCE: 1003
DIQMTQSPSS LSASVGDRVT ITCRASQSIS SYLNWYQQKP GKAPKLLIYA ASSLQSGVPS 60
RFSGSGSGTD FTLTISSLQP EDFATYYCQQ FYSTPFTFGQ GTKLEIK 107

| | |
|---|---|
| SEQ ID NO: 1004 | moltype = AA   length = 107 |
| FEATURE | Location/Qualifiers |
| source | 1..107 |
| | mol_type = protein |
| | organism = synthetic construct |
| | note = 1A7[CD28]_L1.67 |

SEQUENCE: 1004
DIQMTQSPSS LSASVGDRVT ITCRASQSIS SYLNWYQQKP GKAPKLLIYA ASSLQSGVPS 60
RFSGSGSGTD FTLTISSLQP EDFATYYCQQ HYSTPFTFGQ GTKLEIK 107

| | |
|---|---|
| SEQ ID NO: 1005 | moltype = AA   length = 107 |
| FEATURE | Location/Qualifiers |
| source | 1..107 |
| | mol_type = protein |
| | organism = synthetic construct |
| | note = 1A7[CD28]_L1.68 |

SEQUENCE: 1005
DIQMTQSPSS LSASVGDRVT ITCRASQSIS SYLNWYQQKP GKAPKLLIYA ASSLQSGVPS 60
RFSGSGSGTD FTLTISSLQP EDFATYYCQQ KYSTPFTFGQ GTKLEIK 107

```
SEQ ID NO: 1006          moltype = AA   length = 107
FEATURE                  Location/Qualifiers
source                   1..107
                         mol_type = protein
                         organism = synthetic construct
                         note = 1A7[CD28]_L1.69
SEQUENCE: 1006
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ LYSTPFTFGQ GTKLEIK                 107

SEQ ID NO: 1007          moltype = AA   length = 107
FEATURE                  Location/Qualifiers
source                   1..107
                         mol_type = protein
                         organism = synthetic construct
                         note = 1A7[CD28]_L1.70
SEQUENCE: 1007
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ TYSTPFTFGQ GTKLEIK                 107

SEQ ID NO: 1008          moltype = AA   length = 107
FEATURE                  Location/Qualifiers
source                   1..107
                         mol_type = protein
                         organism = synthetic construct
                         note = 1A7[CD28]_L1.71
SEQUENCE: 1008
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ VYSTPFTFGQ GTKLEIK                 107

SEQ ID NO: 1009          moltype = AA   length = 107
FEATURE                  Location/Qualifiers
source                   1..107
                         mol_type = protein
                         organism = synthetic construct
                         note = 1A7[CD28]_L1.72
SEQUENCE: 1009
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ YYSTPFTFGQ GTKLEIK                 107

SEQ ID NO: 1010          moltype = AA   length = 107
FEATURE                  Location/Qualifiers
source                   1..107
                         mol_type = protein
                         organism = synthetic construct
                         note = 1A7[CD28]_L1.73
SEQUENCE: 1010
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SASTPFTFGQ GTKLEIK                 107

SEQ ID NO: 1011          moltype = AA   length = 107
FEATURE                  Location/Qualifiers
source                   1..107
                         mol_type = protein
                         organism = synthetic construct
                         note = 1A7[CD28]_L1.74
SEQUENCE: 1011
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SDSTPFTFGQ GTKLEIK                 107

SEQ ID NO: 1012          moltype = AA   length = 107
FEATURE                  Location/Qualifiers
source                   1..107
                         mol_type = protein
                         organism = synthetic construct
                         note = 1A7[CD28]_L1.75
SEQUENCE: 1012
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SFSTPFTFGQ GTKLEIK                 107

SEQ ID NO: 1013          moltype = AA   length = 107
FEATURE                  Location/Qualifiers
source                   1..107
                         mol_type = protein
                         organism = synthetic construct
                         note = 1A7[CD28]_L1.76
```

-continued

```
SEQUENCE: 1013
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SHSTPFTFGQ GTKLEIK                 107

SEQ ID NO: 1014          moltype = AA   length = 107
FEATURE                  Location/Qualifiers
source                   1..107
                         mol_type = protein
                         organism = synthetic construct
                         note = 1A7[CD28]_L1.77
SEQUENCE: 1014
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SKSTPFTFGQ GTKLEIK                 107

SEQ ID NO: 1015          moltype = AA   length = 107
FEATURE                  Location/Qualifiers
source                   1..107
                         mol_type = protein
                         organism = synthetic construct
                         note = 1A7[CD28]_L1.78
SEQUENCE: 1015
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SLSTPFTFGQ GTKLEIK                 107

SEQ ID NO: 1016          moltype = AA   length = 107
FEATURE                  Location/Qualifiers
source                   1..107
                         mol_type = protein
                         organism = synthetic construct
                         note = 1A7[CD28]_L1.79
SEQUENCE: 1016
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SQSTPFTFGQ GTKLEIK                 107

SEQ ID NO: 1017          moltype = AA   length = 107
FEATURE                  Location/Qualifiers
source                   1..107
                         mol_type = protein
                         organism = synthetic construct
                         note = 1A7[CD28]_L1.80
SEQUENCE: 1017
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SVSTPFTFGQ GTKLEIK                 107

SEQ ID NO: 1018          moltype = AA   length = 107
FEATURE                  Location/Qualifiers
source                   1..107
                         mol_type = protein
                         organism = synthetic construct
                         note = 1A7[CD28]_L1.81
SEQUENCE: 1018
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SWSTPFTFGQ GTKLEIK                 107

SEQ ID NO: 1019          moltype = AA   length = 107
FEATURE                  Location/Qualifiers
source                   1..107
                         mol_type = protein
                         organism = synthetic construct
                         note = 1A7[CD28]_L1.82
SEQUENCE: 1019
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYATPFTFGQ GTKLEIK                 107

SEQ ID NO: 1020          moltype = AA   length = 107
FEATURE                  Location/Qualifiers
source                   1..107
                         mol_type = protein
                         organism = synthetic construct
                         note = 1A7[CD28]_L1.83
SEQUENCE: 1020
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYDTPFTFGQ GTKLEIK                 107

SEQ ID NO: 1021          moltype = AA   length = 107
FEATURE                  Location/Qualifiers
```

```
                        source          1..107
                                        mol_type = protein
                                        organism = synthetic construct
                                        note = 1A7[CD28]_L1.84
SEQUENCE: 1021
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYGTPFTFGQ GTKLEIK                 107

SEQ ID NO: 1022         moltype = AA   length = 107
FEATURE                 Location/Qualifiers
source                  1..107
                        mol_type = protein
                        organism = synthetic construct
                        note = 1A7[CD28]_L1.85
SEQUENCE: 1022
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYHTPFTFGQ GTKLEIK                 107

SEQ ID NO: 1023         moltype = AA   length = 107
FEATURE                 Location/Qualifiers
source                  1..107
                        mol_type = protein
                        organism = synthetic construct
                        note = 1A7[CD28]_L1.86
SEQUENCE: 1023
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYKTPFTFGQ GTKLEIK                 107

SEQ ID NO: 1024         moltype = AA   length = 107
FEATURE                 Location/Qualifiers
source                  1..107
                        mol_type = protein
                        organism = synthetic construct
                        note = 1A7[CD28]_L1.87
SEQUENCE: 1024
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYNTPFTFGQ GTKLEIK                 107

SEQ ID NO: 1025         moltype = AA   length = 107
FEATURE                 Location/Qualifiers
source                  1..107
                        mol_type = protein
                        organism = synthetic construct
                        note = 1A7[CD28]_L1.88
SEQUENCE: 1025
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYQTPFTFGQ GTKLEIK                 107

SEQ ID NO: 1026         moltype = AA   length = 107
FEATURE                 Location/Qualifiers
source                  1..107
                        mol_type = protein
                        organism = synthetic construct
                        note = 1A7[CD28]_L1.89
SEQUENCE: 1026
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYTTPFTFGQ GTKLEIK                 107

SEQ ID NO: 1027         moltype = AA   length = 107
FEATURE                 Location/Qualifiers
source                  1..107
                        mol_type = protein
                        organism = synthetic construct
                        note = 1A7[CD28]_L1.90
SEQUENCE: 1027
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYVTPFTFGQ GTKLEIK                 107

SEQ ID NO: 1028         moltype = AA   length = 107
FEATURE                 Location/Qualifiers
source                  1..107
                        mol_type = protein
                        organism = synthetic construct
                        note = 1A7[CD28]_L1.91
SEQUENCE: 1028
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYYTPFTFGQ GTKLEIK                 107

SEQ ID NO: 1029         moltype = AA   length = 107
```

```
FEATURE                 Location/Qualifiers
source                  1..107
                        mol_type = protein
                        organism = synthetic construct
                        note = 1A7[CD28]_L1.92
SEQUENCE: 1029
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSAPFTFGQ GTKLEIK                 107

SEQ ID NO: 1030         moltype = AA  length = 107
FEATURE                 Location/Qualifiers
source                  1..107
                        mol_type = protein
                        organism = synthetic construct
                        note = 1A7[CD28]_L1.93
SEQUENCE: 1030
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSDPFTFGQ GTKLEIK                 107

SEQ ID NO: 1031         moltype = AA  length = 107
FEATURE                 Location/Qualifiers
source                  1..107
                        mol_type = protein
                        organism = synthetic construct
                        note = 1A7[CD28]_L1.94
SEQUENCE: 1031
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSFPFTFGQ GTKLEIK                 107

SEQ ID NO: 1032         moltype = AA  length = 107
FEATURE                 Location/Qualifiers
source                  1..107
                        mol_type = protein
                        organism = synthetic construct
                        note = 1A7[CD28]_L1.95
SEQUENCE: 1032
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSIPFTFGQ GTKLEIK                 107

SEQ ID NO: 1033         moltype = AA  length = 107
FEATURE                 Location/Qualifiers
source                  1..107
                        mol_type = protein
                        organism = synthetic construct
                        note = 1A7[CD28]_L1.96
SEQUENCE: 1033
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSKPFTFGQ GTKLEIK                 107

SEQ ID NO: 1034         moltype = AA  length = 107
FEATURE                 Location/Qualifiers
source                  1..107
                        mol_type = protein
                        organism = synthetic construct
                        note = 1A7[CD28]_L1.97
SEQUENCE: 1034
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSLPFTFGQ GTKLEIK                 107

SEQ ID NO: 1035         moltype = AA  length = 107
FEATURE                 Location/Qualifiers
source                  1..107
                        mol_type = protein
                        organism = synthetic construct
                        note = 1A7[CD28]_L1.98
SEQUENCE: 1035
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSQPFTFGQ GTKLEIK                 107

SEQ ID NO: 1036         moltype = AA  length = 107
FEATURE                 Location/Qualifiers
source                  1..107
                        mol_type = protein
                        organism = synthetic construct
                        note = 1A7[CD28]_L1.99
SEQUENCE: 1036
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSSPFTFGQ GTKLEIK                 107
```

```
SEQ ID NO: 1037          moltype = AA   length = 107
FEATURE                  Location/Qualifiers
source                   1..107
                         mol_type = protein
                         organism = synthetic construct
                         note = 1A7[CD28]_L1.100
SEQUENCE: 1037
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSVPFTFGQ GTKLEIK                 107

SEQ ID NO: 1038          moltype = AA   length = 107
FEATURE                  Location/Qualifiers
source                   1..107
                         mol_type = protein
                         organism = synthetic construct
                         note = 1A7[CD28]_L1.101
SEQUENCE: 1038
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSYPFTFGQ GTKLEIK                 107

SEQ ID NO: 1039          moltype = AA   length = 107
FEATURE                  Location/Qualifiers
source                   1..107
                         mol_type = protein
                         organism = synthetic construct
                         note = 1A7[CD28]_L1.102
SEQUENCE: 1039
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPITFGQ GTKLEIK                 107

SEQ ID NO: 1040          moltype = AA   length = 107
FEATURE                  Location/Qualifiers
source                   1..107
                         mol_type = protein
                         organism = synthetic construct
                         note = 1A7[CD28]_L1.103
SEQUENCE: 1040
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPLTFGQ GTKLEIK                 107

SEQ ID NO: 1041          moltype = AA   length = 107
FEATURE                  Location/Qualifiers
source                   1..107
                         mol_type = protein
                         organism = synthetic construct
                         note = 1A7[CD28]_L1.104
SEQUENCE: 1041
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPWTFGQ GTKLEIK                 107

SEQ ID NO: 1042          moltype = AA   length = 107
FEATURE                  Location/Qualifiers
source                   1..107
                         mol_type = protein
                         organism = synthetic construct
                         note = 1A7[CD28]_L1.105
SEQUENCE: 1042
DIQMTQSPSS LSASVGDRVT ITCRASQSIS SYLTWYQQKP GKAPKLLIYA ASSLQSGVPS    60
RFSGSGSGTD FTLTISSLQP EDFATYYCQQ VYSTPFTFGQ GTKLEIK                 107

SEQ ID NO: 1043          moltype = AA   length = 107
FEATURE                  Location/Qualifiers
source                   1..107
                         mol_type = protein
                         organism = synthetic construct
                         note = 1A7[CD28]_L1.106
SEQUENCE: 1043
DIQMTQSPSS LSASVGDRVT ITCRASQSIS SYLTWYQQKP GKAPKLLIYA ASSLQSGVPS    60
RFSGSGSGTD FTLTISSLQP EDFATYYCQQ SYNTPFTFGQ GTKLEIK                 107

SEQ ID NO: 1044          moltype = AA   length = 4
FEATURE                  Location/Qualifiers
source                   1..4
                         mol_type = protein
                         organism = synthetic construct
SEQUENCE: 1044
YMNM                                                                 4

SEQ ID NO: 1045          moltype = AA   length = 5
```

```
FEATURE                 Location/Qualifiers
source                  1..5
                        mol_type = protein
                        organism = synthetic construct
SEQUENCE: 1045
GSGGS                                                                      5

SEQ ID NO: 1046         moltype = AA  length = 5
FEATURE                 Location/Qualifiers
source                  1..5
                        mol_type = protein
                        organism = synthetic construct
SEQUENCE: 1046
GGGGS                                                                      5

SEQ ID NO: 1047         moltype = AA  length = 4
FEATURE                 Location/Qualifiers
source                  1..4
                        mol_type = protein
                        organism = synthetic construct
SEQUENCE: 1047
GGGS                                                                       4

SEQ ID NO: 1048         moltype = AA  length = 479
FEATURE                 Location/Qualifiers
source                  1..479
                        mol_type = protein
                        organism = synthetic construct
                        note = XENP37902 Chain 2 -
                        1A7[CD28]_H1.14_L1_scFv(GKPGS)4_Fc(216)_IgG1_C220S/PVA_/S26
                        7K/S364K/E357Q
SEQUENCE: 1048
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QSYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479

SEQ ID NO: 1049         moltype = AA  length = 479
FEATURE                 Location/Qualifiers
source                  1..479
                        mol_type = protein
                        organism = synthetic construct
                        note = XENP37903 Chain 2 -
                        1A7[CD28]_H1.14_L1.71_scFv(GKPGS)4_Fc(216)_IgG1_C220S/PVA_/
                        S267K/S364K/E357Q
SEQUENCE: 1049
EVQLLESGGG LVQPGGSLRL SCAASGFTFS SYYMSWVRQA PGKGLEWVST ISESGDSTYY    60
ADSVKGRFTI SRDNSKNTLY LQMNSLRAED TAVYYCAKSG PGLRQVGFDY WGQGTLVTVS   120
SGKPGSGKPG SGKPGSGKPG SDIQMTQSPS SLSASVGDRV TITCRASQSI SSYLNWYQQK   180
PGKAPKLLIY AASSLQSGVP SRFSGSGSGT DFTLTISSLQ PEDFATYYCQ QVYSTPFTFG   240
QGTKLEIKEP KSSDKTHTCP PCPAPPVAGP SVFLFPPKPK DTLMISRTPE VTCVVVDVKH   300
EDPEVKFNWY VDGVEVHNAK TKPREEQYNS TYRVVSVLTV LHQDWLNGKE YKCKVSNKAL   360
PAPIEKTISK AKGQPREPQV YTLPPSREQM TKNQVKLTCL VKGFYPSDIA VEWESNGQPE   420
NNYKTTPPVL DSDGSFFLYS KLTVDKSRWQ QGNVFSCSVM HEALHNHYTQ KSLSLSPGK    479
```